US008178552B2

(12) United States Patent
Graczyk et al.

(10) Patent No.: US 8,178,552 B2
(45) Date of Patent: May 15, 2012

(54) 7-AZAINDOLE DERIVATIVES AND THEIR USE IN THE INHIBITION OF C-JUN N-TERMINAL KINASE

(75) Inventors: Piotr Pawel Graczyk, London (GB); Paschalis Dimopoulos, London (GB); Afzal Khan, London (GB); Gurpreet Singh Bhatia, London (GB); Christopher Neil Farthing, London (GB)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 12/536,342

(22) Filed: Aug. 5, 2009

(65) Prior Publication Data

US 2010/0069354 A1 Mar. 18, 2010

Related U.S. Application Data

(63) Continuation of application No. PCT/EP2008/051428, filed on Feb. 5, 2008.

(51) Int. Cl.
*C07D 471/02* (2006.01)
*C07D 491/02* (2006.01)
*C07D 498/02* (2006.01)
*A01N 43/42* (2006.01)
*A61K 31/44* (2006.01)

(52) U.S. Cl. ........................................ 514/300; 546/113

(58) Field of Classification Search .................. 546/113; 514/300

See application file for complete search history.

(56) References Cited

U.S. PATENT DOCUMENTS 7,645,769 B2 * 1/2010 Khan et al. .................... 514/300

OTHER PUBLICATIONS

Manning et al., Nature review Drug Discovery, vol. 2, (2003), 554-565.*

Bennett et al., PNAS, vol. 98, (2001), 13681-13686.*

Bendotti et al., Central nervous System. Agents in Medicinal Chemistry, vol. 6, No. 2, (2006), 1-9.*

Bhattacharya, Birendra K. et al., "Total synthesis of 2'-deoxy-2'-arafluoro-tubercidin,-toyocamycin, -sangivamycin and certain related nucleosides," *J. Chem. Soc. Perkin. Trans. I*, pp. 1543-1550 (1995).

Denmark, Scott E. et al., "Convergence of Mechanistic Pathways in the Palladium(0)-Catalyzed Cross-Coupling of Alkenylsilacyclobutanes and Alkenylsilanols," *Organic Letters*, vol. 2(16):2491-2494 (2000).

Ehrentraut, Andreas et al., "A New Efficient Palladium Catalyst for Heck Reactions of Deactivated Aryl Chlorides," *Synlett*, vol. 11:1589-1592 (2000).

Escoubet, Stéphanie et al., "Thiyl Radical Mediated Racemization of Nonactivated Aliphatic Amines," *J. Org. Chem.*, vol. 71:7288-7292 (2006).

Gu, Xiao-Hui et al., "Syntheses and Biological Activities of Bis(3-indolyl)thiazoles, Analogues of Marine Bis(indole)alkaloid Nortopsentins," *Bioorganic & Medicinal Chemistry Letters*, vol. 9:569-572 (1999).

Hartung, Christian G. et al., "Highly Selective Palladium-Catalyzed Heck Reactions of Aryl Bromides with Cycloalkenes," *Organic Letters*, vol. 1(5):709-711 (1999).

Hatanaka, Yasuo et al., "Cross-Coupling of Organosilanes with Organic Halides Mediated by Palladium Catalyst and Tris(diethylamino)sulfonium Difluorotrimethylsilicate," *J. Org. Chem.*, vol. 53:918-920 (1988).

Hatanaka, Yasuo et al., "Highly Selective Cross-Coupling Reactions of Organosilicon Compounds Mediated by Fluoride Ion and a Palladium Catalyst," *Synlett*, pp. 845-853 (1991).

Hosoya, Takamitsu et al., "Rapid methylation on carbon frameworks useful for the synthesis of $^{11}CH_3$-incorporated PET tracers: Pd(0)-mediated rapid coupling of methyl iodide with an alkenyltributylstannane leading to a 1-methylalkene," *Org. Biomol. Chem.*, vol. 4:410-415 (2006).

Krawczyk, Steven H. et al., "Synthesis and Evaluation of Certain Thiosangivamycin Analogs as Potential Inhibitors of Cell Proliferation and Human Cytomegalovirus," *J. Med. Chem.*, vol. 38:4115-4119 (1995).

Lambert, Joseph B. et al., "Stabilization of Positive Charge by β Silicon," *J. Am. Chem. Soc.*, vol. 109:7838-7845 (1987).

Littke, Adam F. et al., "Pd/P($t$-Bu)$_3$: A Mild and General Catalyst for Stille Reactions of Aryl Chlorides and Aryl Bromides," *J. Am. Chem. Soc.*, vol. 124:6343-6348 (2002).

Littke, Adam F. et al., "Versatile Catalysts for the Suzuki Cross-Coupling of Arylboronic Acids with Aryl and Vinyl Halides and Triflates under Mild Conditions," *J. Am. Chem. Soc.*, vol. 122:4020-4028 (2000).

Mazzola, R.D. et al., "Improved Yields with Added Copper(I) Salts in Carbonylative Stille Couplings of Sterically Hindered Vinylstannanes," *J. Org. Chem.*, vol. 69:220-223 (2004).

Mitchell, Terence N., "Palladium-Catalysed Reactions of Organotin Compounds," *Synthesis*, pp. 803-815 (1992).

Ognyanov, Vassil I. et al., "Design of Potent, Orally Available Antagonists of the Transient Receptor Potential Vanilloid 1. Structure-Activity Relationships of 2-Piperazin-1-yl-1*H*-benzimidazoles," *J. Med. Chem.*, vol. 49:3719-3742 (2006).

Paquette, Leo A. et al., "Total Synthesis of Dumsin. 1. Retrosynthetic Strategy and the Elaboration of Key Intermediates from (-)-Bornyl Acetate," *J. Org. Chem.*, vol. 68:6905-6918 (2003).

Pearson, William H. et al., "Total Synthesis of the *Kopsia lapidilecta* Alkaloid (±)-Lapidilectine B," *J. Org. Chem.*, vol. 69:9109-9122 (2004).

Schwarz, George, "2,4-Dimethylthiazole [Thiazole, 2,4-dimethyl-]," *Organic Syntheses, Coll.*, vol. 3:332 (1955): vol. 25:35 (1945).

Stille, John K., "The Palladium-Catalyzed Cross-Coupling Reactions of Organotin Reagents with Organic Electrophiles," *Chem. Int. Ed. Engl.*, vol. 25:508-524 (1986).

Suzuki, Akira, "Synthetic studies via the cross-coupling reaction of organoboron derivatives with organic halides," *Pure & Appl. Chem.*, vol. 63(3):419-422 (1991).

(Continued)

*Primary Examiner* — Janet Andres
*Assistant Examiner* — Niloofar Rahmani
(74) *Attorney, Agent, or Firm* — Nelson Mullins Riley & Scarborough LLP; John F. Resek; Pankaj N. Desai, J.D.

(57) ABSTRACT

The present invention provides a compound of formula (I); or a pharmaceutically acceptable salt thereof, the use of a compound of formula (I) or a pharmaceutically acceptable salt thereof in the inhibition of c-Jun N-terminal kinase (JNK) activity and the use in medicine and particularly in the treatment of neurodegenerative disorders, inflammatory diseases and/or and autoimmune diseases. The invention also provides processes for the manufacture of said compounds of formula (I) or a pharmaceutically acceptable salt thereof and compositions containing them.

16 Claims, 13 Drawing Sheets

OTHER PUBLICATIONS

Tamao, Kohei et al., "Palladium-Catalyzed Cross-Coupling Reaction of Alkenylalkoxysilanes with Aryl and Alkenyl Halides in the Presence of a Fluoride Ion," *Tetrahedron Letters*, vol. 30(44):6051-6054 (1989).

Thompson, Scott K. et al., "Synthesis and Antiviral Activity of a Novel Class of HIV-1 Protease Inhibitors Containing a Heterocyclic $P_1$'-$P_2$' Amide Bond Isostere," *Bioorganic & Medicinal Chemistry Letters*, vol. 4(20):2441-2446 (1994).

Uozumi, Yasuhiro et al., "Heck Reaction in Water with Amphiphilic Resin-Supported Palladium-Phosphine Complexes," *Synlett*, vol. 12:2045-2047 (2002).

Graczyk, Piotr P., "Gini Coefficient: A New Way to Express Selectivity of Kinase Inhibitors against a Family of Kinases," J. Med. Chem., vol. 50:5773-5779 (2007).

Stariha, Rochelle L., et al., "Mitogen-activated protein kinase signalling in oligodendrocytes: a comparison of primary cultures and CG-4," Int. J. Devl Neuroscience 19 (2001) 427-437.

Takahashi, Hidetoshi, et al., "Extracellular regulated kinase and c-Jun N-terminal kinase are activated in psoriatic involved epidermis," Journal of Dermatological Science 30 (2002) 94-99.

Shin, Taekyun, et al., "Activation of mitogen-activated protein kinases in experimental autoimmune encephalomyelitis," Journal of Neuroimmunology 140 (2003) 118-125.

Gazel, Alix, et al., "Inhibition of JNK Promotes Differentiation of Epidermal Keratinocytes," The Journal of Biological Chemistry vol. 281, No. 29, pp. 20530-20541, Jul. 21, 2006.

* cited by examiner

7-AZAINDOLE DERIVATIVES AND THEIR USE IN THE INHIBITION OF C-JUN N-TERMINAL KINASE

RELATED APPLICATIONS

This application is a continuation of International Application Number PCT/EP2008/051428, filed on Feb. 5, 2008, which claims priority to GB 070226.0, which was filed on Feb. 6, 2007. The entire contents of the aforementioned applications are hereby incorporated herein by reference.

FIELD OF THE INVENTION

The invention relates to 7-azaindole derivatives or pharmaceutically acceptable salts thereof, their use in the inhibition of c-Jun N-terminal kinase (AK) activity, their use in medicine and particularly in the treatment of neurodegenerative disorders, inflammatory diseases, autoimmune diseases and/or organ failure. The invention also provides processes for the manufacture of said 7-azaindole derivatives and compositions containing them.

BACKGROUND OF THE INVENTION

The c-Jun N-terminal kinases (hereinafter referred to as "JNKs") are a family of serine/threonine protein kinases and members of the mitogen-activated protein kinase (MAPK) family. Three distinct genes (JNK1, JNK2 and JNK3) have been identified.

It is known that JNKs are related to neurodegenerative disorders such as multiple sclerosis and autoimmune diseases such as rheumatoid arthritis (WO2004/078756).

Furthermore, the above patent reference also discloses that 7-azaindole derivatives which have a ring on the C3 position and an aromatic group such as a phenyl group or a heterocyclic group such as a morpholino group on the C5 position possess JNK inhibitory activity.

Also, it is known that certain 7-azaindole derivatives having substitution (for example a thiazolyl group) at the C3 position and substitution (for example a heterocyclic group) at the C5 position can show in vitro inhibitory activity against other kinases, namely TEC and JAK kinases (WO2006/004984).

However, there is no disclosure of 7-azaindole derivatives which have a pyrazolyl group on the C3 position and a non-aromatic carbocyclic group on the C5 position.

It is desirable for a JNK inhibitor to have superior selectivity for JNK over other kinases. This is in order to reduce the risk of unexpected side-effects.

DESCRIPTION OF THE INVENTION

Under the circumstances, the present inventors have conducted intensive studies. As a result, they have found that 7-azaindole derivatives which have a pyrazolyl group on C3 position and non-aromatic hydrocarbon cyclic group on C5 position have a superior selectivity for JNK kinases over other kinases and show significant in vivo activity, thereby completing the present invention.

The first aspect of the invention therefore relates to a compound of formula (I); or a pharmaceutically acceptable salt thereof, (I)

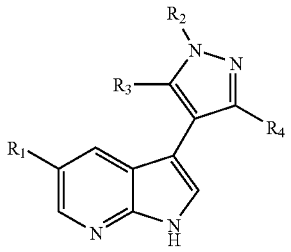

wherein $R^1$ represents a 5-7 membered non-aromatic hydrocarbon cyclic group optionally and independently substituted with 1-4 substituent(s) selected from the group consisting of a halogen atom, a cyano group, a hydroxyl group, an oxo group, an ethylenedioxy group, a $C_{1-6}$ alkyl group, a $C_{1-6}$ alkoxy group, a $C_{1-6}$ hydroxyalkyl group, —C(O)OH, —$CONH_2$, a $NHR^5$ group, a $NR^5R^6$ group and —$R^a$-$R^b$;

wherein $R^a$ represents a single bond or —$CH_2$—;

wherein $R^b$ represents a 4-8 membered non-aromatic heterocyclic group, a $C_{6-10}$ aryl group or a 5-7 membered heteroaryl group, optionally and independently substituted with 1-4 substituent(s) selected from the group consisting of a halogen atom and a $C_{1-6}$ alkyl group;

wherein $R^5$ and $R^6$ are independently selected from a $C_{1-6}$ alkyl group, a $C_{1-6}$ alkoxy group, a $C_{1-6}$ hydroxyalkyl group or a 6-membered non-aromatic heterocyclic group wherein two or more positions on $R^1$ are optionally bridged by a group —X— wherein X is O, $CH_2$, $CH_2$—$CH_2$, $NR^7$, $CH_2$—$CH_2$—$CH_2$, $CH_2$—$CH(CH_2$—)—$CH_2$ or $N(R^7)$—$CH(CH_2$—)$CH_2$ to form a bicyclic or tricyclic ring system, wherein $R^7$ is independently selected from hydrogen or a $C_{1-6}$ alkyl group and wherein said bridge may be optionally and independently substituted with one or more of a $C_{1-6}$ alkyl group, a cyano group, $CO_2NH_2$, a $C_{1-6}$ hydroxyalkyl group, an oxo group, a hydroxy group, a $C_{1-6}$ alkylamino group or a 6-membered non-aromatic heterocyclic group wherein $R^2$ represents a hydrogen atom, a $C_{1-6}$ alkyl group optionally substituted with a 4-7 membered non-aromatic heterocyclic group or a $C_{1-6}$ haloalkyl group $R^3$ represents a hydrogen atom or a $C_{1-6}$ alkyl group and $R^4$ represents a hydrogen atom or a $C_{1-6}$ alkyl group.

In a preferred embodiment, the first aspect of the invention relates to a compound of formula (Ia) or a pharmaceutically acceptable salt thereof (Ia)

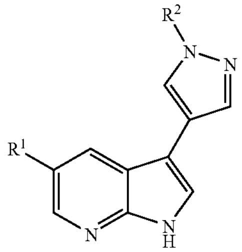

wherein $R^1$ represents a 5-7 membered non-aromatic hydrocarbon cyclic group optionally and independently substituted with 1-4 substituent(s) selected from the group consisting of a halogen atom, an oxo group, an ethylenedioxy group, a $C_{1-6}$ alkyl group, a $C_{1-6}$ alkoxy group, a $C_{1-6}$ hydroxyalkyl group, —C(O)OH, a ($C_{1-6}$ alkyl)amino group, a di($C_{1-6}$ alkyl)amino group and —$R^a$-$R^b$;

wherein $R^a$ represents a single bond or —$CH_2$—;

wherein $R^b$ represents a 4-7 membered non-aromatic heterocyclic group, a $C_{6-10}$ aryl group or a 5-7 membered heteroaryl group, optionally and independently substituted with 1-4 substituent(s) selected from the group consisting of a halogen atom and a $C_{1-6}$ alkyl group;

wherein $R^2$ represents a hydrogen atom, a $C_{1-6}$ alkyl group optionally substituted with a 4-7 membered non-aromatic heterocyclic group or a $C_{1-6}$ haloalkyl group.

Alternatively, the present invention relates to a compound of formula (Ia) or a pharmaceutically acceptable salt thereof wherein $R^1$ represents a 5-7 membered non-aromatic hydrocarbon cyclic group optionally and independently substituted with 1-4 substituent(s) selected from the group consisting of a halogen atom, an oxo group, an ethylenedioxy group, a $C_{1-6}$ alkyl group, a $C_{1-6}$ alkoxy group, a $C_{1-6}$ hydroxyalkyl group, —C(O)OH, and —$R^a$-$R^b$; and wherein $R^a$, $R^b$ and $R^2$ are as defined above for the compound of formula (Ia).

In a preferred embodiment, $R^1$ represents a cyclopentyl group, a cyclohexyl group, a cycloheptyl group, a cyclopentenyl group, a cyclohexenyl group, a cycloheptenyl group, a cyclohexadienyl group, borane, norborane, adamantane, 7-oxabicyclo[2.2.1]hept-2,3-ene, 7-oxabicyclo[2.2.1]heptane, or 7-aminobicyclo[2.2.1]hept-2,3-ene, each of which may optionally and independently substituted with 1-4 substituent(s) selected from the group consisting of a halogen atom, an oxo group, an ethylenedioxy group, a $C_{1-6}$ alkyl group, a $C_{1-6}$ alkoxy group, a $C_{1-6}$ hydroxyalkyl group, —C(O)OH, a ($C_{1-6}$ alkyl)amino group, a di($C_{1-6}$ alkyl)amino group and —$R^a$-$R^b$;

wherein $R^a$ represents a single bond or —$CH_2$—;

wherein $R^b$ represents a 4-7 membered non-aromatic heterocyclic group, a $C_{6-10}$ aryl group or a 5-6 membered heteroaryl group, optionally and independently substituted with 1-4 substituent(s) selected from the group consisting of a halogen atom and a $C_{1-6}$ alkyl group.

Preferably, $R^1$ represents a cyclohexyl group optionally and independently substituted with 1-4 substituent(s) selected from the group consisting of a halogen atom, an oxo group, an ethylenedioxy group, a $C_{1-6}$ alkyl group, a $C_{1-6}$ alkoxy group, a $C_{1-6}$ hydroxyalkyl group, —C(O)OH, a ($C_{1-6}$ alkyl)amino group, a di($C_{1-6}$ alkyl)amino group and —$R^a$-$R^b$;

wherein $R^a$ represents a single bond or —$CH_2$—;

wherein $R^b$ represents a 4-7 membered non-aromatic heterocyclic group, a $C_{6-10}$ aryl group or a 5-6 membered heteroaryl group, optionally and independently substituted with 1-4 substituent(s) selected from the group consisting of a halogen atom and a $C_{1-6}$ alkyl group;

More preferably, $R^1$ represents a 5-7 membered non-aromatic hydrocarbon cyclic group optionally and independently substituted with 1-4 substituent(s) selected from the group consisting of a fluorine atom, an oxo group, an ethylenedioxy group, methyl group, ethyl group, t-butyl group, methoxy group, methylamino group, dimethylamino group, diethylamino group, azetidinyl group, piperidyl group, fluoropiperidyl group, pyrrolidinyl group, methylpiperazinyl group, isopropylpiperazinyl group, methyldiazepanyl group, morpholino group, oxazepanyl group, oxazocanyl group, pyrimidyloxy group and fluorophenoxy group.

In a preferred embodiment, $R^1$ represents a 5-7 membered non-aromatic hydrocarbon cyclic group optionally and independently substituted with 1-4 substituent(s) selected from the group consisting of a methylpiperazinyl group, a morpholino group, oxazepanyl group and an oxazocanyl group.

Preferably, $R^1$ represents a cyclohexyl group optionally and independently substituted with 1-4 substituent(s) selected from the group consisting of a methylpiperazinyl group, a morpholino group oxazepanyl group and an oxazocanyl group.

Preferably, $R^2$ represents a methyl group, a morpholinoethyl group or a trifluoromethyl group. More preferably $R^2$ represents a methyl group. Preferably $R^3$ and $R^4$ independently represent a hydrogen or a methyl group.

In a second aspect, the invention relates to a compound selected from the following group or a pharmaceutically acceptable salt thereof;

I-6

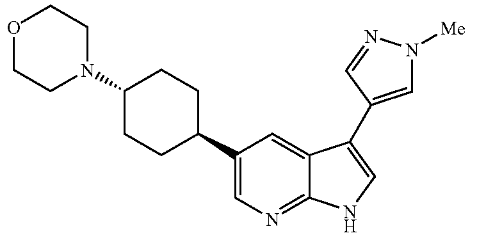

I-7

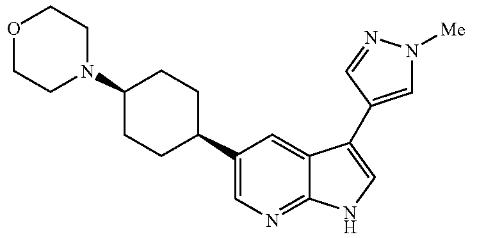

I-23

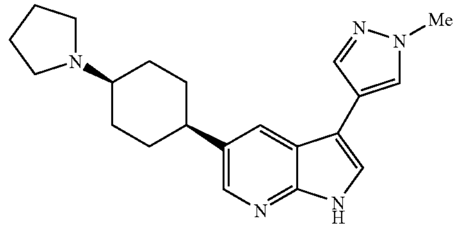

I-24

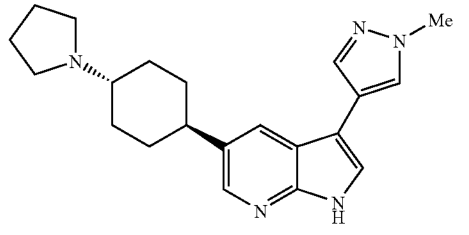

I-25

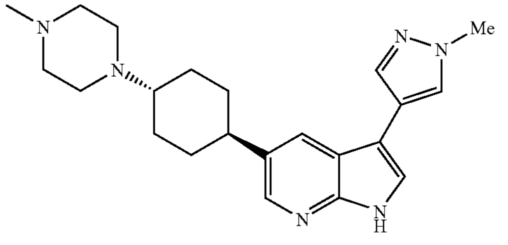

-continued
I-26
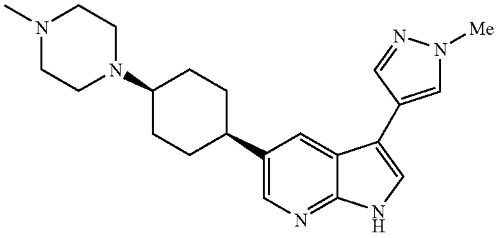
I-37
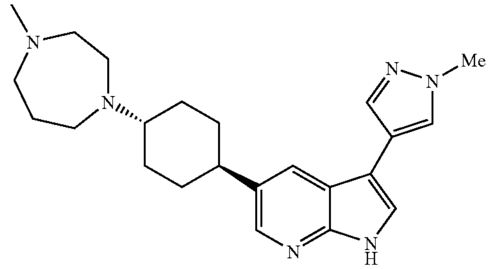
I-38
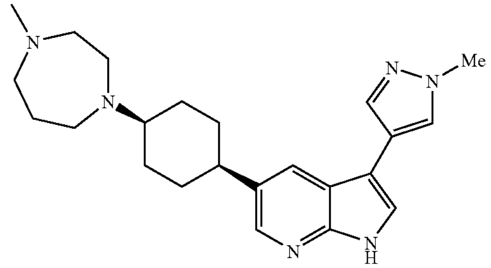
I-39
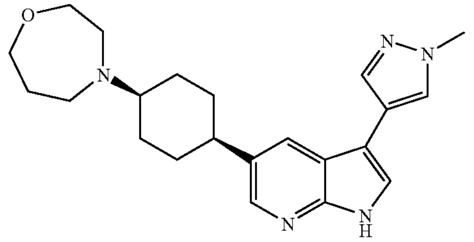
I-40
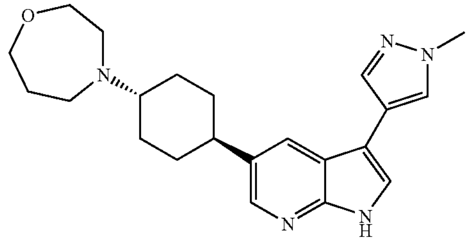
I-41
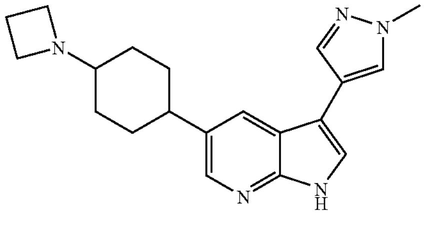
-continued
I-43
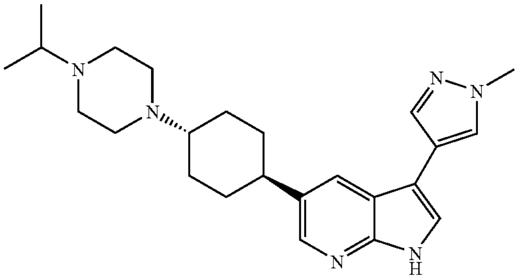
I-44
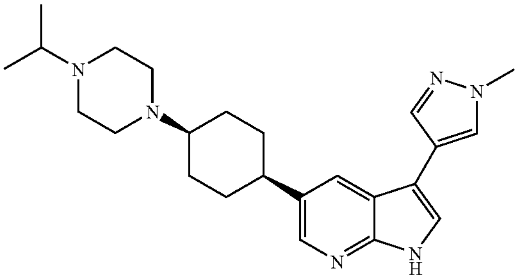
I-45
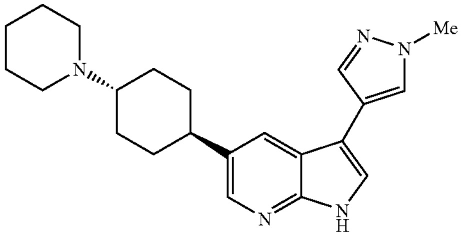
I-46
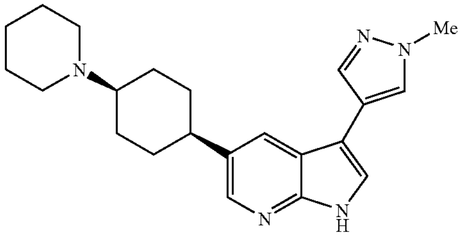
I-71
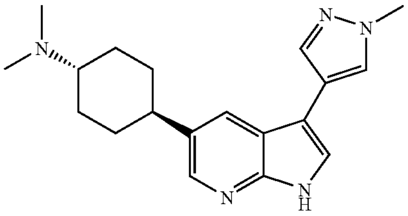
I-72
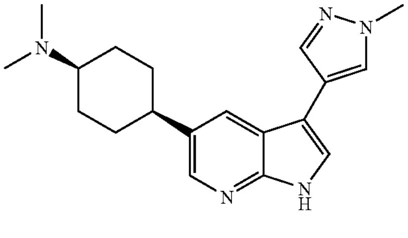

-continued

I-129

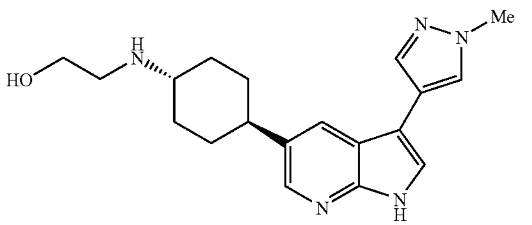

In a third aspect, the invention provides a pharmaceutical composition comprising a compound as defined herein.

In a fourth aspect, the invention provides a compound or a pharmaceutical composition as defined herein for use in medicine.

In a fifth aspect, the invention provides a compound or a pharmaceutical composition as defined herein for use in preventing and/or treating a neurodegenerative disorder, an inflammatory disease, an autoimmune disease and/or organ failure. Preferably, the neurodegenerative disorder is multiple sclerosis. Preferably, the inflammatory disease is is multiple sclerosis. Preferably, the autoimmune disease is rheumatoid arthritis. Preferably the organ failure is heart failure, liver failure or diabetic nephropathy.

In a sixth aspect, the invention provides a method for preventing and/or treating a neurodegenerative disorder (for example multiple sclerosis), an inflammatory disease (for example, multiple sclerosis), an autoimmune disease (for example rheumatoid arthritis) and/or organ failure (for example, heart failure, liver failure or diabetic nephropathy), which comprises administering to a mammalian animal an effective amount of a compound or pharmaceutically salt thereof or a composition as defined herein.

In a seventh aspect, the invention provides the use of a compound or pharmaceutically salt thereof as defined herein, for the manufacture of a medicament for the prevention and/or treatment of a neurodegenerative disorder (for example multiple sclerosis), an inflammatory disease (for example, multiple sclerosis), an autoimmune disease (for example rheumatoid arthritis) and/or organ failure (for example, heart failure, liver failure or diabetic nephropathy).

The invention further provides a process for the manufacture of a compound of formula (I) and intermediates involved in the manufacture of a compound of formula (I). Processes for the manufacture of said compound and intermediates are described hereinafter in Reaction Schemes 1 to 4 and are illustrated by the accompanying examples.

DETAILED DESCRIPTION OF THE INVENTION

Figure 1:
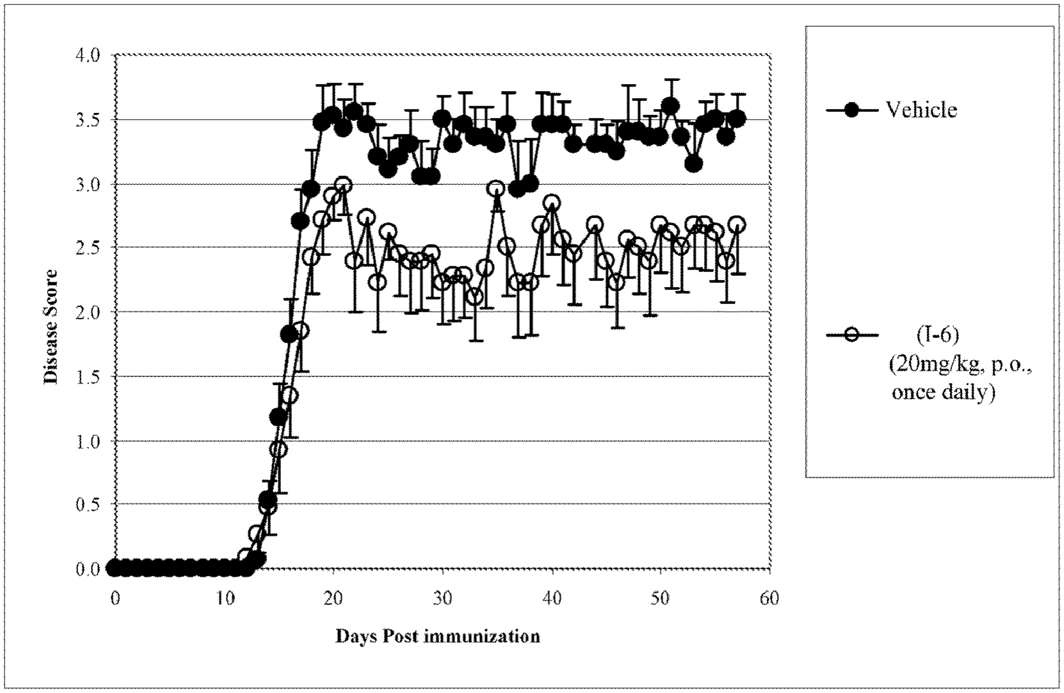
FIG. 1 shows the effect of compound I-6 (20 mg/kg, p.o., once daily) on peak disease score in the EAE experiment in mice.

The meanings of symbols or terms used in the specification of the present application will be explained below, and the present invention will be described in detail.

The compounds of the present invention are provided for the prevention and or treatment of neurodegenerative disorders, inflammatory diseases and/or autoimmune diseases and/or organ failure.

Examples of "neurodegenerative disorders" used herein are: multiple sclerosis, dementia; Alzheimer's disease; Parkinson's disease; Amyotrophic Lateral Sclerosis; Huntington's disease; senile chorea; Sydenham's chorea; hypoglycemia; head and spinal cord trauma including traumatic head injury; acute and chronic pain; epilepsy and seizures; olivopontocerebellar dementia; neuronal cell death; hypoxia-related neurodegeneration; acute hypoxia; glutamate toxicity including glutamate neurotoxicity; cerebral ischemia; dementia linked to meningitis and/or neurosis; cerebrovascular dementia; or dementia in an HIV-infected patient, preferably multiple sclerosis.

Examples of "autoimmune diseases" used herein are: multiple sclerosis, rheumatoid arthritis, systemic lupus erythematosus, glumerulonephritis, scleroderma, chronic thyroiditis, Graves's disease, autoimmune gastritis, diabetes, autoimmune haemolytis anaemia, autoimmune neutropaenia, thrombocytopenia, atopic dermatitis, chronic active hepatitis, myasthenia gravis, multiple sclerosis, ulcerative colitis, Crohn's disease, psoriasis or graft vs host disease, preferably rheumatoid arthritis.

Examples of "inflammatory diseases" used herein are asthma, autoimmune diseases (including multiple sclerosis, systemic Lupus erythematosus), chronic inflammation, chronic prostatitis, glomerulonephritis, hypersensitivity, inflammatory bowel disease, pelvic inflammatory disease, reperfusion injury, rheumatoid arthritis, transplant rejection and vasculitis.

It will be appreciated that an inflammatory disease is a disease accompanied by a cascade of biochemical events including the local vascular system, the immune system and various cells within the injured tissues, e.g. brain, spinal cord, synovial joints, organ systems (heart, liver, kidney lung, gut) and soft tissue, (muscle, skin) etc. For the purposes of the present invention, inflammation can either be acute or chronic. The inflammatory diseases for the present invention include those which involve the immune system (i.e. as demonstrated in allergic reaction and some myopathies). The inflammatory diseases for the present invention further include non-immune diseases with aetiological orgins in inflammatory processes including cancer, atherosclerosis and ischameic heart disease.

The compounds of the present invention are further provided for the prevention and/or treatment of organ failure, particularly of the heart, liver or kidneys. Examples of "organ failure" used herein are chronic or acute cardiac failure, cardiac hypertrophy, dilated, hypertrophic or restrictive cardiomyopathy, acute myocardial infarction, post-myocardial infarction, acute or chronic myocarditis, diastolic dysfunction of the left ventricle, systolic dysfunction of the left ventricle; hypertension and nephropathy and nephritis as complications thereof, diabetic nephropathy, endothelial dysfunction, arteriosclerosis or post-angioplasty restenosis. The invention particularly relates to the prevention and/or treatment of diabetic nephropathy.

The compounds of the present invention are further provided for the prevention and/or treatment of chronic rheumatoid arthritis, osteoarthritis, gout, chronic obstructive pulmonary disease, asthma, bronchitis, cystic fibrosis, inflammatory bowel disease, irritable colon syndrome, mucous colitis, ulcerative colitis, Crohn's disease, gastritis, esophagitis, eczema, dermatitis, hepatitis, glomerulonephritis, ophthalmic diseases, diabetic retinopathy, diabetic macular edema, diabetic nephropathy, diabetic neuropathy, obesity, psoriasis, cancer, cerebral apoplexy, cerebrovascular disorder, an ischemic disorder of an organ selected from the heart, kidney, liver and brain, ischemia reperfusion injury, endotoxin shock or rejection in transplantation.

The term "halogen atom" used herein means a fluorine atom, a chlorine atom, a bromine atom, an iodine atom and the like, preferably a fluorine atom or a chlorine atom, and more preferably a fluorine atom.

The term "$C_{1-6}$ alkyl group" used herein means an alkyl group that is a straight or branched chain with 1 to 6 carbons. The alkyl group therefore has 1, 2, 3, 4, 5 or 6 carbon atoms. Specifically, examples of "$C_{1-6}$ alkyl group" include methyl group, ethyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, n-hexyl group, 1-ethyl-2-methylpropyl group, 1,1,2-trimethylpropyl group, 1-ethylbutyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group and the like.

The term "$C_{1-6}$ haloalkyl group" used herein means $C_{1-6}$ alkyl group as described above is substituted with 1, 2 or 3 halogen atom(s). Specifically, examples of "$C_{1-6}$ haloalkyl group" include fluoromethyl group, difluoromethyl group, trifluoromethyl group, fluoroethyl group, difluroethyl group, trifluoroethyl group, chloromethyl group, bromomethyl group, iodomethyl group and the like.

The term "$C_{1-6}$ alkoxy group" used herein means an oxy group that is bonded to the previously defined "$C_{1-6}$ alkyl group". Specifically, examples of "$C_{1-6}$ alkoxy group" include methoxy group, ethoxy group, n-propoxy group, iso-propoxy group, n-butoxy group, iso-butoxy group, sec-butoxy group, tert-butoxy group, n-pentyloxy group, iso-pentyloxy group, sec-pentyloxy group, n-hexyloxy group, iso-hexyloxy group, 1,1-dimethylpropoxy group, 1,2-1 dimethylpropoxy group, 2,2-dimethylpropoxy group, 2-methylbutoxy group, 1-ethyl-2-methylpropoxy group, 1,1,2-trimethylpropoxy group, 1,1-dimethylbutoxy group, 1,2-dimethylbutoxy group, 2,2-dimethylbutoxy group, 2,3-dimethylbutoxy group, 1,3-dimethylbutoxy group, 2-ethylbutoxy group, 2-methylpentyloxy group, 3-methylpentyloxy group and the like.

The term "($C_{1-6}$ alkyl)amino group" used herein means an amino group which is substituted with a $C_{1-6}$ alkyl group as described above.

The term "di($C_{1-6}$ alkyl)amino group" used herein means an amino group which is substituted with two $C_{1-6}$ alkyl group as described above.

The term "5-7 membered non-aromatic hydrocarbon cyclic group" used herein means 5-7 membered cycloalkyl group, 5-7 membered cycloalkenyl group and 5-7 membered cycloalkadienyl group. The non-aromatic hydrocarbon cyclic group therefore has 5, 6 or 7 ring members. Specifically, examples of "5-7 membered non-aromatic hydrocarbon cyclic group" include cyclopentyl group, cyclohexyl group, cycloheptyl group, cyclopentenyl group, cyclohexenyl group, cycloheptenyl group, cyclopentadienyl group, cyclohexadienyl group cycloheptadienyl group borane, adamantane, 7-oxabicyclo[2.2.1]hept-2,3-ene, 7-oxabicyclo[2.2.1]heptane or 7-aminobicyclo[2.2.1]hept-2,3-ene.

The non-aromatic hydrocarbon cyclic group may be provided as a bicyclic or tricyclic ring system having two or more shared or common atoms. In this case, the non-aromatic hydrocarbon cyclic group comprises a bridging moiety having one or more atoms selected from C, N, O or S, said bridging moiety connecting the two or more shared or common atoms.

Preferably, the non-aromatic hydrocarbon cyclic group is a six membered cycloalkyl group or a six membered cycloalkenyl group with a bridging moiety selected from —$CH_2$—, —O—, —N—, —$(CH_2)_3$—, —$CH_2$—$CH_2$—N—.

The bridging moiety can be attached to two shared or common atoms which are adjacent to each other on the non-aromatic hydrocarbon cyclic group or which are separated by one, two or three ring atoms.

Examples include borane, norborane, adamantane, 7-oxabicyclo[2.2.1]hept-2,3-ene, 7-oxabicyclo[2.2.1]heptane or 7-aminobicyclo[2.2.1]hept-2,3-ene.

The non-aromatic hydrocarbon cyclic group may be optionally and independently substituted at any available position on the ring atoms and/or bridging atoms with 1 to 4 substituent(s) selected from the group consisting of a halogen atom, an oxo group, a $C_{1-6}$ alkyl group, a $C_{1-6}$ hydroxyalkyl group, —$CONH_2$, a hydroxy group, a $C_{1-6}$alkylamino group or a 6-membered non-aromatic heterocyclic group. Preferably, the substituent(s) are selected from the group consisting of methyl, CN, $CO_2NH_2$, $CH_2$—OH, =O, OH, NHMe, or a 6-membered non-aromatic heterocyclic group comprising two nitrogen atoms. When the non-aromatic hydrocarbon cyclic group is substituted on a bridging N-atom, the substituent is preferably hydrogen or a $C_{1-6}$ alkyl group, more preferably hydrogen, methyl, ethyl or propyl.

The term "4-8 membered non-aromatic heterocyclic group" used herein means heterocyclic group, which has no aromaticity and the number of atoms forming the ring is 4, 5, 6, 7 or 8, containing one or more species of heteroatom selected from the group consisting of a nitrogen atom, a sulphur atom and an oxygen atom. Specifically, examples of "4-8 membered non-aromatic heterocyclic group" include azetidinyl group, pyrrolidinyl group, imidazolidinyl group, pyrazolidinyl group, piperidinyl group, piperazinyl group, morpholinyl group, tetrahydropyranyl group, dioxanyl group, diazepanyl, oxazepanyl group, oxazocanyl group and the like.

The term "$C_{6-10}$ aryl group" used herein means an aryl group constituted by 6, 7, 8, 9 or 10 carbon atoms and includes condensed ring groups such as monocyclic ring group, or bicyclic ring group and the like. Specifically, examples of "$C_{6-10}$ aryl group" include phenyl group, indenyl group, naphthyl group or azulenyl group and the like. It should be noted that condensed rings such as indan and tetrahydro naphthalene are also included in the aryl group.

The term "5-7 membered heteroaryl group" used herein means a monocyclic heteroaryl group, in which the number of atoms forming the ring is 5, 6 or 7, containing one or more species of heteroatom selected from the group consisting of a nitrogen atom, a sulphur atom and an oxygen atom. Specifically, examples of "5-7 membered heteroaryl group" include 1) pyrrolyl group, pyridyl group, pyridazinyl group, pyrimidinyl group, pyrazinyl group, triazolyl group, tetrazolyl group, pyrazolyl group, imidazolyl group and the like as a nitrogen-containing heteroaryl group; 2) thienyl group and the like as a sulphur-containing heteroaryl group; 3) furyl group, pyranyl group and the like as an oxygen-containing heteroaryl group; and 4) thiazolyl group, isothiazolyl group, isoxazolyl group, furazanyl group, oxazolyl group, oxadiazolyl group, pyrazolooxazolyl group, imidazothiazolyl group, furopyrrolyl group or pyridooxazinyl group and the like as a heteroaryl group containing two or more different species of heteroatoms.

Subsequently, a substituent in the compounds according to the present invention represented by the formula (I) will be explained.

$R^1$ represents a 5-7 membered non-aromatic hydrocarbon cyclic group optionally and independently substituted with 1-4 substituent(s) selected from the group consisting of a halogen atom, a cyano group, a hydroxyl group, an oxo group, an ethylenedioxy group, a $C_{1-6}$ alkyl group, a $C_{1-6}$ alkoxy group, a $C_{1-6}$ hydroxyalkyl group, —C(O)OH, —$CONH_2$, a $NHR^5$ group, a $NR^5R^6$ group or —$R^a$-$R^b$;

wherein $R^a$ represents a single bond or —$CH_2$—;

wherein $R^b$ represents a 4-8 membered non-aromatic heterocyclic group, $C_{6-10}$ aryl group or a 5-7 membered heteroaryl group, optionally and independently substituted with 1-4 substituent(s) selected from the group consisting of halogen atom or $C_{1-6}$ alkyl group;

wherein $R^5$ and $R^6$ are independently selected from a $C_{1-6}$ alkyl group, a $C_{1-6}$ alkoxy group, a $C_{1-6}$ hydroxyalkyl group or a 6-membered non-aromatic heterocyclic group;

wherein two or more positions on $R^1$ are optionally bridged by a group —X— wherein X is O, $CH_2$, $CH_2$—$CH_2$, $NR^7$, $CH_2$—$CH_2$—$CH_2$, $CH_2$—CH($CH_2$—)—$CH_2$ or N($R^7$)—CH($CH_2$—)$CH_2$ to form a bicyclic or tricyclic ring system, wherein $R^7$ is independently selected from hydrogen or a $C_{1-6}$ alkyl group and wherein said bridge may be optionally and independently substituted with one or more of a $C_{1-6}$ alkyl group, a cyano group, $CO_2NH_2$ a $C_{1-6}$ hydroxyalkyl group, an oxo group, a hydroxyl group, a $C_{1-6}$ alkylamino group or a 6-membered non-aromatic heterocyclic group.

Preferably $R^1$ represents a cyclopentyl group, a cyclohexyl group, a cycloheptyl group, a cyclopentenyl group, a cyclohexenyl group, a cycloheptenyl group, a cyclohexiadienyl group, borane, norborane, adamantane, 7-oxabicyclo[2.2.1]hept-2,3-ene, 7-oxabicyclo[2.2.1]heptane, or 7-aminobicyclo[2.2.1]hept-2,3-ene.

Preferably, $R^1$ represents a cyclohexyl group or a cyclohexenyl group. More preferably $R^1$ represents a cyclohexyl group.

Preferably $R^1$ represents a 5-7 membered non-aromatic hydrocarbon cyclic group optionally and independently substituted with 1-4 substituent(s) selected from the group consisting of a halogen atom, an oxo group, an ethylenedioxy group, a $C_{1-6}$ alkyl group, a $C_{1-6}$ alkoxy group, a $C_{1-6}$ hydroxyalkyl group, —C(O)OH, a ($C_{1-6}$ alkyl)amino group and —$R^a$-$R^b$;

wherein $R^a$ represents a single bond or —$CH_2$—;

wherein $R^b$ represents a 4-7 membered non-aromatic heterocyclic group, a $C_{6-10}$ aryl group or a 5-7 membered heteroaryl group, optionally and independently substituted with 1-4 substituent(s) selected from the group consisting of a halogen atom and a $C_{1-6}$ alkyl group;

Alternatively, $R^1$ represents a 5-7 membered non-aromatic hydrocarbon cyclic group optionally and independently substituted with 1-4 substituent(s) selected from the group consisting of a halogen atom, an oxo group, an ethylenedioxy group, a $C_{1-6}$ alkyl group, a $C_{1-6}$ alkoxy group, a $C_{1-6}$ hydroxyalkyl group, —C(O)OH, and —$R^a$-$R^b$; and wherein $R^a$ represents a single bond or —$CH_2$—;

$R^b$ represents a 4-7 membered non-aromatic heterocyclic group, a $C_{6-10}$ aryl group or a 5-7 membered heteroaryl group, optionally and independently substituted with 1-4 substituent(s) selected from the group consisting of a halogen atom and a $C_{1-6}$ alkyl group.

Preferably $R^1$ represents a cyclopentyl group, a cyclohexyl group, a cycloheptyl group, a cyclopentenyl group, a cyclohexenyl group, a cycloheptenyl group, a cyclohexiadienyl group, borane, norborane, adamantane, 7-oxabicyclo[2.2.1]hept-2,3-ene, 7-oxabicyclo[2.2.1]heptane, or 7-aminobicyclo[2.2.1]hept-2,3-ene, each of which may optionally and independently be substituted with 1-4 substituent(s) selected from the group consisting of a halogen atom, an oxo group, an ethylenedioxy group, a $C_{1-6}$ alkyl group, a $C_{1-6}$ alkoxy group, a $C_{1-6}$ hydroxyalkyl group, —C(O)OH, a ($C_{1-6}$ alkyl)amino group, a di($C_{1-6}$ alkyl)amino group and —$R^a$-$R^b$.

More preferably $R^1$ can be optionally and independently substituted with 1-4 substituent(s) selected from the group consisting of a fluorine atom, an oxo group, an ethylenedioxy group, a methyl group, an ethyl group, a t-butyl group, a methoxy group, a methylamino group, a dimethylamino group, a diethylamino group, an azetidinyl group, a piperidyl group, a fluoropiperidyl group, a pyrrolidinyl group, a methylpiperazinyl group, an isopropylpiperazinyl group, a methyldiazepanyl group, a morpholino group, oxazepanyl group and oxazocanyl group;

More preferably, $R^1$ represents a cyclohexyl group optionally and independently substituted with 1-4 substituent(s) selected from the group consisting of a fluorine atom, an oxo group, an ethylenedioxy group, a methyl group, an ethyl group, a t-butyl group, a methoxy group, a methylamino group, a dimethylamino group, a diethylamino group, an azetidinyl group, a piperidyl group, a fluoropiperidyl group, a pyrrolidinyl group, a methylpiperazinyl group, an isopropylpiperazinyl group, a methyldiazepanyl group, a morpholino group, an oxazepanyl group and an oxazocanyl group Most preferably, $R^1$ represents a cyclohexyl group optionally and independently substituted with a substituent selected from the consisting of a methylpiperazinyl group, a morpholino group, an oxazepanyl group or oxazocanyl group.

$R^2$ represents a hydrogen atom, a $C_{1-6}$ alkyl group optionally substituted with a 4-8 membered non-aromatic heterocyclic group or a $C_{1-6}$ haloalkyl group.

Preferably, $R^2$ represents a hydrogen atom, a methyl group, a morpholinomethyl group, a difluoromethyl group or a trifluoromethyl group. More preferably, $R^2$ represents a methyl group.

Preferably $R^3$ represents a hydrogen or methyl group.

Preferably $R^4$ represents a hydrogen or methyl group.

Preferably $R^5$ and $R^6$ are independently selected from a $C_{1-6}$ alkyl group, a $C_{1-6}$ alkoxy group or a 6-membered non-aromatic heterocyclic group.

More preferably $R^5$ and $R^6$ are independently methyl, ethyl, propyl, isopropyl, —$CH_2$—$CH_2$—O—$CH_2$—$CH_3$, $CH_2$—$CH_2$—O—$CH_3$, —$CH_2$—$CH_2$—OH, or a 6-membered non-aromatic heterocyclic group comprising an oxygen atom.

JNK inhibitory compounds of formula (I) as defined above have significant in vivo activity.

Specifically, the present invention provides one or more of the following compounds (the chemical structures of which are set out in the examples section): I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-50, I-51, I-52, I-53, I-54, I-55, I-56, I-57, I-58, I-59, I-60, I-62, I-63, I-64, I-66, I-67, I-68, I-71, I-72, I-73, I-74, I-75, I-76, I-77, I-78, I-79, I-80, I-93, I-94, I-95, I-96, I-101, I-102, I-103, I-104, I-105, I-106, I-107, I-108, I-109, I-110, I-111, I-112, I-113, I-114, I-115, I-116, I-117, I-118, I-119, I-120, I-121, I-122, I-123, I-124, I-125, I-126, I-127, I-128, I-129, I-130, I-131, I-133, I-136, I-137, I-138, I-139, I-140, I-141, I-142, I-143, I-145, I-146, I-147, I-148, I-149, I-150, I-151, I-153, I-154, I-155, I-156, I-157, I-162 or I-163.

Preferable compounds according to the present invention are following:

I-6

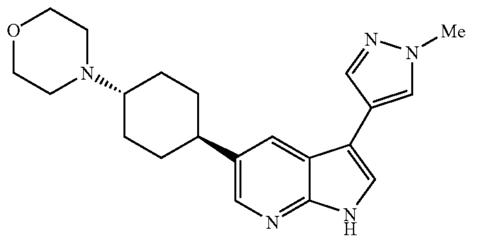

I-7

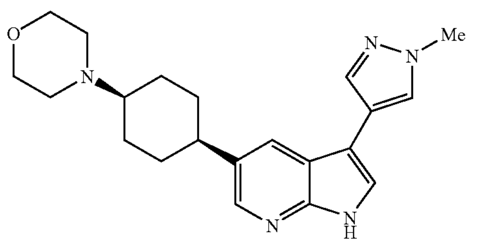

I-23

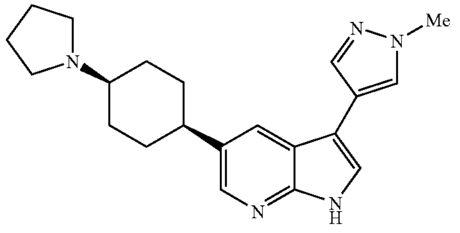

I-24

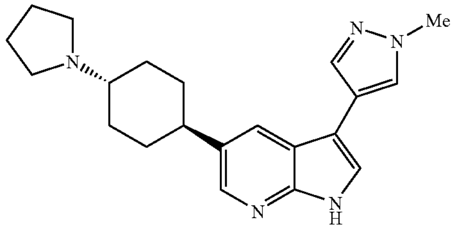

I-25

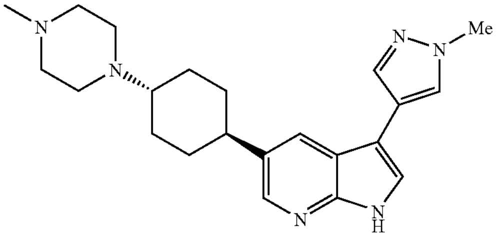

-continued
I-26
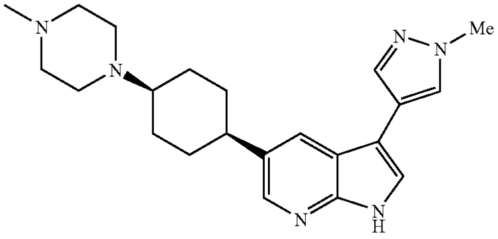
I-37
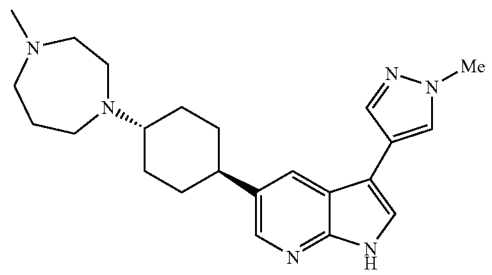
I-38
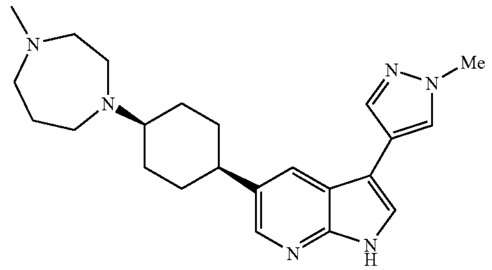
I-39
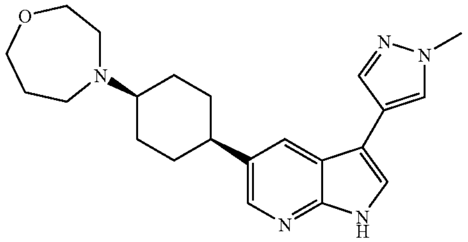
I-40
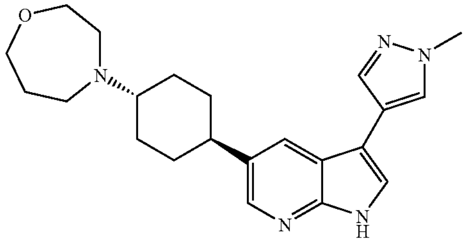
I-41
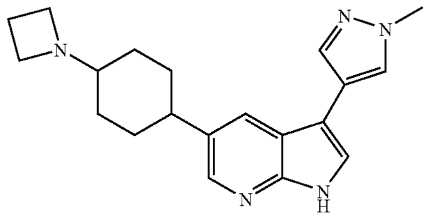
-continued
I-43
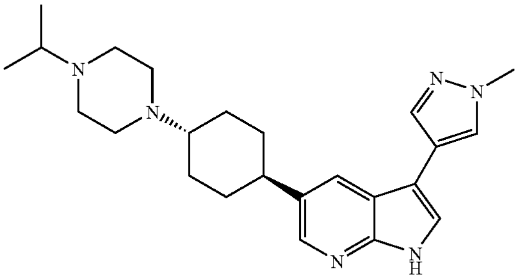
I-44
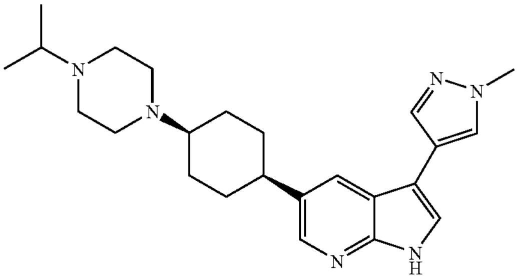
I-45
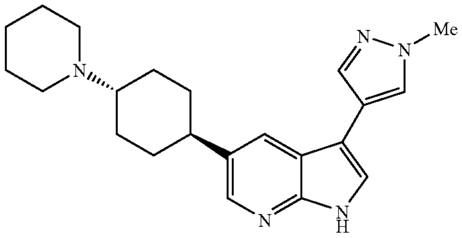
I-46
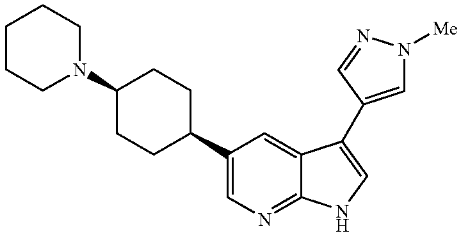
I-71
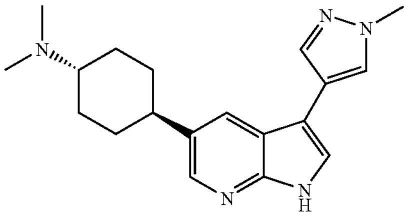
I-72
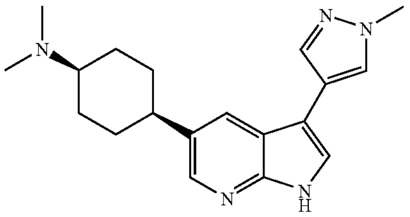

-continued

I-129

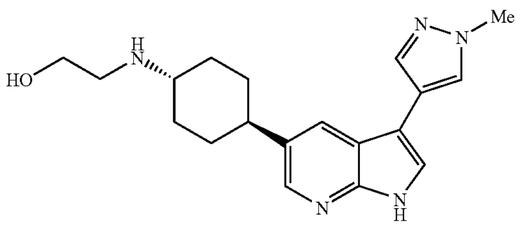

The structural formula of the compound may be described to represent a given isomer for the sake of convenience; however, all isomers of the compound that may occur structurally such as an geometric isomer, an optical isomer, a stereoisomer and a tautomer are included in the present invention, and there is no limitation to the formula described for the sake of convenience, regardless of whether it is an isolated isomer (for instance, an enantiomer), or a mixture of isomers (for instance, a racemic mixture).

When the compound according to the present invention is obtained in free form, it can be converted into a salt or a hydrate thereof by a conventional method.

Herein, there is no limitation on the "salt" according to the present invention as long as it forms a salt with the compound according to the present invention, and is pharmacologically acceptable. The preferred examples of the salt include hydrohalogenates (for instance, hydrochloride salt, hydrobromide salt, hydroiodide salt and the like), inorganic acid salts (for instance, sulphate salt, nitrate salt, perchlorate salt, phosphate salt, carbonate salt, bicarbonate salt and the like), organic carboxylic acid salts (for instance, acetate salt, maleate salt, tartrate salt, fumarate salt, citrate salt and the like), organic sulfonic acid salts (for instance, methanesulfonate salt, ethane sulfonate salt, benzenesulfonate salt, toluenesulfonate salt, camphorsulfonate salt and the like), amino acid salt (for instance, aspartate salt, glutamate salt and the like), quaternary ammonium salts, alkaline metal salts (for instance, sodium salt, potassium salt and the like), alkaline earth metal salts (magnesium salt, calcium salt and the like) and the like. In addition, hydrochloride salt, sulphate salt, methanesulfonate salt, acetate salt and the like are preferable as a "pharmacologically acceptable salt" of compounds according to the present invention.

Further, when the compound according to the present invention may comprise various isomers (for instance, the geometric isomer, the optical isomer, the rotational isomer, the tautomer and the like), it can also be purified into a single isomer by means of a conventional separation method, for instance, recrystallization, optical resolution such as diastereomeric salt method, enzyme fractionation method, various chromatographic methods (for instance, thin layer chromatography, column chromatography, glass chromatography and the like). However, a single isomer herein includes not only the isomer having 100% purity, but also the isomer containing non-target isomers still remaining after undergoing conventional purification operation. In addition, when using the compound according to the present invention as a raw material for medicinal drug, the single isomer mentioned above may be used, in addition, a mixture of isomers in any proportions may be used.

Crystal polymorphism may exist for the compound according to the present invention, salts thereof, or hydrates thereof; however, all the polymorphic crystals thereof are included in the present invention. Crystal polymorphism may exist for a single isomer or a mixture, and both are included in the present invention.

In addition, a compound still demonstrating the desired pharmacological activity after the compound according to the present invention has been subjected to metabolism such as oxidation and hydrolysis in vivo is also included in the present invention.

Furthermore, a compound which when subjected to metabolism such as oxidation, reduction and hydrolysis in vivo, generates the compound according to the present invention, a so-called prodrug, is also included in the present invention.

The compound according to the present invention can be provided as a pharmaceutical composition. The pharmaceutical composition may additionally comprise a pharmaceutically acceptable excipient for example a pharmaceutically acceptable carrier and/or a pharmaceutically acceptable diluent. Suitable carrier and/or diluents are well known in the art and include pharmaceutical grade starch, mannitol, lactose, magnesium stearate, sodium saccharin, talcum, cellulose, glucose, sucrose (or other sugar), magnesium carbonate, gelatin oil, alcohol, detergents, emulsifiers or water (preferably sterile). The composition may be a mixed preparation of a composition or may be a combined preparation for simultaneous separate or sequential use (including administration).

The compound according to the present invention, a salt thereof or a hydrate thereof can be formulated by a conventional method. Examples of the preferred dosage forms include a tablet, a powder, a subtle granule, a granule, a coated tablet, a capsule, a syrup, a troche, a inhalant, a suppository, an injectable, an ointment, an ophthalmic ointment, an eye drop, a nasal drop, an ear drop, a cataplasm, a lotion and the like. For formulation, a diluent, a binder, a disintegration agent, a lubricant, a colorant and a flavoring agent used in general, and as necessary, additives such as a stabilizer, an emulsifier, an absorption enhancer, a surfactant, a pH adjuster, an antiseptic agent, and an antioxidant can be used. In addition, formulation is also possible by combining ingredients that are used in general as raw materials of pharmaceutical formulation, by the conventional method. Examples of these ingredients include (1) soybean oil, animal oil such as beef tallow and synthethic glyceride; (2) hydrocarbon such as liquid paraffin, squalane and solid paraffin; (3) an ester oil such as octyldodecylmyristate and isopropylmyristate; (4) higher alcohol such as cetostearylalcohol and behenyl alcohol; (5) a silicon resin; (6) a silicon oil; (7) a surfactant such as polyoxyethylene fatty acid ester, sorbitan fatty acid ester, glycerin fatty acid ester, polyoxyethylene sorbitan fatty acid ester, polyoxyethylene hardened castor oil and polyoxyethylene polyoxypropylene block co-polymer; (8) a water-soluble polymer such as hydroxyethyl cellulose, polyacrylic acid, carboxyvinyl polymer, polyethyleneglycol, polyvinylpyrrolidone and methyl cellulose; (9) lower alcohol such as ethanol and isopropanol; (10) multivalent alcohol such as glycerin, propylene glucol, dipropylene glycol and sorbitol; (11) a sugar such as glucose and cane sugar; (12) an inorganic powder such as anhydrous silicic acid, magnesium aluminium silicate and aluminium silicate; and (13) purified water and the like.

Among the aforementioned additives, use can be made of 1) lactose, corn starch, sucrose, glucose, mannitol, sorbit, crystalline cellulose, silicon dioxide and the like as a diluting agent; 2) polyvinyl alcohol, polyvinyl ether, methyl cellulose, ethyl cellulose, gum arabic, traganth, gelatine, shellac, hydroxypropyl cellulose, hydroxypropylmethyl cellulose, polyvinylpyrrolidone, polypropyleneglycol.polyoxyethylene block co-polymer, meglumine, calcium citrate, dextrin, pectin and the like as a binder; 3) a starch, agar, gelatine powder, crystalline cellulose, calcium carbonate, sodium bicarbonate, calcium citrate, dextrin, pectin, calcium carboxymethylcellulose and the like as a disintegration agent; 4) magnesium stearate, talc, polyethyleneglycol, silica, hardened plant oil and the like as a lubricant; 5) a colorant, as long as addition thereof to a pharmaceutical drug is authorized, as a colorant; 6) a cocoa powder, menthol, fragrance, a peppermint oil, a cinnamon powder as a flavoring agent; and 7) an antioxidants whose addition to a pharmaceutical drug is authorized such as ascorbic acid and α-tocophenol as an antioxidant.

The compounds of the invention will normally be administered in a daily dosage regimen (for an adult patient) of, for example, an oral dose of between 1 mg and 2000 mg, preferably between 30 mg and 1000 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

General Procedure

The method for preparation of compound represented by formula (I) will be described below.

Compound (I) can be obtained by the methods represented by the following Reaction Schemes 1 to 4 or methods equivalent thereto.

Each reference symbol in the compounds shown in the following Reaction Schemes 1 to 4 has the same meaning as defined above. The compounds shown in the reaction schemes include salts formed from the compounds and examples of the salts include the same ones as the salts of Compound (I), and the like.

Scheme 1

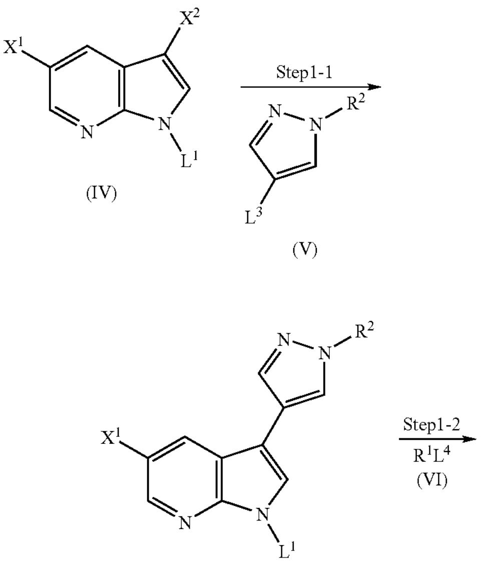

(IV) (V) (III)

-continued

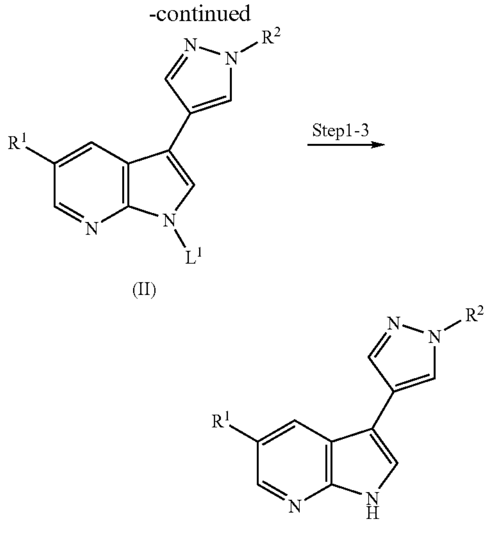

(II) (I)

wherein $R^1$ and $R^2$ have the same meanings as described above; and $X^1$ and $X^2$ represent independently halogen atom, $L^1$ represents amino-protecting group such as phenylsulfonyl group or dimethylamino group, $L^3$ and $L^4$ represent independently trialkyl tin group, $B(OR^{32})_2$ or $SiR^{33}_2$ wherein each of $R^{32}$ independently represent hydrogen or $C_{1-6}$ alkyl or two $R^{32}$ together form a 5-7 membered ring with the boron and oxygen atoms, wherein the ring is optionally substituted with 1-4 $C_{1-6}$ alkyl group(s), and each of $R^{33}$ represents fluoro atom, hydroxyl group or $C_{1-6}$ alkyl group.

Step 1-1

Compound (III) can be produced by coupling compound (IV) with compound (V) in the presence of a metal catalyst as disclosed in WO2004/078756 and WO2006/015123. Coupling reaction includes known coupling reactions; Stille reaction, Suzuki coupling, Hiyama reaction and the like. Stille reaction can be carried out according to Stille (*Angew. Chem., Int. ed, Engl.* 1986, 25, 508); Mitchell (*Synthesis,* 1992, 803) or Littke et al. (*J. Am. Chem. Soc.* 2002, 124, 6343). Suzuki coupling can be carried out according to Suzuki (*Pure Appl. Chem.* 1991, 63, 419) or Littke et al. (*J. Am. Chem. Soc.* 2000, 122, 4020). Hiyama reaction can be carried out according to Hatanaka et al. (*J. Org. Chem.* 1988, 53, 918), Hatanaka et al. (*Synlett,* 1991, 845), Tamao et al. (*Tetrahedron Lett.* 1989, 30, 6051), or Denmark et al. (*Org. Lett.* 2000, 2, 565, ibid. 2491).

Compound (IV) may be commercially available or may be prepared from commercially available product by methods known to those skilled in the art.

Compound (V) may be commercially available or may be prepared from commercially available product by methods known to those skilled in the art.

Step 1-2

Compound (II) can be produced by coupling compound (III) with compound (VI) in the presence of a metal catalyst like in step 1-1.

Compound (VI) may be commercially available or may be prepared from commercially available product by methods known to those skilled in the art. For example, stannane described as (VIa) can be produced from the relevant ketone using several methods well-known in the art (*J. Org. Chem.* 2004, 69, 9109). For instance, ketone can be converted first to enol triflate as shown below

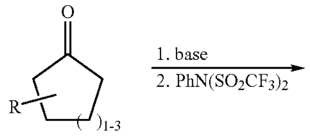

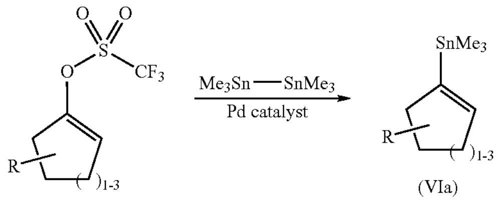

(VIa)

wherein R represents a halogen atom, an oxo group, an ethylenedioxy group, a $C_{1-6}$ alkyl group, a $C_{1-6}$ alkoxy group, a $C_{1-6}$ hydroxyalkyl group, —C(O)OH, a ($C_{1-6}$ alkyl)amino group, a di($C_{1-6}$ alkyl)amino group or —$R^a$-$R^b$;wherein $R^a$ represents a single bond or —$CH_2$—; wherein $R^b$ represents a 4-7 membered non-aromatic heterocyclic group, a $C_{6-10}$ aryl group or a 5-7 membered heteroaryl group, optionally and independently substituted with 1-4 substituent(s) selected from the group consisting of halogen atom or $C_{1-6}$ alkyl group;

As base either NaH (*Org. Biomol. Chem.* 2006, 4(3), 410), $(CH_3Si)_2NLi$, $(CH_3Si)_2NK$ (*J. Org. Chem.* 2003, 68, 6905) or i-$Pr_2NLi$ can be used. Suitable palladium catalysts for the second step include tetrakis(triphenylphoshine)palladium (0) $Pd(PPh_3)_4$. An alternative method (*J. Org. Chem.* 2004, 69, 220) involves the relevant vinyllithium derivative as an intermediate

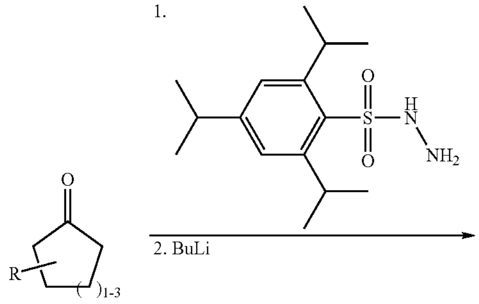

(VII)

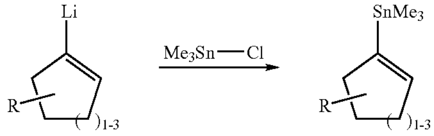

(VIa)

Boronic ester described as (VIb) can also be produced from the relevant ketone (VII) using the methodology well-known in the art (*J. Med. Chem.* 2006, 49, 3719-3742 or WO2005/005422) as shown below:

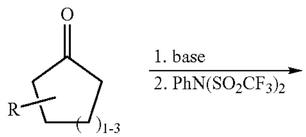

(VII)

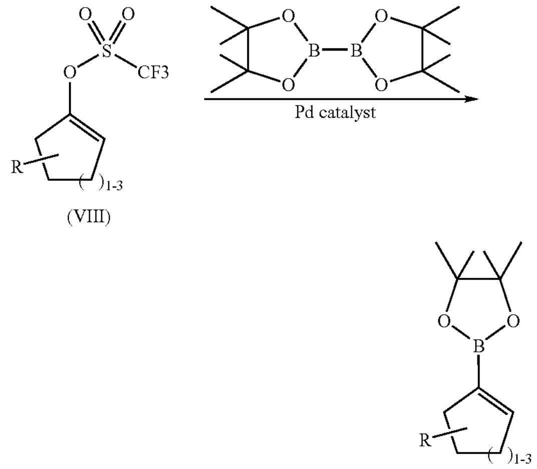

(VIII)

(VIb)

As base either $(CH_3Si)_2NLi$ or i-$Pr_2NLi$ can be used. Suitable palladium catalysts for the reaction of the triflate (VIII) with bis(pinacolato)diboron include palladium (II) chloride complex with 1,1'-bis(diphenylphosphino)ferrocene $PdCl_2dppf$ or palladium (II) chloride complex with triphenylphosphine $PdCl_2(PPh_3)_2$.

Chemistry analogous to that used for the preparation of stannanes described as (VIa) can be used to convert ketones into the relevant silanes described as (VIc) (*J. Am. Chem. Soc.* 1987, 109, 7838).

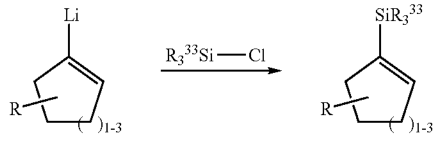

(VIc)

Compound (II) can also be prepared by the Heck reaction as shown below.

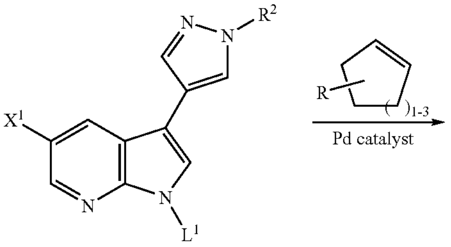

(III)

-continued

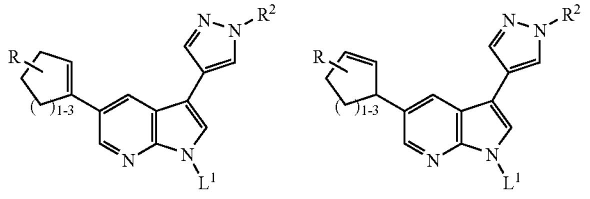

(IIa)

Various regioisomers of (IIa) can be formed depending on the reaction conditions. The reaction may involve $X^1$═I (Synlett 2002, 12, 2045), $X^1$═Br (*Org. Lett.* 1999, 1, 709), $X^1$═Cl (Synlett 2000, 11, 1589) and a variety of palladium catalysts including elemental Pd, chloro[4-(diphenylphosphino-κP)benzamide](η3-2-propenyl)palladium, tris(dibenzylideneacetone)dipalladium, palladium diacetate, etc. The reaction may be run in the presence of phosphine such as butylbis(tricyclo[3.3.1.13,7]dec-1-yl)phosphine, tricyclohexylphosphine, or triphenylphosphine.

Step 1-3

The conditions for the removal of the $L^1$ group will depend on the property of the $L^1$ group. For example, when $L^1$ is phenylsulfonyl group, the compound of formula (I) can be produced by the treatment of the compound of formula (II) under basic conditions, for instance using sodium hydroxide in water/ethanol. Specifically, following working examples will be specified.

If desired, a modification of $R^1$ or $R^2$ might be conducted either prior or subsequent to each step. For example, compound (II) which contains unsaturated ring can be reduced into compound (II) which contains saturated ring. The reduction can be accomplished by using hydrogen gas over catalyst such as palladium, platinum, or rhodium.

In particular, the reduction of cyclohexenyl derivative (IIa) may produce a mixture of cis- and trans-(IIb) as shown below.

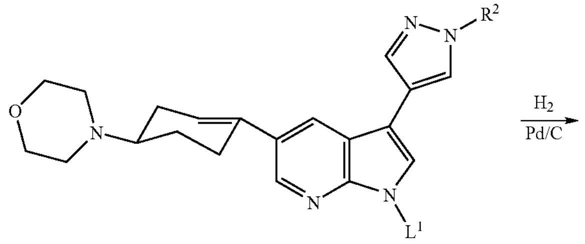

(IIa)

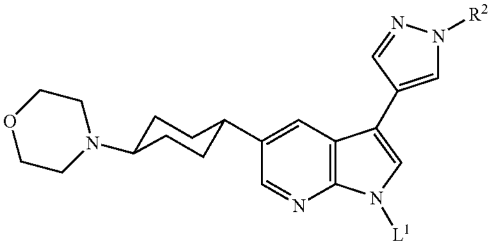

trans-(IIb)

+

-continued

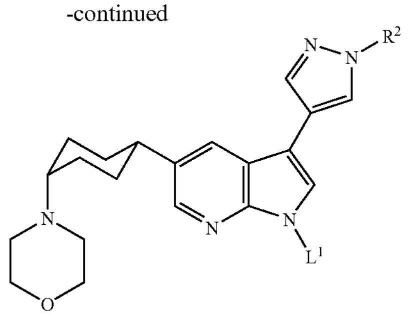

cis-(IIb)

Such mixture, if needed, can be separated using chromatographic methods well known in the art. Alternatively, the cis isomers such as cis-(IIb) can be converted into the more thermodynamically stable trans-isomers such as trans-(IIb) using a free-radical method developed by Bertrand et al. (*J. Org. Chem.* 2006, 71, 7288).

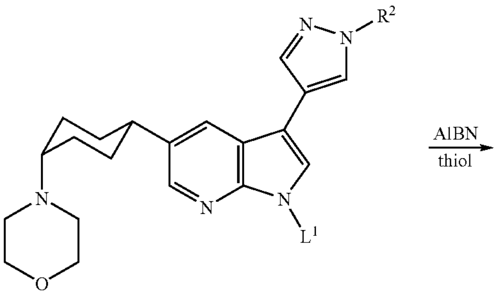

cis-(IIb)

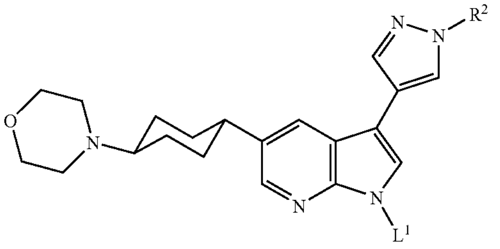

trans-(IIb)

Compound (II) may undergo one or more further reactions to provide a different compound (II). For example, a compound may undergo hydrolysis, reductive amination, reduction, oxidation, elimination, substitution and/or addition reaction. In particular, with regard to reductive amination, following working examples will be specified.

Furthermore, if desired, the sequence between step 1-1 and step 1-2 can be alternated as described below. Alternatively, compound of formula (II) can be prepared by a) reaction of a compound of formula (IX) with stannane (Va) in the presence of a palladium catalyst or b) reaction of a compound of formula (IX) with boronic acid or ester (Vb) in a presence of a suitable palladium catalyst or c) reaction of a compound of formula (IX) with silane (Vc) in the presence of a palladium catalyst

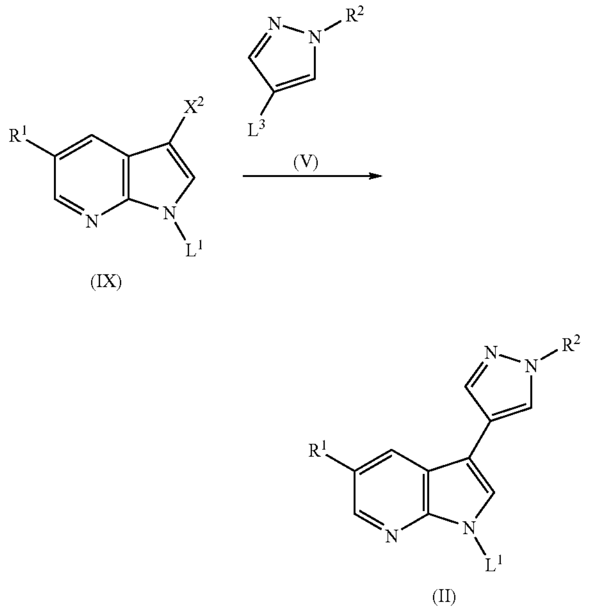

(IX)

(II)

wherein all symbols in the scheme has the same meanings as described above;

Suitable catalysts for the purpose of this invention include $(PPh_3)_2PdCl_2$ or $(PPh_3)_4Pd$, $Pd(OAc)_2$, $[PdCl(\eta^3-C_3H_5]_2$, $Pd_2(dba)_3$ (wherein dba =dibenzylidenacetone), Pd/P(t-Bu)$_3$ It will be appreciated that the reaction set out as option a) is a Stille reaction, which can be carried out according to Stille (*Angew. Chem., Int. ed, Engl.* 1986, 25, 508); Mitchell (*Synthesis,* 1992, 803) or Littke et al. (*J. Am. Chem. Soc.* 2002, 124, 6343), The reaction set out as option b) is a Suzuki reaction which can be carried out according to Suzuki (*Pure Appl. Chem.* 1991, 63, 419) or Littke et al. (*J. Am. Chem. Soc.* 2000, 122, 4020).

It will be appreciated that the reaction set out as option c) is a Hiyama reaction which can be carried out according to Hatanaka et al. (*J. Org. Chem.* 1988, 53, 918), Hatanaka et al. (*Synlett,* 1991, 845), Tamao et al. (*Tetrahedron Lett.* 1989, 30, 6051), or Denmark et al. (*Org. Lett.* 2000, 2, 565, ibid. 2491).

Scheme 2

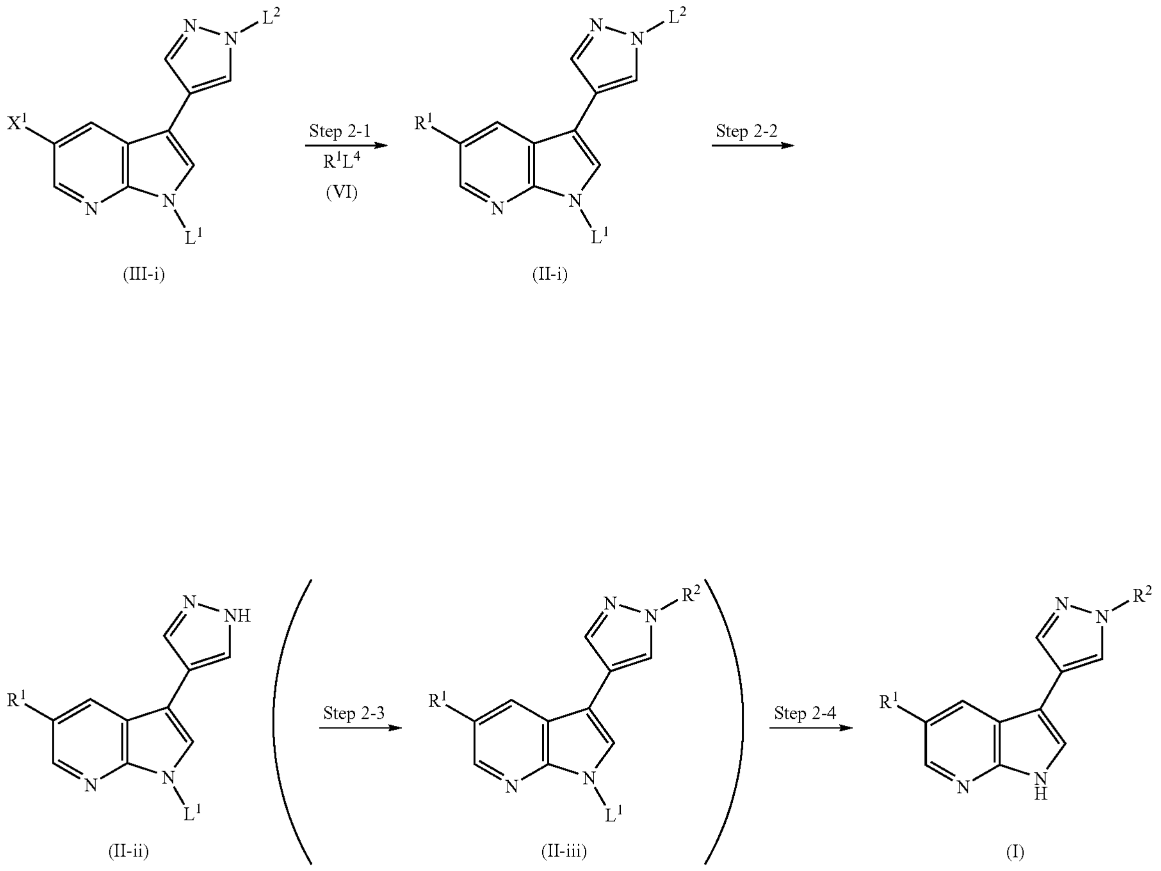

(III-i)

(II-i)

(II-ii)

(II-iii)

(I)

wherein $X^1$, $R^1$ and $L^1$ have the same meanings as described above, $L^2$ represents nitrogen-protecting group.

Step 2-1

Compound (II-i) can be produced by reacting compound (III-i) with $R^1L^4$ (VI) Compound (III-i) can be produced by method disclosed in WO2004/078756. This step can be conducted according to the step 1-2.

Step 2-2

Compound (II-ii) can be produced by deprotection of compound (II-i) as described in the following example (III-g).

Step 2-3

If desired, compound (II-iii) may be produced by introducing $R^2$ group into compound (II-ii).

Step 2-4

Compound (I) can be produced from compound (II-ii) or compound (II-iii) according to step 1-3.

If desired, the sequence among each step can be alternated.

Scheme 3

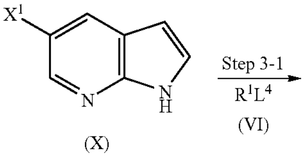

(X)

(VI)

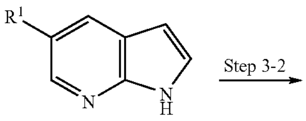

(XI)

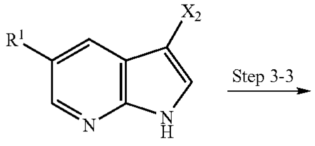

(XII)

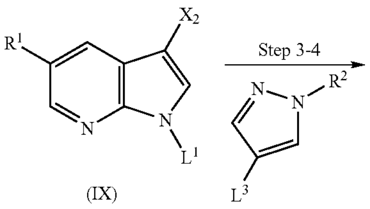

(IX)

(V)

-continued

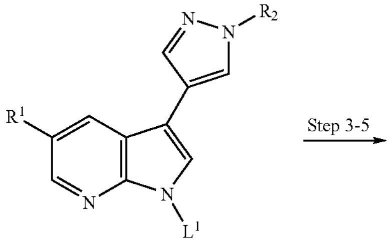

(II)

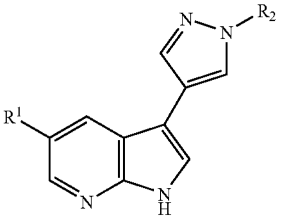

(I)

wherein all symbols in the scheme have the same meanings as described above; Compound (I) can also be prepared via compound (IX). Preparation of compound (IX) follows the general methods disclosed in WO2003/082869 and WO2004/078756 starting from 5-halo-7-azaindole (X). Conversion of compound (X) into compound (XI) follows the methods described in step 1-2. The compound (IX) is provided by the introduction of a $L^1$ group into a compound (XII). However, a skilled person will appreciate that the actual synthetic sequence to prepare compound (XII) will depend on the type of protecting group $L^1$ used. In particular where $L^1$ is a silyl group, introduction of $L^1$ may occur prior to the introduction of $X^2$ as shown in Scheme 4.

Scheme 4

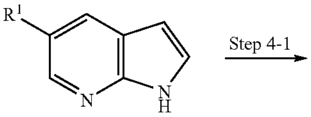

(XI)

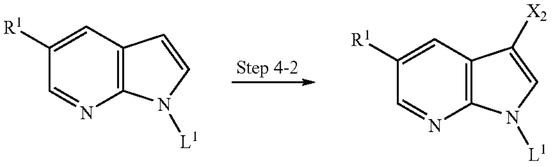

(XIII)

(IX)

wherein all symbols in the scheme have the same meanings as described above:

Step 4-1

The compound (XIII) is provided by the introduction of a $L^1$ group into a compound (XI) as disclosed in WO2003/082868 for $R^1$=aryl.

Step 4-2

This step can be conducted using bromine in the presence of pyridine as disclosed in WO2003/082868.

Scheme 5

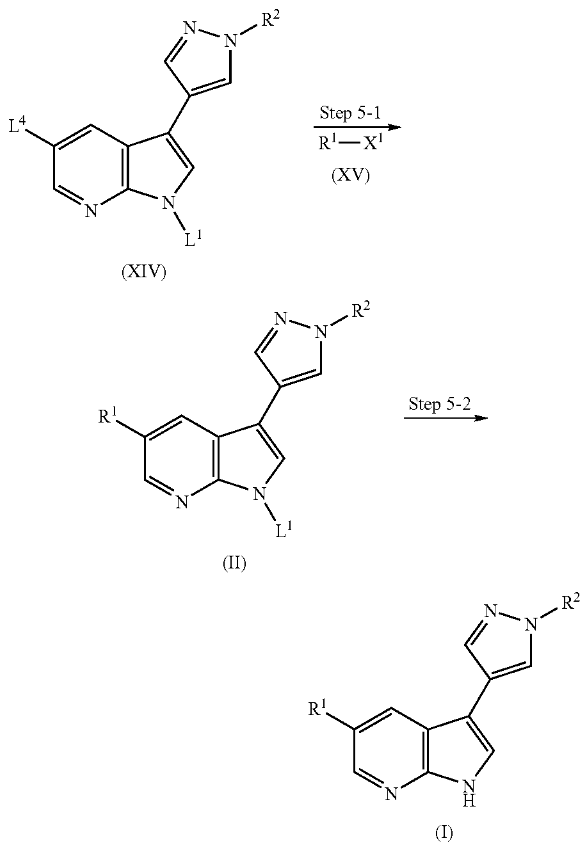

(XIV)
(II)
(I)

wherein all symbols in the scheme have the same meanings as described above:

Step 5-1

Compound (II) can be prepared by reacting compound (XIV) with compound (XV).

Method for installation of the stannane (—$SnBu_3$) and slime (—$SiMe_3$) moieties at C(5) of the 7-azaindole system was disclosed in WO2004/078757. Boronates and boronic acids analogous to (XIV) were also disclosed in WO2006/015123 and WO2005/028475.

Step 5-2

This step can be conducted according to step 1-3.

EXAMPLES

The present invention will be described in more detail with reference to examples, which however shall not be construed as limiting the scope of the invention thereto.

The examples set out below refer to the preparation of compounds falling within the scope of formula (I) which are specific examples of compounds falling within the scope of the invention.

Synthetic Methods for Synthesis of Compounds of the Invention

General Procedure for the Deprotection of 7-azaindoles

Procedure A: Removal of the phenylsulfonyl Group.

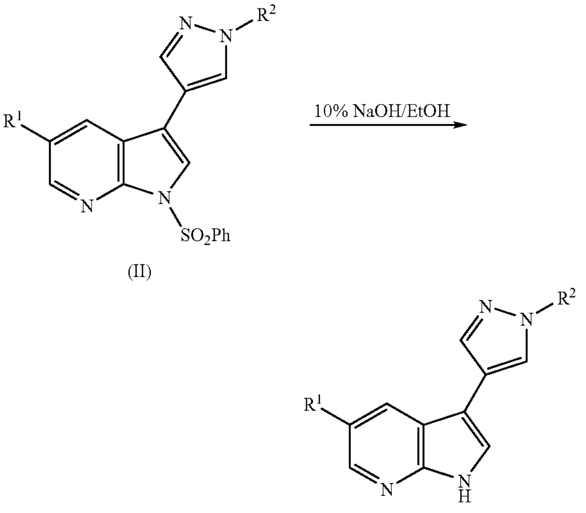

(II)
(I)

The 7-azaindole (II) (1 mmol) was dissolved in EtOH (10 mL). 10% NaOH (5 mL) was added and the reaction was heated to 80° C. for 40 mins. It was allowed to cool down and a saturated solution of $NaHCO_3$ (10 mL) was added. It was then extracted with EtOAc (3×20 mL) and the combined organic extracts were dried over $MgSO_4$ and concentrated. The crude product was purified by silicagel chromatography (SGC) using appropriate solvent as eluent or by preparative TLC (PTLC) using appropriate solvent as the eluent or by LCMS (column LUNA 10μ C18(2) 00G-4253-V0 250×50 mm) using water-MeCN (0.1% AcOH) as eluent (in gradient; flow 80 mL/min).

Procedure B: Removal of the silyl Group

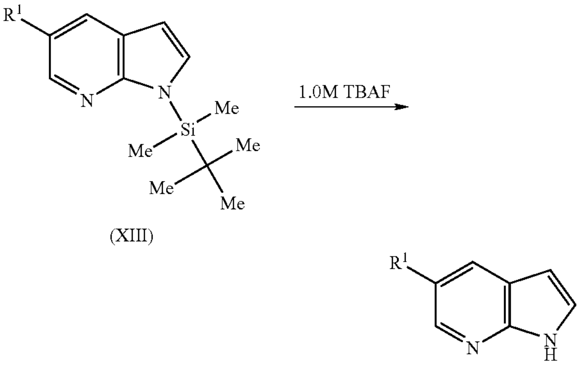

(XIII)
(XI)

To a stirred solution of the silyl-protected azaindole (XIII) (11.4 mmol) in THF (50 mL) was added 1 M tetrabutylammonium fluoride in THF (22.7 mL, 22.7 mmol). After 75 min the mixture was concentrated and the residue was purified by silicagel chromatography (SGC) using appropriate solvent as eluent or by preparative TLC (PTLC) using appropriate solvent as the eluent or by LCMS (column LUNA 10μ C18(2) 00G-4253-V0 250×50 mm) using water-MeCN (0.1% AcOH) as eluent (in gradient; flow 80 mL/min) to afford the azaindole (XI). Yield about 80%.

Procedure C: Removal of the silyl Group

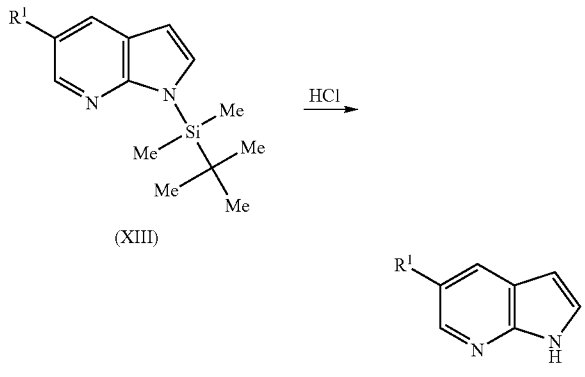

(XIII)

(XI)

Concentrated aqueous HCl (1 mL) was added to a solution of silyl-protected azaindole (XIII) (0.28-0.9 mmol) in methanol (10 mL) and the reaction mixture was stirred at room temperature for 15-30 min. The mixture was then added to saturated aqueous $NaHCO_3$ (50 mL) and extracted with EtOAc (2×40 mL). The combined organic portions were dried ($MgSO_4$), concentrated, and purified by trituration with $Et_2O$ (5 mL) to afford 7-azaindole (XI) as a white powder (50-95%).

General Procedure for the Hydrogenation of 7-azaindoles Containing a Partially Unsaturated Ring at C(5)

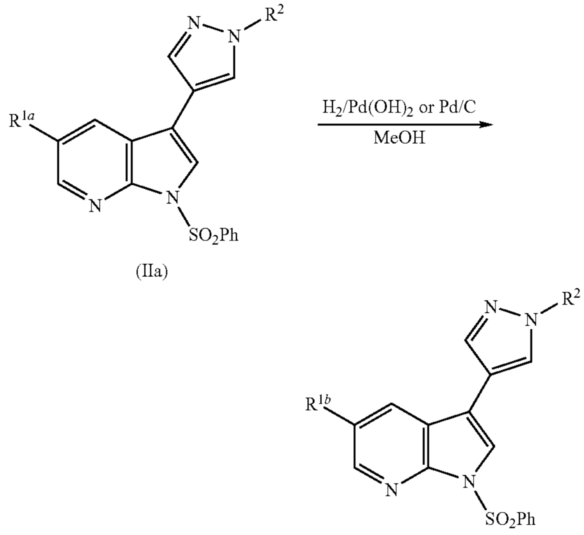

(IIa)

(IIb)

wherein $R^2$ has the same meanings as described above, $R^{1a}$ represents 5-7 membered unsaturated hydrocarbon ring, $R^{1b}$ represents 5-7 membered saturated hydrocarbon ring;

Compound (IIa) (1 mmol) was dissolved in appropriate solvent (MeOH or a mixture of MeOH and $CH_2Cl_2$ or EtOAc to improve solubility) (10-30 mL).

$Pd(OH)_2$ (0.1-0.3 mmol) (20% on C, wet, Degussa type) or Pd/C (0.25-0.50 mmol) (10% on C, wet Degussa type E101) was added in one portion. The reaction was stirred under hydrogen for 1-7 days. The reaction mixture was filtered through a small pad of Celite and washed with copious amount of MeOH. The solvent was removed to give the product (IIb) which was taken forward crude.

General Procedures for the Reductive Amination Involving amines and 7-azaindoles Containing Keto Functionality Procedure A

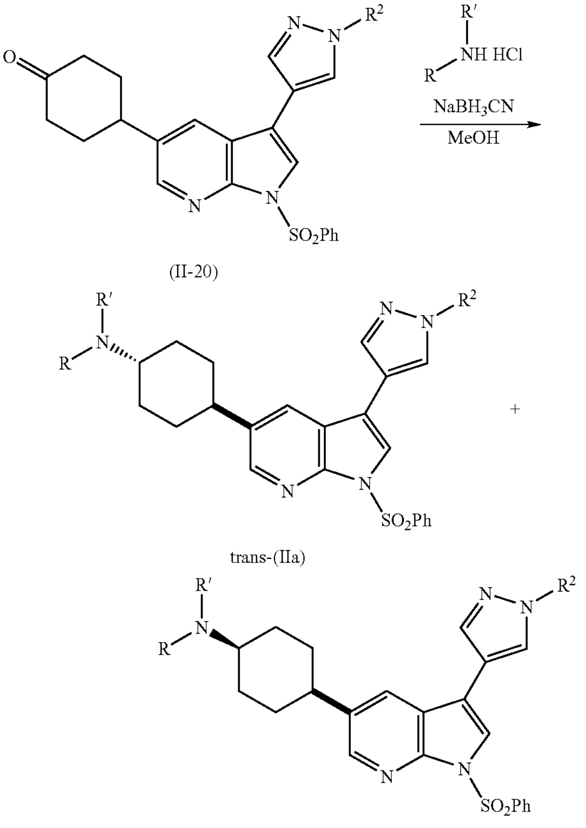

(II-20)

trans-(IIa)

cis-(IIa)

wherein R2 has the same meaning as described above; R and R' independently represents hydrogen atom, C1-6 alkyl group or R and R', together with the nitrogen atom they are bonded to, form a 4-8 membered ring optionally substituted with halogen atom or C1-6 alkyl group:

Ketone (II-20) (1 mmol) was added at room temperature (RT) over 5 min to a solution of secondary amine R'RNH hydrochloride (6 mmol) in dry MeOH (10 mL) under nitrogen and the mixture was then stirred for 5 min at RT. When using free amine, its hydrochloride was prepared in situ by adding dropwise 1.25 M solution of HCl in MeOH (2 mmol) and stirring at RT for 5 min. Solid $NaCNBH_3$ (2 mmol) was added in one portion. The reaction was then stirred at RT overnight. Saturated solution of $NaHCO_3$ (30 mL) was added and the reaction mixture was extracted with EtOAc (4×35 mL). The combined organic extracts were dried over $MgSO_4$ and concentrated. The crude product was purified by silicagel chromatography (SGC) using appropriate solvent as eluent or by preparative TLC (PTLC) using appropriate solvent as the eluent or by LCMS (column LUNA 10μ C18(2) 00G-4253-V0 250×50 mm) using water-MeCN (0.1% AcOH) as eluent (in gradient; flow 80 mL/min) to afford trans-(IIa) and cis-(IIa).

Procedure B

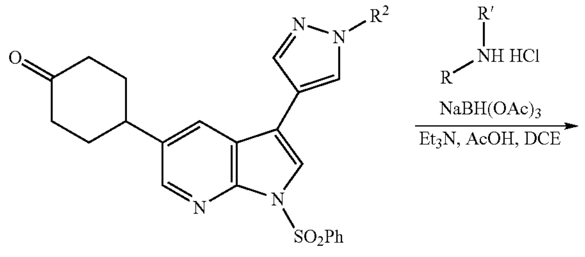

(II-20)

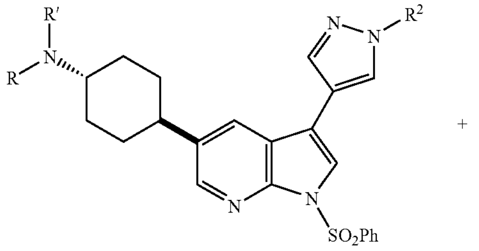

trans-(IIa)

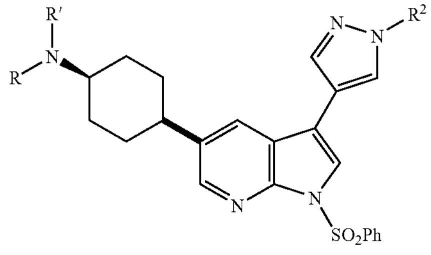

cis-(IIa)

wherein R2 has the same meaning as described above; R and R' independently represents hydrogen atom, C1-6 alkyl group or R and R', together with the nitrogen atom they are bonded to, form a 4-8 membered ring optionally substituted with halogen atom or C1-6 alkyl group:

Triethylamine (204 mg, 2.0 mmol) was added at room temperature (RT) to a mixture of secondary amine R'RNH hydrochloride (1.7 mmol) and ketone (II-20) (1 mmol) in dry 1,2-dichloroethane (7.1 mL), followed by glacial acetic acid (62 mg, 1.0 mmol) and $NaBH(OAc)_3$. When using free amine, triethylamine is not used. The mixture was then stirred at RT overnight. Aqueous 10% NaOH (9 mL) was added, the mixture was stirred vigorously for 10 min and extracted with EtOAc (3×35 mL). The combined organic extracts were dried over $MgSO_4$ and concentrated. The crude product was purified by silicagel chromatography (SGC) using appropriate solvent as eluent or by preparative TLC (PTLC) using appropriate solvent as the eluent or by LCMS (column LUNA 10μ C18(2) 00G-4253-V0 250×50 mm) using water-MeCN (0.1% AcOH) as eluent (in gradient; flow 80 mL/min) to afford trans-(IIa) and cis-(IIa).

General Procedures for the Suzuki Reaction

Procedure A

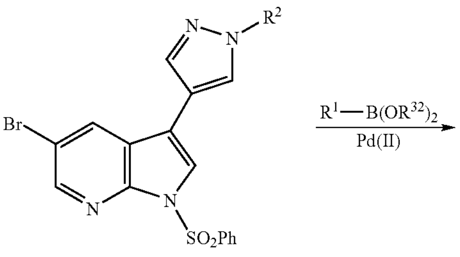

(III)

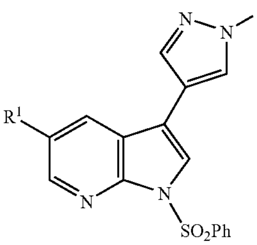

(IIa)

wherein each symbol has the same meanings as described above;

Bromide (III) (1 mmol), boronic acid or boronic acid pinacol ester $R^1$—$B(OR^{32})_2$ (2 mmol), LiCl (3 mmol), and $Pd(PPh_3)_2Cl_2$ (0.1 mmol), were dissolved in EtOH (20 mL) and toluene (20 mL). Then 1.0 M $Na_2CO_3$ solution (20-25 mL) was added and the reaction was heated to 105-110° C. for 8 hours. The reaction mixture was allowed to cool down. It was poured into water (30 mL) and was extracted with EtOAc (3×40 mL). The combined organic extracts were dried over $MgSO_4$ and concentrated. Product (IIa) was isolated by means of silicagel chromatography (SGC) using hexane/EtOAc as the eluent (gradient elution 0%-100% EtOAc) or by preparative TLC (PTLC) using appropriate solvent system as the eluent.

Procedure B

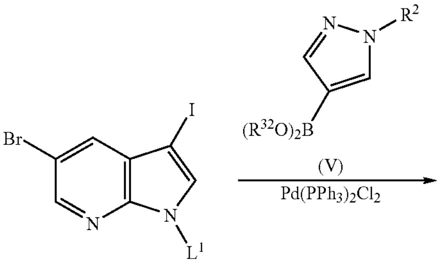

(IV)

-continued

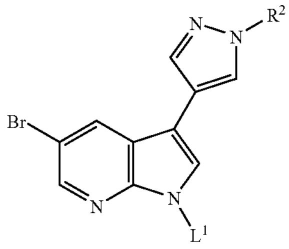

(III)

wherein each symbol has the same meanings as described above:

A mixture of iodide (IV) [10 mmol; preparation of (IV) ($L^1$=$SO_2Ph$) disclosed in WO2004/078756], boronic acid or boronic acid pinacol ester (Vb) (11 mmol), LiCl (30 mmol), $Pd(PPh_3)_2Cl_2$ (0.5 mmol) and 1.0 M $Na_2CO_3$ solution (25 mL) in EtOH (25 mL) and toluene (25 mL) was heated at 100° C. for 3 h.

The reaction mixture was cooled down to RT, diluted with water (35 mL) and extracted with EtOAc (4×40 mL). The combined organic extracts were dried ($MgSO_4$) and concentrated. The product (III) was isolated by crystallization and/or by silicagel chromatography (SGC) using an appropriate solvent system as eluent. Yield 33-80%.

General Procedure for the Synthesis of enol triflates

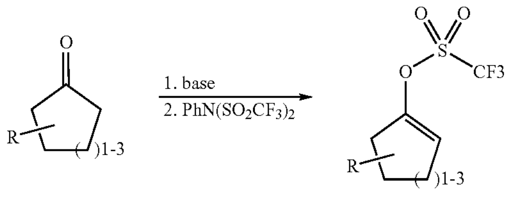

(VII) (VIII)

wherein R has the same meaning as described above;

To a solution of ketone (VII) (10 mmol) in THF (35 mL), cooled to −78° C., was added 1.0 M solution of LiHMDS or NaHMDS in THF (12 mL, 12 mmol,) dropwise. The stirring continued at −78° C. for 1 h. N-phenylbis(trifluoromethanesulfonimide) (3.93 g, 11 mmol) was added in one portion and the stirring continued at −78° C. for 1 h then at RT for 19.5 h. The solvent was evaporated and the crude product purified by column chromatography on alumina (Neutral, Grade I) using hexane:EtOAc=7:1 (v/v) as the eluent. Alternatively, the product can be isolated by SGC using EtOAc:hexane: $Et_3N$=39:60:1 (v/v/v) as eluent (gradient elution starting with 19:80:1) to give triflate (VIII). Yield 62-84%.

General Procedure for the Synthesis of boronic pinacol esters

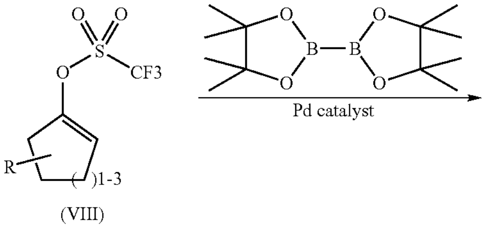

(VIII)

-continued

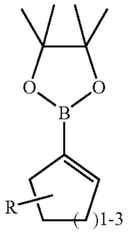

(VI-b)

wherein R has the same meaning as described above;

A mixture of triflate (VIII) (10 mmol), bis(pinacolatodiboron) (3.80 g, 15 mmol), potassium acetate (2.94 g, 30 mmol) and dichloro[1,1'-bis(diphenylphosphino)ferrocene]palladium (II) dichloromethane adduct (0.41 g, 0.5 mmol) in DMF (43 mL) was stirred at 85° C. for 6-17 h to give a homogeneous black solution. Reaction mixture was concentrated and diluted with EtOAc. The solid was filtered off and the filtrate concentrated. The residue was purified by SGC using EtOAe: hexane=1:1 (v/v) as eluent (gradient elution) to give compound (VI-b). Yield 47-67%.

General Procedure for Protection of 7-azaindoles as phenylsulfonamides

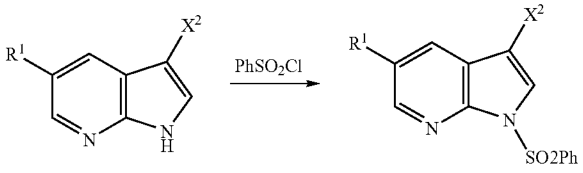

(XII) (XI)

Benzenesulfonyl chloride (15 mmol) was added to a stirred mixture of (XII) (10 mmol), tetrabutylammonium hydrogensulfate (1.5 mmol) and 50% aqueous NaOH (4 mL) in $CH_2Cl_2$ (60 mL). The mixture was stirred at room temperature for 3.5 h while the progress of the reaction was followed by TLC. The mixture was then partitioned between $CH_2Cl_2$ (50 mL) and brine (80 mL). The aqueous layer was extracted with $CH_2Cl_2$ (3×60 mL) and the combined organic extracts dried (MgSO4), filtered and concentrated. The residual semisolid was stirred with cold MeOH (70 mL) for 1.5 h. The resulting solid was filtered off and dried in vacuum to afford (IX) in about 80% yield.

3-(1-methyl-1H-pyrazol-4-yl)-5-(4-methylcyclohex-1-enyl)-1H-pyrrolo[2,3-b]pyridine (I-1)

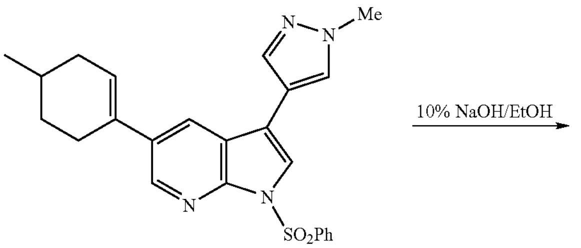

(IIa-1)

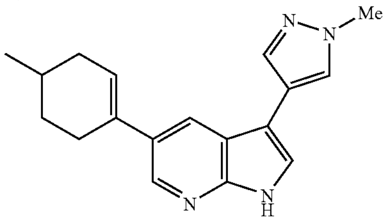

(I-1)

Compound (IIa-1) (49 mg, 0.11 mmol) was deprotected as described in the general procedure A for the deprotection of 7-azaindoles. The crude product was purified by PTLC using EtOAc as the eluent to give (I-1) as a white solid (33 mg, 69%), $^1$H NMR (400 MHz, $CDCl_3$) δ 1.06 (d, J=6.2 Hz, 3H), 1.50-1.40 (m, 1H), 1.97-1.74 (m, 3H), 2.40-2.30 (m, 1H), 2.60-2.53 (m, 2H), 4.00 (s, 3H), 6.12-6.08 (m, 1H), 7.40 (s, 1H), 7.64 (s, 1H), 7.77 (s, 1H), 8.02 (d, J=1.9 Hz, 1H), 8.43 (d, J=1.6 Hz, 1H), 10.31 (br s, NH, 1H).

5-(4-tert-butylcyclohex-1-enyl)-3-(1-methyl-1H-pyrazol-4-yl)-1H-pyrrolo[2,3-b]pyridine (I-2)

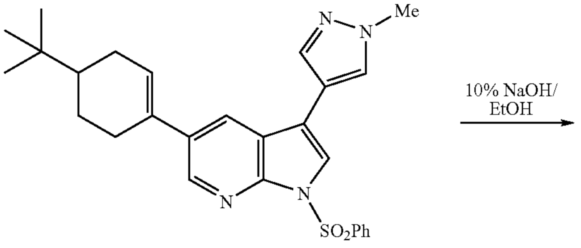

(IIa-2)

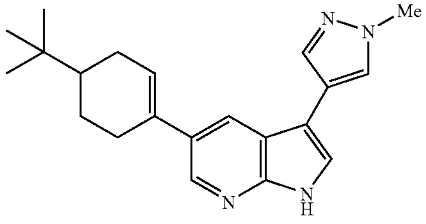

(I-2)

Compound (IIa-2) (55 mg, 0.11 mmol) was deprotected as described in the general procedure A for the deprotection of 7-azaindoles. The crude product was purified by PTLC using EtOAc as the eluent to give (I-2) as a white solid (29 mg, 88%), $^1$H NMR (400 MHz, $CDCl_3$) δ 0.94 (s, 9H), 1.46-1.36 (m, 2H), 2.08-1.98 (m, 2H), 2.35-2.25 (m, 1H), 2.66-2.48 (m, 2H), 4.00 (s, 3H), 6.16-6.12 (m, 1H), 7.40 (d, J=1.8 Hz, 1H), 7.64 (s, 1H), 7.77 (s, 1H), 8.01 (d, J=1.9 Hz, 1H), 8.43 (s, 1H), 10.07 (br s, NH, 1H).

3-(1-methyl-1H-pyrazol-4-yl)-5-(4-methylcyclohexyl)-1H-pyrrolo[2,3-b]pyridine (I-3)

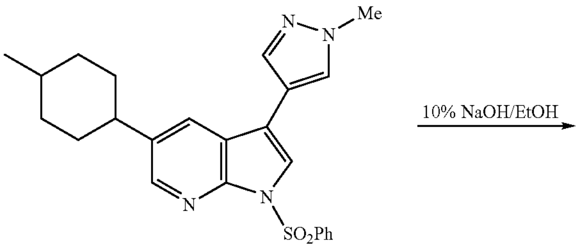

(IIb-3)

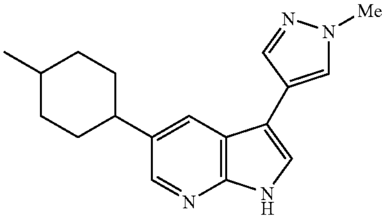

(I-3)

Compound (IIb-3) (41 mg, 0.094 mmol) was deprotected as described in the general procedure A for the deprotection of 7-azaindoles. The crude product was purified by PTLC using EtOAc as the eluent to give (I-3) as a white solid (1.2:1 mixture of isomers) (9 mg, 32%), $^1$H NMR (400 MHz, $CDCl_3$) δ 0.97 (d, J=6.5 Hz, 3H), 1.08 (d, J=6.5 Hz, 3H), 1.20-1.10(m, 2H), 1.65-1.55 (m, 4H), 1.68-1.56 (m, 4H), 1.78-1.69 (m, 4H), 1.98-1.79 (m, 4H), 2.63 (tt, J=3.4 and 12.2 Hz, 1H), 2.72 (tt, J=3.4 and 12.2 Hz, 1H), 4.00 (s, 3H), 4.01 (s, 3H), 7.38 (s, 2H), 7.63 (s, 2H), 7.77 (s, 1H), 7.78 (s, 1H), 7.88 (d, J=1.7 Hz, 1H), 7.91 (d, J=1.9 Hz, 1H), 8.24 (d, J=1.8 Hz, 1H), 8.27 (d, J=1.8 Hz, 1H), 9.79 (br s, NH, 2H).

5-(4-tert-butylcyclohexyl)-3-(1-methyl-1H-pyrazol-4-yl)-1H-pyrrolo[2,3-b]pyridine (I-4)

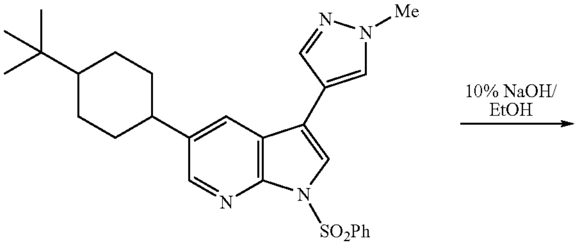

(IIb-4)

-continued

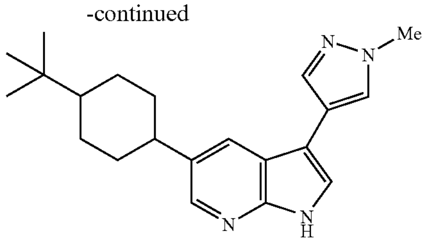

(I-4)

Compound (IIb-4) (46 mg, 0.096 mmol) was deprotected as described in the general procedure A for the deprotection of 7-azaindoles. The crude product was purified by PTLC using EtOAc as the eluent to give (I-4) as a white solid (1.05:1 mixture of isomers) (19 mg, 58%), $^1H$ NMR (400 MHz, $CDCl_3$) δ 0.83 (s, 9H), 0.92 (s, 9H), 1.35-1.13 (m, 6H), 1.70-1.50 (m, 4H), 2.08-1.83 (m, 6H), 2.36-2.29 (m, 2H), 2.63 (tt, J=3.4 and 12.2 Hz, 1H), 3.27-3.21(m, 1H), 4.00 (s, 3H), 4.01 (s, 3H), 7.39 (s, 1H), 7.40 (s, 1H), 7.62 (s, 1H), 7.63 (s, 1H), 7.77 (d, J=0.5 Hz, 1H), 7.78 (d, J=0.5 Hz, 1H), 7.89 (d, J=1.8 Hz, 1H), 8.07 (d, J=1.3 Hz, 1H), 8.25 (d, J=2.0 Hz, 1H), 8.37 (d, J=1.9 Hz, 1H), 10.07 (br s, NH, 2H).

3-(1-Difluoromethyl-1H-pyrazol-4-yl)-5-(4-morpholin-4-yl-cyclohex-1-enyl)-1H-pyrrolo[2,3-b]pyridine (I-5)

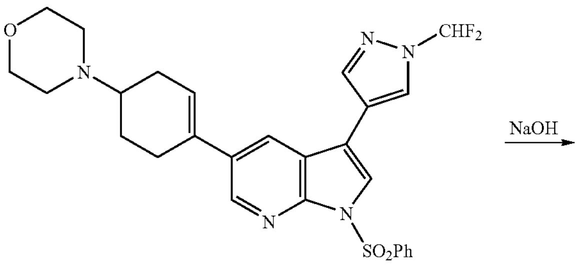

(IIa-5)

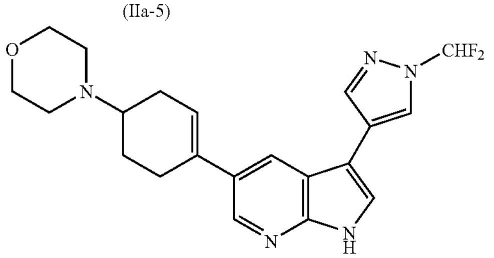

(I-5)

Compound (IIa-5) was deprotected as described in the general procedure A for the deprotection of 7-azaindoles. Thus azaindole (IIa-5) (29.14 mg, 0.054 mmol) and 10% aqueous NaOH (0.2 mL) in EtOH (2 mL) were heated at 105° C. for a period of 2 h 30 min. The crude product was purified by LCMS (column LUNA 10μ C18(2) 00G-4253-V0 250×50 mm) using water-MeCN (0.1% AcOH) as eluent (in gradient; flow 80 mL/min; retention time 21.87 min) to give (I-5) (0.80 mg, 3.7%). $^1H$ NMR (400 MHz, $CDCl_3$) δ 2.15-2.33 (m, 2H), 2.42-2.55 (m, 2H), 2.56-2.74 (m, 7H), 3.75-3.81 (m, 4H), 6.06-6.10 (m, 1H), 7.27 (t, J=60.5 Hz, 1H), 7.44 (d, J=1.4 Hz, 1H), 7.93-7.94 (m, 1H), 7.99 (d, J=2.0 Hz, 1H), 8.05 (s, 1H), 8.41 (d, J=1.8 Hz, 1H), 8.99 (br s, NH, 1H). MS (CI) m/z 400.1 ($MH^+$).

4-((1r,4r)-4-(3-(1-methyl-1H-pyrazol-4-yl)-1H-pyrrolo[2,3-b]pyridin-5-yl)cyclohexyl)morpholine (I-6)

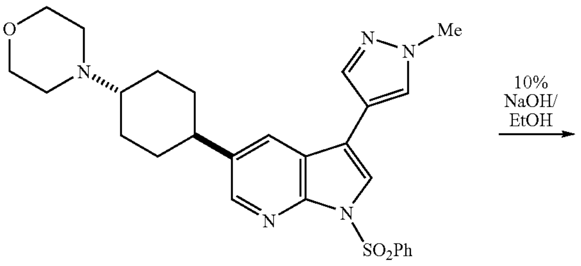

(IIb-6)

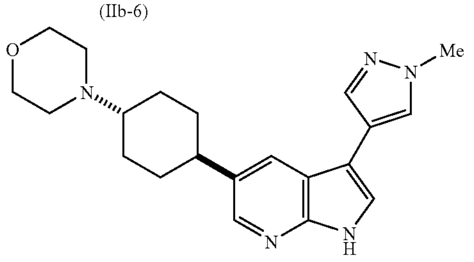

(I-6)

Trans isomer (IIb-6) was deprotected as described in the general procedure A for the deprotection of 7-azaindoles. Thus, (IIb-6) (1.12 g, 2.21 mmol) was dissolved in ethanol (22.1 mL). 10% solution of NaOH (11.05 mL) was added and the reaction was heated to 80° C. for 40 min. It was allowed to cool down and a saturated solution of $NaHCO_3$ (50 mL) was added. The mixture was then extracted with EtOAc (3×100 mL) and the combined organic extracts were dried over $MgSO_4$ and concentrated. The crude product was was washed with MeOH to afford white solid, which was filtered off and dried to give (I-6) (0.66 g, 80%), $^1H$ NMR (400 MHz, $CDCl_3$) δ 1.49-1.40 (m, 2H), 1.65-1.55 (m, 2H), 2.14-1.99 (m, 4H), 2.38-2.31 (tt, J=11.4 and 3.2 Hz, 1H), 2.67-2.59 (m, 4H), 2.68 (t, J=3.2 Hz, 1H), 3.78-3.74 (m, 4H), 3.99 (s, 3H), 7.35 (s, 1H), 7.61 (s, 1H), 7.74 (d, J=0.5 Hz, 1H), 7.86 (d, J=2.0 Hz, 1H), 8.18 (d, J=2.0 Hz, 1H), 9.73 (br s, NH, 1H).

4-((1r,4r)-4-(3-(1-methyl-1H-pyrazol-4-yl)-1H-pyrrolo[2,3-b]pyridin-5-yl)cyclohexyl)morpholine hydrochloride (I-6).HCl

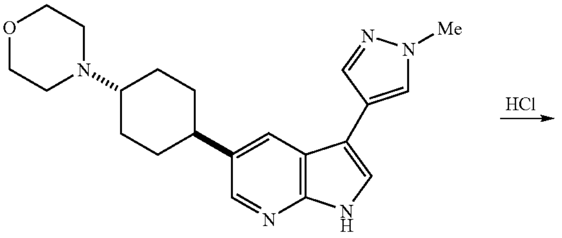

(I-6)

-continued

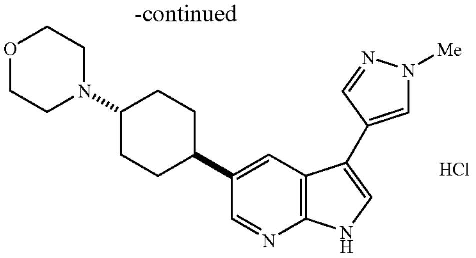

(I-6)•HCl

Compound (I-6) (2.584 g, 7.07 mmol) was dissolved at 50° C. in a mixture of absolute EtOH (6.45 mL)-2.00 M aqueous HCl (3.54 ml, 7.07 mmol) to form a clear yellow solution. The solution was cooled to about 35° C. and a mixture of EtOH: tBuOMe=1:1 (v/v) (12.9 mL) was added via syringe over a period of 30 s. The mixture was left to stand at −20° C. for 3 days. The crystals were filtered off, washed with EtOH:t-BuOMe=1:1 (v/v) (10 mL) and dried in vacuum to give (I-6).HCl (2.762 g, 93%). $^1$H NMR (400 MHz, DMSO-$d_6$) δ 1.61-1.84 (m, 4H), 1.93-2.08 (m, 2H), 2.23-2.38 (m, 2H), 2.64-2.79 (m, 1H), 3.06-3.20 (m, 2H), 3.21-3.33 (m, 1H), 3.34-3.48 (m, 2H), 3.90 (s, 3H), 3.92-4.04 (m, 4H), 7.68 (d, J=2.4 Hz, 1H), 7.84 (s, 1H), 8.09 (d, J=1.7 Hz, 1H), 8.16 (s, 1H), 8.17 (d, J=1.9 Hz, 1H), 11.24 (br s, 1H), 11.69 (brs, 1H).

4-((1s,4s)-4-(3-(1-methyl-1H-pyrazol-4-yl)-1H-pyrrolo[2,3-b]pyridin-5-yl)cyclohexyl)morpholine (I-7)

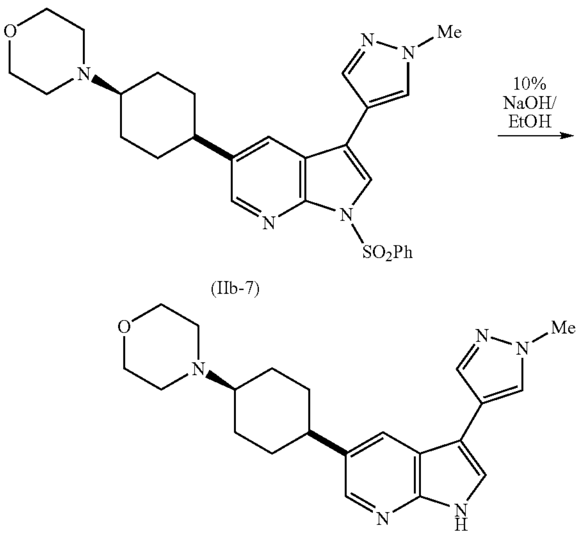

(IIb-7)

(I-7)

Cis isomer (II-7) was deprotected as described in the general procedure A for the deprotection of 7-azaindoles. Thus, (IIb-7) (1.22 g, 2.41 mmol) was dissolved in ethanol (24.1 mL). A 10% solution of NaOH (12.05 mL) was added and the reaction was heated to 80° C. for 40 min. It was allowed to cool down and a saturated solution of $NaHCO_3$ (100 mL) was added. It was then extracted with EtOAc (3×100 mL) and the combined organic extracts were dried over $MgSO_4$ and concentrated. The crude product was purified by SGC using hexane/10:1 $CH_2Cl_2$:MeOH as the eluent (gradient elution 0%-100% 10:1 $CH_2Cl_2$:MeOH) to give the cis isomer (I-7) as a white solid (0.53 g, 60%), $^1$H NMR (400 MHz, $CDCl_3$) δ 1.63-1.54 (m, 2H), 1.73-1.65 (m, 2H), 2.09-1.97 (m, 4H), 2.31-2.26 (m, 1H), 2.55-2.47 (m, 4H), 2.89-2.80 (m, 1H), 3.79-3.75 (m, 4H), 4.01 (s, 3H), 7.39 (d, J=2.3 Hz, 1H), 7.63 (s, 1H), 7.79 (d, J=0.4 Hz, 1H), 7.93 (d, J=1.8 Hz, 1H), 8.30 (d, J=2.0 Hz, 1H), 9.73 (br s, NH, 1H).

5-(4-ethylcyclohex-1-enyl)-3-(1-methyl-1H-pyrazol-4-yl)-1H-pyrrolo[2,3-b]pyridine (I-8)

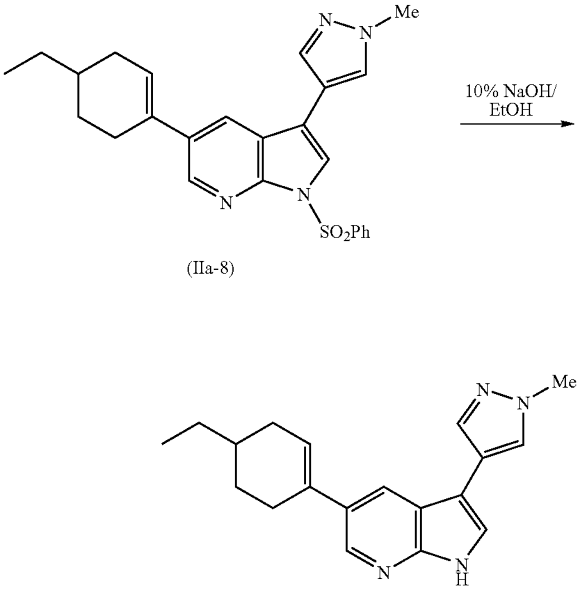

(IIa-8)

(I-8)

Compound (IIa-8) (0.17 g, 0.38 mmol) was deprotected as described in the general procedure A for the deprotection of 7-azaindoles. The crude product was purified by PTLC using EtOAc as the eluent to give (I-8) as a pale yellow solid (79 mg, 68%), $^1$H NMR (400 MHz, $CDCl_3$) δ 0.98 (t, J=7.4 Hz, 1H), 1.47-1.35 (m, 3H), 1.62-1.51 (m, 1H), 1.94-1.82 (m, 1H), 2.03-1.95 (m, 1H), 2.43-2.33 (m, 1H), 2.58-2.53 (m 2H), 4.00 (s, 3H), 6.13-6.09 (m, 1H), 7.39 (d, J=2.4 Hz, 1H), 7.64 (s, 1H), 7.77 (d, J=0.6 Hz, 1H), 8.01 (d, J=2.0 Hz, 1H), 8.43 (d, J=2.0 Hz, 1H), 9.87 (br s, NH, 1H).

N,N-dimethyl-4-(3-(1-methyl-1H-pyrazol-4-yl)-1H-pyrrolo[2,3-b]pyridin-5-yl)cyclohexanamine (I-9)

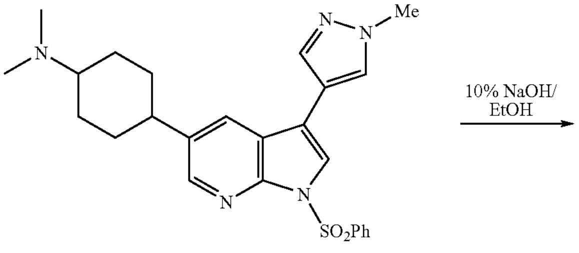

(IIb-9)

-continued

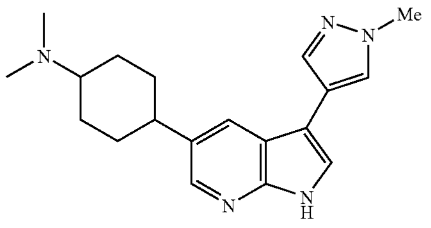

(I-9)

Compound (IIb-9) (0.22 g, 0.47 mmol) was deprotected as described in the general procedure A for the deprotection of 7-azaindoles. The crude product was purified by LCMS (column LUNA 10μ C18(2) 00G-4253-V0 250×50 mm) using water-MeCN (0.1% AcOH) as eluent (in gradient; flow 80 mL/min) to give (I-9) (0.116 g, 76%; retention time 8.2-9.2 min) as a yellow oil; a mixture of 1:1 cis:trans isomers.

5-cyclopentenyl-3-(1-methyl-1H-pyrazol-4-yl)-1H-pyrrolo[2,3-b]pyridine (I-10)

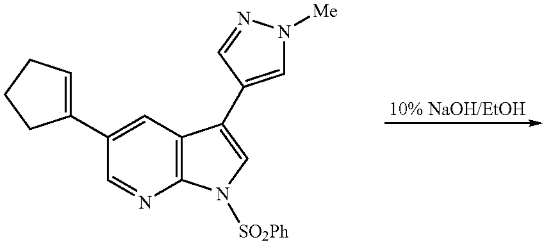

(IIa-10)

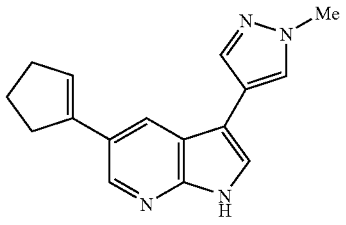

(I-10)

Compound (IIa-10) (0.11 g, 0.28 mmol) was deprotected as described in the general procedure A for the deprotection of 7-azaindoles. The crude product was purified by PTLC using EtOAc as the eluent to give (I-10) as a yellow solid (38 mg, 52%), $^1$H NMR (400 MHz, $CDCl_3$) δ 2.13-2.04 (m, 2H), 2.63-2.56 (m, 2H), 2.86-2.79 (m, 2H), 4.01 (s, 3H), 6.25-6.22 (m, 1H), 7.36 (d, J=2.3 Hz, 1H), 7.63 (s, 1H), 7.77 (d, J=0.4 Hz, 1H), 8.04 (d, J=1.8 Hz, 1H), 8.52 (d, J=1.8 Hz, 1H), 9.06 (br s, NH, 1H).

5-cyclopentyl-3-(1-methyl-1H-pyrazol-4-yl)-1H-pyrrolo[2,3-b]pyridine (I-11)

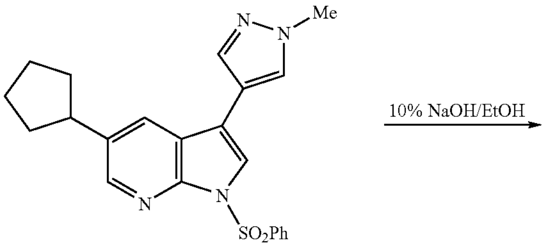

(IIb-11)

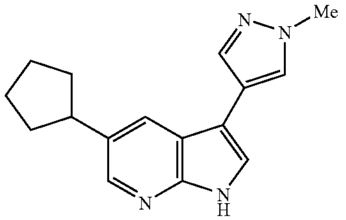

(I-11)

Compound (IIb-11) (45 mg, 0.011 mmol) was deprotected as described in the general procedure A for the deprotection of 7-azaindoles. The crude product was purified by PTLC using EtOAc as the eluent to give (I-11) as a white solid (15.5 mg, 52%), $^1$H NMR (400 MHz, $CDCl_3$) δ 1.81-1.63 (m, 4H), 1.92-1.83 (m, 2H), 2.21-2.12 (m, 2H), 3.20-3.11(m, 1H), 4.00 (s, 3H), 7.36 (d, J=1.9 Hz, 1H), 7.62 (s, 1H), 7.76 (d, J=0.4 Hz, 1H), 7.91 (d, J=1.6 Hz, 1H), 8.26 (s, 1H), 9.04 (br s, NH, 1H).

5-cyclohexenyl-3-(1-methyl-1H-pyrazol-4-yl)-1H-pyrrolo[2,3-b]pyridine (I-12)

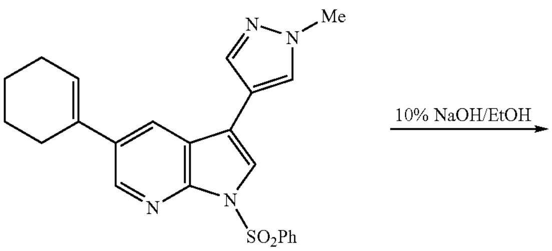

(IIa-12)

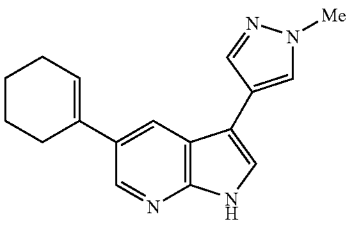

(I-12)

Compound (IIa-12) (30 mg, 0.07 mmol) was deprotected as described in the general procedure A for the deprotection of 7-azaindoles. The crude product was purified by PTLC using EtOAc as the eluent to give (I-12) as a white solid (14.5 mg, 73%), $^{1}$H NMR (400 MHz, $CDCl_3$) δ 1.75-1.68 (m, 2H), 1.88-1.82 (m, 2H), 2.29-2.23 (m, 2H), 2.54-2.49 (m, 2H), 4.00 (s, 3H), 6.15-6.11 (m, 1H), 7.41 (d, J=2.1 Hz, 1H), 7.64 (s, 1H), 7.77 (d, J=0.4 Hz, 1H), 8.01 (d, J=2.0 Hz, 1H), 8.43 (d, J=1.9 Hz, 1H), 10.31 (br s, NH, 1H).

(E)-5-cycloheptenyl-3-(1-methyl-1H-pyrazol-4-yl)-1H-pyrrolo[2,3-b]pyridine (I-13)

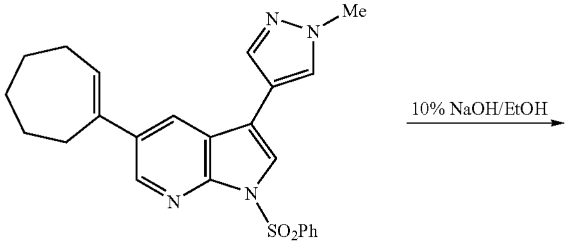

(IIa-13)

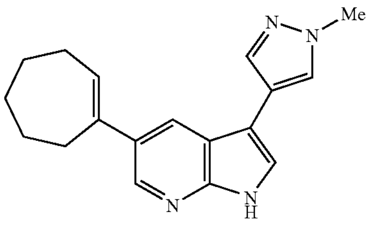

(I-13)

Compound (IIa-13) (48 mg, 0.11 mmol) was deprotected as described in the general procedure A for the deprotection of 7-azaindoles. The crude product was purified by prep TLC using EtOAc as the eluent to give (I-13) as a white solid (25 mg, 78%), $^{1}$H NMR (400 MHz, $CDCl_3$) δ 1.65-1.58 (m, 2H), 1.76-1.69 (m, 2H), 1.92-1.85 (m, 2H), 2.37-2.31 (m, 2H), 2.73-2.69 (m, 2H), 4.00 (s, 3H), 6.12 (t, J=6.6 Hz, 1H), 7.42 (d, J=2.0 Hz, 1H), 7.64 (s, 1H), 7.78 (d, J=0.6 Hz, 1H), 7.96 (d, J=2.0 Hz, 1H), 8.37 (d, J=2.0 Hz, 1H), 10.80 (br s, NH, 1H).

5-(1,4-Dioxa-spiro[4.5]dec-7-en-8-yl)-3-(1-methyl-1H-pyrazol-4-yl)-1H-pyrrolo[2,3-b]pyridine (I-14)

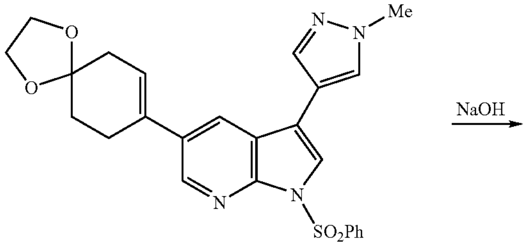

(IIa-14)

-continued

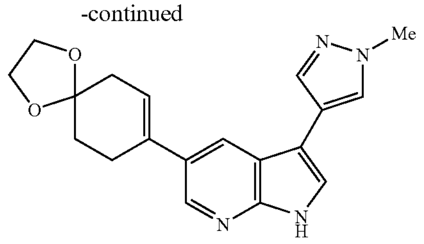

(I-14)

Compound (IIa-14) (30 mg, 0.063 mmol) was deprotected as described in the general procedure A for the deprotection of 7-azaindoles. The crude product was purified by PTLC using EtOAc as the eluent to give product I-14 (15.7 mg, 74%) as a yellow solid; $^{1}$H NMR (400 MHz, $CDCl_3$) δ 1.99 (t, J=6.5 Hz, 2H), 2.55-2.51 (m, 2H), 2.80-2.75 (m, 2H), 4.00 (s, 3H), 4.06 (s, 4H), 6.02-5.98 (m, 1H), 7.40 (d, J=1.9 Hz, 1H), 7.63 (s, 1H), 7.76 (d, J=0.6 Hz, 1H), 8.03 (d, J=1.9 Hz, 1H), 8.44 (d, J=1.9 Hz, 1H), 10.46 (br s, NH, 1H).

5-(4,4-dimethylcyclohex-1-enyl)-3-(1-methyl-1H-pyrazol-4-yl)-1H-pyrrolo[2,3-b]pyridine (I-15)

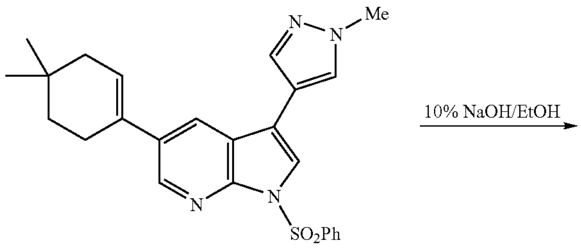

(IIa-15)

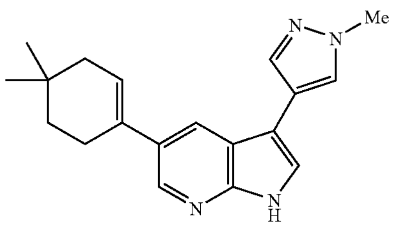

(I-15)

Compound (IIa-15) (78 mg, 0.17 mmol) was deprotected as described in the general procedure A for the deprotection of 7-azaindoles. The crude product was purified by PTLC using EtOAc as the eluent to give (I-15) as a white solid (43 mg, 80%), $^{1}$H NMR (400 MHz, $CDCl_3$) δ 1.02 (s, 6H), 1.59 (t, J=6.4 Hz, 2H), 2.07-2.03 (m, 2H), 2.56-2.50 (m, 2H), 4.00 (s, 3H), 6.10-6.06 (m, 1H), 7.42 (s, 1H), 7.64 (s, 1H), 7.78 (s, 1H), 8.03 (d, J=1.9 Hz, 1H), 8.45 (d, J=1.6 Hz, 1H), 10.87 (br s, NH, 1H).

5-cyclohexyl-3-(1-methyl-1H-pyrazol-4-yl)-1H-pyrrolo[2,3-b]pyridine (I-16)

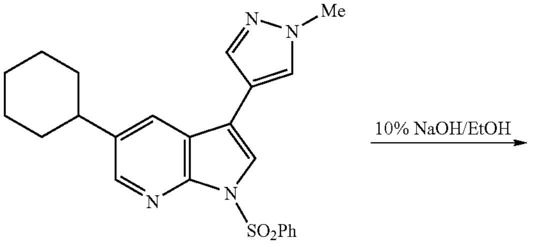

(IIb-16)

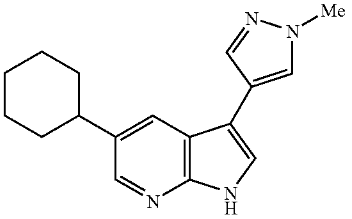

(I-16)

Compound (IIb-16) (16 mg, 0.038 mmol) was deprotected as described in the general procedure A for the deprotection of 7-azaindoles. The crude product was purified by PTLC using EtOAc as the eluent to give (I-16) as a white solid (7.2 mg, 67%), $^1$H NMR (400 MHz, $CDCl_3$) δ 1.37-1.25 (tq, J=3.2 and 12.5 Hz, 1H), 1.61-1.41 (m, 4H), 1.83-1.76 (m, 1H), 2.00-1.85 (m, 4H), 2.68 (tt, J=3.2 and 12.5 Hz, 1H), 4.01 (s, 3H), 7.41(s, 1H), 7.64 (s, 1H), 7.78 (s, 2H), 7.89 d, J=1.9 Hz, 1H), 8.26 (d, J=1.9 Hz, 1H), 10.44 (br s, NH, 1H).

5-cycloheptyl-3-(1-methyl-1H-pyrazol-4-yl)-1H-pyrrolo[2,3-b]pyridine (I-17)

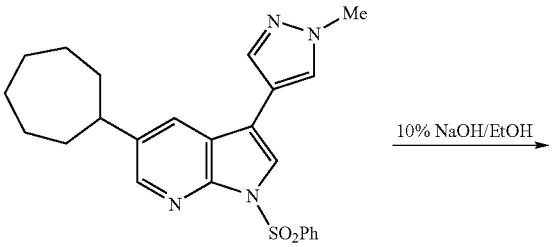

(IIb-17)

-continued

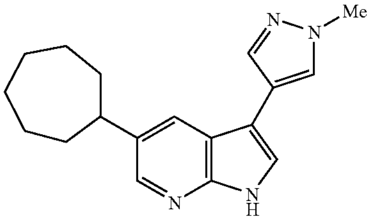

(I-17)

Compound (IIb-17) (46 mg, 0.10 mmol) was deprotected as described in the general procedure A for the deprotection of 7-azaindoles. The crude product was purified by PTLC using EtOAc as the eluent to give (I-17) as a white solid (22 mg, 71%), $^1$H NMR (400 MHz, $CDCl_3$) δ 1.90-1.58 (m, 10H), 2.04-1.96 (m, 2H), 2.84 (tt, J=3.6 and 10.6 Hz, 1H), 4.01 (s, 3H), 7.40 (d, J=1.8 Hz, 1H), 7.64 (s, 1H), 7.77 (d, J=0.4 Hz, 1H), 7.87 (d, J=1.9 Hz, 1H), 8.24 (d, J=1.9 Hz, 1H), 10.20 (br s, NH, 1H).

5-(4,4-dimethylcyclohexyl)-3-(1-methyl-1H-pyrazol-4-yl)-1H-pyrrolo[2,3-b]pyridine (I-18)

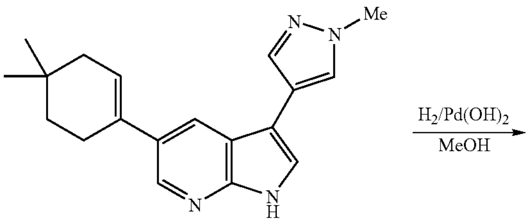

(I-15)

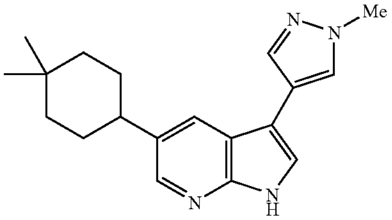

(I-18)

Compound (I-15) was hydrogenated using the general procedure for hydrogenation of 7-azaindoles. Thus, (I-15) (17 mg, 0.055 mmol) in MeOH (2 mL) and $Pd(OH)_2$ (20% on C, wet, Degussa type) (3.86 mg, 0.011 mmol) were used. The crude product was purified by PTLC using EtOAc as the eluent to give (I-18) as a white solid (7.2 mg, 42%), $^1$H NMR (400 MHz, $CDCl_3$) δ 0.99 (s, 3H), 1.03 (s, 3H), 1.45-1.35 (m, 2H), 1.58-1.52 (m, 2H), 1.81-1.67 (m, 4H), 2.64-2.55 (m, 1H), 4.01 (s, 3H), 7.38 (d, J=2.2 Hz, 1H), 7.63 (s, 1H), 7.77 (s, 1H), 7.89 (d, J=1.8 Hz, 1H), 8.26 (d, J=1.9 Hz, 1H), 9.61 (br s, NH, 1H).

5-(1,4-Dioxa-spiro[4.5]dec-8-yl)-3-(1-methyl-1H-pyrazol-4-yl)-1H-pyrrolo[2,3-b]pyridine (I-19)

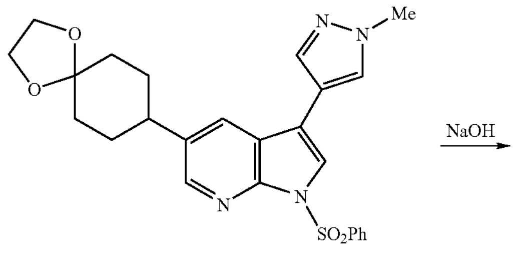

(IIb-19)

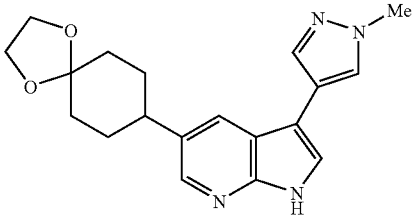

(I-19)

Compound (IIb-19) (40 mg, 0.083 mmol) was deprotected as described in the general procedure A for the deprotection of 7-azaindoles. The crude product was purified by PTLC using EtOAc as the eluent to give product (I-19) (13.3 mg, 74%) as a white solid; $^1$H NMR (400 MHz, $CDCl_3$) δ 1.81-1.71 (m, 2H), 2.00-1.84 (m, 6H), 2.80-2.71 (m, 1H), 4.01 (s, 3H), 4.03-4.02 (m, 4H), 7.40 (d, J=1.4 Hz, 1H), 7.64 (s, 1H), 7.76 (d, J=0.6 Hz, 1H), 7.92 (d, J=2.0 Hz, 1H), 8.27 (d, J=1.7 Hz, 1H), 9.55 (br s, NH, 1H).

4-[3-(1-Methyl-1H-pyrazol-4-yl)-1H-pyrrolo[2,3-b]pyridin-5-yl]-cyclohexanone (I-20)

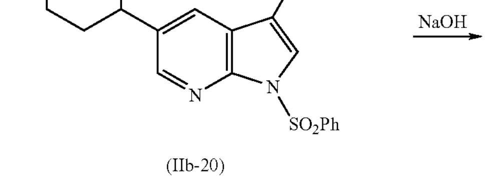

(IIb-20)

-continued

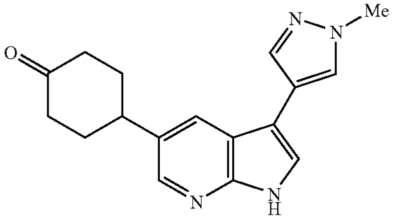

(I-20)

Compound (IIb-20) (22 mg, 0.050 mmol) was deprotected as described in the general procedure A for the deprotection of 7-azaindoles. The crude product was purified by PTLC using EtOAc as the eluent to give product I-20 (5.7 mg, 38%) as a white solid; $^1$H NMR (400 MHz, $CDCl_3$) δ 2.14-2.00 (m, 2H), 2.36-2.28 (m, 2H), 2.65-2.54 (m, 4H), 3.22 (tt, J=3.3 and 12.2 Hz, 1H), 4.01 (s, 3H), 7.40 (d, J=2.2 Hz, 1H), 7.63 (s, 1H), 7.75 (d, J=0.5 Hz, 1H), 7.91 (d, J=1.9 Hz, 1H), 8.29 (d, J=1.9 Hz, 1H), 9.31 (br s, NH, 1H).

5-(4,4-dimethylcyclohexa-1,5-dienyl)-3-(1-methyl-1H-pyrazol-4-yl)-1H-pyrrolo[2,3-b]pyridine (I-21)

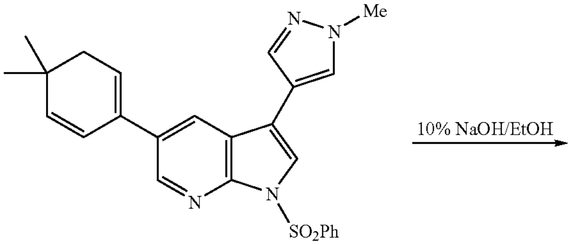

(IIa-21)

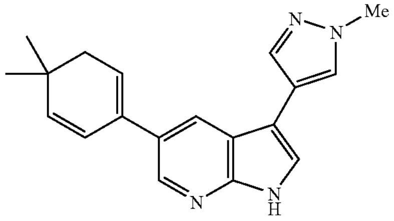

(I-21)

Compound (IIa-21) (77 mg, 0.17 mmol) was deprotected as described in the general procedure A for the deprotection of 7-azaindoles. The crude product was purified by PTLC using EtOAc as the eluent to give (I-21) as a white solid (38 mg, 72%), $^1$H NMR (400 MHz, $CDCl_3$) δ 1.10 (s, 6H), 2.34 (d, J=4.5 Hz, 2H), 4.00 (s, 3H), 5.79 (d, J=9.70 Hz, 1H), 6.03 (t, J=4.5 Hz, 1H), 6.25 (d, J=9.7 Hz, 1H), 7.42 (s, 1H), 7.64 (s, 1H), 7.77 (s, 1H), 8.02 (s, 1H), 8.43 (s, 1H), 10.33 (br s, NH, 1H).

5-(4-ethylcyclohexyl)-3-(1-methyl-1H-pyrazol-4-yl)-1H-pyrrolo[2,3-b]pyridine (I-22)

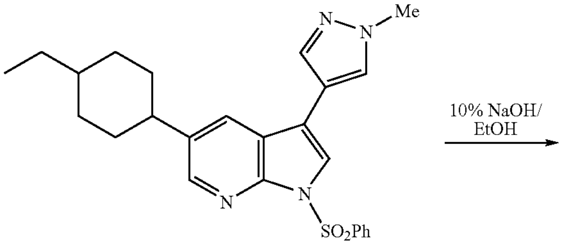

(IIb-22)

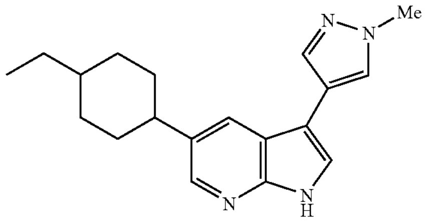

(I-22)

Compound (IIb-22) (0.20 g, 0.45 mmol) was deprotected as described in the general procedure A for the deprotection of 7-azaindoles. The crude product was purified by PTLC using EtOAc as the eluent to give (I-22) as a white solid (1.3:1 mixture of isomers) (0.14 g, 63%), $^1$H NMR (400 MHz, $CDCl_3$) δ 0.94 (t, J=7.1 Hz, 3H), 0.95 (t, J=7.4 Hz, 3H), 1.16-1.05 (m, 2H), 1.34-1.24 (m, 2H), 1.59-1.45 (m, 4H), 1.80-1.60 (m, 10H), 2.02-1.90 (m, 4H), 2.64 (tt, J=3.2 and 12.1 Hz, 1H), 2.79-2.69 (m, 1H), 4.00 (s, 3H), 4.01 (s, 3H), 7.37 (s, 1H), 7.38 (s, 1H), 7.63 (s, 2H), 7.77 (d, J=0.6 Hz, 1H), 7.78 (d, J=0.6 Hz, 1H), 7.88 (d, J=2.0 Hz, 1H), 7.89 (d, J=2.0 Hz, 1H), 8.24 (d, J=2.0 Hz, 1H), 8.26 (d, J=2.0 Hz, 1H), 9.49 (br s, NH, 1H), 9.51 (br s, NH, 1H).

3-(1-methyl-1H-pyrazol-4-yl)-5-((1s,4s)-4-(pyrrolidin-1-yl)cyclohexyl)-1H-pyrrolo[2,3-b]pyridine (I-23)

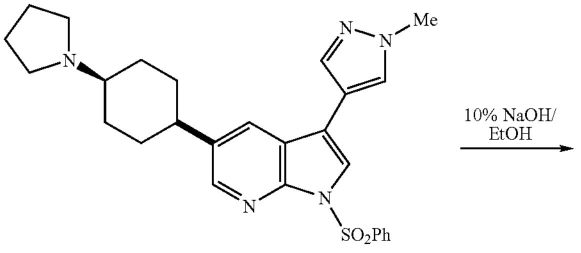

(IIb-23)

-continued

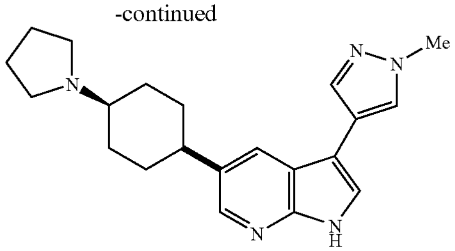

(I-23)

Compound (IIb-23) (150 mg, 0.30 mmol) in EtOH (3.06 mL) and 10% NaOH (1.02 mL) was deprotected following the general procedure for the deprotection of 7-azaindoles. The crude product was purified by LCMS (column LUNA 10μ C18(2) 00G-4253-V0 250×50 mm) using water—MeCN (0.1% AcOH) as eluent (in gradient; flow 80 mL/min) to give a (I-23) (107 mg, 69%; retention time 12.30 min) as a yellow foam. $^1$H NMR (400 MHz, $CDCl_3$) δ 1.83-1.73 (m, 4H), 1.99-1.95 (m, 4H), 2.11-2.03 (m, 2H), 2.33-2.22 (m, 2H), 2.85-2.79 (m, 2H), 3.16-3.10 (m, 4H), 3.99 (s, 3H), 7.38 (s, 1H), 7.74 (d, J=0.6 Hz, 1H), 7.75 (s,1H), 8.02 (d, J=1.8 Hz, 1H), 8.20 (d, J=1.8 Hz, 1H), 10.88 (br s, NH, 1H), MS (CI) m/z 350.1 ($MH^+$).

3-(1-methyl-1H-pyrazol-4-yl)-5-((1r,4r)-4-(pyrrolidin-1-yl)cyclohexyl)-1H-pyrrolo[2,3-b]pyridine (I-24)

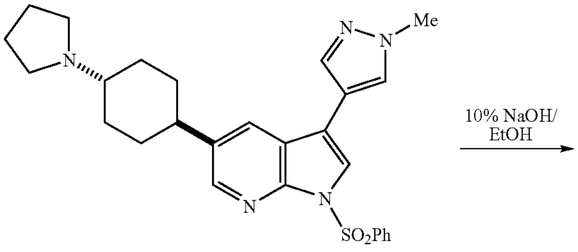

(IIb-24)

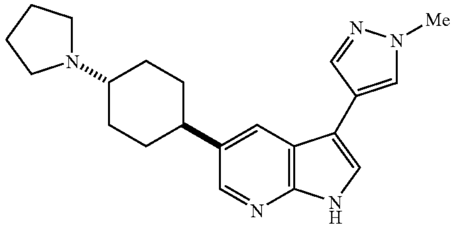

(I-24)

Compound (IIb-24) (188 mg, 0.38 mmol) in EtOH (3.83 mL) and 10% NaOH (1.27 mL) was deprotected following the general procedure for the deprotection of 7-azaindoles. The crude product was purified by LCMS (column LUNA 10μ C18(2) 00G-4253-V0 250×50 mm) using water-MeCN (0.1% AcOH) as eluent (in gradient; flow 80 mL/min) to give a (I-24) (102 mg, 76%; retention time 11.30 min) as a white foam. $^1$H NMR (400 MHz, $CDCl_3$) δ 1.63-1.51 (dq, J=2.4 and 12.6 Hz, 2H), 1.88-1.75 (dq, J=2.5 and 12.5 Hz, 2H), 2.05-1.95 (m, 6H), 2.24-2.16 (m, 2H), 2.76-2.66 (tt, J=3.2 and 12.2 Hz, 1H), 2.87-2.78 (tt, J=3.7 and 11.7 Hz, 1H), 3.24-3.14 (m, 4H), 3.99 (s, 3H), 7.40 (s, 1H), 7.63 (s,1H), 7.74 (d, J=0.6 Hz, 1H), 7.86 (d, J=1.8 Hz, 1H), 8.12 (d, J=1.8 Hz, 1H), 10.88 (br s, NH, 1H), MS (CI) m/z 350.1 ($MH^+$).

3-(1-methyl-1H-pyrazol-4-yl)-5-((1r,4r)-4-(4-methylpiperazin-1-yl)cyclohexyl)-1H-pyrrolo[2,3-b]pyridine (I-25)

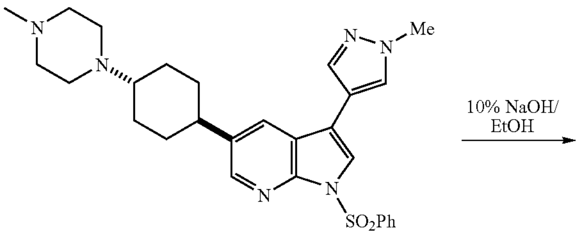

(IIb-25)

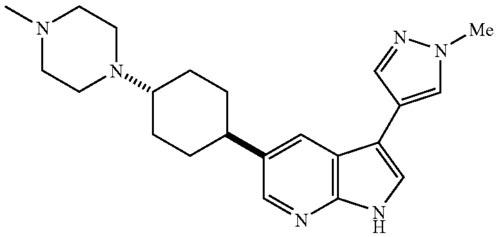

(I-25)

Compound (IIb-25) (175 mg, 0.4 mmol) in EtOH (3.37 mL) and 10% NaOH (1.12 mL) was deprotected following the general procedure for the deprotection of 7-azaindoles. The crude product was purified by LCMS (column LUNA 10μ C18(2) 00G-4253-V0 250×50 mm) using water-MeCN (0.1% AcOH) as eluent (in gradient; flow 80 mL/min) to give compound (I-25) as a yellow solid (79 mg, 62%). $^1$H NMR (400 MHz, $CDCl_3$) δ 1.53-1.42 (dq, J=2.6 and 12.5 Hz, 2H), 1.66-1.54 (dq, J=2.6 and 12.5 Hz, 2H), 2.01-1.95 (br m, 2H), 2.09-2.02 (m, 2H), 2.28 (s, 3H), 2.85-2.48 (m, 11H), 3.99 (s, 3H), 7.39 (s, 1H), 7.61 (s, 1H), 7.74 (d, J=0.4 Hz, 1H), 7.87 (d, J=1.9 Hz, 1H), 8.17 (d, J=1.9 Hz, 1H), 10.79 (br s, NH, 1H).

3-(1-methyl-1H-pyrazol-4-yl)-5-((1s,4s)-4-(4-methylpiperazin-1-yl)cyclohexyl)-1H-pyrrolo[2,3-b]pyridine (I-26)

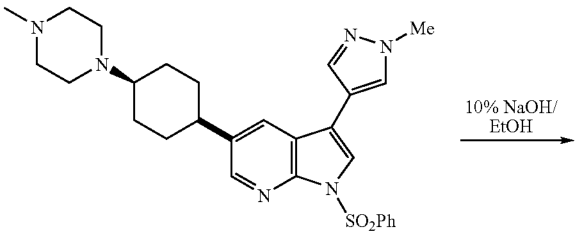

(IIb-26)

-continued

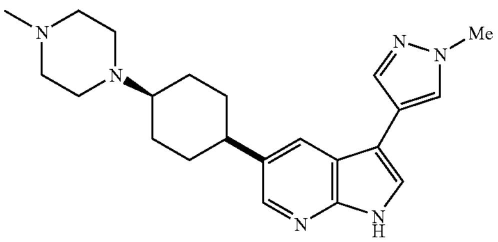

(I-26)

Compound (IIb-26) (110 mg, 0.21 mmol) in EtOH (2.12 mL) and 10% NaOH (0.70 mL) was deprotected following the general procedure for the deprotection of 7-azaindoles. The crude product was washed with MeOH, filtered and dried to give (I-26) (60 mg, 75%) as a white solid. $^1$H NMR (400 MHz, $CDCl_3$) δ 1.72-1.54 (m, 8H), 2.08-1.95 (m, 4H), 2.31 (s, 3H), 2.66-2.43 (br s, 5H), 2.89-2.80 (m, 1H), 3.99 (s, 3H), 7.35 (s, 1H), 7.63 (s, 1H), 7.76 (d, J=0.6 Hz, 1H), 7.94 (d, J=1.9 Hz, 1H), 8.23 (d, J=1.9 Hz, 1H), 9.57 (br s, NH, 1H).

3-(1-methyl-1H-pyrazol-4-yl)-5-(4-phenylcyclohex-1-enyl)-1H-pyrrolo[2,3-b]pyridine (I-27)

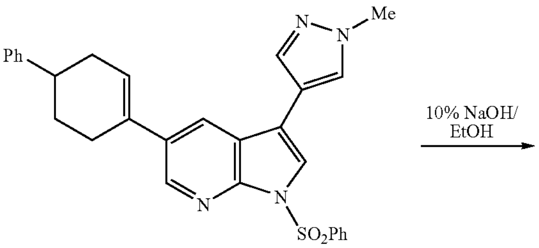

(IIa-27)

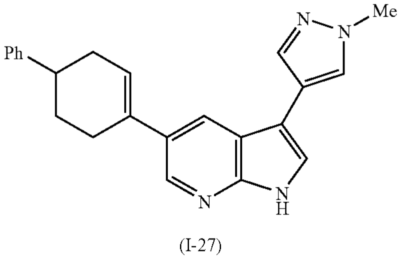

(I-27)

Compound (IIa-27) (0.11 g, 0.22 mmol) was deprotected as described in the general procedure A for the deprotection of 7-azaindoles. The crude product was purified by PTLC using EtOAc as the eluent to give (I-27) as a pale yellow solid (28 mg, 35%), $^1$H NMR (400 MHz, $CDCl_3$) δ 2.05-1.94 (m, 1H), 2.22-2.14 (m, 1H), 2.45-2.35 (m, 1H), 2.62-2.53 (m, 1H), 2.73-2.66 (m, 2H), 2.99-2.90 (m, 1H), 4.00 (s, 3H), 6.24-6.20 (m, 1H), 7.26-7.21 (m, 1H), 7.38-7.29 (m, 4H), 7.40 (s, 1H), 7.64 (s, 1H), 7.78 (d, J=0.6 Hz, 1H), 8.05 (d, J=2.1 Hz, 1H), 8.44 (d, J=2.0 Hz, 1H), 10.15 (br s, NH, 1H).

3-(1-methyl-1H-pyrazol-4-yl)-5-(3,3,5,5-tetramethylcyclohex-1-enyl)-1H-pyrrolo[2,3-b]pyridine (I-28)

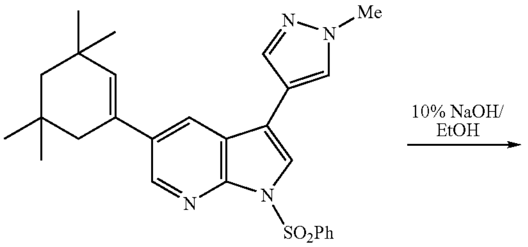

(IIa-28)

-continued

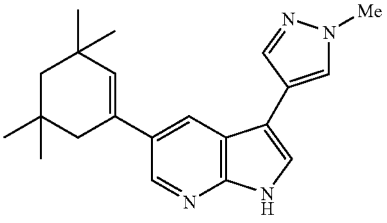

(I-28)

Compound (IIa-28) (60 mg, 0.126 mmol) was deprotected as described in the general procedure. The crude product was purified by PTLC using EtOAc as the eluent to give (I-28) (17 mg, 40%) as a white solid, $^1$H NMR (400 MHz, $CDCl_3$) δ 1.09 (s, 6H), 1.14 (s, 6H), 1.46 (s, 2H), 2.25 (d, J=1.3 Hz, 2H), 4.01 (s, 3H), 5.81 (t, J=1.3 Hz, 1H), 7.40 (d, J=2.4 Hz, 1H), 7.64 (s, 1H), 7.79 (d, J=0.4 Hz, 1H), 7.98 (d, J=2.0 Hz, 1H), 8.41 (d, J=2.0 Hz, 1H), 10.06 (br s, NH, 1H).

Mixture of 3-(1-methyl-1H-pyrazol-4-yl)-5-(5-methylcyclohex-1-enyl)-1H-pyrrolo[2,3-b]pyridine and 3-(1-methyl-1H-pyrazol-4-yl)-5-(3-methylcyclohex-1-enyl)-1H-pyrrolo[2,3-b]pyridine (I-29)

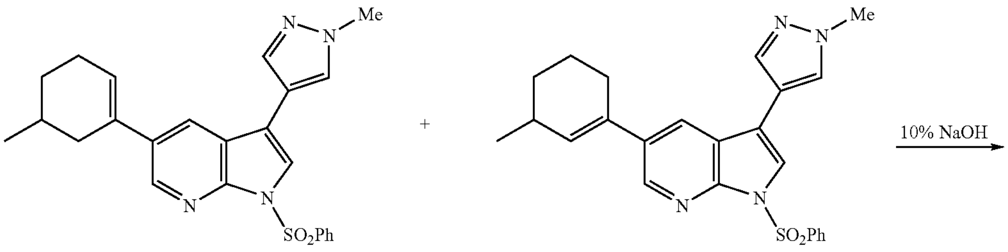

(IIa-29)

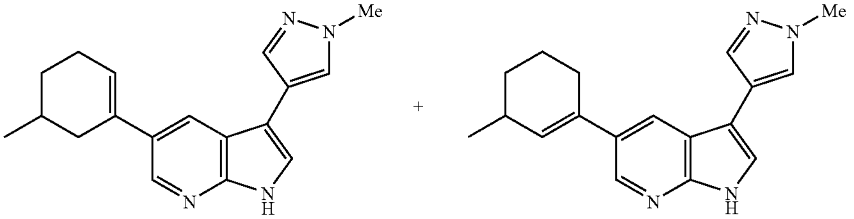

(I-29)

Mixture (IIa-29) (42 mg, 0.10 mmol) was deprotected as described in the general procedure A for the deprotection of 7-azaindoles. The crude product was purified by PTLC using EtOAc as the eluent to afford (I-29) as a 2.4:1 mixture of isomers; white solid (22 mg, 78%), $^1$H NMR (400 MHz, $CDCl_3$) δ 1.10 (d, J=6.6 Hz, 3H, major isomer), 1.12 (d, J=7.0 Hz, 3H, minor isomer), 1.37-1.24 (m, 3H), 2.00-1.69 (m, 5H), 2.19-2.09 (m, 2H), 2.35-2.27 (m, 2H), 2.51-2.46 (m, 1H), 2.61-2.53 (m, 1H), 4.00 (s, 6H,), 5.99-5.96 (m, 1H, minor isomer), 6.14-6.09 (m, 1H, major isomer), 7.42 (d, J=1.2 Hz, 2H), 7.64 (s, 2H), 7.78 (s, 2H), 8.03-8.01 (m, 2H), 8.45-8.43 (m, 2H), 10.78 (br s, 2H).

Mixture of 3-(1-methyl-1H-pyrazol-4-yl)-5-(6-methylcyclohex-1-enyl)-1H-pyrrolo[2,3-b]pyridine and 3-(1-methyl-1H-pyrazol-4-yl)-5-(2-methylcyclohex-1-enyl)-1H-pyrrolo[2,3-b]pyridine (I-30)

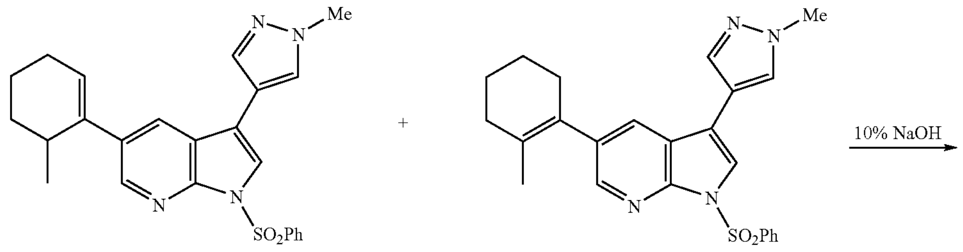

(IIa-30)

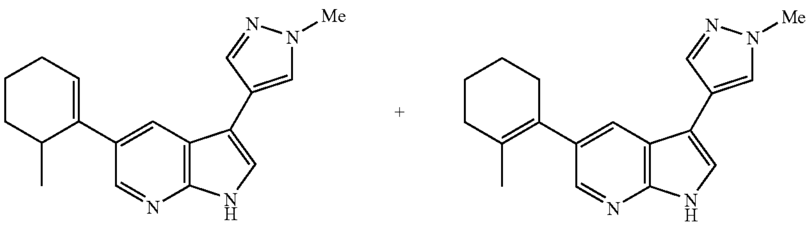

(I-30)

Mixture (IIa-30) (22 mg, 0.05 mmol) was deprotected as described in the general procedure A for the deprotection of 7-azaindoles. The crude product was purified by PTLC using EtOAc as the eluent to give (I-30) as a 4:1 mixture of isomers; white solid (12 mg, 80%), $^1$H NMR (400 MHz, $CDCl_3$) δ 0.97 (d, J=7.1 Hz, 3H, major isomer), 1.60 (s, 3H, minor isomer), 1.84-1.61 (m, 6H), 2.00-1.91 (m, 2H), 2.17-2.11 (m, 2H), 2.24-2.18 (m, 2H), 2.34-2.19 (m, 2H), 2.95-2.85 (m, 1H), 3.99 (s, 3H, minor isomer), 4.00 (s, 3H, major isomer), 5.90 (dt, J=1.0 and 3.9 Hz, 1H), 7.41 (d, J=2.2 Hz, 1H), 7.44 (d, J=2.4 Hz, 1H), 7.62 (s, 1H), 7.65 (s, 1H), 7.74 (d, J=0.6 Hz, 1H), 7.77 (d, J=0.6 Hz, 1H), 7.84 (d, J=1.90 Hz, 1H), 7.95 (d, J=1.9 Hz, 1H), 8.32 (d, J=2.0 Hz, 1H), 8.40 (d, J=2.1 Hz, 1H), 10.08 (br s, 1H), 10.25 (br s, 1H).

5-(2-Methoxy-cyclohex-1-enyl)-3-(1-methyl-1H-pyrazol-4-yl)-1H-pyrrolo[2,3-b]pyridine (I-31)

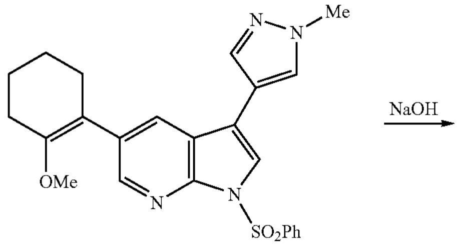

(IIa-31)

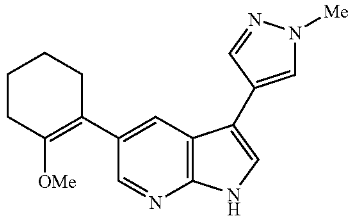

(I-31)

Compound (IIa-31) (19 mg, 0.042 mmol) was deprotected as described in the general procedure A for the deprotection of 7-azaindoles. The crude product was purified by PTLC using EtOAc as the eluent to give (I-31) (1.70 mg, 13%), $^1$H NMR (400 MHz, $CDCl_3$) δ 1.72-1.79 (m, 2H), 1.80-1.88 (m, 2H), 2.31-2.36 (m, 2H), 2.41-2.46 (m, 2H), 3.46 (s, 3H), 3.99 (s, 3H), 7.34 (d, J=2.0 Hz, 1H), 7.63 (s, 1H), 7.76 (d, J=0.6 Hz, 1H), 8.02 (d, J=1.9 Hz, 1H), 8.37 (d, J=1.9 Hz, 1H), 8.98 (br s, NH, 1H).

3-(1-methyl-1H-pyrazol-4-yl)-5-(3-methylcyclohexyl)-1H-pyrrolo[2,3-b]pyridine (I-32)

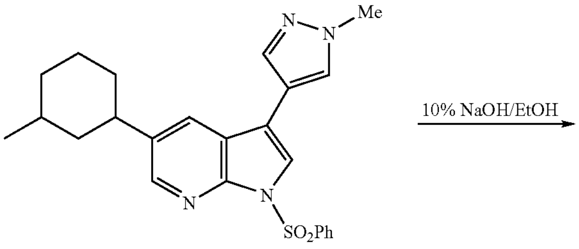

(IIb-32)

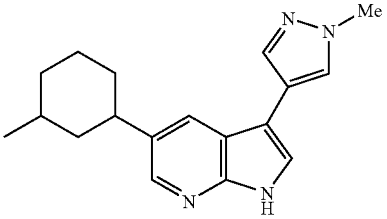

(I-32)

Compound (IIb-32) (0.10 g, 0.24 mmol) was deprotected as described in the general procedure A for the deprotection of 7-azaindoles. The crude product was purified by PTLC using EtOAc as the eluent to give (I-32) as a white solid (1.15:1 mixture of isomers) (43 mg, 62%), $^1$H NMR (400 MHz, $CDCl_3$) δ 0.98 (d, J=6.6 Hz, 3H, major isomer), 1.13 (d, J=7.2 Hz, 3H, minor isomer), 1.99-1.42 (m, 17H), 2.18-2.09 (m, 1H), 2.73 (tt, J=3.2 and 12.0 Hz, 1H), 2.99 (tt, J=3.5 and 11.0 Hz, 1H), 4.00 (s, 6H), 7.43 (s, 2H), 7.64 (s, 2H), 7.78 (s, 2H), 7.89 (d, J=1.8 Hz, 1H), 7.92 (d, J=1.8 Hz, 1H), 8.26 (d, J=1.7 Hz, 1H), 8.28 (d, J=1.7 Hz, 1H), 10.97 (br s, NH, 2H).

3-(1-methyl-1H-pyrazol-4-yl)-5-(2-methylcyclohexyl)-1H-pyrrolo[2,3-b]pyridine (I-33)

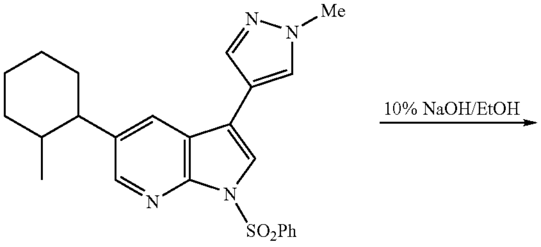

(IIb-33)

-continued

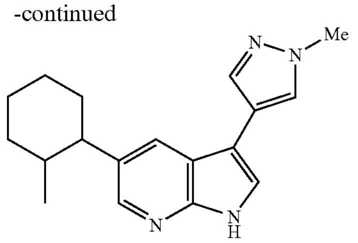

(I-33)

Compound (IIb-33) (60 mg, 0.14 mmol) was deprotected as described in the general procedure A for the deprotection of 7-azaindoles. The crude product was purified by PTLC using EtOAc as eluent to give product (I-33) as a white solid (4:1 mixture of isomers) (22 mg, 54%), $^1$H NMR (400 MHz, $CDCl_3$) δ 0.71 (d, J=6.5 Hz, 3H, minor isomer), 0.74 (d, J=7.2 Hz, 3H, major isomer), 2.02-1.40 (m, 15H), 2.25-2.11 (m, 3H), 2.35-2.20 (m, 1H), 3.02 (dt, J=3.6 and 12.7 Hz, 1H), 3.99 (s, 3H, minor isomer), 4.01 (s, 3H, major isomer), 7.42 (s, 1H), 7.45 (s, 1H), 7.63 (s, 1H), 7.65 (s, 1H), 7.78 (d, J=0.4 Hz, 2H), 7.86-7.84 (m, 2H), 8.18 (d, J=1.6 Hz, 1H), 8.22 (d, J=1.6 Hz, 1H), 10.69 (br s, NH, 1H), 10.78 (br s, NH, 1H).

3-(1-methyl-1H-pyrazol-4-yl)-5-(3,3,5,5-tetramethylcyclohexyl)-1H-pyrrolo[2,3-b]pyridine (I-34)

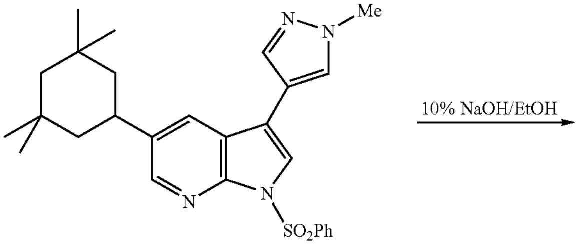

(IIb-34)

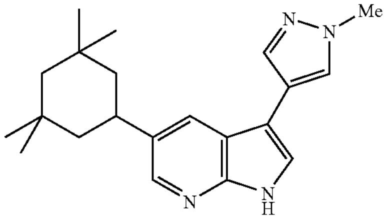

(I-34)

Compound (IIb-34) (0.085 g, 0.18 mmol) was deprotected as described in the general procedure A for the deprotection of 7-azaindoles. The crude product was purified by PTLC using EtOAc as the eluent to give (I-34) as a yellow solid (28 mg, 47%), $^1$H NMR (400 MHz, $CDCl_3$) δ 0.98 (s, 6H), 1.16 (s, 6H), 1.20-1.15 (m, 1H), 1.41-1.32 (m, 2H), 1.66 (d, J=12.6 Hz, 2H), 2.98 (tt, J-=3.0 and 12.6 Hz 1H), 4.01 (s, 3H), 7.44 (d, J=1.3 Hz, 1H), 7.64 (s, 1H), 7.79 (d, J=0.5 Hz, 1H), 7.90 (d, J=1.9 Hz, 1H), 8.28 (d, J=1.8 Hz, 1H), 11.05 (br s, NH, 1H).

3-(1-methyl-1H-pyrazol-4-yl)-5-(4-phenylcyclohexyl)-1H-pyrrolo[2,3-b]pyridine (I-35)

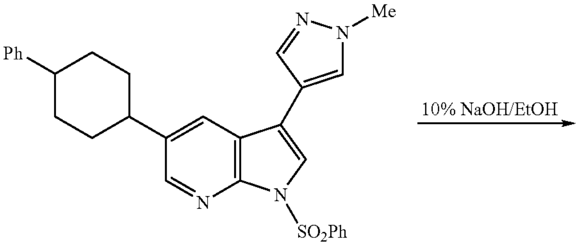

(IIb-35)

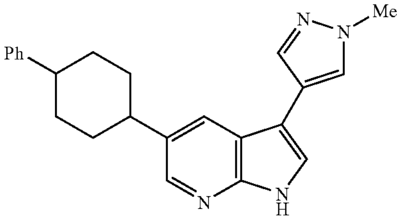

(I-35)

Compound (IIb-35) (0.17 g, 0.35 mmol) was deprotected as described in the general procedure A for the deprotection of 7-azaindoles. The crude product was purified by PTLC using EtOAc as the eluent to give (I-35) as a yellow solid which exists as a 1.2:1 mixture of isomers (88 mg, 71%), $^1$H NMR (400 MHz, $CDCl_3$) δ 1.79-1.67 (dq, J=3.1 and 12.0 Hz, 1H), 1.99-1.89 (m, 4H), 2.16-2.05 (m, 8H), 2.72-2.64 (m, 1H), 2.83-2.75 (m, 1H), 3.00-2.94 (m, 1H), 3.12-3.05 (m, 1H), 3.99 (s, 3H), 4.02 (s, 3H), 7.25-7.17 (m, 2H), 7.39-7.28 (m, 10H), 7.60 (s, 1H), 7.65 (s, 1H), 7.75 (d, J=0.5 Hz, 1H), 7.78

(d, J=0.5 Hz, 1H), 7.93 (d, J=1.4 Hz, 2H), 8.29 (d, J=2.0 Hz, 1H), 8.31 (d, J=2.0 Hz, 1H), 9.09 (br s, NH, 2H).

3-(1-methyl-1H-pyrazol-4-yl)-5-(3,3,5-trimethylcyclohexyl)-1H-pyrrolo[2,3-b]pyridine (I-36)

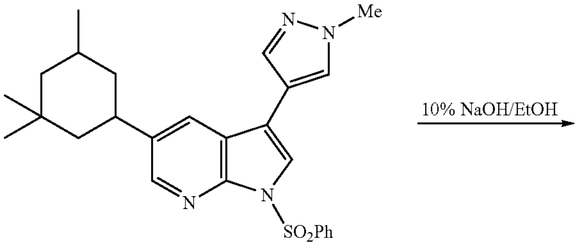

(IIb-36)

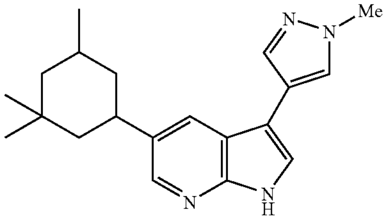

(I-36)

Compound (IIb-36) (0.04 g, 0.084 mmol) was deprotected as described in the general procedure A for the deprotection of 7-azaindoles. The crude product was purified by PTLC using EtOAc as the eluent to give (I-36) as a white solid (2.5:1 mixture of isomers) (6 mg, 22%), $^1$H NMR (400 MHz, $CDCl_3$) δ 0.86 (s, 3H, major isomer), 0.95 (d, J=6.5 Hz, 3H, minor isomer), 0.99 (s, 3H, minor isomer), 1.06 (s, 3H, minor isomer), 1.09 (s, 3H, major isomer), 1.16 (d, J=7.2 Hz, 3H, major isomer), 1.35-1.24 (m, 4H), 1.55-1.44 (dd, J=5.2 and 13.5 Hz, 2H), 1.68-1.53 (m, 6H), 1.91-1.83 (m, 1H), 2.20-2.10 (m, 1H), 2.92 (tt, J=3.8 and 12.6 Hz, 1H), 3.17-3.07 (m, 1H), 4.01 (s, 6H), 7.36 (d, J=2.1 Hz, 2H), 7.63 (s, 2H), 7.77 (s, 2H), 7.86 (d, J=1.8 Hz, 1H), 7.90 (d, J=1.8 Hz, 1H), 8.23 (d, J=1.8 Hz, 1H), 8.28 (d, J=1.8 Hz, 1H), 9.20 (br s, NH, 2H).

5-((1r,4r)-4-(4-methyl-1,4-diazepan-1-yl)cyclohexyl)-3-(1-methyl-1H-pyrazol-4-yl)-1H-pyrrolo[2,3-b]pyridine (I-37) and 5-((1s,4s)-4-(4-methyl-1,4-diazepan-1-yl)cyclohexyl)-3-(1-methyl-1H-pyrazol-4-yl)-1H-pyrrolo[2,3-b]pyridine (I-38)

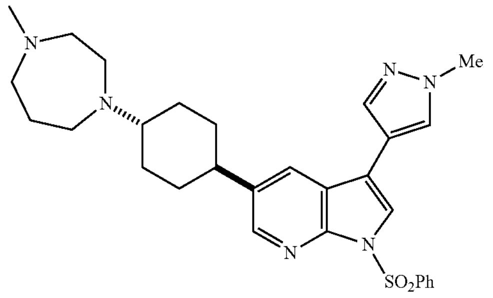

(IIb-37)

+

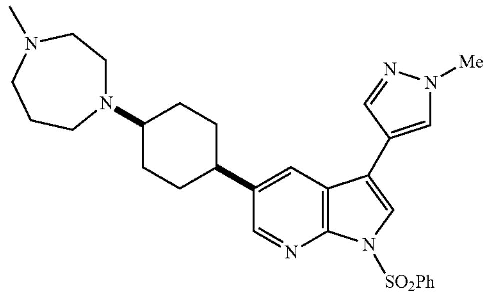

(IIb-38)

10%
NaOH/
EtOH

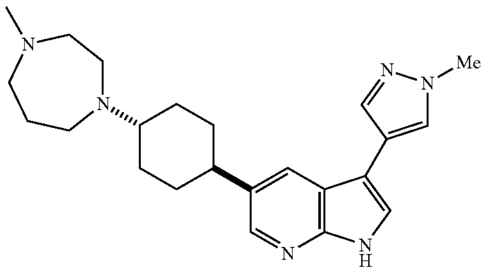

(I-37)

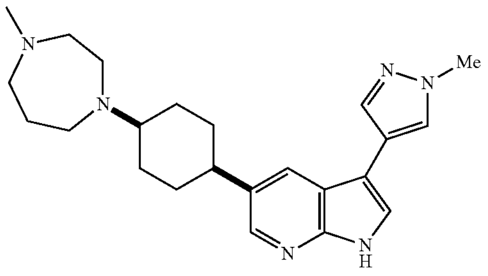

(I-38)

Mixture of (IIb-37) and (IIb-38) (157 mg, 0.29 mmol) in EtOH (2.94 mL) and 10% NaOH (1.0 mL) was deprotected following the general procedure for the deprotection of 7-azaindoles. The crude product was purified by LCMS (column LUNA 10μ C18(2) 00G-4253-V0 250×50 mm) using water-MeCN (0.1% AcOH) as eluent (in gradient; flow 80 mL/min) to give individual isomers (I-37) (38 mg, 33%) and (I-38) (12 mg, 10%) as well as a mixture of (I-37) and (I-38) (22 mg, 19%).

Data for trans compound (I-37): $^1H$ NMR (400 MHz, $CDCl_3$) δ 1.55-1.42 (dq, J=2.5 and 12.6 Hz, 2H), 1.67-1.56 (dq, J=2.5 and 12.6 Hz, 2H), 2.03-1.98 (m, 6H), 2.53 (s, 3H), 2.67-2.57 (tt, J=2.6 and 12.1 Hz, 1H), 2.82-2.72 (tt, J=2.5 and 11.5 Hz, 1H), 3.01-2.91 (m, 8H), 4.00 (s, 3H), 7.39 (s, 1H), 7.62 (s,1H), 7.75 (d, J=0.6 Hz, 1H), 7.87 (d, J=1.8 Hz, 1H), 8.16 (d, J=1.8 Hz, 1H), 10.44 (br s, NH, 1H), MS (CI) m/z 393.1 ($MH^+$).

Data for cis compound (I-38): $^1H$ NMR (400 MHz, $CDCl_3$) δ 1.72-1.62 (m, 2H), 1.82-1.73 (m, 2H), 1.91-1.83 (m, 2H), 2.15-2.01 (m, 4H), 2.60 (s, 3H), 2.80-2.75 (m, 1H), 2.90-2.86 (m, 2H), 3.01-2.91 (m, 5H), 3.07-3.02 (m, 2H), 3.99 (s, 3H), 7.37 (s, 1H), 7.64 (s,1H), 7.76 (d, J=0.6 Hz, 1H), 7.98 (d, J=1.6 Hz, 1H), 8.21 (d, J=1.8 Hz, 1H), 9.99 (br s, NH, 1H), MS (CI) m/z 393.1 ($MH^+$).

4-((1s,4s)-4-(3-(1-methyl-1H-pyrazol-4-yl)-1H-pyrrolo[2,3-b]pyridin-5-yl)cyclohexyl)-1,4-oxazepane (I-39) and 4-((1r,4r)-4-(3-(1-methyl-1H-pyrazol-4-yl)-1H-pyrrolo[2,3-b]pyridin-5-yl)cyclohexyl)-1,4-oxazepane (I-40)

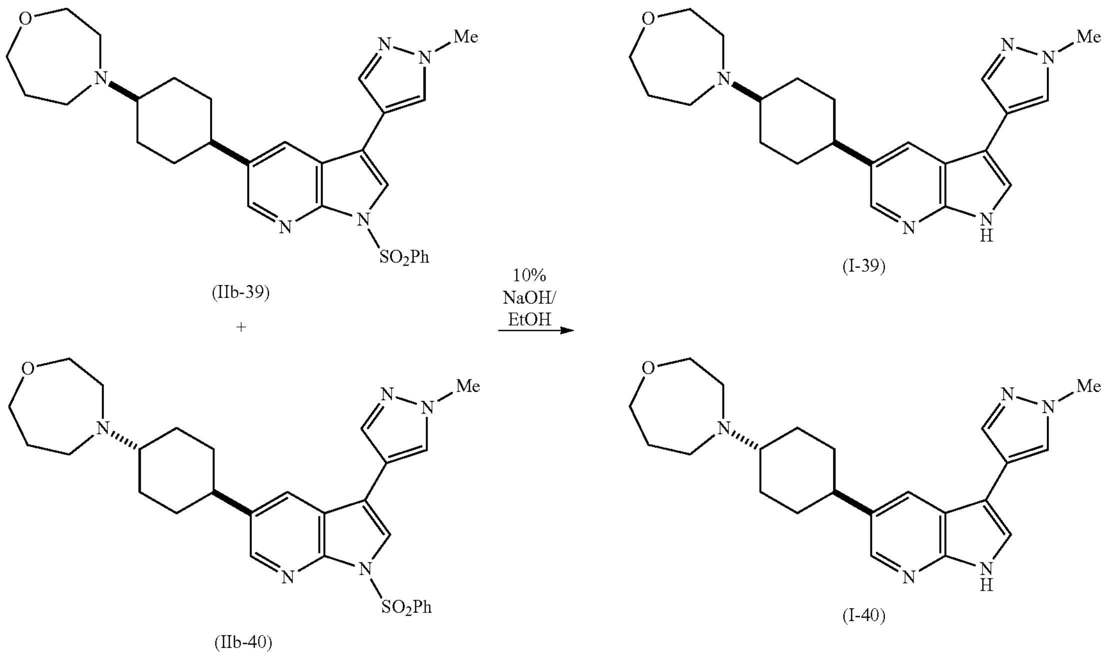

(IIb-39) + (IIb-40) → (I-39), (I-40)

The mixture of cis/trans isomers (IIb-39) and (IIb-40) (71 mg, 0.13 mmol) in EtOH (1.36 mL) and 10% aqueous NaOH (0.34 mL) was deprotected following the general procedure for the deprotection of 7-azaindoles. The crude product was separated by PTLC using 5:1 $CH_2Cl_2$:MeOH as the eluent to give cis isomer (I-39) (14 mg, 27%) and the trans isomer (I-40) (11 mg, 21%).

Data for cis isomer (I-39): $^1$H NMR (400 MHz, $CDCl_3$) δ 1.79-1.58 (m, 5H), 2.01-1.84 (m, 5H), 2.17-2.03 (m, 2H), 2.95-2.83 (m, 6H), 3.81-3.76 (br m, 2H), 3.82 (t, J=5.8 Hz, 2H), 4.01 (s, 3H), 7.39 (d, J=2.2 Hz, 1H), 7.65 (br s, 1H), 7.77 (d, J=0.5 Hz, 1H), 7.97 (br s, 1H), 8.30 (d, J=1.8 Hz, 1H), 9.71 (br s, NH, 1H).

Data for trans compound (I-40): $^1$H NMR (400 MHz, $CDCl_3$) δ 1.70-1.45 (m, 4H), 2.00-1.90 (br m, 2H), 2.12-2.02 (br m, 4H), 2.69-2.60 (m, 1H), 2.80-2.70 (m, 1H), 2.95-2.85 (m, 4H), 3.81-3.76 (m, 2H), 3.83 (t, J=6.0 Hz, 2H), 4.01 (s, 3H), 7.38 (d, J=2.2 Hz, 1H), 7.63 (s, 1H), 7.76 (d, J=0.4 Hz, 1H), 7.87 (d, J=1.9 Hz, 1H), 8.22 (d, J=1.9 Hz, 1H), 9.60 (br s, NH, 1H).

5-(4-(azetidin-1-yl)cyclohexyl)-3-(1-methyl-1H-pyrazol-4-yl)-1H-pyrrolo[2,3-b]pyridine (I-41)

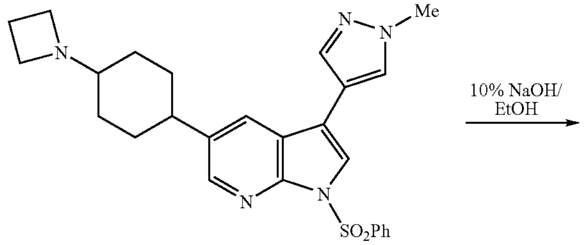

(IIb-41)

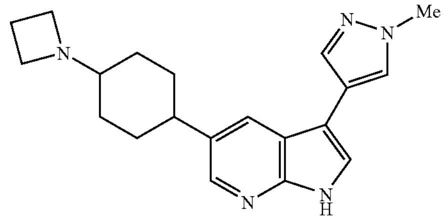

(I-41)

Compound (IIb-41) (156 mg, 0.33 mmol) in EtOH (3.28 mL) and 10% NaOH (1.10 mL) was deprotected following the general procedure for the deprotection of 7-azaindoles. The crude product was purified by LCMS (column LUNA 10μ C18(2) 00G-4253-V0 250×50 mm) using water-MeCN (0.1% AcOH) as eluent (in gradient; flow 80 mL/min) to give (I-41) (93 mg, 84%; retention time 9.50 min) as a yellow foam, a 1.05:1 mixture of trans: cis isomers. $^1$H NMR (400 MHz, $CDCl_3$) δ 1.69-1.45 (m, 8H), 1.89-1.81 (m, 2H), 2.04-1.94 (m, 4H), 2.25-2.15 (m, 2H), 2.34-2.25 (m, 2H), 2.60-2.50 (m, 1H), 2.72-2.63 (m, 3H), 3.58 (t, J=7.5 Hz, 4H), 3.68 (t, J=7.6 Hz, 4H), 3.97 (s, 3H), 3.98 (s, 3H), 7.38 (s, 1H), 7.39 (s, 1H), 7.60 (s, 2H), 7.75-7.73 (s, 4H), 7.84 (d, J=1.9 Hz, 1H), 8.01 (d, J=1.9 Hz, 1H), 8.12 (d, J=1.8 Hz, 1H), 8.21 (d, J=1.7 Hz, 1H), 10.94 (br s, NH, 2H), MS (CI) m/z 336.1 ($MH^+$).

5-(4,4-difluorocyclohexyl)-3-(1-methyl-1H-pyrazol-4-yl)-1H-pyrrolo[2,3-b]pyridine (I-42)

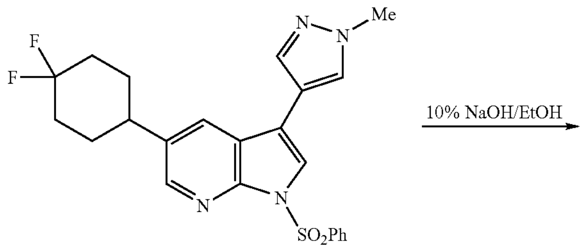

(IIb-42)

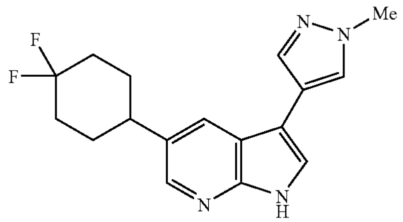

(I-42)

Compound (IIb-42) (77 mg, 0.17 mmol) in ethanol (3.40 mL) and 10% solution of NaOH (1.12 mL) was deprotected following the general procedure for the deprotection of 7-azaindoles. The crude product was purified by PTLC using EtOAc as the eluent to give (I-42) as a white solid (22 mg, 41%), $^1$H NMR (400 MHz, $CDCl_3$) δ 2.05-1.84 (m, 6H), 2.33-2.21 (m, 2H), 2.84-2.75 (m, 1H), 4.02 (s, 3H), 7.39 (d, J=2.4 Hz, 1H), 7.64 (s, 1H), 7.75 (d, J=0.5 Hz, 1H), 7.89 (d, J=2.0 Hz, 1H), 8.24 (d, J=2.0 Hz, 1H), 9.19 (br s, NH, 1H).

5-((1r,4r)-4-(4-isopropylpiperazin-1-yl)cyclohexyl)-3-(1-methyl-1H-pyrazol-4-yl)-1H-pyrrolo[2,3-b]pyridine (I-43)

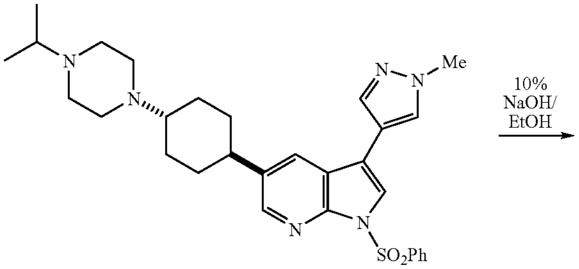

(IIb-43)

-continued

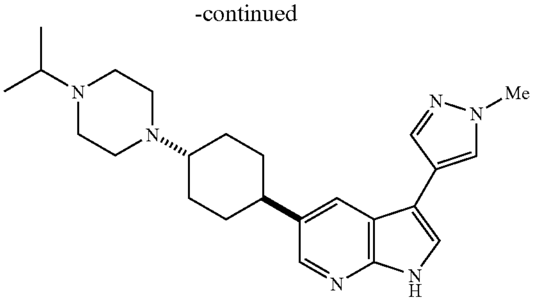

(I-43)

Compound (IIb-43) (129 mg, 0.24 mmol) in EtOH (2.36 mL) and 10% NaOH (1.18 mL) was deprotected following the general procedure for the deprotection of 7-azaindoles. The crude product was purified by preparative LCMS (column LUNA 10μ C18(2) 00G-4253-V0 250×50 mm) using water-MeCN (0.1% AcOH) as eluent (in gradient; flow 80 mL/min) to give compound (I-43) (40 mg, 42%; retention time 11.5-12 min) as a yellow oil. $^1$H NMR (400 MHz, $CDCl_3$) δ 1.19 (d, J=6.60 Hz, 6H), 1.65-1.45 (m, 4H), 2.07-2.01 (m, 2H), 2.16-2.10 (m, 2H), 2.74-2.60 (m, 2H), 3.06-2.94 (br s, 8H), 3.15-3.06 (m, 1H), 4.00 (s, 3H), 7.37 (s, 1H), 7.63 (s, 1H), 7.74 (d, J=0.5 Hz, 1H), 7.90 (d, J=1.7 Hz, 1H), 8.07 (s, 1H), 10.6 (br s, NH, 1H), MS (CI) m/z 407.1 (MH$^+$).

5-((1s,4s)-4-(4-isopropylpiperazin-1-yl)cyclohexyl)-3-(1-methyl-1H-pyrazol-4-yl)-1H-pyrrolo[2,3-b]pyridine (I-44)

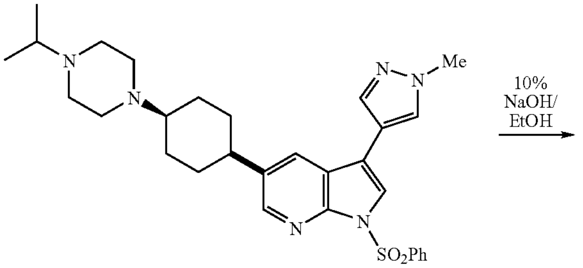

(IIb-44)

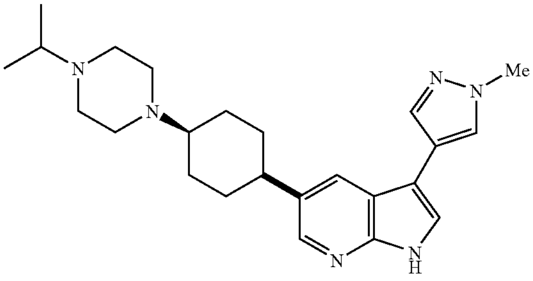

(I-44)

Compound (IIb-44) (200 mg, 0.36 mmol) in EtOH (3.65 mL) and 10% NaOH (1.21 mL) was deprotected following the general procedure for the deprotection of 7-azaindoles. The crude product was purified by preparative LCMS (column LUNA 10μ C18(2) 00G-4253-V0 250×50 mm) using water-MeCN (0.1% AcOH) as eluent (in gradient; flow 80 mL/min) to give (I-44) (63 mg, 42%; retention time 12-13 min) as white solid. $^1$H NMR (400 MHz, $CDCl_3$) δ 1.22 (d, J=6.60 Hz, 6H), 1.75-1.56 (m, 4H), 2.01-1.93 (m, 4H), 2.45-2.40 (m, 1H), 2.99-2.69 (m, 9H) 3.19-3.10 (m, 1H), 4.00 (s, 3H), 7.37 (s, 1H), 7.62 (s, 1H), 7.77 (d, J=0.6 Hz, 1H), 7.95 (d, J=1.7 Hz, 1H), 8.17 (d, J=1.7 Hz, 1H), 10.5 (br s, NH, 1H), MS (CI) m/z 407.1 (MH$^+$).

3-(1-methyl-1H-pyrazol-4-yl)-5-((1r,4r)-4-(piperidin-1-yl)cyclohexyl)-1H-pyrrolo[2,3-b]pyridine (I-45)

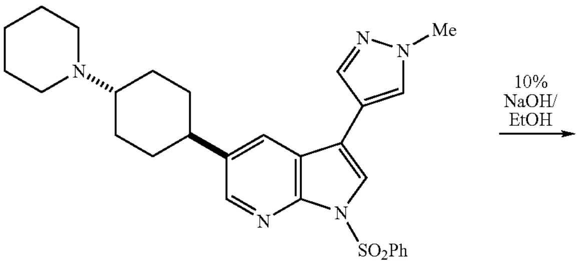

(IIb-45)

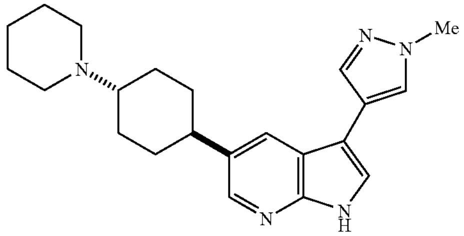

(I-45)

Compound (IIb-45) (0.14 g, 0.28 mmol) in EtOH (2.81 mL) and 10% NaOH (0.94 mL) was deprotected following the general procedure for the deprotection of 7-azaindoles. The crude product was purified by preparative LCMS (column LUNA 10μC18(2) 00G-4253-V0 250×50 mm) using water-MeCN (0.1% AcOH) as eluent (in gradient; flow 80 mL/min) to give (I-45) (54 mg, 53%; retention time 11.5-12.5 min) as white foam. $^1$H NMR (400 MHz, $CDCl_3$) δ 1.46-1.94 (m, 10H), 2.05-2.11 (m, 2H), 2.18-2.25 (m, 2H), 2.30-2.38 (m, 1H), 2.60-2.68 (m, 1H), 2.76-2.85 (m, 1H), 2.95-3.03 (m, 2H), 3.15-3.23 (m, 1H), 4.01 (s, 3H), 7.40 (s, 1H), 7.66 (s, 1H), 7.73 (d, J=0.6 Hz, 1H), 7.88 (d, J=1.6 Hz, 1H), 8.11 (s, 1H), 10.60 (br s, NH, 1H); MS (CI) m/z 364.1 (MH$^+$).

3-(1-methyl-1H-pyrazol-4-yl)-5-((1s,4s)-4-(piperidin-1-yl)cyclohexyl)-1H-pyrrolo[2,3-b]pyridine (I-46)

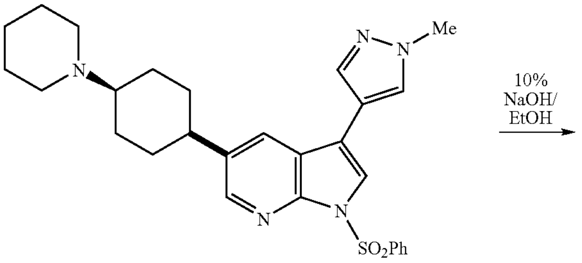

(IIb-46)

-continued

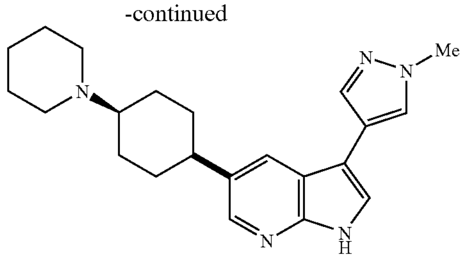

(I-46)

Compound (IIb-46) (0.20 g, 0.40 mmol) in EtOH (4.00 mL) and 10% NaOH (1.32 mL) was deprotected following the general procedure for the deprotection of 7-azaindoles. The crude product was purified by preparative LCMS (column LUNA 10μ C18(2) 00G-4253-V0 250×50 mm) using water-MeCN (0.1% AcOH) as eluent (in gradient; flow 80 mL/min) to give (I-46) (50 mg, 35%; retention time 12.0-13.5 min) as white foam. $^1$H NMR (400 MHz, $CDCl_3$) δ 1.45-1.70 (m, 4H), 1.75-1.95 (m, 7H), 2.05-2.10 (m, 2H), 2.18-2.23 (m, 1H), 2.32-2.40 (m, 1H), 2.82-2.89 (m, 2H), 2.97-3.13 (m, 3H),), 3.99 (s, 3H), 7.39 (s, 1H), 7.67 (s, 1H), 7.74 (d, J=0.6 Hz, 1H), 8.01 (d, J=1.6 Hz, 1H), 8.22 (s, 1H), 10.68 (br s, NH, 1H); MS (CI) m/z 364.1 ($MH^+$).

5-((1r,4r)-4-(3,3-difluoropyrrolidin-1-yl)cyclohexyl)-3-(1-methyl-1H-pyrazol-4-yl)-1H-pyrrolo[2,3-b]pyridine (I-47)

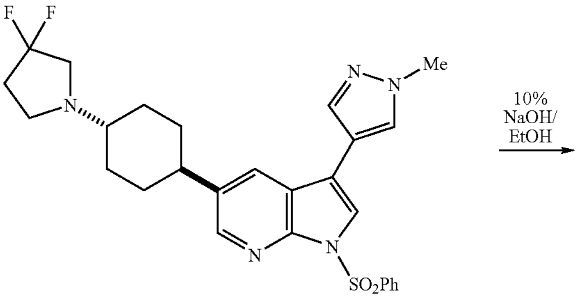

(IIb-47)

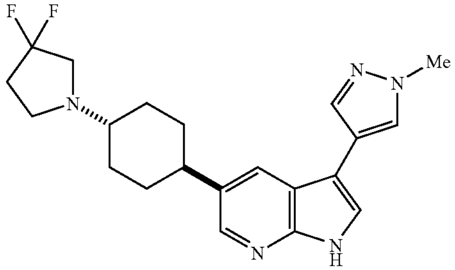

(I-47)

Compound (IIb-47) (85 mg, 0.16 mmol) in EtOH (3.24 mL) and 10% NaOH (1.62 mL) was deprotected following the general procedure for the deprotection of 7-azaindoles. The crude product was purified by PTLC using 10:1 $CH_2Cl_2$:MeOH as the eluent to give (I-47) as a white solid (33 mg, 53%), $^1$H NMR (400 MHz, $CDCl_3$) δ 1.46-1.35 (dq, J=2.9 and 12.6 Hz, 2H), 1.63-1.51 (dq, J=2.8 and 12.8 Hz, 2H), 2.03-1.95 (m, 2H), 2.11-2.04 (m, 2H), 2.34-2.17 (m, 3H), 2.64 (tt, J=3.4 and 12.1 Hz, 1H), 2.83 (t, J=7.0 Hz, 2H), 3.00 (t, J=13.5 Hz, 2H), 3.96 (s, 3H), 7.34 (s, 1H), 7.59 (s, 1H), 7.71 (d, J=0.5 Hz, 1H), 7.84 (d, J=0.6 Hz, 1H), 8.11 (d, J=2.0 Hz, 1H), 10.21 (br s, NH, 1H).

5-((1s,4s)-4-(3,3-difluoropyrrolidin-1-yl)cyclohexyl)-3-(1-methyl-1H-pyrazol-4-yl)-1H-pyrrolo[2,3-b]pyridine (I-48)

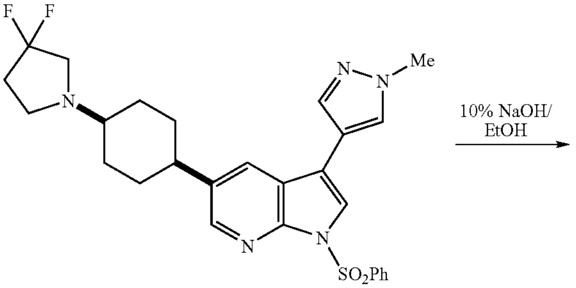

(IIb-48)

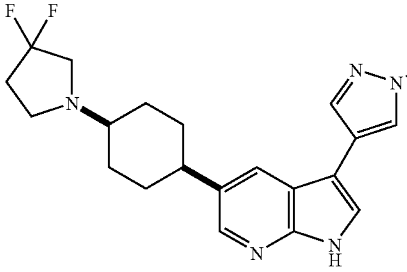

(I-48)

Compound (IIb-48) (6 mg, 0.011 mmol) in EtOH (0.5 mL) and 10% NaOH (0.1 mL) was deprotected following the general procedure for the deprotection of 7-azaindoles to afford (I-48) (3.9 mg, 89%); $^1$H NMR (400 MHz, $CDCl_3$) δ 1.72-1.56 (m, 6H), 2.02-1.92 (m, 4H), 2.38-2.26 (m, 2H), 2.43-2.38 (m, 1H), 2.73 (t, J=3.6 Hz, 1H), 2.78 (t, J=6.9 Hz, 2H), 2.97 (t, J=13.8 Hz, 2H), 4.01 (s, 3H), 7.36 (d, J=2.2 Hz, 1H), 7.64 (s, 1H), 7.77 (d, J=0.5 Hz, 1H), 7.91 (d, J=1.6 Hz, 1H), 8.25 (s, 1H), 9.03 (br s, NH, 1H).

5-((1R,4s)-4-((S)-3-fluoropyrrolidin-1-yl)cyclohexyl)-3-(1-methyl-1H-pyrazol-4-yl)-1H-pyrrolo[2,3-b]pyridine (I-49)

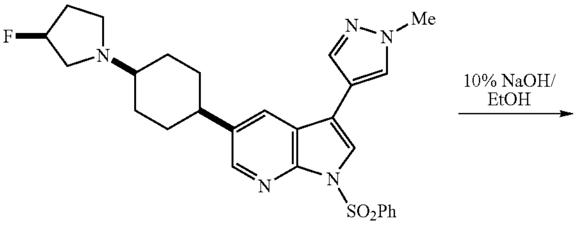

(IIb-49)

-continued

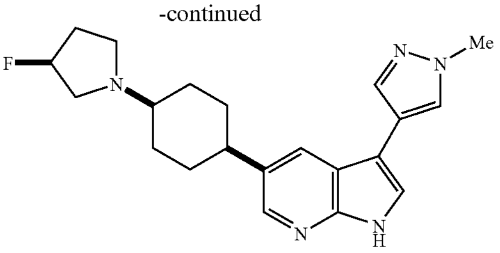

(I-49)

Compound (IIb-49) (20 mg, 0.04 mmol) in EtOH (1.0 mL) and 10% NaOH (0.5 mL) was deprotected following the general procedure for the deprotection of 7-azaindoles. The crude product was purified by PTLC using 5:1 $CH_2Cl_2$:MeOH as the eluent to give (I-49) as a white solid (8.9 mg, 61%), $^1$H NMR (400 MHz, $CDCl_3$) δ 1.72-1.57 (m, 4H), 2.15-1.95 (m, 6H), 2.40-2.35 (m, 1H), 2.56-2.48 (m, 1H), 2.96-2.72 (m, 4H), 4.00 (s, 3H), 5.24 (td, J=5.7 and 55.7 Hz, 1H), 7.37 (d, J=2.2 Hz, 1H), 7.65 (s, 1H), 7.77 (s, 1H), 7.93 (s, 1H), 8.26 (d, J=1.6 Hz, 1H), 9.48 (br s, NH, 1H).

5-((1S,4r)-4-((S)-3-fluoropyrrolidin-1-yl)cyclohexyl)-3-(1-methyl-1H-pyrazol-4-yl)-1H-pyrrolo[2,3-b]pyridine (I-50)

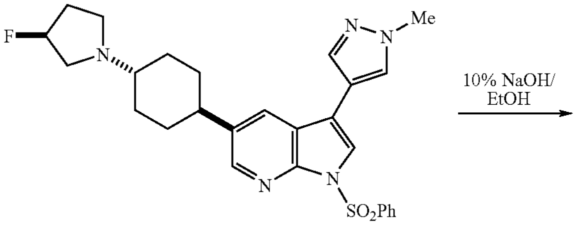

(IIb-50)

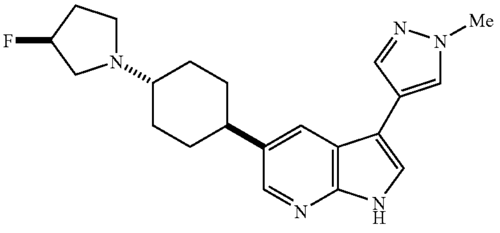

(I-50)

Compound (IIb-50) (75 mg, 0.16 mmol) in EtOH (3.0 mL) and 10% NaOH (1.00 mL) was deprotected following the general procedure for the deprotection of 7-azaindoles. The crude product was purified by PTLC using 5:1 $CH_2Cl_2$:MeOH as the eluent to give (I-50) as a white solid (30 mg, 55%), $^1$H NMR (400 MHz, $CDCl_3$) δ 1.53-1.43 (m, 2H), 1.65-1.54 (dq, J=2.2 and 12.6 Hz, 2H), 2.03-1.96 (m, 2H), 2.28-2.04 (m, 5H), 2.52-2.46 (m, 1H), 2.65-2.55 (m, 1H), 2.66 (tt, J=3.4 and 12.0 Hz, 1H), 3.07-2.80 (m, 3H), 3.97 (s, 3H), 5.22 (td, J=5.4 and 55.1 Hz, 1H), 7.35 (s, 1H), 7.60(s, 1H), 7.72 (d, J=0.6 Hz, 1H), 7.85 (d, J=2.0 Hz, 1H), 8.14 (d, J=2.0 Hz, 1H), 10.21 (br s, NH, 1H).

3-(1-methyl-1H-pyrazol-4-yl)-5-(1,4-dioxaspiro[4.4]non-6-en-7-yl)-1H-pyrrolo[2,3-b]pyridine (I-51)

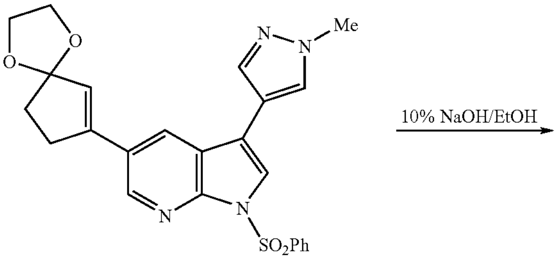

(IIa-51)

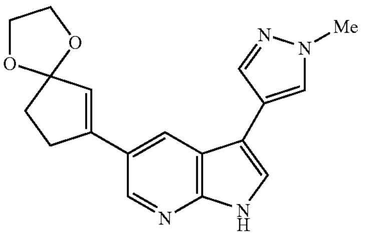

(I-51)

Compound (IIa-51) (40 mg, 0.086 mmol) was deprotected following the general procedure for the deprotection of 7-azaindoles. The crude product was purified by PTLC using 10:1 $CH_2Cl_2$:MeOH as the eluent to give (I-51) as a yellow solid (13 mg, 47%), $^1$H NMR (400 MHz, $CDCl_3$) δ 1.87-1.76 (m, 1H), 2.62-2.45 (m, 3H), 3.99-3.92 (m, 3H), 4.00 (s, 3H), 4.11-4.05 (m, 1H), 4.67-4.65 (m, 1H), 7.40 (d, J=1.5 Hz, 1H), 7.63 (s, 1H), 7.77 (s, 1H), 7.90 (d, J=1.8 Hz, 1H), 8.25 (d, J=1.7 Hz, 1H), 10.05 (br s, 1H).

N,N-diethyl-4-(3-(1-methyl-1H-pyrazol-4-yl)-1H-pyrrolo[2,3-b]pyridin-5-yl)cyclohexanamine (I-52)

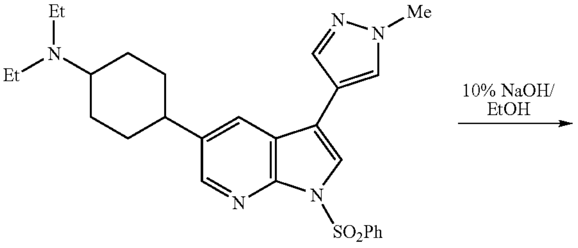

(IIb-52)

-continued

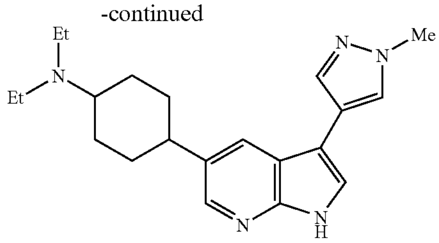

(I-52)

Compound (IIb-52) (61 mg, 0.12 mmol) in EtOH (2.44 mL) and 10% NaOH (1.12 mL) was deprotected following the general procedure for the deprotection of 7-azaindoles. The crude product was purified by LCMS (column LUNA 10μ C18(2) 00G-4253-V0 250×50 mm) using water-MeCN (0.1% AcOH) as eluent (in gradient; flow 80 mL/min) to give a (I-52) (26 mg, 59%; retention time 7.8-8.7 min) as a colourless oil, a 2.5:1 mixture of trans: cis isomers. $^1$H NMR (400 MHz, $CDCl_3$) δ 1.17 (t, J=7.2 Hz, 6H), 1.29 (t, J=7.2 Hz, 6H), 1.76-1.60 (m, 5H), 1.92-1.76 (m, 4H), 2.12-2.05 (m, 2H), 2.25-2.16 (m, 2H), 2.38-2.27 (m, 1H), 2.73-2.63 (m, 1H), 2.09 (q, J=7.2 Hz, 4H), 3.02 (q, J=7.2 Hz, 4H), 3.13-3.07 (m, 1H), 3.26-3.16 (m, 1H), 4.00 (s, 3H), 4.01 (s, 3H), 7.39 (s, 2H), 7.64 (s, 1H), 7.70 (s, 1H), 7.74 (s, 1H), 7.75 (s,1H), 7.78 (d, J=1.8 Hz, 1H), 8.02 (s, 1H), 8.12 (d, J=1.8 Hz, 1H), 8.24 (d, J=1.6 Hz, 1H), 10.52 (br s, NH, 1H) 10.57 (br s, NH, 1H), MS (CI) m/z 352.1 (MH$^+$).

5-((1S,4s)-4-((R)-3-fluoropyrrolidin-1-yl)cyclohexyl)-3-(1-methyl-1H-pyrazol-4-yl)-1H-pyrrolo[2,3-b]pyridine (I-53)

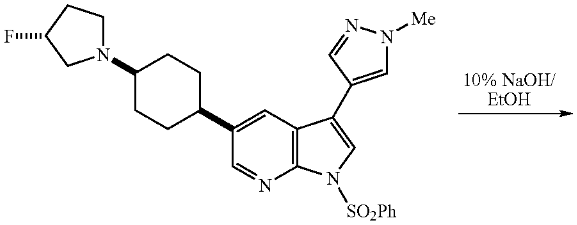

(IIb-53)

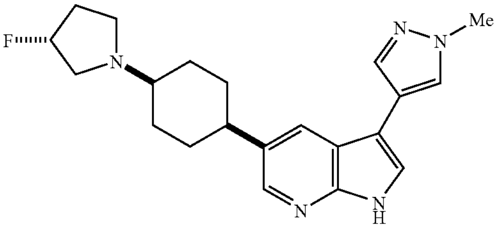

(I-53)

Compound (IIb-53) (40 mg, 0.08 mmol) in EtOH (1.5 mL) and 10% NaOH (0.78 mL) was deprotected following the general procedure for the deprotection of 7-azaindoles. The crude product was purified by PTLC using 5:1 $CH_2Cl_2$: MeOH as the eluent to give (I-53) as a white solid (9 mg, 31%), $^1$H NMR (400 MHz, $CDCl_3$) δ 1.72-1.52 (m, 5H), 2.20-1.95 (m, 6H), 2.40-2.35 (m, 1H), 2.55-2.49 (m, 1H), 2.95-2.72 (m, 3H), 4.00 (s, 3H), 5.23 (td, J=5.5 and 56.2 Hz, 1H), 7.34 (d, J=2.4 Hz, 1H), 7.65 (s, 1H), 7.77 (d, J=0.5 Hz, 1H), 7.92 (d, J=1.80 Hz, 1H), 8.26 (d, J=2.0 Hz, 1H), 8.81 (br s, NH, 1H).

5-((1R,4r)-4-((R)-3-fluoropyrrolidin-1-yl)cyclohexyl)-3-(1-methyl-1H-pyrazol-4-yl)-1H-pyrrolo[2,3-b]pyridine (I-54)

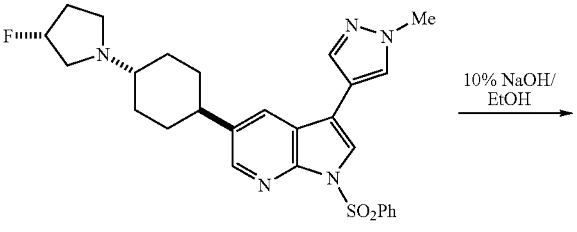

(IIb-54)

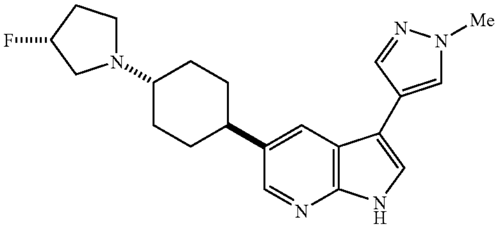

(I-54)

Compound (IIb-54) (60 mg, 0.12 mmol) in EtOH (2.36 mL) and 10% NaOH (1.18 mL) was deprotected following the general procedure for the deprotection of 7-azaindoles. The crude product was purified by PTLC using 5:1 $CH_2Cl_2$: MeOH as the eluent to give (I-54) as a white solid (18 mg, 41%), $^1$H NMR (400 MHz, $CDCl_3$) δ 1.58-1.43 (m, 2H), 1.70-1.59 (dq, J=2.4 and 12.8 Hz, 2H), 2.32-2.00 (m, 7H), 2.68-2.60 (m, 1H), 2.66 (tt, J=3.1 and 12.0 Hz, 1H), 3.10-2.92 (m, 3H), 4.00 (s, 3H), 5.23 (td, J=5.5 and 55.3 Hz, 1H), 7.40 (d, J=2.2 Hz, 1H), 7.63 (s, 1H), 7.76 (d, J=0.5 Hz, 1H), 7.88 (d, J=2.0 Hz, 1H), 8.25 (d, J=2.0 Hz, 1H), 10.21 (br s, NH, 1H).

Ethyl-{4-[3-(1-methyl-1H-pyrazol-4-yl)-1H-pyrrolo[2,3-b]pyridin-5-yl]-cyclohexyl}-amine (I-55)

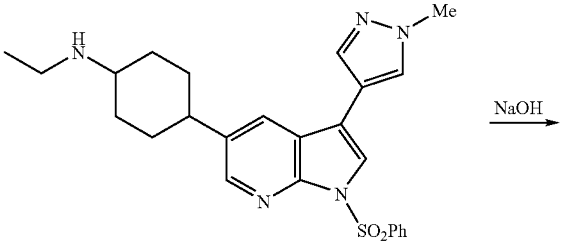

(IIb-55)

-continued

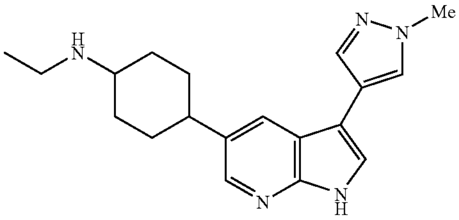

(I-55)

Compound (IIb-55) (66 mg, 0.14 mmol) in EtOH (1.42 mL) and 10% NaOH (1.42 mL) was deprotected following the general procedure for the deprotection of 7-azaindoles. The crude product was purified by LCMS (column LUNA 10μ C18(2) 00G-4253-V0 250×50 mm) using water-MeCN (0.1% AcOH) as eluent (in gradient; flow 80 mL/min) to give a (I-55) (29 mg, 63%; retention time 18.5-19.2 min) as a white foam, a 5.2:1 mixture of trans: cis isomers. $^1$H NMR (400 MHz, $CDCl_3$) δ 1.34 (t, J=7.2 Hz, 3H, major), 1.33 (t, J=7.2 Hz, 3H, minor), 1.54-1.77 (m, 4H, major), 1.82-1.90 (m, 4H, minor), 2.00-2.04 (m, 2H, major), 2.01-2.04 (m, 2H, minor), 2.12-2.21 (m, 2H, minor), 2.25-2.33 (m, 2H, major), 2.65-2.71 (m, 1H, major), 2.76-2.84 (m, 1H, minor), 3.02 (q, J=7.2 Hz, 4H, major and minor), 3.00-3.04 (m, 1H, major), 3.30-3.35 (m, 1H, minor), 3.96 (s, 3H, minor), 3.99 (s, 3H, major), 7.39 (s, 1H, minor), 7.41 (s, 1H, major), 7.61 (s, 1H, major), 7.66 (s, 1H, minor), 7.73 (d, J=0.5 Hz, 1H, minor), 7.74 (d, J=0.6 Hz, 1H, major), 7.86 (d, J=1.8 Hz, 1H, major), 8.02 (s, 1H, minor), 8.07 (s, 1H, major), 8.20 (s 1H, minor), 10.78 (br s, NH 1H, major), 10.98 (br s, NH 1H, minor), MS (CI) m/z 324.1 (MH$^+$).

N,N-dimethyl-4-(3-(1-(2-morpholinoethyl)-1H-pyrazol-4-yl)-1H-pyrrolo[2,3-b]pyridin-5-yl)cyclohexanamine (I-56), (1s,4s)-N,N-dimethyl-4-(3-(1-(2-morpholinoethyl)-1H-pyrazol-4-yl)-1H-pyrrolo[2,3-b]pyridin-5-yl)cyclohexanamine (I-59) and (1r,4r)-N,N-dimethyl-4-(3-(1-(2-morpholinoethyl)-1H-pyrazol-4-yl)-1H-pyrrolo[2,3-b]pyridin-5-yl)cyclohexanamine (I-60)

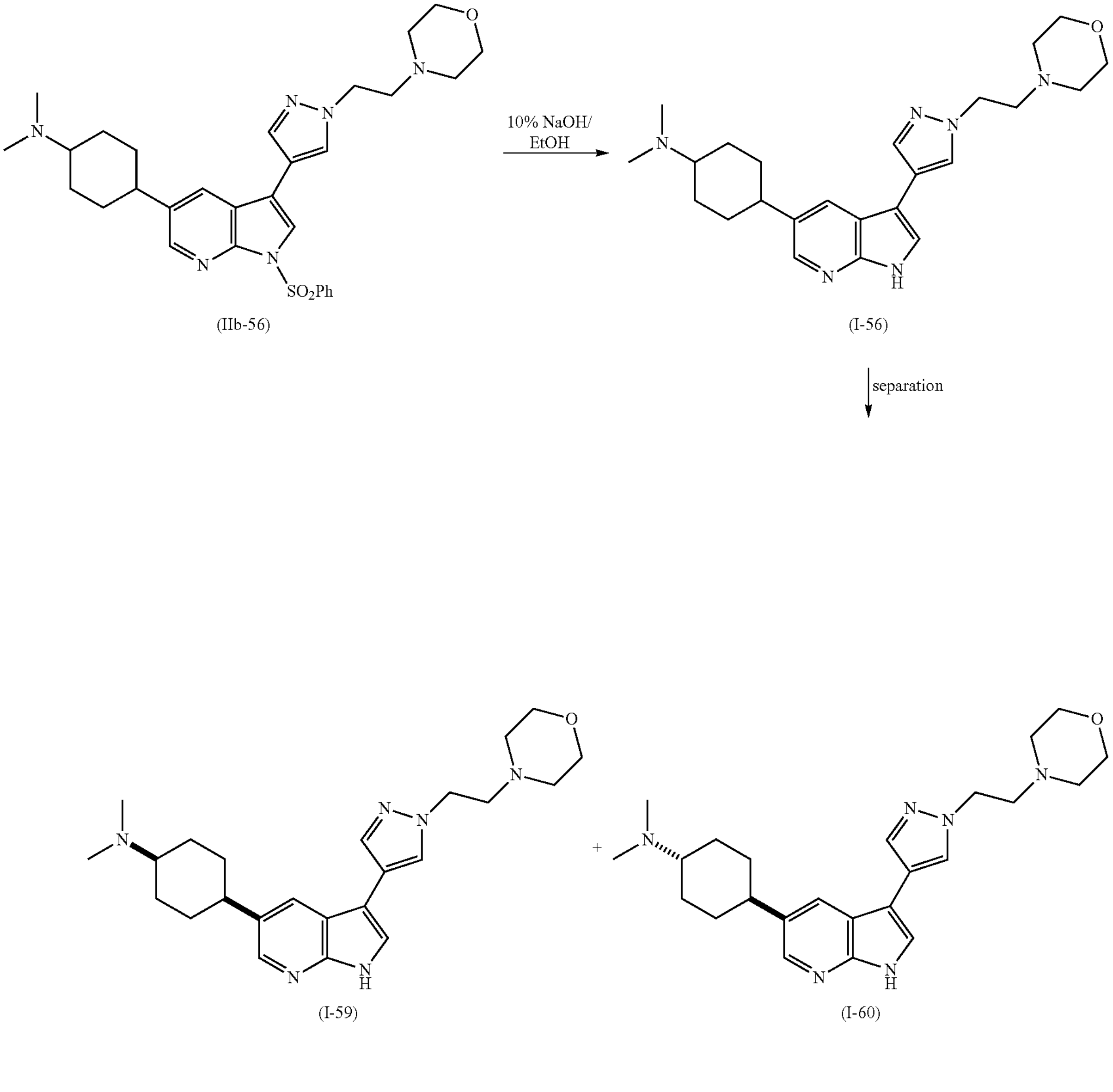

(IIb-56)

(I-56)

(I-59)

(I-60)

Compound (IIb-56) (0.25 g, 0.44 mmol) in EtOH (4.39 mL) and 10% NaOH (1.46 mL) was deprotected following the general procedure for the deprotection of 7-azaindoles. The mixture was allowed to cool down to RT, treated with water (10 mL) and extracted with EtOAc (4×10 mL). The combined organic extracts were dried over $MgSO_4$ and concentrated. The crude product was purified by LCMS (column LUNA 10μ C18(2) 00G-4253-V0 250×50 mm) using water-MeCN (0.1% AcOH) as eluent (in gradient; flow 80 mL/min) to give a (I-56) (0.10 g, 54%; retention time 20.5-22 min) as a yellow oil, a 1.75:1 mixture of isomers. This mixture was further separated by PTLC using 83:15:2 $CHCl_3$:MeOH:$NH_4OH$ as the eluent to give the trans isomer (I-60) and the cis isomer (I-59) as yellow solids.

Data for cis isomer (I-59): $^1H$ NMR (400 MHz, $CDCl_3$) δ 1.84-1.56 (m, 4H), 2.16-2.01 (m, 5H), 2.35 (br s, 6H), 2.55 (t, J=4.6 Hz, 4H), 2.82 (tt, J=3.6 and 11.0 Hz, 1H), 2.92 (t, J=6.7 Hz, 2H), 3.74 (t, J=4.6 Hz, 4H), 4.36 (t, J=6.7 Hz, 2H), 7.38 (d, J=2.2 Hz, 1H), 7.77 (d, J=0.5 Hz, 1H), 7.83(br s, 1H), 8.00 (br s, 1H), 8.27 (d, J=1.4 Hz, 1H), 9.25 (br s, NH 1H), MS (CI) m/z 423.1 ($MH^+$).

Data for trans isomer (I-60): $^1H$ NMR (400 MHz, $CDCl_3$) δ 1.57-1.46 (dq, J=2.2, 12.4 Hz, 2H), 1.70-1.58 (dq, J=2.3, 12.4 Hz, 2H), 2.20-2.05 (m, 5H), 2.44 (s, 6H), 2.54 (t, J=4.6 Hz, 4H), 2.68 (tt, J=3.4 and 12.1 Hz, 1H), 2.90 (t, J=6.6 Hz, 2H), 3.74 (t, J=4.6 Hz, 4H), 4.34 (t, J=6.6 Hz, 2H), 7.37 (d, J=2.3 Hz, 1H), 7.74 (d, J=0.5 Hz, 1H), 7.77 (d, J=0.6 Hz, 1H), 7.87 (d, J=1.9 Hz, 1H), 8.23 (d, J=2.0 Hz, 1H), 8.97 (br s, NH 1H), MS (CI) m/z 423.1 ($MH^+$).

4-(2-(4-(5-((1r,4r)-4-morpholinocyclohexyl)-1H-pyrrolo[2,3-b]pyridin-3-yl)-1H-pyrazol-1-yl)ethyl)morpholine (I-57)

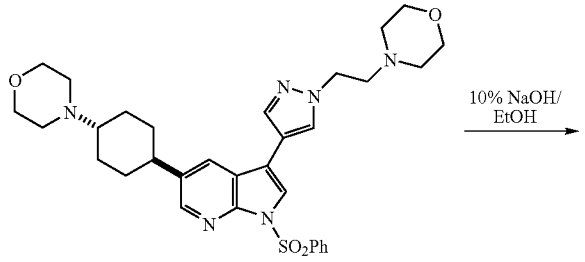

(IIb-57)

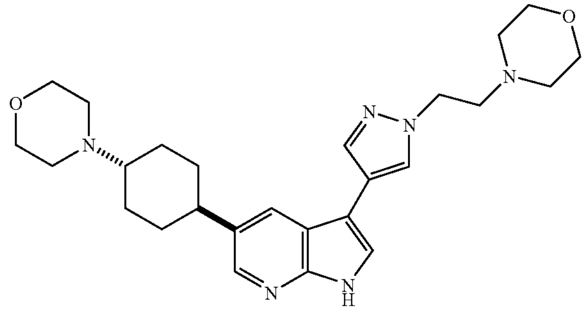

(I-57)

Compound (IIb-57) (0.10 g, 0.17 mmol) in EtOH (4.0 mL) and 10% NaOH (2.0 mL) was deprotected following the general procedure for the deprotection of 7-azaindoles. The product was isolated by PTLC using 10:1 $CH_2Cl_2$:MeOH as the eluent to give (I-57) (47 mg, 60%), $^1H$ NMR (400 MHz, $CDCl_3$) δ 1.53-1.43 (dq, J=2.2, 12.0 Hz, 2H), 1.68-1.57 (dq, J=2.2, 12.5 Hz, 2H), 2.10 (t, J=13.8 Hz, 4H), 2.63 (tt, J=3.2 and 11.3 Hz, 1H), 2.54 (t, J=4.6 Hz, 4H), 2.65 (t, J=4.6 Hz, 4H), 2.70 (t, J=3.3 Hz, 1H), 2.89 (t, J=6.7 Hz, 2H), 3.73 (t, J=4.6 Hz, 4H), 3.77 (t, J=4.6 Hz, 4H), 4.34 (t, J=6.6 Hz, 2H), 7.41 (d, J=2.1 Hz, 1H), 7.75 (s, 1H), 7.77 (d, J=0.6 Hz, 1H), 7.89 (d, J=1.9 Hz, 1H), 8.25 (d, J=2.0 Hz, 1H), 10.31 (br s, NH 1H).

4-(2-(4-(5-((1s,4s)-4-morpholinocyclohexyl)-1H-pyrrolo[2,3-b]pyridin-3-yl)-1H-pyrazol-1-yl)ethyl)morpholine (I-58)

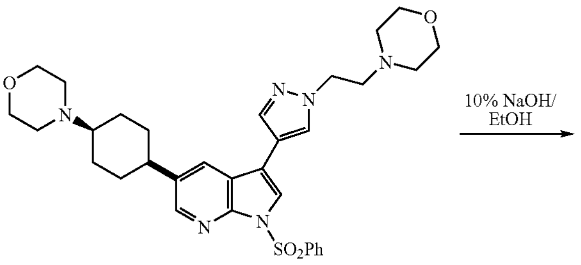

(IIb-58)

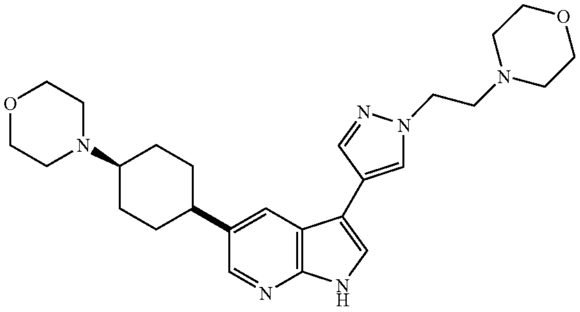

(I-58)

Compound (IIb-58) (0.06 g, 0.10 mmol) in EtOH (2.04 mL) and 10% NaOH (1.02 mL) was deprotected following the general procedure for the deprotection of 7-azaindoles. The product was isolated by PTLC using 10:1 $CH_2Cl_2$:MeOH as the eluent to give (I-58) (20 mg, 43%); $^1H$ NMR (400 MHz, $CDCl_3$) δ 1.65-1.55 (m, 2H), 1.74-1.66 (m, 2H), 2.10-1.98 (m, 4H), 2.54 (t, J=4.6 Hz, 7H), 2.87-2.81 (m,1H), 2.91 (t, J=6.6 Hz, 2H), 2.89 (t, J=6.7 Hz, 2H), 3.73 (t, J=4.6 Hz, 4H), 3.81-3.75 (br s, 4H), 4.34 (t, J=6.7 Hz, 2H), 7.39 (d, J=2.1 Hz, 1H), 7.76 (br s, 1H), 7.79 (s, 1H), 7.95 (br s, 1H), 8.29 (d, J=2.0 Hz, 1H), 9.64 (br s, NH, 1H).

(1s,4s)-N,N-dimethyl-4-(3-(1-(2-morpholinoethyl)-1H-pyrazol-4-yl)-1H-pyrrolo[2,3-b]pyridin-5-yl) cyclohexanamine (I-59)—see the synthesis of (I-56)

(1r,4r)-N,N-dimethyl-4-(3-(1-(2-morpholinoethyl)-1H-pyrazol-4-yl)-1H-pyrrolo[2,3-b]pyridin-5-yl) cyclohexanamine (I-60)—see the synthesis of (I-56)

5-Cyclopent-1-enyl-3-[1-(2-morpholin-4-yl-ethyl)-1H-pyrazol-4-yl]-1H-pyrrolo[2,3-b]pyridine (I-62)

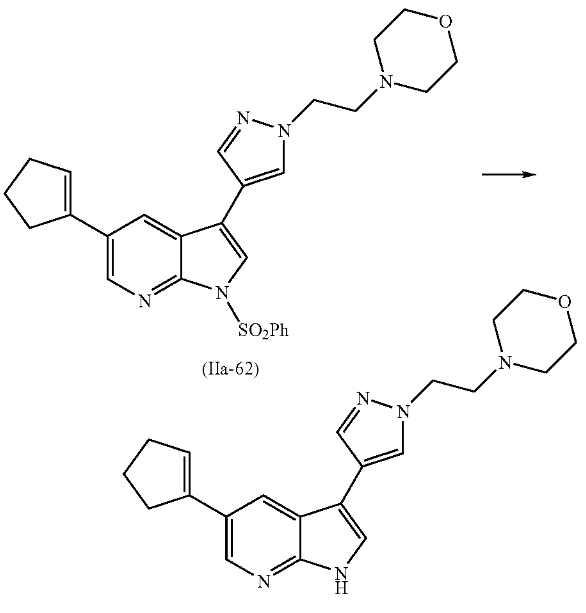

(IIa-62)

(I-62)

Compound (IIa-62) (25 mg, 50 μmol) in EtOH (1.0 mL) and 10% NaOH (0.5 mL) was deprotected following the general procedure for the deprotection of 7-azaindoles to afford (I-62) (17 mg, 47 μmol, 94%) as a white powder, which did not require further purification. $^1$H NMR (400 MHz, $CDCl_3$) δ 2.01 (pentet, J=7.5 Hz, 2H), 2.42-2.56 (m, 6H), 2.71-2.79 (m, 2H), 2.82 (t, J=6.7 Hz, 2H), 3.66 (t, J=6.7 Hz, 4H), 4.26 (t, J=6.7 Hz, 2H) 6.14-6.17 (m, 3H), 7.32 (d, J=2.2 Hz, 1H), 7.68 (s, 1H), 7.71 (s, 1H), 7.97 (d, J=1.7 Hz, 1H), 8.45 (d, J=1.7 Hz, 1H), 9.79 (br s, 1H).

5-(1-methoxycyclopentyl)-3-(1-methyl-1H-pyrazol-4-yl)-1H-pyrrolo[2,3-b]pyridine (I-63)

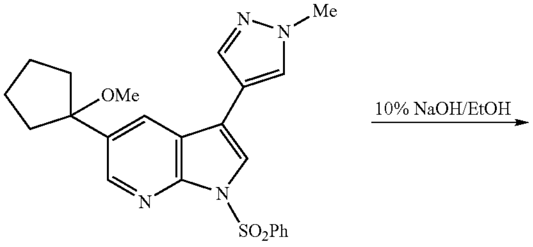

(IIb-63)

-continued

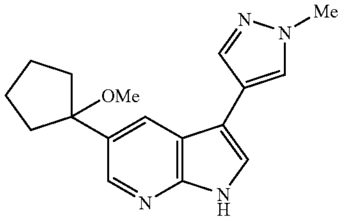

(I-63)

Compound (IIb-63) (32 mg, 0.073 mmol) was deprotected following the general procedure for the deprotection of 7-azaindoles. The crude product was purified by PTLC using EtOAc as the eluent to give (I-63) as a white solid (9.9 mg, 45%), $^1$H NMR (400 MHz, $CDCl_3$) δ 1.86-1.78 (m, 2H), 2.02-1.90 (m, 4H), 2.36-2.27 (m, 2H), 3.00 (s, 3H), 4.01 (s, 3H), 7.44 (d, J=2.1 Hz, 1H), 7.66 (s, 1H), 7.77 (d, J=0.5 Hz, 1H), 8.10 (d, J=1.9 Hz, 1H), 8.46 (d, J=2.0 Hz, 1H), 9.80 (br s, NH, 1H).

5-Cyclopentyl-3-[1-(2-morpholin-4-yl-ethyl)-1H-pyrazol-4-yl]-1H-pyrrolo[2,3-b]pyridine (I-64)

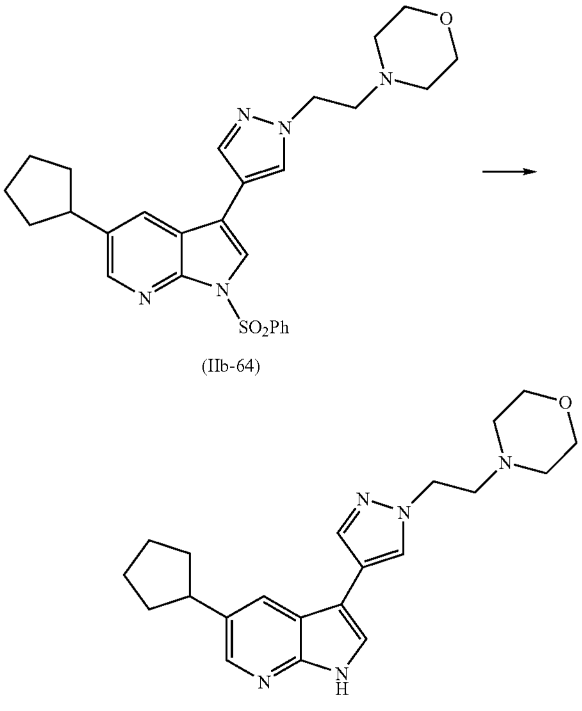

(IIb-64)

(I-64)

Compound (IIb-64) (100 mg, 0.20 mmol) in EtOH (4 mL) and 10% aqueous NaOH (2 mL) was deprotected following the general procedure for the deprotection of 7-azaindoles. The crude product as foam (67 mg) was triturated with $Et_2O$ (5 mL) to afford (I-64) (44 mg, 61%) as a pale yellow powder. $^1$H NMR (400 MHz, $CDCl_3$) δ 1.63-1.83 (m, 4H), 1.84-1.95 (m, 2H), 2.14-2.23 (m, 2H), 2.55 (t, J=4.7 Hz, 4H), 2.91 (d, J=6.6 Hz, 2H), 3.17 (tt, J=7.4, 9.1 Hz, 1H), 3.75 (d, J=4.7 Hz, 4H), 4.35 (d, J=6.7 Hz, 2H), 7.36 (d, J=2.4 Hz, 1H), 7.76 (s, 1H), 7.78 (s, 1H), 7.92 (d, J=1.8 Hz, 1H), 8.28 (d, J=2.0 Hz, 1H), 8.54 (br s, 1H).

5-((1r,4r)-4-(4-methylpiperazin-1-yl)cyclohexyl)-3-(1-(trifluoromethyl)-1H-pyrazol-4-yl)-1H-pyrrolo[2,3-b]pyridine (I-66)

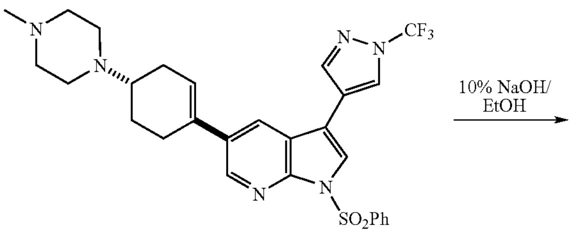

(IIb-66)

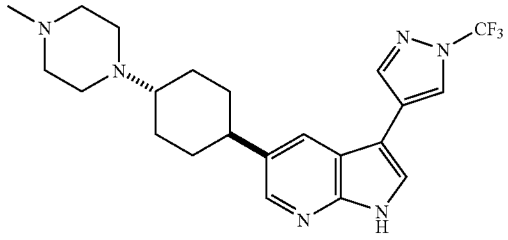

(I-66)

Compound (IIb-66) (30 mg, 0.052 mmol) in EtOH (1.0 mL) and 10% NaOH (0.5 mL) was deprotected following the general procedure for the deprotection of 7-azaindoles. The crude product was purified by PTLC using 5:1 $CH_2Cl_2$:MeOH as the eluent to give (I-66) as a white solid (10 mg, 47%), $^1$H NMR (400 MHz, $CDCl_3$) δ 1.58-1.45 (dq, J=2.4 and 11.3 Hz, 2H), 1.69-1.58 (dq, J=1.8 and 12.8 Hz, 2H), 2.17-2.03 (m, 5H), 2.36 (s, 3H), 2.81-2.44 (m, 9H), 7.48 (s, 1H), 7.85 (d, J=1.9 Hz, 1H), 8.03 (s, 1H), 8.04 (d, J=1.0 Hz, 1H), 8.26 (d, J=2.0 Hz, 1H), 9.97 (br s, NH, 1H).

5-((1s,4s)-4-(4-methylpiperazin-1-yl)cyclohexyl)-3-(1-(trifluoromethyl)-1H-pyrazol-4-yl)-1H-pyrrolo[2,3-b]pyridine (I-67)

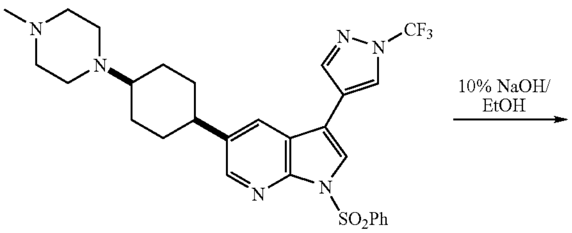

(IIb-67)

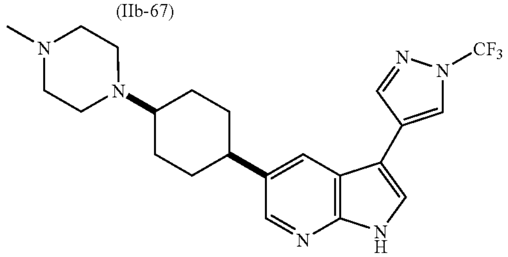

(I-67)

Compound (IIb-67) (18 mg, 0.031 mmol) in EtOH (1.0 mL) and 10% NaOH (0.5 mL) was deprotected following the general procedure for the deprotection of 7-azaindoles. The crude product (I-67) (9.9 mg, 73%) did not require purification, $^1$H NMR (400 MHz, $CDCl_3$) δ 1.74-1.56 (m, 4H), 2.10-1.98 (m, 5H), 2.35-2.32 (m, 1H), 2.35 (s, 3H), 2.72-2.46 (br m, 7H), 2.91-2.83 (m 1H), 7.51 (s, 1H), 7.92 (d, J=2.0 Hz, 1H), 8.05 (s, 1H), 8.06 (s, 1H), 8.33 (d, J=2.0 Hz, 1H), 10.21 (br s, NH, 1H).

Mixture of 3-(1-methyl-1H-pyrazol-4-yl)-5-(3,5,5-trimethylcyclohex-1-enyl)-1H-pyrrolo[2,3-b]pyridine and 3-(1-methyl-1H-pyrazol-4-yl)-5-(3,3,5-trimethylcyclohex-1-enyl)-1H-pyrrolo[2,3-b]pyridine (I-68)

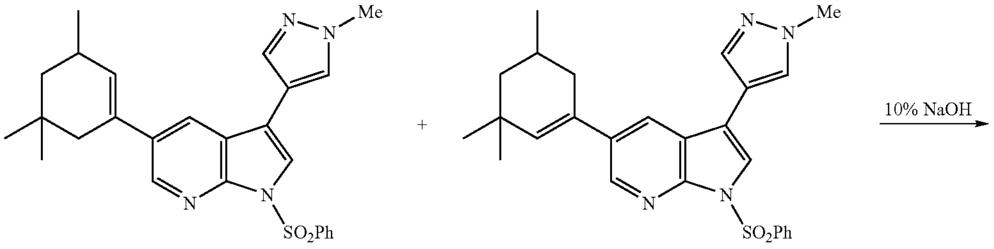

(IIa-68)

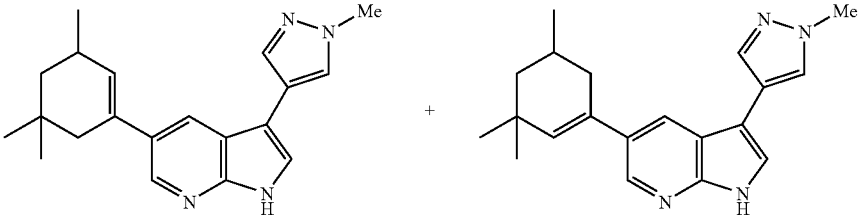

(I-68)

Mixture (IIa-68) (35 mg, 0.076 mmol) was deprotected following the general procedure for the deprotection of 7-azaindoles. The crude product was purified by PTLC using EtOAc as the eluent to give (I-68) as a white solid (14 mg, 57%).

(1r,4r)-N,N-dimethyl-4-(3-(1-methyl-1H-pyrazol-4-yl)-1H-pyrrolo[2,3-b]pyridin-5-yl)cyclohexanamine (I-71) and (1s,4s)-N,N-dimethyl-4-(3-(1-methyl-1H-pyrazol-4-yl)-1H-pyrrolo[2,3-b]pyridin-5-yl)cyclohexanamine (I-72)

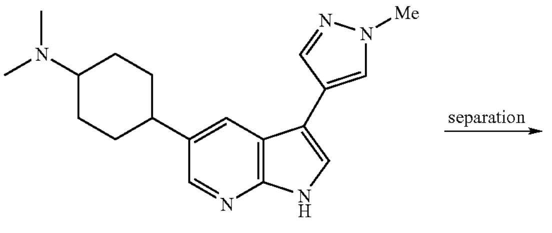

(I-9)

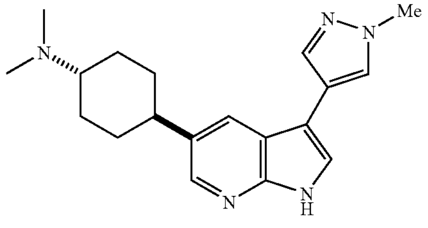

(I-71)

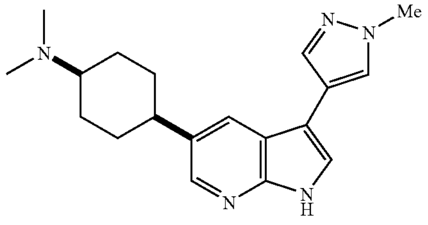

(I-72)

Mixture (I-9) (89 mg) was separated by PTLC using 92:6:1 $CHCl_3$:MeOH:$NH_4OH$ as the eluent to give the trans isomer (I-71) (32 mg, 36%) as a white solid and the cis isomer (I-72) (26 mg, 29%) as a white solid. Data for trans compound (I-71): $^1$H NMR (400 MHz, $CDCl_3$) δ 1.53-1.41 (dq, J=2.5 and 12 Hz, 2H), 1.70-1.57 (dq, J=2.2 and 12.6 Hz, 2H), 2.14-2.03 (m, 4H), 2.38 (s, 6H), 2.45-2.35 (m, 1H), 2.71-2.62 (tt, J=3.2 and 12.1 Hz, 1H), 4.00 (s, 3H), 7.40 (d, J=1.1 Hz, 1H), 7.63 (s, 1H), 7.76 (d, J=0.6 Hz, 1H), 7.88 (d, J=2.0 Hz, 1H), 8.24 (d, J=2.0 Hz, 1H), 10.24 (br s, NH, 1H).

Data for cis compound (I-72): $^1$H NMR (400 MHz, $CDCl_3$) δ 1.65-1.55 (m, 2H), 1.76-1.67 (m, 2H), 2.13-1.96 (m, 4H), 2.21-2.16 (m, 1H), 2.31 (s, 6H), 2.86-2.77 (tt, J=3.6 and 10.9 Hz, 1H), 4.01 (s, 3H), 7.39 (d, J=1.9 Hz, 1H), 7.69 (s, 1H), 7.77 (d, J=0.6 Hz, 1H), 7.98 (s, 1H), 8.29 (d, J=2.0 Hz, 1H), 10.22 (br s, NH, 1H).

3-(1-Methyl-1H-pyrazol-4-yl)-5-(4-morpholin-4-ylmethyl-cyclohexyl)-1H-pyrrolo[2,3-b]pyridine (I-73)

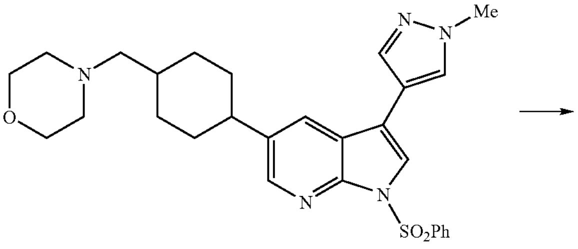

(IIb-73)

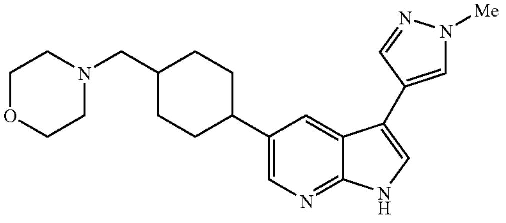

(I-73)

The mixture of diastereomeric amines (IIb-73) (81 mg, 156 μmol) in EtOH (2.0 mL) and 10% NaOH (1 mL) was deprotected following the general procedure for the deprotection of 7-azaindoles. The crude product was not purified further and afforded (I-73) (58 mg, 98%) as a pale yellow powder; 3:2 diastereomeric mixture; $^1$H NMR (400 MHz, $CDCl_3$) δ 0.98-1.13 (m, 1.2H), 1.41-1.76 (m, 4.2H), 1.90 (br d, J=11.3 Hz, 2.4H), 2.15 (d, J=7.1 Hz, 1.2H), 2.40-2.49 (m, 4.8H), 2.53-2.75 (m, 1H), 3.67 (t, J=4.6 Hz, 4H), 3.91 (s, 1.8H), 3.92 (s, 1.2H), 7.28 (s, 0.4H), 7.29 (s, 0.6H), 7.55 (s, 1H), 7.67 (s, 0.6H), 7.68 (s, 0.4H), 7.81 (d, J=2.0 Hz, 0.6H), 7.81 (d, J=2.0 Hz, 0.4H), 8.06 (d, J=2.0 Hz, 0.6H), 8.08 (d, J=2.0 Hz, 0.4H). MS (CI) m/z 380 ($MH^+$).

((1r,4r)-4-(3-(1-methyl-1H-pyrazol-4-yl)-1H-pyrrolo[2,3-b]pyridin-5-yl)cyclohexyl)methanol (I-74)

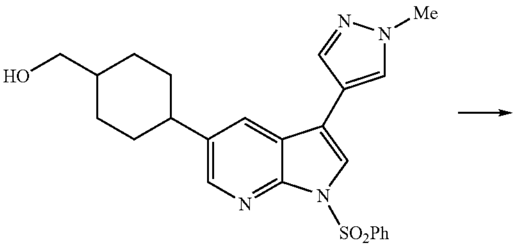

(IIb-74)

-continued

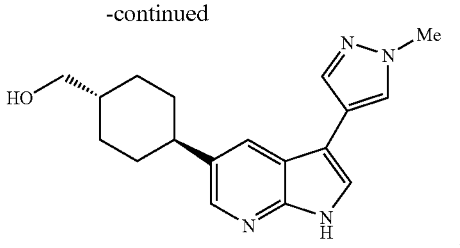

(I-74)

Compound (IIb-74) (10 mg) in EtOH (1.0 mL) and 10% NaOH (0.5 mL) was deprotected following the general procedure for the deprotection of 7-azaindoles. The crude product was purified by preparative LCMS (column LUNA 10μ C18(2) 00G-4253-V0 250×50 mm) using water-MeCN (0.1% AcOH) as eluent (in gradient; flow 80 mL/min) to afford (I-74) (1.2 mg, 3.9 μmol). $^1$H NMR (400 MHz, $CDCl_3$) δ 1.06-1.18 (m, 2H), 1.45-1.62 (m, 3H), 1.87-2.00 (m, 4H), 2.59 (tt, J=3.2, 12.1 Hz, 1H), 3.48 (d, J=6.3 Hz, 2H), 3.93 (s, 3H), 7.29 (s, 1H), 7.55 (s, 1H), 7.68 (d, J=0.6 Hz, 1H), 7.81 (d, J=1.7 Hz, 1H), 8.13 (s, 1H), 9.22 (br s, 1H). MS (CI) m/z 311 ($MH^-$).

3-(1-Methyl-1H-pyrazol-4-yl)-5-(4-morpholin-4-yl-cyclohex-1-enyl)-1H-pyrrolo[2,3-b]pyridine (I-75)

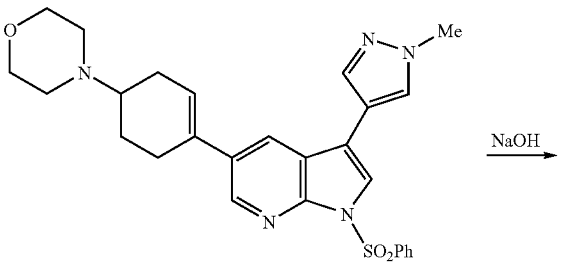

(IIa-75)

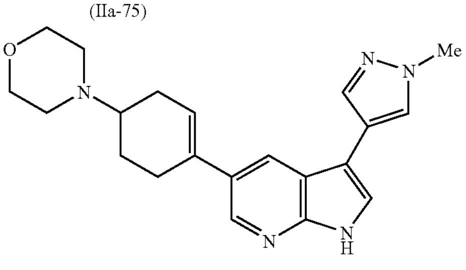

(I-75)

Compound (IIa-75) (50 mg, 0.0993 mmol) and 10% aq. NaOH (409 μL) in EtOH (819 μL) was deprotected following the general procedure for the deprotection of 7-azaindoles. After cooling the solvent was evaporated, DMF (1.5 mL) and acetic acid (77 μL) were added followed by a few drops of water to dissolve the precipitated solid. The product was isolated by preparative LCMS (column LUNA 10μ C18(2) 00G-4253-V0 250×50 mm) using water-MeCN (0.1% AcOH) as eluent (in gradient; flow 80 mL/min) to give (I-75) (25 mg, 69%) as a light orange solid; $^1$H NMR (400 MHz, $CDCl_3$+6 drops $d_4$-MeOH) δ 1.59 (dq, J=12.1, 4 Hz, 1H), 2.10-2.25 (m, 1H), 2.40-2.70 (m, 8H), 3.74 (t, J=9.2 Hz, 4H), 3.93 (s, 3H), 6.00 (m, 1H), 7.27 (s, 1H), 7.32 (s, 1H), 7.59 (s, 1H), 7.69 (s, 1H), 7.95 (d, J=1.9 Hz, 1H), 8.24 (s, 1H); m/z ($CI^+$) 364.1 ($MH^+$).

(1r,4r)-4-(3-(1-methyl-1H-pyrazol-4-yl)-1H-pyrrolo[2,3-b]pyridin-5-yl)cyclohexanecarboxylic acid (I-76) and (1s,4s)-4-(3-(1-methyl-1H-pyrazol-4-yl)-1H-pyrrolo[2,3-b]pyridin-5-yl)cyclohexanecarboxylic acid (I-77)

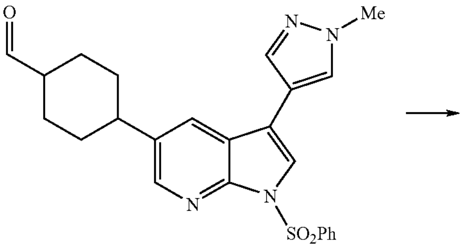

(IIb-90)

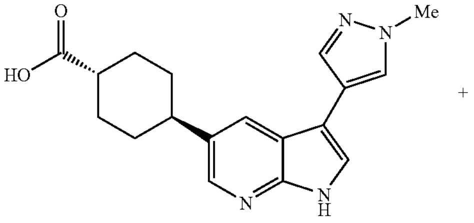

(I-76)

+

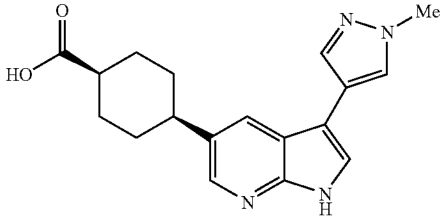

(I-77)

The mixture of diastereomeric aldehydes (IIb-90) (140 mg, 0.31 mmol) was dissolved in 1,4-dioxane (3 mL) and cooled to 0° C. Amidosulfonic acid (50 mg, 0.52 mmol) was added followed by a solution of $NaClO_2$ (35 mg, 0.387 mmol) in water (1 mL). The reaction was stirred for 2 h, diluted with water (10 mL), and extracted with EtOAc (2×25 mL). The combined organic solutions were dried over $MgSO_4$ and concentrated to afford a solid (168 mg). The crude mixture was dissolved in MeOH (5 mL), $SOCl_2$ (60 mg, 0.50 mmol) added, and the reaction allowed to stir for 16 h. The reaction mixture was then poured onto saturated aqueous $NaHCO_3$ (25 mL), and the mixture extracted with EtOAc (2×40 mL). The combined organic portions were dried over $MgSO_4$ and concentrated to afford a crude product (126 mg), which was purified by SGC using $CH_2Cl_2$ containing 10% to 30% EtOAc as eluent. Fractions containing spots at 0.50 or 0.30 in EtOAc:$CH_2Cl_2$=1:4 (v/v) were concentrated to afford a solid (30 mg). The solid was dissolved in EtOH (2 mL) and 10% aqueous NaOH (1 mL) was added. The reaction mixture was heated to reflux for 1 h, cooled, concentrated in vacuo, and purified by preparative LCMS (column LUNA 10μ C18(2) 00G-4253-V0 250×50 mm) using water-MeCN (0.1% AcOH) as eluent (in gradient; flow 80 mL/min). First to elute was trans acid (I-76) (5.1 mg, 5%). $^1$H NMR (400 MHz, DMSO-$d_6$) δ 1.59-1.78 (m, 4H), 2.00-2.09 (m, 2H), 2.13-2.22 (m, 2H), 2.39-2.49 (m, 1H), 2.70-2.79 (m, 1H), 3.99 (s, 3H), 7.54 (s, 1H), 7.81 (s, 1H), 8.00 (s, 1H), 8.05 (d, J=1.8 Hz, 1H), 8.14 (s, 1H). MS (CI) m/z 325 ($MH^+$).

Eluting shortly after was the cis acid (I-77) (1.2 mg, 1%). $^1$H NMR (400 MHz, DMSO-$d_6$) δ 1.67-1.88 (m, 6H), 2.27-2.35 (m, 2H), 2.71-2.83 (m, 2H), 3.99 (s, 3H), 7.53 (s, 1H), 7.79 (s, 1H), 7.97 (s, 1H), 7.99 (d, J=1.9 Hz, 1H), 8.11 (s, 1H). MS (CI) m/z 325 ($MH^+$).

4-((1s,4s)-4-(3-(1H-pyrazol-4-yl)-1H-pyrrolo[2,3-b]pyridin-5-yl)cyclohexyl)morpholine (I-78)

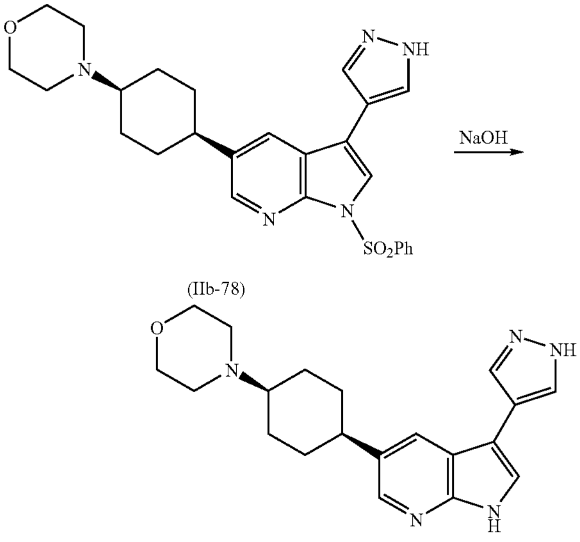

(IIb-78)

(I-78)

Compound (IIb-78) (14.00 mg, 0.028 mmol) and 10% aq. NaOH (70 μL) in EtOH (2.0 mL) was deprotected following the general procedure for the deprotection of 7-azaindoles. The product was isolated by preparative LCMS (column LUNA 10μ C18(2) 00G-4253-V0 250×50 mm) using water-MeCN (0.1% AcOH) as eluent (in gradient; flow 80 mL/min; retention time 15.27 min) to give (I-78) (5.70 mg, 58%); $^1$H NMR (400 MHz; $CDCl_3$) δ 1.44-1.64 (m, 4H), 1.87-1.90 (m, 4H), 1.93-1.95 (m, 1H), 2.14-2.21 (m, 1H), 2.36-2.46 (m, 4H), 3.60-3.70 (m, 4H), 7.28 (s, 1H), 7.71 (s, 1H), 7.83 (s, 1H), 7.87 (d, J=1.9 Hz, 1H), 8.04 (d, J=1.8 Hz, 1H). MS (CI) m/z 352 ($MH^+$).

4-((1r,4r)-4-(3-(1H-pyrazol-4-yl)-1H-pyrrolo[2,3-b]pyridin-5-yl)cyclohexyl)morpholine (I-79)

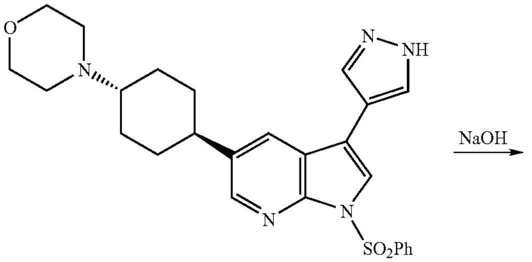

(IIb-79)

-continued

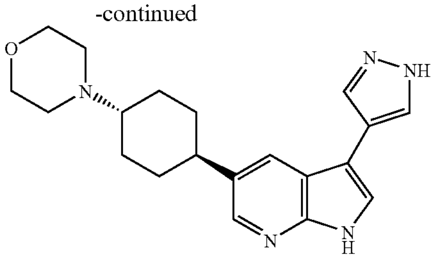

(I-79)

Compound (IIb-79) (7.46 mg, 0.0151 mmol) and 10% aq. NaOH (50 μL) in EtOH (2.0 mL) was deprotected following the general procedure for the deprotection of 7-azaindoles. Purification by PTLC using $CH_2Cl_2$:MeOH=19:1 (v/v) as eluent afforded (I-79) (2.92 mg, 55%). $^1$H NMR (400 MHz; $CDCl_3$) δ 1.38-1.56 (m, 5H), 2.09-2.14 (m, 4H), 2.60-2.66 (m, 5H), 3.73-3.78 (m, 4H), 7.38 (s, 1H), 7.84 (s, 2H), 7.88 (d, J=1.9 Hz, 1H), 8.16 (d, J=1.8 Hz, 1H), 9.59 (bs, 1H). MS (CI) m/z 352 ($MH^+$).

4-((1r,4r)-4-(3-(1-(difluoromethyl)-1H-pyrazol-4-yl)-1H-pyrrolo[2,3-b]pyridin-5-yl)cyclohexyl)morpholine (I-80)

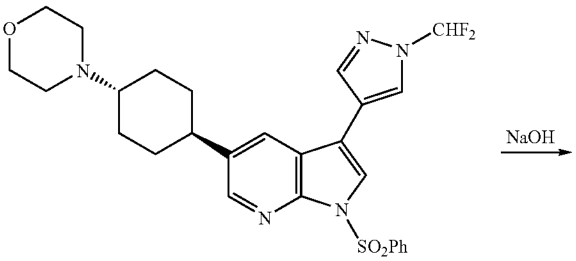

(IIb-80)

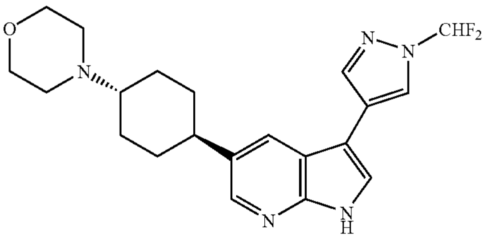

(I-80)

Compound (IIb-80) (6.0 mg, 0.011 mmol) and 10% aq. NaOH (30 μL) in EtOH (2.0 mL) was deprotected following the general procedure for the deprotection of 7-azaindoles. Purification by PTLC using $CH_2Cl_2$:MeOH=19:1 (v/v) afforded (I-80) (3.24 mg, 74%); $^1$H NMR (400 MHz; $CDCl_3$) δ 1.57-1.75 (m, 5H), 2.04-2.16 (m, 4H), 2.38 (tt, J=11.4 Hz, 3.6 Hz, 1H), 2.62-2.66 (m, 4H), 3.74-3.79 (m, 4H), 7.28 (t, J=60.7 Hz, 1H), 7.46 (d, J=2.2 Hz, 1H), 7.86 (d, J=1.9, 1H), 7.93 (d, J=0.3 Hz, 1H), 8.05 (s, 1H), 8.26 (d, J=1.9 Hz, 1H), 9.28 (bs, 1H). MS (CI) m/z (MH+).

5-((1r,4r)-4-(3-(1-methyl-1H-pyrazol-4-yl)-1H-pyrrolo[2,3-b]pyridin-5-yl)cyclohexyl)-1,5-oxazocane (I-93)

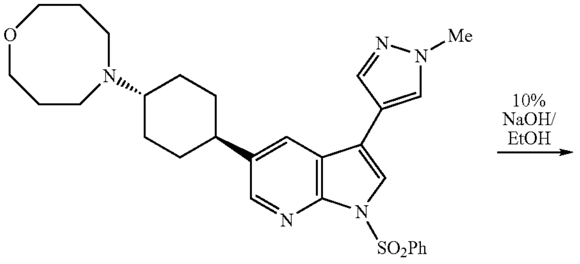

(IIb-93)

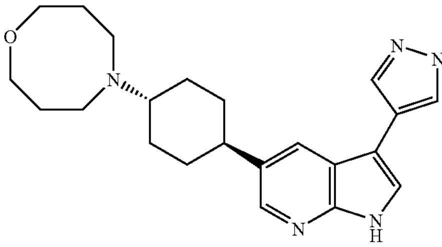

(I-93)

Trans isomer (IIb-93) was deprotected as described in the general procedure A for the deprotection of 7-azaindoles. Thus, (IIb-93) (63.4 mg, 0.11 mmol) was dissolved in ethanol (5.0 mL). 10% solution of NaOH (0.70 mL) was added and the reaction was heated to 100° C. for 50 min. It was allowed to cool down and a saturated solution of $NaHCO_3$ (15 mL) was added. The mixture was then extracted with EtOAc (25 mL). The extract was washed with $NaHCO_3$ (2×15 mL), dried over $MgSO_4$ and concentrated to afford (I-93) (23.2 mg, 49%; purity about 89%); $^1$H NMR (400 MHz; $CDCl_3$) δ 1.56-1.78 (m, 8H), 1.94-2.12 (m, 5H), 2.69-2.89 (m, 5H), 3.79 (t, J=5.2 Hz, 4H), 3.99 (s, 3H), 7.38 (d, J=2.2 Hz, 1H), 7.62 (s, 1H), 7.76 (s, 1H), 7.87 (d, J=1.6 Hz, 1H), 8.23 (d, J=1.6 Hz, 1H), 9.77 (bs, 1H).

5-((1s,4s)-4-(3-(1-methyl-1H-pyrazol-4-yl)-1H-pyrrolo[2,3-b]pyridin-5-yl)cyclohexyl)-1,5-oxazocane (I-94)

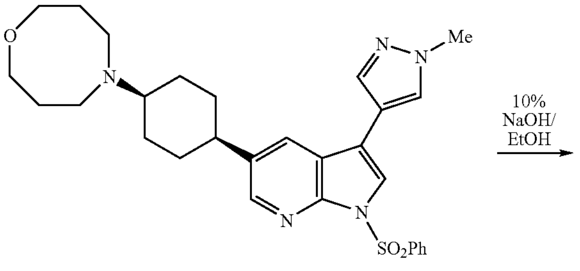

(IIb-94)

-continued

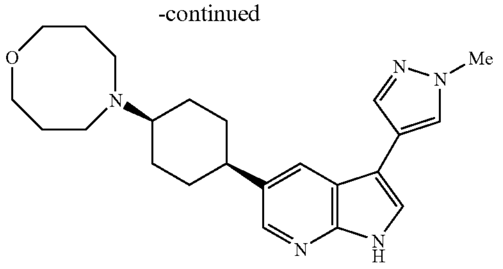

(I-94)

Cis isomer (IIb-94) was deprotected as described in the general procedure A for the deprotection of 7-azaindoles. Thus, (IIb-94) (40.3 mg, 0.08 mmol) was dissolved in ethanol (5.0 mL). 10% solution of NaOH (0.70 mL) was added and the reaction was heated to 100° C. for 40 min. It was allowed to cool down and a saturated solution of $NaHCO_3$ (15 mL) was added. The mixture was then extracted with EtOAc (25 mL). The extract was washed with $NaHCO_3$ (2×15 mL), dried over $MgSO_4$ and concentrated to afford (I-94) (24.6 mg, 83%), $^1$H NMR (400 MHz; $CDCl_3$) δ 1.65-1.79 (m, 8H), 1.94-2.07 (m, 5H), 2.67-2.82 (m, 5H), 3.86 (t, J=5.2 Hz, 4H), 4.00 (s, 3H), 7.38 (d, J=2.2 Hz, 1H), 7.68 (s, 1H), 7.76 (s, 1H), 7.97 (s, 1H), 8.27 (d, J=2.1 Hz, 1H), 9.24 (bs, 1H).

4-((1r,4r)-4-(3-(1,5-dimethyl-1H-pyrazol-4-yl)-1H-pyrrolo[2,3-b]pyridin-5-yl)cyclohexyl)morpholine (I-95)

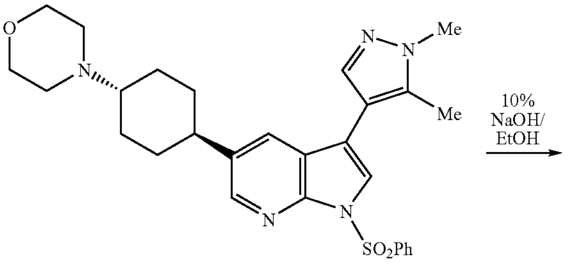

(IIb-95)

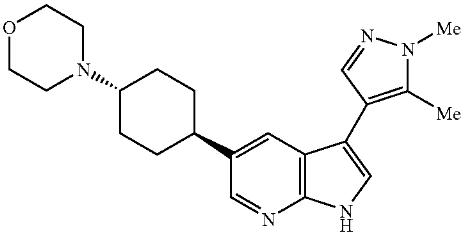

(I-95)

Trans isomer (IIb-95) was deprotected as described in the general procedure A for the deprotection of 7-azaindoles. Thus, (IIb-95) (44.6 mg, 0.09 mmol) was dissolved in ethanol (5.0 mL). 10% solution of NaOH (1.0 mL) was added and the reaction was heated to 90° C. for 1 h 30 min. It was allowed to cool down and diluted with EtOAc (20 mL). The mixture was washed with a saturated solution of $NaHCO_3$ (3×15 mL), dried over $MgSO_4$ and concentrated to afford (I-95) (27.0 mg, 83%); $^1$H NMR (400 MHz; $CDCl_3$) δ 1.32-1.41 (m, 2H), 1.46-1.57 (m, 2H), 1.96-2.03 (m, 5H), 2.27 (s, 3H), 2.54-2.56

(m, 5H), 3.67-3.70 (m, 4H), 3.82 (s, 3H), 7.17 (d, J=2.0 Hz, 1H), 7.36 (s, 1H), 7.70 (d, J=2.0 Hz, 1H), 8.16 (d, J=2.0 Hz, 1H), 9.64 (bs, 1H).

4-((1s,4s)-4-(3-(1,5-dimethyl-1H-pyrazol-4-yl)-1H-pyrrolo[2,3-b]pyridin-5-yl)cyclohexyl)morpholine (I-96)

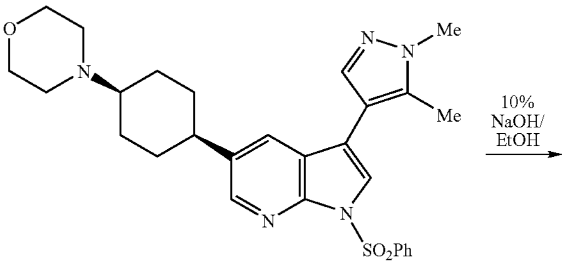

(IIb-96)

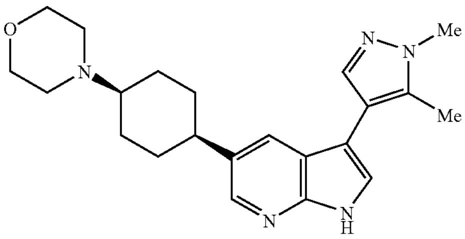

(I-96)

Cis isomer (IIb-96) was deprotected as described in the general procedure A for the deprotection of 7-azaindoles. Thus, (IIb-96) (106.2 mg, 0.20 mmol) was dissolved in ethanol (5.0 mL). 10% solution of NaOH (1.0 mL) was added and the reaction was heated to 90° C. for 1 h 30 min. It was allowed to cool down and diluted with EtOAc (20 mL). The mixture was washed with a saturated solution of $NaHCO_3$ (3×15 mL), dried over $MgSO_4$ and concentrated to afford (I-96) (71.0 mg, 91%); $^1$H NMR (400 MHz; $CDCl_3$) δ 1.46-1.62 (m, 4H), 1.88-1.97 (m, 4H), 2.19 (m, 1H), 2.29 (s, 3H), 2.41 (m, 4H), 2.72-2.79 (m, 1H), 3.68 (t, J=4.7 Hz, 4H), 3.83 (s, 3H), 7.20 (d, J=2.0 Hz, 1H), 7.39 (s, 1H), 7.77 (d, J=2.0 Hz, 1H), 8.23 (d, J=2.0 Hz, 1H), 10.26 (bs, 1H).

4-((1r,4r)-4-(3-(1,3-dimethyl-1H-pyrazol-4-yl)-1H-pyrrolo[2,3-b]pyridin-5-yl)cyclohexyl)morpholine (I-101)

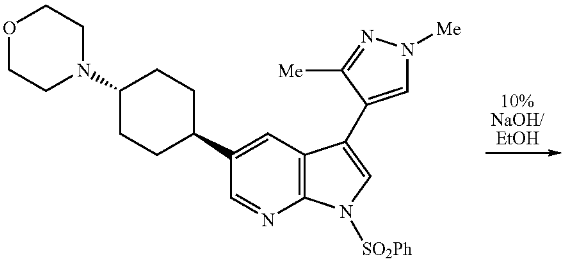

(IIb-101)

-continued

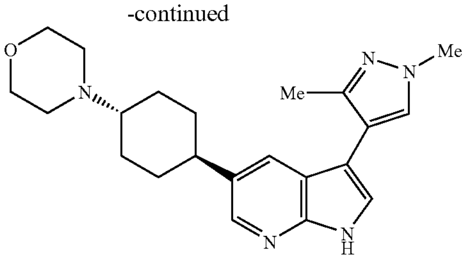

(I-101)

Trans isomer (IIb-101) was deprotected as described in the general procedure A for the deprotection of 7-azaindoles. Thus, (IIb-101) (90.3 mg, 0.16 mmol) was dissolved in ethanol (5.0 mL). 10% solution of NaOH (1.5 mL) was added and the reaction was heated to 90° C. for 1 h. It was allowed to cool down and diluted with EtOAc (25 mL). The mixture was washed with a saturated solution of $NaHCO_3$ (3×25 mL), dried over $MgSO_4$ and concentrated to afford (I-101) (62.0 mg, 100%) as a pale yellow powder; $^1$H NMR (400 MHz; $CDCl_3$) δ 1.40-1.48 (m, 2H), 1.54-1.64 (m, 2H), 2.04-2.11 (m, 5H), 2.35 (s, 3H), 2.62 (t, J=4.6 Hz, 4H), 2.67 (m, 1H), 3.76 (t, J=4.6 Hz, 4H), 3.94 (s, 3H), 7.29 (d, J=2.0 Hz, 1H), 7.51 (s, 1H), 7.74 (d, J=2.0 Hz, 1H), 8.23 (d, J=2.0 Hz, 1H), 9.70 (bs, 1H).

4-((1s,4s)-4-(3-(1,3-dimethyl-1H-pyrazol-4-yl)-1H-pyrrolo[2,3-b]pyridin-5-yl)cyclohexyl)morpholine (I-102)

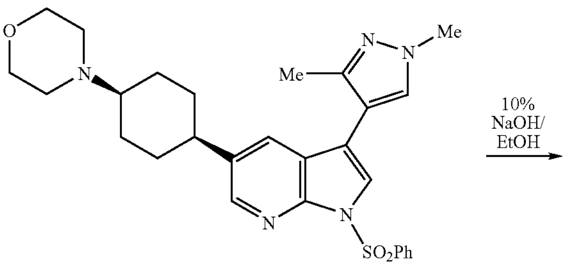

(IIb-102)

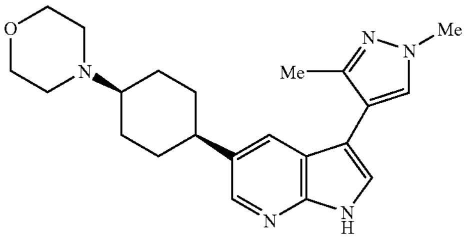

(I-102)

Cis isomer (IIb-102) was deprotected as described in the general procedure A for the deprotection of 7-azaindoles. Thus, (IIb-102) (152.9 mg, 0.29 mmol) was dissolved in ethanol (8.0 mL). 10% solution of NaOH (1.5 mL) was added and the reaction was heated to 90° C. for 1.3 h. It was allowed to cool down and diluted with EtOAc (25 mL). The mixture was washed with a saturated solution of $NaHCO_3$ (3×25 mL), dried over $MgSO_4$ and concentrated to afford (I-102) (87.0 mg, 78%) as a pale yellow powder; $^1$H NMR (400 MHz; $CDCl_3$) δ 1.54-1.68 (m, 4H), 1.93-2.04 (m, 4H), 2.27 (m, 1H), 2.36 (s, 3H), 2.49 (m, 4H), 2.78-2.85 (m, 1H), 3.75 (d, J=4.6 Hz, 4H), 3.94 (s, 3H), 7.27 (d, J=2.3 Hz, 1H), 7.52 (s, 1H), 7.79 (d, J=2.0 Hz, 1H), 8.27 (d, J=2.0 Hz, 1H), 8.89 (bs, 1H).

(S)-3-methyl-4-((1r,4S)-4-(3-(1-methyl-1H-pyrazol-4-yl)-1H-pyrrolo[2,3-b]pyridin-5-yl)cyclohexyl)morpholine (I-103)

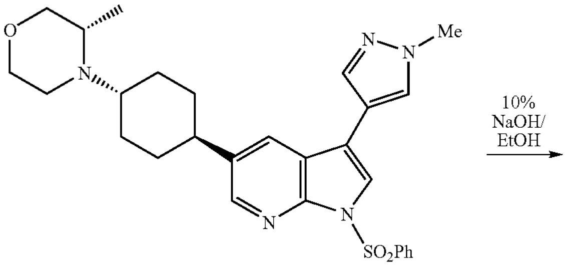

(IIb-103)

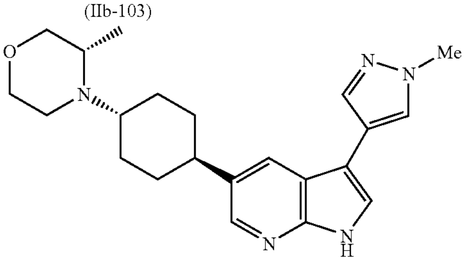

(I-103)

Trans isomer (IIb-103) was deprotected as described in the general procedure A for the deprotection of 7-azaindoles. Thus, (IIb-103) (103 mg, 0.16 mmol) was dissolved in ethanol (7.0 mL). 10% solution of NaOH (1.0 mL) was added and the reaction was heated to 90° C. for 45 min. It was allowed to cool down and diluted with EtOAc (25 mL). The mixture was washed with a saturated solution of $NaHCO_3$ (3×15 mL), dried over $MgSO_4$ and concentrated to afford an oil. This oil was triturated with cold diethyl ether and the solid impurities were filtered off The ethereal solution was concentrated and purified by LCMS (column LUNA 10μ C18(2) 00G-4253-V0 250×50 mm) using water-MeCN (0.1% AcOH) as eluent (in gradient; flow 80 mL/min) to afford the azaindole (I-103) (5.8 mg, 9%). $^1$H NMR (400 MHz; $CDCl_3$) δ 1.07 (d, J=6.4 Hz, 3H), 1.38-1.71 (m, 4H), 1.91-2.09 (m, 4H), 2.61-2.67 (m, 2H), 2.78-2.83 (m, 1H), 2.88-3.00 (m, 2H), 3.36-3.41 (m, 1H), 3.71-3.74 (m, 2H), 3.84-3.88 (m, 1H), 4.00 (s, 3H), 7.35 (s, 1H), 7.61 (s, 1H), 7.75 (m, 1H), 7.91 (d, J=1.9 Hz, 1H), 8.10 (d, J=1.9 Hz, 1H), 10.23 (bs, 1H).

(S)-3-methyl-4-((1s,4R)-4-(3-(1-methyl-1H-pyrazol-4-yl)-1H-pyrrolo[2,3-b]pyridin-5-yl)cyclohexyl)morpholine (I-104)

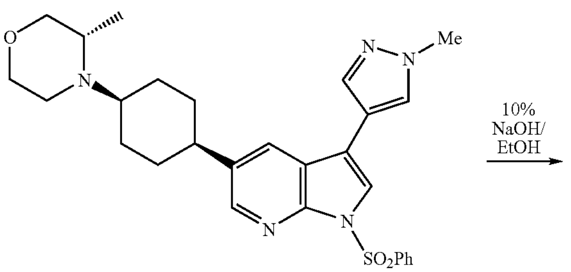

(IIb-104)

-continued

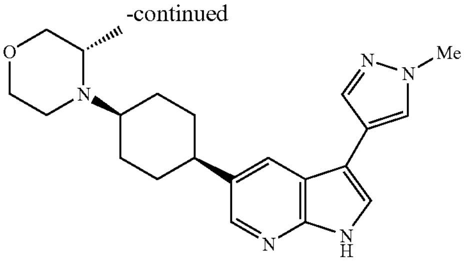

(I-104)

Cis isomer (IIb-104) was deprotected as described in the general procedure A for the deprotection of 7-azaindoles. Thus, (IIb-104) (53.6 mg, 0.10 mmol) was dissolved in ethanol (5.0 mL). 10% solution of NaOH (1.0 mL) was added and the reaction was heated to 90° C. for 45 min. It was allowed to cool down and diluted with EtOAc (20 mL). The mixture was washed with a saturated solution of $NaHCO_3$ (3×15 mL), dried over $MgSO_4$ and concentrated to afford an oil (40 mg). The oil was triturated with cold diethyl ether and the resulting cream solid filtered off to afford (I-104) (6.9 mg, 18%). $^1$H NMR (400 MHz; $CDCl_3$) δ 1.05 (d, J=6.4 Hz, 3H), 1.51-1.74 (m, 4H), 1.87-2.17 (m, 4H), 2.53-2.55 (m, 2H), 2.70 (m, 1H), 2.88-2.96 (m, 2H), 3.53-3.57 (m, 1H), 3.64-3.79 (m, 3H), 4.00 (s, 3H), 7.35 (d, J=2.3 Hz, 1H), 7.62 (s, 1H), 7.77 (s, 1H), 7.94 (d, J=1.7 Hz, 1H), 8.29 (d, J=1.7 Hz, 1H), 8.95 (bs, 1H).

(1r,4r)-N-isopropyl-4-(3-(1-methyl-1H-pyrazol-4-yl)-1H-pyrrolo[2,3-b]pyridin-5-yl)cyclohexanamine (I-105)

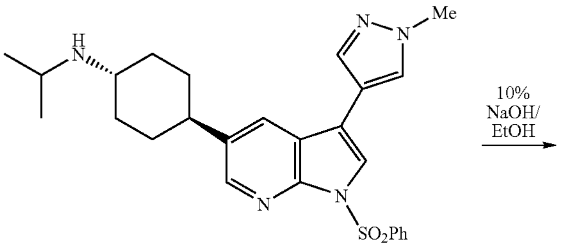

(IIb-105)

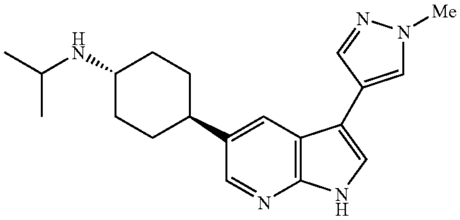

(I-105)

Trans isomer (IIb-105) was deprotected as described in the general procedure A for the deprotection of 7-azaindoles. Thus, (IIb-105) (57.9 mg, 0.12 mmol) was dissolved in ethanol (5.0 mL). 10% solution of NaOH (1.0 mL) was added and the reaction was heated to 90° C. for 1 h. It was allowed to cool down and diluted with EtOAc (20 mL). The mixture was washed with a saturated solution of $NaHCO_3$ (3×15 mL), dried over $MgSO_4$ and concentrated to afford (I-105) (18.1 mg, 44%) as an oil. $^1$H NMR (400 MHz, $CDCl_3$) δ 1.14 (d, J=6.2 Hz, 6H), 1.29-1.42 (m, 4H), 1.56-1.70 (m, 2H), 1.97-

2.05 (m, 2H), 2.09-2.18 (m, 2H), 2.63-2.79 (m, 2H), 3.04-3.14 (m, 1H), 3.99 (s, 3H), 7.37 (d, J=1.5 Hz, 1H), 7.62 (s, 1H), 7.74-7.76 (m, 1H), 7.87 (d, J=2.0 Hz, 1H), 8.21 (d, J=2.0 Hz, 1H), 9.42(bs, 1H).

(1s,4s)-N-isopropyl-4-(3-(1-methyl-1H-pyrazol-4-yl)-1H-pyrrolo[2,3-b]pyridin-5-yl)cyclohexanamine (I-106)

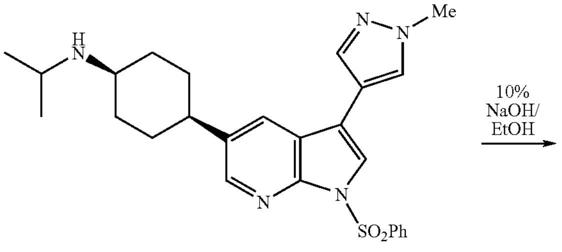

(IIb-106)

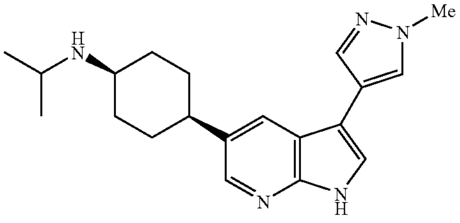

(I-106)

Cis isomer (IIb-106) was deprotected as described in the general procedure A for the deprotection of 7-azaindoles. Thus, (IIb-106) (90.3 mg, 0.19 mmol) was dissolved in ethanol (5.0 mL). 10% solution of NaOH (1.0 mL) was added and the reaction was heated to 90° C. for 1 h. It was allowed to cool down and diluted with EtOAc (20 mL). The mixture was washed with a saturated solution of $NaHCO_3$ (3×15 mL), dried over $MgSO_4$ and concentrated to afford (I-106) (41.5 mg, 65%) as a pale yellow powder. $^1$H NMR (400 MHz, $CDCl_3$) δ 1.10 (d, J=6.2 Hz, 6H), 1.63-1.93 (m, 8H), 2.69-2.78 (m, 1H), 2.88-2.98 (m, 1H), 3.00-3.06 (m, 1H), 3.99 (s, 3H), 7.38 (d, J=1.8 Hz, 1H), 7.64 (bs, 1H), 7.75-7.76 (m, 1H), 7.90-7.93 (m, 1H), 8.26 (d, J=2.0 Hz, 1H), 9.78 (bs, 1H).

(1r,4r)-N-(2-ethoxyethyl)-N-ethyl-4-(3-(1-methyl-1H-pyrazol-4-yl)-1H-pyrrolo[2,3-b]pyridin-5-yl) cyclohexanamine (I-107)

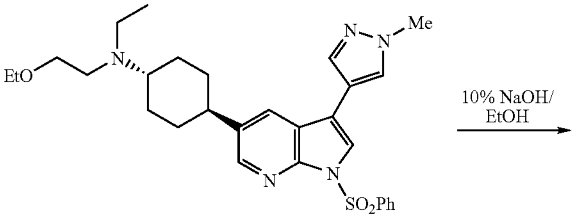

(IIb-107)

-continued

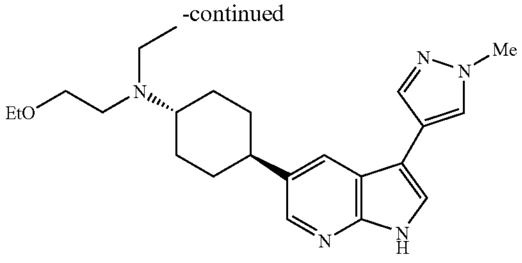

(I-107)

Trans isomer (IIb-107) was deprotected as described in the general procedure A for the deprotection of 7-azaindoles. Thus, (IIb-107) (52.8 mg, 0.10 mmol) was dissolved in ethanol (5.0 mL). 10% solution of NaOH (1.0 mL) was added and the reaction was heated to 90° C. for 1 h. It was allowed to cool down and diluted with EtOAc (20 mL). The mixture was washed with a saturated solution of $NaHCO_3$ (3×15 mL), dried over $MgSO_4$ and concentrated to afford (I-107) (35.5 mg, 91%) as a yellow oil. $^1$H NMR (400 MHz, $CDCl_3$) δ 1.08 (t, J=7.0 Hz, 3H), 1.22 (t, J=7.0 Hz, 3H), 1.41-1.67 (m, 4H), 1.89-2.08 (m, 5H), 2.61-2.77 (m, 5H), 3.45-3.56 (m, 4H), 3.99 (s, 3H), 7.38 (d, J=2.0 Hz, 1H), 7.62 (s, 1H), 7.76 (d, J=0.7 Hz, 1H), 7.87 (d, J=2.0 Hz, 1H), 8.23 (d, J=2.0 Hz, 1H), 9.99 (bs, 1H).

(1s,4s)-N-(2-ethoxyethyl)-N-ethyl-4-(3-(1-methyl-1H-pyrazol-4-yl)-1H-pyrrolo[2,3-b]pyridin-5-yl) cyclohexanamine (I-108)

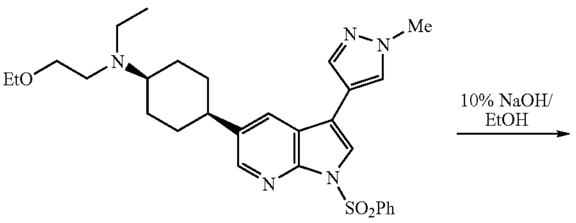

(IIb-108)

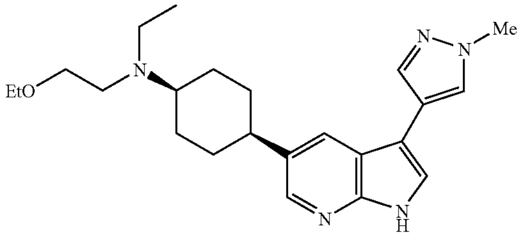

(I-108)

Cis isomer (IIb-108) was deprotected as described in the general procedure A for the deprotection of 7-azaindoles. Thus, (IIb-108) (59.2 mg, 0.11 mmol) was dissolved in ethanol (5.0 mL). 10% solution of NaOH (1.0 mL) was added and the reaction was heated to 90° C. for 1 h. It was allowed to cool down and diluted with EtOAc (20 mL). The mixture was washed with a saturated solution of $NaHCO_3$ (3×15 mL), dried over $MgSO_4$ and concentrated to afford (I-108) (38.5 mg, 88%) as a yellow powder. $^1$H NMR (400 MHz, $CDCl_3$) δ 1.00 (t, J=7.0 Hz, 3H), 1.19 (t, J=7.0 Hz, 3H), 1.55-1.66 (m, 2H), 1.68-1.77 (m, 2H), 1.81-1.94 (m, 2H), 2.05-2.17 (m, 2H), 2.65-2.76 (m, 5H), 2.86-2.94 (m, 1H), 3.45-3.53 (m, 4H), 3.99 (s, 3H), 7.38 (d, J=1.9 Hz, 1H), 7.63 (s, 1H), 7.77 (d, J=0.6 Hz, 1H), 7.94-7.96 (m, 1H), 8.30 (d, J=1.9 Hz, 1H), 9.78 (bs, 1H).

(1r,4r)-N-ethyl-N-methyl-4-(3-(1-methyl-1H-pyrazol-4-yl)-1H-pyrrolo[2,3-b]pyridin-5-yl)cyclohexanamine (I-109)

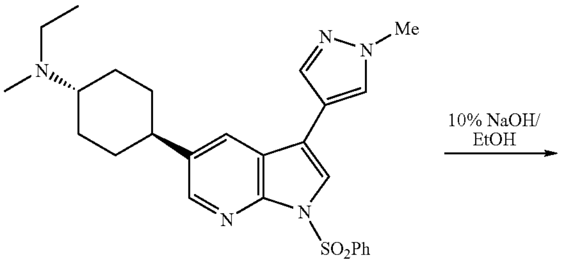

(IIb-109)

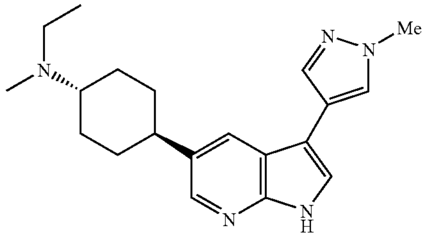

(I-109)

Trans isomer (IIb-109) was deprotected as described in the general procedure A for the deprotection of 7-azaindoles. Thus, (IIb-109) (75.9 mg, 0.16 mmol) was dissolved in ethanol (5.0 mL). 10% solution of NaOH (1.0 mL) was added and the reaction was heated to 90° C. for 1.3 h. It was allowed to cool down and diluted with EtOAc (20 mL). The mixture was washed with a saturated solution of $NaHCO_3$ (3×15 mL), dried over $MgSO_4$ and concentrated to afford (I-109) (21.6 mg, 44%) as a yellow oil. $^1$H NMR (400 MHz, $CDCl_3$) δ 1.11 (t, J=7.0 Hz, 3H), 1.44-1.68 (m, 4H), 1.99-2.10 (m, 4H), 2.33 (s, 3H), 2.54-2.70 (m, 4H), 4.00 (s, 3H), 7.36 (d, J=2.2 Hz, 1H), 7.62 (s, 1H), 7.75 (d, J=0.6 Hz, 1H), 7.86 (d, J=2.0 Hz, 1H), 8.23 (d, J=2.0 Hz, 1H), 9.31 (bs, 1H).

(1s,4s)-N-ethyl-N-methyl-4-(3-(1-methyl-1H-pyrazol-4-yl)-1H-pyrrolo[2,3-b]pyridin-5-yl)cyclohexanamine (I-110)

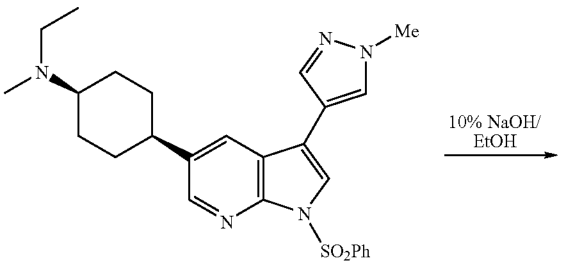

(IIb-110)

-continued

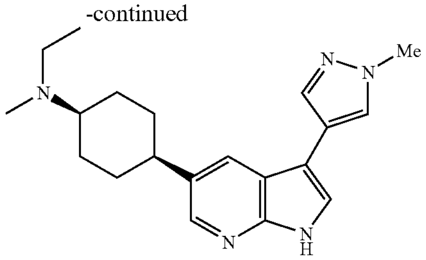

(I-110)

Cis isomer (IIb-110) was deprotected as described in the general procedure A for the deprotection of 7-azaindoles. Thus, (IIb-110) (69.5 mg, 0.15 mmol) was dissolved in ethanol (5.0 mL). 10% solution of NaOH (1.0 mL) was added and the reaction was heated to 90° C. for 1 h. It was allowed to cool down and diluted with EtOAc (20 mL). The mixture was washed with a saturated solution of $NaHCO_3$ (3×15 mL), dried over $MgSO_4$ and concentrated to afford (I-110) (25.8 mg, 52%) as a yellow oil. $^1$H NMR (400 MHz, $CDCl_3$) δ 1.03 (t, J=7.0 Hz, 3H), 1.54-1.66 (m, 2H), 1.67-1.77 (m, 2H), 1.92-2.14 (m, 4H), 2.22-2.34 (m, 3H), 2.46-2.54 (m, 1H), 2.60-2.71 (m, 2H), 2.83-2.91 (m, 1H), 4.00 (s, 3H), 7.37 (d, J=2.0 Hz, 1H), 7.62-7.69 (m, 1H), 7.76 (d, J=0.7 Hz, 1H), 7.93-7.99 (m, 1H), 8.29 (d, J=2.0 Hz, 1H), 9.68 (bs, 1H).

(1r,4r)-N-(2-methoxyethyl)-4-(3-(1-methyl-1H-pyrazol-4-yl)-1H-pyrrolo[2,3-b]pyridin-5-yl)cyclohexanamine (I-111)

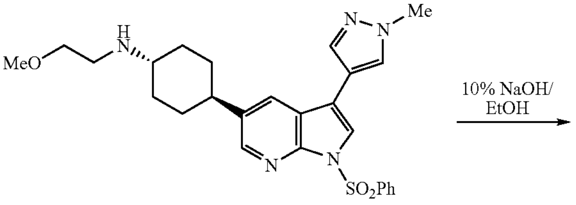

(IIb-111)

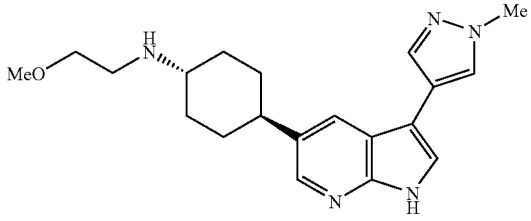

(I-111)

Trans isomer (IIb-111) was deprotected as described in the general procedure A for the deprotection of 7-azaindoles. Thus, (IIb-111) (55.5 mg, 0.11 mmol) was dissolved in ethanol (5.0 mL). 10% solution of NaOH (1.0 mL) was added and the reaction was heated to 90° C. for 50 min. It was allowed to cool down and diluted with EtOAc (20 mL). The mixture was washed with a saturated solution of $NaHCO_3$ (3×15 mL), dried over $MgSO_4$ and concentrated to afford (I-111) (27.2 mg, 68%) as a yellow oil. $^1$H NMR (400 MHz, $CDCl_3$) δ 1.29-1.41 (m, 2H), 1.56-1.70 (m, 2H), 1.96-2.05 (m, 2H), 2.08-2.16 (m, 2H), 2.56-2.73 (m, 2H), 2.88 (t, J=5.1 Hz, 2H), 3.38 (s, 3H), 3.54 (t, J=5.1 Hz, 2H), 3.99 (s, 3H), 7.37 (s, 1H), 7.62 (s, 1H), 7.75 (d, J=0.7 Hz, 1H), 7.87 (d, J=1.9 Hz, 1H), 8.23 (d, J=1.9 Hz, 1H), 9.48 (bs, 1H).

(1s,4s)-N-(2-methoxyethyl)-4-(3-(1-methyl-1H-pyrazol-4-yl)-1H-pyrrolo[2,3-b]pyridin-5-yl)cyclohexanamine (I-112)

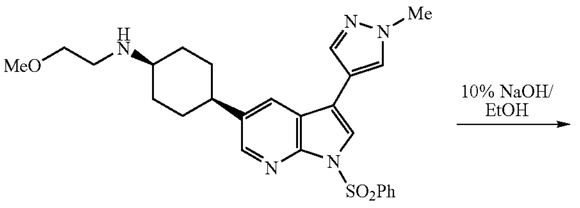

(IIb-112)

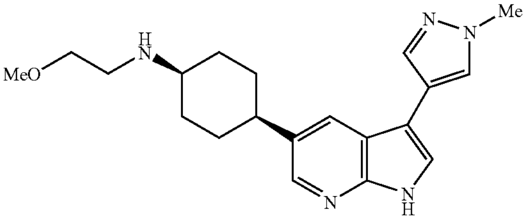

(I-112)

Cis isomer (IIb-112) was deprotected as described in the general procedure A for the deprotection of 7-azaindoles. Thus, (IIb-112) (89.8 mg, 0.18 mmol) was dissolved in ethanol (5.0 mL). 10% solution of NaOH (1.0 mL) was added and the reaction was heated to 90° C. for 1.3 h. It was allowed to cool down and diluted with EtOAc (20 mL). The mixture was washed with a saturated solution of $NaHCO_3$ (3×15 mL), dried over $MgSO_4$ and concentrated to afford (I-112) (52.3 mg, 81%) as a yellow oil. $^1H$ NMR (400 MHz, $CDCl_3$) δ 1.67-1.76 (m, 4H), 1.86-2.02 (m, 5H), 2.69-2.79 (m, 1H), 2.83 (t, J=5.2 Hz, 2H), 2.93-2.97 (m, 1H), 3.38 (s, 3H), 3.56 (t, J=5.1 Hz, 2H), 4.00 (s, 3H), 7.38 (s, 1H), 7.67 (s, 1H), 7.76 (d, J=0.6 Hz, 1H), 7.94 (d, J=1.9 Hz, 1H), 8.25 (d, J=1.9 Hz, 1H), 10.11 (bs, 1H).

(1r,4r)-N-ethyl-4-(3-(1-methyl-1H-pyrazol-4-yl)-1H-pyrrolo[2,3-b]pyridin-5-yl)-N-propylcyclohexanamine (I-113)

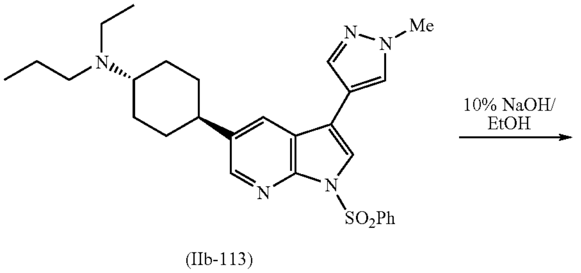

(IIb-113)

-continued

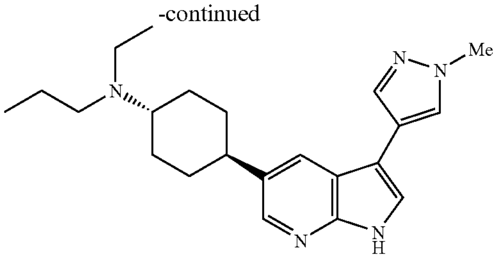

(I-113)

Trans isomer (IIb-113) was deprotected as described in the general procedure A for the deprotection of 7-azaindoles. Thus, (IIb-113) (66.9 mg, 0.13 mmol) was dissolved in ethanol (5.0 mL). 10% solution of NaOH (1.0 mL) was added and the reaction was heated to 90° C. for 1 h. It was allowed to cool down and diluted with EtOAc (20 mL). The mixture was washed with a saturated solution of $NaHCO_3$ (3×15 mL), dried over $MgSO_4$ and concentrated to afford (I-113) (41.2 mg, 85%) as a yellow oil. $^1H$ NMR (400 MHz, $CDCl_3$) δ 0.90 (t, J=7.1 Hz, 3H), 1.08 (t, J=7.1 Hz, 3H), 1.42-1.67 (m, 6H), 1.95-2.08 (m, 4H), 2.44-2.52 (m, 2H), 2.57-2.72 (m, 4H), 3.99 (s, 3H), 7.38 (d, J=2.1 Hz, 1H), 7.62 (s, 1H), 7.78 (d, J=0.7 Hz, 1H), 7.87 (d, J=2.0 Hz, 1H), 8.24 (d, J=2.0 Hz, 1H), 9.88 (bs, 1H).

(1s,4s)-N-ethyl-4-(3-(1-methyl-1H-pyrazol-4-yl)-1H-pyrrolo[2,3-b]pyridin-5-yl)-N-propylcyclohexanamine (I-114)

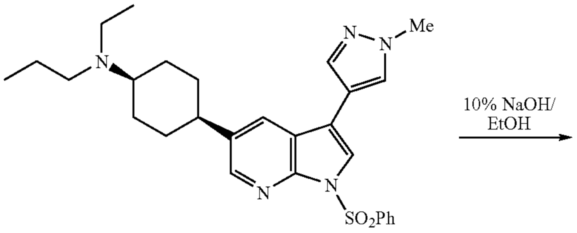

(IIb-114)

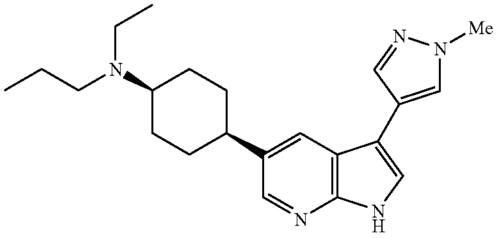

(I-114)

Cis isomer (IIb-114) was deprotected as described in the general procedure A for the deprotection of 7-azaindoles. Thus, (IIb-114) (68.8 mg, 0.14 mmol) was dissolved in ethanol (5.0 mL). 10% solution of NaOH (1.0 mL) was added and the reaction was heated to 90° C. for 1 h. It was allowed to cool down and diluted with EtOAc (20 mL). The mixture was washed with a saturated solution of $NaHCO_3$ (3×15 mL), dried over $MgSO_4$ and concentrated to afford (I-114) (43.8 mg, 61%) as a yellow oil. $^1H$ NMR (400 MHz, $CDCl_3$) δ 0.90 (t, J=7.2 Hz, 3H), 0.98 (t, J=7.1 Hz, 3H), 1.43-1.76 (m, 6H), 1.83-2.19 (m, 4H), 2.43-2.51 (m, 2H), 2.62-2.73 (m, 3H), 2.85-2.94 (m, 1H), 3.99 (s, 3H), 7.38 (d, J=2.1 Hz, 1H), 7.62 (s, 1H), 7.76 (d, J=0.7 Hz, 1H), 7.96 (s, 1H), 8.29 (s, 1H), 9.81 (bs, 1H).

(1r,4r)-N-methyl-4-(3-(1-methyl-1H-pyrazol-4-yl)-1H-pyrrolo[2,3-b]pyridin-5-yl)-N-propylcyclohexanamine (I-115)

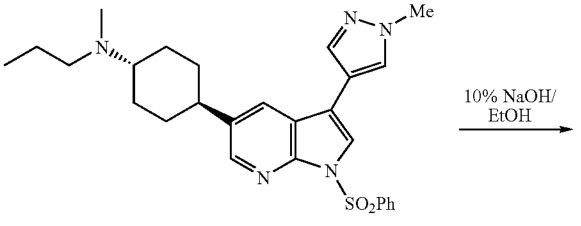

(IIb-115)

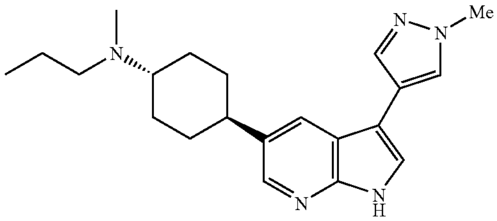

(I-115)

Trans isomer (IIb-115) was deprotected as described in the general procedure A for the deprotection of 7-azaindoles. Thus, (IIb-115) (66.5 mg, 0.14 mmol) was dissolved in ethanol (5.0 mL). 10% solution of NaOH (1.0 mL) was added and the reaction was heated to 90° C. for 1 h. It was allowed to cool down and diluted with EtOAc (20 mL). The mixture was washed with a saturated solution of $NaHCO_3$ (3×15 mL), dried over $MgSO_4$ and concentrated to afford (I-115) (36.1 mg, 76%) as an off-white foam. $^1$H NMR (400 MHz, $CDCl_3$) δ 0.92 (t, J=7.3 Hz, 3H), 1.43-1.68 (m, 6H), 1.97-2.09 (m, 4H), 2.33 (s, 3H), 2.43-2.49 (m, 2H), 2.53-2.69 (m, 2H), 3.99 (s, 3H), 7.38 (d, J=2.1 Hz, 1H), 7.62 (s, 1H), 7.75 (d, J=0.7 Hz, 1H), 7.87 (d, J=2.1 Hz, 1H), 8.23 (d, J=2.1 Hz, 1H), 9.71 (bs, 1H).

(1s,4s)-N-methyl-4-(3-(1-methyl-1H-pyrazol-4-yl)-1H-pyrrolo[2,3-b]pyridin-5-yl)-N-propylcyclohexanamine (I-116)

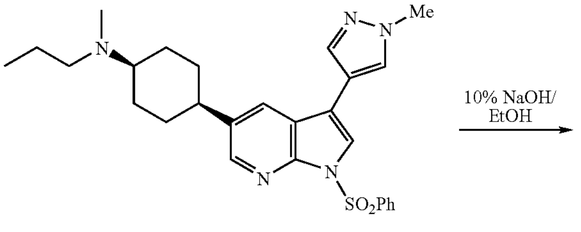

(IIb-116)

-continued

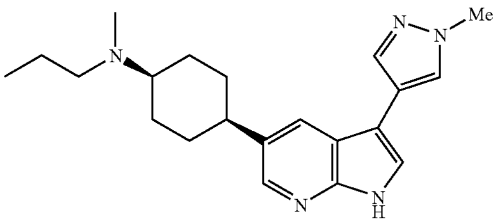

(I-116)

Cis isomer (IIb-116) was deprotected as described in the general procedure A for the deprotection of 7-azaindoles. Thus, (IIb-116) (61.5 mg, 0.13 mmol) was dissolved in ethanol (5.0 mL). 10% solution of NaOH (1.0 mL) was added and the reaction was heated to 90° C. for 1 h. It was allowed to cool down and diluted with EtOAc (20 mL). The mixture was washed with a saturated solution of $NaHCO_3$ (3×15 mL), dried over $MgSO_4$ and concentrated to afford (I-116) (38.2 mg, 87%) as a yellow oil. $^1$H NMR (400 MHz, $CDCl_3$) δ 0.92 (t, J=7.2 Hz, 3H), 1.44-1.76 (m, 6H), 1.94-2.15 (m, 4H), 2.26 (s, 3H), 2.37-2.53 (m, 3H), 2.82-2.91 (m, 1H), 3.99 (s, 3H), 7.38 (d, J=2.1 Hz, 1H), 7.39-7.69 (m, 1H), 7.76 (s, 1H), 7.91-8.00 (m, 1H), 8.29 (d, J=1.7 Hz, 1H), 9.73 (bs, 1H)

(1r,4r)-N-(2-methoxyethyl)-N-methyl-4-(3-(1-methyl-1H-pyrazol-4-yl)-1H-pyrrolo[2,3-b]pyridin-5-yl)cyclohexanamine (I-117)

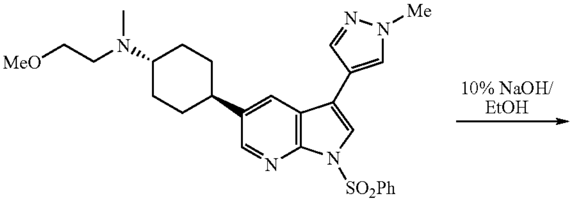

(IIb-117)

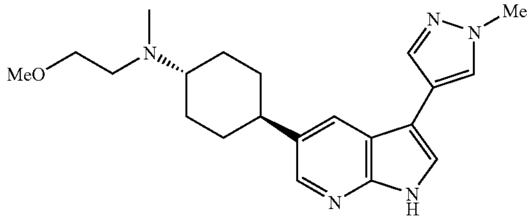

(I-117)

Trans isomer (IIb-117) was deprotected as described in the general procedure A for the deprotection of 7-azaindoles. Thus, (IIb-117) (74.2 mg, 0.15 mmol) was dissolved in ethanol (5.0 mL). 10% solution of NaOH (1.0 mL) was added and the reaction was heated to 90° C. for 1 h. It was allowed to cool down and diluted with EtOAc (20 mL). The mixture was washed with a saturated solution of $NaHCO_3$ (3×15 mL), dried over $MgSO_4$ and concentrated to afford (I-117) (42.6 mg, 79%) as a pale yellow oil. $^1$H NMR (400 MHz, $CDCl_3$) δ 1.42-1.68 (m, 4H), 1.97-2.09 (m, 4H), 2.38 (s, 3H), 2.53-2.68 (m, 2H), 2.71 (t, J=5.9 Hz, 2H), 3.38 (s, 3H), 3.51 (t, J=5.9 Hz, 2H), 3.99 (s, 3H), 7.38 (d, J=2.1 Hz, 1H), 7.62 (s, 1H), 7.75 (d, J=0.7 Hz, 1H), 7.86 (d, J=2.1 Hz, 1H), 8.22 (d, J=2.1 Hz, 1H), 9.75 (bs, 1H).

(1s,4s)-N-(2-methoxyethyl)-N-methyl-4-(3-(1-methyl-1H-pyrazol-4-yl)-1H-pyrrolo[2,3-b]pyridin-5-yl)cyclohexanamine (I-118)

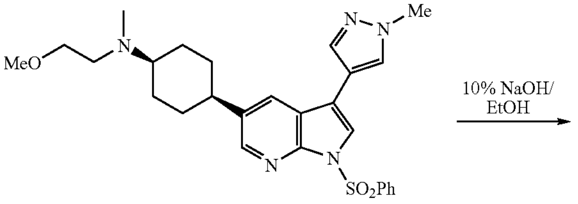

(IIb-118)

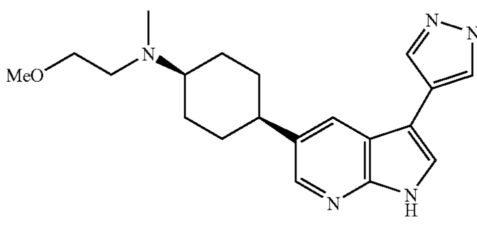

(I-118)

Cis isomer (IIb-118) was deprotected as described in the general procedure A for the deprotection of 7-azaindoles. Thus, (IIb-118) (68.5 mg, 0.13 mmol) was dissolved in ethanol (5.0 mL). 10% solution of NaOH (1.0 mL) was added and the reaction was heated to 90° C. for 1 h. It was allowed to cool down and diluted with EtOAc (20 mL). The mixture was washed with a saturated solution of $NaHCO_3$ (3×15 mL), dried over $MgSO_4$ and concentrated to afford (I-118) (41.7 mg, 84%) as an off-white foam. $^1H$ NMR (400 MHz, $CDCl_3$) δ 1.56-1.66 (m, 2H), 1.68-1.77 (m, 2H), 1.90-2.01 (m, 2H), 2.03-2.16 (m, 2H), 2.32 (s, 3H), 2.47-2.53 (m, 1H), 2.69 (t, J=6.3 Hz, 2H), 2.85-2.93 (m, 1H), 3.37 (s, 3H), 3.51 (t, J=6.3 Hz, 2H), 4.00 (s, 3H), 7.38 (d, J=2.1 Hz, 1H), 7.63 (s, 1H), 7.77 (d, J=0.5 Hz, 1H), 7.95 (s, 1H), 8.30 (d, J=2.1 Hz, 1H), 9.84 (bs, 1H).

(1r,4r)-N-(2-ethoxyethyl)-4-(3-(1-methyl-1H-pyrazol-4-yl)-1H-pyrrolo[2,3-b]pyridin-5-yl)cyclohexanamine (I-119)

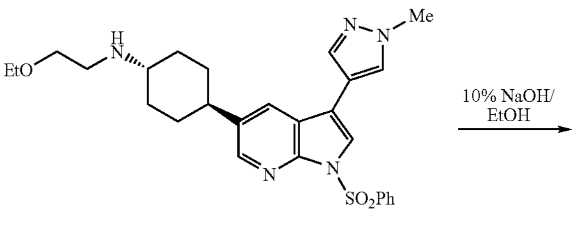

(IIb-119)

-continued

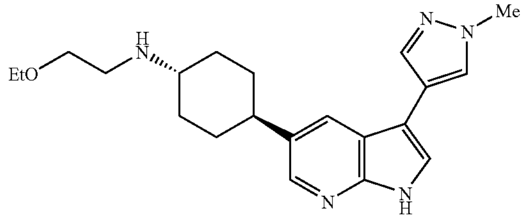

(I-119)

Trans isomer (IIb-119) was deprotected as described in the general procedure A for the deprotection of 7-azaindoles. Thus, (IIb-119) (66.5 mg, 0.13 mmol) was dissolved in ethanol (5.0 mL). 10% solution of NaOH (1.0 mL) was added and the reaction was heated to 90° C. for 1 h. It was allowed to cool down and diluted with EtOAc (20 mL). The mixture was washed with a saturated solution of $NaHCO_3$ (3×15 mL), dried over $MgSO_4$ and concentrated to afford (I-119) (40.6 mg, 84%) as a pale yellow oil. $^1H$ NMR (400 MHz, $CDCl_3$) δ 1.21-1.26 (m, 1H), 1.22 (t, J=7.0 Hz, 3H), 1.29-1.41 (m, 2H), 1.57-1.69 (m, 2H), 1.97-2.04 (m, 2H), 2.07-2.16 (m, 2H), 2.55-2.73 (m, 2H), 2.87 (t, J=5.2 Hz, 2H), 3.58 (t, J=5.2 Hz, 2H), 3.99 (s, 3H), 7.37 (s, 1H), 7.62 (s, 1H), 7.75 (d, J=0.7 Hz, 1H), 7.87 (d, J=2.0 Hz, 1H), 8.23 (d, J=2.0 Hz, 1H), 9.69 (bs, 1H).

(1s,4s)-N-(2-ethoxyethyl)-4-(3-(1-methyl-1H-pyrazol-4-yl)-1H-pyrrolo[2,3-b]pyridin-5-yl)cyclohexanamine (I-120)

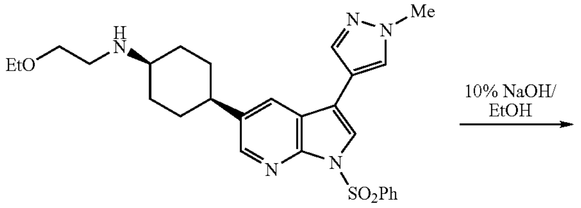

(IIb-120)

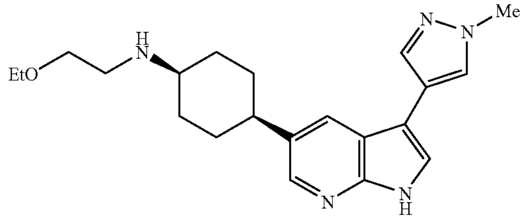

(I-120)

Cis isomer (IIb-120) was deprotected as described in the general procedure A for the deprotection of 7-azaindoles. Thus, (IIb-120) (104.7 mg, 0.21 mmol) was dissolved in ethanol (5.0 mL). 10% solution of NaOH (1.0 mL) was added and the reaction was heated to 90° C. for 1 h. It was allowed to cool down and diluted with EtOAc (20 mL). The mixture was washed with a saturated solution of $NaHCO_3$ (3×15 mL), dried over $MgSO_4$ and concentrated to afford (I-120) (65.7 mg, 87%) as a pale yellow oil. $^1H$ NMR (400 MHz, $CDCl_3$) δ 1.21-1.26 (m, 1H), 1.22 (t, J=7.1 Hz, 3H), 1.64-1.76 (m, 4H), 1.85-2.02 (m, 4H), 2.69-2.78 (m, 1H), 2.82 (t, J=5.3 Hz, 2H), 2.92-2.99 (m, 1H), 3.53 (q, J=7.1 Hz, 2H), 3.60 (t, J=5.3 Hz, 2H), 3.99 (s, 3H), 7.39 (s, 1H), 7.66 (s, 1H), 7.75 (d, J=0.6 Hz, 1H), 7.93 (s, 1H), 8.26 (d, J=2.0 Hz, 1H), 10.20 (bs, 1H).

(1r,4r)-N-(2-methoxyethyl)-4-(3-(1-methyl-1H-pyrazol-4-yl)-1H-pyrrolo[2,3-b]pyridin-5-yl)-N-propylcyclohexanamine (I-121)

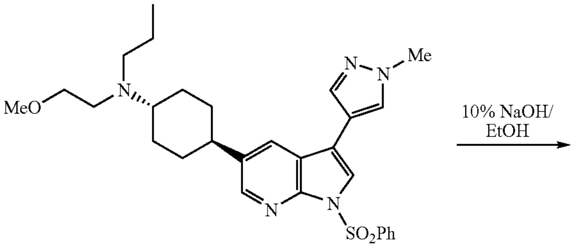

(IIb-121)

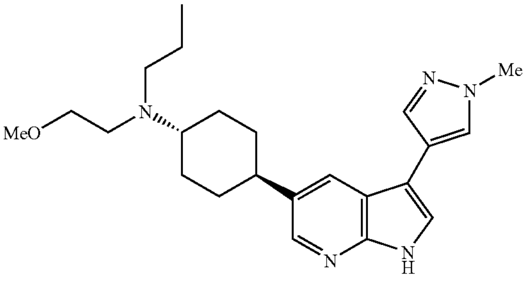

(I-121)

Trans isomer (IIb-121) was deprotected as described in the general procedure A for the deprotection of 7-azaindoles. Thus, (IIb-121) (87.7 mg, 0.16 mmol) was dissolved in ethanol (5.0 mL). 10% solution of NaOH (1.0 mL) was added and the reaction was heated to 90° C. for 1 h. It was allowed to cool down and diluted with EtOAc (20 mL). The mixture was washed with a saturated solution of $NaHCO_3$ (3×15 mL), dried over $MgSO_4$ and concentrated to afford (I-121) (64.6 mg, 99%) as a pale yellow oil. $^1H$ NMR (400 MHz, $CDCl_3$) δ 0.89 (t, J=7.3 Hz, 3H), 1.40-1.54 (m, 4H), 1.54-1.67 (m, 2H), 1.92-2.08 (m, 4H), 2.50 (t, J=7.4 Hz, 2H), 2.58-2.68 (m, 2H), 2.71 (t, J=6.8 Hz, 2H), 3.38 (s, 3H), 3.43 (t, J=6.8 Hz, 2H), 3.99 (s, 3H), 7.39 (d, J=2.2 Hz, 1H), 7.62 (s, 1H), 7.76 (d, J=0.8 Hz, 1H), 7.87 (d, J=1.9 Hz, 1H), 8.23 (d, J=2.0 Hz, 1H), 10.03 (bs, 1H).

(1s,4s)-N-(2-methoxyethyl)-4-(3-(1-methyl-1H-pyrazol-4-yl)-1H-pyrrolo[2,3-b]pyridin-5-yl)-N-propylcyclohexanamine (I-122)

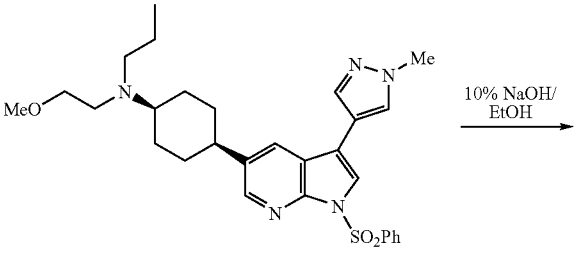

(IIb-122)

-continued

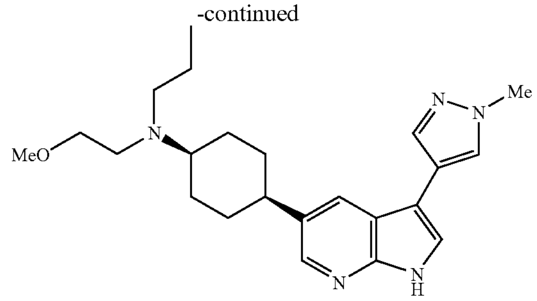

(I-122)

Cis isomer (IIb-122) was deprotected as described in the general procedure A for the deprotection of 7-azaindoles. Thus, (IIb-122) (75.7 mg, 0.13 mmol) was dissolved in ethanol (5.0 mL). 10% solution of NaOH (1.0 mL) was added and the reaction was heated to 90° C. for 1 h. It was allowed to cool down and diluted with EtOAc (20 mL). The mixture was washed with a saturated solution of $NaHCO_3$ (3×15 mL), dried over $MgSO_4$ and concentrated to afford (I-122) (55.3 mg, 98%) as a pale yellow oil. $^1H$ NMR (400 MHz, $CDCl_3$) δ 0.88 (t, J=7.2 Hz, 3H), 1.41-1.53 (m, 2H), 1.55-1.66 (m, 2H), 1.68-1.78 (m, 2H), 1.80-1.92 (m, 2H), 2.07-2.20 (m, 2H), 2.48-2.58 (m, 2H), 2.72 (t, J=6.9 Hz, 3H), 2.88-2.97 (m, 1H), 3.34 (s, 3H), 3.44 (t, J=6.9 Hz, 2H), 3.99 (s, 3H), 7.39 (d, J=2.1 Hz, 1H), 7.62 (s, 1H), 7.77 (s, 1H), 7.96 (d, J=1.7 Hz, 1H), 8.31 (d, J=2.0 Hz, 1H), 9.92 (bs, 1H).

(1r,4r)-N-ethyl-N-(2-methoxyethyl)-4-(3-(1-methyl-1H-pyrazol-4-yl)-1H-pyrrolo[2,3-b]pyridin-5-yl)cyclohexanamine (I-123)

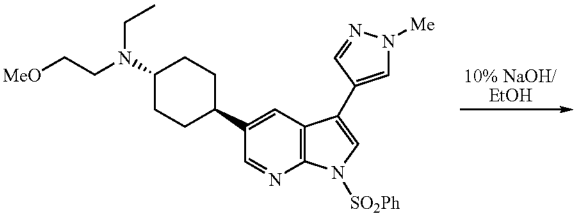

(IIb-123)

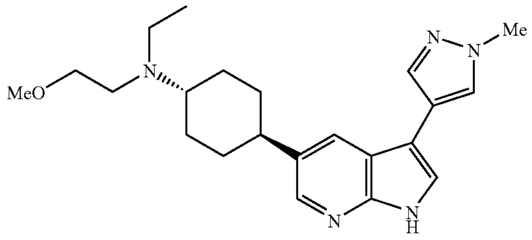

(I-123)

Trans isomer (IIb-123) was deprotected as described in the general procedure A for the deprotection of 7-azaindoles. Thus, (IIb-123) (42.6 mg, 0.08 mmol) was dissolved in ethanol (5.0 mL). 10% solution of NaOH (1.0 mL) was added and the reaction was heated to 90° C. for 1 h. It was allowed to cool down and diluted with EtOAc (20 mL). The mixture was washed with a saturated solution of $NaHCO_3$ (3×15 mL), dried over $MgSO_4$ and concentrated to afford (I-123) (32.4 mg, 99%) as a pale yellow oil. $^1H$ NMR (400 MHz, $CDCl_3$) δ

1.08 (t, J=7.0 Hz, 3H), 1.41-1.54 (m, 2H), 1.55-1.67 (m, 2H), 1.93-2.09 (m, 4H), 2.58-2.77 (m, 6H), 3.38 (s, 3H), 3.45 (t, J=6.6 Hz, 2H), 4.00 (s, 3H), 7.37 (d, J=2.3 Hz, 1H), 7.62 (s, 1H), 7.75 (d, J=0.7 Hz, 1H), 7.86 (d, J=2.0 Hz, 1H), 8.23 (d, J=2.0 Hz, 1H), 9.57 (bs, 1H).

(1s,4s)-N-ethyl-N-(2-methoxyethyl)-4-(3-(1-methyl-1H-pyrazol-4-yl)-1H-pyrrolo[2,3-b]pyridin-5-yl)cyclohexanamine (I-124)

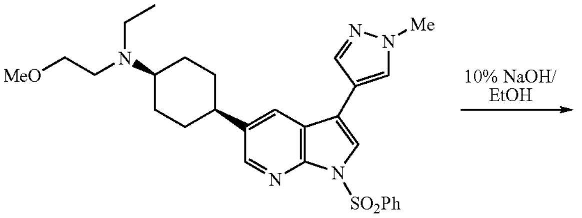

(IIb-124)

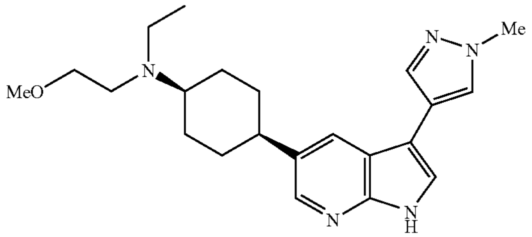

(I-124)

Cis isomer (IIb-124) was deprotected as described in the general procedure A for the deprotection of 7-azaindoles. Thus, (IIb-124) (44.1 mg, 0.08 mmol) was dissolved in ethanol (5.0 mL). 10% solution of NaOH (1.0 mL) was added and the reaction was heated to 90° C. for 1 h. It was allowed to cool down and diluted with EtOAc (20 mL). The mixture was washed with a saturated solution of $NaHCO_3$ (3×15 mL), dried over $MgSO_4$ and concentrated to afford (I-124) (30.4 mg, 94%) as an off-white solid. $^1H$ NMR (400 MHz, $CDCl_3$) δ 1.00 (t, J=7.0 Hz, 3H), 1.56-1.66 (m, 2H), 1.68-1.79 (m, 2H), 1.82-1.93 (m, 2H), 2.06-2.19 (m, 2H), 2.66-2.77 (m, 5H), 2.88-2.96 (m, 1H), 3.35 (s, 3H), 3.44 (t, J=6.8 Hz, 2H), 4.00 (s, 3H), 7.38 (d, J=2.2 Hz, 1H), 7.63 (s, 1H), 7.77 (d, J=0.6 Hz, 1H), 7.95 (d, J=1.9 Hz, 1H), 8.31 (d, J=1.9 Hz, 1H), 9.70 (bs, 1H).

2-(((1r,4r)-4-(3-(1-methyl-1H-pyrazol-4-yl)-1H-pyrrolo[2,3-b]pyridin-5-yl)cyclohexyl)(propyl)amino)ethanol (I-125)

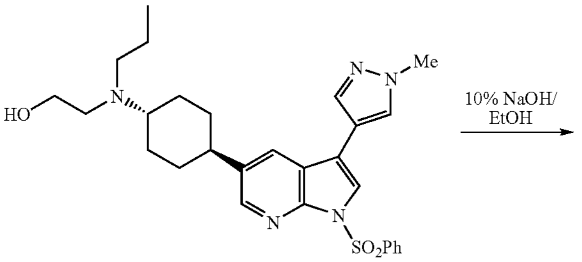

(IIb-125)

-continued

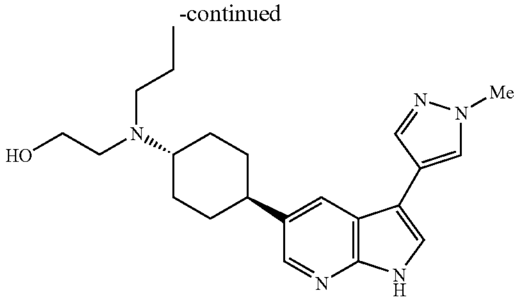

(I-125)

Trans isomer (IIb-125) was deprotected as described in the general procedure A for the deprotection of 7-azaindoles. Thus, (IIb-125) (67.2 mg, 0.13 mmol) was dissolved in ethanol (5.0 mL). 10% solution of NaOH (1.0 mL) was added and the reaction was heated to 90° C. for 1.2 h. It was allowed to cool down and diluted with EtOAc (20 mL). The mixture was washed with a saturated solution of $NaHCO_3$ (3×15 mL), dried over $MgSO_4$ and concentrated to afford (I-125) (40.5 mg, 82%) as a pale yellow oil. $^1H$ NMR (400 MHz, $CDCl_3$) δ 0.91 (t, J=7.4 Hz, 3H), 1.42-1.70 (m, 6H), 1.89-1.98 (m, 2H), 2.00-2.10 (m, 2H), 2.50 (t, J=7.4 Hz, 2H), 2.59-2.73 (m, 4H), 3.54 (t, J=5.3 Hz, 2H), 3.99 (s, 3H), 7.38 (d, J=2.0 Hz, 1H), 7.62 (s, 1H), 7.76 (d, J=0.6 Hz, 1H), 7.87 (d, J=2.0 Hz, 1H), 8.23 (d, J=2.0 Hz, 1H), 9.87 (bs, 1H).

2-(((1s,4s)-4-(3-(1-methyl-1H-pyrazol-4-yl)-1H-pyrrolo[2,3-b]pyridin-5-yl)cyclohexyl)(propyl)amino)ethanol (I-126)

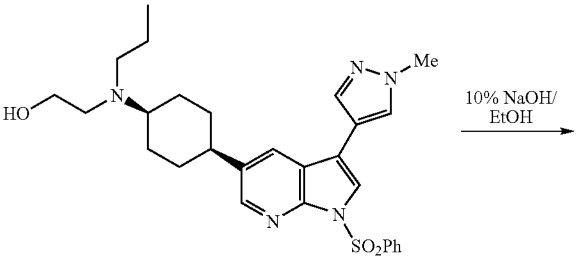

(IIb-126)

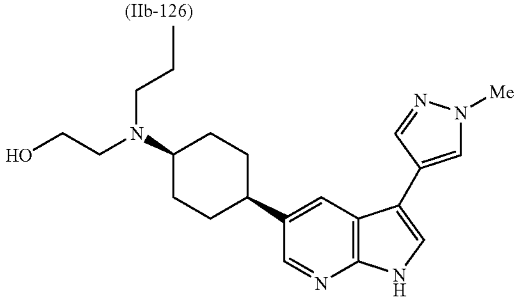

(I-126)

Cis isomer (IIb-126) was deprotected as described in the general procedure A for the deprotection of 7-azaindoles. Thus, (IIb-126) (69.9 mg, 0.11 mmol) was dissolved in ethanol (5.0 mL). 10% solution of NaOH (1.0 mL) was added and the reaction was heated to 90° C. for 1 h. It was allowed to cool down and diluted with EtOAc (20 mL). The mixture was washed with a saturated solution of $NaHCO_3$ (3×15 mL), dried over $MgSO_4$ and concentrated to afford (I-126) (44.3 mg, 87%) as an off-white solid. $^1$H NMR (400 MHz, $CDCl_3$) δ 0.86 (t, J=7.4 Hz, 3H), 1.41-1.54 (m, 2H), 1.59-1.88 (m, 6H), 2.18-2.29 (m, 2H), 2.44-2.56 (m, 2H), 2.59-2.81 (m, 3H), 3.02-3.09 (m, 1H), 3.48-3.58 (m, 2H), 4.00 (s, 3H), 7.40 (d, J=1.9 Hz, 1H), 7.62 (s, 1H), 7.76 (s, 1H), 8.00(s, 1H), 8.32 (d, J=1.9 Hz, 1H), 9.97 (bs, 1H).

N-((1 r,4r)-4-(3-(1-methyl-1H-pyrazol-4-yl)-1H-pyrrolo[2,3-b]pyridin-5-yl)cyclohexyl)tetrahydro-2H-pyran-4-amine (I-127)

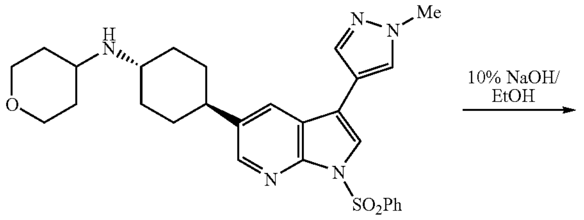

(IIb-127)

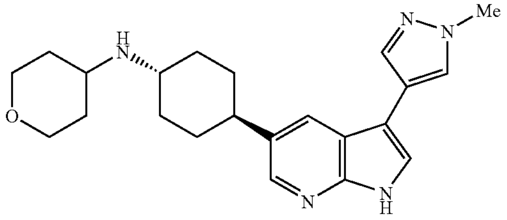

(I-127)

Trans isomer (IIb-127) was deprotected as described in the general procedure A for the deprotection of 7-azaindoles. Thus, (IIb-127) (45.7 mg, 0.09 mmol) was dissolved in ethanol (5.0 mL). 10% solution of NaOH (1.0 mL) was added and the reaction was heated to 90° C. for 1.2 h. It was allowed to cool down and diluted with EtOAc (20 mL). The mixture was washed with a saturated solution of $NaHCO_3$ (3×15 mL), dried over $MgSO_4$ and concentrated to afford (I-127) (21.1 mg, 63%) as a pale yellow oil. $^1$H NMR (400 MHz, $CDCl_3$) δ 1.23-1.47 (m, 5H), 1.36-1.70 (m, 2H), 1.82-1.92 (m, 2H), 1.96-2.13 (m, 4H), 2.63-2.82 (m, 2H), 2.83-2.92 (m, 1H), 3.38-3.48 (m, 2H), 3.93-4.05 (m, 2H), 3.99 (s, 3H), 7.36 (d, J=2.2 Hz, 1H), 7.61 (s, 1H), 7.75 (d, J=0.6 Hz, 1H), 7.86 (d, J=2.1 Hz, 1H), 8.23 (d, J=2.1 Hz, 1H), 9.22 (bs, 1H).

N-((1s,4s)-4-(3-(1-methyl-1H-pyrazol-4-yl)-1H-pyrrolo[2,3-b]pyridin-5-yl)cyclohexyl)tetrahydro-2H-pyran-4-amine (I-128)

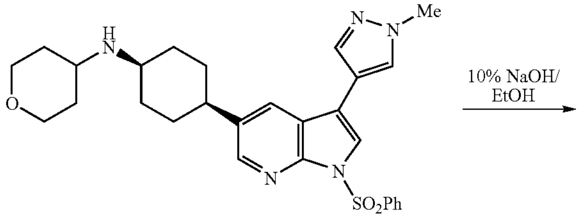

(IIb-128)

-continued

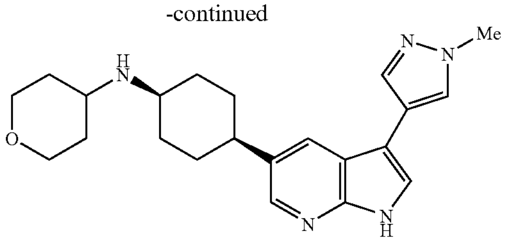

(I-128)

Cis isomer (IIb-128) was deprotected as described in the general procedure A for the deprotection of 7-azaindoles. Thus, (IIb-128) (73.5 mg, 0.14 mmol) was dissolved in ethanol (5.0 mL). 10% solution of NaOH (1.0 mL) was added and the reaction was heated to 90° C. for 1 h. It was allowed to cool down and diluted with EtOAc (20 mL). The mixture was washed with a saturated solution of $NaHCO_3$ (3×15 mL), dried over $MgSO_4$ and concentrated to afford (I-128) (33.0 mg, 61%) as an off-white solid. $^1$H NMR (400 MHz, $CDCl_3$) δ 1.36-1.51 (m, 3H), 1.63-1.98 (m, 10H), 2.70-2.82 (m, 2H), 2.83-2.92 (m, 1H), 3.12 (s, 1H), 3.38-3.48 (m, 2H), 3.96-4.03 (m, 2H), 3.99 (s, 3H), 7.36 (d, J=2.1 Hz, 1H), 7.63 (s, 1H), 7.76 (d, J=0.6 Hz, 1H), 7.91 (s, 1H), 8.25 (d, J=2.1 Hz, 1H), 9.45 (bs, 1H).

2-((1r,4r)-4-(3-(1-methyl-1H-pyrazol-4-yl)-1H-pyrrolo[2,3-b]pyridin-5-yl)cyclohexylamino)ethanol (I-129)

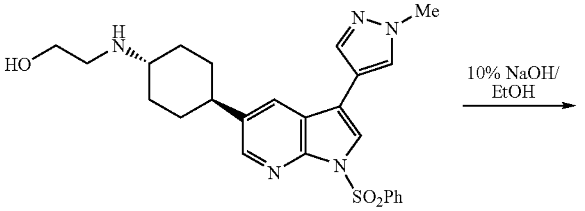

(IIb-129)

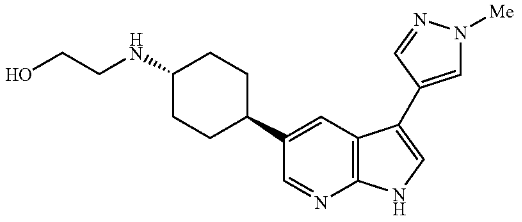

(I-129)

Trans isomer (IIb-129) was deprotected as described in the general procedure

A for the deprotection of 7-azaindoles. Thus, (IIb-129) (31.6 mg, 0.07 mmol) was dissolved in ethanol (5.0 mL). 10% solution of NaOH (1.0 mL) was added and the reaction was heated to 90° C. for 1.3 h. It was allowed to cool down, filtered and purified by LCMS (column LUNA 10μ C18(2) 00G-4253-V0 250×50 mm) using water—MeCN (0.1% AcOH) as eluent (in gradient; flow 80 mL/min) to afford (I-129) (26.7 mg, 99%) as an oil. $^1$H NMR (400 MHz, $CDCl_3$) δ 1.54-1.74 (m, 4H), 2.02-2.17 (m, 4H), 2.25-2.33 (m, 2H), 2.67-2.77 (m, 1H), 2.93-3.05 (m, 1H), 3.06-3.14 (m, 2H), 3.89-3.95 (m, 2H), 3.99 (s, 3H), 7.38 (s, 1H), 7.61 (s, 1H), 7.74 (d, J=0.6 Hz, 1H), 7.86 (d, J=2.0 Hz, 1H), 8.11 (d, J=1.9 Hz, 1H), 10.13 (bs, 1H).

2-((1s,4s)-4-(3-(1-methyl-1H-pyrazol-4-yl)-1H-pyrrolo[2,3-b]pyridin-5-yl)cyclohexylamino)ethanol (I-130)

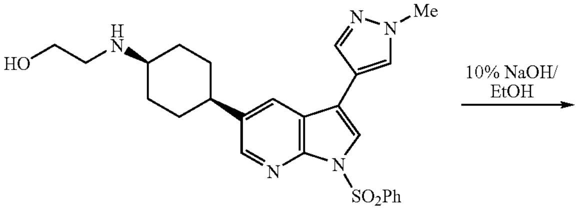

(IIb-130)

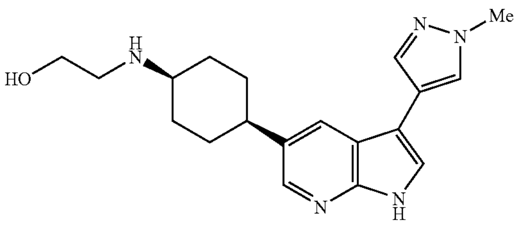

(I-130)

Cis isomer (IIb-130) was deprotected as described in the general procedure A for the deprotection of 7-azaindoles. Thus, (IIb-130) (39.7 mg, 0.08 mmol) was dissolved in ethanol (5.0 mL). 10% solution of NaOH (1.0 mL) was added and the reaction was heated to 90° C. for 1.1 h. It was allowed to cool down, filtered and purified by LCMS (column LUNA 10μ C18(2) 00G-4253-V0 250×50 mm) using water—MeCN (0.1% AcOH) as eluent (in gradient; flow 80 mL/min) to afford (I-130) (34.0 mg, 99%) as an oil. $^1$H NMR (400 MHz, $CDCl_3$) δ 1.78-1.90 (m, 4H), 2.02-2.19 (m, 6H), 2.72-2.82 (m, 1H), 3.08-3.15 (m, 2H), 3.32-3.38 (m, 1H), 3.88-3.94 (m, 2H), 3.95 (s, 3H), 7.36 (s, 1H), 7.69 (s, 1H), 7.72 (s, 1H), 8.00 (d, J=1.8 Hz, 1H), 8.13 (s, 1H), 10.65 (bs, 1H).

2-(ethyl(4-(3-(1-methyl-1H-pyrazol-4-yl)-1H-pyrrolo[2,3-b]pyridin-5-yl)cyclohexyl)amino)ethanol (I-131)

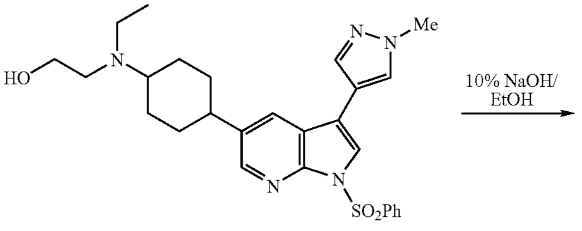

(IIb-131)

-continued

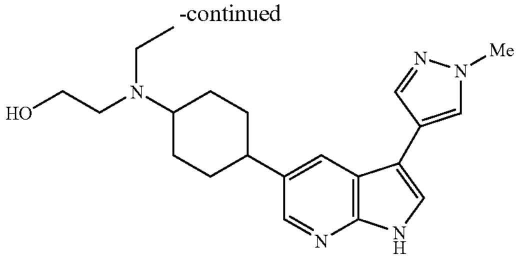

(I-131)

Cis isomer (IIb-131) was deprotected as described in the general procedure A for the deprotection of 7-azaindoles. Thus, (IIb-131) (101.8 mg, 0.20 mmol) was dissolved in ethanol (5.0 mL). 10% solution of NaOH (1.0 mL) was added and the reaction was heated to 90° C. for 1 h. It was allowed to cool down and diluted with EtOAc (20 mL). The mixture was washed with a saturated solution of $NaHCO_3$ (2×15 mL), dried over $MgSO_4$, concentrated and purified by LCMS (column LUNA 10μ C18(2) 00G-4253-V0 250×50 mm) using water—MeCN (0.1% AcOH) as eluent (in gradient; flow 80 mL/min) to afford (I-131) (37.2 mg, 50%), mixture of isomers, as an oil. Selected resonances in $^1$H NMR (400 MHz, $CDCl_3$) δ 1.20 (t, J=7.2 Hz, $CH_2CH_3$, minor), 1.31 (t, J=7.2 Hz, $CH_2CH_3$, major), 3.99 (s, 3H; minor), 4.00 (s, 3H; major).

N-ethyl-N-isopropyl-4-(3-(1-methyl-1H-pyrazol-4-yl)-1H-pyrrolo[2,3-b]pyridin-5-yl)cyclohexanamine (I-133)

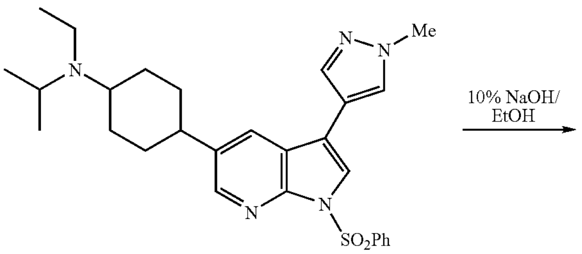

(IIb-133)

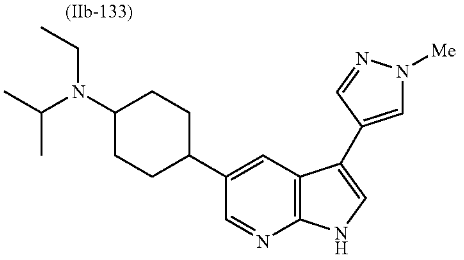

(I-133)

Azaindole (IIb-133) was deprotected as described in the general procedure A for the deprotection of 7-azaindoles. Thus, (IIb-133) (50.7 mg, 0.10 mmol) was dissolved in ethanol (5.0 mL). 10% solution of NaOH (1.0 mL) was added and the reaction was heated to 90° C. for 1 h. It was allowed to cool down and diluted with EtOAc (20 mL). The mixture was washed with a saturated solution of $NaHCO_3$ (2×15 mL), dried over $MgSO_4$ and concentrated to afford (I-133) (21.6 mg, 57%), mixture of isomers, a yellow oil. Selected resonances from $^1$H NMR (400 MHz, $CDCl_3$) δ 3.99 (s, 3H;

minor), 4.00 (s, 3H; major), 7.36 (d, J=1.8 Hz, 1H; major), 7.62 (s, 1H; major), 7.75 (s, 1H; major), 7.86 (d, J=1.8 Hz, 1H; major), 8.21 (d, J=1.8 Hz, 1H; major), 9.40 (bs, major).

5-(bicyclo[2.2.1]hept-2-en-2-yl)-3-(1-methyl-1H-pyrazol-4-yl)-1H-pyrrolo[2,3-b]pyridine (I-136)

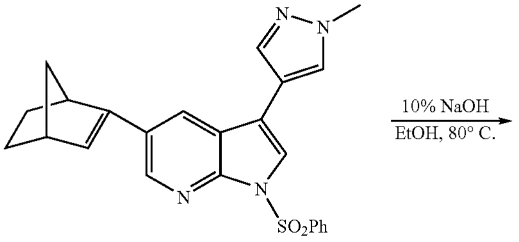

(IIa-136)

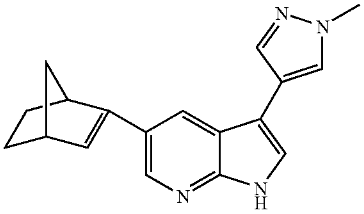

(I-136)

5-(bicyclo[2.2.1]hept-2-en-2-yl)-3-(1-methyl-1H-pyrazol-4-yl)-1-(phenylsulfonyl)-1H-pyrrolo[2,3-b]pyridine 2 (63 mg, 0.146 mmol) in EtOH (1.50 mL) and 10% aqueous NaOH (0.75 mL), was deprotected as described in the general procedure A for the deprotection of 7-azaindoles by refluxing for 20 min. The reaction was quenched by addition of a saturated solution of $NaHCO_3$ (15 mL) and the mixture was stirred for 20 minutes. It was extracted with EtOAc (3×15 mL). The combined organic extracts were dried over $MgSO_4$ and concentrated. The crude product purified by PTLC using EtOAc as the eluent to give (I-136) (24.8 mg, 58%). $^1H$ NMR (400 MHz, $CDCl_3$) δ 1.16-1.25 (m, 2H), 1.32 (d, J=8.2 Hz, 1H), 1.59-1.63 (m, 1H), 1.80-1.89 (m, 2H), 3.04-3.08 (m, 1H), 3.42-3.45 (br s, 1H), 4.01 (s, 3H), 6.35 (d, J=3.1 Hz, 1H), 7.39 (d, J=2.3 Hz, 1H), 7.64 (s, 1H), 7.78 (d, J=0.5 Hz, 1H), 8.04 (d, J=2.0 Hz, 1H), 8.49 (d, J=2.0 Hz, 1H), 10.09 (br s, NH, 1H).

5-(bicyclo[2.2.1]heptan-2-yl)-3-(1-methyl-1H-pyrazol-4-yl)-1H-pyrrolo[2,3-b]pyridine (I-137)

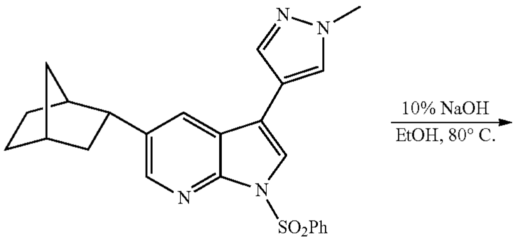

(IIb-137)

-continued

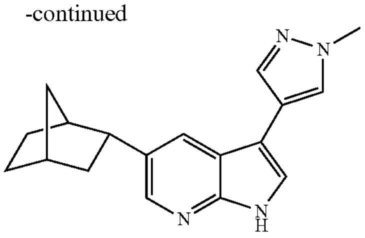

(I-137)

Compound (IIb-137) (0.46 g, 1.06 mmol) in EtOH (21.2 mL) and 10% aqueous NaOH (10.6 mL), was deprotected as described in the general procedure A for the deprotection of 7-azaindoles by refluxing for 20 mins. The reaction was quenched by addition of water (50 mL) and the mixture was extracted with EtOAc (3×70 mL). The combined organic extracts were dried over $MgSO_4$ and concentrated. The crude product purified by SGC using EtOAc:hexane as eluent (gradient elution, from 0:100 to 100:0, v/v) to give (I-137) (0.19 g, 63%) as a white solid. $^1H$ NMR (400 MHz, $CDCl_3$) δ 1.26-1.36 (m, 3H), 1.48-1.56 (m, 2H), 1.56-1.63 (m, 1H), 1.63-1.68 (m, 1H), 2.06-2.15 (m, 1H), 2.40 (t, J=4.2 Hz, 1H), 2.50 (br s, 1H), 3.36-3.43 (m, 1H), 4.01 (s, 3H), 7.39 (d, J=2.3 Hz, 1H), 7.62 (s, 1H), 7.78 (d, J=0.7 Hz, 1H), 7.89 (d, J=1.8 Hz, 1H), 8.25 (d, J=2.0 Hz, 1H), 9.65 (br s, NH, 1H).

3-(1-methyl-1H-pyrazol-4-yl)-5-((1R)-1,7,7-trimethylbicyclo[2.2.1]hept-2-en-2-yl)-1H-pyrrolo[2,3-b]pyridine (I-138)

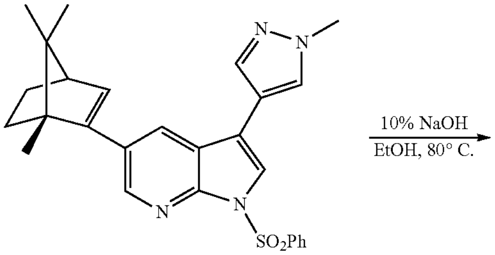

(IIa-138)

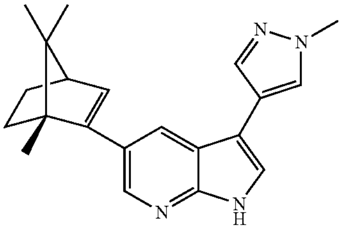

(I-138)

Compound (IIa-138) (32 mg, 0.068 mmol) in EtOH (1.0 mL) and 10% aqueous NaOH (0.5 mL), was deprotected as described in the general procedure A for the deprotection of 7-azaindoles by refluxing for 20 mins. The reaction was quenched by addition of water (15 mL) and was extracted with EtOAc (3×15 mL). The combined organic extracts were dried over $MgSO_4$ and concentrated. The crude product purified by PTLC using EtOAc as the eluent to give (I-138) (11.4 mg, 50%) as a white solid. $^1H$ NMR (400 MHz, $CDCl_3$) δ

0.87 (s, 3H), 0.96 (s, 3H), 1.13 (s, 3H), 1.14-1.19 (m, 1H), 1.32-1.40 (m, 1H), 1.68-1.76 (m, 1H), 1.95-2.03 (m, 1H), 2.44 (t, J=3.4 Hz, 1H), 4.01 (s, 3H), 6.06 (d, J=3.3 Hz, 1H), 7.35 (d, J=2.4 Hz, 1H), 7.61 (s, 1H), 7.77 (s, 1H), 7.87 (d, J=1.8 Hz, 1H), 8.26 (d, J=2.0 Hz, 1H), 8.82 (br s, NH, 1H).

5-(bicyclo[2.2.1]heptan-2-yl)-3-(1-methyl-1H-pyrazol-4-yl)-1H-pyrrolo[2,3-b]pyridine (I-139)

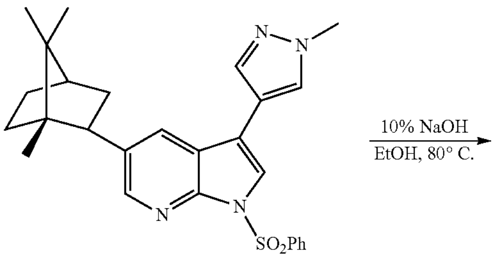

(IIb-139)

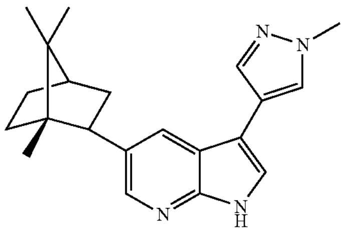

(I-139)

Compound (IIb-139) (45 mg, 0.095 mmol) in EtOH (2.0 mL) and 10% aqueous NaOH (1.0 mL), was deprotected as described in the general procedure A for the deprotection of 7-azaindoles by refluxing for 20 mins. The reaction was quenched by addition of water (10 mL) and was extracted with EtOAc (3x10 mL). The combined organic extracts were dried over $MgSO_4$ and concentrated. The crude product purified by PTLC using EtOAc as the eluent to give (I-139) as a white solid (18 mg, 57%). Compound is a 1.2:1 mixture of diastereoisomers $^1$H NMR (400 MHz, $CDCl_3$) δ 0.77 (s, 3H, minor), 0.81 (s, 3H, minor), 0.87 (s, 3H, major), 0.89 (s, 3H, major), 0.98 (s, 3H, minor), 1.09 (s, 3H, major), 1.34-1.46 (m, 5H), 1.57-1.63 (dd, J=5.2 and 13.2 Hz, 1H), 1.67-1.80 (m, 2H), 1.81-1.94 (m, 4H), 2.25 (tt, J=3.8 and 12.2 Hz, 1H), 2.38-2.45 (m, 1H), 3.08 (t, J=8.6 Hz, 1H), 3.20-3.26 (m, 1H), 4.01 (2xs, 2x3H), 7.37 (s, 1H, major), 7.39 (s, 1H, minor), 7.59 (s, 1H, major), 7.62 (s, 1H, minor), 7.76 (d, J=0.5 Hz, 1H, major), 7.78 (d, J=0.5 Hz, 1H, minor), 7.92 (d, J=1.6 Hz, 1H, minor), 7.98 (d, J=1.4 Hz, 1H, major), 8.20 (s, 1H, minor), 8.27 (s, 1H, major), 9.70 (br s, NH, 1H, major), 9.73 (br s, NH, 1H, minor).

(5-(3-(1-methyl-1H-pyrazol-4-yl)-1H-pyrrolo[2,3-b]pyridin-5-yl)bicyclo[2.2.1]heptane-2,3-diyl)dimethanol (I-140)

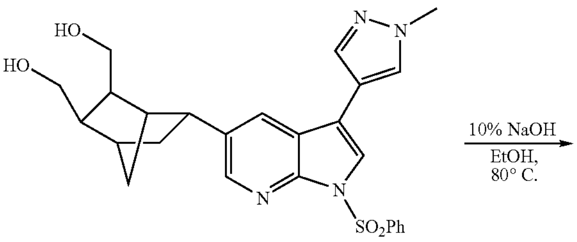

(IIb-140)

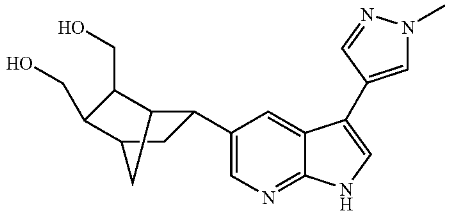

(I-140)

Compound (IIb-140) (31 mg, 0.063 mmol) in EtOH (2.0 mL) and 10% aqueous NaOH (1.0 mL), was deprotected as described in the general procedure A for the deprotection of 7-azaindoles by refluxing for 20 min. The reaction was quenched by addition of water (10 mL) and was extracted with EtOAc (3x10 mL). The combined organic extracts were dried over $MgSO_4$ and concentrated. The crude product purified by PTLC using $CH_2Cl_2$:MeOH=5:1 (v/v) as the eluent to give (I-140) (10.5 mg, 47%) as a white solid; $^1$H NMR (400 MHz, $CDCl_3$) δ 1.47 (d, J=9.9 Hz, 1H), 1.59 (dt, J=4.8 and 13.5 Hz, 1H), 1.68 (d, J=9.90 Hz, 1H), 1.96-2.05 (m, 1H), 2.30-2.43 (m, 2H), 2.46 (br s, 2H), 3.05 (t, J=7.3 Hz, 1H), 3.69-3.74 (dd, J=3.2 and 11 Hz, 2H), 3.78-3.83 (dd, J=3.2 and 11 Hz, 2H), 3.98 (s, 3H), 4.00 (t, J=10.4 Hz, 1H), 4.18 (t, J=10.4 Hz, 1H), 7.33 (s, 1H), 7.58 (s, 1H), 7.72 (s, 1H), 7.82 (s, 1H), 8.10 (d, J=1.2 Hz, 1H), 9.93 (br s, 1H).

5-(7,7-dimethylbicyclo[4.1.0]hept-2-en-2-yl)-3-(1-methyl-1H-pyrazol-4-yl)-1H-pyrrolo[2,3-b]pyridine (I-141)

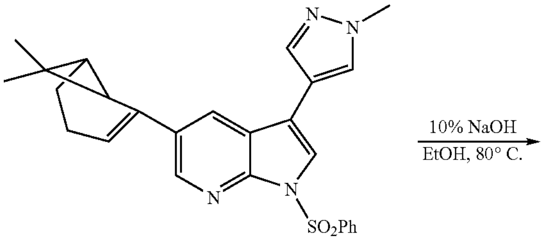

(IIa-141)

-continued

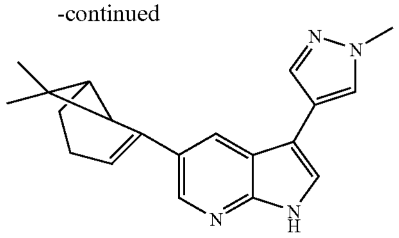

(I-141)

Compound (IIa-141) (41 mg, 0.089 mmol) in EtOH (1.80 mL) and 10% aqueous NaOH (0.90 mL), was deprotected as described in the general procedure A for the deprotection of 7-azaindoles by refluxing for 20 mins. The crude product purified by PTLC using EtOAc as the eluent to give (I-141) (21.2 mg, 75%) as a pale white solid. $^1$H NMR (400 MHz, $CDCl_3$) δ 0.97 (s, 3H), 1.40 (d, J=8.8 Hz, 1H), 1.41 (s, 3H), 2.19-2.21 (m, 1H), 2.47 (t, J=3.0 Hz, 1H), 2.50 (t, J=3.0 Hz, 1H), 2.60 (dd, J=5.5 and 14.4 Hz, 1H), 2.77 (td, J=1.5 and 5.6 Hz, 1H), 4.01 (s, 3H), 5.90-5.93 (m, 1H), 7.41 (d, J=2.1 Hz, 1H), 7.63 (s, 1H), 7.78 (d, J=0.5 Hz, 1H), 7.94 (d, J=1.9 Hz, 1H), 8.37 (d, J=2.0 Hz, 1H), 10.47 (br s, NH, 1H).

5-(7,7-dimethylbicyclo[4.1.0]heptan-2-yl)-3-(1-methyl-1H-pyrazol-4-yl)-1H-pyrrolo[2,3-b]pyridine (I-142)

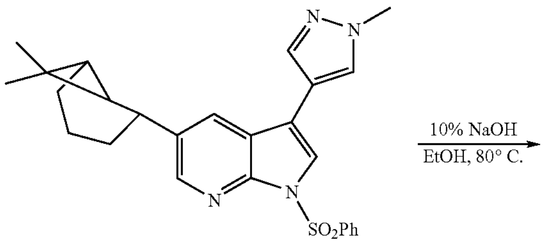

(IIb-142)

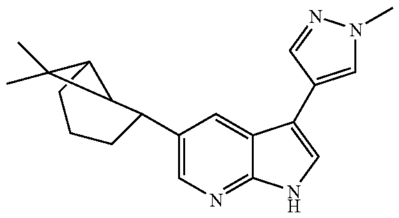

(I-142)

Compound (IIb-142) (0.18 g, 3.93 mmol) in EtOH (4.0 mL) and 10% aqueous NaOH (2.0 mL), was deprotected as described in the general procedure for the deprotection of 7-azaindoles by refluxing for 20 mins. The crude product purified by PTLC using EtOAc as the eluent to give (I-142) (89 mg, 71%) as a pale white solid. $^1$H NMR (400 MHz, $CDCl_3$) δ 0.93 (s, 3H), 1.19 (d, J=9.7 Hz, 1H), 1.35 (s, 3H), 1.99-2.11 (m, 4H), 2.44-2.60 (m, 2H), 2.63-2.67 (m, 1H), 3.57-3.65 (m, 1H), 4.00 (s, 3H), 7.38 (d, J=2.2 Hz, 1H), 7.61 (s, 1H), 7.77 (s, 1H), 7.90 (d, J=1.2, 1H), 8.26 (d, J=1.9 Hz, 1H), 9.64 (br s, NH, 1H).

3-(1-methyl-1H-pyrazol-4-yl)-5-(8-methyl-8-azabicyclo[3.2.1]oct-3-en-3-yl)-1H-pyrrolo[2,3-b]pyridine (I-143)

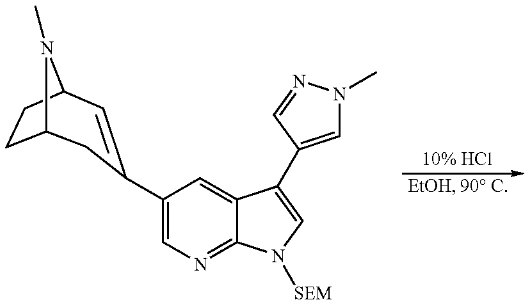

(IIa-143)

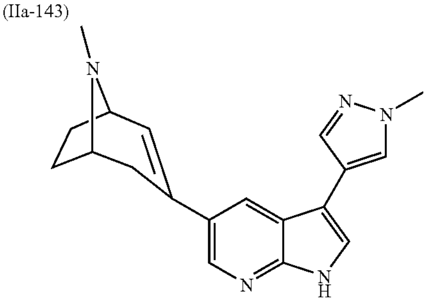

(I-143)

A mixture of compound (IIa-143) (53 mg, 0.12 mmol) and 10% HCl (1.10 mL) in EtOH (1.10 mL) was stirred at 90° C. overnight. The reaction was allowed to cool to RT and was poured slowly into a saturated solution of $NaHCO_3$ (20 mL). The mixture was extracted with $CH_2Cl_2$ (4×20 mL). The combined organic extracts were dried ($MgSO_4$) and concentrated. The residue was purified by LCMS (column LUNA 10μ, C18(2) 00G-4253-V0 250×50 mm) using water—MeCN (0.1% AcOH) as eluent (in gradient; flow 80 mL/min) to afford (I-143) (13 mg, 34%) as a yellow solid. δ $^1$H NMR (400 MHz, $CDCl_3$) δ 1.70-1.79 (m 1H), 1.99-2.04 (m, 1H), 2.18-2.38 (m, 2H), 2.54 (s, 3H), 3.03 (d, J=14.2 Hz, 2H), 3.613742 (s, 1H), 7.62 (s, 1H), 7.76 (s, 1H), 7.99 (d, J=2.1 Hz, 1H), 8.38 (d, J=2.1 Hz, 1H), 9.33 (br s, NH, 1H); MS (CI) m/z 320.1 ($MH^+$).

7-(3-(1-methyl-1H-pyrazol-4-yl)-1H-pyrrolo[2,3-b]pyridin-5-yl)bicyclo[3.3.1]non-6-en-3-one (I-145)

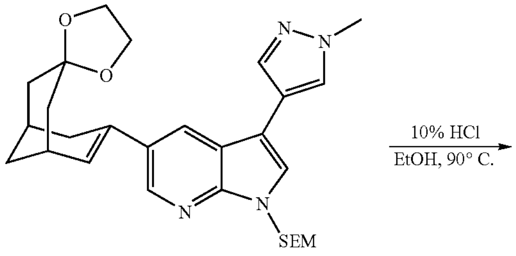

(IIa-144)

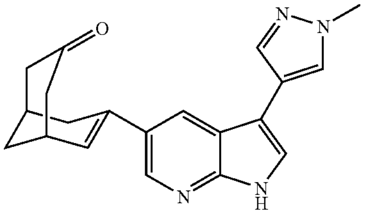

(I-145)

A mixture of (IIa-144) (0.46 g, 0.90 mmol) and 10% HCl (9.0 mL) in EtOH (9.0 mL) was stirred at 90° C. overnight. The mixture was allowed to cool to RT and was poured slowly into a saturated solution of $NaHCO_3$ (50 mL). It was then extracted with $CH_2Cl_2$ (4×50 mL). The combined organic extracts were dried ($MgSO_4$) and concentrated. The residue was triturated with MeOH and the solid was filtered of to give (I-145) (0.26 g, 87%) as a yellow solid. $^1H$ NMR (400 MHz, $CDCl_3$) δ 2.15 (br s, 1H), 2.40-2.53 (m, 3H), 2.56-2.69 (m, 2H), 2.79-2.93 (m, 2H), 2.95-3.00 (br s, 1H), 4.01 (s, 3H), 6.12-6.14 (m, 1H), 7.37(s, 1H), 7.63 (s, 1H), 7.74 (d, J=0.6 Hz, 1H), 7.92 (d, J=1.7 Hz, 1H), 8.35 (d, J=2.1 Hz, 1H), 9.37 (br s, NH, 1H).

7-(3-(1-methyl-1H-pyrazol-4-yl)-1H-pyrrolo[2,3-b]pyridin-5-yl)bicyclo[3.3.1]non-6-en-3-ol (I-146) and (I-147)

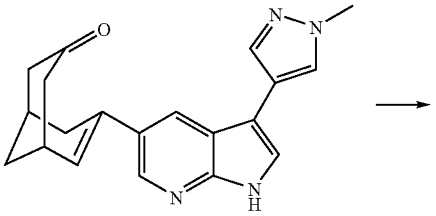

(I-145)

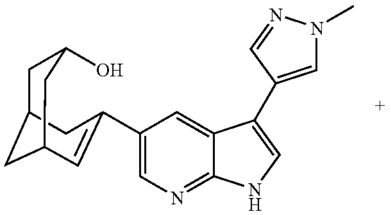

(I-146)

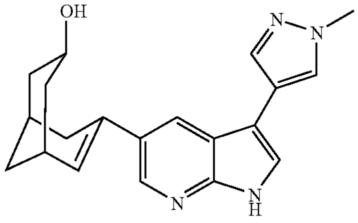

(I-147)

A solution of HCl (0.90 mL, 1.25 M in MeOH, 1.13 mmol) in MeOH was added dropwise via syringe into a 2.0 M solution of methylamine in THF (3.76 mL, 7.52 mmol) at RT under nitrogen and was stirred for 10 minutes. This solution was then added via syringe into a solution of ketone (I-145) (0.125 g, 0.38 mmol) in THF/MeOH/DCE=1:1:1 (6 mL, v/v/v). The mixture was stirred at RT for 1 hr. Solid $NaCNBH_3$ (0.047 g, 0.75 mmol) was added in one portion. The reaction was stirred at RT overnight. A saturated solution of $NaHCO_3$ (30 mL) was added and the mixture was extracted with EtOAc (4×30 mL). The combined organic extracts were dried ($MgSO_4$) and concentrated. The residue was purified by LCMS (column LUNA 10μ C18(2) 00G-4253-V0 250×50 mm) using water—MeCN (0.1% AcOH) as eluent (in gradient; flow 80 mL/min) to afford the trans alcohol (I-147) (3 mg, 2.4%; retention time 17.08 min.) and cis alcohol (I-146) (42 mg, 34%; retention time 18.8-19.5 min). None of the desired amines (I-150) and (I-151) could be isolated.

Data for cis alcohol (I-146) $^1H$ NMR (400 MHz, $CDCl_3$) δ 1.70 (d, J=12.2 Hz, 1H), 1.85 (t, J=4.2 Hz, 1H), 1.89 (t, J=4.2 Hz, 1H), 2.04-2.12 (m, 3H), 2.45-2.51 (br s, 1H), 2.61-2.67 (br s, 1H), 2.76-2.78 (br s, 1H), 2.83 (d, J=6.89 Hz, 1H), 4.01 (s, 3H), 4.02-4.06 (m, 1H), 6.57 (d, J=5.7 Hz, 1H), 7.38 (s, 1H), 7.64 (s, 1H), 7.75 (d, J=0.6 Hz, 1H), 8.02 (d, J=2.1 Hz, 1H), 8.43 (d, J=2.1 Hz, 1H), 9.43 (br s, NH, 1H); MS (CI) m/z 335.1 ($MH^+$).

Data for trans alcohol (I-147) $^1H$ NMR (400 MHz, $CDCl_3$) δ 1.43 (td, J=3.5 and 11.6 Hz, 1H), 1.57 (td, J=3.5 and 11.6 Hz, 1H), 1.67 (d, J=12.1 Hz, 1H), 1.76-1.82 (m, 1H), 2.05-2.13 (m, 3H), 2.47-2.52 (m, 1H), 2.64-2.71 (m, 1H), 2.77-2.85 (dd, J=7.0 and 18.5 Hz, 1H), 4.01 (s, 3H), 4.00-4.09 (m, 1H), 6.23 (d, J=6.3 Hz, 1H), 7.36 (s, 1H), 7.64 (s, 1H), 7.76 (d, J=0.6 Hz, 1H), 8.0 (d, J=2.0 Hz, 1H), 8.34 (d, J=2.1 Hz, 1H), 9.65 (br s, NH, 1H); MS (CI) m/z 335.1 ($MH^+$).

Cis-3-(1-methyl-1H-pyrazol-4-yl)-5-(7-(4-methylpiperazin-1-yl)bicyclo[3.3.1]non-2-en-3-yl)-1H-pyrrolo[2,3-b]pyridine (I-148) and trans-3-(1-methyl-1H-pyrazol-4-yl)-5-(7-(4-methylpiperazin-1-yl)bicyclo[3.3.1]non-2-en-3-yl)-1H-pyrrolo[2,3-b]pyridine (I-149)

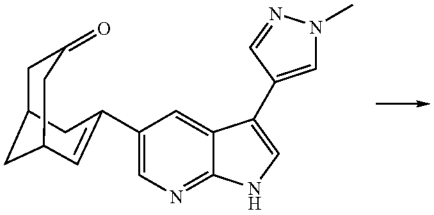

(I-145)

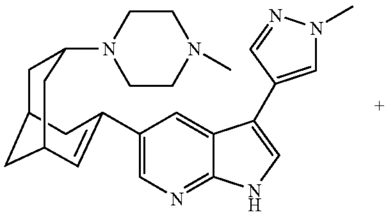

(I-148)

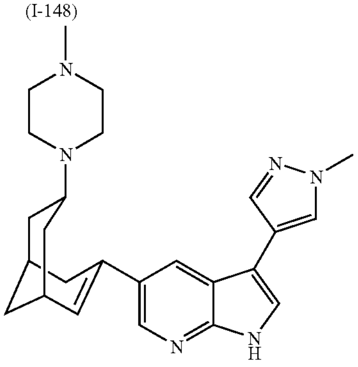

(I-149)

Ketone (I-145) (60 mg, 0.18 mmol), N-methylpiperazine (0.18 g, 1.80 mmol), 1.25 M HCl in MeOH (0.43 mL, 0.54 mmol) and $NaCNBH_3$ (12 mg, 0.36 mmol) in anhydrous MeOH (1.80 mL): THF (0.5 mL) were reacted following the general procedure A for the reductive amination. The crude product was purified by LCMS (column LUNA 10μ C18(2) 00G-4253-V0 250×50 mm) using water—MeCN (0.1% AcOH) as eluent (in gradient; flow 80 mL/min) to afford the trans isomer (I-149) (4.6 mg, 6%; retention time 11.8-12.3 min) and the cis isomer (I-148) (4 mg, 5%; retention time 12.4-12.7 min.). Data for cis isomer (I-148): $^1$H NMR (400 MHz, $CDCl_3$) δ 1.41-1.54 (m, 2H), 1.59-1.70 (m, 2H), 1.78 (d, J=12.2 Hz, 2H), 1.87-1.97 (m, 2H), 2.28 (s, 3H), 2.42-2.52 (m, 4H), 2.56-2.66 (br m, 4H), 2.67-2.72 (m, 1H), 2.74-2.86 (m, 2H), 4.01 (s, 3H), 6.21 (d, J=6.5 Hz, 1H), 7.36 (d, J=2.2 Hz, 1H), 7.65 (s, 1H), 7.76 (d, J=0.6 Hz, 1H), 8.00 (d, J=1.9 Hz, 1H), 8.41 (d, J=1.8 Hz, 1H), 9.08 (br s, NH, 1H); MS (CI) m/z 417.2 ($MH^+$).

Data for trans isomer (I-149): $^1$H NMR (400 MHz, $CDCl_3$) δ 1.42-1.51 (m, 2H), 1.53-1.60 (dd, J=8.9 and 13.3 Hz, 1H), 1.64-1.71 (m, 1H), 1.76-1.81 (m, 1H), 1.95-2.03 (dd, J=6.6 and 13.1 Hz, 1H), 2.08-2.17 (m, 1H), 2.36 (s, 3H), 2.38-2.71 (m, 12H), 4.00 (s, 3H), 6.24 (d, J=5.9 Hz, 1H), 7.36 (s, 1H), 7.65 (s, 1H), 7.77 (d, J=0.6 Hz, 1H), 7.99 (d, J=2.0 Hz, 1H), 8.37 (d, J=2.0 Hz, 1H), 9.55 (br s, NH, 1H); MS (CI) m/z 417.2 ($MH^+$).

Cis N-methyl-7-(3-(1-methyl-1H-pyrazol-4-yl)-1H-pyrrolo[2,3-b]pyridin-5-yl)bicyclo[3.3.1]non-6-en-3-amine (I-150) and trans N-methyl-7-(3-(1-methyl-1H-pyrazol-4-yl)-1H-pyrrolo[2,3-b]pyridin-5-yl)bicyclo[3.3.1]non-6-en-3-amine (I-151)

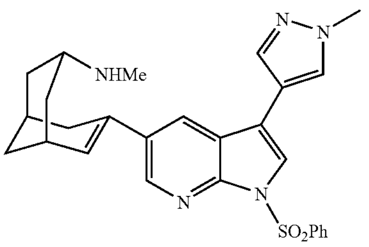

(IIa-150)

+

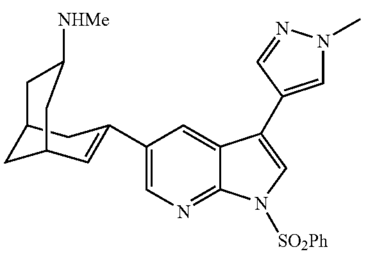

(IIa-151)

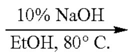

-continued

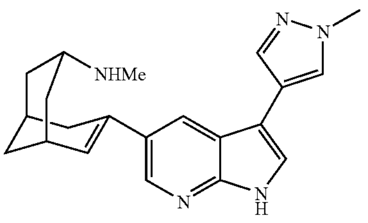

(I-150)

+

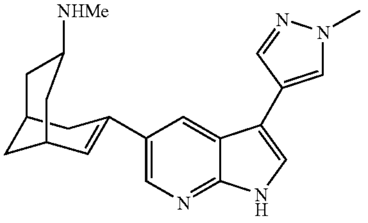

(I-151)

A 2:1 trans:cis mixture of amines (IIa-151) and (IIa-150) (22 mg, 45 μmol) in EtOH (1.0 mL) and 10% aqueous NaOH (0.5 mL), was deprotected as described in the general procedure A for the deprotection of 7-azaindoles by refluxing for 20 mins. The crude product was purified by PTLC using $CHCl_3$:MeOH:$NH_4OH$=83:15:2 (v/v/v) as the eluent to give cis isomer (I-150) (2.29 mg, 14%) as a yellow solid and the trans isomer (I-151) (9 mg, 58%) as a yellow solid.

Data for cis isomer (I-150) $^1$H NMR (400 MHz, $CDCl_3$) δ 1.24-1.28 (d, J=5.3 Hz, 1H), 1.69-1.89 (m, 3H), 1.96-2.08 (m, 2H), 2.37 (s, 3H), 2.41-2.48 (m, 1H), 2.58-2.65 (m, 2H), 2.79 (d, J=6.8 Hz, 1H), 2.82-2.87 (m, 1H), 4.01 (s, 3H), 6.44 (d, J=6.3 Hz, 1H), 7.34 (s, 1H), 7.71 (s, 1H), 7.74 (s, 1H), 8.01 (d, J=2.0 Hz, 1H), 8.38 (d, J=1.9 Hz, 1H), 9.20 (br s, NH, 1H).

Data for trans isomer (I-151) $^1$H NMR (400 MHz, $CDCl_3$) δ 1.26-1.36 (td, J=3.4 and 12.3 Hz, 1H), 1.38-1.47 (td, J=3.4 and 12.3 Hz, 1H), 1.63-1.72 (m, 2H), 1.81 (d, J=12.0 Hz, 1H), 2.01-2.11 (m, 2H), 2.43 (s, 3H), 2.43-2.48 (m, 1H), 2.64-2.70 (br s, 1H), 2.78-2.88 (m, 2H), 4.01 (s, 3H), 6.24 (d, J=6.2 Hz, 1H), 7.40 (s, 1H), 7.64 (s, 1H), 7.77 (s, 1H), 8.02 (d, J=2.1 Hz, 1H), 8.42 (d, J=1.9 Hz, 1H), 9.91 (br s, NH, 1H).

Azaadamantane derivative (I-153)

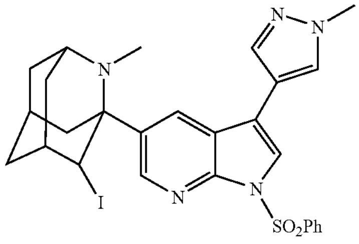

(IIb-152)

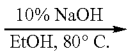

-continued

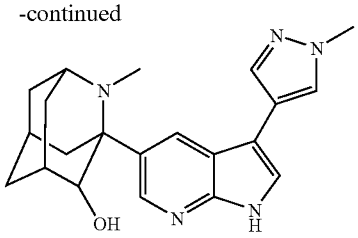

(I-153)

Compound (IIb-152) (9.5 mg, 15.5 μmol) in EtOH (0.6 mL) and 10% aqueous NaOH (0.3 mL), was deprotected and transformed into (I-153) under the conditions described in the general procedure for the deprotection of 7-azaindoles by refluxing for 20 mins. The crude product was purified by PTLC using $CHCl_3$:MeOH:$NH_4OH$=90:8:2 (v/v/v) as the eluent to give (I-153) (3.2 mg, 57%) as a white solid. $^1H$ NMR (400 MHz, $CDCl_3$) δ 1.41 (d, J=12.0 Hz, 1H), 1.66 (d, J=11.7 Hz, 1H), 1.96 (d, J=11.8 Hz, 1H), 2.14 (s, 3H), 2.17-2.37 (m, 7H), 3.00 (br s, 1H), 4.01 (s, 3H), 4.14 (br s, 1H), 7.34 (s, 1H), 7.64 (s, 1H), 7.73 (s, 1H), 8.02 (br s, 1H), 8.45 (br s, 1H), 9.45 (br s, 1H); MS (CI) m/z 364.3 ($MH^+$).

3-(1-Methyl-1H-pyrazol-4-yl)-5-tricyclo[3.3.1.1~3,7~]dec-2-yl-1H-pyrrolo[2,3-b]pyridine (I-154)

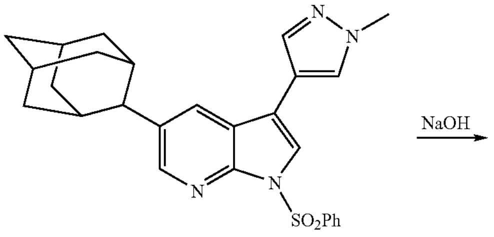

(IIb-154)

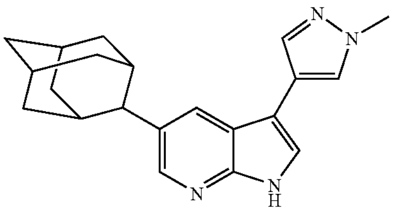

(I-154)

Crude compound (IIb-154) (35.8 mg) in EtOH (5 mL) and 10% aqueous NaOH (1.0 mL), was deprotected and transformed into (I-154) under the conditions described in the general procedure for the deprotection of 7-azaindoles by stirring at 90° C. for 45 min. The crude product was purified by PTLC using $CH_2Cl_2$:MeOH=97:3 (v/v) to afford (I-154) (18 mg. 23% for 2 steps) as an off-white solid; $^1H$ NMR (400 MHz, $CDCl_3$) δ 1.23-1.29 (m, 2H), 1.59-1.65 (m, 2H), 1.78-1.85 (m, 2H), 1.88-1.95 (m, 2H), 1.98-2.10 (m, 4H), 2.54-2.59 (m, 2H), 3.19-3.23 (m, 1H), 3.98 (s, 3H), 7.37 (s, 1H), 7.60 (s, 1H), 7.76 (s, 1H), 8.02 (s, 1H), 8.37 (d, J=1.9 Hz, 1H), 9.67 (brs, NH).

(1R,2S,4R)-5-(3-(1-methyl-1H-pyrazol-4-yl)-1H-pyrrolo[2,3-b]pyridin-5-yl)-7-oxabicyclo[2.2.1]hept-5-ene-2-carbonitrile endo-(I-155), (1R,2R,4R)-5-(3-(1-methyl-1H-pyrazol-4-yl)-1H-pyrrolo[2,3-b]pyridin-5-yl)-7-oxabicyclo[2.2.1]hept-5-ene-2-carbonitrile exo-(I-155) and (1R,4R)-5-(3-(1-methyl-1H-pyrazol-4-yl)-1H-pyrrolo[2,3-b]pyridin-5-yl)-7-oxabicyclo[2.2.1]hept-5-ene-2-carboxamide (I-156)

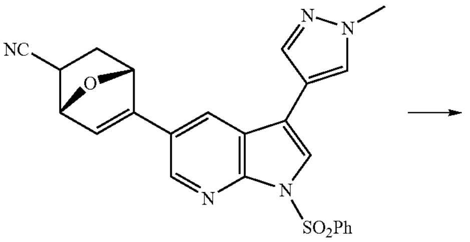

(IIa-155)

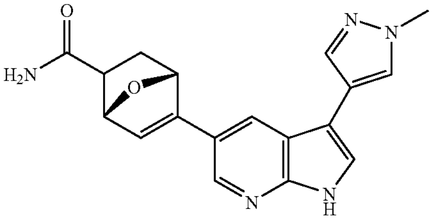

+

(I-156)

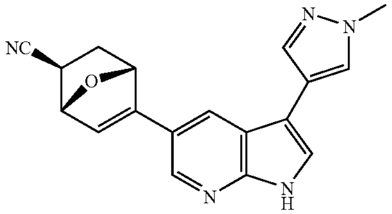

+ exo-(I-155)

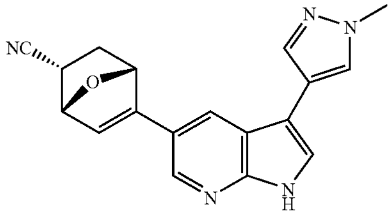

endo-(I-155)

Compound (IIa-155) (195 mg, 0.43 mmol, approx 1:1 mixture of exo/endo) in EtOH (4.0 mL) and 10% aqueous NaOH (2.0 mL), was deprotected and partially transformed into (I-156) under the conditions described in the general procedure for the deprotection of 7-azaindoles by refluxing for 30 mins. The crude product (84 mg, oil) was purified by LCMS (column LUNA 10μ C18(2) 00G-4253-V0 250×50 mm) using water—MeCN (0.1% AcOH) as eluent (in gradient; flow 80 mL/min). Eluting first, with $MH^+$ 336 was (I-156) (15.6 mg, 47 μmol, 11%, approx. 3:2 exo:endo). $^1H$ NMR (400 MHz, $CDCl_3$) δ 1.62 (dd, J=4.0, 11.4 Hz, 1H, minor isomer), 1.81 (dd, J=9.2, 11.4 Hz, 1H, major isomer), 2.05-2.14 (m, 1H, minor isomer), 2.21 (ddd, J=4.6, 10.4, 14.0 Hz, 1H, minor isomer), 2.47 (dd, J=3.0, 8.5 Hz, 1H, major isomer), 3.15-3.22 (m, 1H, major isomer), 3.94 (s, 3H), 5.19 (s, 1H, major isomer), 5.23 (d, J=2.2 Hz, 1H, major isomer), 5.45 (d, J=4.5 Hz, 1H, minor isomer), 5.53 (d, J=4.3 Hz, 1H, major isomer), 6.47 (s, 1H, minor isomer), 6.50 (s, 1H, major isomer), 7.34 (s, 1H, minor isomer), 7.36 (s, 1H, major isomer), 7.60-7.70 (m, 2H), 7.96 (s, 1H, major isomer), 7.99 (s, 1H, minor isomer), 8.27 (s, 1H). Next to elute, with $MH^+$ 318, was endo-(I-155) (9.4 mg, 30 μmol, 7%). $^1$H NMR (400 MHz, $CDCl_3$) δ 1.73 (dd, J=3.6, 11.6 Hz, 1H), 2.50 (dt, J=4.5, 14.0 Hz, 1H), 3.17 (dt, J=4.5, 9.5 Hz, 1H), 4.03 (s, 3H), 5.41 (d, J3.0 Hz, 1H), 5.64 (d, J=4.5 Hz, 1H), 6.73 (s, 1H), 7.45 (s, 1H), 7.65 (s, 1H), 7.78 (s, 1H), 7.69 (s, 1H), 8.08 (s, 1H), 8.45 (s, 1H), 10.31 (br s, 1H). Last to elute was exo-(I-155) (5.1 mg, 16 μmol, 4%). $^1$H NMR (400 MHz, $CDCl_3$) δ 1.84 (dd, J=8.6, 11.7 Hz, 1H), 2.25 (dt, J=4.2, 11.6 Hz, 1H), 2.58 (dd, J=3.8, 8.5 Hz, 1H), 3.93 (s, 3H), 5.34 (d, J 1.1 Hz, 1H), 5.59 (d, J=4.6 Hz, 1H), 6.44 (d, J=1.4 Hz, 1H), 7.33 (s, 1H), 7.56 (s, 1H), 7.66 (s, 1H), 7.69 (s, 1H), 7.92 (d, J=1.8 Hz, 1H), 8.24 (d, J=1.8 Hz, 1H).

(1R,4R,5S)-5-(3-(1-methyl-1H-pyrazol-4-yl)-1H-pyrrolo[2,3-b]pyridin-5-yl)-7-oxabicyclo[2.2.1]heptane-2-carbonitrile (I-157)

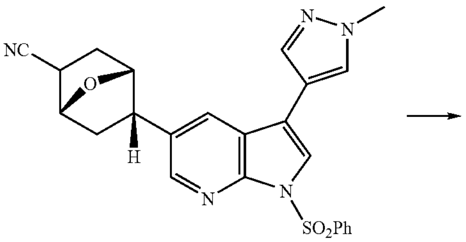

(IIb-157)

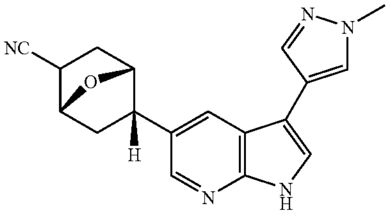

(I-157)

To a stirred solution of (IIb-157) (99 mg, 0.21 mmol, unassigned 2:1 mixture of isomers) in THF (2 mL) was added 1.0 M solution of $nBu_4NF$ in THF (1 mL, 1 mmol), and the solution was heated to reflux and stirred for 3 d. The reaction mixture was then cooled, diluted with EtOAc (100 mL) and extracted with saturated aqueous $NaHCO_3$ (2×40 mL). The organic portion was dried over $MgSO_4$ and concentrated to afford an oil (86 mg), which was purified by LCMS (column LUNA 10μ C18(2) 00G-4253-V0 250×50 mm) using water—MeCN (0.1% AcOH) as eluent (in gradient; flow 80 mL/min) to afford the (I-157) as an unnasigned 3:1 mixture of isomers. (41 mg, 0.13 mmol, 61%). $^1$H NMR (400 MHz, $CDCl_3$) δ 1.80-2.14 (m, 4H, both isomers), 2.35-2.53 (m, 2H, both isomers), 2.76 (dd, J=4.5, 9.1 Hz, 1H, minor isomer), 3.02-3.08 (m, 1H, major isomer), 3.73 (dt, J=5.7, 11.8 Hz, 1H, minor isomer), 3.83 (dt, J=5.7, 11.8 Hz, 1H, major isomer), 3.98 (s, 3H, major isomer), 4.02 (s, 3H, minor isomer), 4.77-4.81 (m, 1H, major isomer), 4.92-5.01 (m, 1H in major isomer & 2H in minor isomer), 7.46 (s, 1H, minor isomer), 7.52 (s, 1H, major isomer), 7.61 (s, 1H, minor isomer), 7.76 (s, 1H, minor isomer), 7.79 (s, 1H, major isomer), 7.82 (d, J=1.8 Hz, 1H, minor isomer), 7.97 (s, 1H, major isomer), 8.17 (d, J=1.9 Hz, 1H, minor isomer), 8.25 (d, J=2.0 Hz, 1H, major isomer), 8.26 (d, J=2.0 Hz, 1H, major isomer), 10.56 (br s, 1H).

4-((1s,4s)-4-fluoro-4-(3-(1-methyl-1H-pyrazol-4-yl)-1H-pyrrolo[2,3-b]pyridin-5-yl)cyclohexyl)morpholine (I-162)

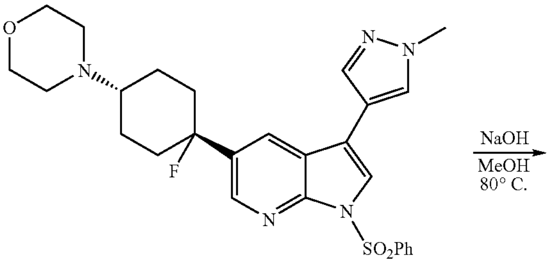

(IIb-162)

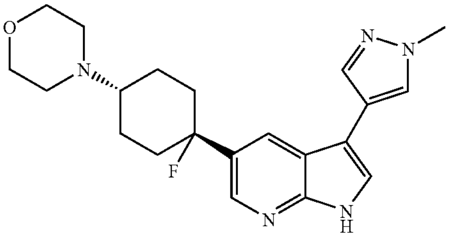

(I-162)

Compound (IIb-162) (25 mg, 0.05 mmol) in EtOH (1.0 mL) and 10% aqueous NaOH (0.5 mL), was deprotected under the conditions described in the general procedure for the deprotection of 7-azaindoles by heating to 80° C. for 20 min. The crude product was purified by PTLC using $CH_2Cl_2$:MeOH=9:1 (v/v) as the eluent to give a 1.3:1 mixture of product (I-162) and elimination product (I-75) as a yellow solid (7 mg, 38%). The mixture was purified further by PTLC using $CH_2Cl_2$:MeOH=95:5 (v/v) as the eluent (15 elutions) to give (I-162) as a yellow solid (2.5 mg, 11%) and the elimination product (I-75) (2.0 mg, 11%).

Data for compound (I-162): $^1$H NMR (400 MHz, $CDCl_3$) δ 1.50-1.78 (m, 2H), 1.83-1.91 (m, 2H), 1.91-2.04 (m, 3H), 2.24-2.37 (m, 2H), 2.45 (br s, 4H), 3.64-3.75 (br s, 4H), 4.01

(s, 3H), 7.39 (d, J=0.5 Hz, 1H), 7.64 (s, 1H), 7.77 (s, 1H), 8.14 (s, 1H), 8.47 (d, J=1.9 Hz, 1H), 9.11 (br s, NH, 1H).

4-((1s,4s)-4-methoxy-4-(3-(1-methyl-1H-pyrazol-4-yl)-1H-pyrrolo[2,3-b]pyridin-5-yl)cyclohexyl)morpholine (I-163)

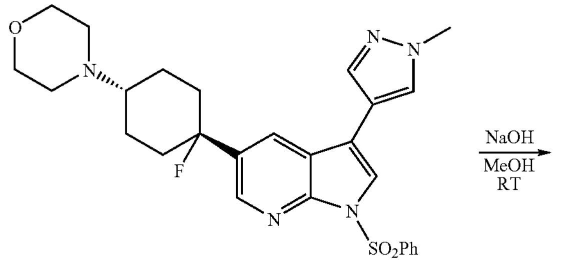

(IIb-162)

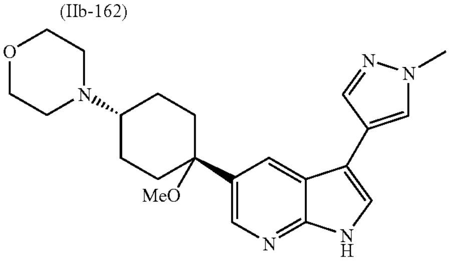

(I-163)

10% aqueous NaOH (0.72 mL, 1.80 mmol) was added to a solution of (IIb-162) (20.5 mg, 0.052 mmol) in MeOH (3.6 mL) and the reaction mixture was stirred at RT for 17 h. A saturated solution of $NaHCO_3$ (18 mL) was then added and the mixture extracted with EtOAc (3×27 mL). The combined organic extracts were dried over $MgSO_4$, filtered and concentrated in vacuo. The crude product was purified by PTLC using (v/v) as the eluent to give (I-163) as a white oil (9.0 mg, 44%); $R_f$=0.64 ($CH_2Cl_2$:MeOH=90:10); $^1$H NMR (400 MHz, $CDCl_3$) δ 1.54-1.67 (m, 2H), 1.82-2.02 (m, 5H), 2.28-2.36 (m, 1H), 2.39-2.55 (m, 5H), 2.98 (s, 3H), 3.70 (app. t, J=4.1 Hz, 4H), 4.01 (s, 3H), 7.45 (br s, 1H), 7.66 (s, 1H), 7.79 (s, 1H), 8.14 (d, J=1.8 Hz, 1H), 8.48 (d, J=1.9 Hz, 1H), 10.15 (br s, 1H).

4-((1s,4s)-1-methyl-4-(3-(1-methyl-1H-pyrazol-4-yl)-1H-pyrrolo[2,3-b]pyridin-5-yl)cyclohexyl)morpholine (I-165)

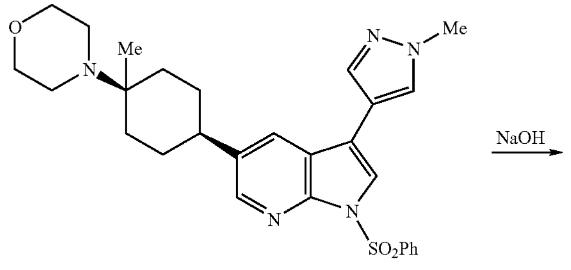

(IIb-165)

-continued

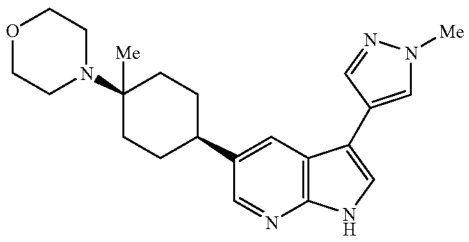

(I-165)

Compound cis (IIb-165) (135 mg, 259.8 μmol) in EtOH (1.2 mL) and 10% aqueous NaOH (1.0 mL), was deprotected and transformed into (I-165) under the conditions described in the general procedure for the deprotection of 7-azaindoles by heating at 85° C. for 2 h and worked up to produce (I-165) (90 mg, 91%), yellow oil; $^1$H NMR (400 MHz, $CDCl_3$) δ 0.92 (s, 3H), 1.33 (td, J=13.3, 2.4 Hz, 2H), 1.61 (dd, J=13.3, 2.4 Hz, 2H), 1.93-2.10 (m, 4H), 2.56 (t, J=3.9 Hz, 4H), 2.71 (tt, J=12.2, 4.0 Hz, 1H), 3.78 (t, J=4.4 Hz, 4H), 4.01 (s, 3H), 7.41 (s, 1H), 7.65 (s, 1H), 7.79 (s, 1H), 7.95 (s, 1H), 8.29 (d, J=1.8 Hz, 1H), 10.04 (bs, 1H).

4-((1r,4r)-1-methyl-4-(3-(1-methyl-1H-pyrazol-4-yl)-1H-pyrrolo[2,3-]pyridin-5-yl)cyclohexyl)morpholine (I-166)

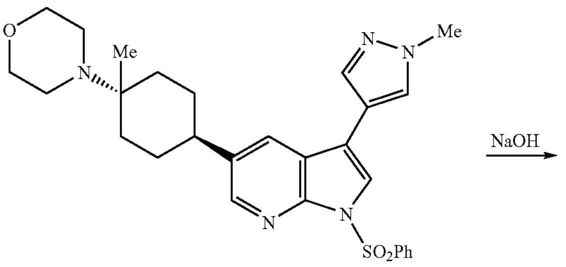

(IIb-166)

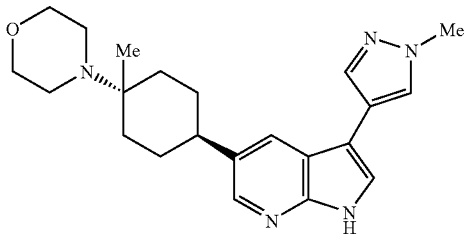

(I-166)

Compound trans (IIb-166) (228 mg, 438.7 μmol) in EtOH (2.0 mL) and 10% aqueous NaOH (1.8 mL), was deprotected and transformed into (I-166) under the conditions described in the general procedure for the deprotection of 7-azaindoles by refluxing for 2 h. The crude product was purified by PTLC using $CH_2Cl_2$:MeOH=94:6 (v/v) as the eluent to afford (I-166) (80 mg, 48%) as a yellow solid. $^1$H NMR (400 MHz, $CDCl_3$) δ 1.12 (s, 3H), 1.59-1.78 (m, 4H), 1.82-2.03 (m, 4H), 2.67 (bs, 5H), 3.77 (bs, 4H), 4.01 (s, 3H), 7.36 (d, J=2.4 Hz, 1H), 7.63 (s, 1H), 7.77 (s, 1H), 7.87 (d, J=2.0 Hz, 1H), 8.24 (d, J=2.0 Hz, 1H), 8.95 (bs, 1H).

3-(1-methyl-1H-pyrazol-4-yl)-5-(4-methylcyclohex-1-enyl)-1-(phenylsulfonyl)-1H-pyrrolo[2,3-b]pyridine (IIa-1)

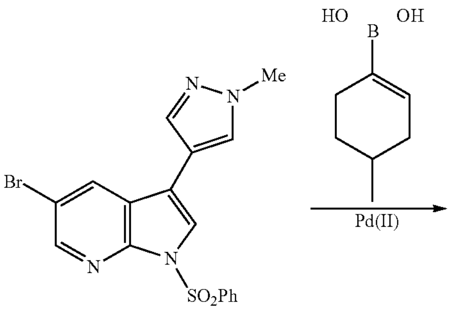

(III-a)

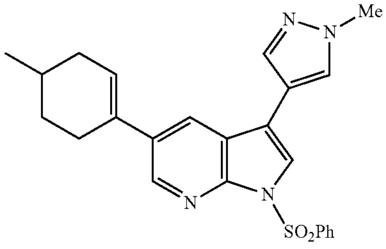

(IIa-1)

Bromide (III-a) (0.15 g, 0.36 mmol), 4-methylcyclohexen-1-yl boronic acid (0.10 g, 0.72 mmol), lithium chloride (46 mg, 1.08 mmol), and $Pd(PPh_3)_2Cl_2$ (25 mg, 0.036 mmol), in EtOH (0.90 mL), toluene (0.90 mL) and 1M $Na_2CO_3$ solution (0.90 mL) were reacted using the general procedure A for the Suzuki reaction. The crude product was purified by PTLC using hexane:EtOAc=1:1 (v/v) as the eluent to give (IIa-I) as a white foam (0.11 g, 71%), $^1$H NMR (400 MHz, $CDCl_3$) δ 1.02 (d, J=6.4 Hz, 3H), 1.44-1.35 (m, 1H), 1.93-1.70 (m, 3H), 2.36-2.27 (m, 1H), 2.50-2.44 (m, 2H), 4.00 (s, 3H), 6.10-6.06 (m, 1H), 7.51-7.46 (m, 2H), 7.59-7.55 (m, 1H), 7.64 (s, 1H), 7.73 (s, 1H), 7.76 (d, J=0.6 Hz, 1H), 7.87 (d, J=2.2 Hz, 1H), 8.22-8.19 (m, 2H), 8.50 (d, J=2.1 Hz, 1H).

5-(4-tert-butylcyclohex-1-enyl)-3-(1-methyl-1H-pyrazol-4-yl)-1-(phenylsulfonyl)-1H-pyrrolo[2,3-b]pyridine (IIa-2)

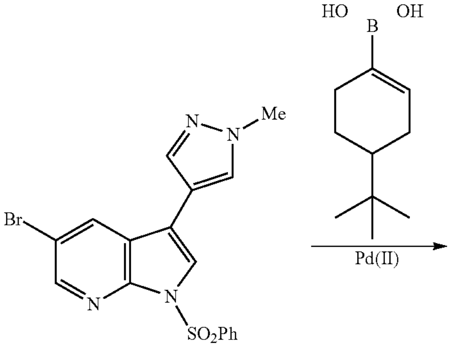

(III-a)

-continued

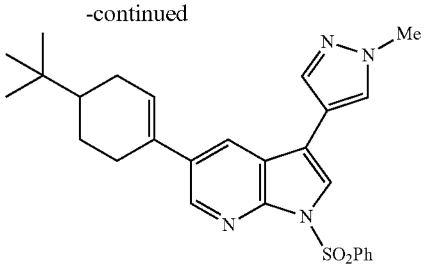

(IIa-2)

Bromide (III-a) (0.15 g, 0.36 mmol), 4-t-butylcyclohexen-1-yl boronic acid (0.13 g, 0.72 mmol), lithium chloride (46 mg, 1.08 mmol), and $Pd(PPh_3)_2Cl_2$ (25 mg, 0.036 mmol), in EtOH (0.90 mL), toluene (0.90 mL) and 1 M $Na_2CO_3$ solution (0.90 mL) were reacted using the general procedure A for the Suzuki reaction. The crude product was purified by PTLC using 1:1 hexane:EtOAc as the eluent to give (IIa-2) as a white solid (0.11 g, 67%), $^1$H NMR (400 MHz, $CDCl_3$) δ 0.92 (s, 9H), 1.42-1.30 (m, 2H), 2.04-1.94 (m, 2H), 2.32-2.22 (m, 1H), 2.57-2.40 (m, 2H), 3.99 (s, 3H), 6.13-6.09 (m, 1H), 7.51-7.46 (m, 2H), 7.60-7.54 (m, 1H), 7.64 (s, 1H), 7.73 (s, 1H), 7.76 (s, 1H), 7.87 (d, J=2.0 Hz, 1H), 8.22-8.19 (m, 2H), 8.50 (d, J=2.0 Hz, 1H).

3-(1-methyl-1H-pyrazol-4-yl)-5-(4-methylcyclohexyl)-1-(phenylsulfonyl)-1H-pyrrolo[2,3-b]pyridine (IIb-3)

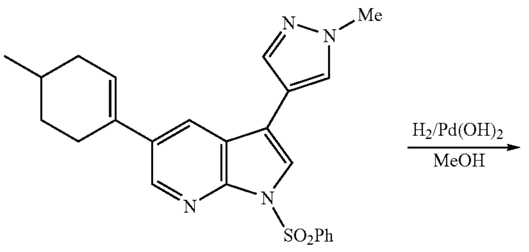

(IIa-1)

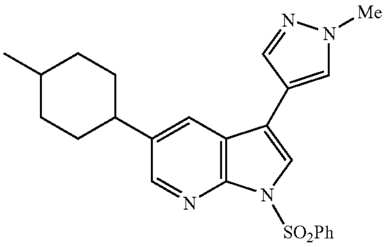

(IIb-3)

Compound (IIa-1) was hydrogenated using the general procedure for hydrogenation of 7-azaindoles. Thus, (IIa-1) (48 mg, 0.11 mmol) in MeOH (5 mL) and $Pd(OH)_2$ (20% on C, wet, Degussa type) (15.6 mg, 0.011 mmol) were used to give (IIb-3) as a 1.2:1 mixture of isomers (41 mg, 85%), $^1$H NMR (400 MHz, $CDCl_3$) δ 0.94 (d, J=6.5 Hz, 3H), 1.03 (d, J=7.1 Hz, 3H), 1.16-1.06 (m, 2H), 1.58-1.48 (m, 4H), 2.00-1.63 (m, 12H), 2.58 (tt, J=3.2 and 12.2 Hz, 1H), 2.72-2.64 (m, 1H), 3.99 (s, 3H), 4.00 (s, 3H), 7.51-7.45 (m, 4H), 7.59-7.54 (m, 2H), 7.64 (s, 2H), 7.73 (2xs, 2H), 7.75 (d, J=0.6 Hz, 1H), 7.76 (d, J=0.6 Hz, 1H), 7.78 (s, 1H), 7.79 (s, 1H), 8.23-8.19 (m, 4H), 8.34 (d, J=2.0 Hz, 1H), 8.37 (d, J=2.1 Hz, 1H).

5-(4-tert-butylcyclohexyl)-3-(1-methyl-1H-pyrazol-4-yl)-1-(phenylsulfonyl)-1H-pyrrolo[2,3-b]pyridine (IIb-4)

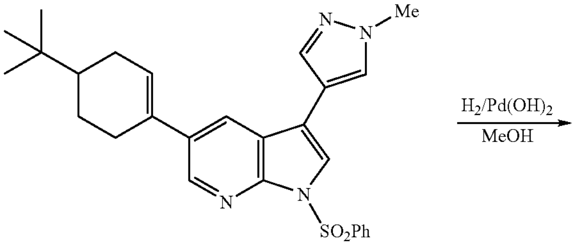

(IIa-2)

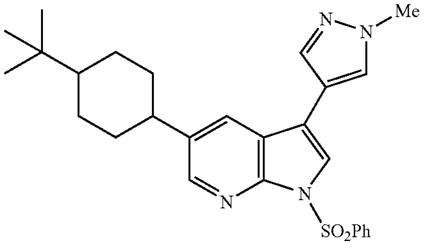

(IIb-4)

Compound (IIa-2) was hydrogenated using the general procedure for hydrogenation of 7-azaindoles. Thus, (IIa-2) (47 mg, 0.10 mmol) in MeOH (5 mL) and $Pd(OH)_2$ (20% on C, wet, Degussa type) (7 mg, 0.010 mmol) were used to give the product (IIb-4) as a 1.1:1 mixture of isomers (45 mg, 95%), $^1$H NMR (400 MHz, $CDCl_3$) δ 0.80 (s, 9H), 0.89 (s, 9H), 1.21-1.11 (m, 6H), 1.53-1.40 (m, 2H), 1.66-1.60 (m, 2H), 1.99-1.79 (m, 6H), 2.26-2.19 (m, 2H), 2.58 (tt, J=3.1 and 12.2 Hz, 1H), 3.18-3.13 (m, 1H), 3.99 (s, 6H), 7.50-7.45 (m, 4H), 7.59-7.54 (m, 2H), 7.63 (s, 1H), 7.64 (s, 1H), 7.73 (s, 2H), 7.77-7.75 (m, 3H), 7.95-7.93 (m, 1H), 8.23-8.19 (m, 4H), 8.34 (d, J=2.1 Hz, 1H), 8.48 (d, J=2.1 Hz, 1H).

1-Benzenesulfonyl-3-(1-difluoromethyl-1H-pyrazol-4-yl)-5-(4-morpholin-4-yl-cyclohex-1-enyl)-1H-pyrrolo[2,3-b]pyridine (IIa-5)

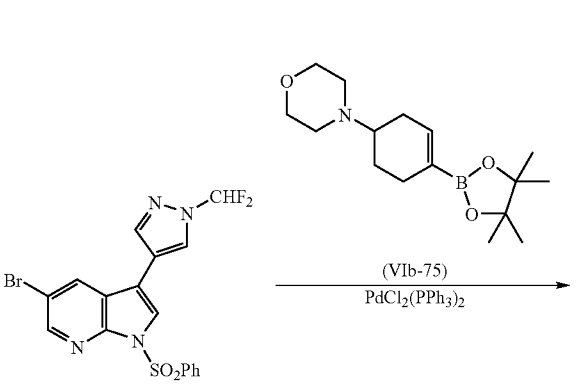

(III-h)

-continued

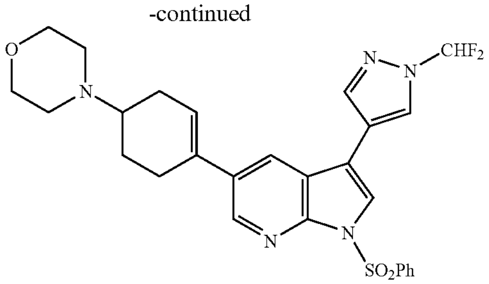

(IIa-5)

Bromide (III-h) (24.60 mg, 0.054 mmol), boronic pinacol ester (VIb-75) (18.77 mg, 0.064 mmol), LiCl (6.87 mg, 0.162 mmol), $Pd(PPh_3)_2Cl_2$ (3.51 mg, 0.005 mMol) and 1.0 M aqueous $Na_2CO_3$ (0.135 mL) in EtOH (2 mL), toluene (2 mL) were reacted using the general procedure A for the Suzuki reaction. The crude product was partially purified by PTLC using $CH_2Cl_2$:MeOH=19:1 (v/v) as eluent and used (whole amount, assuming 29 mg) for the synthesis of (I-5) without additional purification.

4-(1r,4r)-4-(3-(1-methyl-1H-pyrazol-4-yl)-1-(phenylsulfonyl)-1H-pyrrolo[2,3-b]pyridin-5-yl)cyclohexyl)morpholine (IIb-6) and 4-((1s,4s)-4-(3-(1-methyl-1H-pyrazol-4-yl)-1-(phenylsulfonyl)-1H-pyrrolo[2,3-b]pyridin-5-yl)cyclohexyl)morpholine (IIb-7)

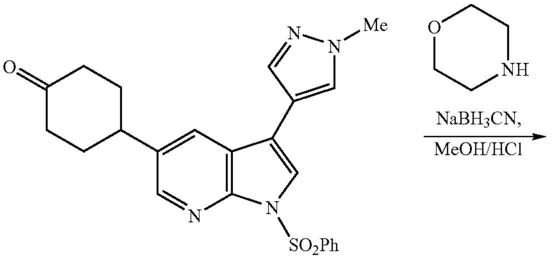

(IIb-20)

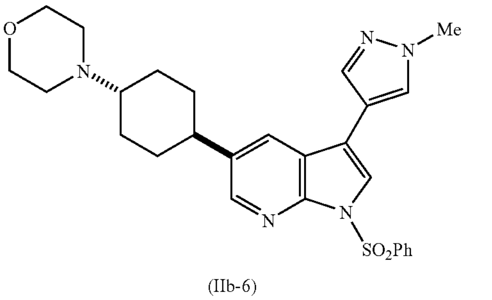

+

(IIb-6)

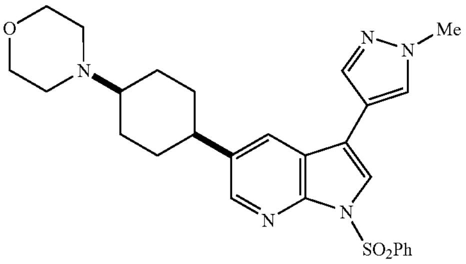

(IIb-7)

Morpholine (10.20 g, 119.90 mmol) was dissolved in dry MeOH (20 mL) under nitrogen. A 1.25 M solution of HCl/MeOH (38.36 ml, 47.96 mmol) was added and the mixture was stirred at RT for 15 min. A solution of (IIb-20) (5.21 g, 11.99 mmol) in MeOH (60 mL) was then added via syringe at RT. The mixture was then stirred at RT for 20 min. Solid $NaCNBH_3$ (1.50 g, 23.98 mmol) was added in one portion. The reaction was then stirred at RT overnight. Saturated solution of $NaHCO_3$ (100 mL) was added, the mixture was stirred at RT for 15 min and extracted with EtOAc (3×100 mL). The combined organic extracts were dried over $MgSO_4$, concentrated and separated by SGC using hexane/10:1 $CH_2Cl_2$:MeOH as the eluent (gradient elution 0%-100% 10:1 $CH_2Cl_2$:MeOH) to give the trans isomer (IIb-6) as a white solid (1.94 g, 32%) and the cis isomer (IIb-7) as a white foam (1.22 g, 20%).

Data for trans isomer (IIb-6): $^1$H NMR (400 MHz, $CDCl_3$) δ 1.59-1.36 (m, 4H), 2.11-2.96 (m, 4H), 2.36-2.29 (tt, J=11.3 and 3.2 Hz, 1H), 2.65-2.57 (m, 5H), 3.76-3.72 (m, 4H), 3.99 (s, 3H), 7.51-7.46 (m, 2H), 7.60-7.55 (m, 1H), 7.63 (s, 1H), 7.73 (s, 1H), 7.75 (d, J=0.3 Hz, 1H), 7.76 (s, 1H), 8.23-8.19 (m, 2H), 8.33 (d, J=2.0 Hz, 1H).

Data for cis isomer (IIb-7): $^1$H NMR (400 MHz, $CDCl_3$) δ 1.64-1.50 (m, 4H), 2.01-1.90 (m, 4H), 2.27-2.23 (m, 1H), 2.52-2.43 (br m, 4H), 2.83-2.75 (m, 1H), 3.76-3.72 (m, 4H), 4.00 (s, 3H), 7.51-7.46 (m, 2H), 7.60-7.55 (m, 1H), 7.65 (s, 1H), 7.73 (s, 1H), 7.77 (d, J=0.6 Hz, 1H), 7.81 (d, J=2.0 Hz, 1H), 8.23-8.19 (m, 2H), 8.40 (d, J=2.0 Hz, 1H).

1-Benzenesulfonyl-3-(1-methyl-1H-pyrazol-4-yl)-5-(4-morpholin-4-yl-cyclohexyl)-1H-pyrrolo[2,3-b]pyridine—Mixture of Isomers (IIb-6) and (IIb-7)—an Alternative Method of Preparation

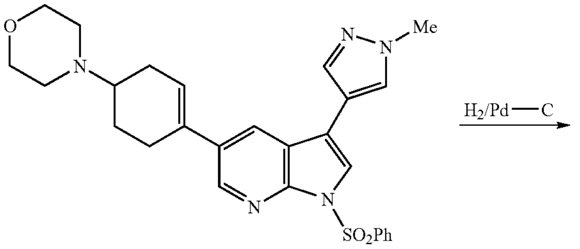

(IIa-75)

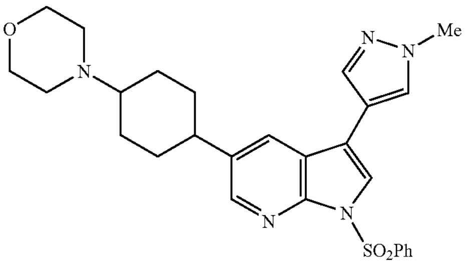

(IIb-6):(IIb-7) = 64:36

General procedure: (IIa-75) (30 mg, 0.0596 mmol), 10% Pd.C (60 mg, Degussa type E101) in EtOAc (2 mL), was de-aerated by evacuation then purging with hydrogen (3×) then left overnight to stir under $H_2$. TLC showed starting material so the catalyst was filtered off on a pad of Celite, which was washed with MeOH:$CH_2Cl_2$=1:1 (v/v). The combined filtrates were concentrated, EtOAc and Pd/C (60 mg) were added and the hydrogenation continued overnight after de-aeration. The solution was filtered through Celite, washed with MeOH:$CH_2Cl_2$=1:1 (v/v) to give the pure product as a mixture of isomers (IIb-6):(IIb-7)=64:36; clear oil (30.6 mg, 102%). This mixture can be separated into individual isomers as shown in the previous preparation.

4-((1r,4r)-4-(3-(1-methyl-1H-pyrazol-4-yl)-1-(phenylsulfonyl)-1H-pyrrolo[2,3-b]pyridin-5-yl)cyclohexyl)morpholine (IIb-6)—Synthesis from (IIb-7)

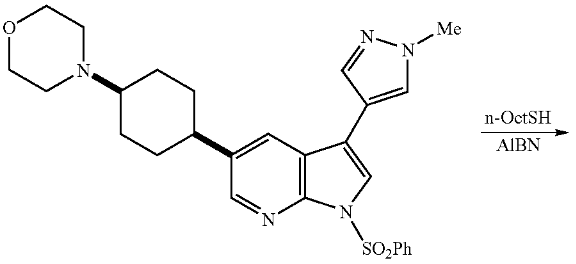

(IIb-7)

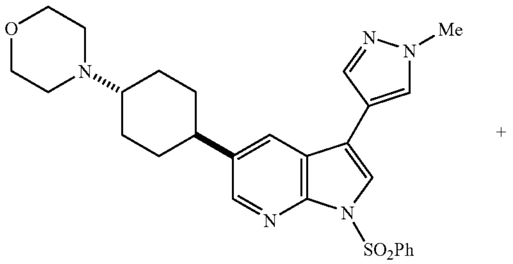

+

(IIb-6)

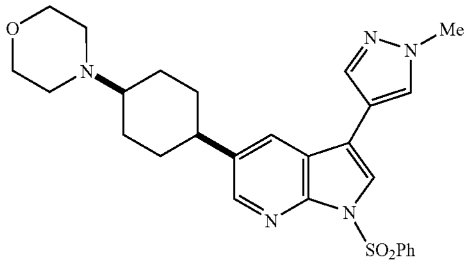

(IIb-7)

AIBN (10 mg, 0.06 mmol) was added in one portion to a solution of (IIb-7) (0.50 g, 0.988 mmol) and 1-octanethiol (0.188 ml, 1.08 mmol) in anhydrous benzene (9.88 mL), and the mixture was heated to reflux. AIBN (71.11 mg, 4.33 mmol) in anhydrous benzene (5 mL) was then added in small portions using a dropping funnel (5 drops every 15 minutes) over 4 h period. When the addition of AIBN was completed the mixture was refluxed overnight, cooled to RT and concentrated. The crude product was purified by SGC using EtOAc initially as the eluent to remove the thiol followed by MeOH:EtOAc=1:9 (v/v) to give the unreacted cis isomer (IIb-7) (68 mg, 13.6%) and then using $MeOH:CH_2Cl_2=1:9$ (v/v) to give the trans isomer (IIb-6) (0.377 g, 75%) as a white solid.

5-(4-ethylcyclohex-1-enyl)-3-(1-methyl-1H-pyrazol-4-yl)-1-(phenylsulfonyl)-1H-pyrrolo[2,3-b]pyridine (IIa-8)

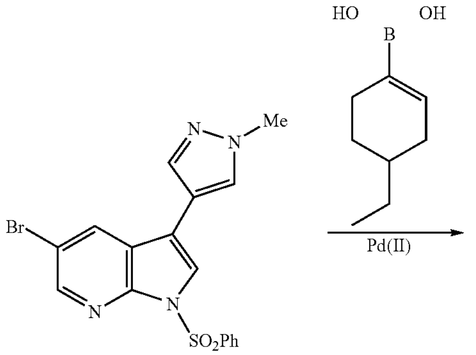

(III-a)

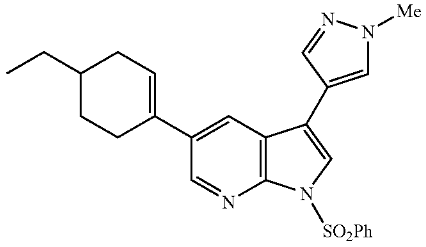

(IIa-8)

Bromide (III-a) (0.50 g, 1.20 mmol), 4-ethylcyclohexen-1-yl boronic acid (0.22 g, 1.44 mmol), lithium chloride (0.10 g, 2.40 mmol), and $Pd(PPh_3)_2Cl_2$ (84 mg, 0.12 mmol), in EtOH (3.0 mL), toluene (3.0 mL) and 1M $Na_2CO_3$ solution (3.0 mL) were reacted using the general procedure A for the Suzuki reaction. The crude product was purified by PTLC using 2:1 hexane:EtOAc as the eluent to give (IIa-8) as a white solid (0.38 g, 72%), $^1$H NMR (400 MHz, $CDCl_3$) δ 0.96 (t, J=7.4 Hz, 3H), 1.43-1.32 (m, 3H), 1.57-1.46 (m, 1H), 1.89-1.79 (m, 1H), 1.99-1.92 (m, 1H), 2.40-2.30 (m, 1H), 2.50-2.43 (m, 2H), 4.00 (s, 3H), 6.11-6.07 (m, 1H), 7.51-7.46 (m, 2H), 7.59-7.54 (m, 1H), 7.64 (s, 1H), 7.73 (s, 1H), 7.76 (s, 1H), 7.87 (d, J=2.1 Hz, 1H), 8.22-8.19 (m, 2H), 8.51 (d, J=2.1 Hz, 1H).

N,N-dimethyl-4-(3-(1-methyl-1H-pyrazol-4-yl)-1-(phenylsulfonyl)-1H-pyrrolo[2,3-b]pyridin-5-yl)cyclohexanamine (IIb-9)

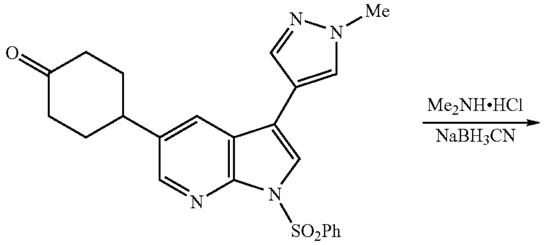

(IIb-20)

-continued

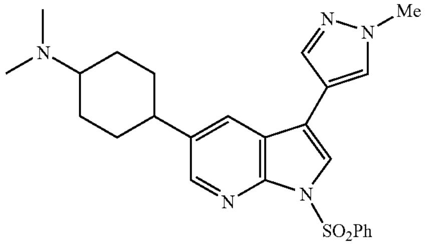

(IIb-9)

Ketone (IIb-20) (0.60 g, 1.38 mmol) was added in one portion to a solution of dimethylamine hydrochloride (0.67 g, 8.28 mmol) in dry MeOH (13.80 mL) at RT under $N_2$. The mixture was then stirred at RT for 5 min. Solid $NaCNBH_3$ (0.17 g, 2.76 mmol) was added in one portion. The reaction was then stirred at RT overnight. Saturated solution of $NaHCO_3$ (40 mL) was added and the reaction mixture was extracted with EtOAc (4×50 mL). The combined organic extracts were dried over $MgSO_4$ and concentrated. The crude product was purified by LCMS (column LUNA 10μ C18(2) 00G-4253-V0 250×50 mm) using water—MeCN (0.1% AcOH) as eluent (in gradient; flow 80 mL/min) to give a (IIb-9) (0.30 g, 47%; retention time 13.5-14.5 min) as a yellow oil, a 1.05:1 mixture of trans:cis isomers. $^1$H NMR (400 MHz, $CDCl_3$) δ 1.65-1.52 (m, 4H), 1.79-1.68 (m, 4H),1.97-1.87 (m, 2H), 2.07-2.02 (m, 2H), 2.22-2.10 (m, 4H), 2.47 (s, 6H), 2.58 (s, 6H), 2.70-2.62 (m, 2H), 2.93-2.85 (m, 1H), 3.03-2.94 (m, 1H), 4.00 (s, 6H), 7.50-7.45 (m, 4H), 7.59-7.55 (m, 2H), 7.66 (s, 1H), 7.76-7.72 (m, 4H), 7.77 (s, 1H), 7.93 (d, J=2 Hz, 1H), 8.21-8.18 (m, 4H), 8.30 (d, J=2.0 Hz, 2H), 8.38 (d, J=2.0 Hz, 1H), MS (CI) m/z 464.1 ($MH^+$).

5-cyclopentenyl-3-(1-methyl-1H-pyrazol-4-yl)-1-(phenylsulfonyl)-1H-pyrrolo[2,3-b]pyridine (IIa-10)

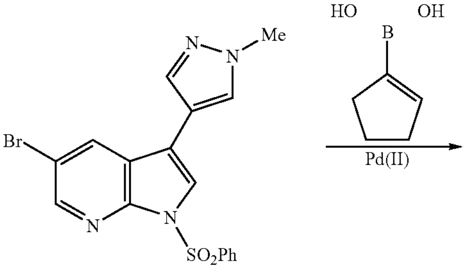

(III-a)

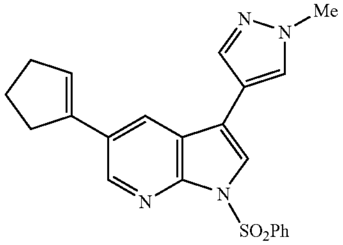

(IIa-10)

Bromide (III-a) (0.50 g, 1.20 mmol), cyclopenten-1-yl boronic acid (0.27 g, 2.40 mmol), lithium chloride (0.15 g, 3.60 mmol), and $Pd(PPh_3)_2Cl_2$ (84 mg, 0.012 mmol), in EtOH (3.0 mL), toluene (3.0 mL) and 1M $Na_2CO_3$ solution (3.0 mL) were reacted using the general procedure A for the Suzuki reaction. The crude product was purified by SGC using 3:1-2:1-1:1 hexane:EtOAc as the eluent to give the product (IIa-10) as a white solid (0.40 g, 83%), $^1$H NMR (400 MHz, $CDCl_3$) δ 2.10-2.01 (m, 2H), 2.60-2.53 (m, 2 H), 2.79-2.72 (m, 2H), 4.00 (s, 3H), 6.26-6.23 (m, 1H), 7.51-7.46 (m, 2H), 7.60-7.55 (m, 1H), 7.64 (s, 1H), 7.73 (s, 1H), 7.76 (d, J=0.6 Hz, 1H), 7.91 (d, J=2.0 Hz, 1H), 8.22-8.18 (m, 2H), 8.60 (d, J=2.0 Hz, 1H).

5-cyclopentyl-3-(1-methyl-1H-pyrazol-4-yl)-1-(phenylsulfonyl)-1H-pyrrolo[2,3-b]pyridine (IIb-11)

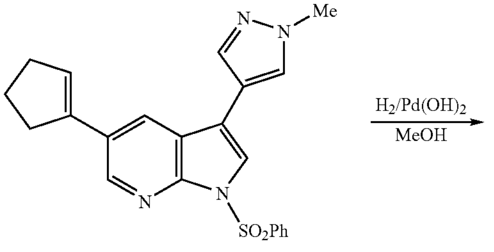

(IIa-10)

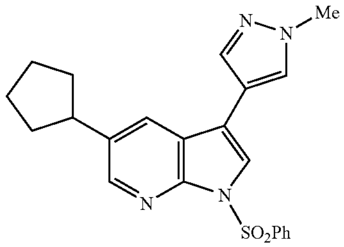

(IIb-11)

Compound (IIa-10) was hydrogenated using the general procedure for hydrogenation of 7-azaindoles. Thus, 7-azaindole (IIa-10) (52 mg, 0.13 mmol) in MeOH (2 mL) and $Pd(OH)_2$ (20% on C, wet, Degussa type) (35 mg, 0.05 mmol) were used to give the product (IIb-11) (45 mg, 86%), $^1$H NMR (400 MHz, $CDCl_3$) δ 1.65-1.54 (m, 2H), 1.76-1.68 (m, 2H), 1.87-1.79 (m, 2H), 2.16-2.07 (m, 2H), 3.14-3.04 (m, 1H), 3.99 (s, 3H), 7.51-7.46 (m, 2H), 7.59-7.54 (m, 1H), 7.64 (s, 1H), 7.72 (s, 1H), 7.75 (s, 1H), 7.79 (d, J=1.9 Hz, 1H), 8.23-8.18 (m, 2H), 8.37 (d, J=2.0 Hz, 1H).

5-cyclohexenyl-3-(1-methyl-1H-pyrazol-4-yl)-1-(phenylsulfonyl)-1H-pyrrolo[2,3-b]pyridine (IIa-12)

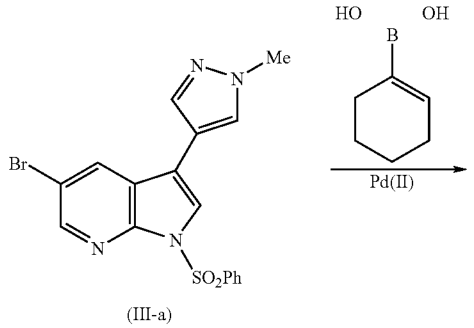

(III-a)

-continued

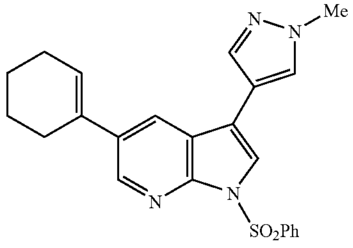

(IIa-12)

Bromide (III-a) (0.15 g, 0.36 mmol), cyclohexen-1-yl boronic acid (0.09 g, 0.72 mmol), LiCl (46 mg, 1.08 mmol), and $Pd(PPh_3)_2Cl_2$ (25 mg, 0.036 mmol), in EtOH (0.72 mL), toluene (0.72 mL) and 1.0 M $Na_2CO_3$ solution (0.72 mL) were reacted using the general procedure A for the Suzuki reaction. The crude product was purified by PTLC using 1:1 hexane:EtOAc as the eluent to give product (IIa-12) as a white solid (81 mg, 54%), $^1$H NMR (400 MHz, $CDCl_3$) δ 1.71-1.65 (m, 2H), 1.84-1.77 (m, 2 H), 2.25-2.20 (m, 2H), 2.45-2.39 (m, 2H), 3.99 (s, 3H), 6.12-6.08 (m, 1H), 7.51-7.45 (m, 2H), 7.59-7.55 (m, 1H), 7.65 (s, 1H), 7.73 (s, 1H), 7.76 (s, 1H), 7.87 (d, J=2.1 Hz, 1H), 8.22-8.19 (m, 2H), 8.50 (d, J=2.1 Hz, 1H).

(E)-5-cycloheptenyl-3-(1-methyl-1H-pyrazol-4-yl)-1-(phenylsulfonyl)-1H-pyrrolo[2,3-b]pyridine (IIa-13)

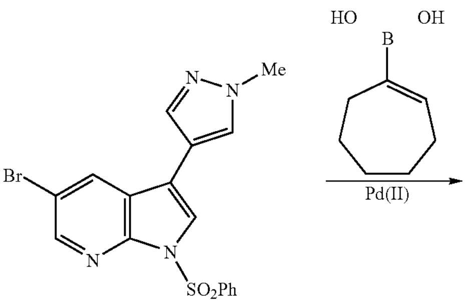

(III-a)

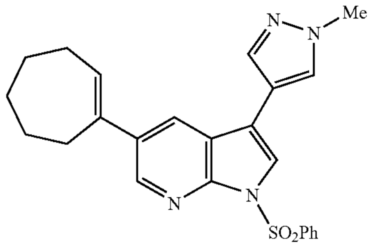

(IIa-13)

Bromide (III-a) (0.15 g, 0.36 mmol), cyclohepten-1-yl boronic acid (0.10 g, 0.72 mmol), lithium chloride (46 mg, 1.08 mmol), and $Pd(PPh_3)_2Cl_2$ (25 mg, 0.036 mmol), in EtOH (0.72 mL), toluene (0.72 mL) and 1M $Na_2CO_3$ solution (0.72 mL) were reacted using the general procedure A for the Suzuki reaction. The crude product was purified by PTLC using 1:1 hexane:EtOAc as the eluent to give (IIa-13) as a white solid (0.12 g, 79%), $^1$H NMR (400 MHz, $CDCl_3$) δ 1.60-1.53 (m, 2H), 1.69-1.62 (m, 2 H), 1.88-1.81 (m, 2H), 2.34-2.27 (m, 2H), 2.64-2.60 (m, 2H), 3.99 (s, 3H), 6.07 (t, J=6.7 Hz, 1H), 7.50-7.45 (m, 2H), 7.59-7.54 (m, 1H), 7.64 (s, 1H), 7.73 (s, 1H), 7.76 (d, J=0.4 Hz, 1H), 7.81 (s, 1H), 8.21-8.18 (m, 2H), 8.43 (d, J=2.1 Hz, 1H).

3-(1-Methyl-1H-pyrazol-4yl)-1-(phenylsulfonyl)-5-(1,4-dioxaspiro[4.5]dec-7-en-8-yl)-1H-pyrrolo[2,3-b]pyridine (IIa-14)

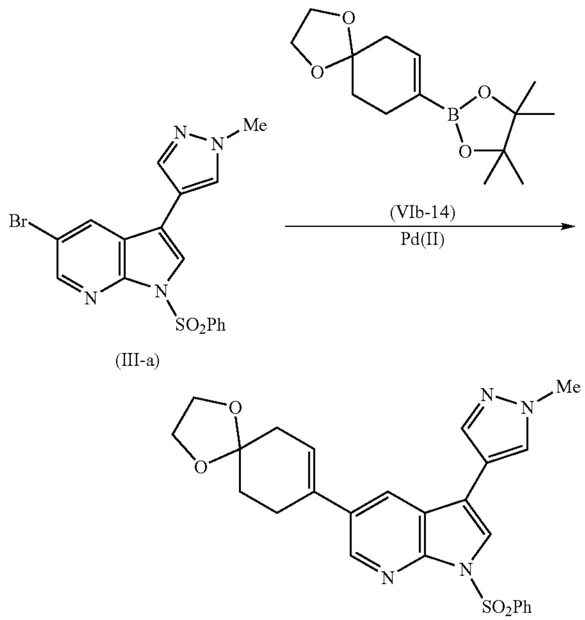

(III-a)

(IIa-14)

Bromide (III-a) (10.00 g, 24.03 mmol), 1,4-diospiro[4,5]dec-7-ene-8-boronic acid pinacol ester (VIb-14) (8.31 g, 31.25 mmol), lithium chloride (3.05 g, 72.09 mmol), $Pd(PPh_3)_2Cl_2$ (1.68 g, 2.40 mmol) and 1.0 M aqueous $Na_2CO_3$ solution (60 mL) in EtOH (60mL) and toluene (60 mL) were reacted following the general protocol A for the Suzuki reaction. The crude product was purified by SGC using hexane/EtOAc as the eluent (gradient elution 0%-100% EtOAc) to afford (IIa-14) as a pale yellow solid (9.66 g, 82%), $^1H$ NMR (400 MHz, $CDCl_3$) δ 1.95 (t, J=6.5 Hz, 2H), 2.50-2.48 (m, 2 H), 2.70-2.67 (m, 2H), 3.99 (s, 3H), 4.04 (s, 4H), 5.99-5.96 (m, 1H), 7.48 (t, J=7.6 Hz, 2H), 7.59-7.55 (m, 1H), 7.64 (s, 1H), 7.74 (s, 1H), 7.75 (d, J=0.6 Hz, 1H), 7.90 (d, J=2.2 Hz, 1H), 8.21-8.18 (m, 2H), 8.52 (d, J=2.1 Hz, 1H).

5-(4,4-dimethylcyclohex-1-enyl)-3-(1-methyl-1H-pyrazol-4-yl)-1-(phenylsulfonyl)-1H-pyrrolo[2,3-b]pyridine (IIa-15)

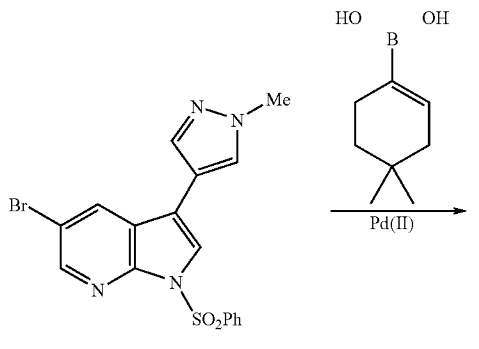

(III-a)

-continued

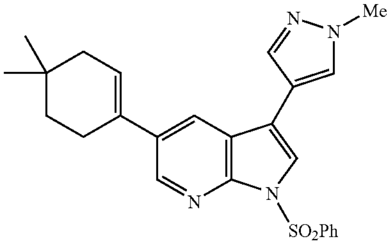

(IIa-15)

Bromide (III-a) (0.15 g, 0.36 mmol), 4,4-dimethylcyclohex-1-enylboronic acid (0.11 g, 0.72 mmol), lithium chloride (46 mg, 1.08 mmol), and $Pd(PPh_3)_2Cl_2$ (25 mg, 0.036 mmol), in EtOH (0.90 mL), toluene (0.90 mL) and 1M $Na_2CO_3$ solution (0.90 mL) were reacted using the general procedure A for the Suzuki reaction. The crude product was purified by PTLC using 1:1 hexane:EtOAc as the eluent to give (IIa-15) as a yellow foam (0.12 g, 78%), $^1H$ NMR (400 MHz, $CDCl_3$) δ 0.97 (s, 6H), 1.54 (t, J=6.4 Hz, 2H), 2.02-1.98 (m, 2H), 2.46-2.40 (m, 2H), 3.98 (s, 3H), 6.06-6.02 (m, 1H), 7.49-7.44 (m, 2H), 7.57-7.53 (m, 1H), 7.65 (s, 1H), 7.72 (s, 1H), 7.76 (d, J=0.5 Hz, 1H), 7.88 (d, J=2.1 Hz, 1H), 8.20-8.17 (m, 2H), 8.51 (d, J=2.1 Hz, 1H).

5-cyclohexyl-3-(1-methyl-1H-pyrazol-4-yl)-1-(phenylsulfonyl)-1H-pyrrolo[2,3-b]pyridine (IIb-16)

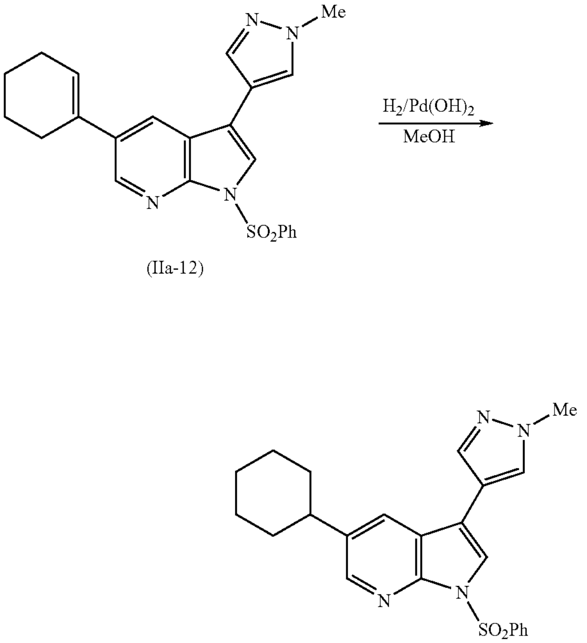

(IIa-12)

(IIb-16)

Compound (IIa-12) was hydrogenated using the general procedure for hydrogenation of 7-azaindoles. Thus, 7-azaindole (IIa-12) (18 mg, 0.043 mmol) in MeOH (2 mL) and $Pd(OH)_2$ (20% on C, wet, Degussa type) (3 mg, 4.3 μmol) were used to give product (IIb-16) (16 mg, 88%), $^1H$ NMR (400 MHz, $CDCl_3$) δ 1.51-1.37 (m, 4 H), 1.91-1.73 (m, 6H), 2.67-2.58 (m, 1H), 4.00 (s, 3H), 7.51-7.46 (m, 2H), 7.59-7.54 (m, 1H), 7.65 (s, 1H), 7.73 (s, 1H), 7.76 (s, 2H), 8.22-8.19 (m, 2H), 8.34 (d, J=2.1 Hz, 1H).

5-cycloheptyl-3-(1-methyl-1H-pyrazol-4-yl)-1-(phenylsulfonyl)-1H-pyrrolo[2,3-b]pyridine (IIb-17)

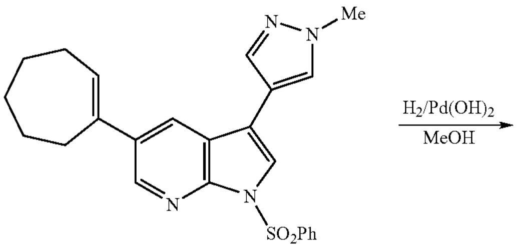

(IIa-13)

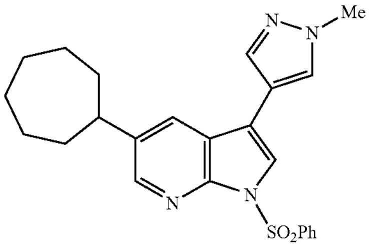

(IIb-17)

Compound (IIa-13) was hydrogenated using the general procedure for hydrogenation of 7-azaindoles. Thus, 7-azaindole (IIa-13) (65 mg, 0.15 mmol) in MeOH (2 mL) and $Pd(OH)_2$ (20% on C, wet, Degussa type) (10 mg, 15 μmol) were used to give (IIb-17) (46 mg, 70%), $^1$H NMR (400 MHz, $CDCl_3$) δ 1.94-1.51 (m, 12H), 2.79 (tt, J=3.7 and 10.5 Hz, 1H), 4.00 (s, 3H), 7.51-7.45 (m, 2H), 7.60-7.54 (m, 1H), 7.64 (s, 1H), 7.72 (s, 1H), 7.74 (d, J=2.0 Hz, 1H), 7.76 (s, 1H), 8.22-8.18 (m, 2H), 8.32 (d, J=2.0 Hz, 1H).

3-(1-methyl-1H-pyrazol-4-yl)-1-(phenylsulfonyl)-5-(1,4-dioxaspiro[4.5]decan-8-yl)-1H-pyrrolo[2,3-b]pyridine (IIb-19)

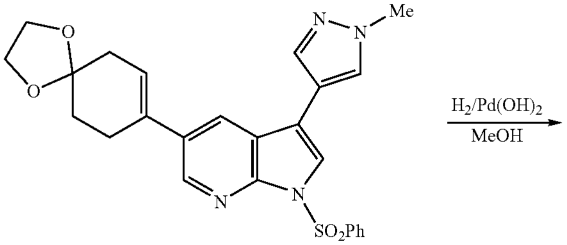

(IIa-14)

-continued

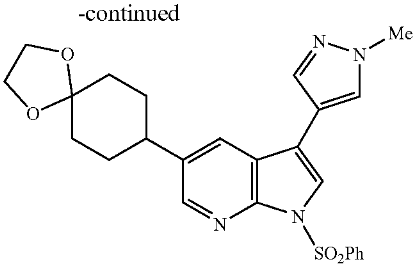

(IIb-19)

Compound (IIa-14) (9.66 g, 20.27 mmol) was dissolved in MeOH (101 mL) and EtOAc (101 mL). $Pd(OH)_2$ on carbon (20% wet Degussa type; 1.41 g, 2.02 mmol) was added in one portion. The reaction mixture was shaken overnight under a $H_2$ atmosphere (40 psi) using the Parr apparatus. The reaction was filtered through a small pad of Celite and was washed with copious amount of MeOH. The solvent was removed to give (IIb-19) as a white foam (7.25 g, 75%), $^1$H NMR (400 MHz, $CDCl_3$) δ 1.90 (m, 8H), 2.74-2.65 (m, 1H), 3.98 (s, 4H), 3.99 (s, 3H), 7.48-7.43 (m, 2H), 7.57-7.51 (m, 1H), 7.64 (s, 1H), 7.72 (s, 1H), 7.74 (d, J=0.4 Hz, 1H), 7.79 (d, J=2.0 Hz, 1H), 8.21-8.18 (m, 2H), 8.34 (d, J=2.0 Hz, 1H).

4-(3-(1-methyl-1H-pyrazol-4-yl)-1-(phenylsulfonyl)-1H-pyrrolo[2,3-b]pyridin-5-yl)cyclohexanone (IIb-20)

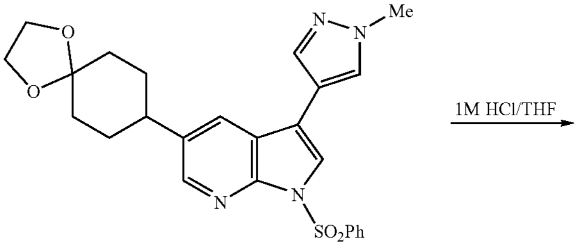

(IIb-19)

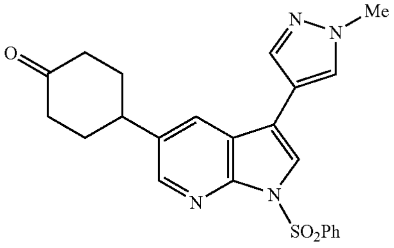

(IIb-20)

Aqueous 7 M HCl (22.7 mL) was added at RT in small portions over 10 minutes to a solution of compound (IIb-19) (7.25 g, 15.15 mmol) in THF (68 mL). The reaction mixture was stirred at RT overnight and quenched by slow addition of a saturated aqueous solution of $NaHCO_3$ (150 mL). After stirring for 15 min the mixture was extracted with EtOAc (3×200 mL). The combined extracts were dried over $MgSO_4$ and concentrated to give (IIb-20) as a white foam (6.50 g, 99%), $^1$H NMR (400 MHz, $CDCl_3$) δ 2.03-1.94 (m, 2H), 2.27-2.21 (m, 2H), 2.57-2.51 (m, 1H), 3.22-3.14 (tt, J=12.2 and 3.3 Hz, 1H), 4.00 (s, 3H), 7.52-7.48 (m, 2H), 7.61-7.57

(m, 1H), 7.64 (s, 1H), 7.75 (d, J=0.5 Hz, 1H), 7.77 (s, 1H), 7.80 (d, J=2.1 Hz, 1H), 8.24-8.21 (m, 2H), 8.40 (d, J=2.1 Hz, 1H).

5-(4,4-dimethylcyclohexa-1,5-dienyl)-3-(1-methyl-1H-pyrazol-4-yl)-1-(phenylsulfonyl)-1H-pyrrolo[2,3-b]pyridine (IIa-21)

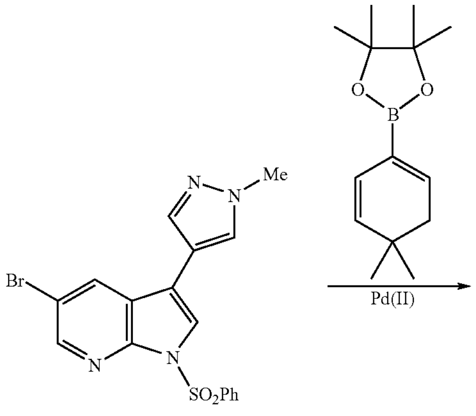

(III-a)

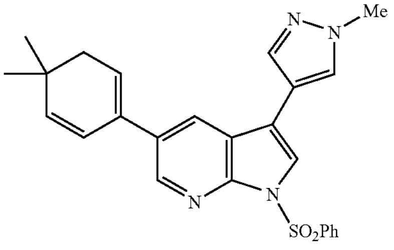

(IIa-21)

Bromide (III-a) (0.20 g, 0.48 mmol), 2-(4,4-dimethylcyclohexa-1,5-dienyl)-4,4,5,5-tetramethyl-1,3,2-dioxaborolane (0.17 g, 0.72 mmol), lithium chloride (61 mg, 1.44 mmol), and $Pd(PPh_3)_2Cl_2$ (34 mg, 0.048 mmol), in EtOH (0.96 mL), toluene (0.96 mL) and 1.0 M $Na_2CO_3$ solution (0.96 mL) were reacted using the general procedure A for the Suzuki reaction. The crude product was purified by PTLC using 1:1 hexane:EtOAc as the eluent to give (IIa-21) as a yellow solid (0.14 g, 64%), $^1$H NMR (400 MHz, $CDCl_3$) δ 1.06 (s, 6H), 2.30 (d, J=4.60 Hz, 2H), 4.00 (s, 3H), 5.76 (d, J=9.70 Hz, 1H), 6.00 (t, J=4.6 Hz, 1H), 6.13 (dd, J=1.3 and 9.7 Hz, 1H), 7.51-7.45 (m, 2H), 7.59-7.54 (m, 1H), 7.65 (s, 1H), 7.75 (s, 1H), 7.77 (s, 1H), 7.88 (d, J=1.9 Hz, 1H), 8.22-8.18 (m, 2H), 8.51 (d, J=1.90 Hz, 1H).

5-(4-ethylcyclohexyl)-3-(1-methyl-1H-pyrazol-4-yl)-1-(phenylsulfonyl)-1H-pyrrolo[2,3-b]pyridine (IIb-22)

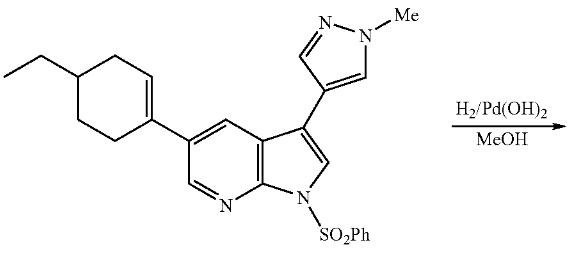

(IIa-8)

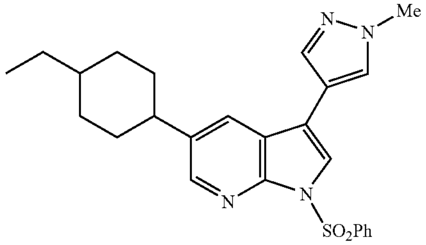

(IIb-22)

Compound (IIa-8) was hydrogenated using the general procedure for hydrogenation of 7-azaindoles. Thus, 7-azaindole (IIa-8) (0.20 g, 0.45 mmol) and $Pd(OH)_2$ (20% on C, wet, Degussa type) (31.5 mg, 0.045 mmol) in MeOH (5 mL) were used to give (IIb-22) as a 1.16:1 mixture of isomers (0.20 g, 100%), $^1$H NMR (400 MHz, $CDCl_3$) δ 0.91 (t, J=7.4 Hz, 6H), 1.12-1.01 (m, 2H), 1.30-1.23 (m, 2H), 1.53-1.38 (m, 4H), 1.71-1.56 (m, 8H), 1.93-1.86 (m, 4H), 2.59 (tt, J=2.8 and 12.2 Hz, 1H), 2.73-2.65 (m, 1H), 3.99 (s, 3H), 4.00 (s, 1H), 7.50-7.45 (m, 4H), 7.59-7.54 (m, 2H), 7.64 (s, 2H), 7.72 (s, 2H), 7.78-7.75 (m, 4H), 8.22-8.19 (m, 4H), 8.34 (d, J=2.1 Hz, 1H), 8.36 (d, J=2.1 Hz, 1H).

3-(1-methyl-1H-pyrazol-4-yl)-1-(phenylsulfonyl)-5-((1s,4s)-4-(pyrrolidin-1-yl)cyclohexyl)-1H-pyrrolo[2,3-b]pyridine (IIb-23) and 3-(1-methyl-1H-pyrazol-4-yl)-1-(phenylsulfonyl)-5-((1r,4r)-4-(pyrrolidin-1-yl)cyclohexyl)-1H-pyrrolo[2,3-b]pyridine (IIb-24)

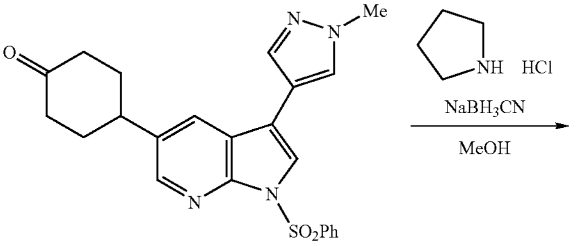

(IIb-20)

-continued

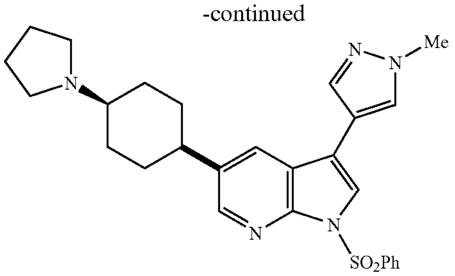

(IIb-23)

+

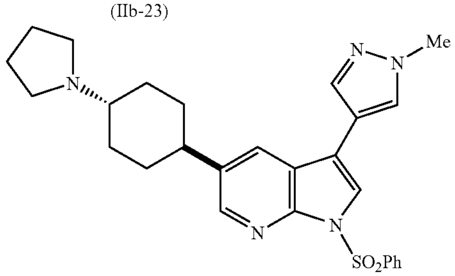

(IIb-24)

-continued

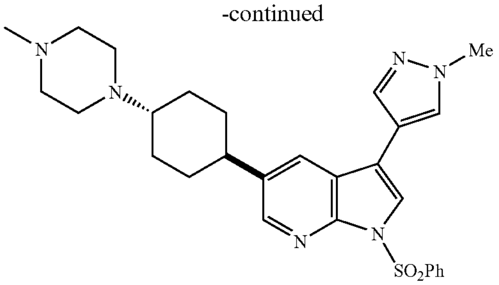

(IIb-25)

+

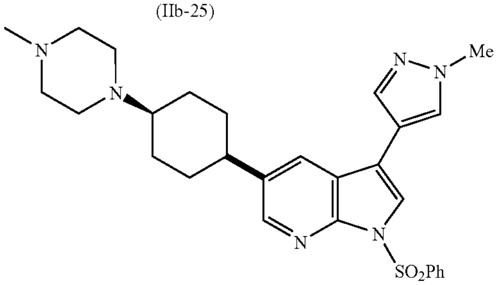

(IIb-26)

Ketone (IIb-20) (0.60 g, 1.38 mmol), pyrrolidine (0.69 ml, 8.28 mmol), 1.25 M HCl in MeOH (2.20 ml, 2.76 mmol) and $NaCNBH_3$ (0.173 g, 2.73 mmol) in anhydrous MeOH (13.8 mL) were reacted following the general procedure A for the reductive amination. The crude product was purified by PTLC using 5:1 $CH_2Cl_2$:MeOH as the eluent to give the trans isomer (IIb-24) as a yellow solid (188 mg, 28%) and the cis isomer (IIb-23) as a white solid (150 mg, 22%).

Data for trans isomer (IIb-24): $^1$H NMR (400 MHz, $CDCl_3$) δ 1.60-1.38 (m, 4H), 1.83-1.77 (m, 4H), 1.97-1.80 (m, 2H), 2.19-2.06 (m, 3H), 2.66-2.57 (m, 5H), 3.98 (s, 3H), 7.49-7.45 (m, 2H), 7.58-7.53 (m, 1H), 7.64 (s, 1H), 7.72 (s,1H), 7.74 (s, 1H), 7.75 (d, J=2.0 Hz, 1H), 8.20-8.18 (m, 2H), 8.33 (d, J=2.0 Hz, 1H).

Data for cis isomer (IIb-23): $^1$H NMR (400 MHz, $CDCl_3$) δ 2.52-1.45 (m, 16H), 2.79-2.70 (tt, J=11.6 and 2.5 Hz, 1H), 3.19-3.10 (m, 1H), 4.09 (s, 3H), 7.51-7.46 (m, 2H), 7.60-7.54 (m, 1H), 7.74 (d, J=0.6 Hz, 1H), 7.78 (s, 1H), 8.11 (s, 1H), 8.13 (d, J=1.5 Hz, 1H), 8.20-8.16 (m, 2H), 8.28 (d, J=2.0 Hz, 1H).

3-(1-methyl-1H-pyrazol-4-yl)-5-((1r,4r)-4-(4-methylpiperazin-1-yl)cyclohexyl)-1-(phenylsulfonyl)-1H-pyrrolo[2,3-b]pyridine (IIb-25) and 3-(1-methyl-1H-pyrazol-4-yl)-5-((1s,4s)-4-(4-methylpiperazin-1-yl)cyclohexyl)-1-(phenylsulfonyl)-1H-pyrrolo[2,3-b]pyridine (IIb-26)

Ketone (IIb-20) (0.60 g, 1.38 mmol), N-methylpiperazine (0.83 g, 8.28 mmol), 1.25 M solution of HCl/MeOH (2.21 ml, 2.76 mmol) and $NaCNBH_3$ (0.17 g, 2.76 mmol) in dry MeOH (13.8 mL) were reacted following the general procedure A for the reductive amination. The crude product was separated by PTLC using 5:1 $CH_2Cl_2$:MeOH as the eluent to give the trans isomer (IIb-25) (178 mg, 25%) as a yellow solid and the cis isomer (IIb-26) (110 mg, 15%) as a yellow solid.

Data for trans isomer (IIb-25): $^1$H NMR (400 MHz, $CDCl_3$) δ 1.58-1.37 (m, 4H), 2.00-1.93 (m, 2H), 2.09-2.02 (m, 2H), 2.29 (s, 3H), 2.72-2.34 (m, 10H), 3.97 (s, 3H), 7.49-7.44 (m, 2H), 7.57-7.52 (m, 1H), 7.63 (s, 1H), 7.71 (s, 1H), 7.75-7.73 (m, 2H), 8.20-8.16 (m, 2H), 8.31 (d, J=2.0 Hz, 1H).

Data for cis isomer (IIb-26): $^1$H NMR (400 MHz, $CDCl_3$) δ 1.67-1.52 (m, 2H), 2.00-1.87 (m, 2H), 2.42-2.36 (m, 1H), 2.41 (s, 3H), 2.73-2.55 (br m, 9H), 2.85-2.73(m, 2H), 3.98 (s, 3H), 7.50-7.43 (m, 2H), 7.57-7.52 (m, 1H), 7.69 (s, 1H), 7.70 (s, 1H), 7.74 (d, J=0.5 Hz, 1H), 7.83 (d, J=2.0 Hz, 1H), 8.17-8.14 (m, 2H), 8.37 (d, J=2.0 Hz, 1H).

3-(1-methyl-1H-pyrazol-4-yl)-5-((1r,4r)-4-(4-methylpiperazin-1-yl)cyclohexyl)-1-(phenylsulfonyl)-1H-pyrrolo[2,3-b]pyridine (IIb-25) and 3-(1-methyl-1H-pyrazol-4-yl)-5-((1s,4s)-4-(4-methylpiperazin-1-yl)cyclohexyl)-1-(phenylsulfonyl)-1H-pyrrolo[2,3-b]pyridine (IIb-26)—an Alternative Method of Preparation of the Mixture

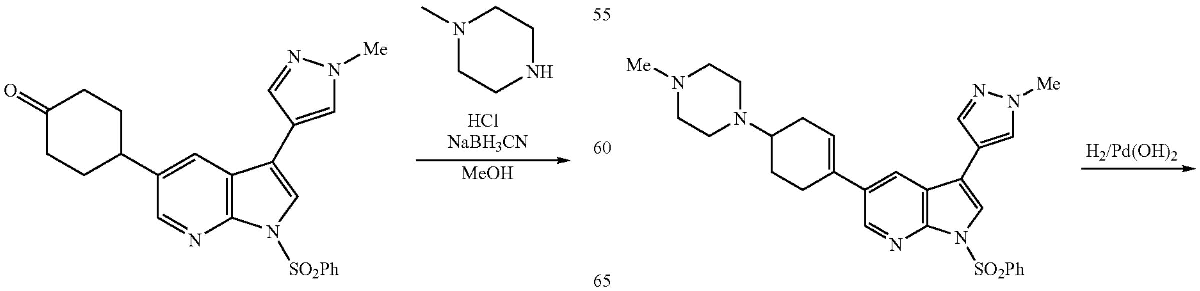

(IIb-20)

(IIa-135)

-continued

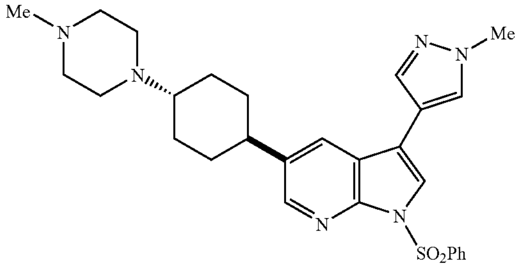

+

(IIb-25)

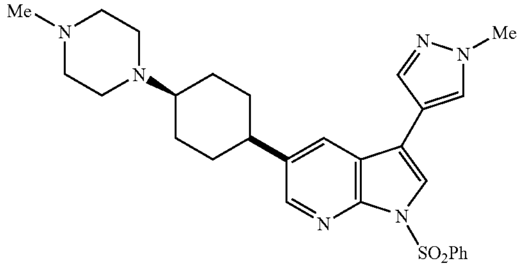

(IIb-26)

Compound (IIa-135) was hydrogenated using the general procedure for hydrogenation of 7-azaindoles. Thus, (IIa-135) (10.01 g, 19.37 mmol) and $Pd(OH)_2$ (20% on C, wet, Degussa type) (2.0 g) in EtOH:THF=1:1 (150 mL) were reacted over a period of 18 h. The reaction mixture was filtered through Celite, washing with EtOH (500 mL), and concentrated to afford a 5:4 mixture (IIb-25) and (IIb-26) (10.05 g, 19.37 mmol, quant.) as a white foam, which was used in the next step (isomerisation) without separation.

3-(1-methyl-1H-pyrazol-4-yl)-5-((1r,4r)-4-(4-methylpiperazin-1-yl)cyclohexyl)-1-(phenylsulfonyl)-1H-pyrrolo[2,3-b]pyridine (IIb-25)—Preparation from a Mixture of (II-25) and (IIb-26) by Isomerization

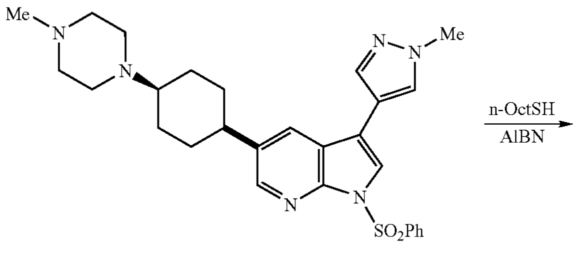

(IIb-26)

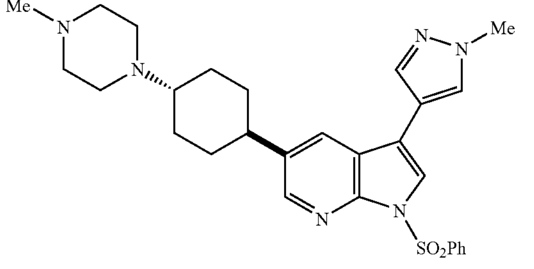

+

(IIb-25)

-continued

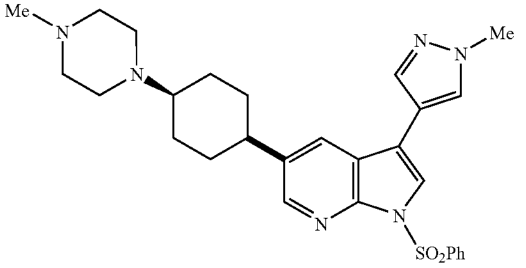

(IIb-26)

To a stirred solution of a 5:4 mixture (IIb-25) and (IIb-26) (10.05 g, 19.37 mmol) in benzene (25 mL) was added octane-1-thiol (3.12 g, 21.31 mmol) and the reaction mixture was heated to reflux. 2,2'-azobis(2-methylpropionitrile) (1.59 g, 9.69 mmol) was then added dropwise over 3 h as a solution in benzene (25 mL). Reflux was continued for 16 h, and the reaction mixture was then concentrated to dryness and purified by SGC using $CH_2Cl_2$:hexanes=1:1 (v/v) and $CH_2Cl_2$:MeOH (gradient from 100:0 to 85:15, v/v). Eluting first was the recovered cis isomer (IIb-26) (1.36g, 2.62 mmol, 14%). Further elution afforded trans isomer (IIb-25) (8.05 g, 15.53 mmol, 80%). NMR data as above.

3-(1-methyl-1H-pyrazol-4-yl)-5-(4-phenylcyclohex-1-enyl)-1-(phenylsulfonyl)-1H-pyrrolo[2,3-b]pyridine (IIa-27)

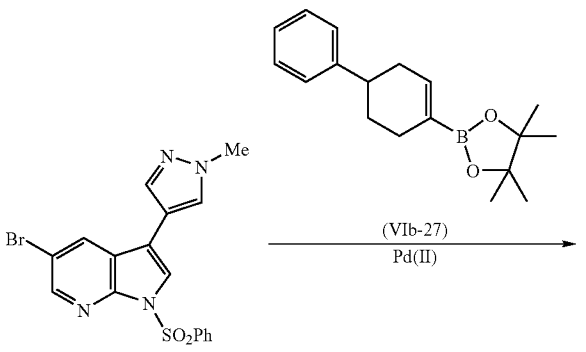

(III-a)

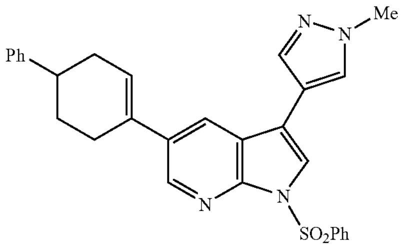

(IIa-27)

Bromide (III-a) (0.37 g, 0.90 mmol), boronic ester (VIb-27) (0.51 g, 1.80 mmol), lithium chloride (76 mg, 1.80 mmol), and $Pd(PPh_3)_2Cl_2$ (63 mg, 0.096 mmol), in EtOH (9.0 mL), toluene (9.0 mL) and 1.0 M $Na_2CO_3$ solution (2.24 mL)

were reacted using the general procedure A for the Suzuki reaction. The crude product was purified by PTLC using 1:1 hexane:EtOAc as the eluent to give (IIa-27) as a yellow solid (0.33 g, 76%), $^1$H NMR (400 MHz, $CDCl_3$) δ 2.00-1.90 (m, 1H), 2.19-2.11 (m, 1H), 2.43-2.32 (m, 1H), 2.70-2.51 (m, 3H), 2.96-2.86 (m, 1H), 4.00 (s, 3H), 6.23-6.19 (m, 1H), 7.30-7.21 (m, 3H), 7.37-7.30 (m, 2H), 7.52-7.47 (m, 2H), 7.61-7.56 (m, 1H), 7.66 (s, 1H), 7.75 (s, 1H), 7.77 (d, J=0.6 Hz, 1H), 7.92 (d, J=2.2 Hz, 1H), 8.23-8.20 (m, 2H), 8.55 (d, J=2.0 Hz, 1H).

3-(1-methyl-1H-pyrazol-4-yl)-1-(phenylsulfonyl)-5-(3,3,5,5-tetramethylcyclohex-1-enyl)-1H-pyrrolo[2,3-b]pyridine (IIa-28)

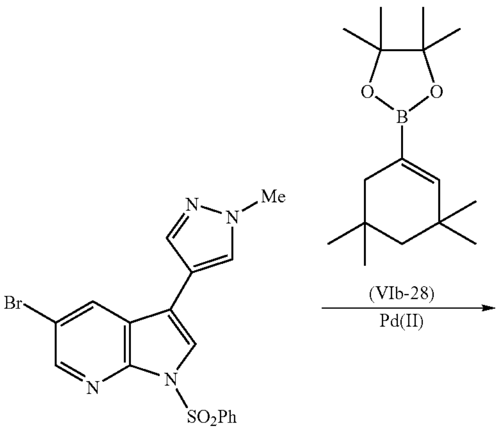

(III-a)

-continued

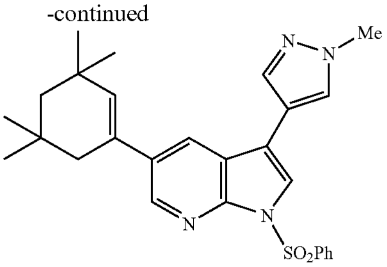

(IIa-28)

Bromide (III-a) (0.27 g, 0.65 mmol), boronic ester (VIb-28) (0.51 g, 1.95 mmol), lithium chloride (82 mg, 1.95 mmol), and $Pd(PPh_3)_2Cl_2$ (45 mg, 0.065 mmol), in EtOH (1.62 mL), toluene (1.62 mL) and 1M $Na_2CO_3$ solution (1.62 mL) were reacted using the general procedure A for the Suzuki reaction. The crude product was purified by PTLC using 1:1 hexane:EtOAc as the eluent to give (IIa-28) as a white solid (0.16 g, 53%), $^1$H NMR (400 MHz, $CDCl_3$) δ 1.04 (s, 6H), 1.10 (s, 6H), 1.42 (s, 2H), 2.16 (d, J=1.3 Hz, 2H), 4.00 (s, 3H), 5.77 (t, J=1.4 Hz, 1H), 7.51-7.46 (m, 2H), 7.60-7.48 (m, 1H), 7.65 (s, 1H), 7.73 (s, 1H), 7.78 (d, J=0.6 Hz, 1H), 7.84 (d, J=2.1 Hz, 1H), 8.22-8.19 (m, 2H), 8.49 (d, J=2.1 Hz, 1H).

Mixture of 3-(1-methyl-1H-pyrazol-4-yl)-5-(5-methylcyclohex-1-enyl)-1-(phenylsulfonyl)-1H-pyrrolo[2,3-b]pyridine and 3-(1-methyl-1H-pyrazol-4-yl)-5-(3-methylcyclohex-1-enyl)-1-(phenylsulfonyl)-1H-pyrrolo[2,3-b]pyridine (IIa-29)

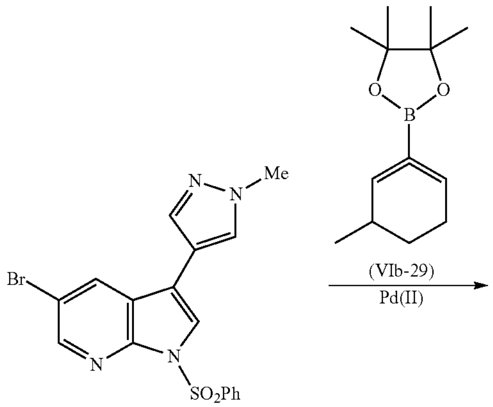

(III-a)

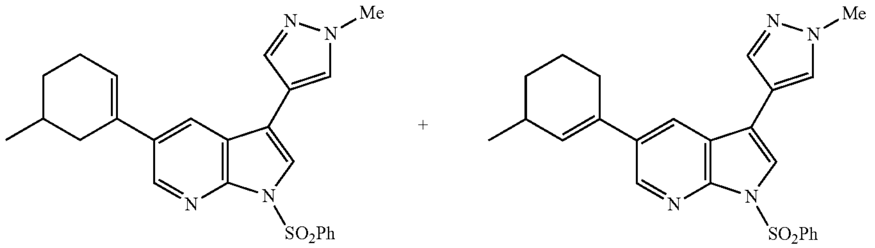

(IIa-29)

5-Bromo-3-(1-methyl-1H-pyrazol-4-yl)-1-(phenyl sulfonyl)-1H-pyrrolo[2,3-b]pyridine (III-a) (0.30 g, 0.72 mmol), boronic ester (VIb-29) (0.40 g, 1.80 mmol), lithium chloride (92 mg, 2.16 mmol), and $Pd(PPh_3)_2Cl_2$ (50 mg, 0.072 mmol), in EtOH (1.80 mL), toluene (1.80 mL) and 1M $Na_2CO_3$ solution (1.80 mL) were reacted using the general procedure. The crude product was purified by PTLC using 1:1 hexane: EtOAc as the eluent to give product (IIa-29) (ratio of isomers 2.4:1) as a yellow solid (0.17 g, 54%), $^1$H NMR (400 MHz, $CDCl_3$) δ 1.06 (d, J=6.6 Hz, 3H, major isomer), 1.07 (J=7.0 Hz, 3H, minor isomer), 1.95-1.64 (m, 6H), 2.12-2.00 (m, 2H), 2.30-2.22 (m, 3H), 2.49-2.34 (m, 3H), 3.99 (s, 6H), 5.94-5.92 (m, 1H, minor isomer), 6.10-6.06 (m, 1H, major isomer), 7.50-7.44 (m, 4H), 7.59-7.53 (m, 2H), 7.65 (s, 2H), 7.72 (s, 2H), 7.76 (d, J=0.5 Hz, 2H), 7.86 (d, J=2.1 Hz, 1H), 7.87 (d, J=2.1 Hz, 1H), 8.22-8.18 (m, 4H), 8.51-8.49 (m, 2H).

Mixture of 3-(1-methyl-1H-pyrazol-4-yl)-5-(6-methylcyclohex-1-enyl)-1-(phenylsulfonyl)-1H-pyrrolo[2,3-b]pyridine and 3-(1-methyl-1H-pyrazol-4-yl)-5-(2-methylcyclohex-1-enyl)-1-(phenylsulfonyl)-1H-pyrrolo[2,3-b]pyridine (IIa-30)

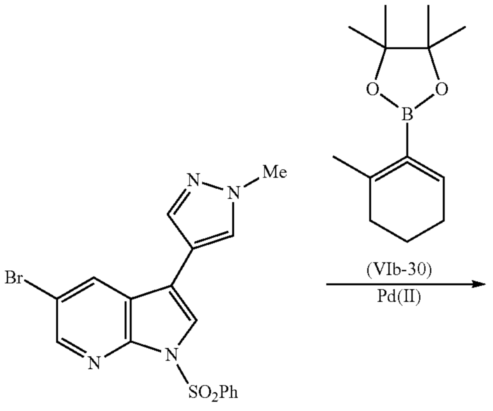

(III-a)

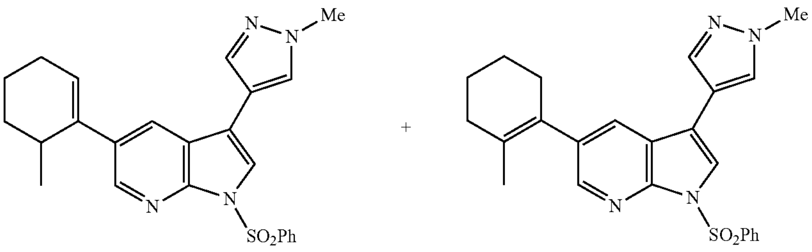

(IIa-30)

5-Bromo-3-(1-methyl-1H-pyrazol-4-yl)-1-(phenylsulfonyl)-1H-pyrrolo[2,3-b]pyridine (III-a) (0.30 g, 0.72 mmol), boronic ester (VIb-30) (0.40 g, 1.80 mmol), lithium chloride (92 mg, 2.16 mmol), and $Pd(PPh_3)_2Cl_2$ (50 mg, 0.072 mmol), in EtOH (1.80 mL), toluene (1.80 mL) and 1.0 M $Na_2CO_3$ solution (1.80 mL) were reacted using the general procedure A for the Suzuki reaction. The crude product was purified by PTLC using 1:1 hexane:EtOAc as eluent to give (IIa-30) (ratio of isomers 35:36 4.3:1) as a white foam (0.091 g, 29%), $^1H$ NMR (400 MHz, $CDCl_3$) δ 0.90 (d, J=7.0 Hz, 3H, major isomer), 1.53 (s, 3H, minor isomer), 1.78-1.55 (m, 9H), 1.94-1.86 (m, 1H), 2.13-2.04 (m, 1H), 2.20-2.14 (m, 2H), 2.25-2.20 (m, 1H), 2.86-2.76 (m, 1H), 3.98 (s, 3H, minor isomer), 3.99 (s, 3H, major isomer), 5.85 (dt, J=1.1 and 3.6 Hz, 1H), 7.52-7.46 (m, 4H), 7.60-7.55 (m, 2H), 7.64 (s, 1H), 7.65 (s, 1H), 7.74 (s, 1H), 7.75 (s, 1H), 7.76 (d, J=0.6 Hz, 1H), 7.78 (s, 1H), 7.81 (d, J=2.0 Hz, 1H), 8.08 (d, J=2.1 Hz, 1H), 8.24-8.19 (m, 4H), 8.41 (d, J=2.0 Hz, 1H), 8.48 (d, J=2.1 Hz, 1H).

5-(2-methoxycyclohex-1-enyl)-3-(1-methyl-1H-pyrazol-4-yl)-1-(phenylsulfonyl)-1H-pyrrolo[2,3-b]pyridine (IIa-31)

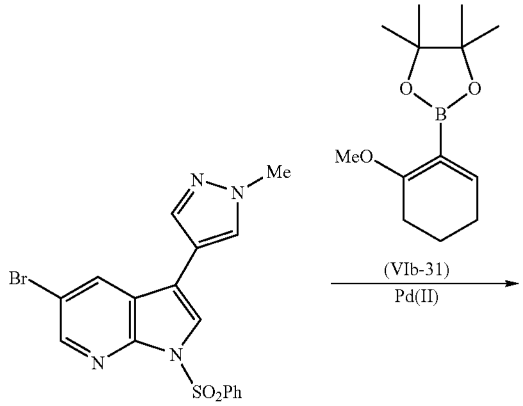

(III-a)

-continued

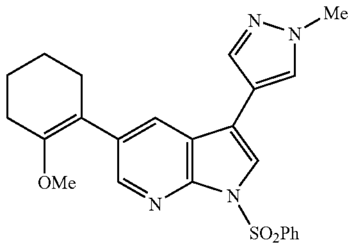

(IIa-31)

5-Bromo-3-(1-methyl-1H-pyrazol-4-yl)-1-(phenyl sulfonyl)-1H-pyrrolo[2,3-b]pyridine (III-a) (0.25 g, 0.60 mmol), boronic ester (VIb-31) (0.71 g, 3.00 mmol), lithium chloride (50 mg, 1.20 mmol), and $Pd(PPh_3)_2Cl_2$ (42 mg, 0.060 mmol), in EtOH (1.50 mL), toluene (1.50 mL) and 1.0 M $Na_2CO_3$ solution (1.50 mL) were reacted using the general procedure A for the Suzuki reaction. The crude product was purified by PTLC using hexane:EtOAc=1:1 (v/v) as eluent to give (IIa-31) (single isomer) as a yellow oil (81 mg, 30%); $^1H$ NMR (400 MHz, $CDCl_3$) δ 1.67-1.75 (m, 2H), 1.77-1.85 (m, 2H), 2.29-2.38 (m, 4H), 3.46 (s, 3H), 3.98 (s, 3H), 7.45-7.50 (m, 2H), 7.53-7.58 (m, 1H), 7.63 (s, 1H), 7.71 (s, 1H), 7.75 (d, J=0.8 Hz, 1H), 7.93 (d, J=2.0 Hz, 1H), 8.19-8.22 (m, 2H), 8.48 (d, J=2.0 Hz, 1H).

3-(1-methyl-1H-pyrazol-4-yl)-5-(3-methylcyclohexyl)-1-(phenylsulfonyl)-1H-pyrrolo[2,3-b]pyridine (IIb-32)

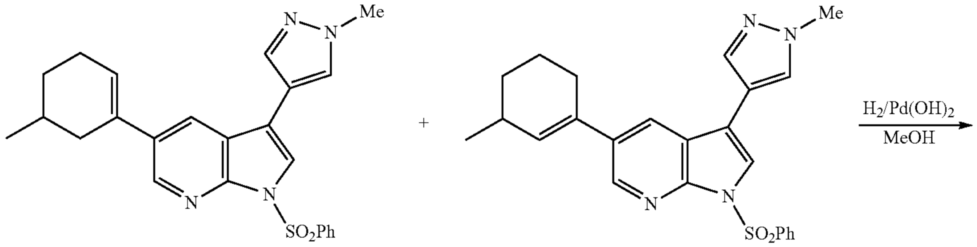

(IIa-29)

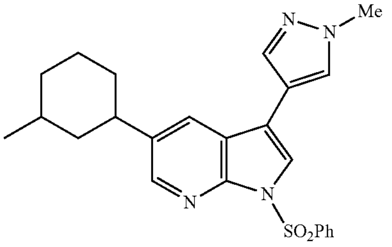

(IIb-32)

Mixture (IIa-29) was hydrogenated using the general procedure for hydrogenation of 7-azaindoles. Thus, (IIa-29) (117 mg, 0.27 mmol) and $Pd(OH)_2$ (20% on C, wet, Degussa type) (19 mg, 0.027 mmol) in MeOH (2.70 mL) were used to give the product (IIb-32) as a 1.26:1 mixture of isomers (103 mg, 88%), $^1$H NMR (400 MHz, $CDCl_3$) δ 0.94 (d, J=6.6 Hz, 3H, major isomer), 1.08 (d, J=7.0 Hz, 3H, minor isomer), 1.66-1.32 (m, 10H), 1.80-1.72 (m, 3H), 1.90-1.81 (m, 4H), 2.11-2.04 (m, 1H), 2.67 (tt, J=3.0 and 12.1 Hz, 1H), 2.93 (tt, J=3.6 and 11.0 Hz, 1H), 4.01 (s, 6H,), 7.52-7.46 (m, 4H), 7.60-7.54 (m, 2H), 7.65 (s, 2H), 7.73 (s, 2H), 7.78-7.75 (m, 4H), 8.23-8.20 (m, 4H), 8.34 (d, J=2.0 Hz, 1H), 8.36 (d, J=2.0 Hz, 1H).

3-(1-methyl-1H-pyrazol-4-y)-5-(2-methylcyclohexyl)-1-(phenylsulfonyl)-1H-pyrrolo[2,3-b]pyridine (IIb-33)

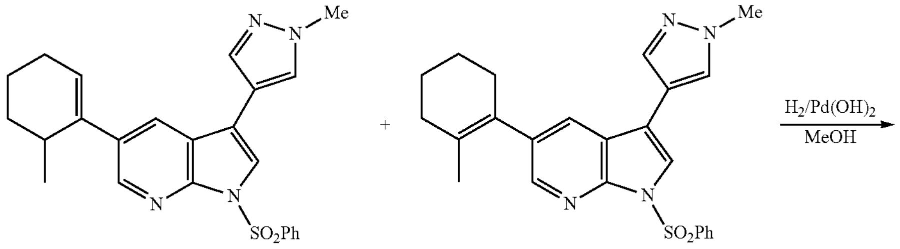

(IIa-30)

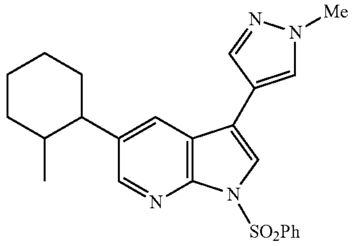

(IIb-33)

Mixture (IIa-30) was hydrogenated using the general procedure for hydrogenation of 7-azaindoles. Thus, (IIa-30) (60 mg, 0.14 mmol) and $Pd(OH)_2$ (20% on C, wet, Degussa type) (9.7 mg, 0.014 mmol) in MeOH (1.40 mL) were used to give the product (IIb-33) as a 4:1 mixture of isomers (56 mg, 94%), $^1$H NMR (400 MHz, $CDCl_3$) δ 0.63 (d, J=6.8 Hz, 3H, minor isomer), 0.66 (d, J=7.1 Hz, 3H, major isomer), 1.96-1.33 (m, 16H), 2.14-2.07 (m, 2H), 2.25-2.15 (m, 1H), 2.95 (td, J=3.8 and 12.4 Hz, 1H), 3.99 (s, 3H, minor isomer), 4.00 (s, 3H, major isomer), 7.52-7.46 (m, 4H), 7.60-7.54 (m, 2H), 7.68-7.63 (m, 2H), 7.79-7.70 (m, 6H), 8.25-8.20 (m, 4H), 8.26 (d, J=1.8 Hz, 1H), 8.32 (d, J=1.9 Hz, 1H).

3-(1-methyl-1H-pyrazol-4-yl)-1-(phenylsulfonyl)-5-(3,3,5,5-tetramethylcyclohexyl)-1H-pyrrolo[2,3-b]pyridine (IIb-34)

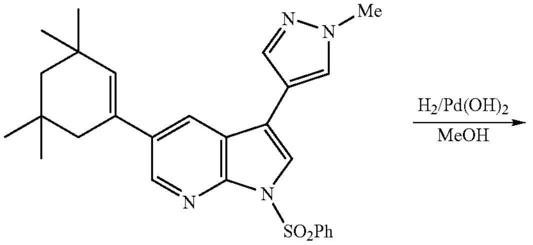

(IIa-28)

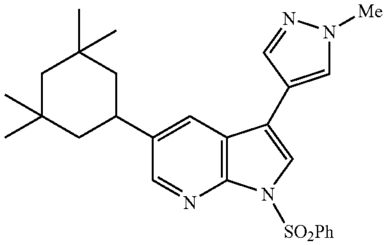

(IIb-34)

Compound (IIa-28) was hydrogenated using the general procedure for hydrogenation of 7-azaindoles. Thus, (IIa-28) (0.10 g, 0.21 mmol) and $Pd(OH)_2$ (20% on C, wet, Degussa type) (15 mg, 0.021 mmol) in MeOH (2.10 mL) were used to give the crude product (IIb-34) (0.085 g, 83%). $^1$H NMR (400 MHz, $CDCl_3$) δ 0.93 (s, 6H), 1.10 (s, 6H), 1.17-1.03 (m, 2H), 1.36-1.21 (m, 2H), 1.56 (d, J=12.7 Hz, 2H), 2.98 (tt, J=2.8 and 12.7 Hz 1H), 4.01 (s, 3H), 7.51-7.46 (m, 2H), 7.59-7.54 (m, 1H), 7.67 (s, 1H), 7.73 (s, 1H), 7.75 (d, J=1.5 Hz, 1H), 7.78 (s, 1H), 8.22-8.19 (m, 2H), 8.35 (d, J=1.4 Hz, 1H).

3-(1-methyl-1H-pyrazol-4-yl)-5-(4-phenyleyelohexyl)-1-(phenylsulfonyl)-1H-pyrrolo[2,3-b]pyridine (IIb-35)

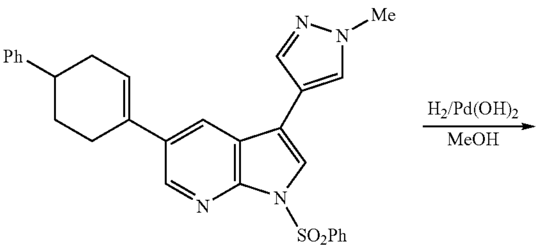

(IIa-27)

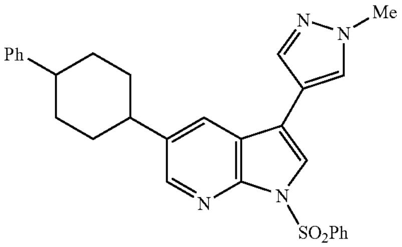

(IIb-35)

Compound (IIa-27) was hydrogenated using the general procedure for hydrogenation of 7-azaindoles. Thus, (IIa-27) (0.22 g, 0.44 mmol) and $Pd(OH)_2$ (20% on C, wet, Degussa type) (31 mg, 0.044 mmol) in MeOH (12.3 mL) were used to give (IIb-35) as a 1.2:1 mixture of isomers (0.17g, 78%), $^1$H NMR (400 MHz, $CDCl_3$) δ 1.68 (t, J=10.5 Hz, 1H), 1.94-1.84 (m, 4 H), 2.09-1.97 (m, 8H), 2.68-2.58 (m, 1H), 2.79-2.71 (m, 1H), 2.98-2.91 (m, 1H), 3.06-2.99 (m, 1H), 3.99 (s, 3H), 4.01 (s, 3H), 7.36-7.18 (m, 10H), 7.52-7.46 (m, 4H), 7.60-7.55 (m, 2H), 7.62 (s, 1H), 7.67 (s, 1H), 7.74 (s, 1H), 7.75 (s, 1H), 7.76 (s, 1H), 7.79 (s, 1H), 8.83-8.81 (m, 2H), 8.25-8.20 (m, 4H), 8.40 (d, J=1.9 Hz, 1H), 8.43 (d, J=2.0 Hz, 1H).

3-(1-methyl-1H-pyrazol-4yl)-1-(phenylsulfonyl)-5-(3,3,5-trimethylcyclohexyl)-1H-pyrrolo[2,3-b]pyridine (IIb-36)

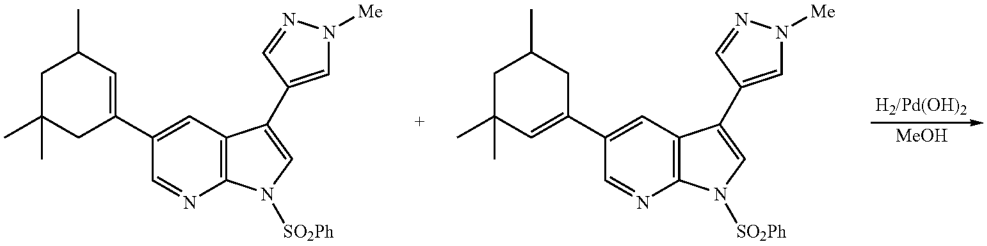

(IIa-68)

-continued

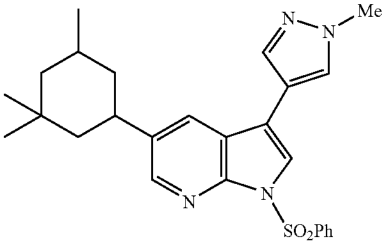

(IIb-36)

Mixture (IIa-68) was hydrogenated using the general procedure for hydrogenation of 7-azaindoles. Thus, (IIa-68) (60 mg, 0.13 mmol) and $Pd(OH)_2$ (20% on C, wet, Degussa type) (9 mg, 0.013 mmol) in MeOH (1.30 mL) were used to give the crude product (IIb-36). The material was not purified and the NMR was not clean for the peaks to be unambiguously assigned.

3-(1-methyl-1H-pyrazol-4-yl)-5-((1r,4r)-4-(4-methyl-1,4-diazepan-1-yl)cyclohexyl)-1-(phenylsulfonyl)-1H-pyrrolo[2,3-b]pyridine (IIb-37) and 3-(1-methyl-1H-pyrazol-4-yl)-5-(1s,4s)-4-(4-methyl-1,4-diazepan-1-yl)cyclohexyl)-1-(phenylsulfonyl)-1H-pyrrolo[2,3-b]pyridine (IIb-38)

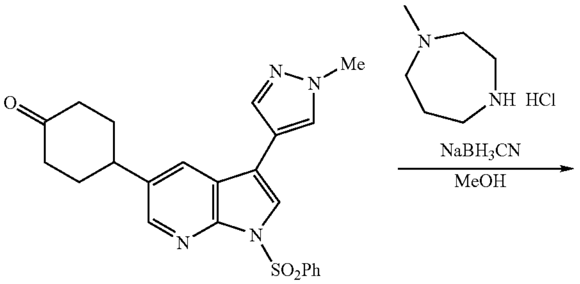

(IIb-20)

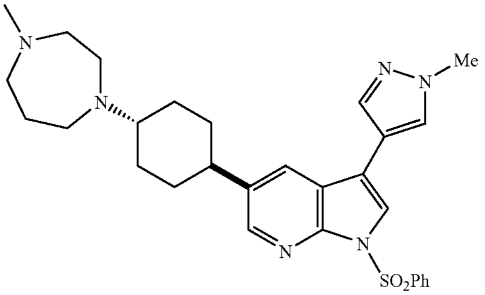

(IIb-37)

+

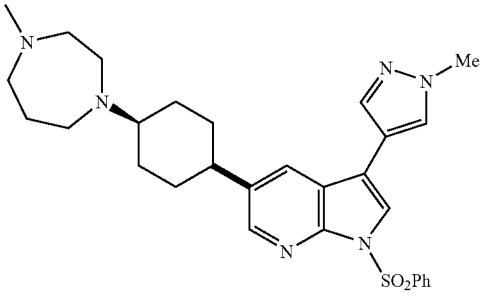

(IIb-38)

Ketone (IIb-20) (0.25 g, 0.57 mmol), N-methylhomopiperazine (0.43 ml, 3.45 mmol), 1.25 M HCl/MeOH (0.92 ml, 1.15 mmol) and $NaCNBH_3$ (0.072 g, 1.15 mmol) in anhydrous methanol (5.75 mL) were reacted following the general procedure A for the reductive amination. The crude product was purified by LCMS (column LUNA 10μ C18(2) 00G-4253-V0 250×50 mm) using water—MeCN (0.1% AcOH) as eluent (in gradient; flow 80 mL/min) to give a 1.5:1 mixture of (IIb-37) and (IIb-38) (157 mg, 51%; retention time 12-13 min) as colourless oil. $^1H$ NMR (400 MHz, $CDCl_3$) δ 1.60-1.41 (m, 4H), 1.89-1.61 (m, 4H), 2.11-1.97 (m, 16H), 2.60 (s, 3H) 2.63 (s, 3H), 2.93-2.78 (m, 4H), 3.11-2.96 (m, 12H), 4.01 (s, 3H), 4.01 (s, 3H), 7.52-7.46 (m, 4H), 7.60-7.55 (m, 2H), 7.65 (s, 1H), 7.70 (s,1H), 7.76-7.73 (m, 6H), 8.22-8.19 (m, 4H), 8.31 (d, J=2.0 Hz, 1H), 8.41 (d, J=2.0 Hz, 1H), MS (CI) m/z 533.3 ($MH^+$).

4-((1s,4s)-4-(3-(1-methyl-1H-pyrazol-4-yl)-1-(phenylsulfonyl)-1H-pyrrolo[2,3-b]pyridin-5-yl)cyclohexyl)-1,4-oxazepane (IIb-39) and 4-((1r,4r)-4-(3-(1-methyl-1H-pyrazol-4-yl)-1-(phenylsulfonyl)-1H-pyrrolo[2,3-b]pyridin-5-yl)cyclohexyl)-1,4-oxazepane (IIb-40)

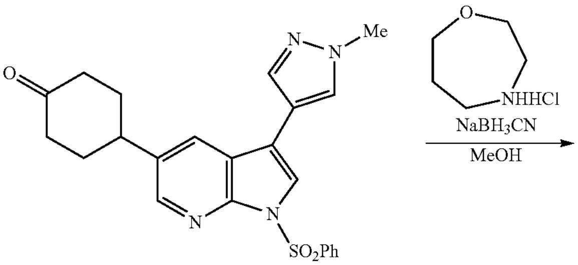

(IIb-20)

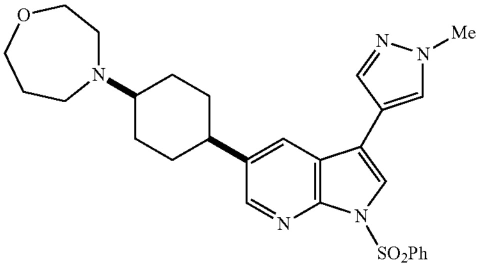

(IIb-39)

+

-continued

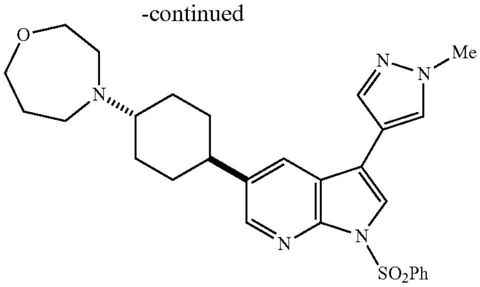

(IIb-40)

Compound (IIb-20) (0.29 g, 0.67 mmol), homomorpholine hydrochloride (0.55 g, 4.00 mmol) and $NaCNBH_3$ (0.08 g, 1.33 mmol) in dry MeOH (6.67 mL) were reacted following the general procedure A for the reductive amination. The crude product was purified by PTLC using 10:1 $CH_2Cl_2$:MeOH as the eluent to give a 1:1.1 mixture of (IIb-39) and (IIb-40) as a white foam (0.07 g, 20%), $^1H$ NMR (400 MHz, $CDCl_3$) δ 1.62-1.5 (m, 5H), 1.78-1.68 (m, 4H), 2.16-1.93 (m, 12H), 2.68-2.51 (m, 1H), 2.91-2.83 (m, 1H), 3.11-2.93 (m, 9H), 3.87-3.79 (m, 8H), 4.00 (s, 3H), 4.02 (s, 3H), 7.51-7.46 (m, 4H), 7.60-7.55 (m, 2H), 7.68 (s, 1H), 7.75 (d, J=2 Hz, 2H), 7.76 (d, J=0.6 Hz, 1H), 7.77 (d, J=2 Hz, 1H), 7.79 (s, 1H), 7.92 (d, J=1.8 Hz, 2H), 8.21-8.18 (m, 4H), 8.31 (d, J=2.0 Hz, 1H), 8.38 (d, J=2.0 Hz, 1H).

4-((1s,4s)-4-(3-(1-methyl-1H-pyrazol-4-yl)-1-(phenylsulfonyl)-1H-pyrrolo[2,3-b]pyridin-5-yl)cyclohexyl)-1,4-oxazepane (IIb-39) and 4-((1r,4r)-4-(3-(1-methyl-1H-pyrazol-4-yl)-1-(phenylsulfonyl)-1H-pyrrolo[2,3-b]pyridin-5-yl)cyclohexyl)-1,4-oxazepane (IIb-40)—an Alternative Method of Preparation

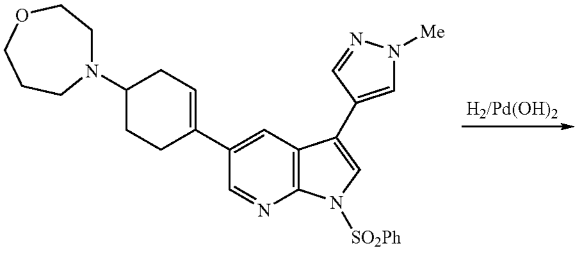

(IIa-134)

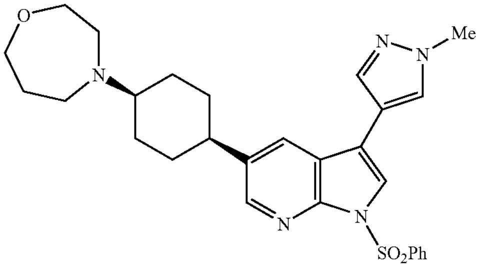

+

(IIb-39)

-continued

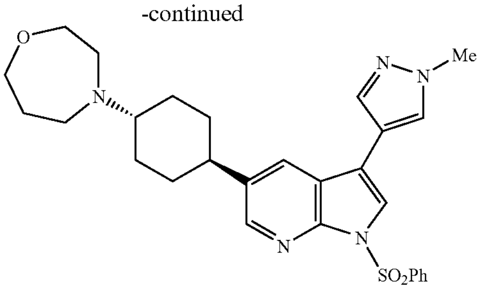

(IIb-40)

Compound (IIa-134) was hydrogenated using the general procedure for hydrogenation of 7-azaindoles. Thus, (IIa-27) (6.04 g, 11.67 mmol) and $Pd(OH)_2$ (20% on C, wet, Degussa type) (1.0 g) in EtOH:THF=1:1 (50 mL) were reacted over a period of 46 h. The reaction mixture was filtered through Celite, washing with EtOH (500 mL), and concentrated to afford a white foam (5.76 g). It was purified by SGC using $CH_2Cl_2$:MeOH (gradient elution from 100:0 to 95:5, v/v). Eluting first was the cis isomer (IIb-39) (1.74 g, 3.36 mmol, 29%). Further elution afforded the trans isomer (IIb-40) (3.76 g, 7.24 mmol, 62%). $^1H$ NMR data as described earlier.

4-((1r,4r)-4-(3-(1-methyl-1H-pyrazol-4-yl)-1-(phenylsulfonyl)-1H-pyrrolo[2,3-b]pyridin-5-yl)cyclohexyl)-1,4-oxazepane (IIb-40)—Synthesis from (IIb-39)

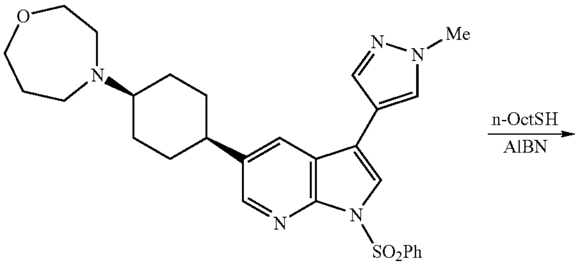

(IIb-39)

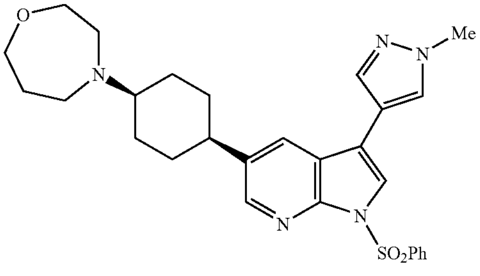

+

(IIb-39)

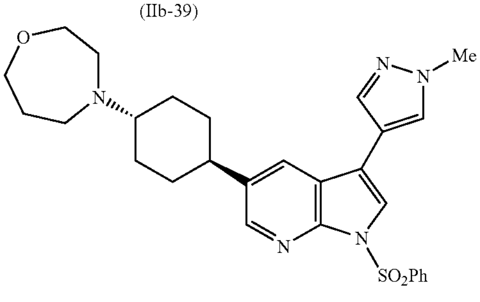

(IIb-40)

To a stirred solution of (IIb-39) (1.74 g, 3.36 mmol) in benzene (10 mL) was added octane-1-thiol (540 mg, 3.69 mmol) and the reaction mixture was heated to reflux. 2,2'-azobis(2-methylpropionitrile) (276 mg, 1.68 mmol) was then added dropwise over 3 h as a solution in benzene (10 mL). Reflux was continued for 18 h, and the reaction mixture was then concentrated to dryness and purified by SGC using $CH_2Cl_2$:hexanes=1:1 (v/v), neat $CH_2Cl_2$ and $CH_2Cl_2$:MeOH=95:5 (v/v). Eluting first was the recovered cis isomer (IIb-39) (68 mg, 0.13 mmol, 4%). Further elution afforded trans isomer (IIb-40) (1.47 g, 2.83 mmol, 84%). NMR data as above.

5-(4-(azetidin-1-yl)cyclohexyl)-3-(1-methyl-1H-pyrazol-4-yl)-1-(phenylsulfonyl)-1H-pyrrolo[2,3-b]pyridine (IIb-41)

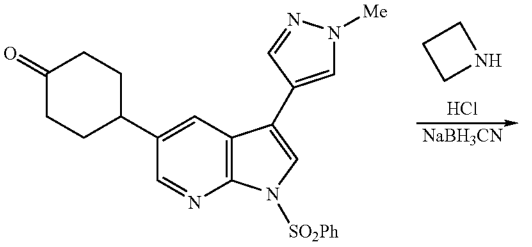

(IIb-20)

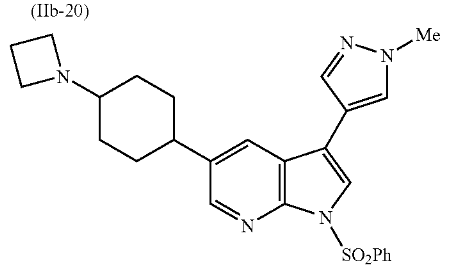

(IIb-41)

Ketone (IIb-20) (0.34 g, 0.78 mmol), azetidine (0.32 ml, 4.69 mmol), 1.25 M HCl in MeOH (1.25 ml, 1.56 mmol) and $NaCNBH_3$ (0.10 g, 1.56 mmol) in anhydrous methanol (7.82 mL) were reacted following the general procedure A for the reductive amination. The crude product was purified by LCMS (column LUNA 10μ C18(2) 00G-4253-V0 250×50 mm) using water—MeCN (0.1% AcOH) as eluent (in gradient; flow 80 mL/min) to give (IIb-41) (156 mg, 42%; retention time 13-14 min) as a colourless oil, a 1.2:1 mixture of trans:cis isomers. $^1$H NMR (400 MHz, $CDCl_3$) δ 1.66-1.40 (m, 8H), 1.92-1.82 (m, 2H), 2.05-1.95 (m, 6H), 2.37-2.22 (m, 4H), 2.74-2.58 (m, 3H), 2.90-2.83 (m, 1H), 3.80-3.71 (m, 8H), 3.99 (, 3H), 4.01 (s, 3H), 7.50-7.44 (m, 4H), 7.59-7.52 (m, 2H), 7.64 (s, 1H), 7.75-7.73 (m, 4H), 7.77 (d, J=0.6 Hz, 1H), 7.87 (s, 1H), 7.95 (s, 1H), 7.93 (d, J=2 Hz, 1H), 8.20-8.16 (m, 4H), 8.31-8.21 (m, 2H), MS (CI) m/z 476.0 ($MH^+$).

5-(4,4-difluorocyclohexyl)-3-(1-methyl-1H-pyrazol-4-y)-1-(phenylsulfonyl)-1H-pyrrolo[2,3-b]pyridine (IIb-42)

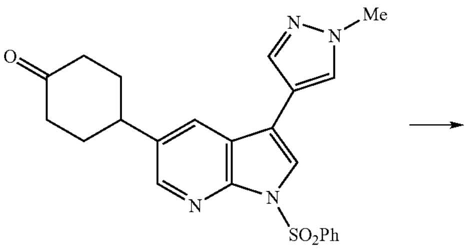

(IIb-20)

-continued

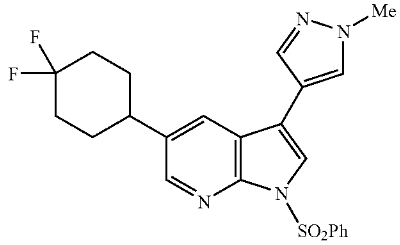

(IIb-42)

A solution of [bis(2-methoxyethyl)amino]sulphur trifluoride (0.09 ml, 0.48 mmol) in anhydrous toluene (6.90 mL) was cooled to 0° C. under nitrogen and $BF_3$.$OEt_2$ (4.23 μl, 0.034 mmol) was added. The resulting solution was allowed to stand at 0° C. for 90 min. Ketone (IIb-20) (0.15 g, 0.34 mmol) was added in one portion and the reaction mixture was heated to 55° C. for 24 h. The mixture was poured at 0° C. into a 10% solution of NaOH (10 mL) and EtOAc (10 mL). The two layers were separated. The organic layer was dried over $MgSO_4$ and concentrated. The crude product was purified by PTLC using 1:1 EtOAc:hexane as the eluent to give (IIb-42) (77 mg, 49%), $^1$H NMR (400 MHz, $CDCl_3$) δ 1.99-1.79 (m, 6H), 2.29-2.19 (m, 2H), 2.76 (t, J=10.5 Hz, 1H), 4.00 (s, 3H), 7.52-7.47 (m, 2H), 7.61-7.56 (m, 1H), 7.64 (s, 1H), 7.75 (d, J=0.4 Hz, 1H), 7.76 (s, 1H), 7.77, (d, J=2.1 Hz, 1H), 8.23-8.20 (m, 2H), 8.35 (d, J=2.1 Hz, 1H).

5-((1r,4r)-4-(4-isopropylpiperazin-1-yl)cyclohexyl)-3-(1-methyl-1H-pyrazol-4-yl)-1-(phenylsulfonyl)-1H-pyrrolo[2,3-b]pyridine (IIb-43) and 5-((1s,4s)-4-(4-isopropylpiperazin-1-yl)cyclohexyl)-3-(1-methyl-1H-pyrazol-4-yl)-1-(phenylsulfonyl)-1H-pyrrolo[2,3-b]pyridine (IIb-44)

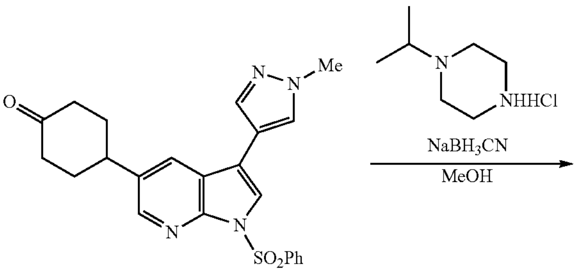

(IIb-20)

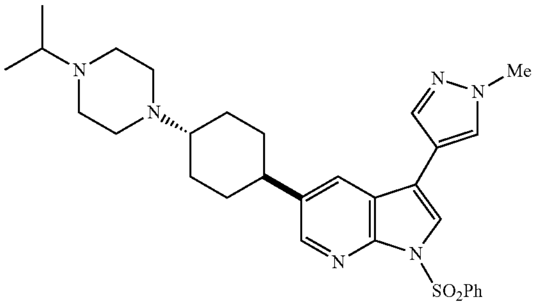

+

(IIb-43)

-continued

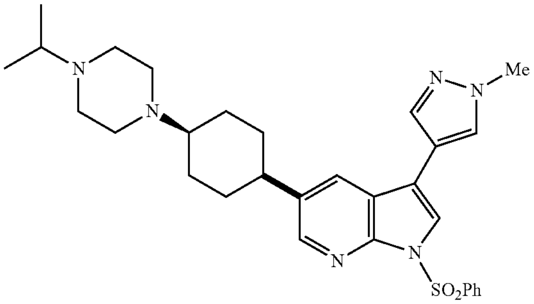

(IIb-44)

Ketone (IIb-20) (0.60 g, 1.38 mmol), 1-isopropylpiperazine (1.18 ml, 8.28 mmol), 1.25 M HCl/MeOH (2.20 ml, 2.76 mmol) and $NaCNBH_3$ (0.17 g, 2.76 mmol) in anhydrous methanol (13.80 mL) were reacted following the general procedure A for the reductive amination. The crude product was purified by preparative LCMS (column LUNA 10μ C18 (2) 00G-4253-V0 250×50 mm) using water—MeCN (0.1% AcOH) as eluent (in gradient; flow 80 mL/min) to give the trans isomer (IIb-43) as a yellow foam (129 mg, 17%; retention time 14.5 min) and the cis isomer (IIb-44) as a yellow foam (200 mg, 27%; retention time 16.6 min).

Data for trans isomer (IIb-43): $^1$H NMR (400 MHz, $CDCl_3$) δ 1.15 (d, J=6.60 Hz, 6H), 1.60-1.41 (m, 4H), 2.02-1.95 (br m, 2H), 2.13-2.06 (br m, 2H), 2.68-2.55 (m, 2H), 2.96-2.85 (br s, 8H), 3.06-2.97 (m, 1H), 3.99 (s, 3H), 7.50-7.45 (m, 2H), 7.59-7.53 (m, 1H), 7.64 (s, 1H), 7.75-7.71 (m, 3H), 8.21-8.17 (m, 2H), 8.30 (d, J=2.0 Hz, 1H), MS (CI) m/z 547.3 ($MH^+$).

Data for cis isomer (IIb-44): $^1$H NMR (400 MHz, $CDCl_3$) δ 1.06 (d, J=6.60 Hz, 3H), 1.22 (d, J=6.60 Hz, 3H), 1.65-1.52 (m, 2H), 1.98-1.88 (m, 2H), 2.24-2.18 (m, 1H), 2.46-2.39 (m, 1H), 2.55-2.48 (m, 2H), 2.87-2.74 (m, 5H), 3.05-2.95 (m, 3H), 3.17-3.10 (m, 2H), 3.30-3.19 (m, 1H), 3.98 (s, 3H), 7.50-7.43 (m, 2H), 7.59-7.53 (m, 1H), 7.65 (s, 1H), 7.75-7.72 (m, 2H), 7.78 (d, J=1.7 Hz, 1H), 8.20-8.16 (m, 2H), 8.37 (d, J=1.7 Hz, 1H), MS (CI) m/z 547.3 ($MH^+$).

3-(1-methyl-1H-pyrazol-4-yl)-1-(phenylsulfonyl)-5-((1r,4r)-4-(piperidin-1-yl)cyclohexyl)-1H-pyrrolo[2,3-b]pyridine (IIb-45) and 3-(1-methyl-1H-pyrazol-4-yl)-1-(phenylsulfonyl)-5-((1s,4s)-4-(piperidin-1-yl)cyclohexyl)-1H-pyrrolo[2,3-b]pyridine (IIb-46)

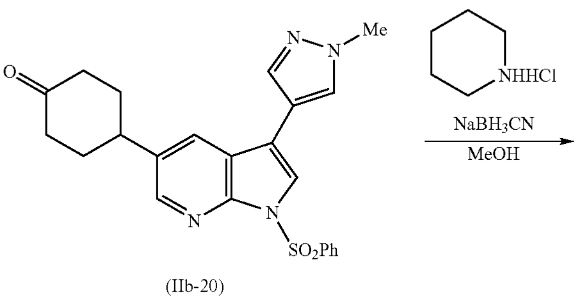

(IIb-20)

-continued

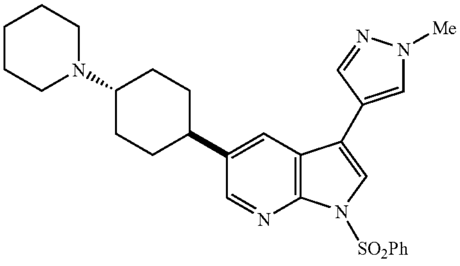

(IIb-45)

+

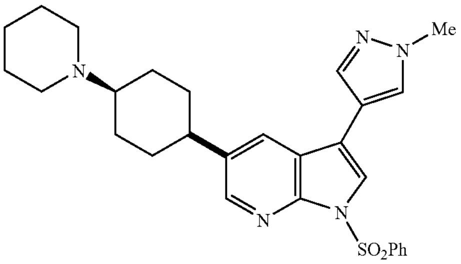

(IIb-46)

Ketone (IIb-20) (0.60 g, 1.38 mmol), piperidine (0.82 mL, 8.28 mmol), 1.25 M

HCl/MeOH (2.20 ml, 2.76 mmol) and $NaCNBH_3$ (0.17 g, 2.76 mmol) in anhydrous methanol (13.8 mL) were reacted following the general procedure A for the reductive amination. The crude product was purified by preparative LCMS (column LUNA 10μ C18(2) 00G-4253-V0 250×50 mm) using water—MeCN (0.1% AcOH) as eluent (in gradient; flow 80 mL/min) to give the trans isomer (IIb-45) as a white foam (142 mg, 20%; retention time 15 min) and the cis isomer (IIb-46) as a white foam (200 mg, 27%; retention time 17.5 min). Data for trans isomer (IIb-45) $^1$H NMR (400 MHz, $CDCl_3$) δ 1.54-1.72 (m, 1H), 1.76-1.96 (m, 6H), 1.97-2.05 (m, 2H), 2.16-2.27 (m, 2H), 2.50-2.62 (m, 1H), 2.88-3.15 (m, 3H), 4.00 (s, 3H), 7.44-7.51 (m, 2H), 7.54-7.59 (m, 1H), 7.73 (s, 1H), 7.74 (s, 1H), 7.75 (s, 1H), 7.79 (d, J=2.0 Hz, 1H), 8.16-8.20 (m, 2H), 8.28 (d, J=2.0 Hz, 1H), MS (CI) m/z 504.2 ($MH^+$).

Data for cis isomer (IIb-46) $^1$H NMR (400 MHz, $CDCl_3$) δ 1.43-1.63 (m, 4H), 1.73-1.89 (m, 6H), 1.94-2.00 (m, 2H), 2.14-2.31 (m, 2H), 2.55-2.69 (m, 1H), 2.81-2.91 (m, 2H), 2.95-3.08 (m, 2H), 3.15-3.25 (m, 1H), 3.95 (s, 3H), 7.42-7.47 (m, 2H), 7.50-7.56 (m, 1H), 7.68 (s, 1H), 7.73 (d, J=2.1 Hz, 1H), 7.76 (s, 1H), 7.88 (d, J=2.1 Hz, 1H), 8.13-8.17 (m, 2H), 8.37 (d, J=2.0 Hz, 1H), MS (CI) m/z 504.2 ($MH^+$).

5-(1r,4r)-4-(3,3-difluoropyrrolidin-1-yl)cyclohexyl)-3-(1-methyl-1H-pyrazol-4-yl)-1-(phenylsulfonyl)-1H-pyrrolo[2,3-b]pyridine (IIb-47) and 5-((1s,4s)-4-(3,3-difluoropyrrolidin-1-yl)cyclohexyl)-3-(1-methyl-1H-pyrazol-4-yl)-1-(phenylsulfonyl)-1H-pyrrolo[2,3-b]pyridine (IIb-48)

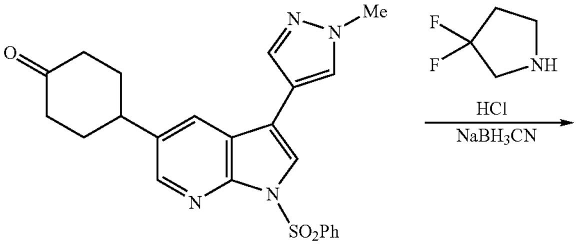

(IIb-20)

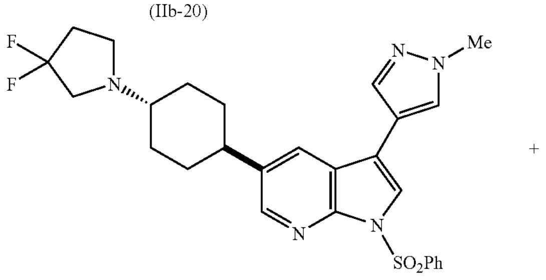

(IIb-47)

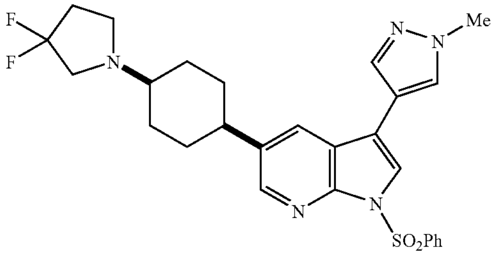

(IIb-48)

Compound (IIb-20) (0.15 g, 0.35 mmol), 3,3-difluoropyrrolidine hydrochloride (0.20 g, 1.39 mmol) and $NaCNBH_3$ (0.04 g, 0.69 mmol) in dry MeOH (3.47 mL) were reacted following the general procedure A for the reductive amination. The crude product was separated by preparative LCMS (column LUNA 10μ C18(2) 00G-4253-V0 250×50 mm) using water—MeCN (0.1% AcOH) as eluent (in gradient; flow 80 mL/min) to give the trans isomer (IIb-47) (85 mg, 47%; retention time 23 min) and impure fractions containing the cis isomer (IIb-48) (retention time 26-27.5 min). The impure fractions were combined and purified further by PTLC using 20:1 $CH_2Cl_2$:MeOH as the eluent to give pure cis isomer (IIb-48) (6 mg, 3%).

Data for trans isomer (IIb-47): $^1$H NMR (400 MHz, $CDCl_3$) δ 1.60-1.40 (m, 4H), 2.01-1.93 (m, 2H), 2.14-2.03 (m, 2H), 2.39-2.25 (m, 3H), 2.69-2.59 (m, 1H), 2.92 (t, J=7.0 Hz, 2H), 3.09 (t, J=7.0 Hz, 2H), 4.00 (s, 3H), 7.51-7.46 (m, 2H), 7.59-7.54 (m, 1H), 7.64 (s, 1H), 7.73 (s, 1H), 7.75 (d, J=2.0 Hz, 1H), 7.76 (d, J=0.6 Hz, 1H), 8.22-8.18 (m 2H), 8.33 (d, J=2.0 Hz, 1H), MS (CI) m/z 526.2 ($MH^+$).

Data for cis isomer (IIb-48): $^1$H NMR (400 MHz, $CDCl_3$) δ 1.65-1.55 (m, 5H), 1.98-1.86 (m, 2H), 2.36-2.24 (m, 2H), 2.41-2.37 (m, 1H), 2.75 (t, J=7.0 Hz, 2H), 2.94 (t, J=13.7 Hz, 2H), 4.00 (s, 3H), 7.52-7.47 (m, 2H), 7.60-7.55 (m, 1H), 7.65 (s, 1H), 7.74 (s, 1H), 7.77 (d, J=0.6 Hz, 1H), 7.80 (d, J=2.0 Hz, 1H), 8.23-8.20 (m 2H), 8.37 (d, J=2.0 Hz, 1H), MS (CI) m/z 526.2 ($MH^+$).

5-((1R,4s)-4-((S)-3-fluoropyrrolidin-1-yl)cyclohexyl)-3-(1-methyl-1H-pyrazol-4yl)-1-(phenylsulfonyl)-1H-pyrrolo[2,3-b]pyridine (IIb-49) and 5-((1S,4r)-4-((S)-3-fluoropyrrolidin-1-yl)cyclohexyl)-3-(1-methyl-1H-pyrazol-4-yl)-1-(phenylsulfonyl)-1H-pyrrolo[2,3-b]pyridine (IIb-50)

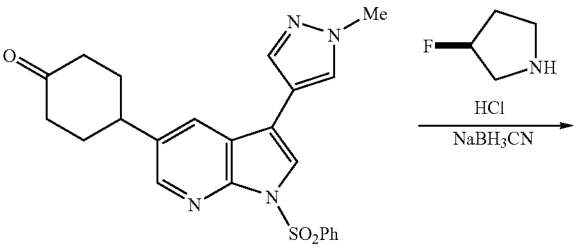

(IIb-20)

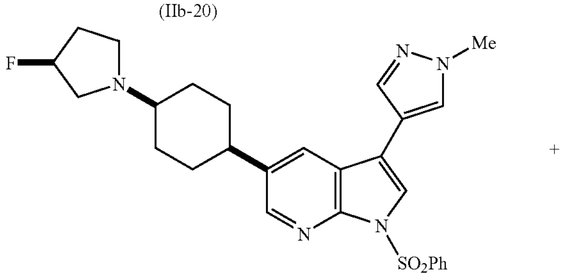

(IIb-49)

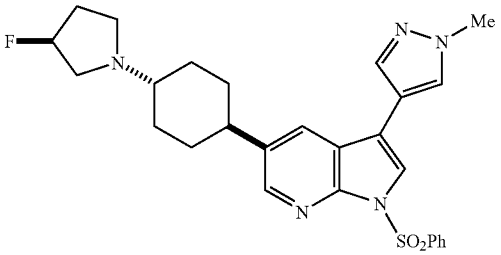

(IIb-50)

Ketone (IIb-20) (0.17 g, 0.39 mmol), (S)-(+)-3-fluoropyrrolidine hydrochloride (0.20 g, 1.57 mmol) and $NaCNBH_3$ (0.05 g, 0.78 mmol) in anhydrous methanol (3.93 mL) were reacted following the general procedure A for the reductive amination. The crude product was purified by LCMS (column LUNA 10μ C18(2) 00G-4253-V0 250×50 mm) using water—MeCN (0.1% AcOH) as eluent (in gradient; flow 80 mL/min) to give a 1:2 mixture of (IIb-49) and (IIb-50) (retention time 16.2-17 min) MS (CI) m/z 508.2 ($MH^+$). The mixture was separated by PTLC using 10:1 $CH_2Cl_2$:MeOH as eluent to give trans isomer (IIb-50) (6 mg, 37%) and the cis isomer (IIb-49) (20 mg, 10%).

Data for cis isomer (IIb-49): $^1$H NMR (400 MHz, $CDCl_3$) δ 1.65-1.57 (m, 4H), 2.00-1.90 (m, 4H), 2.22-2.04 (m, 2H), 2.38-2.33 (m, 1H), 2.46 (q, J=7.0 Hz, 1H), 2.95-2.68 (m, 4H), 4.00 (s, 3H), 5.20 (td, J=5.4 and 55.2 Hz, 1H), 7.52-7.46 (m, 2H), 7.60-7.55 (m, 1H), 7.66 (s, 1H), 7.73 (s, 1H), 7.77 (d, J=0.3 Hz, 1H), 7.82 (d, J=1.6 Hz, 1H), 8.23-8.19 (m 2H), 8.37 (d, J=1.6 Hz, 1H).

Data for trans isomer (IIb-50): $^1H$ NMR (400 MHz, $CDCl_3$) δ 1.61-1.41 (m, 4H), 2.01-1.94 (m, 2H), 2.22-2.08 (m, 4H), 2.45-2.37 (m, 1H), 2.71-2.62 (m, 1H), 2.91-2.86 (m, 1H), 2.98-2.96 (dd, J=8.5 and 15.6 Hz, 1H), 3.08-2.96 (dd, J=12.1 and 28.4 Hz, 1H), 3.25-3.12 (2xdd, J=12.1 and 28.4 Hz, 1H), 4.00 (s, 3H), 5.22 (td, J=4.6 and 55.6 Hz, 1H), 7.52-7.47 (m, 2H), 7.60-7.55 (m, 1H), 7.64 (s, 1H), 7.75-7.74 (m, 3H), 8.23-8.20(m, 2H), 8.34 (d, J=2.1 Hz, 1H).

3-(1-methyl-1H-pyrazol-4-yl)-1-(phenylsulfonyl)-5-(1,4-dioxaspiro[4.4]non-6-en-7-yl)-1H-pyrrolo[2,3-b]pyridine (IIa-51)

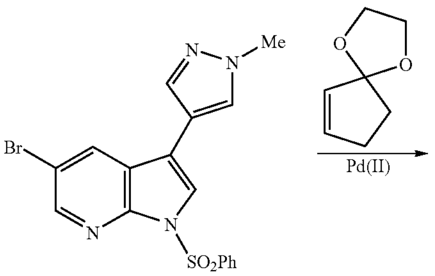

(III-a)

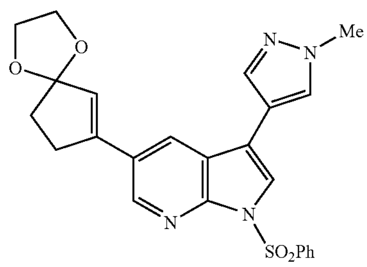

(IIa-51)

A mixture of bromide (III-a) (0.50 g, 1.20 mmol), cyclopent-1-enone ethylene acetal (0.60 g, 4.80 mmol), 2-(di-t-butyl)phosphinobiphenyl (0.072 g, 0.24 mmol), $Pd(OAc)_2$ (27 mg, 0.12 mmol) and $Et_3N$ (0.84 ml, 6.0 mmol) in dry DMF (4 mL) was heated to 110° C. for 24 h. The reaction mixture was allowed to cool down, poured into a saturated solution of $NaHCO_3$ solution (30 mL) and was extracted with EtOAc (3×50 mL). The combined organic extracts were dried over $MgSO_4$ and concentrated. The crude product was purified by SGC using hexane:EtOAc (0%400% EtOAc) as eluent (gradient elution) to give the product (IIa-51) as a yellow oil (0.065 g, 18%), $^1H$ NMR (400 MHz, $CDCl_3$) δ 1.76-1.69 (m, 1H), 2.60-2.39 (m, 3H), 3.94-3.88 (m, 4H), 4.00 (s, 3H), 4.57-4.55 (m, 1H), 7.52-7.46 (m, 2H), 7.60-7.55 (m, 1H), 7.64 (s, 1H), 7.74 (s, 1H), 7.76 (d, J=0.6 Hz, 1H), 7.78 (d, J=2.0 Hz, 1H), 8.23-8.19 (m, 2H), 8.35 (d, J=2.0 Hz, 1H).

N,N-diethyl-4-(3-(1-methyl-1H-pyrazol-4-yl)-1-(phenylsulfonyl)-1H-pyrrolo[2,3-b]pyridin-5-yl) cyclohexanamine (IIb-52)

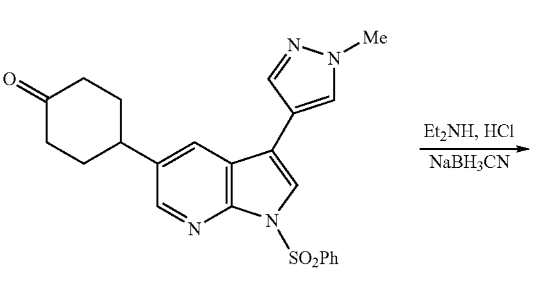

(IIb-20)

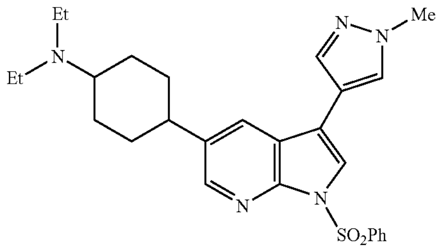

(IIb-52)

Ketone (IIb-20) (0.15 g, 0.35 mmol), diethylamine (0.21 g, 2.08 mmol), 1.0 M solution of HCl in MeOH (0.69 ml, 0.69 mmol) and $NaCNBH_3$ (43 mg, 0.69 mmol) in dry MeOH (3.5 mL) were reacted at 55° C. for 3 h following the general procedure A for the reductive amination. The crude product was purified by LCMS (column LUNA 10μ C18(2) 00G-4253-V0 250×50 mm) using water—MeCN (0.1% AcOH) as eluent (in gradient; flow 80 mL/min) to give (IIb-52) (62 mg, 36%; retention time 13.8-14.6 min) as a colourless oil, a 2.1:1 mixture of trans: cis isomers. $^1H$ NMR (400 MHz, $CDCl_3$) was difficult to assign as some impurities were still present. MS (CI) m/z 464.1 ($MH^+$).

5-((1S,4s)-4-((R)-3-fluoropyrrolidin-1-yl)cyclohexyl)-3-(1-methyl-1H-pyrazol-4yl)-1-(phenylsulfonyl)-1H-pyrrolo[2,3-b]pyridine (IIb-53) and 5-((1R,4r)-4-((R)-3-fluoropyrrolidin-1-yl)cyclohexyl)-3-(1-methyl-1H-pyrazol-4-yl)-1-(phenylsulfonyl)-1H-pyrrolo[2,3-b]pyridine (IIb-54)

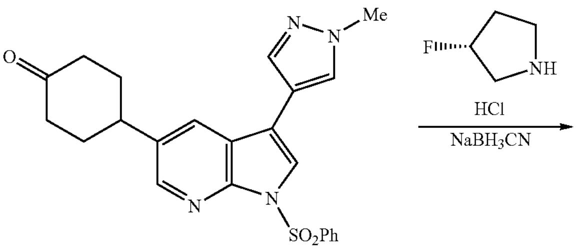

(IIb-20)

-continued

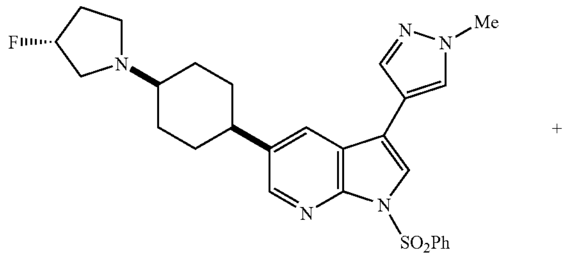

(IIb-53)

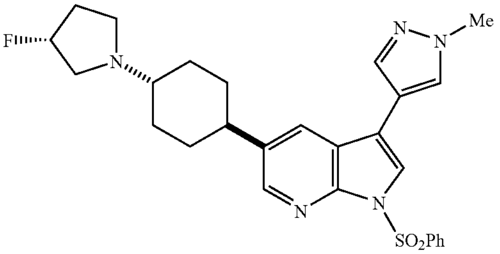

(IIb-54)

Ketone (IIb-20) (0.15 g, 0.35 mmol), (R)-(−)-3-fluoropyrrolidine hydrochloride (0.17 g, 1.39 mmol) and $NaCNBH_3$ (0.04 g, 0.69 mmol) in anhydrous MeOH (3.47 mL) were reacted following the general procedure A for the reductive amination. The crude product was purified by PTLC using 10:1 $CH_2Cl_2$:MeOH as the eluent to give the trans isomer (IIb-54) (61 mg, 35%) and the cis isomer (IIb-53) (40 mg, 23%).

Data for cis isomer (IIb-53): $^1H$ NMR (400 MHz, $CDCl_3$) δ 1.63-1.53 (m, 4H), 2.01-1.90 (m, 4H), 2.21-2.08 (m, 2H), 2.38-2.33 (m, 1H), 2.49-2.41 (m, 1H), 2.96-2.68 (m, 4H), 3.99 (s, 3H), 5.20 (td, J=5.3 and 55.6 Hz, 1H), 7.52-7.47 (m, 2H), 7.60-7.55 (m, 1H), 7.66 (m, 1H), 7.73 (s, 1H), 7.77, (d, J=0.7 Hz, 1H 7.82 (d, J=1.5 Hz, 1H), 8.23-8.20 (m, 2H), 8.37 (d, J=1.70 Hz, 1H).

Data for trans isomer (IIb-54): $^1H$ NMR (400 MHz, $CDCl_3$) δ 1.61-1.41 (m, 4H), 2.00-1.93 (m, 2H), 2.27-2.02 (m, 5H), 2.69-2.55 (m, 2H), 3.08-2.88 (m, 3H), 4.00 (s, 3H), 5.22 (td, J=5.5 and 55.4 Hz, 1H), 7.52-7.47 (m, 2H), 7.60-7.55 (m, 1H), 7.64 (s, 1H), 7.74 (s, 1H), 7.76-7.75 (m, 2H), 8.23-8.20 (m, 2H), 8.34 (d, J=2.0 Hz, 1H).

N-ethyl-4-(3-(1-methyl-1H-pyrazol-4-yl)-1-(phenylsulfonyl)-1H-pyrrolo[2,3-b]pyridin-5-yl)cyclohexanamine (IIb-55)

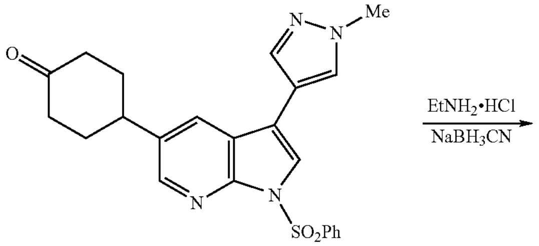

(IIb-20)

-continued

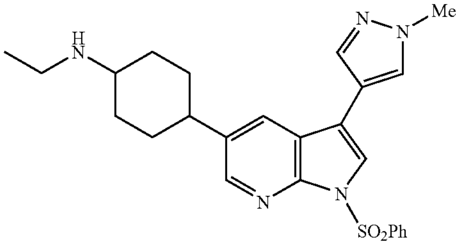

(IIb-55)

Ketone (IIb-20) (0.15 g, 0.34 mmol), 2 M ethylamine in THF (1.72 mL, 3.45 mmol), 1.25 M solution of HCl/MeOH (1.03 mL, 1.03 mmol) and $NaCNBH_3$ (0.043 g, 0.69 mmol) in anhydrous MeOH (3.45 mL) were reacted following the general procedure A for the reductive amination. The product was purified by LCMS (column LUNA 10μ C18(2) 00G-4253-V0 250×50 mm) using water—MeCN (0.1% AcOH) as eluent (in gradient; flow 80 mL/min) to give (IIb-55) (66 mg, 41%; retention time 20.2-21.2 min) as a yellow oil, a 4.2:1 mixture of trans: cis isomers. $^1H$ NMR (400 MHz, $CDCl_3$) δ 1.30 (t, J=7.2 Hz, 3H, major), 1.33 (t, J=7.2 Hz, 3H, minor), 1.48-1.68 (m, 4H, major), 1.67-1.82 (m, 4H, minor), 1.93-2.03 (m, 2H, major), 1.95-2.02 (m, 2H, minor), 2.09-2.16 (m, 2H, minor), 2.18-2.26 (m, 2H, major), 2.63-2.73 (m, 2H, major and minor), 2.98 (q, J=7.2 2H, major), 3.01 (q, J=7.2 Hz, 2H, minor), 3.28-3.31 (m, 1H, minor), 3.42-3.50 (m, 1H, major), 3.97 (s, 3H, major), 3.97 (s, 3H, minor), 7.43-7.49 (m, 4H, major and minor), 7.51-7.58 (m, 2H, major and minor), 7.65 (s, 1H, major), 7.72 (s, 2H, major), 7.73 (s, 1H, minor), 7.76 (d, J=0.6 Hz, 1H, minor), 7.79 (s, 1H, major), 7.87 (s, 1H, minor), 7.97 (d, J=2.0 Hz, 1H, minor), 8.13-8.18 (m, 4H, major and minor), 8.27 (d, J=2.0 Hz, 1H, major), 8.31 (d, J=2.0 Hz, 1H, major), MS (CI) m/z 464.1 ($MH^+$).

N,N-dimethyl-4-(3-(1-(2-morpholinoethyl)-1H-pyrazol-4-yl)-1-(phenylsulfonyl)-1H-pyrrolo[2,3-b]pyridin-5-yl)cyclohexanamine (IIb-56)

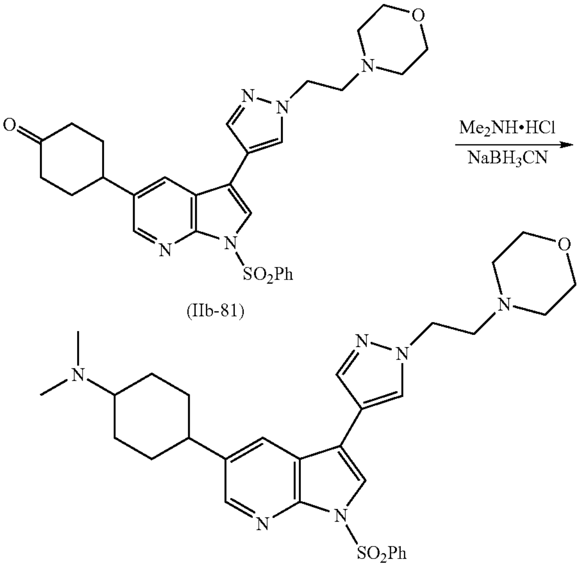

(IIb-81)

(IIb-56)

Ketone (IIb-81) (0.53 g, 1.00 mmol), dimethylamine hydrochloride (0.81 g, 9.94 mmol) and $NaCNBH_3$ (0.12 g, 2.00 mmol) in anhydrous MeOH (9.94 mL) were reacted following the general procedure A for the reductive amination. The product was purified by LCMS (column LUNA 10μ C18(2) 00G-4253-V0 250×50 mm) using water—MeCN (0.1% AcOH) as eluent (in gradient; flow 80 mL/min) to give (IIb-56) (0.25 g, 44%; retention time 23-24.5 min) as a yellow oil, a 1.68:1 mixture of isomers. $^1$H NMR (400 MHz, $CDCl_3$) δ 1.66-1.54 (m, 6H), 1.84-1.75 (m, 4H), 1.99-1.96 (m, 2H), 2.06-2.00 (m, 2H), 2.24-2.13 (m, 4H), 2.52 (t, J=4.4 Hz, 8H), 2.55 (s, 6H), 2.64 (s, 6H), 2.88 (2x t, J=6.6 Hz, 4H), 2.98-2.90 (m, 1H), 3.15-3.05 (m, 1H), 3.69 (t, J=4.6 Hz, 8H), 4.32 (t, J=6.6 Hz, 4H), 7.48-7.44 (m, 4H), 7.58-7.53 (m, 2H), 7.77-7.73 (m, 6H), 7.87 (s, 1H), 7.94 (d, J=1.9 Hz, 1H), 8.20-8.15 (m, 4H), 8.28 (d, J=2.0 Hz, 1H), 8.38 (d, J=2.0 Hz, 1H), MS (CI) m/z 563.2 ($MH^+$).

4-(2-(4-(5-((1r,4r)-4-morpholino cyclohexyl)-1-(phenylsulfonyl)-1H-pyrrolo[2,3-b]pyridin-3-yl)-1H-pyrazol-1-yl)ethyl)morpholine (IIb-57) and 4-(2-(4-(5-((1s,4s)-4-morpholinocyclohexyl)-1-(phenylsulfonyl)-1H-pyrrolo[2,3-b]pyridin-3-yl)-1H-pyrazol-1-yl)ethyl)morpholine (IIb-58)

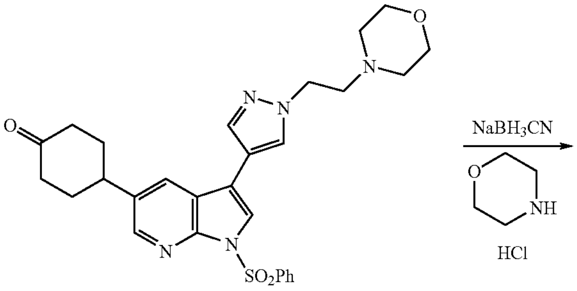

(IIb-81)

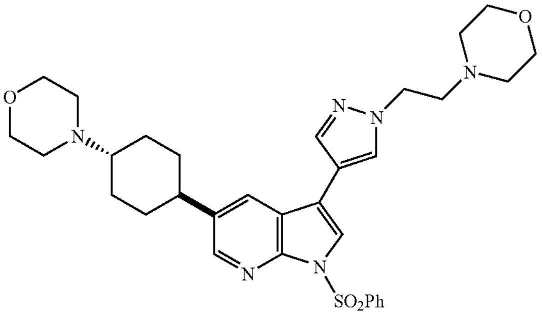

(IIb-57)

+

-continued

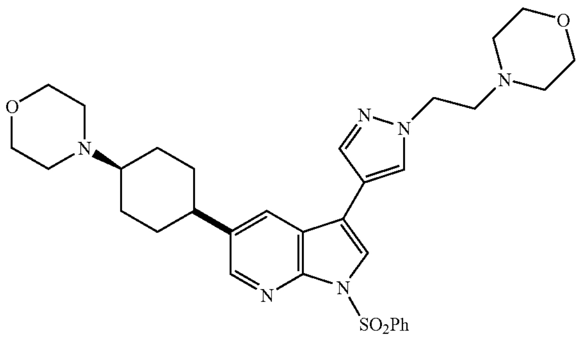

(IIb-58)

Ketone (IIb-81) (0.53 g, 1.00 mmol), morpholine (0.87 g, 10.00 mmol), 1.0 M solution of HCl/MeOH (4.00 ml, 4.00 mmol) and $NaCNBH_3$ (0.12 g, 2.00 mmol) in anhydrous MeOH (10 mL) were reacted following the general procedure A for the reductive amination. The crude product was purified by LCMS (column LUNA 10μ C18(2) 00G-4253-V0 250×50 mm) using water—MeCN (0.1% AcOH) as eluent (in gradient; flow 80 mL/min) to give a mixture of (IIb-57) and (IIb-58) (retention time 23-25 min) as a colourless oil. This mixture was separated by PTLC using 10:1 $CH_2Cl_2$:MeOH as the eluent to give trans isomer (IIb-57) (103 mg, 17%) and the cis isomer (IIb-58) (62 mg, 10%).

Data for trans isomer (IIb-57): $^1$H NMR (400 MHz, $CDCl_3$) δ 1.63-1.43 (m, 4H), 2.07-1.97 (m, 4H), 2.16-2.05 (m 2H), 2.54 (t, J=4.6 Hz, 5H), 2.63 (tt, J=3.3 and 11.6 Hz, 1H), 2.75 (t, J=4.6 Hz, 4H), 2.89 (t, J=6.6 Hz, 2H), 3.72 (t, J=4.6 Hz, 4H), 3.80 (t, J=4.6 Hz, 4H), 4.34 (t, J=6.6 Hz, 2H), 7.51-7.46 (m, 2H), 7.60-7.55 (m, 1H), 7.74 (s, 1H), 7.77-7.75 (m, 3H), 8.22-8.20 (m, 2H), 8.33 (d, J=2.0 Hz, 1H).

Data for cis isomer (IIb-58): $^1$H NMR (400 MHz, $CDCl_3$) δ 1.69-1.52 (m, 4H), 2.05-1.92 (m, 4H), 2.56-2.46 (m, 8H), 2.85-2.75 (m,1H), 2.89 (t, J=6.6 Hz, 2H), 3.78-3.70 (m, 9H), 4.34 (t, J=6.6 Hz, 2H), 7.52-7.47 (m, 2H), 7.61-7.56 (m, 1H), 7.75 (s, 1H), 7.77 (br s, 1H), 7.79 (s, 1H), 7.82 (br s, 1H), 8.23-8.20 (m, 2H), 8.41 (d, J=2.0 Hz, 1H).

1-Benzenesulfonyl-5-cyclopent-1-enyl-3-[1-(2-morpholin-4-yl-ethyl)-1H-pyrazol-4-y1]-1H-pyrrolo[2,3-b]pyridine (IIa-62)

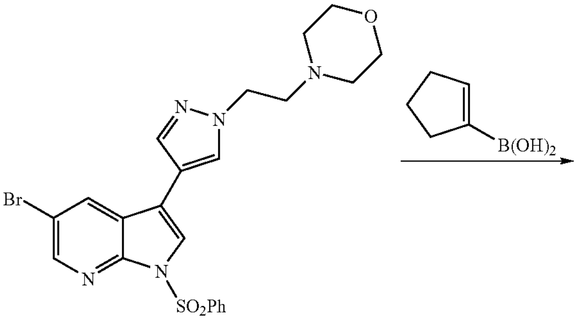

(III-b)

-continued

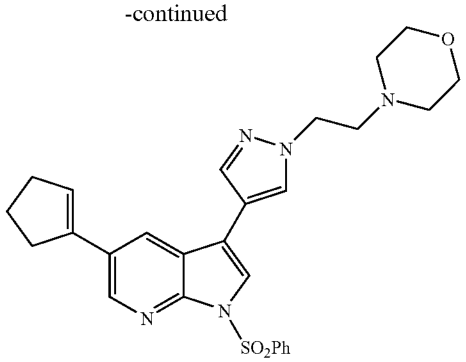

(IIa-62)

A mixture of (III-b) (173 mg, 0.34 mmol), cyclopentenylboronic acid (50 mg, 0.45 mmol), $Pd(PPh_3)_2Cl_2$ (30 mg, 43 μmol), LiCl (50 mg, 1.19 mmol) and 1.0 M aqueous $Na_2CO_3$ (0.5 mL) in toluene (1 mL):ethanol (1 mL) were reacted for 3 h using the general procedure A for the Suzuki reaction. The crude product (219 mg) was purified by SGC using EtOAc: $CH_2Cl_2$:MeOH=49:49:2 (v/v/v) to afford (IIa-62) (134 mg, 79%) as an off-white powder. $^1$H NMR (400 MHz, $CDCl_3$) δ 2.05 (pentet, J=7.5 Hz, 2H), 2.49-2.59 (m, 6H), 2.71-2.78 (m, 1H), 2.87 (t, J 6.5 Hz, 2H), 3.69-3.74 (m, 4H), 4.32 (t, J 6.5 Hz, 2H), 6.21-6.25 (m, 1H), 7.48 (t, J=7.6 Hz, 2H), 7.57 (t, J=7.3 Hz, 1H), 7.74 (s, 1H), 7.77 (d, J=2.5 Hz, 2H), 7.90 (d, J=2.0 Hz, 1H), 8.18-8.22 (m, 2H)), 8.14 (s, 1H), 8.20-8.25 (m, 3H), 8.59 (d, J=2.0 Hz, 1H).

5-(1-methoxycyclopentyl)-3-(1-methyl-1H-pyrazol-4-yl)-1-(phenylsulfonyl)-1H-pyrrolo[2,3-b]pyridine (IIb-63)

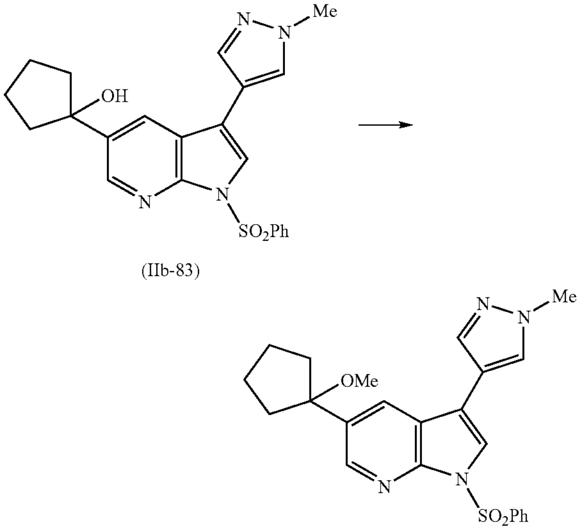

(IIb-83)

(IIb-63)

NaH (60% in mineral oil) (7.10 mg, 0.18 mmol) was added in one portion to a solution of alcohol (IIb-83) (50 mg, 0.12 mmol) in anhydrous DMF (1.18 mL) at 0° C. under nitrogen. The yellow suspension that was formed was stirred at 0° C. for 20 min. MeI (0.073 ml, 1.18 mmol) was injected at 0° C. and after 15 min the reaction was allowed to warm up to RT and stirred for 4 h. Saturated $NaHCO_3$ solution (10 mL) was added and the mixture was extracted with EtOAc (3×10 mL). The combined organic extracts were dried over $MgSO_4$ and concentrated. The crude product was purified by PTLC using EtOAc as the eluent to give (IIb-63) (32 mg, 63%), $^1$H NMR (400 MHz, $CDCl_3$) δ 1.82-1.75 (m, 2H), 1.93-1.83 (m, 4H), 2.28-2.20 (m, 2H), 2.96 (s, 3H), 4.00 (s, 3H), 7.54-7.49 (m, 2H), 7.62-7.57 (m, 1H), 7.66 (s, 1H), 7.77, (d, J=0.6 Hz, 1H), 7.78 (s, 1H), 8.00 (d, J=2.1 Hz, 1H), 8.26-8.23 (m, 2H), 8.53 (d, J=2.1 Hz, 1H).

1-Benzenesulfonyl-5-cyclopentyl-3-[1-(2-morpholin-4-yl-ethyl)-1H-pyrazol-4-yl]-1H-pyrrolo[2,3-b]pyridine (IIb-64)

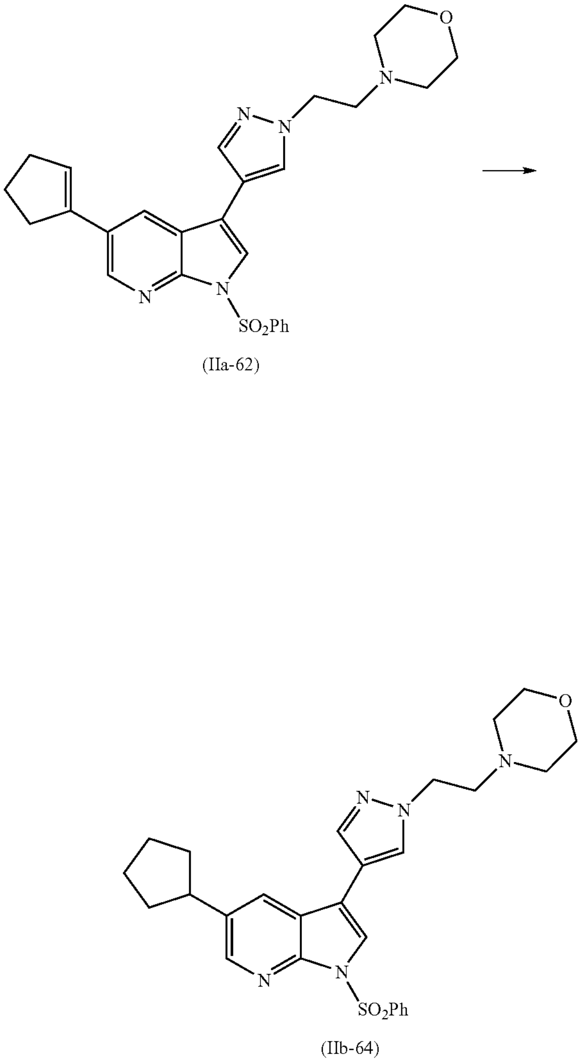

(IIa-62)

(IIb-64)

Compound (IIa-62) was hydrogenated using the general procedure for hydrogenation of 7-azaindoles. Thus, (IIa-62) (110 mg, 0.22 mmol) and $Pd(OH)_2$ (20% on C, wet, Degussa type) (50 mg, 0.071 mmol) in MeOH:$CH_2Cl_2$=2:1 (6 mL; v/v) were used to give (IIb-64) (100 mg, 91%) as a foam. $^1$H NMR (400 MHz, $CDCl_3$) δ 1.57-1.80 (m, 4H), 1.83-1.93 (m, 2H), 2.09-2.20 (m, 2H), 2.83-3.00 (m, 4H), 3.12 (tt, J=7.5, 9.2 Hz, 1H), 3.44-3.54 (m, 2H), 3.93-4.08 (m, 4H), 4.78-4.89 (m, 2H), 7.50 (t, J=7.7 Hz, 2H), 7.59 (t, J=7.3 Hz, 1H), 7.78 (s, 1H), 7.83 (s, 1H), 7.84 (d, J=1.8 Hz, 1H), 8.04 (s, 1H), 8.23 (d, J=7.4 Hz, 1H), 8.39 (d, J=1.8 Hz, 1H).

5-((1r,4r)-4-(4-methylpiperazin-1-yl)cyclohexyl)-1-(phenylsulfonyl)-3-(1-(trifluoromethyl)-1H-pyrazol-4-yl)-1H-pyrrolo[2,3-b]pyridine (IIb-66) and 5-((1s,4s)-4-(4-methylpiperazin-1-yl)cyclohexyl)-1-(phenylsulfonyl)-3-(1-(trifluoromethyl)-1H-pyrazol-4-yl)-1H-pyrrolo[2,3-b]pyridine (IIb-67)

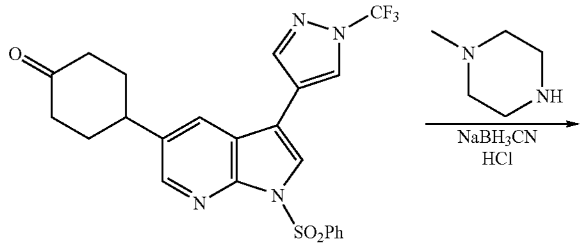

(IIb-84)

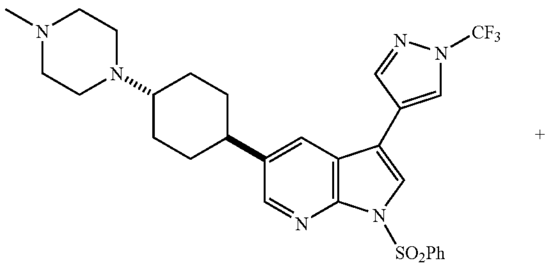

(IIb-66)

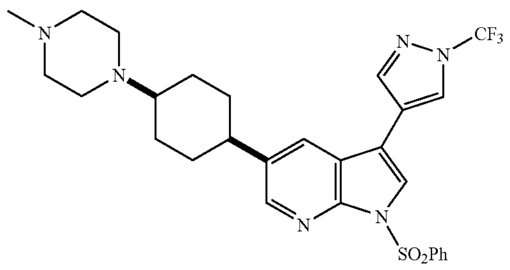

(IIb-67)

Ketone (IIb-84) (0.12 g, 0.24 mmol), N-methylpiperazine (0.14 g, 1.42 mmol), 1.25 M solution of HCl/MeOH (0.38 ml, 0.47 mmol) and $NaCNBH_3$ (29 mg, 0.47 mmol) in anhydrous MeOH (2.4 mL) were reacted following the general procedure A for the reductive amination. The crude product was purified by PTLC using 10:1 $CH_2Cl_2$:MeOH as the eluent to give the trans isomer (IIb-66) (30 mg, 22%) and the cis isomer (IIb-67) (18 mg, 13%).

Data for trans isomer (IIb-66): $^1$H NMR (400 MHz, $CDCl_3$) δ 1.62-1.40 (m, 4H), 2.04-1.95 (m, 2H), 2.12-2.05 (m, 2H), 2.32 (s, 3H), 2.58-2.37 (m, 5H), 2.74-2.59 (m, 5H), 7.54-7.48 (m, 2H), 7.63-7.57 (m, 1H), 7.85 (s, 1H), 8.03 (s, 1H), 8.05 (s, 1H), 8.25-8.22 (m, 2H), 8.37 (d, J=2.0 Hz, 1H).

Data for cis isomer (IIb-67): $^1$H NMR (400 MHz, $CDCl_3$) δ 1.67-1.51 (m, 4H), 2.07-1.91 (m, 7H), 2.22-2.15 (m, 1H), 2.34 (s, 3H), 2.64-2.43 (br m, 4H), 2.95-2.77 (m, 2H), 7.55-7.50 (m, 2H), 7.63-7.59 (m, 1H), 7.79 (d, J=2.0 Hz, 1H), 7.86 (s, 1H), 8.05 (s, 1H), 8.08 (s, 1H), 8.25-8.22 (m, 2H), 8.44 (d, J=2.0 Hz, 1H).

Mixture of 3-(1-methyl-1H-pyrazol-4-yl)-1-(phenylsulfonyl)-5-(3,5,5-trimethylcyclohex-1-enyl)-1H-pyrrolo[2,3-b]pyridine and 3-(1-methyl-1H-pyrazol-4-yl)-1-(phenylsulfonyl)-5-(3,3,5-trimethylcyclohex-1-enyl)-1H-pyrrolo[2,3-b]pyridine (IIa-68)

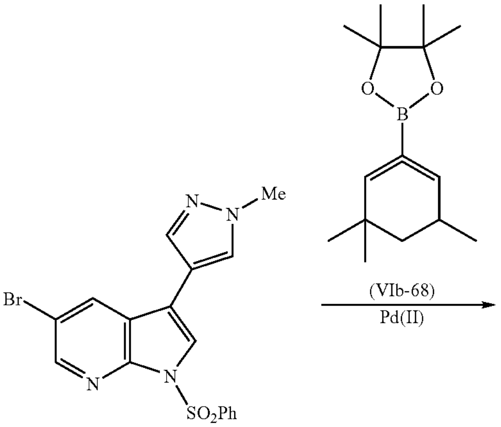

(III-a)

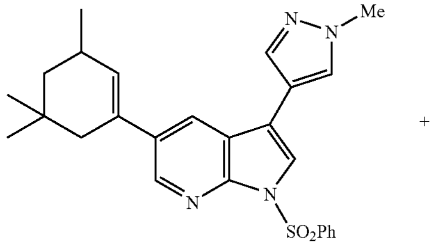

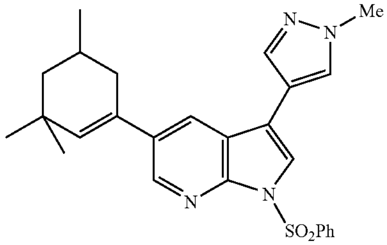

(IIa-68)

Bromide (III-a) (0.30 g, 0.72 mmol), boronic pinacol ester (VIb-68) (0.54 g, 2.16 mmol), lithium chloride (61 mg, 1.44 mmol), and $Pd(PPh_3)_2Cl_2$ (50 mg, 0.072 mmol), in EtOH (1.80 mL), toluene (1.80 mL) and 1M $Na_2CO_3$ solution (1.80 mL) were reacted using the general procedure A for the Suzuki reaction. The crude product was purified by PTLC using 1:1 hexane:EtOAc as the eluent to give (IIa-68) (ratio of isomers 1.33:1) as a brown solid (0.10 g, 31%), $^1$H NMR (400 MHz, $CDCl_3$) δ 0.94 (s, 3H), 1.09-1.05 (m, 15H,), 1.57-1.49 (m, 2H), 1.96-1.92 (m, 1H), 2.07-1.99 (m, 4H), 2.32-2.24 (m, 1H), 2.43-2.35 (m, 2H), 4.00 (s, 6H), 5.79-5.76 (m, 1H, minor isomer), 5.90-5.87 (m, 1H, major isomer), 7.51-7.45 (m, 4H), 7.59-7.54 (m, 2H), 7.65 (s, 2H), 7.73 (s, 2H), 7.77 (s, 2H), 7.85 (d, J=2.1 Hz, 2H), 8.22-8.14 (m, 4H), 8.49 (t, J=2.4 Hz, 2H).

5-(cyclopent-2-enyl)-3-(1-methyl-1 H-pyrazol-4-yl)-1-(phenylsulfonyl)-1H-pyrrolo[2,3-b]pyridine (IIa-69)—See the Synthesis of (IIb-61)

4-(1-(phenylsulfonyl)-3-(1H-pyrazol-4-yl)-1H-pyrrolo[2,3-b]pyridin-5-yl)cyclohexanone (IIb-70)

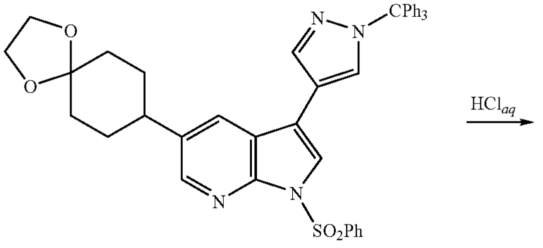

(IIb-92)

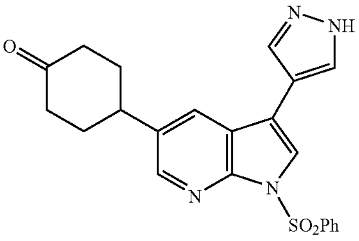

(IIb-70)

A mixture of (IIb-92) (402 mg, 0.568 mmol) and 6 N HCl (3.2 mL) in THF (9.1 mL) was stirred for 18 h. A second aliquot of 6 N HCl was added and stirring continued for another 6 h. The mixture was poured onto saturated aqueous $NaHCO_3$ (20 mL) and extracted with EtOAc. Combined organic solutions were dried ($MgSO_4$) and concentrated to afford pure (IIb-70) (239 mg, quant.). $^1H$ NMR (400 MHz; $CDCl_3$) δ 2.18-2.31 (m, 3H), 2.43-2.62 (m, 5H), 3.19 (tt, J=12.2 Hz, 3.34 Hz, 1H), 7.46-7.54 (m, 2H), 7.55-7.63 (m, 1H), 7.82 (s, 2H), 7.88 (s, 2H), 8.24 (dd, J=7.3 Hz, 1.4 Hz, 2H), 8.42 (d, J=2.0 Hz, 1H). MS (CI) m/z 421 ($MH^+$).

1-Benzenesulfonyl-3-(1-methyl-1H-pyrazol-4-yl)-5-(4-morpholin-4-ylmethyl-cyclohexyl)-1H-pyrrolo[2,3-b]pyridine (IIb-73) and {4-[1-Benzenesulfonyl-3-(1-methyl-1H-pyrazol-4-yl)-1H-pyrrolo[2,3-b]pyridin-5-yl]-cyclohexyl}-methanol (IIb-74)

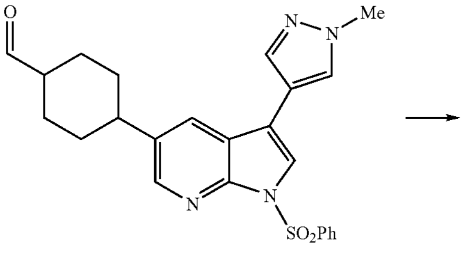

(IIb-90)

-continued

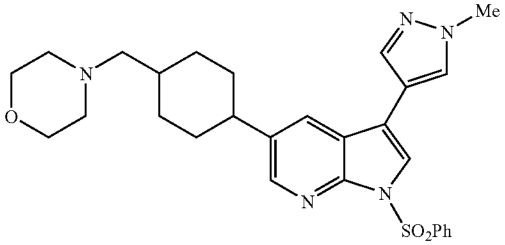

\+

(IIb-73)

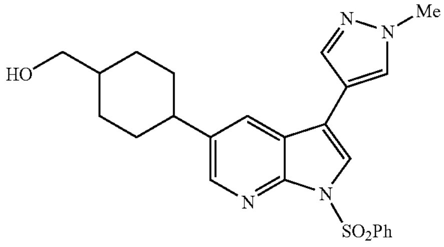

(IIb-74)

A mixture of diastereomeric aldehydes (IIb-90) (85 mg, 190 μmol), morpholine (150 mg, 1.72 mmol), 1.25 N solution of HCl in MeOH (0.60 mL, 0.75 mmol) and $NaBH_3CN$ (50 mg, 0.80 mmol) in MeOH (2 mL) were reacted following the general procedure A for the reductive amination. The crude product (an oil; 110 mg) was purified by SGC using hexanes: $CH_2Cl_2$:EtOAc as eluent in gradient from 1:1:0 to 1:1:2 (v/v). First to elute was a crude mixture presumed to be of the two diastereomeric alcohols (IIb-74) (10 mg), and which was used without further purification or analysis. Further elution gave an unassigned 3:2 mixture of the desired amines (IIb-73) (81 mg, 82%).

Data for (IIb-73): $^1H$ NMR (400 MHz, $CDCl_3$) δ 1.03-1.16 (m, 1.2H), 1.44-1.80 (m, 4.2H), 1.91-2.03 (m, 2.4H), 2.21 (d, J=7.2 Hz, 1.2H), 2.36 (d, J=7.6 Hz, 0.8H), 2.40-2.49 (m, 4H), 2.58-2.69 (m, 0.6H), 2.70-2.78 (m, 0.4H), 3.70-3.78 (m, 4H), 4.01 (s, 1.8H), 4.02 (s, 1.2H), 7.47-7.54 (m, 2H), 7.56-7.62 (m, 1H), 7.65 (s, 1H), 7.74 (s, 1H), 7.76-7.80 (m, 2H), 8.20-8.25 (m, 2H), 8.36 (d, J=2.0 Hz, 0.6H), 8.38 (d, J=2.0 Hz, 0.4H).

1-Benzenesulfonyl-3-(1-methyl-1H-pyrazol-4-yl)-5-(4-morpholin-4-yl-cyclohex-1-enyl)-1H-pyrrolo[2,3-b]pyridine (IIa-75)

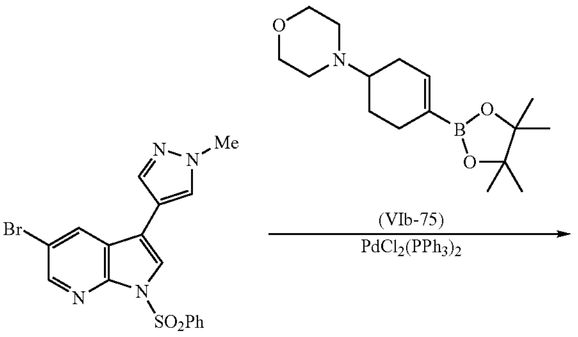

(III-a)

-continued

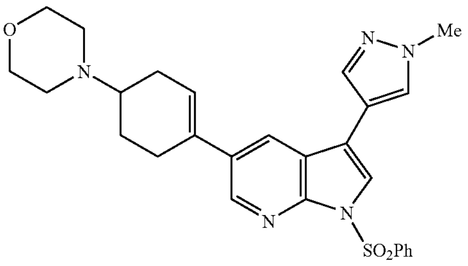

(IIa-75)

A mixture of (III-a) (4.65 g, 11.1 mmol), (VIb-75) (4.90 g, 16.7 mmol), $PdCl_2(PPh_3)_2$ (782 mg, 1.11 mmol), LiCl (1.42 g, 33.4 mmol), 1.0 M aq. $Na_2CO_3$ (27.9 mL, 27.9 mmol), ethanol (50 mL) and toluene (50 mL) was reacted following the general procedure A for the Suzuki reaction. The crude product was purified by SGC using EtOAc:MeOH=8:2 (v/v) as eluent (gradient elution) to give (IIa-75) (4.59 g, 82%) as an orange foam; $^1$H NMR (400 MHz, $CDCl_3$) δ 1.61 (octet, 5.8 Hz, 1H), 2.10-2.30 (m, 2H), 2.40-2.70 (m, 9H), 3.76 (t, J=4.6 Hz, 4H), 4.00 (s, 3H), 7.48 (m, 2H), 7.57 (tt, J=6.5 , 1.3 Hz, 1H), 7.64 (s, 1H), 7.73 (s, 1H), 7.76 (d, J=0.7 Hz, 1H), 7.87 (d, J=2.1 Hz, 1H), 8.21 (m, 2H), 8.50 (d, J=2.1 Hz, 1H).

4-((1s,4s)-4-(1-(phenylsulfonyl)-3-(1H-pyrazol-4-yl)-1H-pyrrolo[2,3-b]pyridin-5-yl)cyclohexyl)morpholine (IIb-78) and 4-((1r,4r)-4-(1-(phenylsulfonyl)-3-(1H-pyrazol-4-yl)-1H-pyrrolo[2,3-b]pyridin-5-yl)cyclohexyl)morpholine (IIb-79)

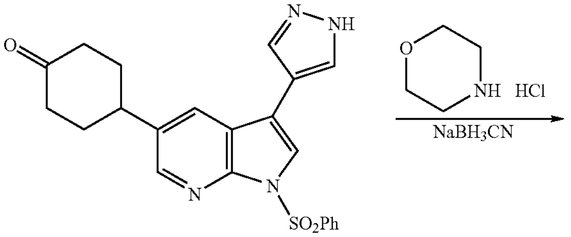

(IIb-70)

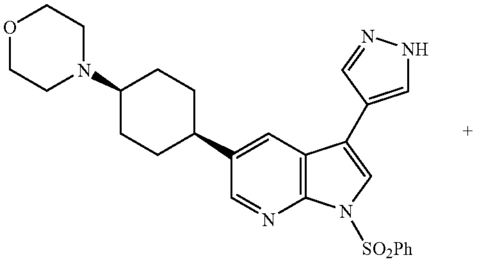

+

(IIb-78)

-continued

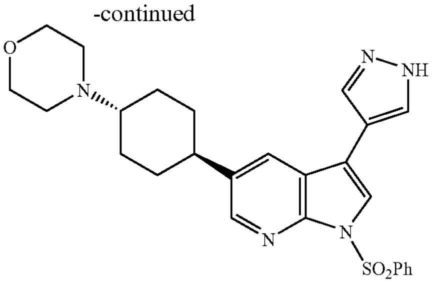

(IIb-79)

Ketone (IIb-70) (100 mg, 0.237 mmol), morpholine (206.5 mg, 2.37 mmol), 1.25 M solution of HCl/MeOH (0.758 mL, 0.95 mmol) and $NaCNBH_3$ (29 mg, 0.47 mmol) in anhydrous MeOH (1.2 mL) were reacted following the general procedure A for the reductive amination. The crude product was purified by PTLC using $CH_2Cl_2$:MeOH+19:1 (v/v) as the eluent to give the cis isomer (IIb-78) (14 mg, 12%) and the trans isomer (IIb-79) (25 mg, 22%).

Data for cis isomer (IIb-78): $^1$H NMR (400 MHz; $CDCl_3$+$CD_3OD$) δ 1.49-1.67 (m, 5H), 1.84-2.02 (m, 4H), 2.40-2.52 (m, 4H), 2.74-2.84 (m, 1H), 3.69-3.78 (m, 4H), 7.48 (tt, J=8.1 Hz, 1.7 Hz, 2H), 7.56 (tt, J=7.2 Hz, 1.3 Hz, 1H), 7.75 (s, 1H), 7.85 (d, J=1.7 Hz, 1H), 7.86 (s, 2H), 8.18 (dd, J=7.2 Hz, 1.39 Hz, 2H), 8.37 (d, J=2.1 Hz, 1H). MS (CI) m/z 492 ($MH^+$).

Data for trans isomer (IIb-79): $^1$H NMR (400 MHz; $CDCl_3$+$CD_3OD$) δ 1.36-1.60 (m, 4H), 1.63-1.67 (m, 1H), 1.95-2.02 (m, 2H), 2.05-2.12 (m, 2H), 2.58 (t, J=3.5 Hz, 1H), 2.63-2.68 (m, 4H), 3.74-3.78 (m, 4H), 7.47 (tt, J=8.0 Hz, 1.60 Hz, 2H), 7.56 (tt, J=7.3 Hz, 1.20 Hz, 1H), 7.75 (s, 1H), 7.77 (d, J=2.0 Hz, 1H), 7.83 (s, 2H), 8.17 (dd, J=7.2 Hz, 1.5 Hz, 2H), 8.30 (d, J=2.0 Hz, 1H). MS (CI) m/z 492 ($MH^+$).

4-((1r,4r)-4-(3-(1-(difluoromethyl)-1H-pyrazol-4-yl)-1-(phenylsulfonyl)-1H-pyrrolo[2,3-b]pyridin-5-yl)cyclohexyl)morpholine (IIb-80)

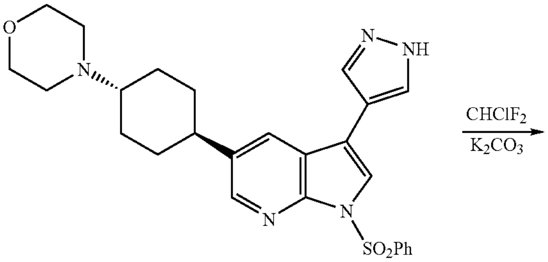

(IIb-79)

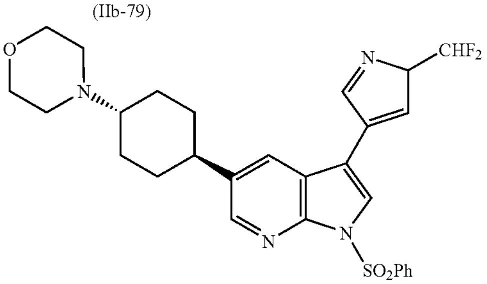

(IIb-80)

Gaseous $CHClF_2$ (96.7 mg, 1.12 mmol) was introduced into a cooled (−78° C.) mixture of (IIb-79) (25 mg, 0.050 mmol), $K_2CO_3$ (21.16 mg, 0.153 mmol) and DMF (0.5 mL) in a CEM microwavaeable tube. The tube was then sealed and heated at 90° C. for 1 h 40 min. The reaction mixture was allowed to cool to RT, and the excess of gas was released. The crude reaction mixture was separated by LCMS (column LUNA 10μ C18(2) 00G-4253-V0 250×50 mm) using water—MeCN (0.1% AcOH) as eluent (in gradient; flow 80 mL/min; retention time 22.91 min) to give (IIb-80) (6.0 mg, 22%) and recovered starting material (IIb-79) (4.91 mg, 20%).

Data for (IIb-80): $^1$H NMR (400 MHz; $CDCl_3$+1 drop of $CD_3OD$) δ 1.38-1.59 (m, 4H), 1.59-1.62 (m, 1H), 1.97-2.05 (m, 2H), 2.06-2.14 (m, 2H), 2.38 (tt, J=11.3 Hz, 3.6 Hz, 1H), 2.57-2.70 (m, 4H), 3.70-3.80 (m, 4H), 7.28 (t, J=61 Hz, 1H), 7.48-7.54 (m, 2H), 7.60 (tt, J=7.3 Hz, 1.3 Hz, 1H), 7.74 (d, J=2.0 Hz, 1H), 7.84 (s, 1H), 7.93 (s, 1H), 8.07 (s, 1H), 8.24 (dd, J=7.2 Hz, 2.0 Hz, 2H), 8.37 (d, J=2.1 Hz, 1H). MS (CI) m/z 542.3 ($MH^+$).

4-(3-(1-(2-morpholinoethyl)-1H-pyrazol-4-yl)-1-(phenylsulfonyl)-1H-pyrrolo[2, 3-b]pyridin-5-yl) cyclohexanone (IIb-81)

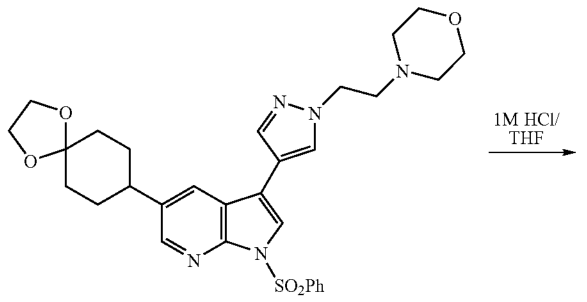

(IIb-85)

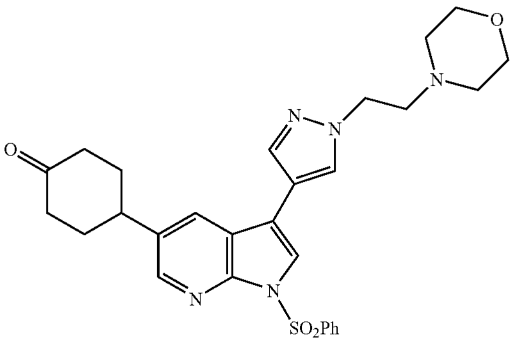

(IIb-81)

7 M aqueous HCl (3.33 mL) was added at RT in small portions over 10 min to a solution of (IIb-85) (1.35 g, 2.33 mmol) in THF (23.3mL). The reaction mixture was stirred at RT overnight, and quenched by slow addition over 15 minutes of a saturated solution of $NaHCO_3$ (30 mL). The mixture was then extracted with EtOAc (4×50 mL). The combined extracts were dried over $MgSO_4$ and concentrated to give crude (IIb-81) (1.11 g, 93%), which was used in further steps without being fully characterised.

2-(3-(1-methyl-1H-pyrazol-4-yl)-1-(phenylsulfonyl)-1H-pyrrolo[2,3-b]pyridin-5-yl)cyclopentanol (IIb-82) and 1-(3-(1-methyl-1H-pyrazol-4-yl)-1-(phenylsulfonyl)-1H-pyrrolo[2,3-b]pyridin-5-yl) cyclopentanol (IIb-83)

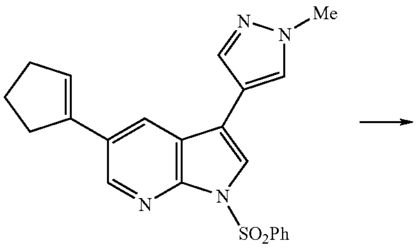

(IIa-10)

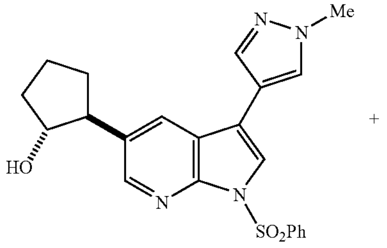

(IIb-82)

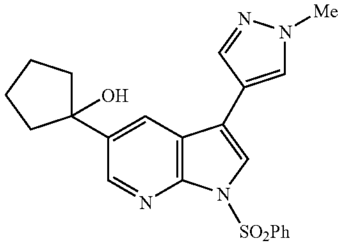

(IIb-83)

1.0 M $BH_3THF$ solution (5.56 ml, 5.56 mmol) was added dropwise to a solution of 5-cyclopentenyl-3-(1-methyl-1H-pyrazol-4-yl)-1-(phenylsulfonyl)-1H-pyrrolo[2,3-b]pyridine (IIa-10) (0.45 g, 1.11 mmol) in anhydrous THF (33.4 mL) at RT under nitrogen. The yellow reaction mixture was stirred at RT for 3 h and cooled to 0° C. Then, 27.5% aqueous $H_2O_2$ (15 mL) was added dropwise at 0° C. and the mixture was stirred for 10 min. Saturated solution of $NaHCO_3$ (50 mL) was added and the mixture was stirred at 0° C. for 1 h. The mixture was extracted with $CH_2Cl_2$ (3×50 mL). The combined organic extracts were dried ($MgSO_4$) and concentrated. The crude product was separated by PTLC using EtOAc as the eluent to give tertiary alcohol (IIb-83) (53 mg, 11%) as a white solid and the trans secondary alcohol (IIb-82) (0.16 g, 33%) as a white solid.

Data for alcohol (IIb-82): $^1$H NMR (400 MHz, $CDCl_3$) δ 1.95-1.65 (m, 4H), 2.26-2.09 (m, 2H), 3.01-2.93 (m, 1H), 3.61 (br s, OH, 1H), 3.99 (s, 3H), 4.34 (q, J=7.8 Hz, 1H), 7.47-7.43 (m, 2H), 7.56-7.52 (m, 2H), 7.69 (s, 1H), 7.70 (s, 1H), 7.82 (d, J=2.0 Hz, 1H), 8.14-8.11 (m, 2H), 8.23 (d, J=2.0 Hz, 1H).

Data for alcohol (IIb-83): $^1$H NMR (400 MHz, $CDCl_3$) δ 1.90-1.85 (m, 2H), 2.08-2.02 (m, 7H), 3.97 (s, 3H), 7.51-7.46

(m, 2H), 7.60-7.55 (m, 1H), 7.66 (s, 1H), 7.73 (s, 1H), 7.74 (d, J=0.6 Hz, 1H), 8.12 (d, J=2.2 Hz, 1H), 8.21-8.18 (m, 2H), 8.56 (d, J=2.1 Hz, 1H), MS (CI) m/z 423.3 ($MH^+$).

4-(1-(phenylsulfonyl)-3-(1-(trifluoromethyl)-1H-pyrazol-4-yl)-1H-pyrrolo[2,3-b]pyridin-5-yl)cyclohexanone (IIb-84)

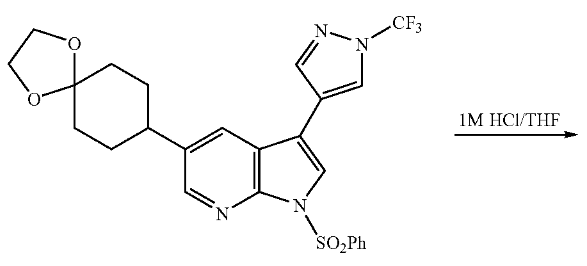

(IIb-86)

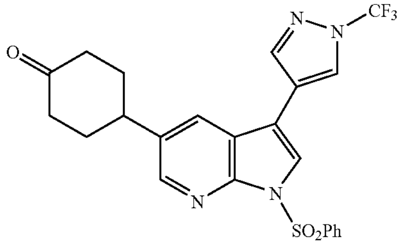

(IIb-84)

Mixture of (IIb-86) (0.23 g, 0.43 mmol) and 7 M HCl (2.0 mL) in THF (6.0 mL) was stirred at room temperature for 4 h and 20 min. The reaction was quenched by slow addition of a saturated solution of $NaHCO_3$ (50 mL). After stirring for 15 minutes at RT the mixture was extracted with EtOAc (3×50 mL). The combined extracts were dried over $MgSO_4$ and concentrated. The crude product was purified by PTLC using 1:1 EtOAc:hexane as the eluent to give (IIb-84) (0.12 g, 55%) as a white solid, $^1H$ NMR (400 MHz, $CDCl_3$) δ 2.13-1.94 (m, 2H), 2.27-2.21 (m, 2H), 2.57-2.51 (m, 4H), 3.22-3.14 (tt, J=12.2 and 3.3 Hz, 1H), 7.54-7.49 (m, 2H), 7.63-7.59 (m, 1H), 7.79 (d, J=2.0 Hz, 1H), 7.88 (s, 1H), 8.01 (s, 1H), 8.07 (s, 1H), 8.26-8.23 (m, 2H), 8.43 (d, J=2.1 Hz, 1H).

4-(2-(4-(1-(phenylsulfonyl)-5-(1,4-dioxaspiro[4.5]decan-8-yl)-1H-pyrrolo[2,3-b]pyridin-3-yl)-1H-pyrazol-1-yl)ethyl)morpholine (IIb-85)

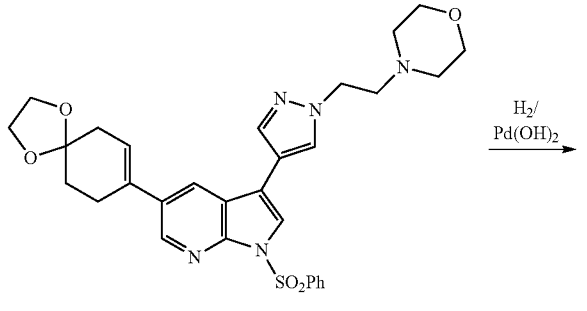

(IIa-87)

-continued

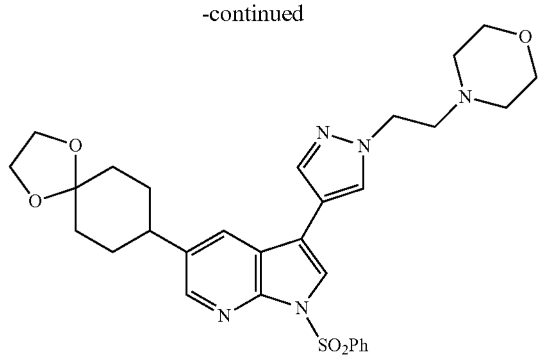

(IIb-85)

Following the general method for hydrogenation of 7-azaindoles, compound (IIa-87) (9.66 g, 20.27 mmol) and $Pd(OH)_2$ on carbon (20% wet Degussa type; 0.22 g, 0.32 mmol) in MeOH (31.6 mL) and EtOAc (10 mL) were converted into (IIb-85) by stirring for 5 days under a $H_2$ atmosphere. The catalyst was filtered off on a small pad of celite and washed with copious amount of MeOH/EtOAc. The solvent was evaporated to give (IIb-85) (1.35 g, 74%), $^1H$ NMR (400 MHz, $CDCl_3$) δ 1.98-1.70 (m, 9H), 2.82-2.70 (m, 6H), 3.93-3.80 (br s, 4H), 3.99 (s, 4H), 4.68-4.50 (br s, 2H), 7.52-7.47 (m, 2H), 7.60-7.55 (m, 1H), 7.76 (s, 1H), 7.79 (s, 1H), 7.81 (d, J=2.1 Hz, 1H), 7.89 (, 1H), 8.24-8.20 (m, 2H), 8.37 (d, J=2.0 Hz, 1H).

1-(phenylsulfonyl)-5-(1,4-dioxaspiro[4.5]decan-8-yl)-3-(1-(trifluoromethyl)-1H-pyrazol-4-yl)-1H-pyrrolo[2,3-b]pyridine (IIb-86)

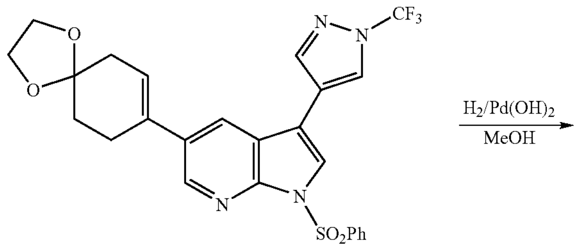

(IIa-88)

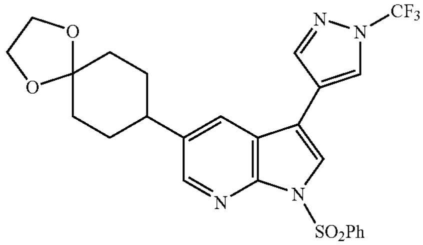

(IIb-86)

Following the general method for hydrogenation of 7-azaindoles, compound (IIa-88) (0.24 g, 0.45 mmol) was hydrogenated in MeOH (9.0 mL) and EtOAc (9.0 mL) in the presence of $Pd(OH)_2$ on carbon (20% wet Degussa type; 31.7 mg, 0.045 mmol) to give crude product (IIb-86) as a white foam (0.23 g, 96%), $^1H$ NMR (400 MHz, $CDCl_3$) δ 1.91-1.64 (m, 8H), 2.76-2.66 (m, 1H), 3.98 (s, 4H), 7.52-7.47 (m, 2H), 7.61-7.56 (m, 1H), 7.76 (d, J=2.0 Hz, 1H), 7.85 (s, 1H), 8.02 (s, 1H), 8.06 (s, 1H), 8.24-8.21 (m, 2H), 8.38 (d, J=2.0 Hz, 1H).

4-(2-(4-(1-(phenylsulfonyl)-5-(1,4-dioxaspiro[4.5]dec-7-en-8-yl)-1H-pyrrolo[2,3-b]pyridin-3-yl)-1H-pyrazol-1-yl)ethyl)morpholine (IIa-87)

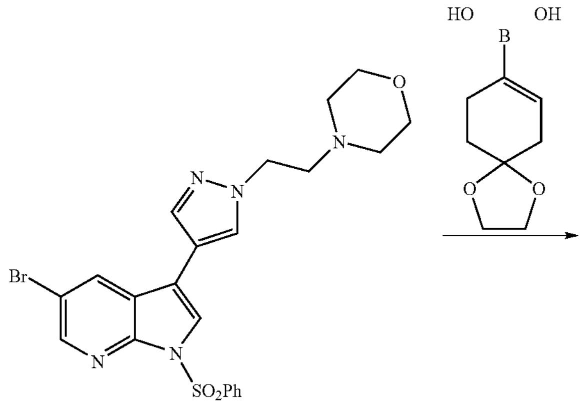

(III-b)

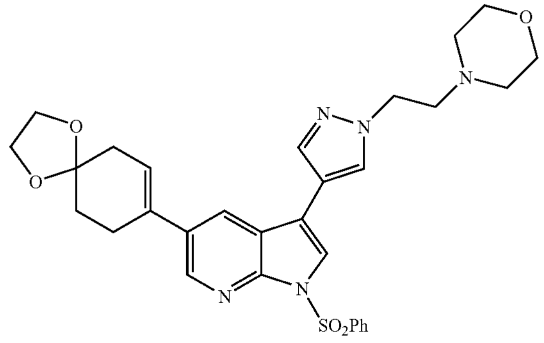

(IIa-87)

A mixture of (III-b) (3.10 g, 6.00 mmol), 1,4-diospiro[4,5]dec-7-ene-8-boronic acid pinacol ester (1.60 g, 6.00 mmol), lithium chloride (0.76 g, 18.00 mmol), 1M $Na_2CO_3$ solution (15 ml, 15 mmol) and $Pd(PPh_3)_2Cl_2$ (0.42 g, 0.60 mmol) in EtOH (30 mL) and toluene (30 mL) was reacted following the general protocol A for the Suzuki reaction. The product was purified by SGC using EtOAc/10% MeOH in EtOAc as the eluent (gradient elution 0%-100% of 10% MeOH in EtOAc mixture) to give (IIa-87) as an orange foam (1.82 g, 53%), $^1$H NMR (400 MHz, $CDCl_3$) δ 1.95 (t, J=6.5 Hz, 2H), 2.51-2.48 (m, 2H), 2.52 (t, J=4.6 Hz, 4H), 2.72-2.66 (m, 2H), 2.87 (t, J=6.5 Hz, 2H), 3.72 (t, J=4.6 Hz, 4H), 4.04 (s, 4H), 4.32 (t, J=6.5 Hz, 2H), 5.99-5.96 (m, 1H), 7.51-7.46 (m, 2H), 7.60-7.55 (m, 1H), 7.75 (s, 1H), 7.77 (s, 2H), 7.91 (d, J=2.1 Hz, 1H), 8.22-8.18 (m, 2H), 8.52 (d, J=2.1 Hz, 1H).

1-(phenylsulfonyl)-5-(1,4-dioxaspiro[4.5]dec-7-en-8-yl)-3-(1-(trifluoromethyl)-1H-pyrazol-4-yl)-1H-pyrrolo[2,3-b]pyridine (IIa-88)

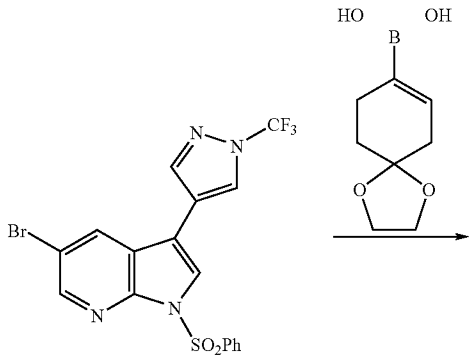

(III-c)

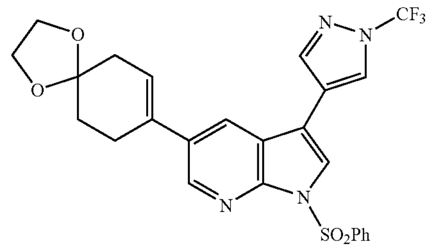

(IIa-88)

Compound (III-c) (0.34 g, 0.72 mmol), 1,4-diospiro[4,5]dec-7-ene-8-boronic acid pinacol ester (0.58 g, 2.16 mmol), lithium chloride (91.6 mg, 2.16 mmol), and $Pd(PPh_3)_2Cl_2$ (50.6 mg, 0.07 mmol) and 1M $Na_2CO_3$ solution (1.80 ml, 1.80 mmol) in EtOH (1.80 mL), toluene (1.80 mL) were reacted following the general procedure A for the Suzuki reaction. The crude product was purified by PTLC using 1:1 EtOAc:hexane as the eluent to give (IIa-88) as a yellow solid (0.24 g, 63%), $^1$H NMR (400 MHz, $CDCl_3$) δ 1.94 (t, J=6.5 Hz, 2H), 2.51-2.46 (m, 2H), 2.71-2.65 (m, 2H), 4.02 (s, 4H), 5.99-5.96 (m, 1H), 7.51-7.46 (m, 2H), 7.61-7.56 (m, 1H), 7.85 (s, 1H), 7.86 (d, J=2.1 Hz, 1H), 8.03 (s, 1H), 8.07 (s, 1H), 8.23-8.20 (m, 2H), 8.53 (d, J=2.1 Hz, 1H).

1-Benzenesulfonyl-5-(4-methoxymethylene-cyclohexyl)-3-(1-methyl-1H-pyrazol-4-yl)-1H-pyrrolo[2,3-b]pyridine (IIb-89)

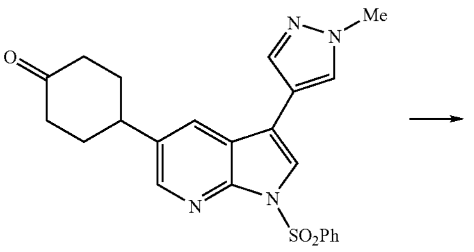

(IIb-20)

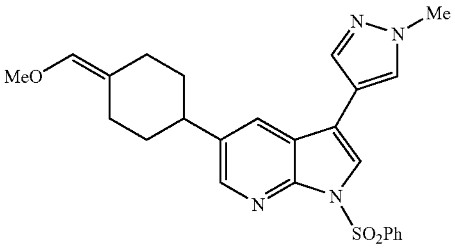

(IIb-89)

To a suspension of (methoxymethyl)triphenylphosphonium chloride (1.82 g, 5.31 mmol) in anhydrous $Et_2O$ (10 mL) at 0° C. was added 1.8 N phenyllithium in $Bu_2O$ (2.95 mL, 5.31 mmol) dropwise. The reaction mixture was stirred at 0° C. for a further 15 min, and a solution of (IIb-20) (923 mg, 2.12 mmol) in THF (10 mL) was added. After stirring at 0° C. for a further 4 h, the reaction mixture was poured onto water (100 mL) and extracted with EtOAc (2×100 mL). The combined organic portions were dried over $MgSO_4$ and concentrated to afford an oil (2.38 g). This crude product was purified by SGC using hexanes:$CH_2Cl_2$:EtOAc=1:1:1 (v/v/v) as eluent to afford (IIb-89) as a clear oil (671 mg, 1.45 mmol, 68%). $^1H$ NMR (400 MHz, $CDCl_3$) δ 1.43-1.57 (m, 2H), 1.77-1.88 (m, 1H), 1.90-2.01 (m, 2H), 2.08-2.25 (m, 2H), 2.78 (tt, J=3.3, 12.1 Hz, 1H), 2.94 (br d, J=13.8 Hz, 1H), 3.59 (s, 3H), 4.01 (s, 3H), 5.86 (t, J=1.5 Hz, 1H), 7.50 (t, J=7.7 Hz, 2H), 7.58 (tt, J=1.3, 7.4 Hz, 1H), 7.65 (s, 1H), 7.73-7.78 (m, 3H), 8.20-8.25 (m, 2H), 8.35 (d, J=2.0 Hz, 1H), 8.54 (br s, 1H).

4-[1-Benzenesulfonyl-3-(1-methyl-1H-pyrazol-4-yl)-1H-pyrrolo[2,3-b]pyridin-5-yl]-cyclohexanecarbaldehyde (IIb-90)

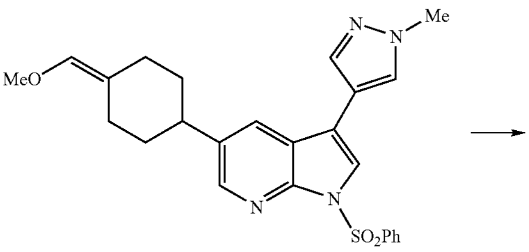

(IIb-89)

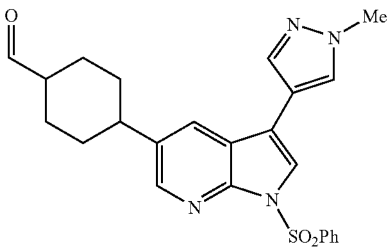

(IIb-90)

A stirred solution of (IIb-89) (280 mg, 0.61 mmol) in THF (15 mL) was cooled to 0° C., and 1.0 N aqueous HCl (5 mL) was added. After stirring at 0° C. for 2 h, the reaction mixture was allowed to warm to RT. After a further 22 h, the solution was poured onto saturated aqueous $NaHCO_3$ (100 mL) and extracted with EtOAc (2×100 mL). The combined organic solutions were dried over $MgSO_4$ and concentrated to afford an oil (324 mg). The crude product was purified by SGC using hexanes:$CH_2Cl_2$:EtOAc=1:1:1 (v/v/v) as eluent to afford aldehyde (IIb-90) (222 mg, 82%) as a clear oil, a mixture of diastereomers in a ratio of 3:2; $^1H$ NMR (400 MHz, $CDCl_3$) δ 1.31-2.63 (m, 10H), 3.92 (s, 1.8H), 3.93 (s, 1.2H), 4.01 (s, 3H), 7.37-7.44 (m, 2H), 7.47-7.53 (m, 1H), 7.54-7.70 (m, 4H), 8.11-8.16 (m, 2H), 8.21 (d, J=2.0 Hz, 0.4H), 8.27 (d, J=2.0 Hz, 0.6H), 9.61, (d, J=2.0 Hz, 0.6H), 9.71 (s, 0.4H).

1-Benzenesulfonyl-5-(1,4-dioxa-spiro[4.5]dec-7-en-8-yl)-3-(1-trityl-1H-pyrazol-4-yl)-1H-pyrrolo[2,3-b]pyridine (IIa-91)

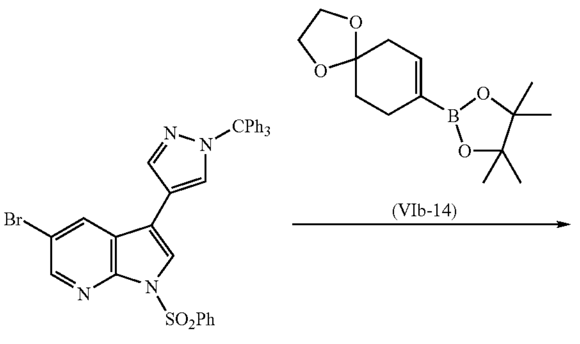

(III-f)

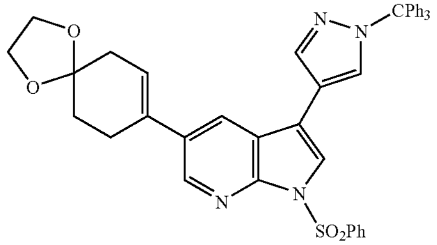

(IIa-91)

Compound (III-f) (1.00 g, 1.55 mmol; preparation disclosed in WO2004/078756), 1,4-diospiro[4,5]dec-7-ene-8-boronic acid pinacol ester (VIb-14) (907.4 mg, 3.41 mmol), LiCl (197.1 mg, 4.65 mmol), $Pd(PPh_3)_2Cl_2$ (105.28 mg, 0.15 mmol) and 1.0 M $Na_2CO_3$ solution (3.87 ml, 3.87 mmol) in EtOH (60 mL), toluene (60 mL) were reacted following the general procedure A for the Suzuki reaction. The crude product was dissolved in hot EtOAc and precipitated by addition of hexane to afford (IIa-91) (0.993 g, 91%) that was used in the next step; $^1$H NMR (400 MHz; $CDCl_3$) δ 1.84-1.89 (m, 2H), 2.39-2.43 (m, 2H), 2.51-2.57 (m, 2H), 3.96 (s, 4H), 5.87 (m, 1H), 7.10-7.17 (m, 6H), 7.25-7.31 (m, 9H), 7.35-7.41 (m, 2H), 7.45-7.51 (m, 1H), 7.54 (d, J=0.7 Hz, 1H), 7.63 (s, 1H), 7.68 (d, J=2.1 Hz, 1H), 7.87 (d, J=0.7 Hz, 1H), 8.09 (dd, J=7.3, 1.4 Hz, 2H), 8.43 (d, J=2.1 Hz, 1H). MS (CI) m/z ($MH^+$).

1-(phenylsulfonyl)-5-(1,4-dioxaspiro[4.5]decan-8-yl)-3-(1-trityl-1H-pyrazol-4-yl)-1H-pyrrolo[2,3-b]pyridine (IIb-92)

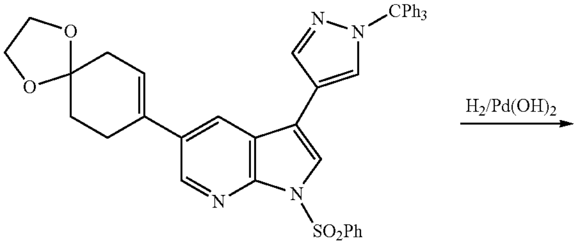

(IIa-91)

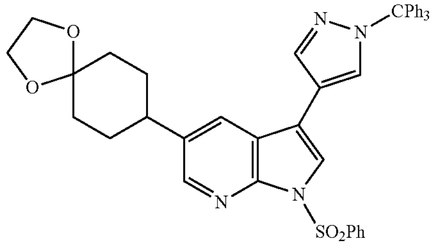

(IIb-92)

Following the general method for hydrogenation of 7-azaindoles, compound (IIa-91) (547 mg, 0.776 mmol) was hydrogenated in EtOAc:MeOH=4:1 (v/v, 20 mL) in the presence of $Pd(OH)_2$ on carbon (20% wet Degussa type; 10.87 mg, 0.0776 mmol) to give crude product (IIb-92) (402 mg, 73%). $^1$H NMR (400 MHz; $CDCl_3$) δ 1.23-1.25 (m, 1H), 1.65-1.75 (m, 4H), 1.76-1.81 (m, 2H), 1.83-1.90 (m, 2H), 3.98 (s, 4H), 7.07-7.14 (m, 6H), 7.23-7.31 (m, 9H), 7.41-7.50 (m, 2H), 7.51-7.58 (m, 1H), 7.76 (s, 1H), 7.81 (dd, J=1.4 Hz, 1H), 7.87 (s, 2H), 8.20 (dd, J=7.5 Hz, 2H), 8.37 (d, J=1.9 Hz, 1H). MS (CI) m/z ($MH^+$).

5-((1r,4r)-4-(3-(1-methyl-1H-pyrazol-4-yl)-1-(phenylsulfonyl)-1H-pyrrolo[2,3-b]pyridin-5-yl)cyclohexyl)-1,5-oxazocane (IIb-93) and 5-((1s,4s)-4-(3-(1-methyl-1H-pyrazol-4-yl)-1-yl)-1H-pyrrolo[2,3-b]pyridin-5-yl)cyclohexyl)-1,5-oxazocane (IIb-94)

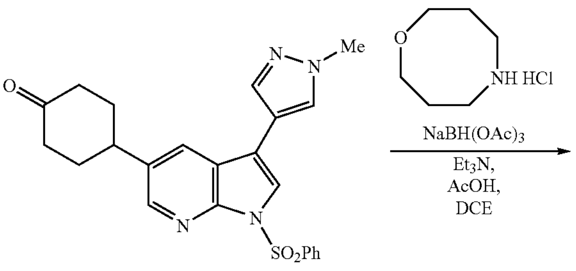

(IIb-20)

-continued

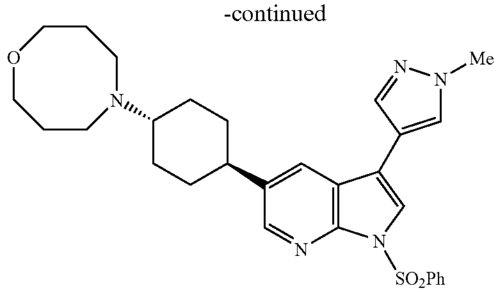

(IIb-93)

+

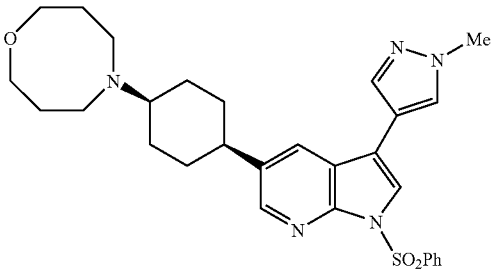

(IIb-94)

Ketone (IIb-20) (0.245 g, 0.56 mmol), 1,5-oxazocane hydrochloride (0.145 g, 0.96 mmol), $Et_3N$ (114 mg, 1.13 mmol), AcOH (34.6 mg, 0.58 mmol) and $NaBH(OAc)_3$ (0.1673 g, 0.79 mmol) in anhydrous 1,2-dichloroethane (4.0 mL) were reacted following the general procedure B for the reductive amination. The crude product was purified by PTLC using $CHCl_3$:MeOH:$NH_4OH$=93:6:1 (v/v/v) as the eluent to give the trans isomer (IIb-93) as a solid (63.4 mg, 21%) and the cis isomer (IIb-94) (40.3 mg, 13%) as a white solid.

Data for trans isomer (IIb-93): $^1H$ NMR (400 MHz; $CDCl_3$) δ 1.40-1.60 (m, 4H), 1.63-1.82 (m, 4H), 1.89-2.08 (m, 5H), 2.54-2.85 (m, 5H), 3.76 (t, J=5.2 Hz, 4H), 3.99 (s, 3H), 7.46-7.51 (m, 2H), 7.57 (tt, J=7.4, 1.5 Hz, 1H), 7.63 (s, 1H), 7.73 (s, 1H), 7.74-7.76 (m, 2H), 8.18-8.22 (m, 2H), 8.32 (d, J=2.0 Hz, 1H).

Data for cis isomer (IIb-94): $^1H$ NMR (400 MHz; $CDCl_3$) δ 1.51-1.78 (m, 9H), 1.85-2.04 (m, 4H), 2.65-2.83 (m, 5H), 3.82 (t, J=5.2 Hz, 4H), 3.99 (s, 3H), 7.46-7.51 (m, 2H), 7.57 (tt, J=7.3, 1.5 Hz, 1H), 7.70 (s, 1H), 7.74 (s, 1H), 7.77 (d, J=0.7 Hz, 1H), 7.86 (s, 1H), 8.18-8.23 (m, 2H), 8.38 (s, 1H).

4-((1r,4r)-4-(3-(1,5-dimethyl-1H-pyrazol-4-yl)-1-(phenylsulfonyl)-1H-pyrrolo[2,3-b]pyridin-5-yl)cyclohexyl)morpholine (IIb-95) and 4-((1s,4s)-4-(3-(1,5-dimethyl-1H-pyrazol-4-yl)-1-(phenylsulfonyl)-1H-pyrrolo[2,3-b]pyridin-5-yl)cyclohexyl)morpholine (IIb-96)

-continued

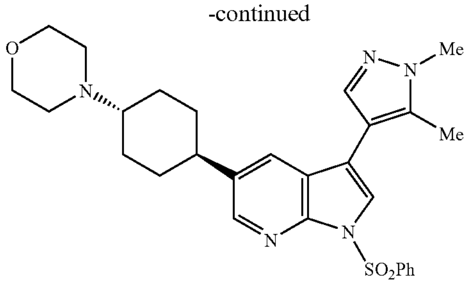

(IIb-95)

+

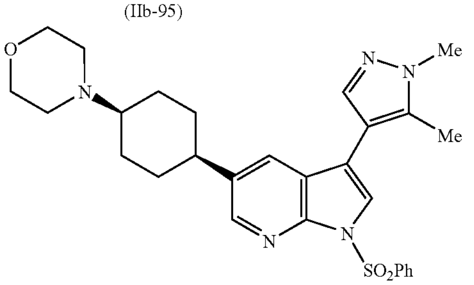

(IIb-96)

Ketone (IIb-98) (0.250 g, 0.56 mmol), morpholine (0.242 g, 2.79 mmol), AcOH (35 mg, 0.58 mmol) and $NaBH(OAc)_3$ (0.165 g, 0.79 mmol) in anhydrous 1,2-dichloroethane (3.0 mL) were reacted following the general procedure B for the reductive amination. The crude product was purified by PTLC using $CHCl_3$:MeOH:$NH_4OH$=93:6:1 (v/v/v) as the eluent to give the trans isomer (IIb-95) as a solid (44.6 mg, 15%) and the cis isomer (IIb-96) (106.2 mg, 37%) as a white solid.

Data for trans isomer (IIb-95): $^1H$ NMR (400 MHz; $CDCl_3$) δ 1.30-1.48 (m, 4H), 1.89-1.93 (m, 2H), 1.98-2.02 (m, 3H), 2.28 (s, 3H), 2.52-2.56 (m, 5H), 3.67-3.69 (m, 4H), 3.82 (s, 3H), 7.40-7.44 (m, 2H), 7.49-7.53 (m, 3H), 7.59 (d, J=2.0 Hz, 1H), 8.13-8.15 (m, 2H), 8.26 (d, J=2.0 Hz, 1H).

Data for cis isomer (IIb-96): $^1H$ NMR (400 MHz; $CDCl_3$) δ 1.43-1.54 (m, 4H), 1.81-1.92 (m, 4H), 2.17 (m, 1H), 2.29 (s, 3H), 2.39 (m, 4H), 2.66-2.72 (m, 1H), 3.63-3.66 (m, 4H), 3.82 (s, 3H), 7.40-7.44 (m, 2H), 7.50 (tt, J=7.2, 1.3 Hz, 1H), 7.51 (s, 1H), 7.54 (s, 1H), 7.65 (d, J=2.0 Hz, 1H), 8.13-8.16 (m, 2H), 8.32 (d, J=2.0 Hz, 1H).

3-(1,5-dimethyl-1H-pyrazol-4-yl)-1-(phenylsulfonyl)-5-(1,4-dioxaspiro[4.5]decan-8-yl)-1H-pyrrolo[2,3-b]pyridine (IIb-97)

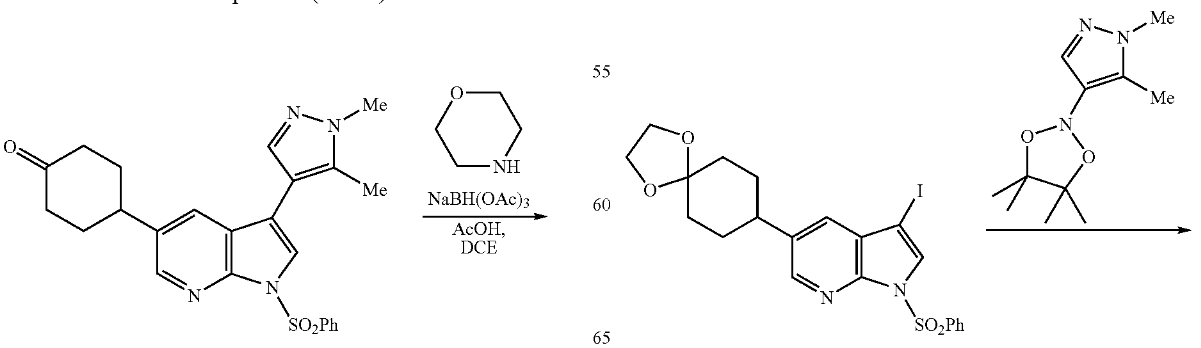

(IIb-98)

(IXb-19)

-continued

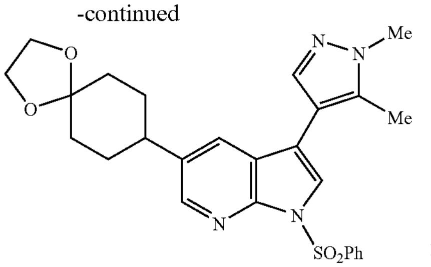

(IIb-97)

A mixture of iodide (IXb-19) (1.00 g, 1.91 mmol), 1,5-dimethyl-4-(4,4,5,5-tetramethyl-1,3,2-dioxaborolan-2-yl)-1H-pyrazole (0.47 g, 2.10 mmol), LiCl (0.24 g, 5.72 mmol) and $Pd(PPh_3)_2Cl_2$ (0.07 g, 0.10 mmol), 1 M $Na_2CO_3$ solution (4.77 mL), in toluene (20 mL) and EtOH (20 mL) was reacted at 105° C. for 4.5 h following the general procedure B for the Suzuki reaction. The mixture was allowed to cool to RT and brine (30 mL) was added. The mixture was extracted with EtOAc (3×60 mL). The combined organic extracts were dried ($MgSO_4$) and the solvent was removed under vacuum to give an orange oil. The crude product was purified by SGC using hexane:EtOAc as the eluent in gradient to give (IIb-97) (0.55 g, 59%). $^1$H NMR (400 MHz; $CDCl_3$) δ 1.68-1.90 (m, 8H), 2.36 (s, 3H), 2.67-2.73 (m, 1H), 3.91 (s, 3H), 3.99 (s, 4H), 7.49-7.54 (m, 2H), 7.58-7.63 (m, 3H), 7.72 (d, J=2.0 Hz, 1H), 8.23-8.26 (m, 2H), 8.37 (d, J=2.0 Hz, 1H).

4-(3-(1,5-dimethyl-1H-pyrazol-4-yl)-1-(phenylsulfonyl)-1H-pyrrolo[2,3-b]pyridin-5-yl)cyclohexanone (IIb-98)

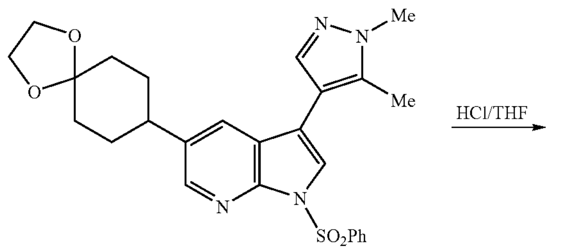

(IIb-97)

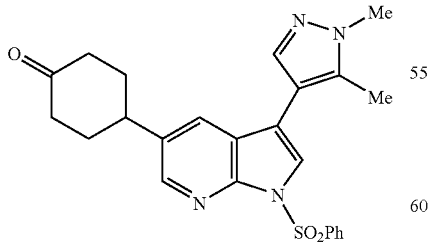

(IIb-98)

Aqueous 6 M HCl (5.6 ml, 33.6 mmol) was added at RT in small portions over 1 minute to a solution of compound (IIb-97) (0.55 g, 1.12 mmol) in THF (20 mL). The reaction mixture was stirred at RT for 2 h and quenched by slow addition of a saturated aqueous solution of $NaHCO_3$ (50 mL). After stirring for 15 min the mixture was extracted with EtOAc (3×60 mL). The combined extracts were dried over $MgSO_4$ and concentrated to give (IIb-98) as an off-white crystalline solid (0.56 g, 111%), $^1$H NMR (400 MHz; $CDCl_3$) δ 1.83-1.93 (m, 2H), 2.10-2.19 (m, 2H), 2.28 (s, 3H), 2.43-2.47 (m, 4H), 3.08 (tt, J=12.2, 3.2 Hz, 1H), 3.82 (s, 3H), 7.42-7.46 (m, 2H), 7.51-7.54 (m, 3H), 7.63 (d, J=2.2 Hz, 1H), 8.14-8.17 (m, 2H), 8.32 (d, J=2.0 Hz, 1H).

3-(1,3-dimethyl-1H-pyrazol-4-yl)-1-yl)-5-(1,4-dioxaspiro[4.5]decan-8-yl)-1H-pyrrolo[2,3-b]pyridine (IIb-99)

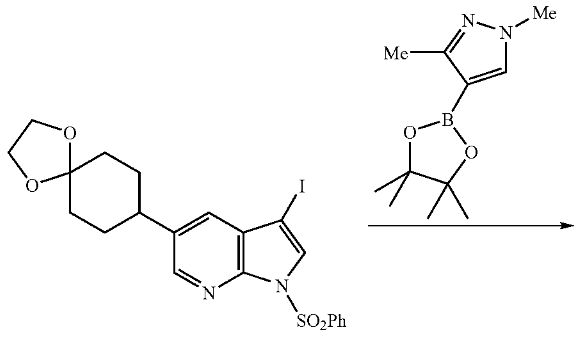

(IXb-19)

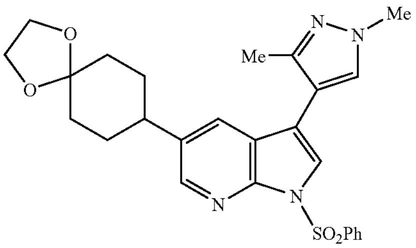

(IIb-99)

A mixture of iodide (IXb-19) (1.00 g, 1.91 mmol), 1,5-dimethyl-4-(4,4,5,5-tetramethyl-1,3,2-dioxaborolan-2-yl)-1H-pyrazole (0.47 g, 2.10 mmol), LiCl (0.24 g, 5.72 mmol) and $Pd(PPh_3)_2Cl_2$ (0.07 g, 0.10 mmol), 1 M $Na_2CO_3$ solution (4.77 mL) in toluene (20 mL) and EtOH (20 mL) was reacted at 105° C. for 3.5 h following the general procedure B for the Suzuki reaction. The mixture was allowed to cool to RT and brine (30 mL) was added. The mixture was extracted with EtOAc (3×60 mL). The combined organic extracts were dried ($MgSO_4$) and the solvent was removed under vacuum to give an orange oil. The crude product was purified by SGC using hexane:EtOAc as the eluent in gradient to give (IIb-99) (0.3125 g, 33%); $^1$H NMR (400 MHz; $CDCl_3$) δ 1.67-1.88 (m, 8H), 2.34 (s, 3H), 2.65-2.72 (m, 1H), 3.93 (s, 3H), 3.98 (s, 4H), 7.47-7.51 (m, 3H), 7.57 (tt, J=7.3, 1.5 Hz, 1H), 7.64 (s, 1H), 7.67 (d, J=2.0 Hz, 1H), 8.21-8.23 (m, 2H), 8.35 (d, J=2.0 Hz, 1H).

4-(3-(1,3-dimethyl-1H-pyrazol-4yl)-1-(phenylsulfonyl)-1H-pyrrolo[2,3-b]pyridin-5-yl)cyclohexanone (IIb-100)

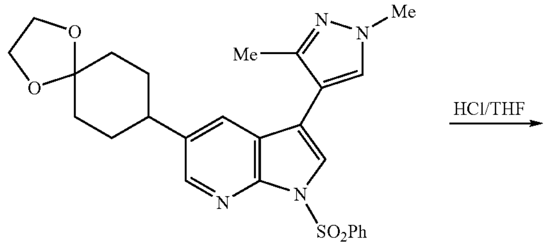

(IIb-99)

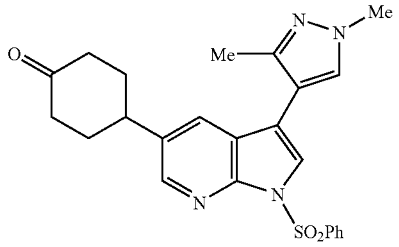

(IIb-100)

Aqueous 6 M HCl (3.5 ml, 21.0 mmol) was added at RT in small portions over 1 minute to a solution of compound (IIb-97) (0.3125 g, 0.63 mmol) in THF (20 mL). The reaction mixture was stirred at RT for 1.3 h and quenched by slow addition of a saturated aqueous solution of $NaHCO_3$ (40 mL). After stirring for 15 min the mixture was extracted with EtOAc (1×60 mL then 3×40 mL). The combined extracts were dried over $MgSO_4$ and concentrated to give (IIb-100) as a yellow solid (0.328 g, 97%; purity 84%). This material was used in further steps without any additional purification. $^1H$ NMR (400 MHz; $CDCl_3$) δ 1.94-1.99 (m, 2H), 2.19-2.24 (m, 2H), 2.34 (s, 3H), 2.51-2.55 (m, 4H), 3.16 (t, J=12.3, 3.3 Hz, 1H), 3.93 (s, 3H), 7.48-7.52 (m, 3H), 7.59 (tt, J=7.4, 1.5 Hz, 1H), 7.66 (m, 2H), 8.21-8.23 (m, 2H), 8.39 (d, J=2.1 Hz, 1H).

4-((1r,4r)-4-(3-(1,3-dimethyl-1H-pyrazol-4-yl)-1-(phenylsulfonyl)-1H-pyrrolo[2,3-b]pyridin-5-yl) cyclohexyl)morpholine (IIb-101) and 4-((1s,4s)-4-(3-(1,3-dimethyl-1H-pyrazol-4-yl)-1-yl)-1H-pyrrolo [2,3-b]pyridin-5-yl)cyclohexyl)morpholine (IIb-102)

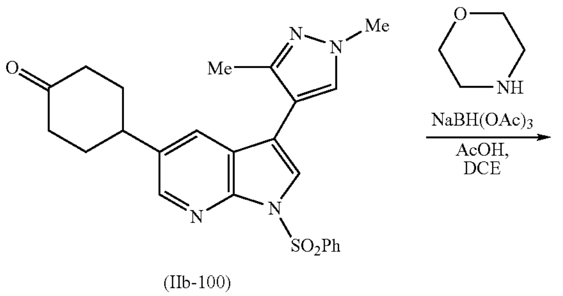

(IIb-100)

-continued

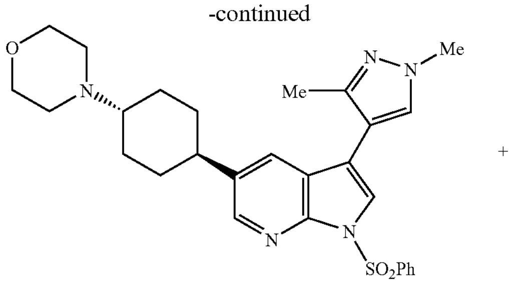

(IIb-101)

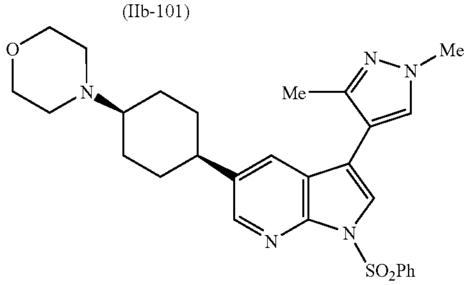

(IIb-102)

Ketone (IIb-100) (0.328 g, 0.73 mmol), morpholine (0.319 g, 3.66 mmol), AcOH (44 mg, 0.73 mmol) and $NaBH(OAc)_3$ (0.217 g, 1.03 mmol) in anhydrous 1,2-dichloroethane (6.0 mL) were reacted following the general procedure B for the reductive amination. The crude product was purified by PTLC using $CHCl_3$:MeOH:$NH_4OH$=93:6:1 (v/v/v) as the eluent to give the trans isomer (IIb-101) as a solid (90.3 mg, 22%; purity 93%) and the cis isomer (IIb-102) (152.9 mg, 40%).

Data for trans isomer (IIb-101): $^1H$ NMR (400 MHz; $CDCl_3$) δ 1.98-1.99 (m, 2H), 2.05-2.08 (m, 2H), 2.30 (bs, 1H), 2.33 (s, 3H), 2.60 (m, 5H), 3.74 (m, 4H), 3.92 (s, 3H), 7.47-7.51 (m, 3H), 7.57 (tt, J=7.4, 1.5 Hz, 1H), 7.61 (d, J=2.0 Hz, 1H), 7.63 (s, 1H), 8.20-8.22 (m, 2H), 8.32 (d, J=2.0 Hz, 1H).

Data for cis isomer (IIb-102): $^1H$ NMR (400 MHz; $CDCl_3$) δ 1.49-1.61 (m, 4H), 1.88-2.00 (m, 4H), 2.25 (bs, 1H), 2.35 (s, 3H), 2.46 (m, 4H), 2.72-2.80 (m, 1H), 3.71-3.74 (m, 4H), 3.92 (s, 3H), 7.49-7.51 (m, 3H), 7.58 (tt, J=7.3, 1.5 Hz, 1H), 7.63 (s, 1H), 7.66 (m, 1H), 8.20-8.23 (m, 2H), 8.39 (d, J=2.0 Hz, 1H).

(S)-3-methyl-4-((1r,4S)-4-(3-(1-methyl-1H-pyrazol-4-yl)-1-(phenylsulfonyl)-1H-pyrrolo[2,3-b]pyridin-5-yl)cyclohexyl)morpholine (IIb-103) and (S)-3-methyl-4-((1s,4R)-4-(3-(1-methyl-1H-pyrazol-4-yl)-1-(phenylsulfonyl)-1H-pyrrolo[2,3-b]pyridin-5-yl) cyclohexyl)morpholine (IIb-104)

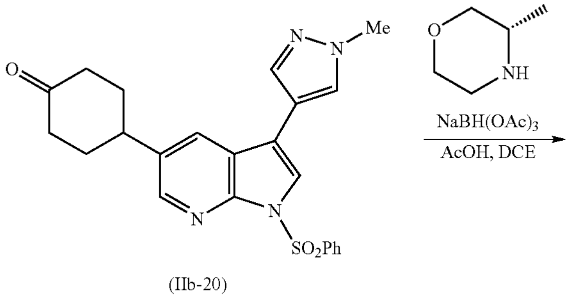

(IIb-20)

-continued

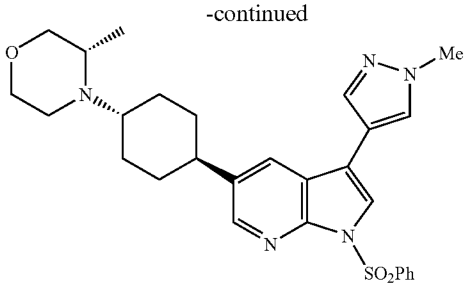

+

(IIb-103)

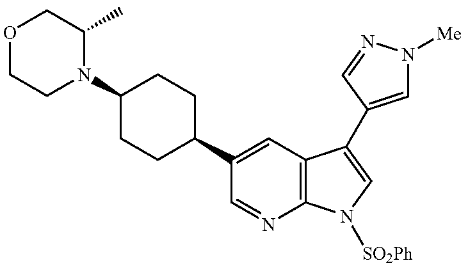

(IIb-104)

Ketone (IIb-20) (0.250 g, 0.58 mmol), (S)-3-methylmorpholine (0.117 g, 1.16 mmol), AcOH (34.6 mg, 0.58 mmol) and $NaBH(OAc)_3$ (0.171 g, 0.81 mmol) in anhydrous 1,2-dichloroethane (3.0 mL) were reacted following the general procedure B for the reductive amination. The crude product was purified by PTLC using $CHCl_3$:MeOH:$NH_4OH$=93:6:1 (v/v/v) as the eluent to give the trans isomer (IIb-103) as a solid (103.6 mg, 21%; 60% purity) and the cis isomer (IIb-104) (53.6 mg, 18%).

Data for cis isomer (IIb-104): $^1H$ NMR (400 MHz; $CDCl_3$) δ 1.03 (d, J=6.4 Hz, 3H), 1.51-1.72 (m, 4H), 1.82-2.06 (m, 4H), 2.51 (m, 2H), 2.67 (m, 1H), 2.83-2.92 (m, 2H), 3.53-3.57 (m, 1H), 3.60-3.79 (m, 3H), 3.99 (s, 3H), 7.45-7.50 (m, 2H), 7.56 (tt, J=7.4, 1.6 Hz, 1H), 7.64 (m, 1H), 7.72 (s, 1H), 7.76 (d, J=0.7 Hz, 1H), 7.82 (m, 1H), 8.19-8.21 (m, 2H), 8.41 (d, J=2.0 Hz, 1H).

(1r,4r)-N-isopropyl-4-(3-(1-methyl-1H-pyrazol-4-yl)-1-(phenylsulfonyl)-1H-pyrrolo[2,3-b]pyridin-5-yl)cyclohexanamine (IIb-105) and (1s,4s)-N-isopropyl-4-(3-(1-methyl-1H-pyrazol-4-yl)-1-(phenylsulfonyl)-1H-pyrrolo[2,3-b]pyridin-5-yl) cyclohexanamine (IIb-106)

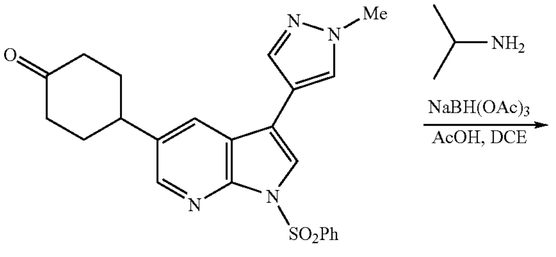

(IIb-20)

-continued

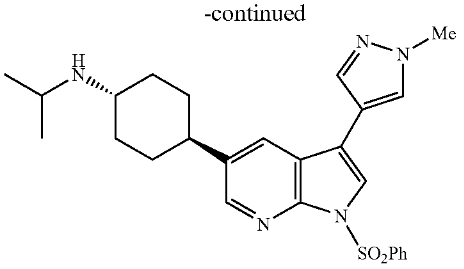

+

(IIb-105)

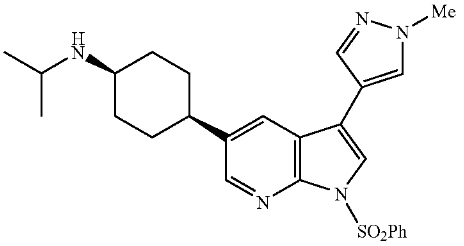

(IIb-106)

Ketone (IIb-20) (0.250 g, 0.58 mmol), isopropylamine (0.200 g, 3.38 mmol), AcOH (34.6 mg, 0.58 mmol) and $NaBH(OAc)_3$ (0.171 g, 0.81 mmol) in anhydrous 1,2-dichloroethane (3.0 mL) were reacted for 19 h following the general procedure B for the reductive amination. The crude product was purified by PTLC using $CHCl_3$:MeOH:$NH_4OH$=93:6:1 (v/v/v) as the eluent to give the trans isomer (IIb-105) as a solid (57.9 mg, 21%) and the cis isomer (IIb-106) (90.3 mg, 33%) as a white solid.

Data for trans isomer (IIb-105): $^1H$ NMR (400 MHz, $CDCl_3$) δ 1.10 (d, J=6.2 Hz, 6H), 1.21-1.36 (m, 2H), 1.49-1.61 (m, 2H), 1.89-1.97 (m, 2H), 2.04-2.13 (m, 2H), 2.59-2.72 (m, 2H), 3.00-3.09 (m, 1H), 3.99 (s, 3H), 7.45-7.51 (m, 2H), 7.57 (tt, J=7.3, 1.5 Hz, 1H), 7.63 (bs, 1H), 7.72 (bs, 1H), 7.73-7.76 (m, 2H), 8.19-8.22 (m, 2H), 8.33 (d, J=2.0 Hz, 1H).

Data for cis isomer (IIb-106): $^1H$ NMR (400 MHz, $CDCl_3$) δ 1.08 (d, J=6.1 Hz, 6H), 1.62-1.71 (m, 4H), 1.75-1.88 (m, 4H), 2.64-2.74 (m, 1H), 2.84-2.96 (m, 1H), 2.98-3.05 (m, 1H), 3.99 (s, 3H), 7.45-7.50 (m, 2H), 7.56 (tt, J=7.3, 1.6 Hz, 1H), 7.64-7.71 (m, 1H), 7.72 (bs, 1H), 7.75-7.76 (m, 1H), 7.80-7.84 (m, 1H), 8.18-8.22 (m, 2H), 8.36 (d, J=2.0 Hz, 1H).

(1r,4r)-N-(2-ethoxyethyl)-N-ethyl-4-(3-(1-methyl-1H-pyrazol-4-yl)-1-(phenylsulfonyl)-1H-pyrrolo[2,3-b]pyridin-5-yl)cyclohexanamine (IIb-107) and (1s,4s)-N-(2-ethoxyethyl)-N-ethyl-4-(3-(1-methyl-1H-pyrazol-4-yl)-1-(phenylsulfonyl)-1H-pyrrolo[2,3-b]pyridin-5-yl)cyclohexanamine (IIb-108)

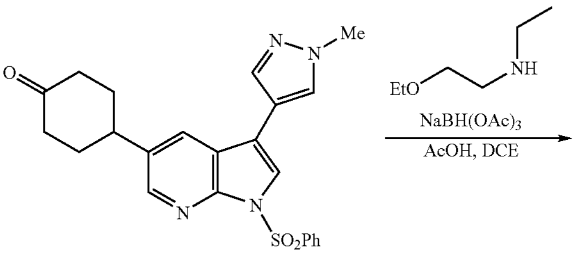

(IIb-20)

-continued

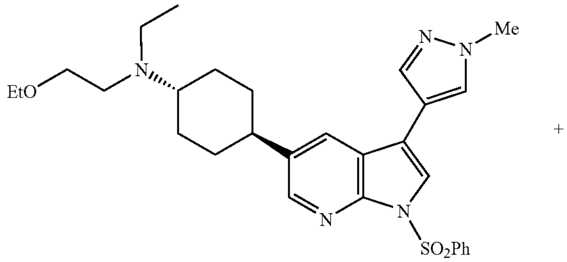

(IIb-107)

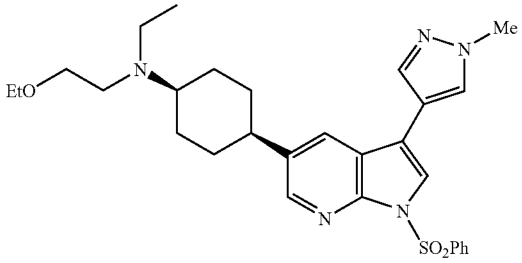

(IIb-108)

Ketone (IIb-20) (0.250 g, 0.58 mmol), 2-ethoxy-N-ethylethanamine (0.135 g, 1.15 mmol), AcOH (34.6 mg, 0.58 mmol) and $NaBH(OAc)_3$ (0.171 g, 0.81 mmol) in anhydrous 1,2-dichloroethane (3.0 mL) were reacted for 21 h following the general procedure B for the reductive amination. The crude product was purified by PTLC using $CHCl_3$:MeOH:$NH_4OH$=93:6:1 (v/v/v) as the eluent to give the trans isomer (IIb-107) (52.8 mg, 17%) and the cis isomer (IIb-108) (59.2 mg, 19%).

Data for trans isomer (IIb-107): $^1H$ NMR (400 MHz, $CDCl_3$) δ 1.06 (t, J=7.0 Hz, 3H), 1.21 (t, J=7.0 Hz, 3H), 1.37-1.58 (m, 4H), 1.67-1.79 (m, 1H), 1.90-2.01 (m, 4H), 2.53-2.77 (m, 6H), 3.43-3.49 (m, 2H), 3.51 (q, J=7.0 Hz, 2H), 3.99 (s, 3H), 7.45-7.51 (m, 2H), 7.57 (tt, J=7.4, 1.5 Hz, 1H), 7.63 (bs, 1H), 7.72 (s, 1H), 7.74-7.73 (m, 2H), 8.19-8.22 (m, 2H), 8.32 (d, J=1.9 Hz, 1H).

Data for cis isomer (IIb-108): $^1H$ NMR (400 MHz, $CDCl_3$) δ 0.98 (t, J=6.9 Hz, 3H), 1.17 (t, J=6.9 Hz, 3H), 1.21 (d, J=3.1 Hz, 2H), 1.52-1.61 (m, 1H), 1.62-1.72 (m, 1H), 1.78-1.88 (m, 2H), 1.97-2.08 (m, 2H), 2.59-2.74 (m, 5H), 2.80-2.89 (m, 1H), 3.42-3.51 (m, 4H), 3.99 (s, 3H), 7.46-7.51 (m, 2H), 7.57

(tt, J=7.3, 1.5 Hz, 1H), 7.64 (bs, 1H), 7.72 (s, 1H), 7.75-7.77 (m, 1H), 7.81-7.84 (m, 1H), 8.18-8.23 (m, 2H), 8.41 (d, J=1.8 Hz, 1H).

(1r,4r)-N-ethyl-N-methyl-4-(3-(1-methyl-1H-pyrazol-4-yl)-1-(phenylsulfonyl)-1H-pyrrolo[2,3-b]pyridin-5-yl)cyclohexanamine (IIb-109) and (1s,4s)-N-ethyl-N-methyl-4-(3-(1-methyl-1H-pyrazol-4-yl)-1-(phenylsulfonyl)-1H-pyrrolo[2,3-b]pyridin-5-yl) cyclohexanamine (IIb-110)

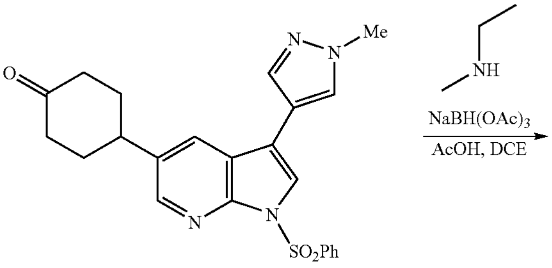

(IIb-20)

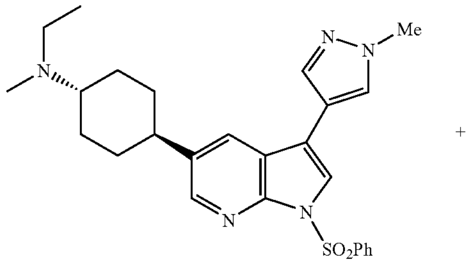

(IIb-109)

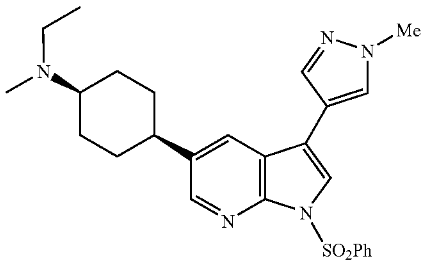

(IIb-110)

Ketone (IIb-20) (0.250 g, 0.58 mmol), N-methylethanamine (0.068 g, 1.15 mmol), AcOH (34.6 mg, 0.58 mmol) and $NaBH(OAc)_3$ (0.171 g, 0.81 mmol) in anhydrous 1,2-dichloroethane (3.0 mL) were reacted for 24 h following the general procedure B for the reductive amination. The crude product was purified by PTLC using $CHCl_3$:MeOH:$NH_4OH$=93:6:1 (v/v/v) as the eluent to give the trans isomer (IIb-109) (75.9 mg, 28%) and the cis isomer (IIb-110) (69.5 mg, 25%).

Data for trans isomer (IIb-109): $^1H$ NMR (400 MHz, $CDCl_3$) δ 1.09 (t, J=7.0 Hz, 3H), 1.39-1.60 (m, 4H), 1.95-2.03 (m, 4H), 2.30 (s, 3H), 2.50-2.65 (m, 4H), 3.99 (s, 3H), 7.45-7.51 (m, 2H), 7.57 (tt, J=7.4, 1.5 Hz, 1H), 7.63 (s, 1H), 7.72 (s, 1H), 7.73-7.76 (m, 2H), 8.18-8.22 (m, 2H), 8.33 (d, J=2.0 Hz, 1H).

Data for cis isomer (IIb-110): $^1H$ NMR (400 MHz, $CDCl_3$) δ 0.98-1.06 (m, 3H), 1.30-1.70 (m, 4H), 1.89-2.06 (m, 4H), 2.19-2.30 (m, 3H), 2.41-2.51 (m, 1H), 2.56-2.68 (m, 2H), 2.76-2.85 (m, 1H), 3.99 (s, 3H), 7.45-7.50 (m, 2H), 7.56 (tt, J=7.4, 1.5 Hz, 1H), 7.61-7.70 (m, 1H), 7.72 (s, 1H), 7.76 (d, J=0.7 Hz, 1H), 7.79-7.90 (m, 1H), 8.18-8.23 (m, 2H), 8.39 (d, J=1.8 Hz, 1H).

(1r,4r)-N-(2-methoxyethyl)-4-(3-(1-methyl-1H-pyrazol-4-yl)-1-(phenylsulfonyl)-1H-pyrrolo[2,3-b]pyridin-5-yl)cyclohexanamine (IIb-111) and (1s,4s)-N-(2-methoxyethyl)-4-(3-(1-methyl-1H-pyrazol-4-yl)-1-(phenylsulfonyl)-1H-pyrrolo[2,3-b]pyridin-5-yl) cyclohexanamine (IIb-112)

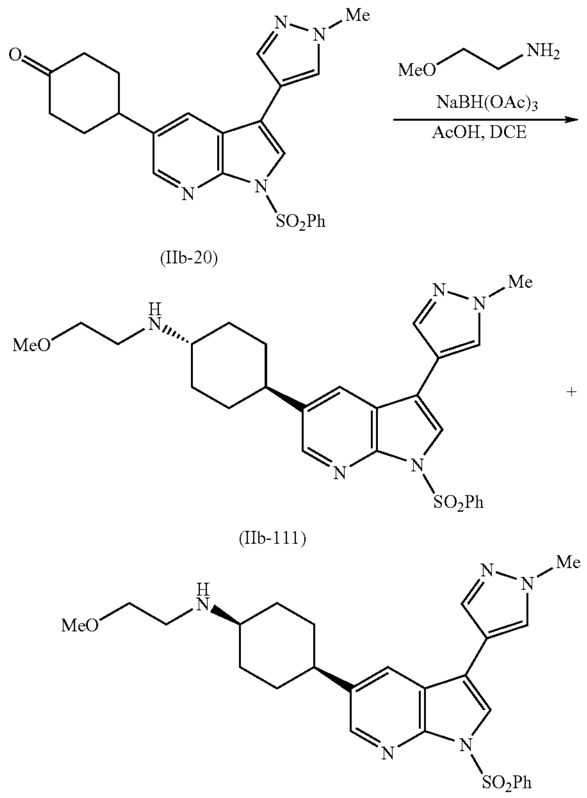

(IIb-20)

(IIb-111)

+

(IIb-112)

Ketone (IIb-20) (0.250 g, 0.58 mmol), 2-methoxyethanamine (0.086 g, 1.15 mmol), AcOH (34.6 mg, 0.58 mmol) and $NaBH(OAc)_3$ (0.171 g, 0.81 mmol) in anhydrous 1,2-dichloroethane (3.0 mL) were reacted for 24 h following the general procedure B for the reductive amination. The crude product was purified by PTLC using $CHCl_3$:MeOH:$NH_4OH$=93:6:1 (v/v/v) as the eluent to give the trans isomer (IIb-111) (55.5 mg, 19%) and the cis isomer (IIb-112) (89.8 mg, 32%).

Data for trans isomer (IIb-111): $^1$H NMR (400 MHz, $CDCl_3$) δ 1.23-1.37 (m, 2H), 1.48-1.61 (m, 2H), 1.89-1.98 (m, 3H), 2.04-2.13 (m, 2H), 2.52-2.68 (m, 2H), 2.85 (t, J=5.1 Hz, 2H), 3.37 (s, 3H), 3.53 (t, J=5.1 Hz, 2H), 3.99 (s, 3H), 7.45-7.51 (m, 2H), 7.57 (tt, J=7.5, 1.5 Hz, 1H), 7.63 (s, 1H), 7.72 (s, 1H), 7.74-7.76 (m, 2H), 8.18-8.23 (m, 2H), 8.33 (d, J=2.0 Hz, 1H).

Data for cis isomer (IIb-112): $^1$H NMR (400 MHz, $CDCl_3$) δ 1.59-1.69 (m, 4H), 1.80-1.94 (m, 4H), 1.98 (s, 1H), 2.65-2.74 (m, 1H), 2.78 (t, J=5.2 Hz, 2H), 2.89-2.93 (m, 1H), 3.35 (s, 3H), 3.52 (t, J=5.2 Hz, 2H), 3.99 (s, 3H), 7.45-7.50 (m, 2H), 7.56 (t, J=7.5 Hz, 1H), 7.68 (s, 1H), 7.72 (s, 1H), 7.75 (s, 1H), 7.81 (d, J=1.8 Hz, 1H), 8.18-8.22 (m, 2H), 8.35 (d, J=1.9 Hz, 1H).

(1r,4r)-N-ethyl-4-(3-(1-methyl-1H-pyrazol-4-yl)-1-(phenylsulfonyl)-1H-pyrrolo[2,3-b]pyridin-5-yl)-N-propylcyclohexanamine (IIb-113) and (1s,4s)-N-ethyl-4-(3-(1-methyl-1H-pyrazol-4-yl)-1-(phenylsulfonyl)-1H-pyrrolo[2,3-b]pyridin-5-yl)-N-propylcyclohexanamine (IIb-114)

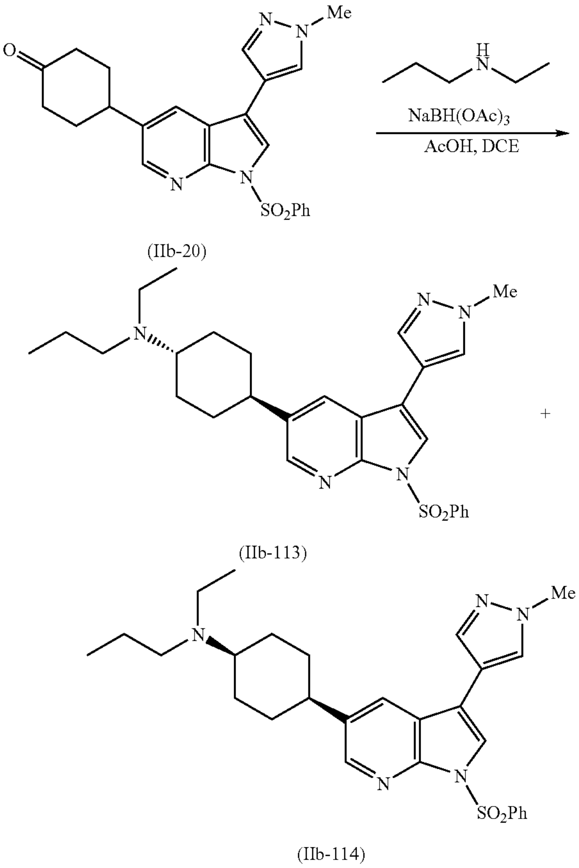

(IIb-20)

(IIb-113)

+

(IIb-114)

Ketone (IIb-20) (0.250 g, 0.58 mmol), N-ethylpropan-1-amine (0.100 g, 1.15 mmol), AcOH (34.6 mg, 0.58 mmol) and $NaBH(OAc)_3$ (0.171 g, 0.81 mmol) in anhydrous 1,2-dichloroethane (3.0 mL) were reacted for 19.5 h following the general procedure B for the reductive amination. The crude product was purified by PTLC using $CHCl_3$:MeOH:$NH_4OH$=93:6:1 (v/v/v) as the eluent to give the trans isomer (IIb-113) (66.9 mg, 23%) and the cis isomer (IIb-114) (68.8 mg, 24%).

Data for trans isomer (IIb-113): $^1$H NMR (400 MHz, $CDCl_3$) δ 0.89 (t, J=7.4 Hz, 3H), 1.04-1.11 (m, 3H), 1.41-1.59 (m, 6H), 1.93-2.01 (m, 4H), 2.38-2.70 (m, 6H), 3.99 (s, 3H), 7.45-7.51 (m, 2H), 7.57 (tt, J=7.5, 1.5 Hz, 1H), 7.63 (s, 1H), 7.72 (s, 1H), 7.74-7.76 (m, 2H), 8.18-8.22 (m, 2H), 8.33 (d, J=2.0 Hz, 1H).

Data for cis isomer (IIb-114): $^1$H NMR (400 MHz, $CDCl_3$) δ 0.88 (t, J=7.0 Hz, 3H), 0.96 (t, J=6.8 Hz, 3H), 1.40-1.68 (m, 6H), 1.81-2.15 (m, 4H), 2.41-2.48 (m, 2H), 2.58-2.70 (m, 3H), 2.79-2.87 (m, 1H), 4.00 (s, 3H), 7.46-7.50 (m, 2H), 7.53-7.59 (m, 1H), 7.62 (s, 1H), 7.71-7.76 (m, 3H), 8.18-8.22 (m, 2H), 8.33 (d, J=2.0 Hz, 1H).

(1r,4r)-N-methyl-4-(3-(1-methyl-1H-pyrazol-4-yl)-1-(phenylsulfonyl)-1H-pyrrolo[2,3-b]pyridin-5-yl)-N-propylcyclohexanamine (IIb-115) and (1s,4s)-N-methyl-4-(3-(1-methyl-1H-pyrazol-4-yl)-1-(phenylsulfonyl)-1H-pyrrolo[2,3-b]pyridin-5-yl)-N-propylcyclohexanamine (IIb-116)

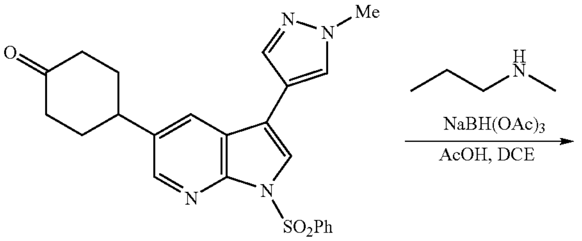

(IIb-20)

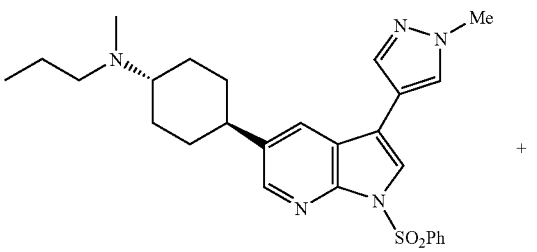

(IIb-115)

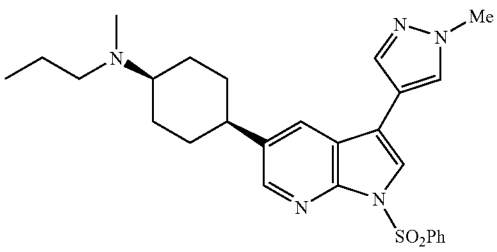

(IIb-116)

Ketone (IIb-20) (0.250 g, 0.58 mmol), N-methylpropan-1-amine (0.084 g, 1.15 mmol), AcOH (34.6 mg, 0.58 mmol) and $NaBH(OAc)_3$ (0.171 g, 0.81 mmol) in anhydrous 1,2-dichloroethane (3.0 mL) were reacted for 21 h following the general procedure B for the reductive amination. The crude product was purified by PTLC using $CHCl_3$:MeOH:$NH_4OH$=93:6:1 (v/v/v) as the eluent to give the trans isomer (IIb-115) (66.5 mg, 23%) and the cis isomer (IIb-116) (61.5 mg, 22%).

Data for trans isomer (IIb-115): $^1H$ NMR (400 MHz, $CDCl_3$) δ 0.90 (t, J=7.3 Hz, 3H), 1.40-1.59 (m, 6H), 1.94-2.02 (m, 4H), 2.31 (s, 3H), 2.42-2.48 (m, 2H), 2.50-2.65 (m, 2H), 3.99 (s, 3H), 7.45-7.51 (m, 2H), 7.57 (tt, J=7.5, 1.5 Hz, 1H), 7.63 (s, 1H), 7.72 (s, 1H), 7.74-7.75 (m, 2H), 8.18-8.22 (m, 2H), 8.33 (d, J=2.0 Hz, 1H).

Data for cis isomer (IIb-116): $^1H$ NMR (400 MHz, $CDCl_3$) δ 0.90 (t, J=7.1 Hz, 3H), 1.43-1.68 (m, 6H), 1.90-2.05 (m, 4H), 2.22 (s, 3H), 2.36-2.46 (m, 3H), 2.76-2.85 (m, 1H), 3.99 (s, 3H), 7.45-7.51 (m, 2H), 7.56 (tt, J=7.4, 1.5 Hz, 1H), 7.62-7.67 (m, 1H), 7.72 (s, 1H), 7.75 (d, J=0.7 Hz, 1H), 7.80-7.87 (m, 1H), 8.18-8.22 (m, 2H), 8.37-8.40 (m, 1H).

(1r,4r)-N-(2-methoxyethyl)-N-methyl-4-(3-(1-methyl-1H-pyrazol-4-yl)-1-(phenylsulfonyl)-1H-pyrrolo[2,3-b]pyridin-5-yl)cyclohexanamine (IIb-117) and (1s,4s)-N-(2-methoxyethyl)-N-methyl-4-(3-(1-methyl-1H-pyrazol-4-yl)-1-(phenylsulfonyl)-1H-pyrrolo[2,3-b]pyridin-5-yl)cyclohexanamine (IIb-118)

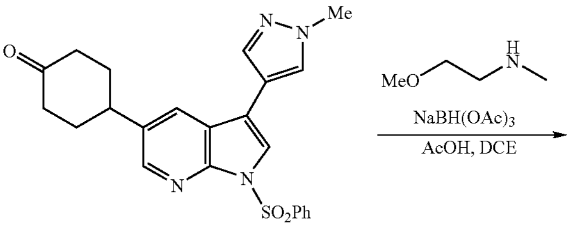

(IIb-20)

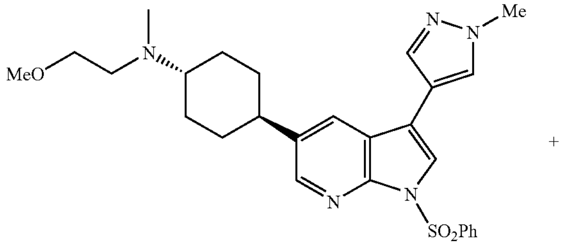

(IIb-117)

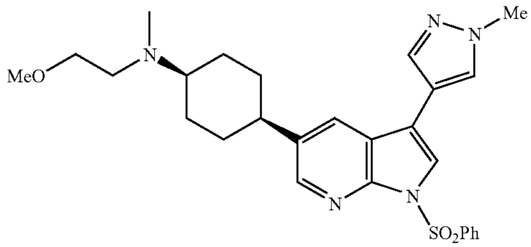

(IIb-118)

Ketone (IIb-20) (0.250 g, 0.58 mmol), 2-methoxy-N-methylethanamine (0.103 g, 1.15 mmol), AcOH (34.6 mg, 0.58 mmol) and $NaBH(OAc)_3$ (0.171 g, 0.81 mmol) in anhydrous 1,2-dichloroethane (3.0 mL) were reacted for 21 h following the general procedure B for the reductive amination. The crude product was purified by PTLC using $CHCl_3$:MeOH:$NH_4OH$=93:6:1 (v/v/v) as the eluent to give the trans isomer (IIb-117) (74.2 mg, 25%) and the cis isomer (IIb-118) (68.5 mg, 24%).

Data for trans isomer (IIb-117): $^1H$ NMR (400 MHz, $CDCl_3$) δ 1.38-1.59 (m, 4H), 1.93-2.03 (m, 4H), 2.36 (s, 3H), 2.50-2.64 (m, 2H), 2.69 (t, J=5.9 Hz, 2H), 3.37 (s, 3H), 3.49 (t, J=5.9 Hz, 2H), 3.99 (s, 3H), 7.45-7.51 (m, 2H), 7.57 (tt, J=7.5, 1.5 Hz, 1H), 7.63 (s, 1H), 7.72 (s, 1H), 7.74-7.75 (m, 2H), 8.18-8.22 (m, 2H), 8.32 (d, J=2.0 Hz, 1H).

Data for cis isomer (IIb-118): $^1H$ NMR (400 MHz, $CDCl_3$) δ 1.52-1.72 (m, 4H), 1.85-2.07 (m, 4H), 2.28 (s, 3H), 2.43-2.50 (m, 1H), 2.66 (t, J=6.0 Hz, 2H), 2.79-2.87 (m, 1H), 3.34 (s, 3H), 3.48 (t, J=6.0 Hz, 2H), 3.99 (s, 3H), 7.45-7.51 (m, 2H), 7.57 (tt, J=7.5, 1.5 Hz, 1H), 7.64 (s, 1H), 7.72 (s, 1H), 7.75 (d, J=0.7 Hz, 1H), 7.82 (s, 1H), 8.19-8.22 (m, 2H), 8.40 (d, J=1.8 Hz, 1H).

(1r,4r)-N-(2-ethoxyethyl)-4-(3-(1-methyl-1H-pyrazol-4-yl)-1-(phenylsulfonyl)-1H-pyrrolo[2,3-b]pyridin-5-yl)cyclohexanamine (IIb-119) and (1s,4s)-N-(2-ethoxyethyl)-4-(3-(1-methyl-1H-pyrazol-4-yl)-1-(phenylsulfonyl)-1H-pyrrolo[2,3-b]pyridin-5-yl) cyclohexanamine (IIb-120)

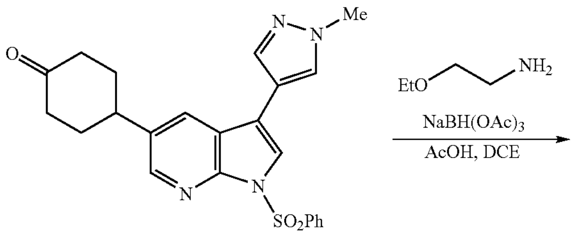

(IIb-20)

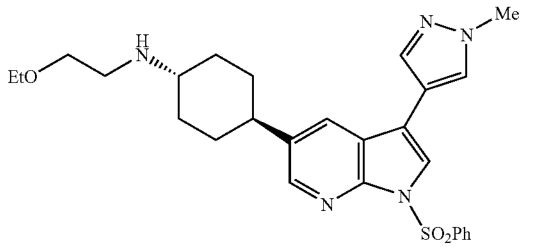

+

(IIb-119)

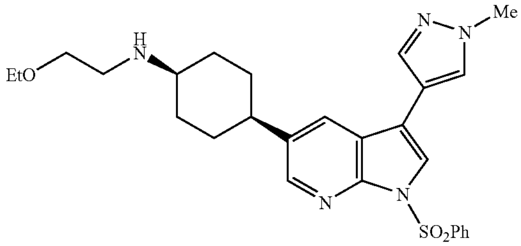

(IIb-120)

Ketone (IIb-20) (0.250 g, 0.58 mmol), 2-ethoxyethanamine (0.103 g, 1.15 mmol), AcOH (34.6 mg, 0.58 mmol) and $NaBH(OAc)_3$ (0.171 g, 0.81 mmol) in anhydrous 1,2-dichloroethane (3.0 mL) were reacted for 21 h following the general procedure B for the reductive amination. The crude product was purified by PTLC using $CHCl_3$:MeOH:$NH_4OH$=93:6:1 (v/v/v) as the eluent to give the trans isomer (IIb-119) (66.5 mg, 23%) and the cis isomer (IIb-120) (104.7 mg, 36%).

Data for trans isomer (IIb-119): $^1$H NMR (400 MHz, $CDCl_3$) δ 1.21 (t, J=6.9 Hz, 3H), 1.23-1.35 (m, 3H), 1.48-1.61 (m, 2H), 1.89-1.97 (m, 2H), 2.03-2.12 (m, 2H), 2.30-2.68 (m, 2H), 2.84 (t, J=5.1 Hz, 2H), 3.52 (q, J=7.2 Hz, 2H), 3.56 (t, J=5.1 Hz, 2H), 3.99 (s, 3H), 7.45-7.51 (m, 2H), 7.56 (tt, J=7.5, 1.5 Hz, 1H), 7.63 (s, 1H), 7.72 (s, 1H), 7.74-7.76 (m, 2H), 8.18-8.22 (m, 2H), 8.33 (d, J=2.0 Hz, 1H).

Data for cis isomer (IIb-120): $^1$H NMR (400 MHz, $CDCl_3$) δ 1.21 (t, J=7.0 Hz, 3H), 1.59-1.72 (m, 6H), 1.78-1.95 (m, 4H), 2.64-2.74 (m, 1H), 2.77 (t, J=5.2 Hz, 2H), 2.88-2.92 (m, 1H), 3.52 (q, J=7.0 Hz, 2H), 3.55 (q, J=5.2 Hz, 2H), 3.99 (s, 3H), 7.44-7.51 (m, 2H), 7.56 (tt, J=7.3, 1.5 Hz, 1H), 7.65 (s, 1H), 7.72 (s, 1H), 7.75 (d, J=0.7 Hz, 1H), 7.79 (d, J=2.0 Hz, 1H), 8.18-8.22 (m, 2H), 8.36 (d, J=2.0 Hz, 1H).

(1r,4r)-N-(2-methoxyethyl)-4-(3-(1-methyl-1H-pyrazol-4-yl)-1-(phenylsulfonyl)-1H-pyrrolo[2,3-b]pyridin-5-yl)-N-propylcyclohexanamine (IIb-121) and (1s,4s)-N-(2-methoxyethyl)-4-(3-(1-methyl-1H-pyrazol-4-yl)-1-(phenylsulfonyl)-1H-pyrrolo[2,3-b]pyridin-5-yl)-N-propylcyclohexanamine (IIb-122)

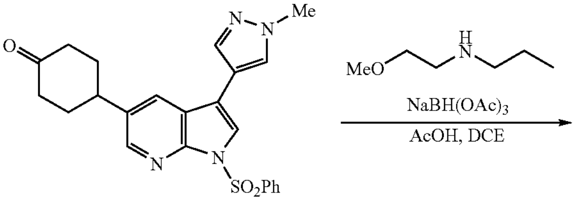

(IIb-20)

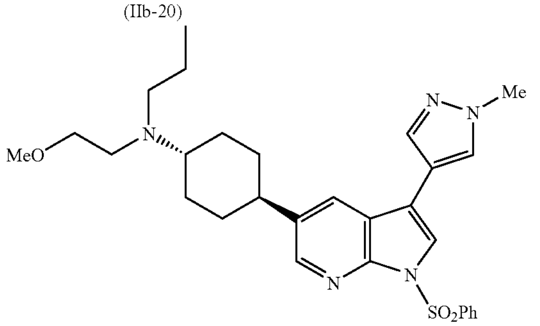

+

(IIb-121)

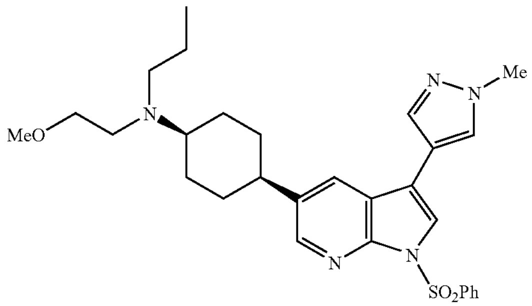

(IIb-122)

Ketone (IIb-20) (0.250 g, 0.58 mmol), N-(2-methoxyethyl) propan-1-amine (0.135 g, 1.15 mmol), AcOH (34.6 mg, 0.58 mmol) and $NaBH(OAc)_3$ (0.171 g, 0.81 mmol) in anhydrous 1,2-dichloroethane (3.0 mL) were reacted for 21 h following the general procedure B for the reductive amination. The crude product was purified by PTLC using $CHCl_3$:MeOH:$NH_4OH$=93:6:1 (v/v/v) as the eluent to give the trans isomer (IIb-121) (87.7 mg, 28%) and the cis isomer (IIb-122) (75.7 mg, 25%).

Data for trans isomer (IIb-121): $^1$H NMR (400 MHz, $CDCl_3$) δ 0.88 (t, J=7.1 Hz, 3H), 1.37-1.58 (m, 6H), 1.89-2.00 (m, 4H), 2.44-2.51 (m, 2H), 2.53-2.64 (m, 2H), 2.68 (t, J=6.6 Hz, 2H), 3.36 (s, 3H), 3.41 (t, J=6.7 Hz, 2H), 3.99 (s, 3H), 7.45-7.51 (m, 2H), 7.56 (tt, J=7.4, 1.5 Hz, 1H), 7.63 (s, 1H), 7.72 (s, 1H), 7.73-7.75 (m, 2H), 8.18-8.22 (m, 2H), 8.32 (d, J=2.0 Hz, 1H).

Data for cis isomer (IIb-122): $^1$H NMR (400 MHz, $CDCl_3$) δ 0.86 (t, J=7.1 Hz, 3H), 1.40-1.51 (m, 2H), 1.52-1.61 (m, 2H), 1.62-1.71 (m, 2H), 1.76-1.85 (m, 2H), 1.99-2.09 (m, 2H), 2.45-2.53 (m, 2H), 2.69 (t, J=7.0 Hz, 3H), 2.82-2.90 (m, 1H), 3.33 (s, 3H), 3.41 (t, J=7.0 Hz, 2H), 3.99 (s, 3H), 7.45-7.52 (m, 2H), 7.57 (t, J=7.5 Hz, 1H), 7.63 (s, 1H), 7.71-7.77 (m, 2H), 7.83 (d, J=2.0 Hz, 1H), 8.18-8.23 (m, 2H), 8.41 (d, J=2.0 Hz, 1H).

(1r,4r)-N-ethyl-N-(2-methoxyethyl)-4-(3-(1-methyl-1H-pyrazol-4-yl)-1-(phenylsulfonyl)-1H-pyrrolo[2,3-b]pyridin-5-yl)cyclohexanamine (IIb-123) and (1s,4s)-N-ethyl-N-(2-methoxyethyl)-4-(3-(1-methyl-1H-pyrazol-4-yl)-1-(phenylsulfonyl)-1H-pyrrolo[2,3-b]pyridin-5-yl)cyclohexanamine (IIb-124)

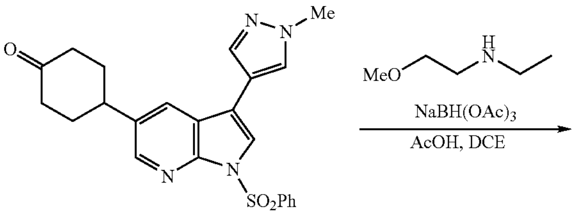

(IIb-20)

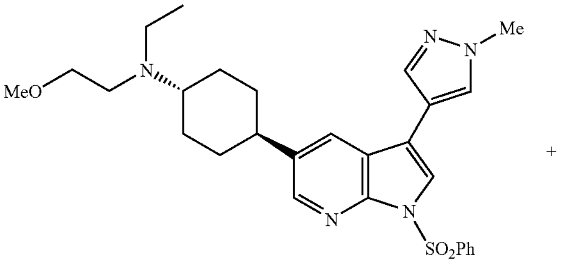

(IIb-123)

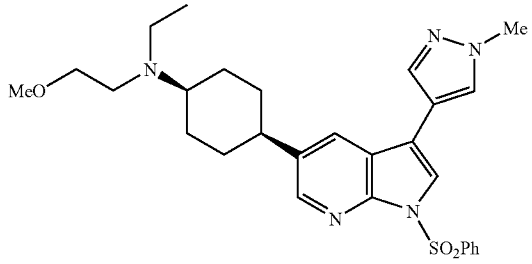

(IIb-124)

Ketone (IIb-20) (0.250 g, 0.58 mmol), N-ethyl-2-methoxyethanamine (0.119 g, 1.15 mmol), AcOH (34.6 mg, 0.58 mmol) and $NaBH(OAc)_3$ (0.171 g, 0.81 mmol) in anhydrous 1,2-dichloroethane (6.0 mL) were reacted for 18 h following the general procedure B for the reductive amination. The crude product was purified by PTLC using $CHCl_3$:MeOH:$NH_4OH$=93:6:1 (v/v/v) as the eluent to give the trans isomer (IIb-123) (42.6 mg, 14%) and the cis isomer (IIb-124) (44.1 mg, 15%).

Data for trans isomer (IIb-123): $^1H$ NMR (400 MHz, $CDCl_3$) δ 1.08 (t, J=6.7 Hz, 3H), 1.39-1.60 (m, 4H), 1.92-2.02 (m, 4H), 2.54-2.78 (m, 6H), 3.36 (s, 3H), 3.42-3.49 (m, 2H), 3.99 (s, 3H), 7.45-7.51 (m, 2H), 7.57 (tt, J=7.5, 1.5 Hz, 1H), 7.63 (s, 1H), 7.72 (s, 1H), 7.73-7.76 (m, 2H), 8.18-8.22 (m, 2H), 8.32 (d, J=2.0 Hz, 1H).

Data for cis isomer (IIb-124): $^1H$ NMR (400 MHz, $CDCl_3$) δ 0.98 (t, J=6.7 Hz, 3H), 1.51-1.73 (m, 4H), 1.75-1.90 (m, 2H), 1.97-2.11 (m, 2H), 2.61-2.76 (m, 5H), 2.81-2.89 (m, 1H), 3.33 (s, 3H), 3.38-3.46 (m, 2H), 3.99 (s, 3H), 7.45-7.52 (m, 2H), 7.57 (tt, J=7.4, 1.5 Hz, 1H), 7.64 (s, 1H), 7.72 (s, 1H), 7.76 (d, J=0.7 Hz, 1H), 7.83 (s, 1H), 8.18-8.22 (m, 2H), 8.41 (s, 1H).

2-(((1r,4r)-4-(3-(1-methyl-1H-pyrazol-4-yl)-1-(phenylsulfonyl)-1H-pyrrolo[2,3-b]pyridin-5-yl)cyclohexyl)(propyl)amino)ethanol (IIb-125) and 2-(((1s,4s)-4-(3-(1-methyl-1H-pyrazol-4-yl)-1-(phenylsulfonyl)-1H-pyrrolo[2,3-b]pyridin-5-yl)cyclohexyl)(propyl)amino)ethanol (IIb-126)

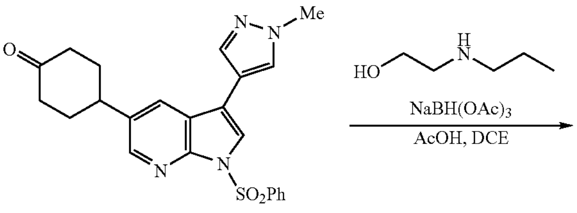

(IIb-20)

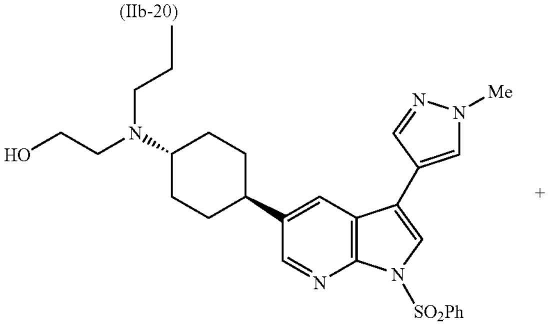

(IIb-125)

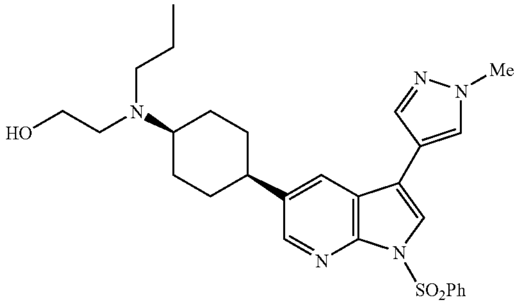

(IIb-126)

Ketone (IIb-20) (0.250 g, 0.58 mmol), 2-(propylamino)ethanol (0.119 g, 1.15 mmol), AcOH (34.6 mg, 0.58 mmol) and $NaBH(OAc)_3$ (0.171 g, 0.81 mmol) in anhydrous 1,2-dichloroethane (3.0 mL) were reacted for 21 h following the general procedure B for the reductive amination. The crude product was purified by PTLC using $CHCl_3$:MeOH:$NH_4OH$=93:6:1 (v/v/v) as the eluent to give the trans isomer (IIb-125) (67.2 mg, 23%) and the cis isomer (IIb-126) (69.9 mg, 23%).

Data for trans isomer (IIb-125): $^1H$ NMR (400 MHz, $CDCl_3$) δ 0.90 (t, J=7.3 Hz, 3H), 1.41-1.59 (m, 6H), 1.86-2.02 (m, 4H), 2.48 (t, J=7.3 Hz, 2H), 2.62-2.69 (m, 4H), 3.52 (t, J=5.2 Hz, 2H), 3.99 (s, 3H), 7.46-7.51 (m, 2H), 7.57 (tt, J=7.4, 1.5 Hz, 1H), 7.63 (s, 1H), 7.73 (s, 1H), 7.74-7.76 (m, 2H), 8.18-8.23 (m, 2H), 8.32 (d, J=2.0 Hz, 1H).

Data for cis isomer (IIb-126): $^1$H NMR (400 MHz, $CDCl_3$) δ 0.85 (t, J=7.2 Hz, 3H), 1.38-1.82 (m, 7H), 1.86-2.02 (m, 1H), 2.07-2.20 (m, 2H), 2.38-2.52 (m, 2H), 2.56-2.78 (m, 4H), 2.94-3.02 (m, 1H), 3.46-3.57 (m, 2H), 3.99 (s, 3H), 7.46-7.51 (m, 2H), 7.57 (tt, J=7.5, 1.5 Hz, 1H), 7.67 (s, 1H), 7.73-7.76 (m, 2H), 7.87 (s, 1H), 8.18-8.23 (m, 2H), 8.43 (d, J=1.7 Hz, 1H).

N-((1r,4r)-4-(3-(1-methyl-1H-pyrazol-4-yl)-1-(phenylsulfonyl)-1H-pyrrolo[2,3-b]pyridin-5-yl)cyclohexyl)tetrahydro-2H-pyran-4-amine (IIb-127) and N-((1s,4s)-4-(3-(1-methyl-1H-pyrazol-4-yl)-1-(phenylsulfonyl)-1H-pyrrolo[2,3-b]pyridin-5-yl)cyclohexyl)tetrahydro-2H-pyran-4-amine (IIb-128)

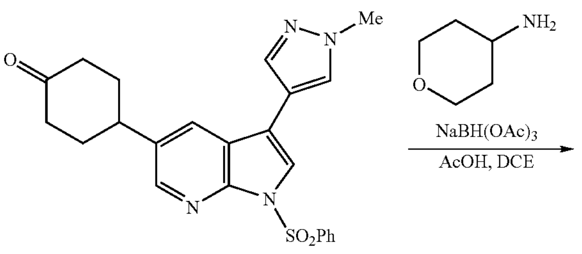

(IIb-20)

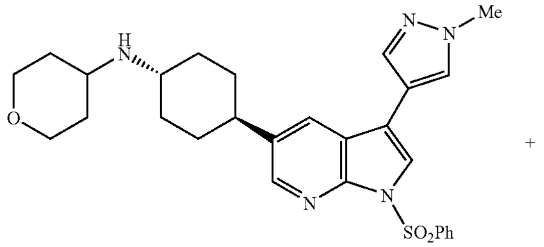

(IIb-127)

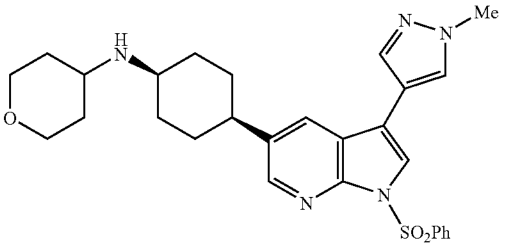

(IIb-128)

Ketone (IIb-20) (0.250 g, 0.58 mmol), tetrahydro-2H-pyran-4-amine (0.116 g, 1.15 mmol), AcOH (34.6 mg, 0.58 mmol) and $NaBH(OAc)_3$ (0.171 g, 0.81 mmol) in anhydrous 1,2-dichloroethane (3.0 mL) were reacted for 18 h following the general procedure B for the reductive amination. The crude product was purified by PTLC using $CHCl_3$:MeOH:$NH_4OH$=93:6:1 (v/v/v) as the eluent to give the trans isomer (IIb-127) (45.7 mg, 15%) and the cis isomer (IIb-128) (73.5 mg, 25%).

Data for trans isomer (IIb-127): $^1$H NMR (400 MHz, $CDCl_3$) δ 1.26-1.36 (m, 2H), 1.37-1.48 (m, 2H), 1.49-1.62 (m, 3H), 1.83-1.98 (m, 4H), 2.02-2.11 (m, 2H), 2.59-2.68 (m, 1H), 2.71-2.81 (m, 1H), 2.83-2.93 (m, 1H), 3.35-3.46 (m, 2H), 3.94-4.03 (m, 2H), 3.99 (s, 3H), 7.45-7.51 (m, 2H), 7.57 (tt, J=7.5, 1.5 Hz, 1H), 7.62 (s, 1H), 7.72 (s, 1H), 7.74-7.76 (m, 2H), 8.18-8.23 (m, 2H), 8.33 (d, J=2.0 Hz, 1H).

Data for cis isomer (IIb-128): $^1$H NMR (400 MHz, $CDCl_3$) δ 1.35-1.48 (m, 3H), 1.60-1.71 (m, 4H), 1.74-1.94 (m, 6H), 2.65-2.79 (m, 2H), 3.11 (s, 1H), 3.35-3.44 (m, 2H), 3.93-3.98 (m, 2H), 3.99 (s, 3H), 7.45-7.52 (m, 2H), 7.57 (tt, J=7.4, 1.5 Hz, 1H), 7.67 (s, 1H), 7.72 (s, 1H), 7.76 (d, J=0.6 Hz, 1H), 7.82 (s, 1H), 8.18-8.23 (m, 2H), 8.36 (d, J=2.0 Hz, 1H).

2-((1r,4r)-4-(3-(1-methyl-1H-pyrazol-4-yl)-1-(phenylsulfonyl)-1H-pyrrolo[2,3-b]pyridin-5-yl)cyclohexylamino)ethanol (IIb-129) and 2-((1s,4s)-4-(3-(1-methyl-1H-pyrazol-4-yl)-1-(phenylsulfonyl)-1H-pyrrolo[2,3-b]pyridin-5-yl)cyclohexylamino)ethanol (IIb-130)

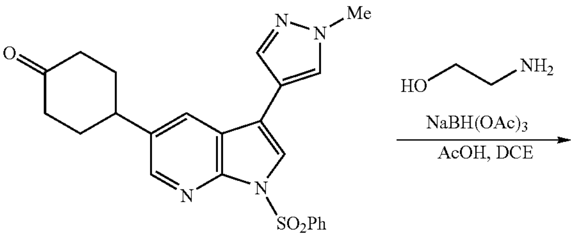

(IIb-20)

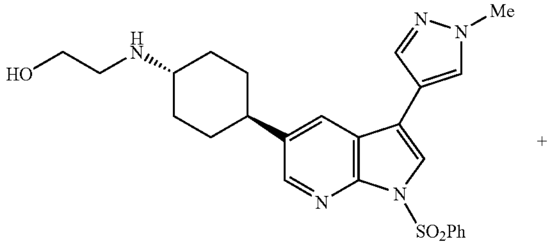

(IIb-129)

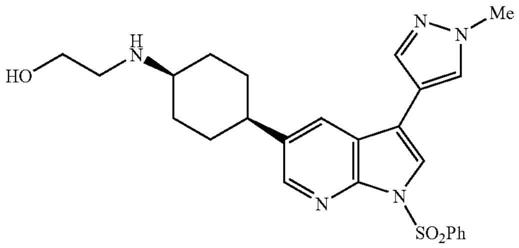

(IIb-130)

Ketone (IIb-20) (0.250 g, 0.58 mmol), 2-aminoethanol (0.16 g, 2.88 mmol), AcOH (34.6 mg, 0.58 mmol) and $NaBH(OAc)_3$ (0.171 g, 0.81 mmol) in anhydrous 1,2-dichloroethane (3.0 mL) were reacted for 18 h following the general procedure B for the reductive amination. The crude product was purified by PTLC using $CHCl_3$:MeOH:$NH_4OH$=93:6:1 (v/v/v) as the eluent to give the trans isomer (IIb-129) (31.6 mg, 12%) and the cis isomer (IIb-130) (39.7 mg, 14%).

Data for trans isomer (IIb-129): $^1$H NMR (400 MHz, $CDCl_3$) δ 1.20-1.37 (m, 2H), 1.48-1.62 (m, 2H), 1.89-2.00 (m, 2H), 2.08-2.17 (m, 2H), 2.20-2.42 (m, 2H), 2.55-2.72 (m, 2H), 2.87 (t, J=5.1 Hz, 2H), 3.69 (t, J=5.1 Hz, 2H), 3.99 (s, 3H), 7.46-7.51 (m, 2H), 7.57 (tt, J=7.5, 1.5 Hz, 1H), 7.63 (s, 1H), 7.73 (s, 1H), 7.74-7.76 (m, 2H), 8.18-8.23 (m, 2H), 8.33 (d, J=2.0 Hz, 1H).

Data for cis isomer (IIb-130): $^1$H NMR (400 MHz, $CDCl_3$) δ 1.62-1.73 (m, 4H), 1.78-1.92 (m, 4H), 2.09-2.32 (m, 2H), 2.65-2.74 (m, 1H), 2.80 (t, J=5.1 Hz, 2H), 2.93-2.99 (m, 1H), 3.68 (t, J=5.1 Hz, 2H), 3.99 (s, 3H), 7.45-7.51 (m, 2H), 7.57 (tt, J=7.4, 1.5 Hz, 1H), 7.68 (s, 1H), 7.72 (s, 1H), 7.75 (d, J=0.6 Hz, 1H), 7.81 (d, J=2.1 Hz, 1H), 8.19-8.22 (m, 2H), 8.35 (d, J=2.1 Hz, 1H).

2-(ethyl(4-(3-(1-methyl-1H-pyrazol-4-yl)-1-(phenylsulfonyl)-1H-pyrrolo[2,3-b]pyridin-5-yl)cyclohexyl)amino)ethanol (IIb-131)

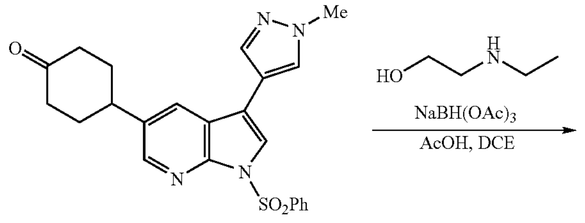

(IIb-20)

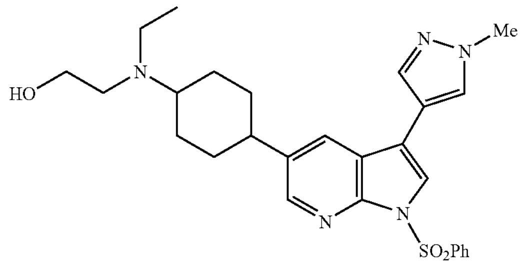

(IIb-131)

Ketone (IIb-20) (0.250 g, 0.58 mmol), 2-(ethylamino)ethanol (0.103 g, 1.16 mmol), AcOH (34.6 mg, 0.58 mmol) and $NaBH(OAc)_3$ (0.171 g, 0.81 mmol) in anhydrous 1,2-dichloroethane (3.0 mL) were reacted for 18 h following the general procedure B for the reductive amination. The crude product was purified by PTLC using $CHCl_3$:MeOH:$NH_4OH$=93:6:1 (v/v/v) as the eluent to give (IIb-131) (101.8 mg, 35%) as a mixture of isomers. Selected resonances from $^1H$ NMR (400 MHz, $CDCl_3$) δ 1.09 (t, J=7.1 Hz, $CH_2CH_3$, minor), 1.20 (t, J=7.1 Hz, $CH_2CH_3$, major), 3.37 (q, J=7.2 Hz, $CH_2CH_3$, major), 3.43 (q, J=7.2 Hz, $CH_2CH_3$, minor), 3.99 (s, 3H; major), 4.00 (s, 3H; minor).

N-isopropyl-4-(3-(1-methyl-1H-pyrazol-4-yl)-1-(phenylsulfonyl)-1H-pyrrolo[2,3-b]pyridin-5-yl)cyclohexanamine (IIb-132)

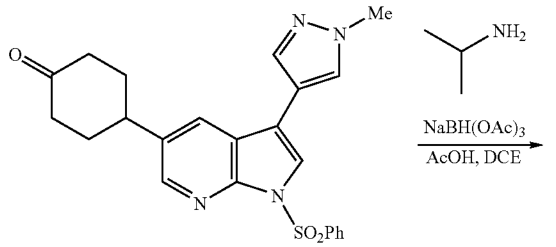

(IIb-20)

-continued

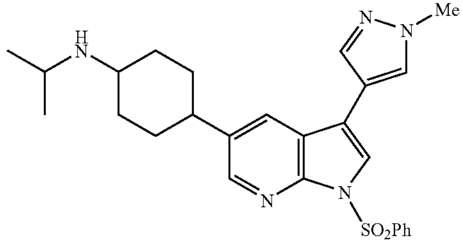

(IIb-132)

Ketone (IIb-20) (0.250 g, 0.58 mmol), isopropylamine (0.414 g, 7.0 mmol), AcOH (71.6 mg, 1.20 mmol) and $NaBH(OAc)_3$ (0.353 g, 1.67 mmol) in anhydrous 1,2-dichloroethane (5.0 mL) were reacted for 19.5 h following the general procedure B for the reductive amination. The crude product after workup was purified by LCMS (column LUNA 10μ C18(2) 00G-4253-V0 250×50 mm) using water—MeCN (0.1% AcOH) as eluent (in gradient; flow 80 mL/min) to afford PTLC using $CHCl_3$:MeOH:$NH_4OH$=93:6:1 (v/v/v) as the eluent to give (IIb-132) (391.9 mg, 69%) as an oil; mixture of isomers. Selected resonances from $^1H$ NMR (400 MHz, $CDCl_3$) δ 1.29 (d, J=6.2 Hz, $(CH_3)_2C$, minor), 1.30 (d, J=6.2 Hz, $(CH_3)_2C$, major), 3.99 (s, 3H; minor), 4.00 (s, 3H; major).

N-ethyl-N-isopropyl-4-(3-(1-methyl-1H-pyrazol-4-yl)-1-yl)-1H-pyrrolo[2,3-b]pyridin-5-yl)cyclohexanamine (IIb-133)

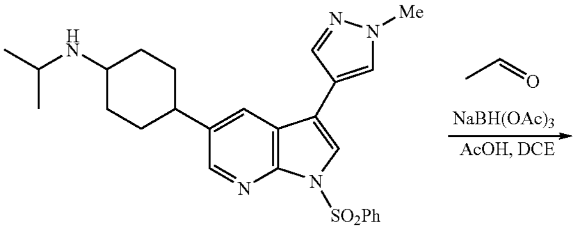

(IIb-132)

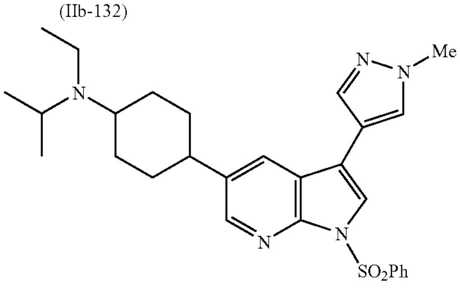

(IIb-133)

Amine (IIb-132) (0.100 g, 0.21 mmol), acetaldehyde (0.50 mL, 8.91 mmol), AcOH (12.5 mg, 0.21 mmol) and $NaBH(OAc)_3$ (0.067 g, 0.31 mmol) in anhydrous 1,2-dichloroethane (1.5 mL) were reacted for 17 h following the general procedure B for the reductive amination. The reaction mixture was treated with 10% aqueous NaOH solution (7 mL) and stirred for 15 min. The mixture was extracted with EtOAc (3×20 mL). The combined extracts were dried ($MgSO_4$), concentrated and purified by PTLC using $CHCl_3$:MeOH:$NH_4OH$=93:6:1 (v/v/v) as the eluent to give (IIb-133) (50.7 mg, 48%). Selected resonances from $^1$H NMR (400 MHz, $CDCl_3$) δ 1.03 (d, J=6.3 Hz, $(CH_3)_2C$, minor), 1.07 (d, J=6.3 Hz, $(CH_3)_2C$, major), 3.92 (s, 3H; minor), 3.93 (s, 3H; major).

4-(4-(3-(1-methyl-1H-pyrazol-4-yl)-1-(phenylsulfonyl)-1H-pyrrolo[2,3-b]pyridin-5-yl)cyclohex-3-enyl)-1,4-oxazepane (IIa-134)

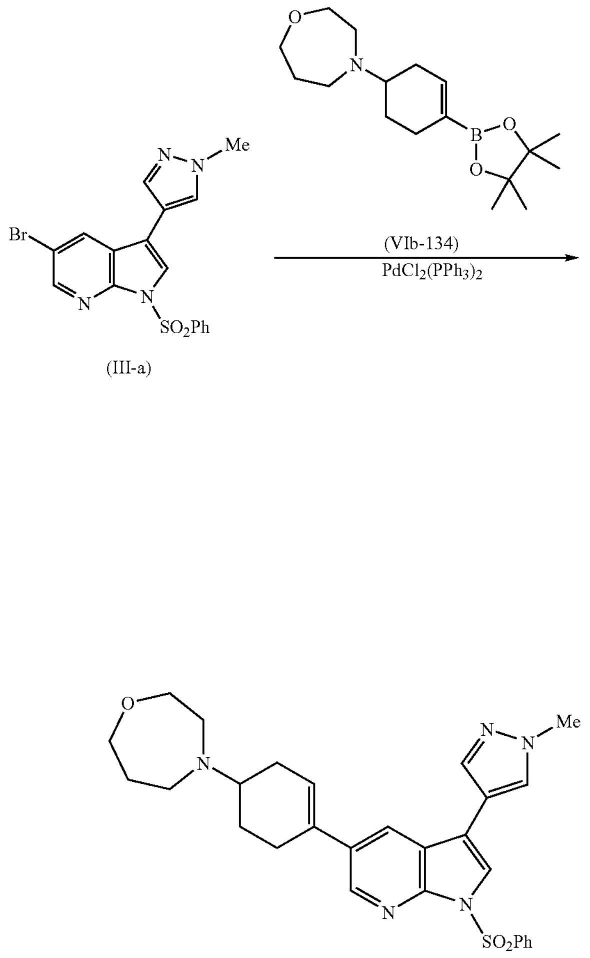

(III-a)

(IIa-134)

Compound (III-a) (8.66 g, 20.77 mmol), boronic ester (VIb-134) (6.38 g, 20.77 mmol), LiCl (2.20 g, 51.91 mmol), $Pd(PPh_3)_2Cl_2$ (1.17 g, 1.66 mmol) and 1.0 M $Na_2CO_3$ solution (25 ml, 25 mmol) in EtOH (30 mL), toluene (30 mL) were reacted for 3 h following the general procedure A for the Suzuki reaction. The crude product (14.30 g, dark brown oil) was purified by SGC using $CH_2Cl_2$:MeOH as eluent (gradient from 100:0 to 95:5; v/v) to afford a foam (6.72 g, estimated purity 95%). The product was further purified by trituration with $Et_2O$ (50 mL) to afford (IIa-134) as an off-white powder (6.04 g, 11.67 mmol, 56%). $^1$H NMR (400 MHz, $CDCl_3$) δ 1.61-1.75 (m, 1H), 1.87-1.96 (m, 2H), 2.06-2.15 (m, 1H), 2.19-2.31 (m, 1H), 2.38-2.50 (m, 1H), 2.55-2.64 (m, 2H), 2.80-3.00 (m, 5H), 3.77 (t, J=4.5 Hz, 2H), 3.85 (t, J=6.0 Hz, 2H), 4.02 (s, 3H), 6.06-6.10 (m, 1H), 7.50 (t, J=7.7 Hz, 2H), 7.59 (tt, J=1.4, 7.3 Hz, 1H), 7.65 (s, 1H), 7.75 (s, 1H), 7.78 (s, 1H), 7.88 (d, J=2.1 Hz, 1H), 8.22 (d, J=7.7 Hz, 2H), 8.51 (d, J=2.1 Hz, 1H).

1-Benzenesulfonyl-5-[4-(4-methyl-piperazin-1-yl)-cyclohex-1-enyl]-3-(1-methyl-1H-pyrazol-4-yl)-1H-pyrrolo[2,3-b]pyridine (IIa-135)

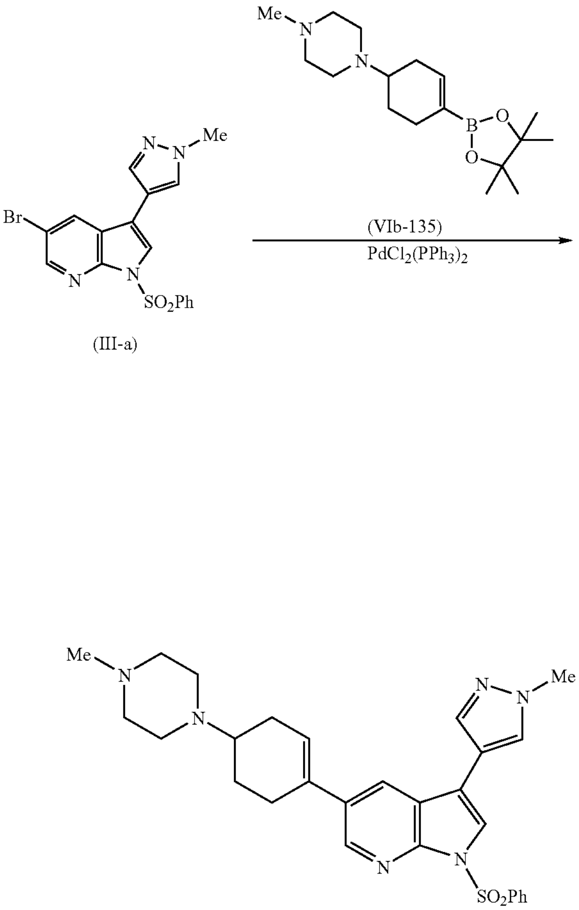

(III-a)

(IIa-135)

Compound (III-a) (10.79 g, 25.85 mmol), boronic ester (VIb-135) (9.50 g, 31.02 mmol), LiCl (2.74 g, 64.62 mmol), $Pd(PPh_3)_2Cl_2$ (1.45 g, 2.07 mmol) and 1.0 M $Na_2CO_3$ solution (40 ml, 40 mmol) in EtOH (80 mL), toluene (80 mL) were reacted for 1 h following the general procedure A for the Suzuki reaction. The crude product (20.21 g, dark brown oil) was purified by trituration with $Et_2O$ (100 mL) to afford a pale brown powder (13.72 g, estimated purity 90%). The product was further purified by SGC on amino silica (Chromatorex NH, Fuji Silysia) using $CH_2Cl_2$:hexane=1:1 (v/v) followed by $CH_2Cl_2$ and then $CH_2Cl_2$:EtOAc=1:1 (v/v) as eluent to afford (IIa-135) (11.60 g, 22.45 g, 87%) as an off-white powder. $^1$H NMR (400 MHz, $CDCl_3$) δ 1.59-1.70 (m, 1H), 2.15-2.31 (m, 2H), 2.33 (s, 3H), 2.41-2.83 (m, 12H), 4.01 (s, 3H), 6.06-6.11 (m, 1H), 7.50 (t, J=7.7 Hz, 2H), 7.59 (tt, J=1.4, 7.5 Hz, 1H), 7.65 (s, 1H), 7.75 (s, 1H), 7.77 (s, 1H), 7.88 (d, J=2.1 Hz, 1H), 8.22 (d, J=7.3 Hz, 2H), 8.52 (d, J=2.1 Hz, 1H).

5-(bicyclo[2.2.1]hept-2-en-2-yl)-3-(1-methyl-1H-pyrazol-4-yl)-1-(phenylsulfonyl)-1H-pyrrolo[2,3-b]pyridine (IIa-136)

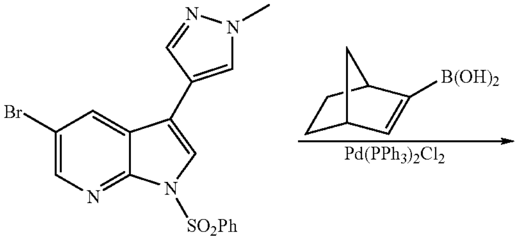

(III-a)

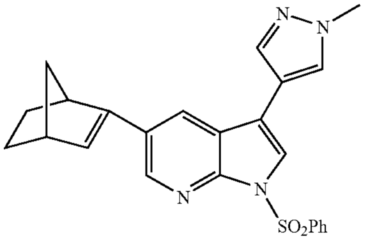

(IIa-136)

Bromide (III-a) (2.23 g, 5.37 mmol), bicyclo[2.2.1]hept-2-en-2-ylboronic acid (0.89 g, 6.45 mmol), lithium chloride (0.68 g, 16.11 mmol), and $Pd(PPh_3)_2Cl_2$ (0.38 g, 0.54 mmol), in EtOH (13.4 mL), toluene (13.4 mL) and 1.0 M $Na_2CO_3$ solution (13.4 mL) were reacted for 4 h following the general procedure A for the Suzuki reaction. The crude product was purified by SGC using EtOAc:hexane (gradient elution from 0:100 to 100:0, v/v) as the eluent to give the product (IIa-136) (1.79 g, 77%) as a white solid. $^1H$ NMR (400 MHz, $CDCl_3$) δ 1.08-1.19 (m, 2H), 1.27-1.31 (m, 1H), 1.53-1.58 (m, 1H), 1.76-1.86 (m, 2H), 3.02-3.05 (m, 1H), 3.34 (br s, 1H), 4.00 (s, 3H), 6.37 (d, J=3.1 Hz, 1H), 7.46-7.51 (m, 2H), 7.54-7.59 (m, 1H), 7.64 (s, 1H), 7.72 (s, 1H), 7.77 (d, J=0.6 Hz, 1H), 7.88 (d, J=2.0 Hz, 1H), 8.18-8.21 (m, 2H), 8.55 (d, J=2.0 Hz, 1H).

5-(bicyclo[2.2.1]heptan-2-yl)-3-(1-methyl-1H-pyrazol-4-yl)-1-(phenylsulfonyl)-1H-pyrrolo[2,3-b]pyridine (IIb-137)

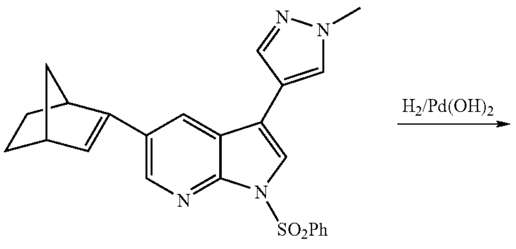

(IIa-136)

-continued

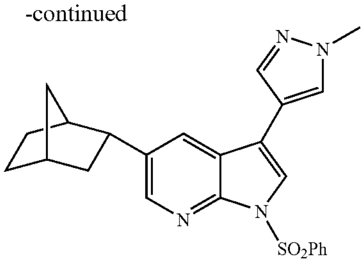

(IIb-137)

Compound (IIa-136) (0.55 g, 1.27 mmol) was hydrogenated using the general procedure for hydrogenation of 7-azaindoles using 20% $Pd(OH)_2/C$ (Degussa type, 0.45 g) in MeOH (25 mL)—EtOAc (25 mL) over a period of 20 h. The reaction mixture was then filtered through Celite and was washed copious amount of $CH_2Cl_2$:MeOH (1:1) (v/v). The solvent was removed to give the crude product (IIb-137) (0.46 g, 84%) as a white solid. $^1H$ NMR (400 MHz, $CDCl_3$) δ 1.20-1.28 (m, 2H), 1.41-1.51 (m, 2H), 1.55-1.66 (m, 3H), 2.02-2.12 (m, 1H), 2.38 (t, J=4.3 Hz, 1H), 2.45 (t, J=3.8 Hz, 1H), 3.28-3.35 (m, 1H), 4.00 (s, 3H), 7.47-7.52 (m, 2H), 7.55-7.60 (m, 1H), 7.63 (s, 1H), 7.73 (s, 1H), 7.77 (m, 2H), 8.18-8.20-8.23 (m, 2H), 8.36 (d, J=2.0 Hz, 1H).

3-(1-methyl-1H-pyrazol-4-yl)-1-(phenylsulfonyl)-5-((1R)-1,7,7-trimethylbicyclo[2.2.1]hept-2-en-2-yl)-1H-pyrrolo[2,3-b]pyridine (IIa-138)

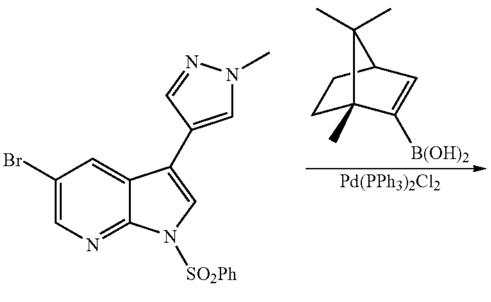

(III-a)

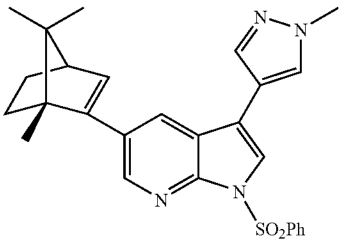

(IIa-138)

Bromide (III-a) (100 mg, 0.24 mmol), (1S)-1,7,7-trimethylbicyclo[2.2.1]hept-2-en-2-ylboronic acid (65 mg, 0.36 mmol), lithium chloride (30.5 mg, 0.72 mmol), and $Pd(PPh_3)_2 Cl_2$ (17 mg, 0.024 mmol), in EtOH (1.20 mL), toluene (1.20 mL) and 1.0 M $Na_2CO_3$ solution (0.60 mL)

were reacted for 4 h following the general procedure A for the Suzuki reaction. The crude product was purified by PTLC using EtOAc:hexane=2:1 (v/v) as eluent to give (IIa-138) (84 mg, 74%) as a white solid. $^1$H NMR (400 MHz, $CDCl_3$) δ 0.83 (s, 3H), 0.89 (s, 3H), 1.08 (s, 3H), 1.05-1.13 (m, 1H), 1.27-1.31 (m, 1H), 1.66-1.73 (m, 1H), 1.92-2.00 (m, 1H), 2.42 (t, J=3.5 Hz, 1H), 3.99 (s, 3H), 6.05 (d, J=3.3 Hz, 1H), 7.46-7.51 (m, 2H), 7.54-7.59 (m, 1H), 7.63 (s, 1H), 7.73 (s, 1H), 7.76 (d, J=0.6 Hz, 1H), 7.77 (d, J=2.0 Hz, 1H), 8.19-8.22 (m, 2H), 8.37 (d, J=2.0 Hz, 1H).

3-(1-methyl-1H-pyrazol-4-yl)-1-(phenylsulfonyl)-5-((1S)-1,7,7-trimethylbicyclo[2.2.1]heptan-2-yl)-1H-pyrrolo[2,3-b]pyridine (IIb-139)

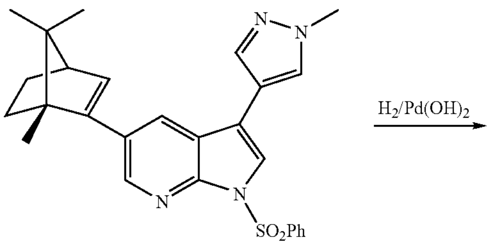

(IIa-138)

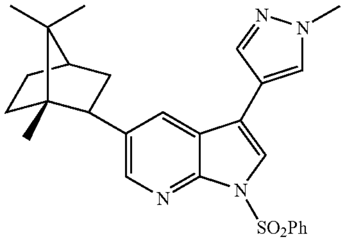

(IIb-139)

Compound (IIa-138) (47 mg, 0.099 mmol) was hydrogenated using the general procedure for hydrogenation of 7-azaindoles using 20% $Pd(OH)_2/C$ (Degussa type, 37 mg) in EtOAc (10 mL) over a period of 20 h. The reaction mixture was then filtered through Celite and was washed with copious amount of $CH_2Cl_2$:MeOH (1:1) (v/v). The solvent was removed to give the crude product as a 1.25:1 mixture of diastereoisomers (45 mg, 96%). $^1$H NMR (400 MHz, $CDCl_3$) δ 0.72 (s, 3H, minor), 0.77 (s, 3H, minor), 0.81 (s, 3H, major), 0.85 (s, 3H, major), 0.95 (s, 3H, minor), 1.05 (s, 3H, major), 1.29-1.43 (m, 5H), 1.48-1.54 (dd, J=5.4 and 13.2 Hz, 1H, minor), 1.65-1.73 (m, 2H), 1.79-1.91 (m, 4H), 2.19-2.36 (m, 2H), 2.99 (t, J=8.6 Hz, 1H, major), 3.13-3.19 (dd, J=2.1 and 5.4 Hz, 1H, minor), 4.00 (2×s, 2×3H), 7.45-7.52 (m, 4H), 7.54-7.59 (m, 2H), 7.60 (s, 1H, major), 7.63 (s, 1H, minor), 7.72 (s, 1H, major), 7.73 (s, 1H, minor), 7.74 (s, 1H, major), 7.76 (s, 1H, minor), 7.77 (d, J=2.2 Hz, 1H, minor), 7.85 (d, J=1.7 Hz, 1H, major), 8.18-8.23 (m, 4H), 8.32 (d, J=2.0 Hz, 1H, minor), 8.38 (d, J=1.7 Hz, 1H, major).

(5-(3-(1-methyl-1H-pyrazol-4-yl)-1-(phenylsulfonyl)-1H-pyrrolo[2,3-b]pyridin-5-yl)bicyclo[2.2.1]heptane-2,3-diyl)dimethanol (IIb-140)

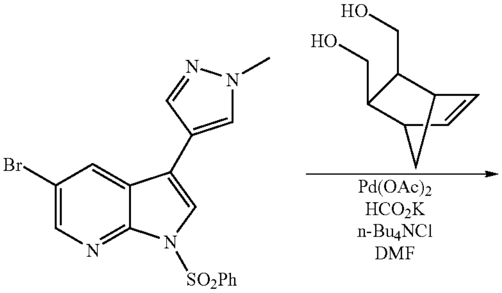

(III-a)

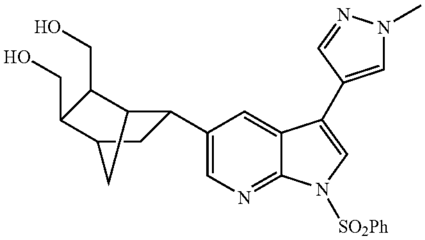

(IIb-140)

Bromide (III-a) (100 mg, 0.24 mmol), 5-norbornene-2-endo-3-endo dimethanol (148 mg, 0.96 mmol), palladium acetate (5.4 mg, 0.024 mmol), n-$Bu_4NCl$ (6.7 mg, 0.024 mmol) and $HCO_2K$ (17 mg, 0.024 mmol), in anhydrous DMF (2.40 mL) were heated to 100° C. in a sealed tube overnight. The reaction mixture was allowed to cool to RT. A saturated solution of $NaHCO_3$ (10 mL) was added and the reaction was extracted with EtOAc (3×20 mL). The combined organic extracts were dried over $MgSO_4$ and concentrated. The crude product purified by prep LCMS (column LUNA 10μ C18(2) 00G-4253-V0 250×50 mm) using water—MeCN (0.1% AcOH) as eluent (in gradient; flow 80 mL/min) to give (IIb-140) (31 mg, 30%; retention time 16.4-17 min) as a white solid. $^1$H NMR (400 MHz, $CDCl_3$) δ 1.46-1.57 (m, 2H), 1.64 (dt, J=1.6 and 10.1 Hz, 1H), 1.96-2.04 (m, 1H), 2.30-2.42 (m, 2H), 2.45-2.50 (m, 2H), 3.00-3.05 (dd, J=6.1 and 8.2 Hz, 1H), 3.73-3.83 (m, 2H), 4.00 (s, 3H), 4.02 (t, J=10.4 Hz, 1H), 4.18 (t, J=10.4 Hz, 1H), 7.46-7.51 (m, 2H), 7.55-7.60 (m, 1H), 7.62 (s, 1H), 7.72 (d, J=2.0 Hz, 1H), 7.73 (s, 1H), 7.75 (d, J=0.5 Hz, 1H), 8.19-8.21 (m, 2H), 8.31 (d, J=2.1 Hz, 1H), MS (CI) m/z 493.2 ($MH^+$).

5-(7,7-dimethylbicyclo[4.1.0]hept-2-en-2-yl)-3-(1-methyl-1H-pyrazol-4-yl)-1-(phenylsulfonyl)-1H-pyrrolo[2,3-b]pyridine (IIa-141)

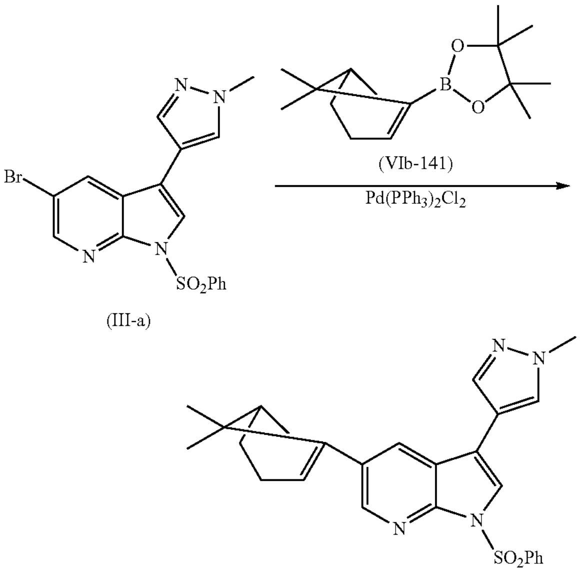

(III-a) (VIb-141) (IIa-141)

Bromide (III-a) (0.30 g, 0.72 mmol), 2-(7,7-dimethylbicyclo[4.1.0]hept-2-en-2-yl)-4,4,5,5-tetramethyl-1,3,2-dioxaborolane (VIb-141) (0.27 g, 1.08 mmol), lithium chloride (0.092 g, 2.16 mmol), and $Pd(PPh_3)_2Cl_2$ (50 mg, 0.072 mmol), in EtOH (1.80 mL), toluene (1.80 mL) and 1.0 M $Na_2CO_3$ solution (1.80 mL) were reacted for 16 h following the general procedure A for the Suzuki reaction. The crude product was purified by SGC using EtOAc:hexane (gradient elution from 0:100 to 100:0, v/v) to give (IIa-141) (0.21 g, 63%) as a white solid. $^1$H NMR (400 MHz, $CDCl_3$) δ 0.90 (s, 3H), 1.33 (d, J=8.5 Hz, 1H), 1.38 (s, 3H), 2.18-2.24 (m, 1H), 2.43 (t, J=3.0 Hz, 1H), 2.47 (t, J=3.0 Hz, 1H), 2.50-2.56 (m, 1H), 2.66 (td, J=1.6 and 5.6 Hz, 1H), 4.00 (s, 3H), 5.88-5.91 (m, 1H), 7.46-7.53 (m, 2H), 7.55-7.59 (m, 1H), 7.64 (s, 1H), 7.73 (s, 1H), 7.76 (d, J=0.5 Hz, 1H), 7.79 (d, J=2.1 Hz, 1H), 8.19-8.22 (m, 2H), 8.44 (d, J=2.1 Hz, 1H).

5-(7,7-dimethylbicyclo[4.1.0]heptan-2-yl)-3-(1-methyl-1H-pyrazol-4-yl)-1-(phenylsulfonyl)-1H-pyrrolo[2,3-b]pyridine (IIb-142)

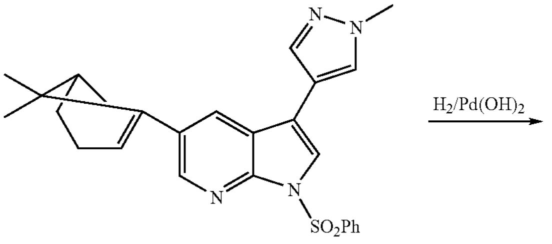

(IIa-141)

-continued

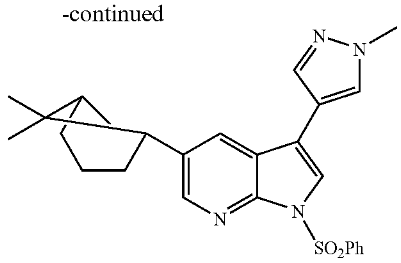

(IIb-142)

Compound (IIa-141) (0.21 g, 0.46 mmol) was hydrogenated using the general procedure for hydrogenation of 7-azaindoles using 20% $Pd(OH)_2/C$ (Degussa type, 0.16 g) in MeOH (22.5 mL)—EtOAc (22.5 mL) overnight. The reaction mixture was then filtered through Celite and was washed copious amount of EtOAc:MeOH (1:1). The solvent was removed to give the crude product (IIb-142) (0.18 g, 87%) as a white solid. $^1$H NMR (400 MHz, $CDCl_3$) δ 0.85 (s, 3H), 1.14 (d, J=9.2 Hz, 1H), 1.32 (s, 3H), 1.93-2.05 (m, 4H), 2.39-2.60 (m, 3H), 3.49-3.55 (dd, J=5.8 and 10.5 Hz, 1H), 4.00 (s, 3H), 7.45-7.50 (m, 2H), 7.54-7.59 (m, 1H), 7.62 (s, 1H), 7.72 (s, 1H), 7.75 (s, 1H), 7.78 (dd, J=1.0 and 2.1 Hz, 1H), 8.18-8.21 (m, 2H), 8.37 (d, J=2.1 Hz, 1H).

3-(1-methyl-1H-pyrazol-4-yl)-5-(8-methyl-8-azabicyclo[3.2.1]oct-3-en-3-yl)-1-((2-(trimethylsilyl)ethoxy)methyl)-1H-pyrrolo[2,3-b]pyridine (IIa-143)

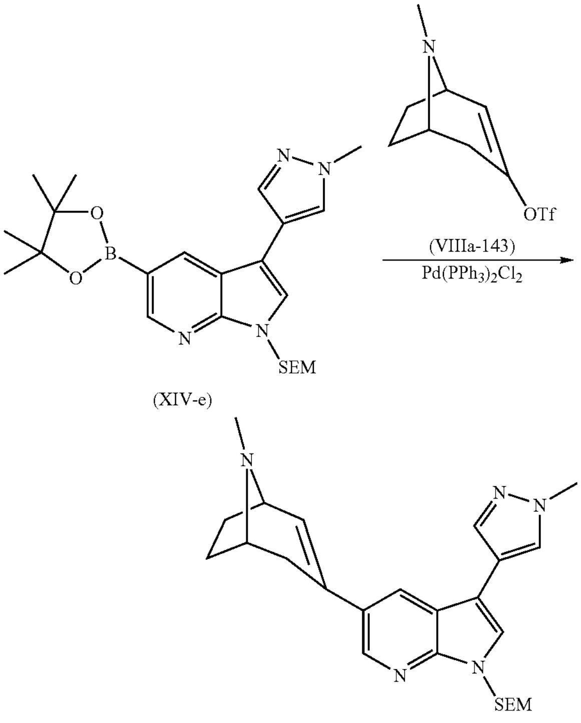

(XIV-e) (VIIIa-143) (IIa-143)

Compound (XIV-e) (200 mg, 0.44 mmol), enol triflate (VIIIa-143) (358 mg, 1.32 mmol; crude), lithium chloride (56 mg, 1.32 mmol), and $Pd(PPh_3)_2Cl_2$ (31 mg, 0.044 mmol), in EtOH (1.1 mL), toluene (1.10 mL) and 1.0 M $Na_2CO_3$ solution (1.10 mL) were reacted for 16 h following a modified general procedure A for the Suzuki reaction. The reaction was allowed to cool to RT. Water (50 mL) was added and the mixture was extracted with EtOAc (4×50 mL). The combined organic extracts were dried ($MgSO_4$) and concentrated. The crude product was purified by prep LCMS (column LUNA 10μ C18(2) 00G-4253-V0 250×50 mm) using water—MeCN (0.1% AcOH) as eluent (in gradient; flow 80 mL/min) to give (IIa-143) (53 mg, 27%) as a brown oil. $^1$H NMR (400 MHz, $CDCl_3$) δ −0.05 (s, 9H), 0.93 (dd, J=7.8 and 8.2 Hz, 2H), 1.81-1.90 (m 1H), 2.15 (dt, J=2.5 and 10.6 Hz, 1H), 2.32-2.41 (m, 1H), 2.69 (s, 3H), 2.45 (d, J=18 Hz, 2H), 3.08-3.18 (m, 1H), 3.56 (dd, J=7.8 and 8.2 Hz, 2H), 3.92 (t, J=5.7 Hz, 1H), 3.97 (t, J=5.7 Hz, 1H), 4.02 (s, 3H), 5.68 (s, 2H), 6.28 (td, J=1.3 and 5.7 Hz, 1H), 7.42 (s, 1H), 7.64 (s, 1H), 7.75 (d, J=0.5 Hz, 1H), 7.96 (d, J=2.1 Hz, 1H), 8.42 (d, J=2.1 Hz, 1H); MS (CI) m/z 451.3 ($MH^+$).

3-(1-methyl-1H-pyrazol-4-yl)-5-(spiro[bicyclo[3.3.1]non[6]ene-3,2'-[1,3]dioxolane]-7-yl)-1-((2-(trimethylsilyl)ethoxy)methyl)-1H-pyrrolo[2,3-b]pyridine (IIa-144)

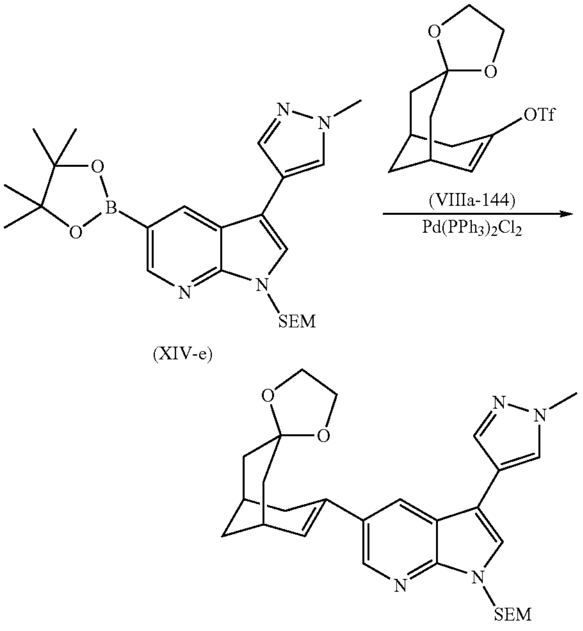

(XIV-e)

(IIa-144)

Boronate (XIV-e) (1.58 g, 3.49 mmol), enol triflate (VIIIa-144) (1.49 g, 4.54 mmol), lithium chloride (0.44 g, 10.47 mmol), and $Pd(PPh_3)_2Cl_2$ (0.24 g, 0.35 mmol), in EtOH (8.70 mL), toluene (8.70 mL) and 1.0 M $Na_2CO_3$ solution (8.70 mL) were reacted for 12 h following a modified general procedure A for the Suzuki reaction. The reaction was allowed to cool to room temperature. Water (50 mL) was added and was extracted with EtOAc (4×50 mL). The combined organic extracts were dried over $MgSO_4$ and concentrated. The crude product purified by SCG using EtOAc: hexane as eluent (gradient elution from 0:100 to 100:0, v/v) to give (IIa-144) (0.59 g, 33%) as yellow oil. $^1$H NMR (400 MHz, $CDCl_3$) δ −0.04 (s, 9H), 0.92 (t, J=8.2 Hz, 2H), 1.72 (dt, J=12.2 and 2.6 Hz, 1H), 1.81-1.96 (m, 6H), 2.43-2.52 (m, 2H), 2.65-2.71 (m, 1H), 2.72-2.80 (dd, J=7.4 and 17.6 Hz, 1H), 3.56 (t, J=8.2 Hz, 2H), 3.75-3.87 (m, 2H), 3.88-3.93 (m, 2H), 4.00 (s, 3H), 5.68 (s, 2H), 6.10 (d, J=6.2 Hz, 1H), 7.38 (s, 1H), 7.63 (s, 1H), 7.78 (d, J=0.5 Hz, 1H), 7.97 (d, J=2.0 Hz, 1H), 8.42 (d, J=2.0 Hz, 1H).

7-(3-(1-methyl-1H-pyrazol-4-yl)-1-(phenylsulfonyl)-1H-pyrrolo[2,3-b]pyridin-5-yl)bicyclo[3.3.1]non-6-en-3-one (IIa-145)

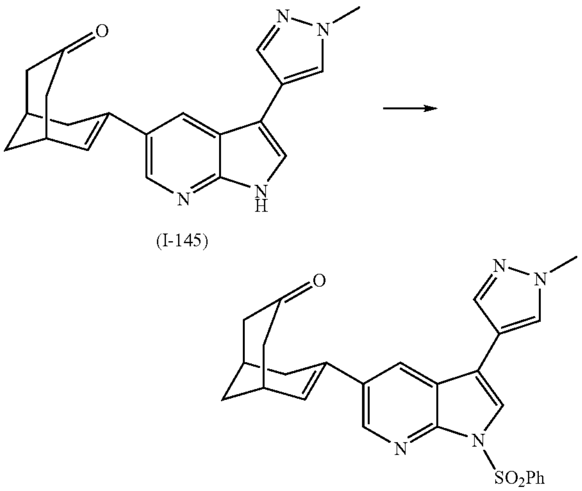

(I-145)

(IIa-145)

Ketone (I-145) was converted into (IIa-145) following the eneral procedure for protection of 7-azaindoles as phenylsulfonamides. Thus, (I-145) (167 mg, 0.52 mmol), $PhSO_2Cl$ (0.10 mL, 0.80 mmol), n-$Bu_4NCl$ (27 mg, 0.078 mmol) and 50% NaOH (0.5 mL) in $CH_2Cl_2$ (5.20 mL) were stirred at RT overnight. Brine (30 mL) was added and was extracted with $CH_2Cl_2$ (3×30 mL). The combined organic extracts were dried over $MgSO_4$ and concentrated. The crude product was triturated with MeOH and the solid was filtered off to give (IIa-145) (233 mg, 95%) as a yellow solid. $^1$H NMR (400 MHz, $CDCl_3$) δ 2.0-2.15 (m, 1H), 2.31-2.47 (m, 3H), 2.52-2.65 (m, 2H), 2.74-2.85 (m, 2H), 2.91-2.97 (br s, 1H), 3.99 (s, 3H), 6.11 (d, J=5.8 Hz, 1H), 7.44-7.49 (m, 2H), 7.54-7.59 (m, 1H), 7.64 (s, 1H), 7.72 (s, 1H), 7.73 (s, 1H), 7.79 (d, J=2.1 Hz, 1H), 8.16-8.20 (m, 2H), 8.42 (d, J=2.1 Hz, 1H).

Cis N-methyl-7-(3-(1-methyl-1H-pyrazol-4-yl)-1-(phenylsulfonyl)-1H-pyrrolo[2,3-b]pyridin-5-yl)bicyclo[3.3.1]non-6-en-3-amine (IIa-150) and trans N-methyl-7-(3-(1-methyl-1H-pyrazol-4-yl)-1-(phenylsulfonyl)-1H-pyrrolo[2,3-b]pyridin-5-yl)bicyclo[3.3.1]non-6-en-3-amine (IIa-151)

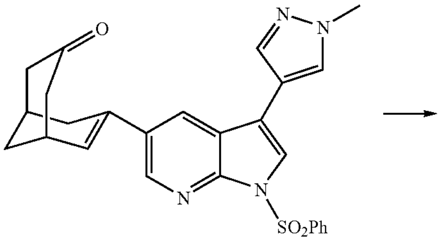

(IIa-145)

-continued

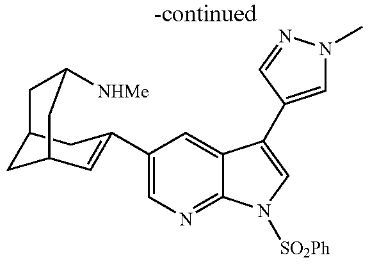

(IIa-150)

+

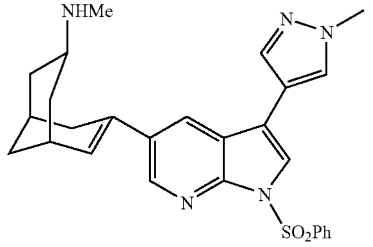

(IIa-151)

A 1.25 M solution of HCl in MeOH (0.40 mL, 0.51 mmol) was added dropwise via syringe into a 2.0 M solution of $MeNH_2$ in THF (1.27 mL, 2.54 mmol) at RT under nitrogen and was stirred for 5 min. This solution was then added via syringe into ketone (IIa-145) (120 mg, 0.25 mmol) in THF: MeOH=1:1 (5 mL). The mixture then heated to 50° C. for 1 hr. The reaction was then allowed to cool to RT and solid $NaCNBH_3$ (32 mg, 0.51 mmol) was added in one portion. The reaction was stirred at RT for 72 hrs. A saturated solution of $NaHCO_3$ (20 mL) was added and the mixture was extracted with EtOAc (3×20 mL). The combined organic extracts were dried ($MgSO_4$) and concentrated. The crude product was purified by prep LCMS (column LUNA 10μ C18(2) 00G-4253-V0 250×50 mm) using water—MeCN (0.1% AcOH) as eluent (in gradient; flow 80 mL/min) to give the product at 18.7-19.2 minutes (retention time) as a 2:1 mixture of cis and trans isomers (IIa-150) and (IIa-151) (39 mg, 32%). δ $^1H$ NMR (400 MHz, $CDCl_3$) δ 1.60-1.78 (m, 7H), 1.91-1.96 (m, 1H), 2.04-2.20 (m, 7H), 2.45 (s, 3H, cis isomer), 2.49 (s, 3H, trans isomer), 2.65-2.75 (m, 5H), 3.09-3.18 (m, 1H, trans isomer), 3.18-3.25 (m 1H, cis isomer), 4.00 (s, 3H, trans isomer), 4.01 (s, 3H, cis isomer), 6.18 (d, J=6.3 Hz, 1H, trans isomer), 6.48 (d, J=6.3 Hz, 1H, cis isomer), 7.45-7.51 (m, 4H), 7.54-7.59 (m, 2H), 7.74 (s, 1H, trans isomer), 7.76 (s, 1H, cis isomer), 7.77 (d, J=2.1 Hz, 1H, trans isomer), 7.81 (d, J=0.6 Hz, 1H, cis isomer), 7.92 (d, J=2.1 Hz, 1H, trans isomer), 8.02 (s, 1H, cis isomer), 8.13 (d, J=2.1 Hz, 1H, cis isomer), 8.16-8.20 (m, 5H), 8.49 (d, J=2.1 Hz, 1H, trans isomer), 8.50 (d, J=2.1 Hz, 1H, cis isomer); MS (CI) m/z 488.2 ($MH^+$).

Azaadamantyl Derivative (IIb-152)

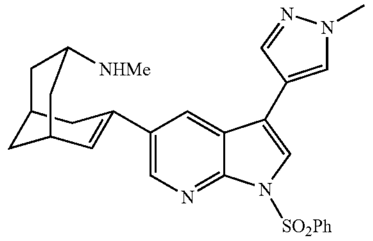

(IIa-150)

+

-continued

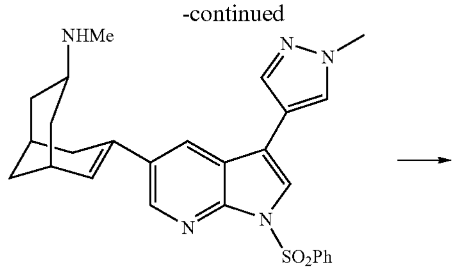

(IIa-151)

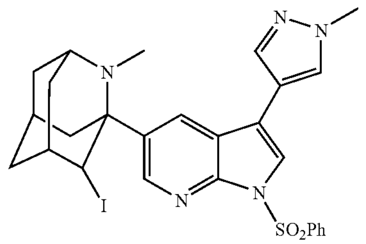

(IIb-152)

A 2:1 cis:trans mixture of amines (IIa-150) and (IIa-151) (39 mg, 80 μmol) was dissolved in anhydrous $CH_3CN$ (1.50 mL) at RT under nitrogen. Iodine (24 mg, 96 μmol) was added in one portion at RT. The reaction was stirred overnight. A saturated solution of $NaHCO_3$ (5 mL) and a solution of $Na_2S_2O_3$ (5 mL) were added to quench the reaction and the mixture was extracted with $CH_2Cl_2$ (3×20 mL). The combined organic extracts were dried over $MgSO_4$ and concentrated. The crude product purified by prep LCMS (column LUNA 10μ C18(2) 00G-4253-V0 250×50 mm) using water—MeCN (0.1% AcOH) as eluent (in gradient; flow 80 mL/min) to give (IIb-152) (9.5 mg, 19%; retention time 16.5-17.3 min). $^1H$ NMR (400 MHz, $CDCl_3$) δ 1.43 (d, J=11.8 Hz, 1H), 1.64 (d, J=13.2 Hz, 1H), 1.89 (d, J=12.3 Hz, 1H), 1.97 (d, J=12.7 Hz, 1H), 2.02 (s, 3H), 2.17-2.30 (m, 6H), 2.93 (br s, 1H), 3.97 (s, 3H), 5.19 (s, 1H), 7.43-7.49 (m, 2H), 7.52-7.56 (m, 1H), 7.73 (s, 1H), 7.74 (d, J=0.6 Hz, 1H), 7.78 (br s, 1H), 8.11 (br s, 1H), 8.14-8.18 (m, 2H), 8.35 (br s, 1H).

Adamantyl Derivative (IIb-154)

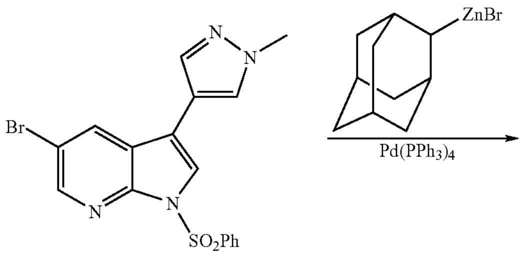

(III-a)

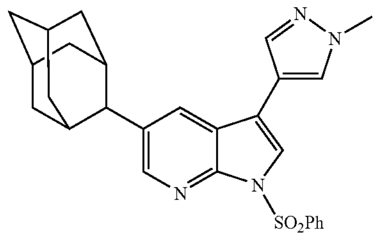

(IIb-154)

To a stirred solution of the bromide (III-a) (100 mg, 0.24 mmol), $Pd(PPh_3)_4$ (28 mg, 0.02 mmol) in THF (2.5 mL) and PhMe (2.5 mL) in a sealed tube was added a 0.5 M solution of 2-adamantylzinc bromide (0.72 mL, 0.36 mmol) dropwise over 1 min. The resulting mixture was allowed to stir at room temperature for a further 1 min and then lowered into a preheated 100° C. bath and stirred vigorously. After 22 h a further amount of $Pd(PPh_3)_4$ (80 mg) and the 2-adamantylzinc bromide solution (0.80 mL) was added and the mixture was stirred at 100° C. for a further 26 h. It was cooled to RT and filtered through a silica pad. The resulting filtrate was concentrated and the residue diluted with EtOAc and washed with saturated $NaHCO_3$ (2×) and saturated brine (1×). The organic layer was dried ($MgSO_4$), filtered and concentrated. The crude material was purified by prep LCMS (column LUNA 10μ C18(2) 00G-4253-V0 250×50 mm) using water—MeCN (0.1% AcOH) as eluent (in gradient; flow 80 mL/min) to give a mixture that was comprised of the Negishi adduct (IIb-154) and phosphine residues (35.8 mg). This material was used directly in preparation of (I-154) without additional purification. MS (CI) m/z 473.2 ($MH^+$).

Synthesis of Mixture of Nitriles Exo-(IIa-155) and Endo-(IIa-155)

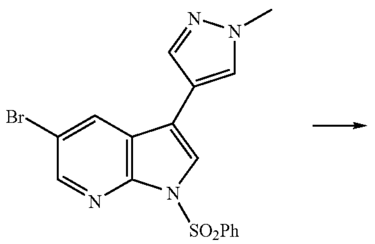

(III-a)

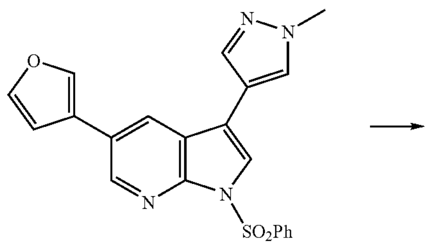

10

-continued

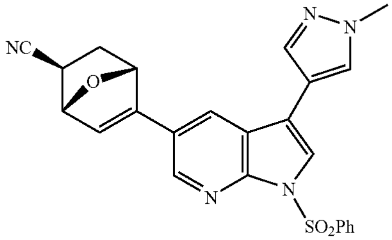

+ exo-(IIa-155)

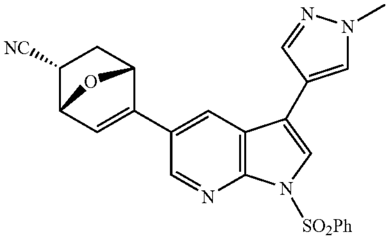

endo-(IIa-155)

5-(furan-3-yl)-3-(1-methyl-1H-pyrazol-4-yl)-1-(phenylsulfonyl)-1H-pyrrolo[2,3-b]pyridine (10)

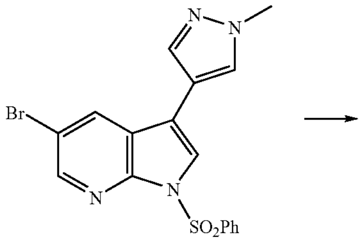

(III-a)

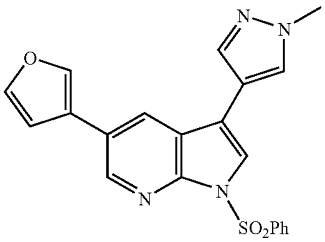

10

Bromide (III-a) (1.00 g, 2.40 mmol), furan-3-boronic acid (300 mg, 2.70 mmol), LiCl (400 mg, 9.44 mmol), and $Pd(PPh_3)_2Cl_2$ (100 mg, 0.14 mmol) in EtOH (5 mL), toluene (5 mL) and 1.0 M $Na_2CO_3$ solution (2.5 mL) were reacted for 2.5 h following the general procedure A for the Suzuki reaction. The crude product (1.61 g, dark brown oil) was purified by SGC using $CH_2Cl_2$:EtOAc:hexane=1:1:1 (v/v/v) to afford 10 as a foam (968 mg, 2.40 mol, quant.). $^1H$ NMR (400 MHz, $CDCl_3$) δ 4.03 (s, 3H), 6.73 (dd, J=0.9, 1.8 Hz, 1H), 7.50-7.56

(m, 3H), 7.61 (tt, J=1.5, 7.4 Hz, 1H), 7.68 (s, 1H), 7.76-7.81 (m, 3H), 8.00 (d, J=2.1 Hz, 2H), 8.23-8.27 (m, 2H), 8.63 (d, J=2.1 Hz, 2H).

(1R,2R,4R)-5-(3-(1-methyl-1H-pyrazol-4-yl)-1-(phenylsulfonyl)-1H-pyrrolo[2,3-b]pyridin-5-yl)-7-oxabicyclo[2.2.1]hept-5-ene-2-carbonitrile exo-(IIa-155) and (1R,2S,4R)-5-(3-(1-methyl-1H-pyrazol-4-yl)-1-(phenylsulfonyl)-1H-pyrrolo[2,3-b]pyridin-5-yl)-7-oxabicyclo[2.2.1]hept-5-ene-2-carbonitrile endo-(IIa-155)

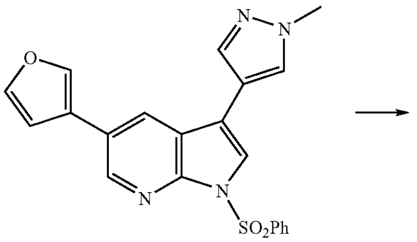

10

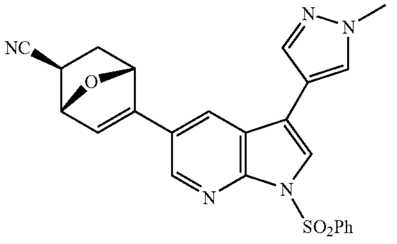

+ exo-(IIa-155)

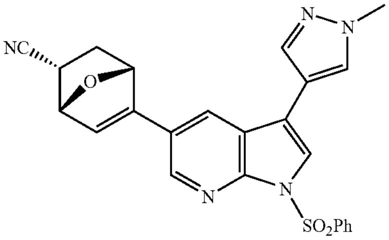

endo-(IIa-155)

To a solution of 10 (373 mg, 0.92 mmol) in acrylonitrile (5 mL) was added zinc (II) iodide (300 mg, 0.94 mmol) portion-wise over 1 h. The mixture was stirred at RT for 26 h, and a further portion of zinc (II) iodide (100 mg, 0.31 mmol) was added. After stirring for a further 16 h, water (25 mL) was added. The mixture was then extracted with EtOAc (2×50 mL) and the combined organic solutions concentrated in vacuo to an oil (620 mg).The oil was purified by SGC using EtOAc:$CH_2Cl_2$ (gradient elution from 1:6 to 1:3, v/v). Eluting first was exo-(IIa-155) (82 mg, 0.18 mmol, 19%). $^1$H NMR (400 MHz, $CDCl_3$) δ 1.77 (dd, J=8.5, 11.7 Hz, 1H), 2.22 (dt, J=4.2, 11.7 Hz, 1H), 2.53 (dd, J=3.8, 8.5 Hz, 1H), 3.93 (s, 3H), 5.30-5.32 (m, 1H), 5.51 (d, J=4.6 Hz, 1H), 6.47 (d, J=1.8 Hz, 1H), 7.43 (t, J=7.7 Hz, 2H), 7.52 (tt, J=1.4, 7.4 Hz, 1H), 7.57 (s, 1H), 7.66 (s, 1H), 7.70 (s, 1H), 7.79 (d, J=2.0 Hz, 2H), 8.10-8.15 (m, 2H), 8.38 (d, 2.0 Hz, 1H). Further elution afforded endo-(IIa-155) (110 mg, 0.24 mmol, 26%). $^1$H NMR (400 MHz, $CDCl_3$) δ 1.59 (dd, J=3.9, 11.6 Hz, 1H), 2.38 (ddd, J=4.6, 9.5, 11.7 Hz, 1H), 3.05 (dd, J=4.1, 9.4 Hz, 1H), 3.93 (s, 3H), 5.29 (dd, J 1.1, 4.1 Hz, 1H), 5.47 (d, J=4.4 Hz, 1H), 6.66 (d, J=1.7 Hz, 1H), 7.43 (t, J=7.7 Hz, 2H), 7.52 (tt, J=1.4, 7.4 Hz, 1H), 7.58 (s, 1H), 7.67 (s, 1H), 7.69 (s, 1H), 7.83 (d, J=2.0 Hz, 2H), 8.10-8.15 (m, 2H), 8.43 (d, 2.0 Hz, 1H). A further sample (111 mg), containing a mixture of the above two compounds was also isolated.

(5S)-5-(3-(1-methyl-1H-pyrazol-4-yl)-1-(phenylsulfonyl)-1H-pyrrolo[2,3-b]pyridin-5-yl)-7-oxabicyclo[2.2.1]heptane-2-carbonitrile (IIb-157)

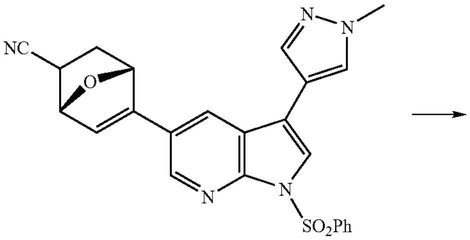

(IIa-155)

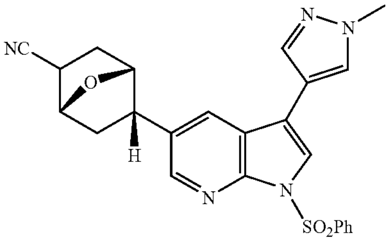

(IIb-157)

A mixture of (IIa-155) (111 mg, unassigned 2:1 mixture of isomers, 0.24 mmol) and 10% Pd/C (50 mg, cat.) in methanol: $CH_2Cl_2$=5:1 (12 mL) was stirred vigorously overnight under hydrogen. After 18 h, the reaction mixture was filtered through Celite, washing with MeoH:$CH_2Cl_2$=1:1 (50 mL), and concentrated to afford (IIb-157) (99 mg, 0.21 mmol, unassigned 2:1 mixture of isomers, 87%) as an oil. $^1$H NMR (400 MHz, $CDCl_3$) δ 1.63-1.96 (m, 2H, both isomers), 2.20-2.38 (m, 2H, both isomers), 2.62 (dd, J=4.1, 8.4 Hz, 1H, minor isomer), 2.90-2.97 (m, 1H, major isomer), 3.56 (dt, J=5.5, 11.8 Hz, 1H, minor isomer), 3.68 (dt, J=5.6, 11.0 Hz, 1H, major isomer), 3.87 (s, 3H, major isomer), 3.93 (s, 3H, minor isomer), 4.66 (t, J 4.1 Hz, 1H, major isomer), 4.80-4.90 (m, 1H in major isomer & 2H in minor isomer), 7.39-7.67 (m, 4H in major isomer, 5H in minor isomer), 7.70 (s, 1H, minor isomer), 7.72 (s, 1H, major isomer), 7.76 (s, 1H, major isomer), 7.90 (s, 1H, major isomer), 8.07 (d, J=1.8 Hz, 1H, major isomer), 8.10-8.17 (m, 1H in major isomer, 3H in minor isomer), 8.20 (s, 1H, minor isomer), 8.26 (d, J 1.7 Hz, 1H, major isomer).

8-(3-1-methyl-1H-pyrazol-4-yl)-1-(phenylsulfonyl)-1H-pyrrolo[2,3-b]pyridin-5-yl)-1,4-dioxaspiro[4.5]decan-8-ol (IIb-158) and 8-(3-1-methyl-1H-pyrazol-4-yl)-1-(phenylsulfonyl)-1H-pyrrolo[2,3-b]pyridin-5-yl)-1,4-dioxaspiro[4.5]decan-7-ol (IIb-159)

(dq, J=2.1, 12.6 Hz, 1H), 2.55-2.63 (m, 1H), 2.66 (d, J=3.3 Hz, 1H), 3.98 (s, 3H), 3.99-4.07 (m, 5H), 7.44-7.49 (m, 2H), 7.53-7.58 (m, 1H), 7.60 (s, 1H), 7.67 (s, 1H), 7.68 (d, J=0.6 Hz, 1H), 7.84 (d, J=2.0 Hz, 1H), 8.15-8.18 (m, 2H), 8.27 (d, J=2.0 Hz, 1H).

5-(8-fluoro-1,4-dioxaspiro[4.5]decan-8-yl)-3-1-methyl-1H-pyrazol-4-yl)-1-(phenylsulfonyl)-1H-pyrrolo[2,3-b]pyridine (IIb-160)

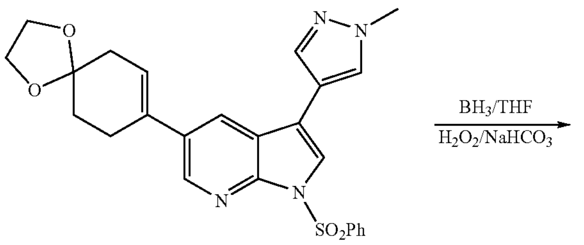

(IIa-14)

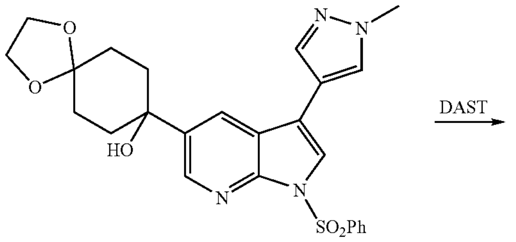

(IIb-158)

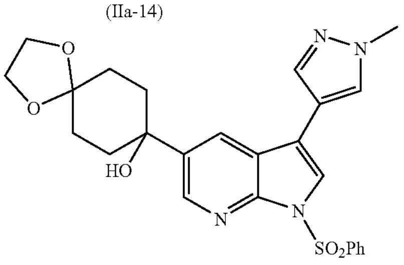

(IIb-158)

+

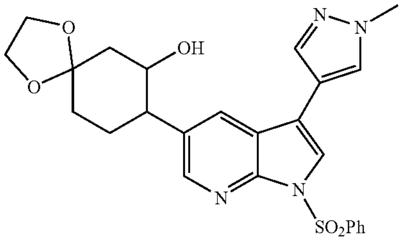

(IIb-159)

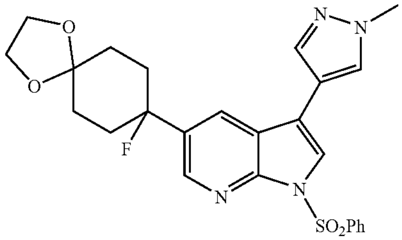

(IIb-160)

1.0 M borane-THF complex in THF (6.30 mL, 6.30 mmol) was added dropwise via syringe at RT to a solution of compound (IIa-14) (1.00 g, 2.11 mmol) in anhydrous THF (21 mL). The reaction was stirred at RT for 3 h and 28% aqueous solution of $H_2O_2$ (10 mL) was added slowly at RT over 20 min. (gas evolution). A saturated solution of $NaHCO_3$ (50 mL) was added and the mixture was stirred at RT for 15 min. The mixture was then extracted with $CH_2Cl_2$ (4×50 mL). The combined organic extracts were dried over $MgSO_4$ and concentrated. The crude product was purified by SGC using EtOAc:hexane (gradient elution from 0:100 to 100:0, v/v) as the eluent to give the tertiary alcohol (IIb-158) as a white foam (0.14 g, 14%) and the secondary alcohol (IIb-159) (0.43 g, 41%).

Data for the tertiary alcohol (IIb-158): $^1$H NMR (400 MHz, $CDCl_3$) δ 1.72 (d, J=12.0 Hz, 2H), 1.87 (d, J=12.0 Hz, 2H), 2.07-2.27 (m, 4H), 3.98 (s, 3H), 3.99-4.01 (dd, J=3.1, 4.5 Hz, 4H), 7.46-7.51 (m, 2H), 7.55-7.60 (m, 1H), 7.66 (s, 1H), 7.73 (d, J=0.6 Hz, 1H), 7.74 (s, 1H), 8.13 (d, J=2.1 Hz, 1H), 8.20-8.23 (m, 2H), 8.63 (d, J=2.2 Hz, 1H).

Data for the secondary alcohol (IIb-159): $^1$H NMR (400 MHz, $CDCl_3$) δ 1.67-1.75 (m, 1H), 1.76-1.85 (m, 4H), 2.28

Diethylaminosulfur trifluoride (DAST) (456 mg, 2.83 mmol) was added via syringe dropwise to a stirred and cooled (−78° C.) solution of alcohol (IIb-158) (140 mg, 0.28 mmol) in anhydrous $CH_2Cl_2$ (5 mL) under nitrogen. The reaction mixture was stirred at −78° C. for 2 h. A saturated solution of $NaHCO_3$ (50 mL) was added. The mixture was allowed to warm up to RT, diluted with $CH_2Cl_2$ (30 mL) and the two layers were separated. The aqueous layer was extracted with $CH_2Cl_2$ (3×30 mL). The combined organic extracts were dried ($MgSO_4$) and concentrated to give crude product (140 mg, 99%) as a 3:1 mixture of compound (IIb-160) and elimination product (IIa-14). The material wasn't purified and was used crude.

Data for fluoro compound (IIb-160): $^1$H NMR (400 MHz, $CDCl_3$) δ 1.76 (d, J=9.2 Hz, 2H), 2.05-2.16 (m, 5H), 2.25 (td, J=4.0 and 14.9 Hz, 1H), 4.00 (s, 3H), 4.00-4.03 (dd, J=3.7 and 5.8 Hz, 4H), 7.48-7.53 (m, 2H), 7.57-7.62 (m, 1H), 7.66 (s, 1H), 7.76 (s, 1H), 7.79 (s, 1H), 8.01 (d, J=2.1 Hz, 1H), 8.22-8.25 (m, 2H), 8.57 (d, J=1.7 Hz, 1H); MS (CI) m/z 496.8 ($M^+$).

Signals due for compound (IIa-14): $^1$H NMR (400 MHz, $CDCl_3$) δ 1.95 (t, J=6.5 Hz, 2H), 2.50-2.48 (m, 2H), 2.70-2.67 (m, 2H), 3.99 (s, 3H), 4.04 (s, 4H), 5.99-5.96 (m, 1H), 7.48 (t, J=7.6 Hz, 2H), 7.59-7.55 (m, 1H), 7.64 (s, 1H), 7.74 (s, 1H), 7.75 (d, J=0.6 Hz, 1H), 7.90 (d, J=2.2 Hz, 1H), 8.21-8.18 (m, 2H), 8.52 (d, J=2.1 Hz, 1H).

4-fluoro-4-(3-(1-methyl-1H-pyrazol-4-yl)-1-(phenylsulfonyl)-1H-pyrrolo[2,3-b]pyridin-5-yl)cyclohexanone (IIb-161)

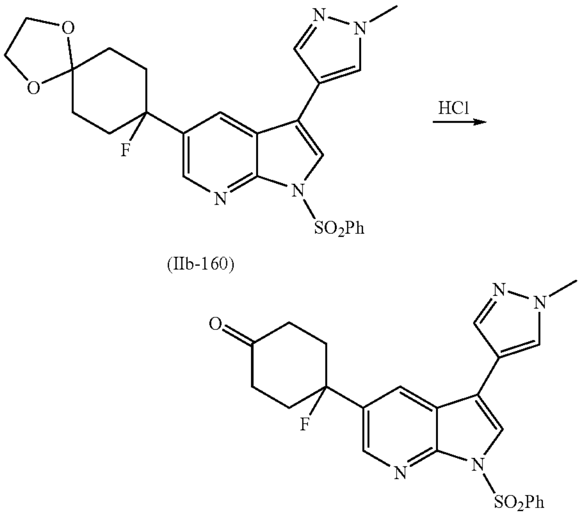

(IIb-160)

(IIb-161)

7 M aqueous HCl (1.00 ml, 7.00 mmol) was added to a solution of compound (IIb-160) (110 mg, 0.22 mmol) in THF (3 mL) and the reaction was stirred at RT for 3 hrs. A saturated solution of $NaHCO_3$ (40 mL) was added slowly over 20 minutes at RT. The mixture was stirred for 15 minutes at RT and extracted with EtOAc (4×30 mL). The combined organic extracts were dried over $MgSO_4$ and concentrated to give crude (IIb-161) (92 mg, 92%). $^1$H NMR (400 MHz, $CDCl_3$) δ 2.23-2.33 (td, J=4.8, 14.0 Hz, 1H), 2.37-2.48 (m, 5H), 2.83-2.94 (m, 2H), 3.99 (s, 3H), 7.47-7.53 (m, 2H), 7.56-7.61 (m, 1H), 7.68 (s, 1H), 7.75 (s, 1H), 7.80 (s, 1H), 8.05 (d, J=2.2 Hz, 1H), 8.19-8.22 (m, 2H), 8.48 (d, J=1.7 Hz, 1H); MS (CI) m/z 452.8 ($M^+$).

4-((1s,4s)-4-fluoro-4-(3-(1-methyl-1H-pyrazol-4-yl)-1-(phenylsulfonyl)-1H-pyrrolo[2,3-b]pyridin-5-yl)cyclohexyl)morpholine (IIb-162) and 4-((1r,4r)-4-fluoro-4-(3-(1-methyl-1H-pyrazol-4-yl)-1-(phenylsulfonyl)-1H-pyrrolo[2,3-b]pyridin-5-yl)cyclohexyl)morpholine (IIb-163)

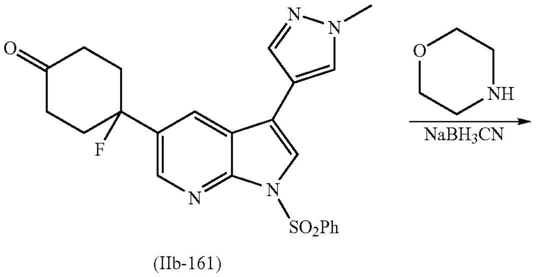

(IIb-161)

-continued

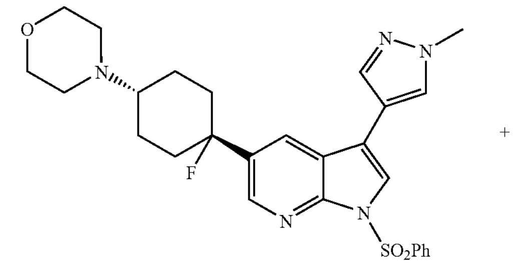

(IIb-162)

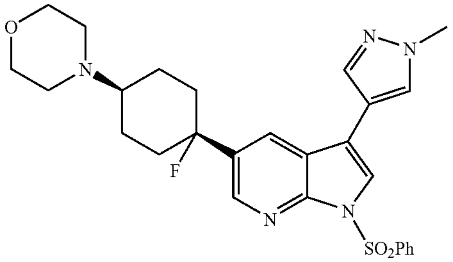

(IIb-163)

Ketone (IIb-161) (110 mg, 0.24 mmol), morpholine (177 mg, 2.03 mmol), 1.25 M HCl in MeOH (0.33 mL, 0.41 mmol) in anhydrous MeOH (9.0 mL) and $NaCNBH_3$ (25.5 mg, 0.41 mmol), which was added as a solution in MeOH (2 mL), were reacted following the general procedure A for the reductive amination. The crude product was purified by PTLC using $CH_2Cl_2$:MeOH=95:5 (v/v) as eluent to give the cis isomer (IIb-163) (32 mg, 25%) as a yellow foam and the trans isomer (IIb-162) (42 mg, 33%) as a yellow foam.

Data for trans isomer (IIb-162):

$^1$H NMR (400 MHz, $CDCl_3$) δ 1.75-1.88 (m, 3H), 1.89-1.98 (m, 3H), 2.14-2.22 (m, 2H), 2.40-62.49 (m, 1H), 2.62-2.67 (t, J=4.2 Hz, 4H), 3.74-3.79 (t, J=4.2 Hz, 4H), 4.00 (s, 3H), 7.47-7.53 (m, 2H), 7.56-7.63 (m, 1H), 7.66 (s, 1H), 7.76 (s, 1H), 7.79 (s, 1H), 8.00 (d, J=2.1 Hz, 1H), 8.20-8.24 (m, 2H), 8.46 (d, J=1.5 Hz, 1H).

$^{13}$C NMR (125 MHz, $CDCl_3$) δ 23.9, 37.0 (d, J=23.4 Hz, $CH_2CF$), 39.3, 49.8, 62.4, 67.4, 95.0 (d, J=175.5 Hz, CF), 112.0, 113.4, 121.4, 122.2, 124.5 (d, J=10.8 Hz, CFC(Ar)), 127.7, 128.1, 129.2, 134.2, 137.6, 138.4, 141.9, 141.9, 146.9.

Data for cis isomer (IIb-163):

$^1$H NMR (500 MHz, $CDCl_3$) δ 1.74-1.86 (t, J=11.7 Hz, 2H), 1.89-1.94 (m, 4H), 2.14-2.37 (m, 3H), 2.43-2.56 (br s, 4H), 3.72-3.80 (t, J=4.3 Hz, 4H), 4.00 (s, 3H), 7.48-7.55 (m, 2H), 7.57-7.62 (m, 1H), 7.67 (s, 1H), 7.78 (d, J=0.6 Hz, 1H), 7.80 (s, 1H), 8.06 (s, 1H), 8.21-8.24 (m, 2H), 8.51 (s, 1H).

$^{13}$C NMR (125 MHz, $CDCl_3$) δ 23.9, 32.5 (d, J=23.6 $CH_2CF$), 39.3, 50.8, 57.6, 67.5, 95.0 (d, J=173.5 Hz, CF), 112.1, 113.6, 121.1, 122.1, 124.6 (d, J=11.3 Hz, CFC(Ar)), 127.7, 128.1, 129.3, 134.2, 137.6, 138.5, 142.4, 142.5, 146.8.

4-(1-methyl-4-(3-(1-methyl-1H-pyrazol-4-yl)-1-(phenylsulfonyl)-1H-pyrrolo[2,3-b]pyridin-5-yl)cyclohex-3-enyl)morpholine (IIa-164)

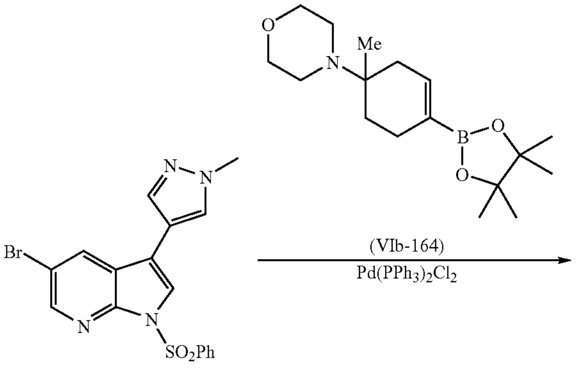

(III-a)

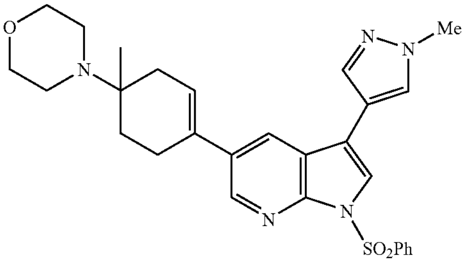

(IIa-164)

Bromide (III-a) (5.68 g, 13.62 mmol), boronic ester (VIb-164) (5.02 g, 16.34 mmol), LiCl (1.73 g, 40.85 mmol), $Pd(PPh_3)_2Cl_2$ (1.74 g, 2.47 mmol) and 1.0 M $Na_2CO_3$ solution (34.04 mL, 34.04 mmol) in EtOH (50 mL) and toluene (50 mL) were reacted for 3.5 h following the general procedure A for the Suzuki reaction. The crude product was purified by SGC using $CH_2Cl_2$:MeOH as eluent (gradient from 100:0 to 95:5; v/v) to afford a yellowish white foam. The product was further purified by dissolving it in $CH_2Cl_2$ and subsequent addition of hexane, after which brown oil appeared at the bottom of the flask. The clear solution was decanted off and evaporated to give (IIa-164) as an off-white foam (3.29 g, 47%). $^1$H NMR (400 MHz, $CDCl_3$) δ 1.03 (s, 3H), 1.68-1.80 (m, 1H), 1.80-1.89 (m, 1H), 2.09-2.19 (m, 1H), 2.32-2.48 (m, 2H), 2.50-2.72 (m, 5H), 3.73 (t, J=4.3 Hz, 4H), 4.01 (s, 3H), 6.00-6.07 (m, 1H), 7.49 (t, J=7.7 Hz, 2H), 7.58 (t, J=7.1 Hz, 1H), 7.64 (s, 1H), 7.78 (d, J=6.6 Hz, 2H), 7.88 (d, J=1.9 Hz, 1H), 8.21 (d, J=7.7 Hz, 2H), 8.53 (d, J=1.7 Hz, 1H).

4-((1s,4s)-1-methyl-4-(3-(1-methyl-1H-pyrazol-4-yl)-1-(phenylsulfonyl)-1H-pyrrolo[2,3-b]pyridin-5-yl)cyclohexyl)morpholine (IIb-165) and 4-((1r,4r)-1-methyl-4-(3-(1-methyl-1H-pyrazol-4-yl)-1-(phenylsulfonyl)-1H-pyrrolo[2,3-b]pyridin-5-yl)cyclohexyl)morpholine (IIb-166)

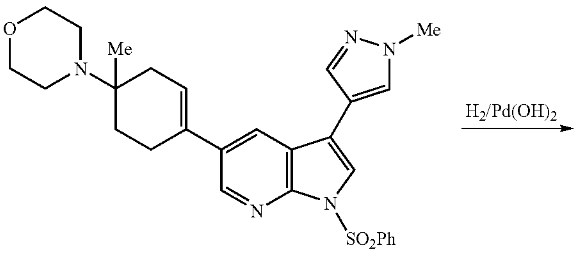

(IIa-164)

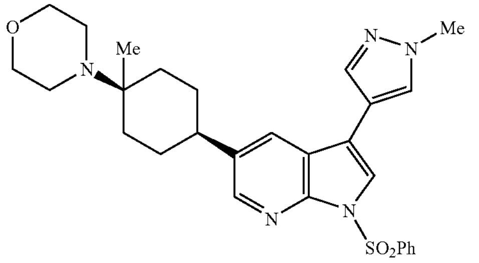

+

(IIb-165)

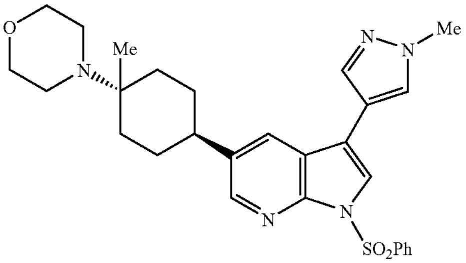

(IIb-166)

Compound (IIa-164) was hydrogenated using the general procedure for hydrogenation of 7-azaindoles. Thus, (IIa-164) (600 mg, 1.16 mmol) and $Pd(OH)_2$ (20% on C, wet, Degussa type) (110 mg) in EtOH:THF=1:1 (20 mL, v/v) were reacted under $H_2$ over a period of 3 d. To effect the completion of the reduction the catalyst was filtered off and the reaction was repeated using $Pd(OH)_2$ (20% on C, wet, Degussa type) (250 mg) in EtOH:THF=1:1 (20 mL). The reaction mixture was filtered through Celite, washing with EtOH:THF=1:1 (300 mL) and concentrated. The residue was purified by SGC using $CH_2Cl_2$:MeOH (gradient elution from 100:0 to 90:10, v/v). Eluting first was the cis isomer (IIb-165; tentative assignment of configuration) (232 mg, 39%) as colourless oil. Further elution afforded the trans isomer (IIb-166; tentative assignment of configuration) (270 mg, 52%), white foam.

Data for (IIb-165): $^1$H NMR (400 MHz, $CDCl_3$) δ 0.88 (s, 3H), 1.26 (td, J=13.4, 3.4 Hz, 2H), 1.52 (dd, J=12.7, 3.5 Hz, 2H), 1.84-2.05 (m, 4H), 2.50 (t, J=4.3 Hz, 4H), 2.64 (tt, J=12.1, 6.0 Hz, 1H), 3.72 (t, J=4.3 Hz, 4H), 3.98 (s, 3H), 7.43-7.51 (m, 2H), 7.52-7.58 (m, 1H), 7.66 (s, 1H), 7.73 (s, 1H), 7.76 (d, J=0.5 Hz, 1H), 7.81 (d, J=2.0 Hz, 1H), 8.16-8.23 (m, 2H), 8.40 (d, J=2.0 Hz, 1H).

Data for (IIb-166): $^1$H NMR (400 MHz, $CDCl_3$) δ 1.02 (s, 3H), 1.54 (hex, J=12.7 Hz, 4H), 1.80 (t, J=12.7 Hz, 4H), 2.59 (bs, 5H), 3.70 (t, J=4.1 Hz, 4H), 3.94 (s, 3H), 7.39-7.47 (m, 2H), 7.48-7.55 (m, 1H), 7.64 (s, 1H), 7.70 (s, 1H), 7.73 (s, 1H), 7.74 (d, J=2.0 Hz, 1H), 8.13-8.19 (m, 2H), 8.31 (d, J=2.0 Hz, 1H).

5-Bromo-3-(1-methyl-1H-pyrazol-4-yl)-1-(phenylsulfonyl)-1H-pyrrolo[2,3-b]pyridine (III-a)

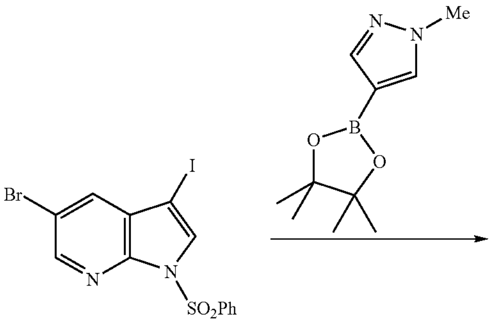

(IV-a)

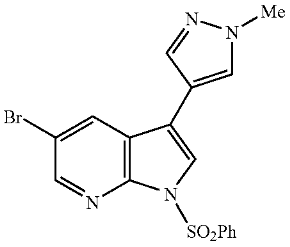

(III-a)

A mixture of iodide (IV-a) (70.00 g, 151.15 mmol; preparation disclosed in WO2004/078756), 1-methyl-4-(4,4,5,5-tetramethyl-1,3,2-dioxaborolan-2-yl)-1H-pyrazole (34.60 g, 166.27 mmol), LiCl (19.22 g, 453.45 mmol) and $Pd(PPh_3)_2Cl_2$ (5.30 g, 7.55 mmol), 1 M $Na_2CO_3$ solution (378 mL), in toluene (378 mL) and EtOH (377.87 mL) was reacted at 100° C. for 3 h following the general procedure B for the Suzuki reaction. The mixture was allowed to cool to RT and water (500 mL) was added. The mixture was extracted with EtOAc (4×500 mL). The combined organic extracts were dried ($MgSO_4$) and the solvent was removed under vacuum. As the solvent was being removed a yellow solid was formed. The solid was filtered to give 9.03 g of product. The mother liquor was concentrated further under vacuum. More solid crushed out of solution which was again filtered to give 12.62 g of the product. The solvent was then removed to give the crude product which was purified by flash chromatography on silica gel using 4:1:1→2:1:1→1:1:1 hexane:EtOAc:$CH_2Cl_2$ as the eluent to give the product (28.80 g) as a yellow solid. Overall yield of (III-a) (50.45 g, 80%). $^1$H NMR (400 MHz, $CDCl_3$) δ 4.00 (s, 3H), 7.54-7.49 (m, 2H), 7.63-7.58 (m, 1H), 7.64 (s, 1H), 7.74 (d, J=0.6 Hz, 1H), 7.78 (s, 1H), 8.08 (d, J=2.2 Hz, 1H), 8.21-8.18 (m, 2H), 8.49 (d, J=2.2 Hz, 1H).

4-(2-(4-(5-bromo-1-(phenylsulfonyl)-1H-pyrrolo[2,3-b]pyridin-3-yl)-1H-pyrazol-1-yl)ethyl)morpholine (III-b)

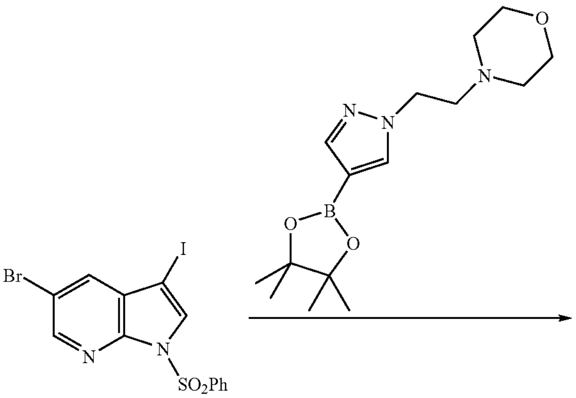

(IV-a)

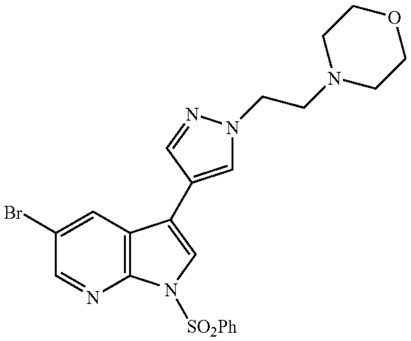

(III-b)

A mixture of iodide (IV-a) (5.26 g, 11.36 mmol; preparation disclosed in WO2004/078756), 4-(2-(4-(4,4,5,5-tetramethyl-1,3,2-dioxaborolan-2-yl)-1H-pyrazol-1-yl)ethyl)morpholine (3.84 g, 12.49 mmol; purchased from Focus Synthesis Cat. No. FS000540), LiCl (1.44 g, 34.07 mmol), 1.0 M $Na_2CO_3$ solution (29.39 ml, 28.39 mmol), and $Pd(PPh_3)_2Cl_2$ (0.80 g, 1.13 mmol in EtOH (85.2 mL) and toluene (85.2 mL) was reacted at 105° C. for 3 h 35 min following the general procedure B for the Suzuki reaction. The crude product was purified by SGC using hexane/EtOAc as the eluent (gradient elution 0%-100% EtOAc) to give (III-b) as a pale yellow oil (3.10 g, 53%), $^1$H NMR (400 MHz, $CDCl_3$) δ 2.52 (t, J=4.6 Hz, 4H), 2.87 (t, J=6.5 Hz, 2H), 3.73 (t, J=4.6 Hz, 4H), 4.32 (t, J=6.5 Hz, 2H), 7.54-7.49 (m, 2H), 7.64-7.59 (m, 1H), 7.74 (s, 1H), 7.76 (s, 1H), 7.80 (s, 1H), 8.09 (d, J=2.1 Hz, 1H), 7.90 (d, J=2.2 Hz, 1H), 8.21-8.18 (m, 2H), 8.49 (d, J=2.1 Hz, 1H).

5-bromo-1-(phenylsulfonyl)-3-(1-(trifluoromethyl)-1H-pyrazol-4-yl)-1H-pyrrolo[2,3-b]pyridine (III-c)

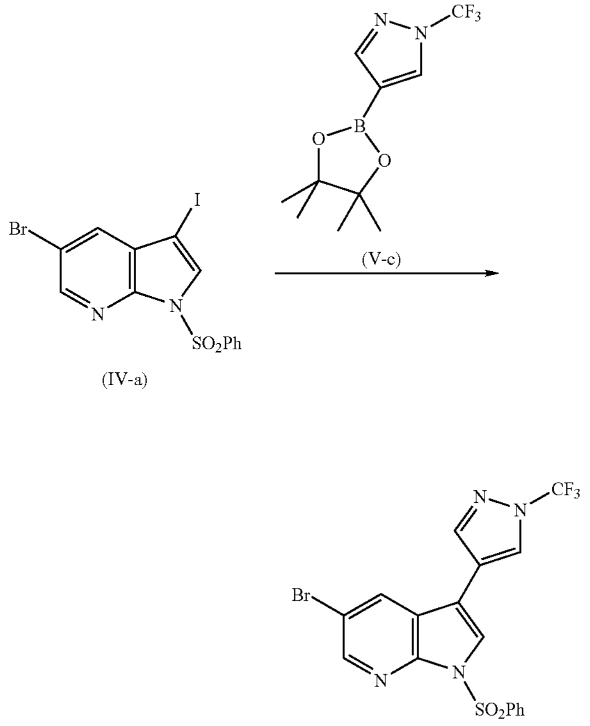

(IV-a)

(V-c)

(III-c)

A mixture of iodide (IV-a) (1.00 g, 2.15 mmol; preparation disclosed in WO2004/078756), boronic ester (V-c) (1.26 g, 4.30 mmol), lithium chloride (0.27 g, 6.45 mmol), 1.0 M $Na_2CO_3$ solution (5.40 ml, 5.40 mmol), and $Pd(PPh_3)_2Cl_2$ (0.15 g, 0.21 mmol) in EtOH (5.40 mL) and toluene (5.40 mL) was reacted following the general procedure B for the Suzuki reaction at 100° C. for 2 h. The crude product was purified by SGC using hexane/EtOAc as the eluent (gradient elution 0%-100% EtOAc) to give (III-c) as a yellow solid (0.34 g, 33%), $^1$H NMR (400 MHz, $CDCl_3$) δ 7.57-7.50 (m, 2H), 7.66-7.60 (m, 1H), 7.91 (s, 1H), 8.02 (s, 1H), 8.08-8.06 (m, 2H), 8.25-8.20 (m, 2H), 8.53 (d, J=2.0 Hz, 1H).

Synthesis of Bromide (III-d)

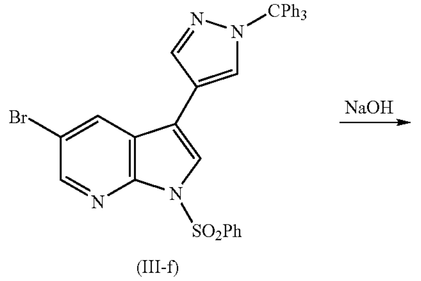

(III-f)

-continued

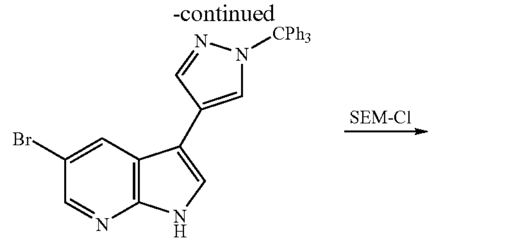

1

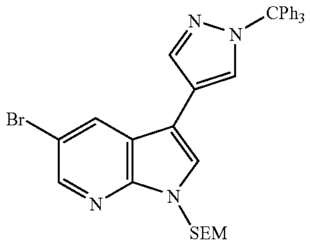

(III-d)

1-Benzenesulfonyl-5-bromo-3-(1-trityl-1H-pyrazol-4-yl)-1H-pyrrolo[2,3-b]pyridine (1)

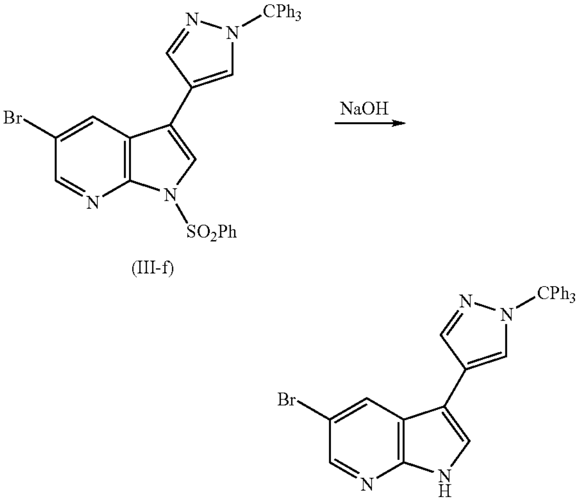

(III-f)

1

A mixture of sulfonamide (III-f) (1.50 g, 2.32 mmol; preparation disclosed in WO2004/078756) and 10% aq. NaOH (22 mL) in EtOH (45 mL) was heated at 100° C. for 8 h. The reaction mixture was cooled, poured onto a mixture of brine (100 mL) and EtOAc (50 mL). The aqueous layer was extracted with EtOAc (4×50 mL), and the combined organic extracts washed with brine (50 mL), dried ($MgSO_4$) and concentrated. The aqueous layer was then extracted with 3% MeOH in $CH_2Cl_2$ (3×50 mL), and the combined organic extracts concentrated without drying. The residual solid was washed with 30% EtOAc in hexane (5×) to give azaindole 1 as an orange solid (0.96 g, 82%).

5-Bromo-1-(2-trimethylsilanyl-ethoxymethyl)-3-(1-trityl-1H-pyrazol-4-yl)-1H-pyrrolo[2,3-b]pyridine (III-d)

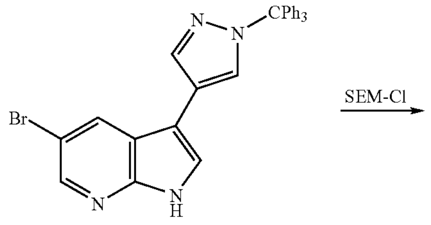

2

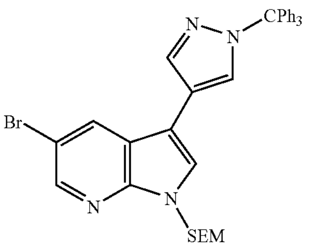

(III-d)

To a solution of azaindole 1 (0.5 g, 0.99 mmol) in DMF (2.5 mL) was added NaH (60% w/w in mineral oil, 59.4 mg, 1.48 mmol) portionwise. Then the reaction mixture was stirred for 0.5 h. SEM-Cl (263 μL, 1.48 mmol) was then added in one portion. The reaction mixture was stirred overnight and poured cautiously onto a stirred mixture of EtOAc (20 mL)/saturated aq. $NH_4Cl$ (20 mL). The layers were separated. The aqueous layer was extracted with EtOAc (2×30 mL), the combined organic extracts dried ($MgSO_4$) and concentrated. The residue was purified by SGC using EtOAc:hexane (gradient elution up to 8:92, v/v) to give (III-d) as a white foam (345 mg, 55%); $^1H$ NMR (400 MHz, $CDCl_3$) δ 0.002 (9H, s), 0.97 (t, J=8.3 Hz, 2H), 3.58 (t, J=8.3 Hz, 2H), 5.69 (s, 2H), 7.30 (m, 6H), 7.40 (m, 9H), 7.46 (s, 1H), 7.65 (s, 1H), 7.98 (d, J=0.7 Hz, 1H), 8.06 (d, J=2.1 Hz, 1H), 8.41 (d, J=2.2 Hz, 1H).

Synthesis of Bromide (III-e)

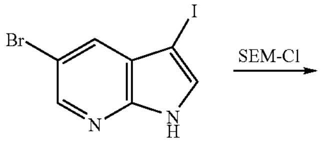

2

-continued

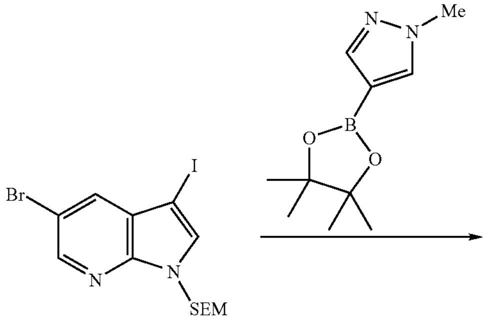

(IV-b)

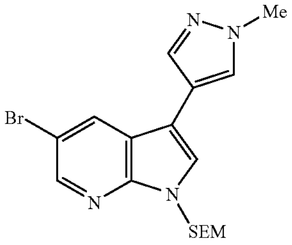

(III-e)

5-Bromo-3-iodo-1-(2-trimethylsilanyl-ethoxymethyl)-1H-pyrrolo[2,3-b]pyridine (IV-b)

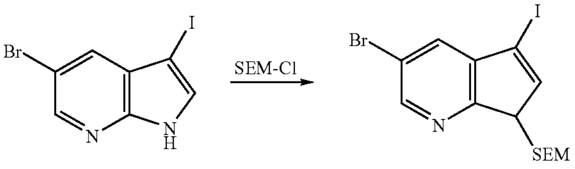

2 (IV-b)

To a solution of 2 (15.0 g, 46.4 mmol; preparation disclosed in WO2004/078756) in DMF (100 mL) was added sodium hydride (2.79 g, 69.7 mmol, 60% in mineral oil) portionwise over 15 min at RT and then the reaction mixture stirred for 0.5 h. 2-(Trimethylsilyl)-ethoxymethyl chloride (SEM-Cl; 12.33 mL, 69.7 mmol) was added in one portion and the reaction mixture stirred overnight. It was then poured onto a mixture of saturated aqueous ammonium chloride (350 mL) and EtOAc (150 mL), the layers were separated, and the aqueous phase was extracted with more EtOAc. The combined organic extracts were dried ($MgSO_4$) and concentrated. The crude product was purified by SGC using 5% EtOAc in hexane as eluent (gradient elution) to give (IV-b) (20.57 g, 98%) as an orange oil; $^1H$ NMR (400 MHz, $CDCl_3$) δ −0.048 (s, 9H), 0.91 (m, 2H), 3.53 (m, 2H), 5.62 (s, 2H), 7.47 (s, 1H), 7.87 (d, J=2.2 Hz, 1H), 8.36 (d, J=2.1 Hz, 1H).

5-Bromo-3-(1-methyl-1H-pyrazol-4-yl)-1-(2-trimethylsilanyl-ethoxymethyl)-1H-pyrrolo[2,3-b]pyridine (III-e)

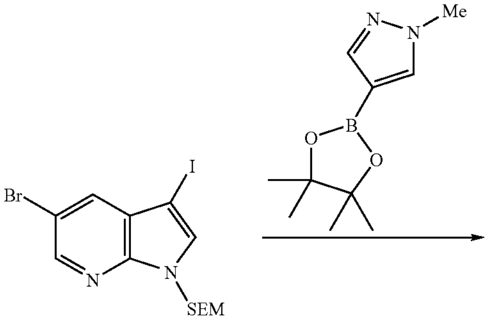

(IV-b)

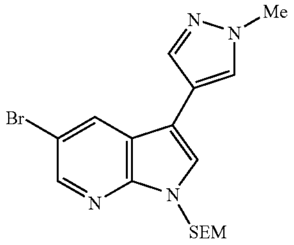

(III-e)

A mixture of iodide (IV-b) (20.0 g, 44.1 mmol), 1-methyl-4-(4,4,5,5-tetramethyl-1,3,2-dioxaborolan-2-yl)-1H-pyrazole (10.10 g, 48.6 mmol), LiCl (5.61 g, 132.4 mmol), $Pd(PPh_3)_2Cl_2$ (1.55 g, 2.21 mmol) and 1 M aqueous $Na_2CO_3$ solution (110 mL), in toluene (110 mL) and EtOH (110 mL) was reacted at reflux for 3 h following the general procedure B for the Suzuki reaction. The crude product was isolated by SGC using 50% EtOAc in hexane as eluent (gradient elution) to give (III-e) as a light orange oil (10.61 g, 59%); $^1$H NMR (400 MHz, $CDCl_3$) δ −0.053 (s, 9H), 0.92 (m, 2H), 3.55 (m, 2H), 3.99 (s, 3H), 5.66 (s, 2H), 7.43 (s, 1H), 7.62 (s, 1H), 7.73 (d, J=0.5 Hz, 1H), 8.13 (d, J=2.2 Hz, 1H), 8.38 (d, J=2.2 Hz, 1H).

1-Benzenesulfonyl-5-bromo-3-(1H-pyrazol-4-yl)-1H-pyrrolo[2,3-b]pyridine (III-g)

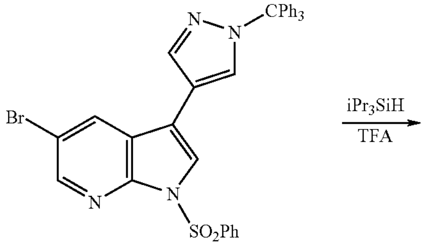

(III-f)

-continued

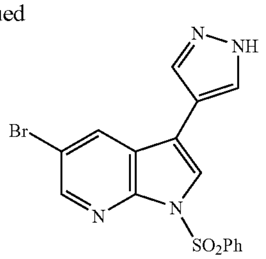

(III-g)

A mixture of azaindole (III-f) (500 mg, 0.774 mmol; preparation disclosed in WO2004/078756), triisopropylsilane (0.43 mL, 2.1 mmol), water (2 drops) and trifluoroacetic acid (1.85 mL, 24 mmol) in $CH_2Cl_2$ (4.4 mL), was stirred vigorously at RT for a period of 1 h 15 min. The reaction was quenched by the addition of $Et_3N$ (2.5 mL) to afford a yellow suspension, which was partitioned between saturated aqueous $NaHCO_3$/EtOAc. The aqueous layer was extracted with EtOAc. Combined organic solutions were dried over $MgSO_4$, concentrated to dryness. The residual solid was washed by MeOH and filtered off to afford (III-g) (241 mg, 77% yield); $^1$H NMR (400 MHz; $CDCl_3$) δ 7.44 (tt, J=8.01 Hz, 1.75 Hz, 2H), 7.53 (tt, J=7.38 Hz, 1.25 Hz, 1H), 7.75 (s, 1H), 7.77 (s, 2H), 8.03 (d, J=2.18 Hz, 1H), 8.11 (dd, J=7.28 Hz, 1.99 Hz, 2H), 8.41 (d, J=2.05 Hz, 1H). MS (CI) m/z ($MH^+$).

1-Benzenesulfonyl-5-bromo-3-(1-difluoromethyl-1H-pyrazol-4-yl)-1H-pyrrolo[2,3-b]pyridine (III-h)

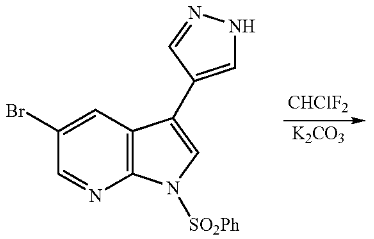

(III-g)

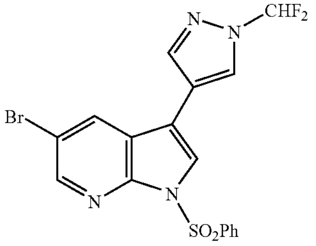

(III-h)

Gaseous $CHClF_2$ (39 g, 0.45 mol) was introduced over a period of 16 min into a heated (90° C.) and stirred mixture of azaindole (III-g) (241 mg, 0.597 mmol) and $K_2CO_3$ (249.3 mg, 1.804 mmol) in DMF (4 mL). The mixture was then stirred at 90° C. for a further 2 h and the mixture was partitioned between EtOAc-water. The aqueous layer was extracted with EtOAc. Combined organic solutions were dried ($MgSO_4$), concentrated and separated by LCMS (column LUNA 10μ C18(2) 00G-4253-V0 250×50 mm) using water—MeCN (0.1% AcOH) as eluent (in gradient; flow 80 mL/min; retention time 29 min) to give (III-h) (24.60 mg, 9%); $^1$H NMR (400 MHz; $CDCl_3$) δ 7.54 (t, J=60.56, 1H), 7.56-7.61 (m, 2H), 7.66-7.72 (m, 1H), 8.17-8.21 (m, 3H), 8.22 (s, 1H), 8.43 (d, J=2.11 Hz, 1H), 8.47 (d, J=2.03 Hz, 1H), 8.61 (d, J=0.53 Hz, 1H). MS (CI) m/z 453/5 ($MH^+$).

5-Bromo-3-iodo-1-(2-trimethylsilanyl-ethoxymethyl)-1H-pyrrolo[2,3-b]pyridine (IV-b)—See Preparation of (III-e)

Synthesis of Boronate (V-c)

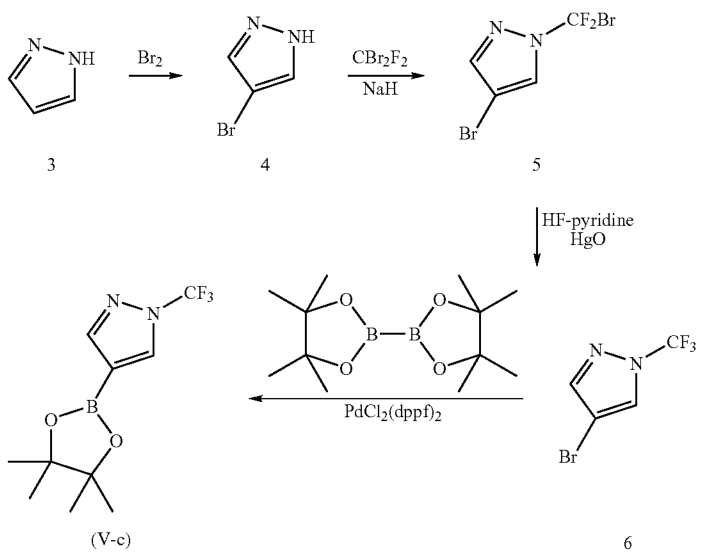

3 4 5

(V-c) 6

4-bromo-1H-pyrazole (4)

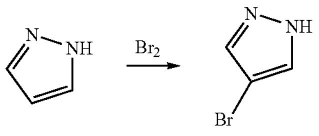

3 4

Bromine (76.4 mL, 1.49 mol) was added dropwise over a period of 2 h to a stirred and cooled (<15° C.; ice bath cooling) solution of pyrazole 3 (97.26 g, 1.43 mol) in water (450 mL). The mixture was stirred for additional 1 h, cooled to 10° C. Excess of acid was neutralized with 50% aqueous NaOH (total of about 120 mL) followed by saturated aqueous $NaHCO_3$ (150 mL). The solid was filtered off, washed with cold water (300 mL) and dried in vacuum overnight to afford 4 (196.49 g, 94%) as white-pink powder. $^1$H NMR (400 MHz, $CDCl_3$) δ 7.60 (s, 2H), 11.70 (bs, 1H).

4-bromo-1-(bromodifluoromethyl)-1H-pyrazole (5)

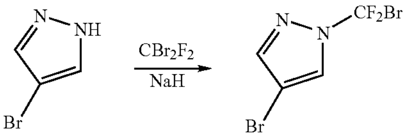

4 5

60% suspension of NaH in oil (19.2 g, 0.48 mol) was washed with hexane (3×150 mL), suspended in DMF (200 mL) and cooled to 0° C. under $N_2$. Then, a solution of bromide 4 (61.7 g, 0.42 mol) in DMF (80 mL) was added dropwise over a period of 30 min while maintaining the temperature of the mixture below 0° C. (acetone-dry ice bath at −10° C.). The mixture was stirred at 0° C. for 5 min and a solution of $CBr_2F_2$ (47.4 mL, 0.515 mol) in DMF (60 mL) was added dropwise at <0° C. over a period of 30 min. Cooling bath was removed and the mixture was stirred for 2 h at RT. Reaction mixture was carefully poured into water (1 L) and extracted with ether (4×400 mL). Combined organic extracts were washed with water (3×200 mL), dried ($MgSO_4$), and concentrated to afford crude 5 (125.68 g) as an orange liquid. A portion of this product (122.73 g) was distilled under reduced pressure to afford 5 (72.68 g, 64%) as colourless liquid b.p. 84-90° C./30 mm Hg. $^1$H NMR (400 MHz, $CDCl_3$) δ 7.76 (s, 1H), 7.88 (s, 1H). Some (about 9% mol) contaminants giving rise to signals at δ 7.60 and 7.68 were also present.

4-bromo-1-(trifluoromethyl)-1H-pyrazole (6)

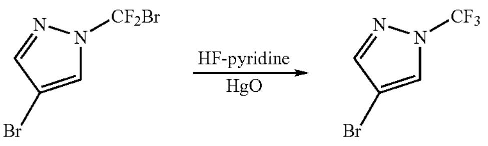

5 6

HF-pyridine complex (129 mL) was added to a stirred and cooled (ice bath) solution of bromide 5 (72.68 g, 0.263 mol) in diisopropyl ether (196 mL) in a polypropylene reaction vessel. Mercuric oxide red (48.4 g, 0.222 mol) was then added in small portions over a period of 3 h at RT. The mixture was stirred for additional 4 h at RT and was poured onto a 25% aqueous KF (650 mL). The solid was filtered off and washed with ether (100 mL). The filtrate was extracted with ether (3×100 mL). Combined extracts were dried ($MgSO_4$), concentrated under reduced pressure and distilled to afford 6 (31.05 g, 55%) as colourless liquid b.p. 35-37° C./25 mm Hg, which crystallized on standing in a refrigerator, m.p. 4° C. $^1$H NMR (400 MHz, $CDCl_3$) δ 7.73 (s, 1H), 7.86 (s, 1H).

4-(4,4,5,5-tetramethyl-1,3,2-dioxaborolan-2-yl)-1-(trifluoromethyl)-1H-pyrazole (V-c)

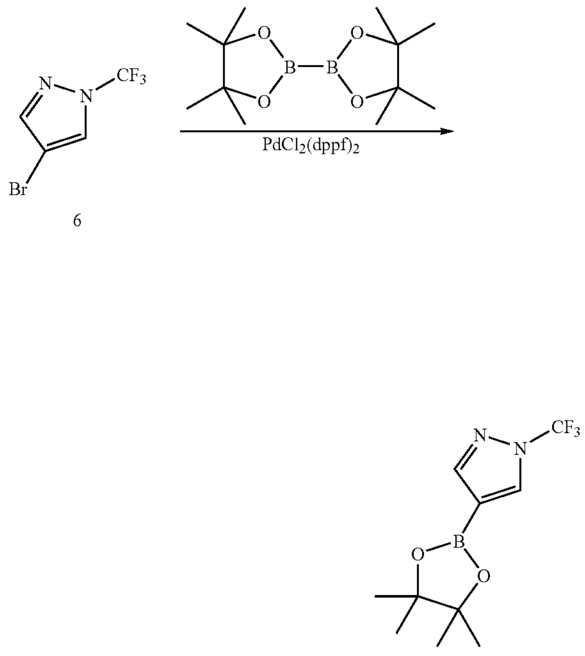

6

(V-c)

The compound was prepared using the general procedure for the synthesis of boronic pinacol esters. Bromide 6 (0.89 g, 4.14 mmol), bis(pinacolato)diboron (1.57 g, 6.2 mmol), $PdCl_2(dppf)_2.CH_2Cl_2$ (38.9 mg, 0.05 mmol) and AcOK (1.22 g, 12.4 mmol) in DMF (24 mL) was stirred under $N_2$ at 80° C. for 16 h. More $PdCl_2(dppf)_2.CH_2Cl_2$ (38.9 mg, 0.05 mmol) was added and stirring continued overnight. The mixture was cooled and partitioned between water (50 mL) and ether (20 mL). The aqueous layer was extracted with ether (4×30 mL). Combined organic solutions were washed with water (10 mL), dried ($MgSO_4$), concentrated and dried in vacuum to afford crude (V-c) (1.47 g) as dark brown semisolid, which was used in further steps without additional purification. The product contains two peaks in $^{19}$F NMR (376 MHz, $CDCl_3$) at δ −60.72 ppm and −60.87 in about 3:1 ratio corresponding to the desired product and an impurity. Data for (V-c): $^1$H NMR (400 MHz, $CDCl_3$) δ 1.33 (s, 12H), 7.97 (s, 1H), 8.12 (s, 1H).

Synthesis of Boronic Ester (VIb-27)

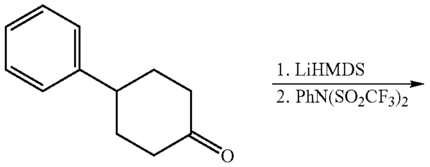

(VII-a)

-continued

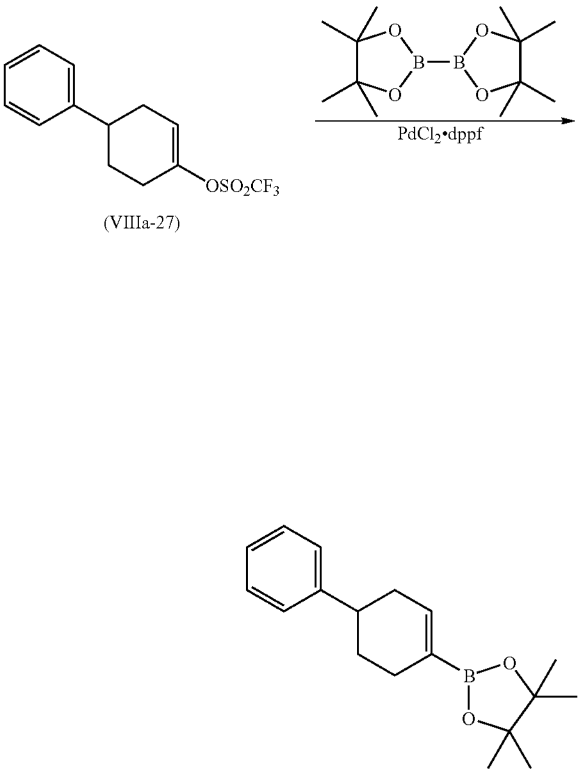

(VIIIa-27)

(VIb-27)

4-Phenylcyclohex-1-enyl trifluoromethanesulfonate (VIIIa-27)

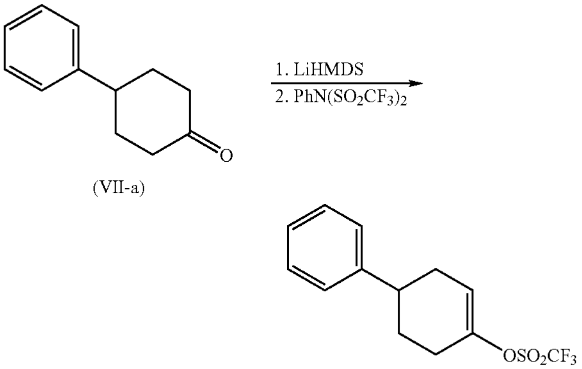

(VII-a)

(VIIIa-27)

Compound (VIIIa-27) was prepared using the general procedure for the synthesis of enol triflates using 4-phenylcyclohexanone (VII-a) (2.21 g, 12.72 mmol), 1 M solution of LiHMDS in THF (15.26 mL, 15.26 mmol) and N-phenylbis (trifluoromethanesulfinimide) (5.00 g, 13.99 mmol) in dry THF (63.6 mL). The crude product was purified by column chromatography on alumina (Neutral, Grade I) and 7:1 hexane:EtOAc (v/v) as the eluent to give (VIIIa-27) (3.06 g, 78%) as a colourless oil. $^1$H NMR (400 MHz, $CDCl_3$) δ 1.92-2.03

(m, 1H), 2.05-2.13 (m, 1H), 2.30-2.62 (m, 4H), 2.82-2.91 (m, 1H), 5.85-5.88 (m, 1H), 7.17-7.25 (m, 3H), 7.28-7.33 (m, 2H).

4,4,5,5-tetramethyl-2-(4-phenylcyclohex-1-enyl)-1,3,2-dioxaborolane (VIb-27)

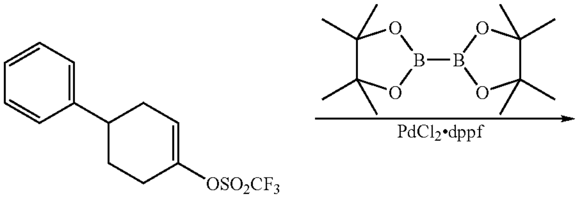

(VIIIa-27)

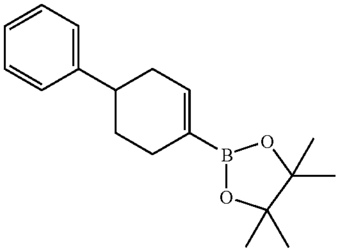

(VIb-27)

The compound was prepared using the general procedure for the synthesis of boronic pinacol esters. The triflate (VIIIa-27) (2.00 g, 6.53 mmol), bis(pinacolatodiboron) (2.48 g, 9.79 mmol), potassium acetate (1.92 g, 19.59 mmol) and dichloro [1,1'-bis(diphenylphosphino)ferrocene]palladium (II) dichloromethane adduct (0.27 g, 0.33 mmol) in DMF (33 mL) was stirred at 85° C. for 10 h. The crude product was purified by SGC using EtOAc:hexane=1:7 (v/v) as eluent to give (VIb-27) (1.35 g, 73%) as a yellow oil; $^1$H NMR (400 MHz, $CDCl_3$) δ 1.29 (s, 12H), 1.65-1.77 (m, 1H), 1.92-2.01 (m, 1H), 2.18-2.47 (m, 4H), 2.74-2.84 (m, 1H), 6.66-6.69 (m, 1H), 7.17-7.25 (m, 3H), 7.28-7.33 (m, 2H).

Synthesis of Boronic Ester (VIb-28)

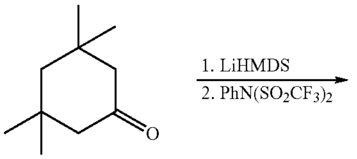

(VII-b)

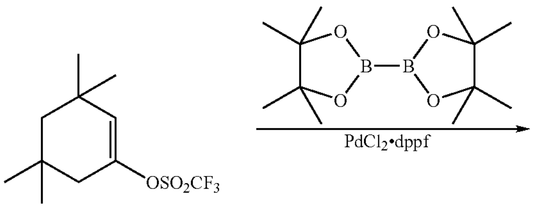

(VIIIa-28)

-continued

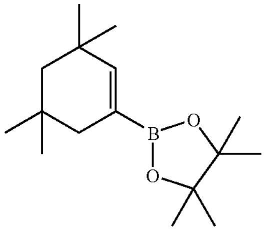

(VIb-28)

3,3,5,5-tetramethylcyclohex-1-enyl trifluoromethanesulfonate (VIIIa-28)

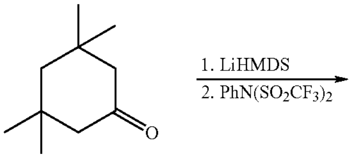

(VII-b)

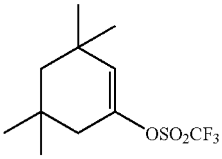

(VIIIa-28)

Compound (VIIIa-28) was prepared using the general procedure for the synthesis of enol triflates using 3,3,5,5-tetramethylcyclohexanone (VII-b) (1.96 g, 12.72 mmol), 1 M solution of LiHMDS in THF (15.26 mL, 15.26 mmol) and N-phenylbis(trifluoromethanesulfinimide) (5.00 g, 13.99 mmol) in dry THF (63.6 mL). The crude product was purified by column chromatography on alumina (Neutral, Grade I) and 7:1 hexane:EtOAc (v/v) as the eluent to give (VIIIa-28) (2.40 g, 66%) as a pale yellow oil. $^1$H NMR (400 MHz, $CDCl_3$) δ 1.05 (s, 6H), 1.10 (s, 6H), 1.36 (s, 2H), 2.10 (d, J=1.2 Hz, 2H), 5.53 (t, J=1.2 Hz, 1H).

4,4,5,5-tetramethyl-2-(3,3,5,5-tetramethylcyclohex-1-enyl)-1,3,2-dioxaborolane (VIb-28)

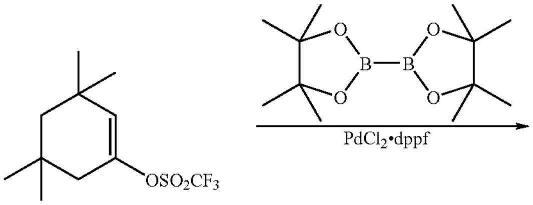

(VIIIa-28)

-continued

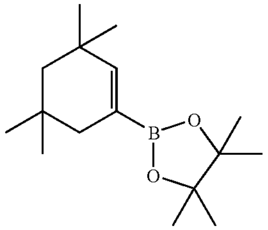

(VIb-28)

The compound was prepared using the general procedure for the synthesis of boronic pinacol esters. Triflate (VIIIa-28) (2.40 g, 8.38 mmol), bis(pinacolatodiboron) (3.19 g, 12.57 mmol), potassium acetate (2.47 g, 125.14 mmol) and dichloro [1,1'-bis(diphenylphosphino)ferrocene]palladium (II) dichloromethane adduct (0.34 g, 0.42 mmol) in DMF (42 mL) was stirred at 85° C. for 8 h. The crude product was purified by SGC using EtOAc:hexane=1:10 (v/v) as eluent to give (VIb-28) (1.05 g, 47%) as a yellow oil; $^{1}H$ NMR (400 MHz, $CDCl_3$) δ 0.93 (s, 6H), 1.02 (s, 6H), 1.28 (s, 12H), 1.32 (s, 2H), 1.85 (d, J=1.8 Hz, 2H), 6.25 (t, J=1.7 Hz, 1H).

Synthesis of Boronic Ester (VIb-29)

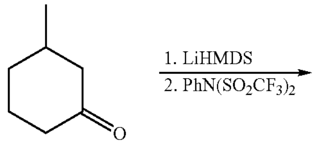

(VII-c)

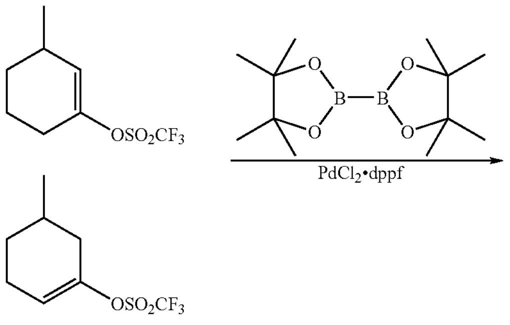

(VIIIa-29)

-continued

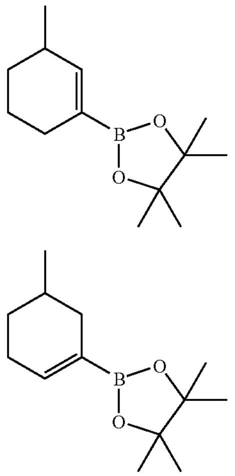

(VIb-29)

Mixture (VIIIa-29) of 5-methylcyclohex-1-enyl trifluoromethanesulfonate and 3-methylcyclohex-1-enyl trifluoromethanesulfonate

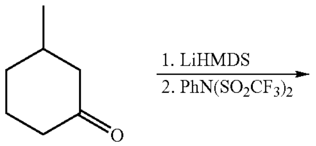

(VII-c)

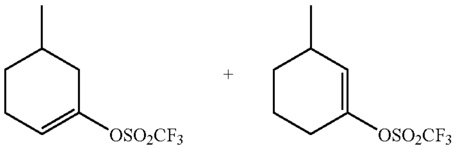

(VIIIa-29)

Mixture (VIIIa-29) was prepared using the general procedure for the synthesis of enol triflates using 3-Methylcyclohexanone (VII-c) (1.54 mL, 12.72 mmol), 1 M solution of LiHMDS in THF (15.26 mL, 15.26 mmol) and N-phenylbis (trifluoromethanesulfinimide) (5.00 g, 13.99 mmol) in dry THF (63.4 mL). The crude product was purified by column chromatography on alumina (Neutral, Grade I) and 8:1 hexane:EtOAc (v/v) as the eluent to give (VIIIa-29) (1.94 g, 62%) as a mixture of regioisomers in 2.7:1 ratio and as a yellow liquid. $^{1}H$ NMR (400 MHz, $CDCl_3$) δ 1.04 (d, J=6.6 Hz, 3H, major isomer), 1.06 (d, J=7.1 Hz, 3H, minor isomer), 1.65-2.05 (m, 8H), 2.18-2.25 (m, 3H), 2.26-2.46 (m, 3H), 5.61-5.63 (m, 1H, minor isomer) 5.73-5.76 (m, 1H, major isomer).

Mixture (VIb-29) of 4,4,5,5-tetramethyl-2-(5-methylcyclohex-1-enyl)-1,3,2-dioxaborolane and 4,4,5,5-tetramethyl-2-(3-methylcyclohex-1-enyl)-1,3,2-dioxaborolane

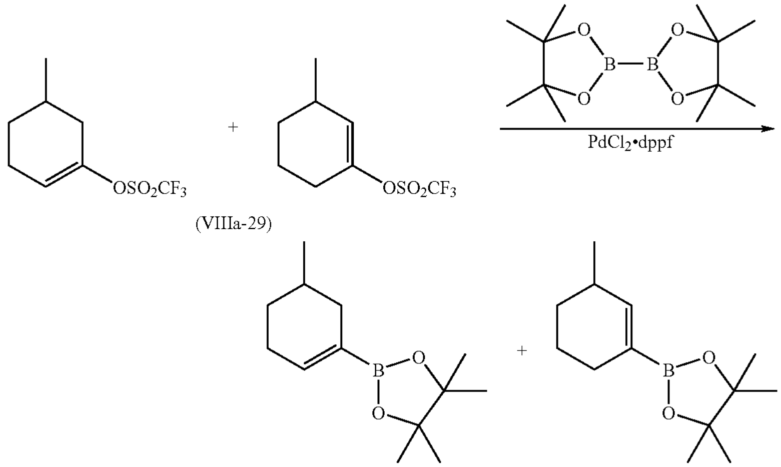

(VIIIa-29)

(VIb-29)

The compound was prepared using the general procedure for the synthesis of boronic pinacol esters. Mixture of triflates (VIIIa-29) (1.94 g, 7.94 mmol), bis(pinacolatodiboron) (3.02 g, 11.91 mmol), potassium acetate (2.34 g, 23.82 mmol) and dichloro[1,1'-bis(diphenylphosphino)ferrocene]palladium (II) dichloromethane adduct (0.32 g, 0.40 mmol) in DMF (40 mL) was stirred at 85° C. for 12 h. The crude product was purified by SGC using EtOAc:hexane=1:8 (v/v) as eluent to give (VIb-29) (1.01 g, 57%) as a yellow oil; a 2.7:1 mixture of regioisomers. $^1H$ NMR (400 MHz, $CDCl_3$) δ 0.95 (d, J=6.4 Hz, 3H, major isomer), 1.01 (d, J=7.2 Hz, 3H, minor isomer), 1.27 (s, 12H), 1.55-1.81 (m, 8H), 2.00-2.28 (m, 6H), 6.39-6.41 (m, 1H, minor isomer) 6.54-6.59 (m, 1H, major isomer).

Synthesis of Boronic Ester (VIb-30)

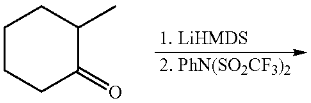

(VII-d)

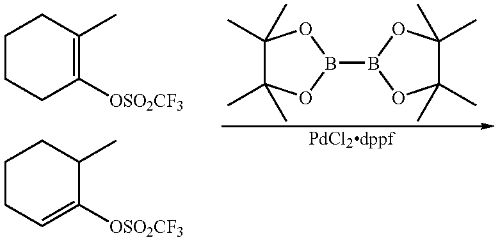

(VIIIa-30)

-continued

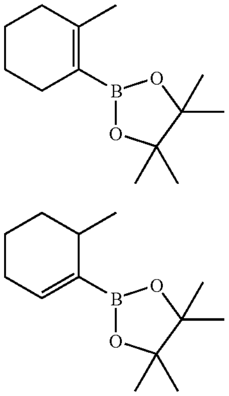

(VIb-30)

Mixture (VIIIa-30) of 6-methylcyclohex-1-enyl trifluoromethanesulfonate and 2-methylcyclohex-1-enyl trifluoromethanesulfonate

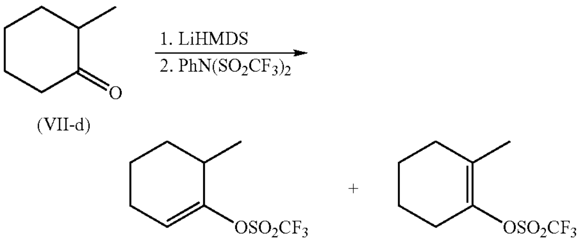

(VII-d)

(VIIIa-30)

Mixture (VIIIa-30) was prepared using the general procedure for the synthesis of enol triflates using 2-methylcyclohexanone (VII-d) (1.54 mL, 12.72 mmol), 1 M solution of LiHMDS in THF (15.26 mL, 15.26 mmol) and N-phenylbis (trifluoromethanesulfinimide) (5.00 g, 13.99 mmol) in dry THF (63.6 mL). The crude product was purified by column chromatography on alumina (Neutral, Grade I) and 8:1 hexane:EtOAc (v/v) as the eluent to give product (VIIIa-30) (2.33 g, 75%) as as a mixture of regioisomers in 12.5:1 ratio; yellow oil.

major isomer $^1$H NMR (400 MHz, $CDCl_3$) 1.15 (d, J=6.1 Hz, 3H), 1.43-1.73 (m, 3H), 1.90-1.98 (m, 1H), 2.15-2.21 (m, 2H), 2.50-2.60 (m, 1H), 5.74 (dt, J=1.4 and 4.1 Hz, 1H).

minor isomer $^1$H NMR (400 MHz, $CDCl_3$) δ 1.55 (s, 3H), 1.74-1.78 (m, 4H), 2.10-2.14 (m, 2H), 2.28-2.34 (m, 2H).

Mixture (VIb-30) of 4,4,5,5-tetramethyl-2-(6-methylcyclohex-1-enyl)-1,3,2-dioxaborolane and 4,4,5,5-tetramethyl-2-(2-methylcyclohex-1-enyl)-1,3,2-dioxaborolane

Synthesis of Boronic Ester (VIb-31)

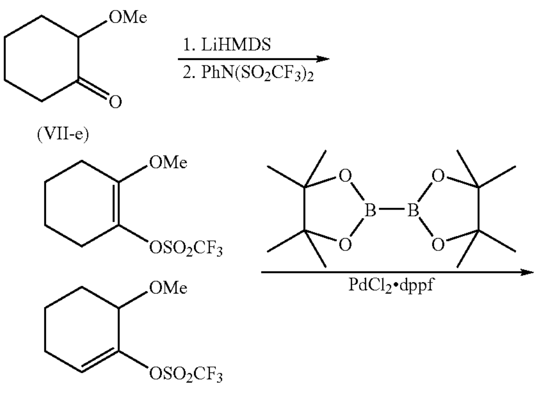

(VII-e)

(VIIIa-31)

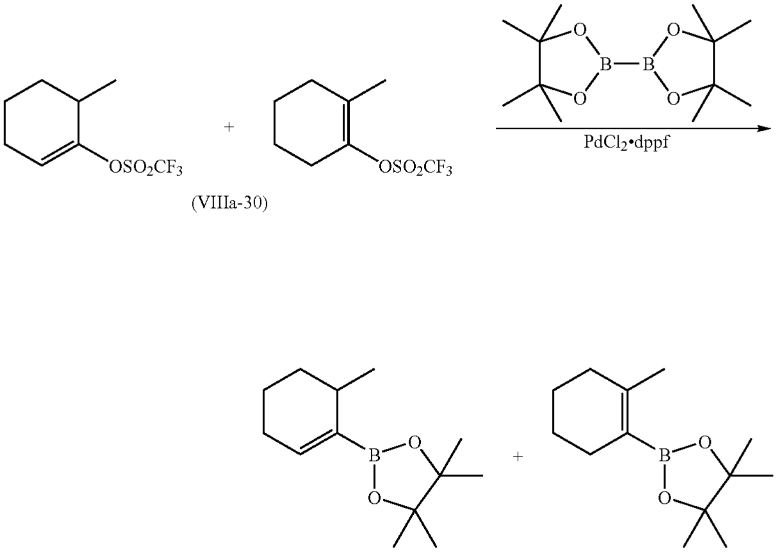

(VIIIa-30)

(VIb-30)

The compound was prepared using the general procedure for the synthesis of boronic pinacol esters. Mixture of triflates (VIIIa-30) (2.29 g, 9.37 mmol), bis(pinacolatodiboron) (3.57 g, 14.06 mmol), potassium acetate (2.76 g, 28.11 mmol) and dichloro[1,1'-bis(diphenylphosphino)ferrocene]palladium (II) dichloromethane adduct (0.38 g, 0.47 mmol) in DMF (47 mL) was stirred at 85° C. for 8 h. The crude product was purified by SGC using EtOAc:hexane=1:8 (v/v) as eluent to give (VIb-30) (1.32 g, 63%) as a yellow oil.

Data for major isomer: $^1$H NMR (400 MHz, $CDCl_3$) δ 1.05 (d, J=7.0 Hz, 3H), 1.26 (s, 12H), 1.46-1.55 (m, 2H), 1.57-1.71 (m, 3H), 2.01-2.07 (m, 2H), 2.33-2.42 (m, 1H), 6.53 (dt, J=1.6 and 3.6 Hz, 1H). Unable to give data for minor isomer as the peaks are overlapping.

-continued

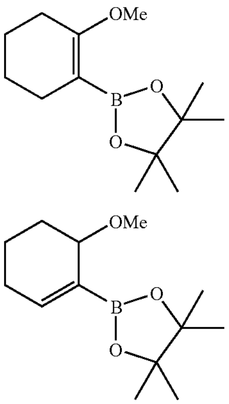

(VIb-31)

Mixture (VIIIa-31) of 6-methoxycyclohex-1-enyl trifluoromethanesulfonate and 2-methoxycyclohex-1-enyl trifluoromethanesulfonate

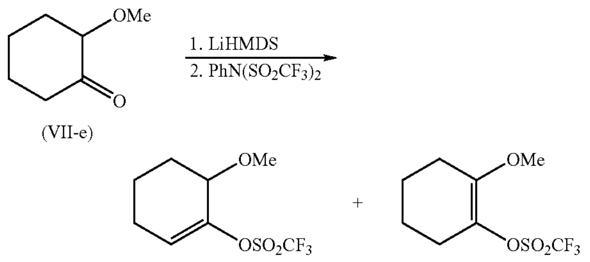

(VII-e)

(VIIIa-31)

Mixture 18 was prepared using the general procedure for the synthesis of enol triflates using 2-methoxycyclohexanone (VII-e) (1.63 g, 12.72 mmol), 1 M solution of LiHMDS in THF (15.26 mL, 15.26 mmol) and N-phenylbis(trifluoromethanesulfinimide) (5.00 g, 13.99 mmol) in dry THF (63.4 mL). The crude product was purified by column chromatography on alumina (Neutral, Grade I) and 10:1 hexane: EtOAc (v/v) as the eluent to give product (VIIIa-31) (2.75 g, 83%) as a mixture of regioisomers in 2.55:1 ratio; yellow oil.

Major isomer: $^1$H NMR (400 MHz, $CDCl_3$) δ 1.70-1.75 (m, 4H), 2.30-2.34 (m, 4H), 3.62 (s, 3H)

Minor isomer $^1$H NMR (400 MHz, $CDCl_3$) δ 1.59-1.64 (m, 1H), 1.83-1.88 (m, 1H), 2.00-2.04 (m, 1H), 2.23-2.27 (m, 1H), 3.42 (s,3H), 3.73-3.77 (m, 1H), 3.82-3.86 (m, 1H), 5.94 (dd, J=3.3 and 4.9 Hz, 1H).

Mixture (VIb-31) of 2-(6-methoxycyclohex-1-enyl)-4,4,5,5-tetramethyl-1,3,2-dioxaborolane and 2-(2-methoxycyclohex-1-enyl)-4,4,5,5-tetramethyl-1,3,2-dioxaborolane

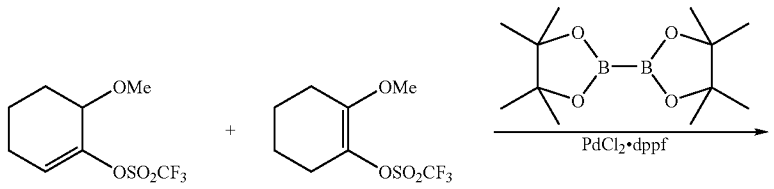

(VIIIa-31)

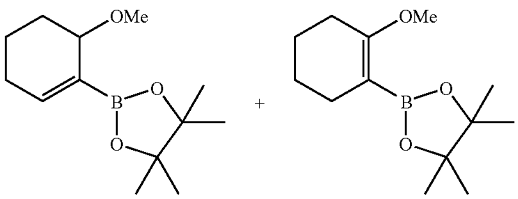

(VIb-31)

The compound was prepared using the general procedure for the synthesis of boronic pinacol esters. Mixture of triflates (VIIIa-31) (2.75 g, 10.56 mmol), bis(pinacolatodiboron) (4.00 g, 15.85 mmol), potassium acetate (3.11 g, 31.68 mmol) and dichloro[1,1'-bis(diphenylphosphino)ferrocene]palladium (II) dichloromethane adduct (0.43 g, 0.53 mmol) in DMF (52.8 mL) was stirred at 85° C. for 6 h. The crude product was purified by SGC using EtOAc:hexane=1:7 (v/v) as eluent to give (VIb-31) (1.26 g, 50%) as a white solid.

Data for major isomer: $^1$H NMR (400 MHz, $CDCl_3$) δ 1.26 (s, 12H), 1.46-1.57 (m, 4H), 2.09-2.19 (m, 4H), 3.58 (s, 3H)

Data for minor isomer $^1$H NMR (400 MHz, $CDCl_3$) δ 1.26 (s, 12H), 1.52-1.57 (m, 1H), 1.64-1.74 (m, 2H), 1.84-1.92 (m, 1H), 1.94-2.04 (m, 1H), 2.09-2.19 (m, 1H), 3.38 (s, 3H), 3.84 (t, J=3.5 Hz, 1H), 6.67 (t, J=3.5 Hz, 1H).

Synthesis of Boronic Ester (VIb-68)

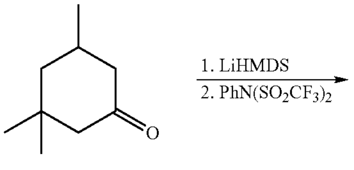

(VII-f)

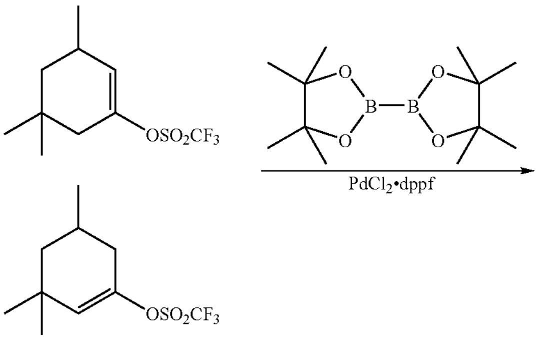

(VIIIa-68)

-continued

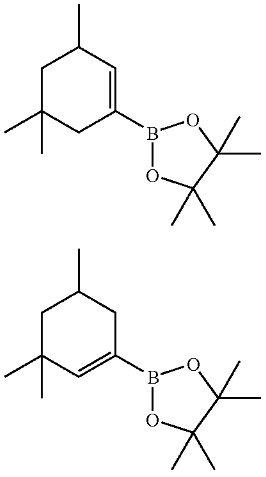

(VIb-68)

Mixture (VIIIa-68) of 3,3,5-trimethylcyclohex-1-enyl trifluoromethanesulfonate and 3,5,5-trimethylcyclohex-1-enyl trifluoromethanesulfonate

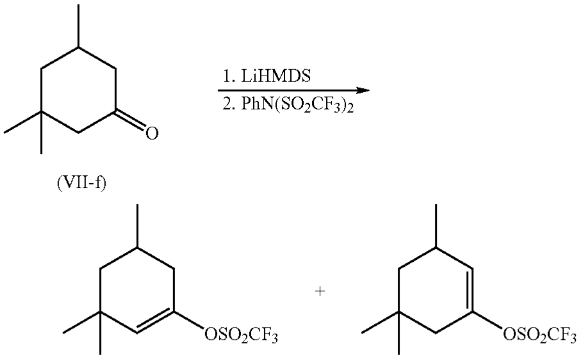

(VII-f)

(VIIIa-68)

Mixture (VIIIa-68) was prepared using the general procedure for the synthesis of enol triflates using 3,3,5-trimethylcyclohexanone (VII-f) (2.00 mL, 12.72 mmol), 1 M solution of LiHMDS in THF (15.26 mL, 15.26 mmol) and N-phenyl-bis(trifluoromethanesulfinimide) (5.00 g, 13.99 mmol) in dry THF (63.6 mL). The crude product was purified by column chromatography on alumina (Neutral, Grade I) and 7:1 hexane:EtOAc (v/v) as the eluent to give product (VIIIa-68) (2.57 g, 74%) as a 2.3:1 ratio of isomers; colourless oil. $^1$H NMR (400 MHz, $CDCl_3$) δ 0.96 (s, 3H, major), 1.03 (d, J=6.3 Hz, 3H, minor), 1.05 (d, J=6.1 Hz, 3H, major), 1.04 (s, 3H, minor), 1.06 (s, 3H, major), 1.07 (s, 3H, minor), 1.43-1.50 (m, 2H), 1.92-1.99 (m, 4H), 2.18-2.33 (m, 2H), 2.36-2.48 (m, 2H), 5.51 (s, 1H, minor), 5.59 (t, J=2.2 Hz, 1H, major).

Mixture (VIb-68) of 4,4,5,5-tetramethyl-2-(3,3,5-trimethylcyclohex-1-enyl)-1,3,2-dioxaborolane and 4,4,5,5-tetramethyl-2-(3,5,5-trimethylcyclohex-1-enyl)-1,3,2-dioxaborolane

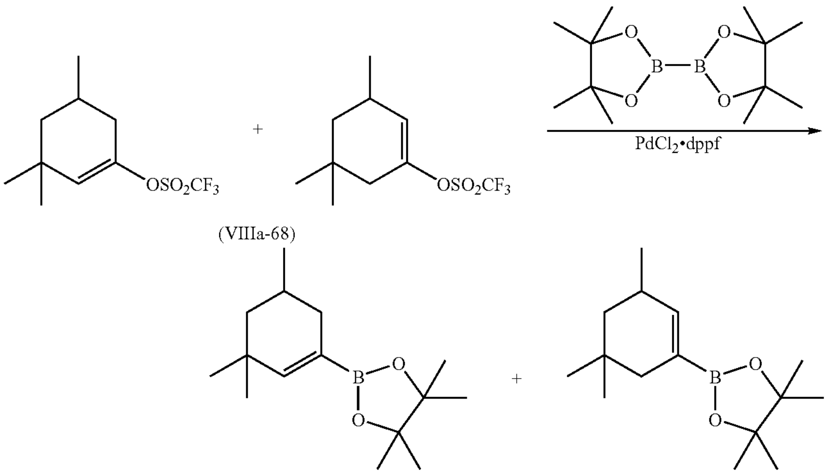

(VIb-68)

The compound was prepared using the general procedure for the synthesis of boronic pinacol esters. Mixture of triflates (VIIIa-68) (1.53 g, 5.62 mmol), bis(pinacolatodiboron) (2.14 g, 8.42 mmol), potassium acetate (1.65 g, 16.86 mmol) and dichloro[1,1'-bis(diphenylphosphino)ferrocene]palladium (II) dichloromethane adduct (0.46 g, 0.56 mmol) in DMF (28.1 mL) was stirred at 85° C. for 10 h. The crude product was purified SGC using EtOAc:hexane=1:10 (v/v) as eluent to give boronic ester (VIb-68) (1.02 g, 73%) as a mixture of isomers in 2.26:1 ratio; dark brown oil; $^{1}H$ NMR (400 MHz, $CDCl_3$) δ 0.89 (s, 3H, major), 0.93 (s, 3H, major), 0.92 (d, J=6.1 Hz, 3H, minor), 0.97 (s, 3H, minor), 0.99 (s, 3H, minor), 1.00 (d, J=7.2 Hz, 3H, major), 1.26 (s, 12H), 1.38-1.47 (m, 3H), 1.50-1.74 (m, 2H), 1.85-1.88 (m, 3H), 2.03-2.30 (m, 2H), 6.23 (s, 1H, minor), 6.36 (t, J=1.7 Hz, 1H, major).

Synthesis of Boronic Ester (VIb-75)

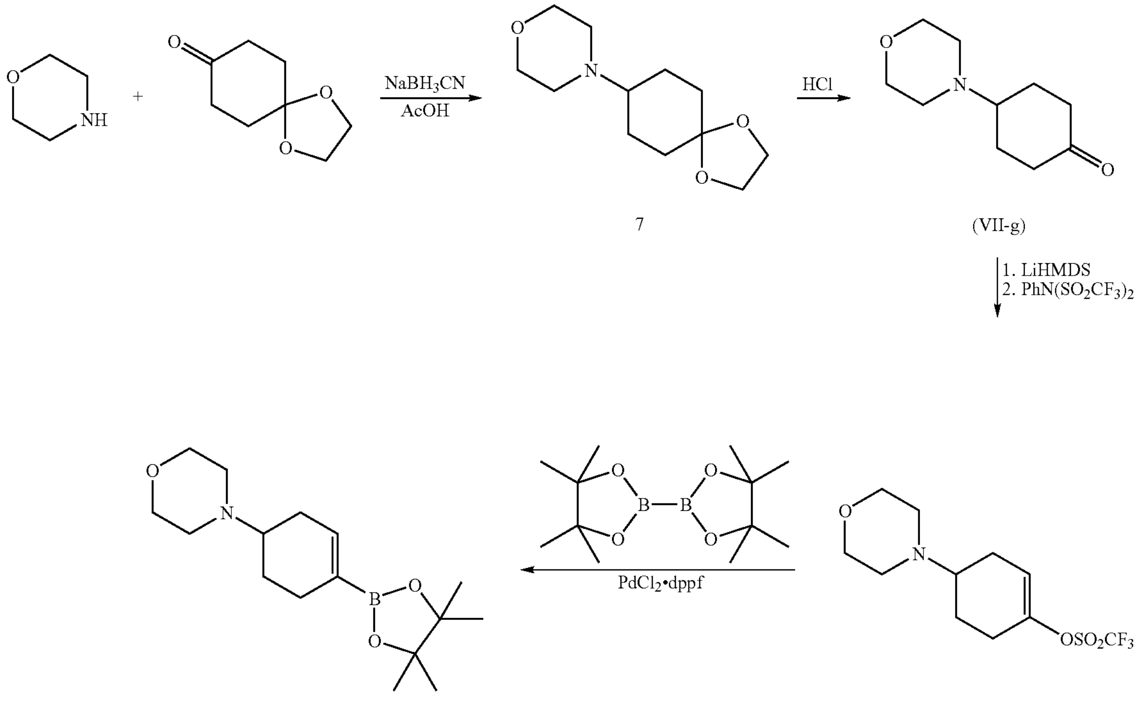

(VIb-75) (VIIIa-75)

4-(1,4-Dioxa-spiro[4.5]dec-8-yl)-morpholine (7)

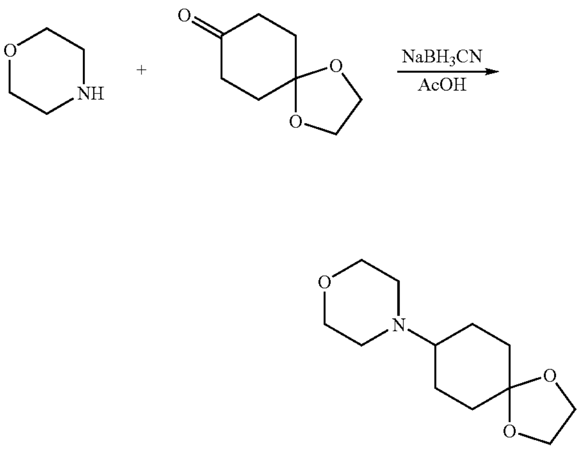

7

A mixture of 1,4-dioxaspiro[4.5]decan-8-one (10.0 g, 64.0 mmol), morpholine (20 mL) and AcOH (1.0 mL) was stirred for 2.5 h. Sodium cyanoborohydride (8.05 g, 128.0 mmol) was then added in one portion followed by more morpholine (15 mL). An exothermic reaction occurred and the mixture was cooled for 2 min with an ice-bath. Then the mixture was stirred at room temperature for 16 h. Ethanol (120 mL) and water (28 mL) were added to the resulting thick slurry and the white solid filtered, washed with ethanol (2×) and the filtrate concentrated. EtOAc was then added, the precipitate filtered off, washed with EtOAc and the filtrate concentrated. The residual oil was purified by Kugelrohr distillation to give 7 (9.03 g, 62%; b.p.140° C./0.05 mmHg) as a clear oil which solidifies on standing.

4-(1,4-Dioxa-spiro[4.5]dec-8-yl)-morpholine (7)—an Alternative Method

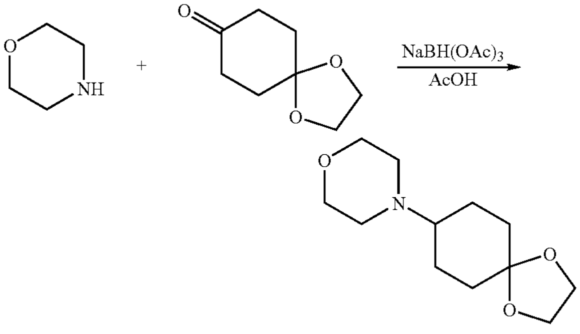

7

Sodium triacetoxyborohydride (382 g, 1.8 mol) was added in one portion to a mixture of 1,4-dioxaspiro[4.5]decan-8-one (200.0 g, 1.28 mol), morpholine (111.4 g, 1.28 mol) and glacial AcOH (73.2 mL, 1.28 mol) in 1,2-dichloroethane (4 L). A slightly exothermic reaction occurred accompanied by increase in temperature by 12° C. Then the mixture was stirred at room temperature overnight. The reaction was quenched by the addition of 10% aqueous NaOH (1.8 L) over a period of 20 min. The organic layer was separated, washed with brine (1 L), dried over $MgSO_4$ and concentrated to afford 7 (237.66 g) as white solid. The aqueous layer was extracted with EtOAc (4×300 mL). Combined extracts were washed with brine (1 L), dried over $MgSO_4$ and concentrated to furnish additional portion of 7 (44 g) as an off-white solid. Total yield of 7 (281.66 g, 97%). $^1$H NMR data identical with the data obtained earlier.

4-Morpholin-4-yl-cyclohexanone (VII-g)

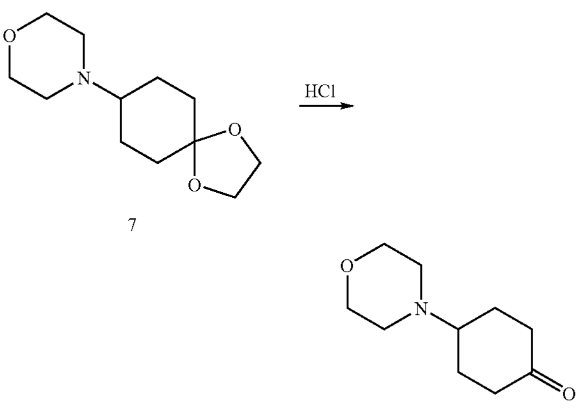

7

(VII-g)

To a solution of 7 (4.50 g, 19.8 mmol) in THF (100 mL) was added 7 N aqueous HCl (40 mL). The reaction mixture was stirred for 17 h and the reaction was quenched by pouring onto saturated aqueous $NaHCO_3$ (475 mL). The mixture was extracted with EtOAc (1×) then $CH_2Cl_2$ (3×) and the combined organic extracts dried ($MgSO_4$) and concentrated. The resulting oil was purified by Kugelrohr distillation to give (VII-g) (3.17 g, 87%) as a clear oil; $^1$H NMR (400 MHz, $CDCl_3$) δ 1.80-1.94 (m, 2H), 1.80-2.10 (m, 2H), 2.30 (m, 1H), 2.45-2.65 (m, 8H), 3.74 (t, J=4.7 Hz, 4H).

Trifluoromethanesulfonic acid 4-morpholin-4-yl-cyclohex-1-enyl ester (VIIIa-75)

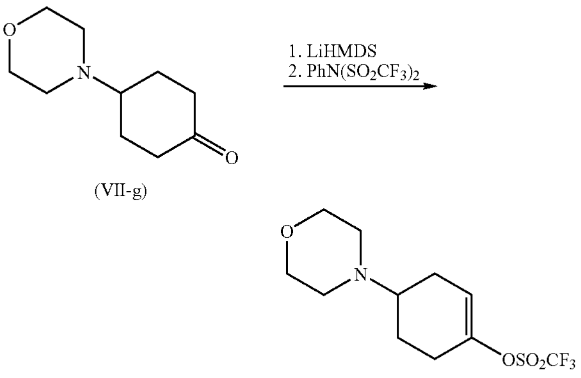

(VII-g)

(VIIIa-75)

Triflate (VIIIa-75) was prepared using the general procedure for the synthesis of enol triflates using ketone (VII-g) (5.30 g, 28.9 mmol), 1 M solution of LiHMDS in THF (34.7 mL, 34.7 mmol) and N-phenylbis(trifluoromethanesulfinimide) (11.37 g, 31.8 mmol) in dry THF (100 mL). The crude product was purified by SGC using EtOAc:hexane:$Et_3N$=39:60:1 (v/v/v) as eluent (gradient elution starting with 19:80:1) to give triflate (VIIIa-75) (7.66 g, 84%) as an orange oil; $^1H$ NMR (400 MHz, $CDCl_3$) δ 1.61-1.72 (m, 1H), 2.07 (m, 1H), 2.20 (m, 1H), 2.30-2.48 (m, 3H), 2.50-2.65 (m, 5H), 3.72 (t, J=4.7 Hz, 4H), 5.72 (m, 1H).

4-[4-(4,4,5,5-Tetramethyl-[1,3,2]dioxazolidin-2-yl)-cyclohex-3-enyl]-morpholine (VIb-75)

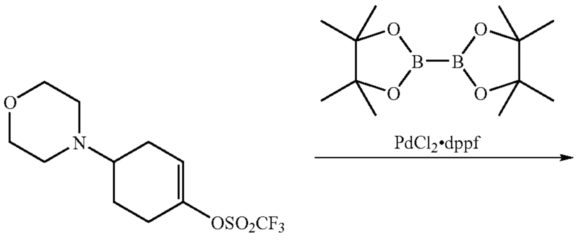

(VIIIa-75)

-continued

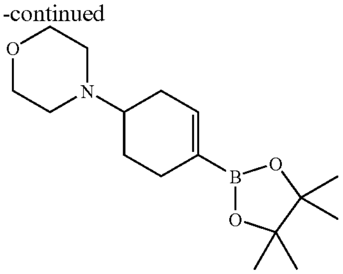

(VIb-75)

The compound was prepared using the general procedure for the synthesis of boronic pinacol esters. Triflate (VIIIa-75) (8.00 g, 25.4 mmol), bis(pinacolatodiboron) (9.66 g, 38.1 mmol), potassium acetate (7.47 g, 76.1 mmol) and dichloro [1,1'-bis(diphenylphosphino)ferrocene]palladium (II) dichloromethane adduct (1.04 g, 1.27 mmol) in DMF (110 mL) was stirred at 85° C. for 17 h. The crude product was purified by SGC using EtOAc:hexane=1:1 (v/v) as eluent (gradient elution) to give (VIb-75) (4.95 g, 67%) as a light orange solid; $^1H$ NMR (400 MHz, $CDCl_3$) δ 1.26 (s, 12H), 1.95-2.10 (m, 2H), 2.05-2.20 (m, 2H), 2.80-2.40 (m, 2H), 2.43-2.65 (m, 5H), 3.74 (t, J=4.7 Hz, 4H),6.51 (m, 1H).

Synthesis of Boronic Ester (VIb-134)

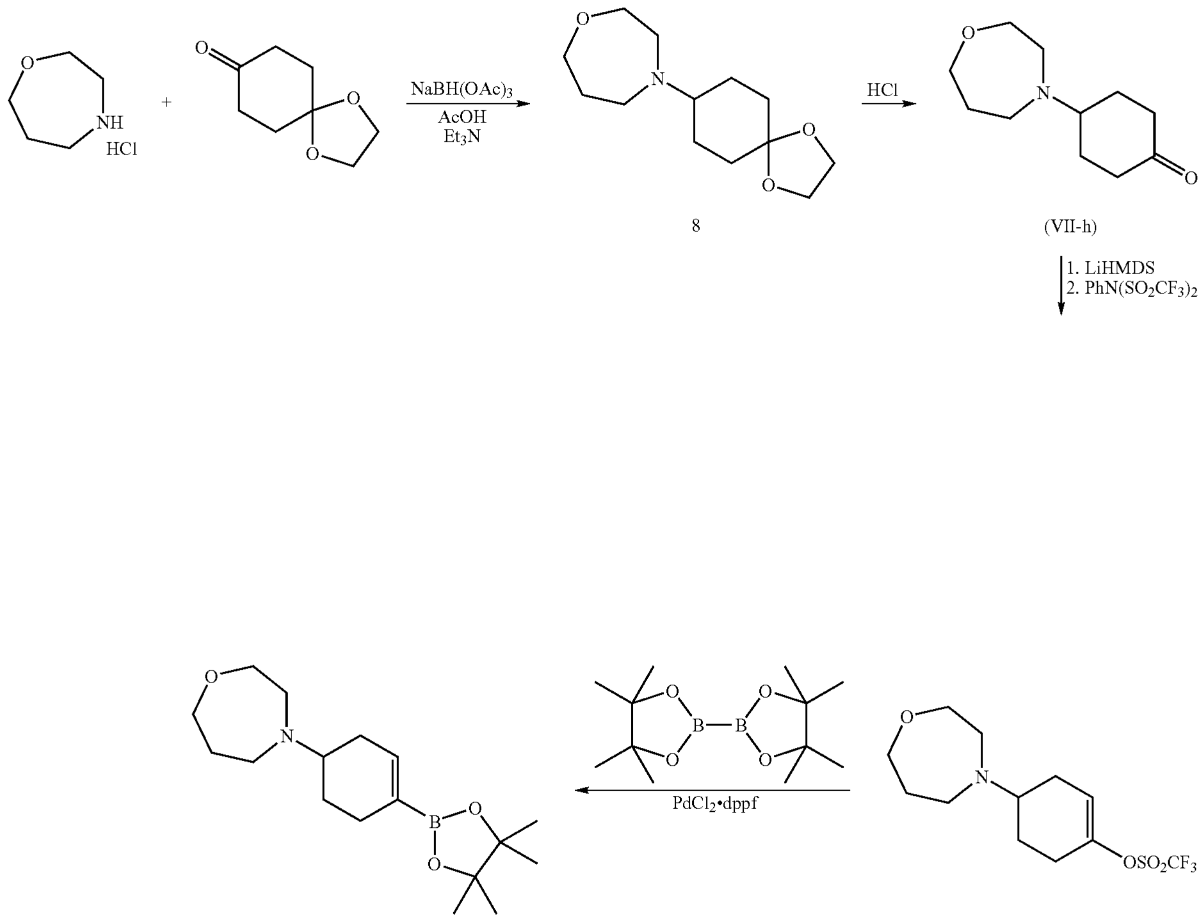

8

(VII-h)

(VIb-134)

(VIIIa-134)

4-(1,4-dioxaspiro[4.5]decan-8-yl)-1,4-oxazepane (8)

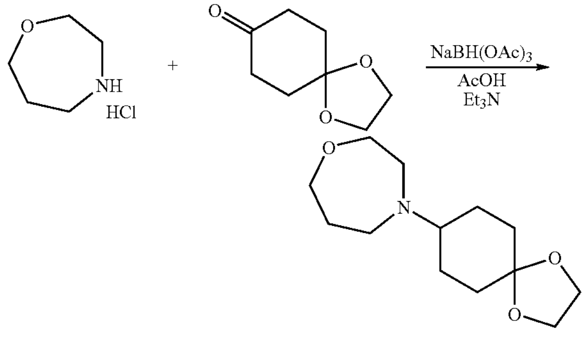

8

$Et_3N$ (96.9 mL, 0.695 mol) was added in one portion to a stirred suspension of homomorpholine hydrochloride (79.76 g, 0.579 mol) and 1,4-dioxaspiro[4.5]decan-8-one (90.5 g, 0.579 mol) in 1,2-dichloroethane (1.81 L). Then glacial acetic acid (34.8 mL, 0.607 mol) was added in one portion followed by solid $NaBH(OAc)_3$ (154 g, 0.727 mol) in one portion as well. This was accompanied by 5° C. increase in the temperature of the reaction mixture. After 2 h 45 min the reaction was quenched by addition of 10% aqueous NaOH (800 mL). The mixture was stirred for 10 min. The organic layer was separated, washed with brine (100 mL), dried ($MgSO_4$) and concentrated to afford an oil (142.36 g) with some suspended solid, which was filtered off (3.00 g). The aqueous part of the reaction mixture was combined with the brine washings and extracted with EtOAc (4×500 mL). Combined extracts were washed with brine (100 mL), dried ($MgSO_4$) and concentrated to afford additional portion of oil (16.82 g). The two oily products were combined and distilled in vacuum to give 8 (101.07 g, 72%) as colorless liquid, b.p. 122° C./8.9·$10^{-3}$ mbar. $^1H$ NMR (400 MHz, $CDCl_3$) δ 1.48-1.64 (m, 4H), 1.70-1.88 (m, 6H), 2.50-2.63 (m, 1H), 2.71-2.81 (m, 4H), 3.66-3.72 (m, 2H), 3.78 (t, J=6.0 Hz, 2H), 3.93 (s, 4H).

4-(1,4-oxazepan-4-yl)cyclohexanone (VII-h)

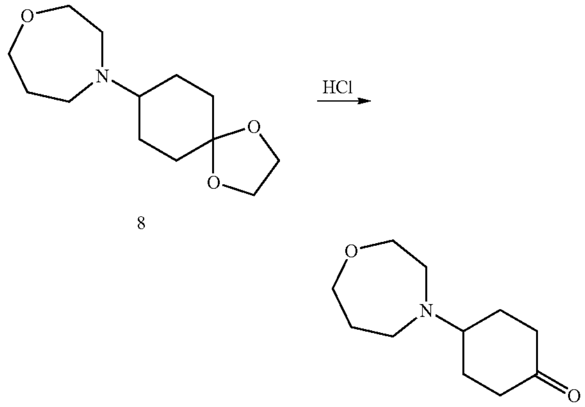

8

(VII-h)

To a cooled (<15° C.) solution of 8 (10.31 g, 42.75 mmol) in THF (216 mL) was added 7 N aqueous HCl (86 mL, 0.602 mol) over a period of 5 min. Cooling bath was then removed and the reaction mixture was stirred overnight at r.t. Then, the reaction mixture was basified to pH 8 by dropwise addition of 50% aqueous NaOH (48 g, 0.602 mol) over a period of 30 min while maintaining the internal temperature at 10-13° C. using an external cooling bath (0° C.). Hexane (50 mL) was added and the organic layer was separated, dried over $MgSO_4$ and concentrated to afford yellowish liquid (7.21 g). The aqueous layer was extracted with EtOAc (4×50 mL). The extracts were combined, dried ($MgSO_4$) and concentrated to afford the second portion of crude product (1.58 g). Both portions of crude product were combined and distilled in vacuum to afford ketone (VII-h) (7.27 g, 86%) as colorless liquid b.p. 98° C./5.3·$10^{-3}$ mbar; $^1H$ NMR (400 MHz, $CDCl_3$) δ 1.73-1.85 (m, 2H), 1.89 (quintet, J=5.9 Hz, 2H), 2.05-2.15 (m, 2H), 2.30-2.42 (m, 2H), 2.43-2.52 (m, 2H), 2.79-2.85 (m, 4H), 3.03 (tt, J=10.4, 6.6 Hz, 1H), 3.72-3.77 (m, 2H), 3.82 (t, J=6.0 Hz, 2H).

4-(1,4-oxazepan-4-yl)cyclohex-1-enyl trifluoromethanesulfonate (VIIIa-134)

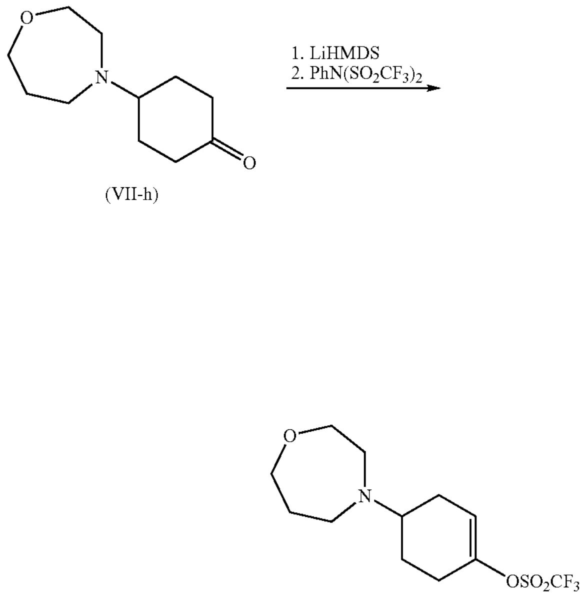

(VII-h)

(VIIIa-134)

Triflate (VIIIa-134) was prepared using the general procedure for the synthesis of enol triflates using ketone (VII-h) (6.49 g, 32.9 mmol), 1 M solution of LiHMDS in THF (39.5 mL, 39.5 mmol) and N-phenylbis(trifluoromethanesulfinimide) (12.94 g, 36.2 mmol) in dry THF (115 mL). The crude reaction mixture was diluted with hexane:EtOAc=4:1 (115 mL) (v/v) and washed with water (50 mL), brine (50 mL), dried ($MgSO_4$) and concentrated. The liquid residue was distilled in vacuum to afford (VIIIa-134) (6.98 g, 64%) as colorless liquid b.p 114° C./5.7·$10^{-3}$ mbar. Purity about 85% by $^1H$ NMR. $^1H$ NMR (400 MHz, $CDCl_3$) δ 1.63-1.76 (m, 1H), 1.86 (quintet, J=6.0 Hz, 2H), 1.95-2.05 (m, 1H), 2.12-

2.24 (m, 1H), 2.26-2.56 (m, 3H), 2.74-2.80 (m, 4H), 2.82-2.92 (m, 1H), 3.68-3.74 (m, 2H), 3.79 (t, J=6.0 Hz, 2H), 5.72 (dt, J=5.7, 2.4 Hz, 1H).

4-(4-(4,4,5,5-tetramethyl-1,3,2-dioxaborolan-2-yl)cyclohex-3-enyl)-1,4-oxazepane (VIb-134)

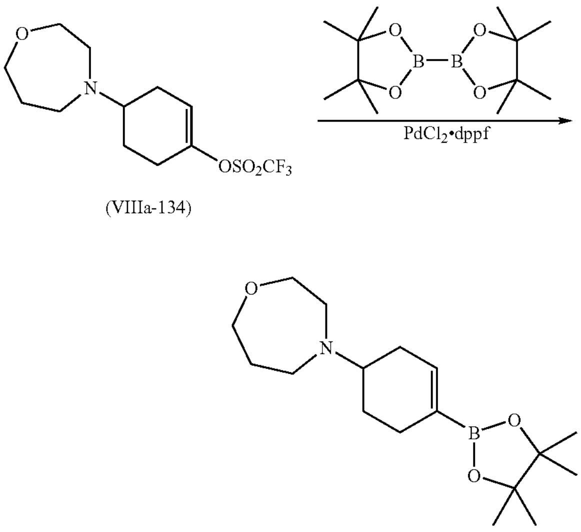

(VIIIa-134)

(VIb-134)

The compound was prepared using the general procedure for the synthesis of boronic pinacol esters. Triflate (VIIIa-134) (6.60 g, 20.06 mmol), bis(pinacolatodiboron) (7.62 g, 30.09 mmol), AcOK (5.90 g, 60.2 mmol) and dichloro[1,1'-bis(diphenylphosphino)ferrocene]palladium (II) dichloromethane adduct (0.82 g, 1.0 mmol) in DMF (86 mL) was stirred at 85° C. for 1 h 45 min when TLC showed absence of the remaining starting material. The mixture was concentrated and separated between EtOAc (125 mL)—water (125 mL). The organic layer was washed with water (120 mL), dried ($MgSO_4$), concentrated and separated by means of chromatography on amino silica (Chromatorex NH, Fuji Silysia) using hexane-EtOAc as eluent (gradient elution) to afford (VIb-134) (2.149 g, 35%) as white solid; $^1H$ NMR (400 MHz, $CDCl_3$) δ 1.26 (s, 12H), 1.33-1.47 (m, 1H), 1.83-1.93 (m, 3H), 2.04-2.22 (m, 2H), 2.23-2.38 (m, 2H), 2.75-2.84 (m, 5H), 3.71 (t, J=4.7 Hz, 2H), 3.80 (t, J=6.0 Hz, 2H), 6.52 (m, 1H).

Synthesis of Boronic Ester (VIb-135)

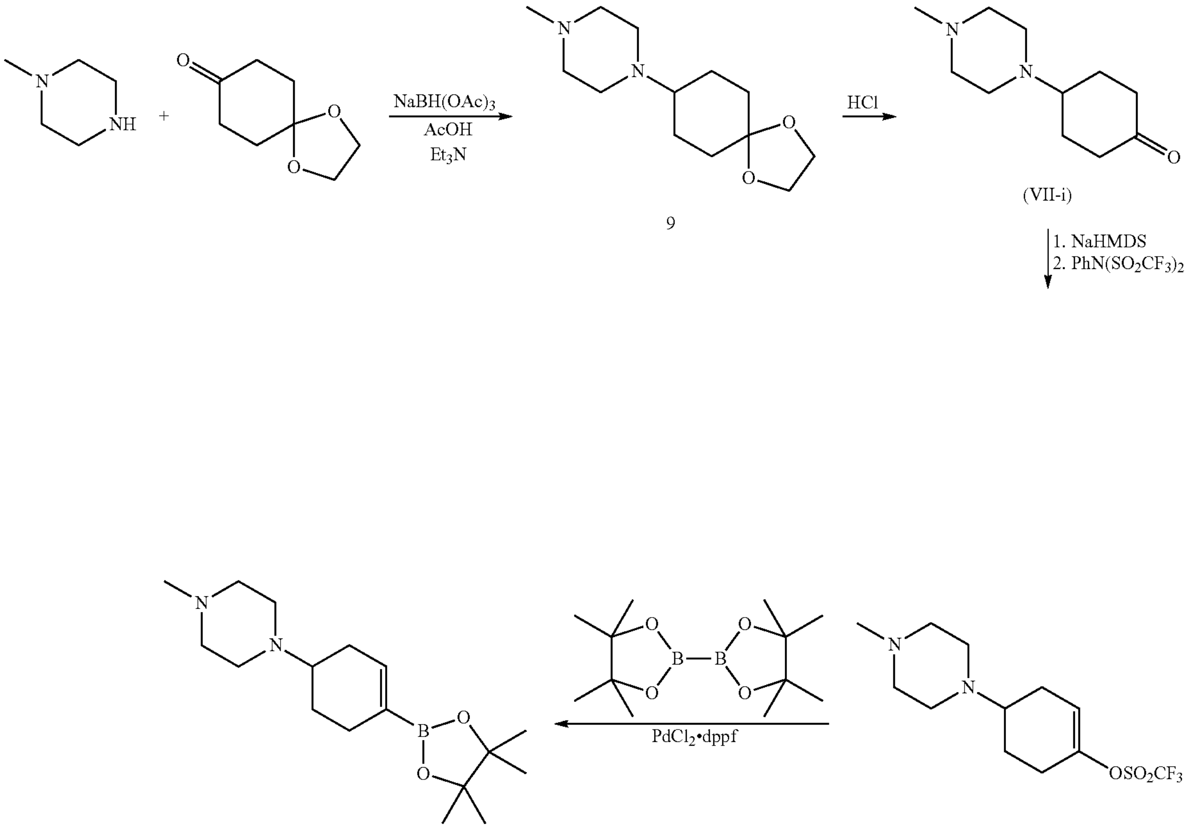

9

(VII-i)

(VIb-135)

(VIIIa-135)

1-methyl-4-(1,4-dioxaspiro[4.5]decan-8-yl)piperazine (9)

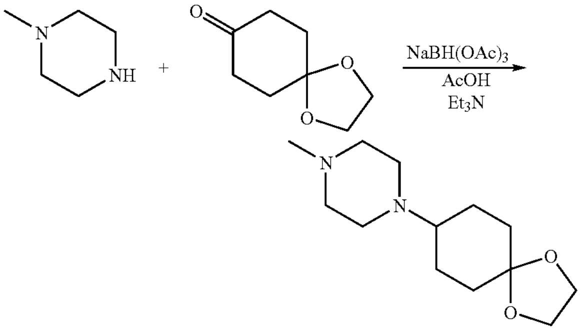

9

1-Methyl-piperazine (128.27 g, 105.90 ml, 1.28 mol) was added in one portion to a stirred and cooled (3° C.) solution of 1,4-dioxaspiro[4.5]decan-8-one (200.00 g, 1.28 mol) in 1,2-dichloroethane (2.0 L). Then glacial acetic acid (76.90 g, 73.31 ml, 1.28 mol) was added in one portion followed by solid $NaBH(OAc)_3$ (379.97 g, 1.79 mol) portionwise over 20 min. The reaction was slowly allowed to warm to RT and was stirred overnight. The reaction was quenched by addition of 10% aqueous NaOH (3×450 mL) with stirring over a period of 25 min. An exotherm of ca. 10° C. was observed. The mixture was stirred for 30 min. The organic layer was separated. Aqueous layer was further extracted with $CH_2Cl_2$ (3×1 L). Brine (1000 mL) was added to the aqueous layer and extracted with EtOAc (2×1000 mL). The combined organic solutions were dried ($MgSO_4$) and concentrated to afford 9 (305.00 g, 1.27 mol, 99.10% yield) as brown/orange oil. $^1H$ NMR (400 MHz, $CDCl_3$) δ 1.45-1.68 (m, 4H), 1.72-1.90 (m, 4H), 1.99 (s, 3H), 2.45 (s, 2H), 2.56-2.67 (m, 1H), 2.87 (bs, 6H), 3.86-3.95 (m, 4H).

4-(4-methylpiperazin-1-yl)cyclohexanone (VII-i)

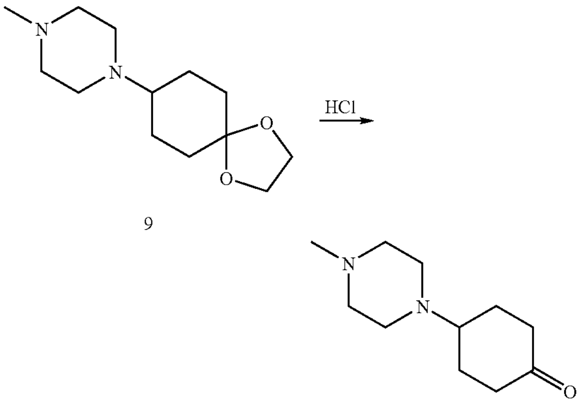

9

(VII-i)

To a cooled (0-5° C.) mixture of 9 (270.00 g, 1,123.39 mmol) and water (1283.00 mL) was added 7 N aqueous HCl (1,283.87 ml, 8,987.08 mmol). Cooling bath was then removed and the reaction mixture was stirred overnight at r.t. Then, the reaction mixture was basified to pH 9 by dropwise addition of 50% aqueous NaOH while maintaining the internal temperature at below 35° C. with an ice bath. The mixture was extracted with EtOAc (3×2 L) followed by $CH_2Cl_2$ (2×2 L). The extracts were dried ($MgSO_4$) and concentrated to afford (VII-i) (142.50 g, 725.96 mmol, 64.62%) as an orange white solid; $^1H$ NMR (400 MHz, $CDCl_3$) δ 1.68-1.81 (m, 2H), 1.88-1.99 (m, 2H), 2.13-2.25 (m, 2H), 2.17 (s, 3H), 2.25-2.43 (m, 5H), 2.43-2.70 (m, 5H).

4-(4-methylpiperazin-1-yl)cyclohex-1-enyl trifluoromethanesulfonate (VIIIa-135)

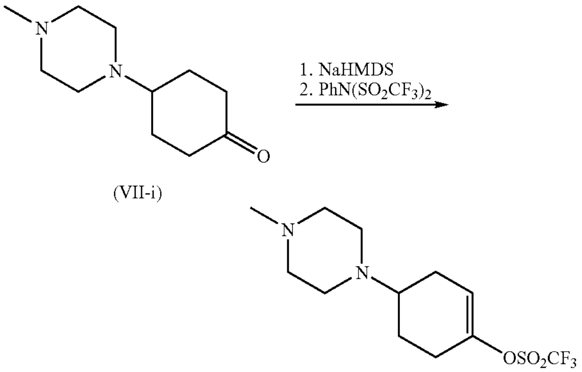

(VII-i)

(VIIIa-135)

Triflate (VIIIa-135) was prepared using a modified procedure for the synthesis of enol triflates using ketone (VII-i) (50.00 g, 254.72 mmol) in THF (1000 mL), 1 M solution of NaHMDS in THF (382.08 ml, 1.00 M, 382.08 mmol), which was added at below −40° C., and N-phenylbis(trifluoromethanesulfinimide) (109.20 g, 305.67 mmol), which was added at −78° C. as a solution in THF (750 mL). The crude reaction mixture was stirred at RT overnight. The reaction was quenched by addition of 5% NaOH solution (1500 mL). The mixture was stirred for 5 min. and extracted with EtOAc (3×2 L). The combined organic extracts were dried over $MgSO_4$ and concentrated. The residue was purified by means of SGC on amino silica (Chromatorex NH, Fuji Silysia) using EtOAc:hexane as eluent (gradient elution from 0:100 to 60:40, v/v) to give (VIIIa-135) (62.00 g, 74%) as a pale yellow oil. $^1H$ NMR (400 MHz, $CDCl_3$) δ 1.58-1.73 (m, 1H), 1.99-2.08 (m, 1H), 2.13-2.25 (m, 1H), 2.26-2.70 (m, 12H), 2.33 (s, 3H), 5.72 (dt, J=5.7, 2.4 Hz, 1H).

1-methyl-4-(4-(4,4,5,5-tetramethyl-1,3,2-dioxaborolan-2-yl)cyclohex-3-enyl)piperazine (VIb-135)

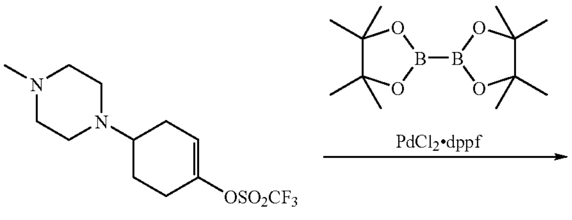

(VIIIa-135)

-continued

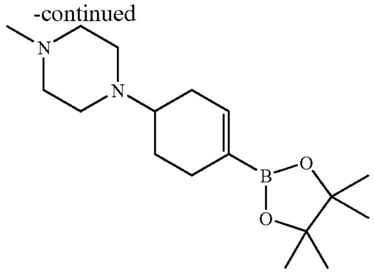

(VIb-135)

Compound (VIb-135) was prepared using the general procedure for the synthesis of boronic pinacol esters. Triflate (VIIIa-135) (66.0 g, 201 mmol), bis(pinacolatodiboron) (61.25 g, 241 mmol), AcOK (59.19 g, 603 mmol) and dichloro[1,1'-bis(diphenylphosphino)ferrocene]palladium (II) dichloromethane adduct (8.28 g, 10.05 mmol) in DMF (500 mL) was stirred at 85° C. for 3 h when TLC showed absence of the remaining starting material. The mixture was concentrated and separated between EtOAc (1000 mL)—water (1000 mL). The organic layer was washed with water (1000 mL), dried ($MgSO_4$), concentrated and separated by means of chromatography on amino silica (Chromatorex NH, Fuji Silysia) using hexane:EtOAc as eluent (gradient elution from 100:0 to 40:60, v/v) to afford (VIb-135) (32.2 g, 52%) as white solid; $^1$H NMR (400 MHz, $CDCl_3$) δ 1.24 (s, 12H), 1.29-1.44 (m, 1H), 1.92-2.03 (m, 1H), 2.04-2.19 (m, 2H), 2.29 (s, 3H), 2.24-2.39 (m, 3H), 2.39-2.55 (m, 4H), 2.55-2.83 (m, 4H), 6.47-6.55 (m, 1H).

Synthesis of Boronic Ester (VIb-141)

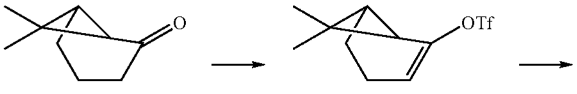

(VII-j) (VIIIa-141)

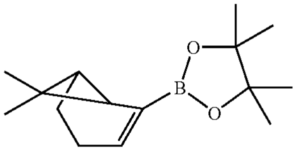

(VIb-141)

7,7-dimethylbicyclo[4.1.0]hept-2-en-2-yl trifluoromethanesulfonate (VIIIa-141)

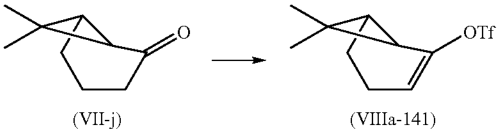

(VII-j) (VIIIa-141)

Triflate (VIIIa-141) was prepared using a procedure for the synthesis of enol triflates using ketone (VII-j) (1.00 g, 7.23 mmol) in THF (72.3 mL), 1.0 M solution of LiHMDS in THF (8.68 mL, 8.68 mmol), which was added at −78° C., and N-phenylbis(trifluoromethanesulfinimide) (3.10 g, 8.68 mmol), which was added in one portion. The reaction was then allowed to warm up to RT and was stirred overnight. The mixture was concentrated and the residue was purified by column chromatography on alumina using hexane: EtOAc=8:1 (v/v) as the eluent to give the product (VIIIa-141) as a colourless oil (1.65 g, 84%), δ $^1$H NMR (400 MHz, $CDCl_3$) δ 0.94 (s, 3H), 1.35 (s, 3H), 1.39 (d, J=9.2 Hz, 1H), 2.12-2.18 (m, 1H), 2.32 (t, J=3.0 Hz, 1H), 2.32-2.37 (m, 2H), 2.54-2.60 (dd, J=5.8 and 14.9 Hz, 1H), 5.53-5.56 (m, 1H).

2-(7,7-dimethylbicyclo[4.1.0]hept-2-en-2-yl)-4,4,5,5-tetramethyl-1,3,2-dioxaborolane (VIb-141)

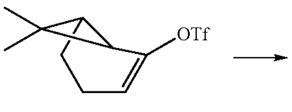

(VIIIa-141)

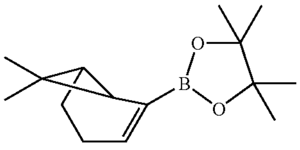

(VIb-141)

Compound (VIb-141) was prepared using the general procedure for the synthesis of boronic pinacol esters. Triflate (VIIIa-141) (1.65 g, 6.10 mmol), bispinacolato(diboron) (2.32 g, 9.15 mmol), $PdCl_2$(dppf) ($_{0.25}$ g, 0.30 mmol) and KOAc (1.79 g, 18.31 mmol) were dissolved in dry DMF (30.5 mL). The reaction mixture was heated to 80° C. for 6 hrs. The mixture was concentrated and the residue was triturated with $Et_2O$ (3×150 mL). The solid was filtered off and the ethereal layer was concentrated to give the crude product, which was purified by SGC using hexane:EtOAc=7:1 (v/v) as the eluent to give (VIb-141) (0.73 g, 48%) as a yellow oil; $^1$H NMR (400 MHz, $CDCl_3$) δ 0.81 (s, 3H), 1.10 (d, J=8.5 Hz, 1H), 1.26 (s, 12H), 1.28 (s, 3H), 2.06-2.11 (m, 1H), 2.32-2.45 (m, 4H), 6.45-6.48 (m, 1H).

Synthesis of Boronic Ester (VIb-164)

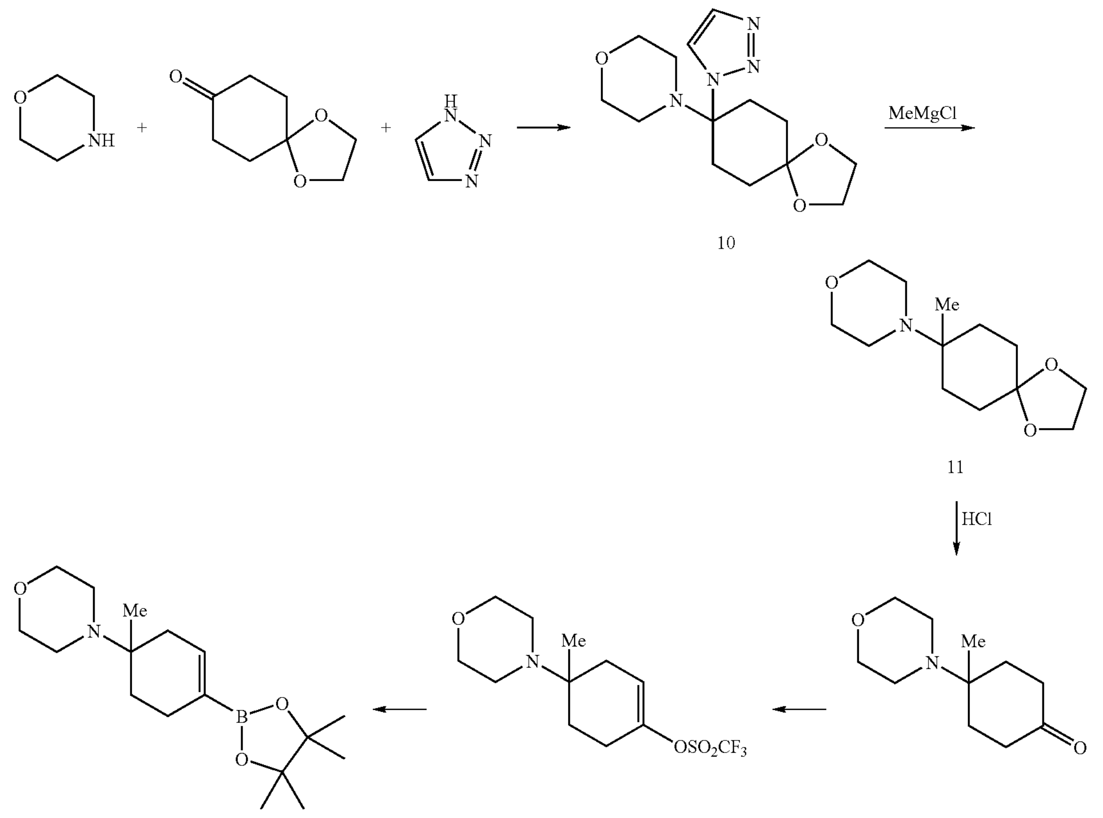

10

11

(VIb-164) (VIIIa-164) (VII-n)

4-(8-methyl-1,4-dioxaspiro[4.5]decan-8-yl)morpholine (11)

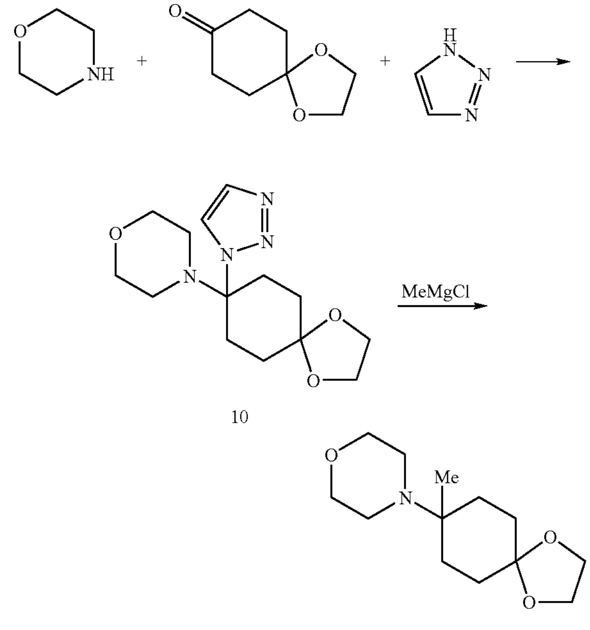

10

11

A mixture of 1,4-cyclohexanedione monoethylene acetal (7.81 g, 50.00 mmol), morpholine (4.81 mL, 55 mmol) and 1H-1,2,3-triazole (3.48 mL, 60 mmol) in toluene (50 mL) was refluxed for 6 hours while collecting water using a Dean-Stark apparatus. The white suspension containing 10 was allowed to cool to RT and added dropwise over 1 hour to a cooled (ice/salt/water bath) 3.0 M MeMgCl solution in THF (66.67 mL, 200 mmol) while maintaining the internal temperature <24° C. The reaction mixture was stirred at RT for a further 2 h. The mixture was then diluted with $Et_2O$ (500 mL). An aqueous solution of $NH_4Cl$ was added in portions until a precipitate formed. The organic layer was decanted off, dried ($MgSO_4$), filtered and concentrated in vacuo. The residue was purified by SGC on amino silica (Chromatorex NH, Fuji Silysia) using hexane:EtOAc as eluent (gradient elution from 100:0 to 50:50, v/v) to give 11 (10.94 g, 91%) as a yellowish white solid. $^1H$ NMR (400 MHz, $CDCl_3$) δ 0.89 (s, 3H), 1.41-1.48 (m, 4H), 1.80-1.94 (m, 4H), 2.50 (t, J=4.2 Hz, 4H), 3.70 (t, J=4.6 Hz, 4H), 3.95 (app. t, J=1.7 Hz, 4H).

4-methyl-4-morpholinocyclohexanone (VII-n)

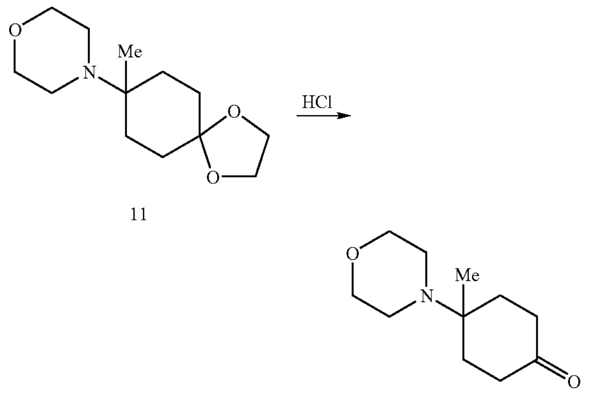

11

(VII-n)

To a cooled (0-5° C.) mixture of 11 (10.00 g, 41.44 mmol) and water (47 mL) was added 7 N aqueous HCl (47 ml, 331.50 mmol). Cooling bath was then removed and the reaction mixture was stirred at RT overnight. Then, the reaction mixture was basified to pH 9 by dropwise addition of 50% aqueous NaOH while maintaining the internal temperature <35° C. with an ice bath. The mixture was extracted with EtOAc (2x73 mL) followed by $CH_2Cl_2$ (2x71 mL). The organic extracts were dried ($MgSO_4$) filtered and concentrated in vacuo to give a white residue that was recrystallised from $CH_2Cl_2$/hexane to afford (VII-n) (6.75 g, 83%) as a white crystalline solid; $^1$H NMR (400 MHz, $CDCl_3$) δ 0.99 (s, 3H), 1.61 (td, J=13.9, 4.3 Hz, 2H), 2.09-2.19 (m, 4H), 2.55-2.65 (m, 6H), 3.74 (t, J=4.6 Hz, 4H).

4-methyl-4-morpholinocyclohex-1-enyl trifluoromethanesulfonate (VIIIa-164)

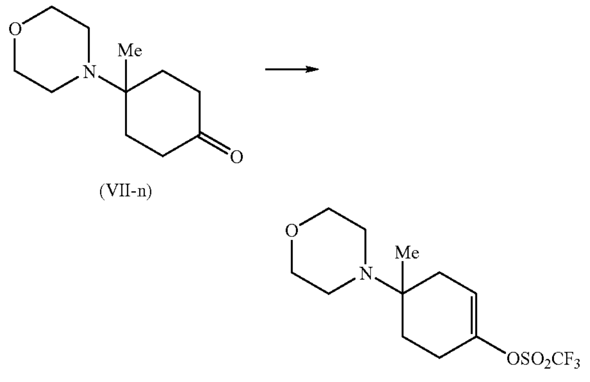

(VII-n)

(VIIIa-164)

Triflate (VIIIa-164) was prepared using a modified procedure for the synthesis of enol triflates using ketone (VII-n) (6.73 g, 34.11 mmol) in THF (167 mL), NaHMDS in THF (51.16 mL, 51.16 mmol, 1.0 M solution in THF), which was added at −78° C., and N-phenylbis(trifluoromethanesulfinimide) (14.62 g, 40.93 mmol), which was added at −78° C. as a solution in THF (167 mL). The crude reaction mixture was allowed to slowly warm to RT overnight. The reaction mixture was cooled to 0° C. and added to a cold 5% aqueous solution of NaOH (167 mL). The mixture was stirred for 20 minutes and subsequently extracted with EtOAc (3x334 mL). The combined organic extracts were dried ($MgSO_4$), filtered and concentrated in vacuo. The residue was taken up in $CH_2Cl_2$ (550 mL) and washed with a cold 5% aqueous solution of NaOH (3x400 mL). The organic phase was dried over MgSO4, filtered and concentrated in vacuo to give (VIIIa-164) (10.42 g, 93%) as a brown oil. $^1$H NMR (400 MHz, $CDCl_3$) δ 1.01 (s, 3H), 1.68-1.77 (m, 1H), 1.78-1.87 (m, 1H), 2.00-2.09 (m, 1H), 2.22-2.49 (m, 3H), 2.50-2.62 (m, 4H), 3.70 (t, J=4.6 Hz, 4H), 5.60-5.65 (m, 1H).

4-(1-methyl-4-(4,4,5,5-tetramethyl-1,3,2-dioxaborolan-2-yl)cyclohex-3-enyl)morpholine (VIb-164)

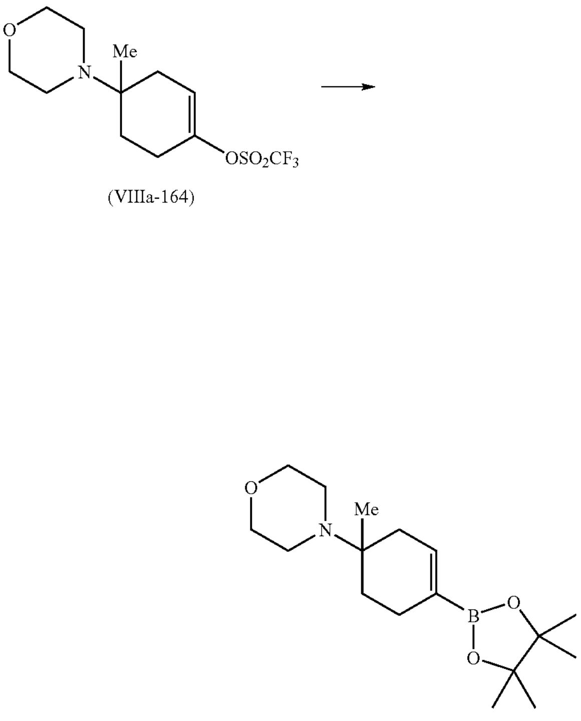

(VIIIa-164)

(VIb-164)

Compound (VIb-164) was prepared using the general procedure for the synthesis of boronic pinacol esters. Triflate (VIIa-164) (10.42 g, 31.64 mmol), bis(pinacolatodiboron) (11.25 g, 44.29 mmol), KOAc (9.32 g, 94.92 mmol) and dichloro[1,1'-bis(diphenylphosphino)ferrocene]palladium (II) dichloromethane adduct (1.29 g, 1.58 mmol) in DMF (280 mL) was stirred at 85° C. overnight. The reaction mixture was cooled down, concentrated and dried under high vacuum. The residue was purified by SGC on amino silica (Chromatorex NH, Fuji Silysia) using hexane:EtOAc as eluent (gradient elution from 100:0 to 50:50, v/v) to give a white residue that was recrystallised from hot hexane to give (VIb-164) (5.02 g, 52%) as a white solid; $^1$H NMR (400 MHz, $CDCl_3$) δ 0.94 (s, 3H), 1.28 (s, 12H), 1.40-1.51 (m, 1H), 1.62-1.70 (m, 1H), 1.93-2.13 (m, 2H), 2.17-2.35 (m, 2H), 2.53-2.66 (m, 4H), 3.71 (t, J=4.6 Hz, 4H), 6.44-6.49 (m, 1H).

8-methyl-8-azabicyclo[3.2.1]oct-3-en-3-yl trifluoromethanesulfonate (VIIIa-143)

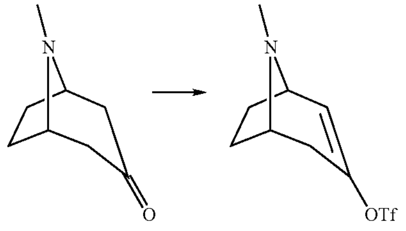

(VII-k) (VIIIa-143)

Triflate (VIIIa-143) was prepared using a procedure for the synthesis of enol triflates using ketone (VII-k) (2.00 g, 14.36 mmol) in THF (71.8 mL), 1.0 M solution of LiHMDS in THF (17.24 mL, 17.24 mmol), which was added at −78° C., and N-phenylbis(trifluoromethanesulfinimide) (6.15 g, 17.24 mmol), which was added in one portion. The reaction mixture was then allowed to warm up to RT and was stirred overnight at RT. Crude yield of (VIIIa-143) (2.68 g).

Synthesis of Triflate (VIIIa-144)

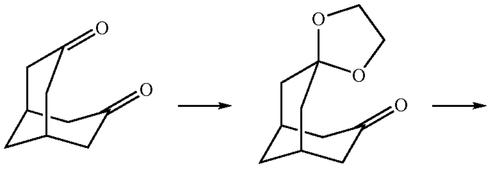

(VII-l) (VII-m)

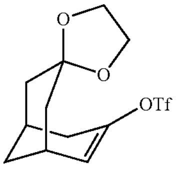

(VIIIa-144)

spiro[bicyclo[3.3.1]nonane-3,2'-[1,3]dioxolan]-7-one (VII-m)

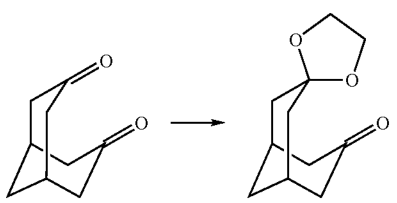

(VII-l) (VII-m)

p-Toluenesulfonic acid (0.29 g, 1.51 mmol) was added to a solution of ketone (VII-l) (2.30 g, 15.11 mmol) in ethylene glycol (3.75 g, 60.45 mmol)—toluene (75 mL) and the reaction mixture was refluxed for 2 h using a Dean-Stark apparatus. The reaction mixture was allowed to cool to RT and was poured into a saturated solution of $NaHCO_3$ (100 mL). The mixture was extracted with EtOAc (3×150 mL), dried ($MgSO_4$) and concentrated. The crude product was purified by SGC using EtOAc:hexane=3:1 (v/v) as the eluent to give (VII-m) (2.33 g, 78%) as a white solid; $^1$H NMR (400 MHz, $CDCl_3$) δ 1.68-1.84 (m, 6H), 2.26-2.34 (dd, J=6.6 and 18.4 Hz, 2H), 2.40-2.48 (m, 4H), 3.77-3.81 (m, 2H), 3.85-3.89 (m, 2H).

spiro[bicyclo[3.3.1]non[6]ene-3,2'-[1,3]dioxolane]-7-yl trifluoromethanesulfonate (VIIIa-144)

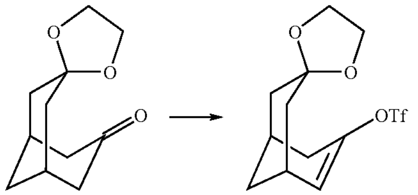

(VII-m) (VIIIa-144)

Triflate (VIIIa-144) was prepared using a procedure for the synthesis of enol triflates using ketone (VII-m) (1.59 g, 8.10 mmol) in THF (40.5 mL), 1.0 M solution of LiHMDS in THF (9.73 mL, 9.73 mmol), which was added at −78° C., and N-phenylbis(trifluoromethanesulfinimide) (3.18 g, 8.91 mmol), which was added in one portion. The crude product was purified by column chromatography on alumina (activated grade I) using hexane:EtOAc 1:1 (v/v) as the eluent to give (VIIIa-144) (1.49 g, 56%) s a yellow oil; $^1$H NMR (400 MHz, $CDCl_3$) δ 1.61-1.66 (dt, J=2.8 and 12.6 Hz, 1H), 1.71-1.87 (m, 6H), 2.43-2.50 (m, 1H), 2.55 (dd, J=7.6 and 7.5 Hz, 1H), 2.65-2.70 (m, 1H), 3.76-3.86 (m, 2H), 3.91-3.96 (m, 2H), 5.80 (d, J=6.8 Hz, 1H).

3-iodo-1-(phenylsulfonyl)-5-(1,4-dioxaspiro[4.5]decan-8-yl)-1H-pyrrolo[2,3-b]pyridine (IXb-19)

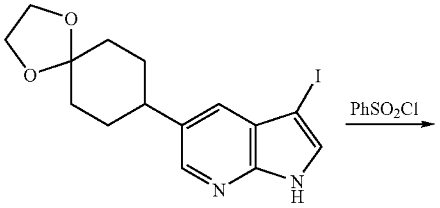

(XIIb-19)

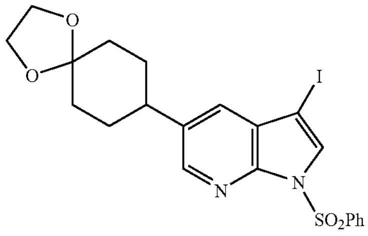

(IXb-19)

Compound (IXb-19) was synthesized following the general procedure for protection of 7-azaindoles as phenylsulfonamides. Thus, crude iodide (XIIb-19) (9.72 mmol), $Bu_4NHSO_4$ (0.494 g, 1.46 mmol), 50% NaOH (4 mL) and $PhSO_2Cl$ (1.92 mL, 15.0 mmol) in $CH_2Cl_2$ (60 mL) were reacted for 3.5 h. Standard workup followed by trituration with cold MeOH (70 mL) for 1.5 h afforded (IXb-19) as a white powder (3.96 g, 78% from (XIb-19)). $^1H$ NMR (400 MHz, $CDCl_3$) δ 1.70-1.81 (m, 2H), 1.83-1.92 (m, 6H), 2.70-2.77 (m, 1H), 4.02 (s, 4H), 7.50-7.54 (m, 3H), 7.61 (tt, J=7.4, 1.6 Hz, 1H), 7.85 (s, 1H), 8.22-8.24 (m, 2H), 8.34 (d, J=2.0 Hz, 1H).

5-Cyclohexenyl-1H-pyrrolo[2,3-b]pyridine (XIa-12)

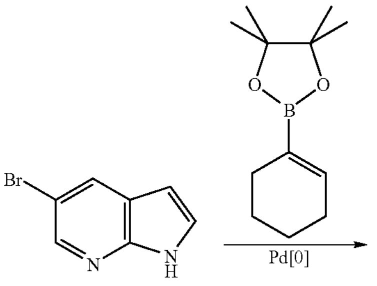

(X-a)

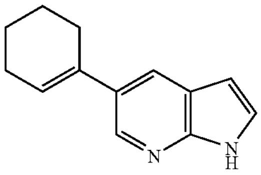

(XIa-12)

A mixture of (X-a) (2.90 g, 14.70 mmol), cyclohexenyl boronic acid pinacol ester (3.40 g, 16.34 mmol), $PdCl_2(PPh_3)_2$ (0.52 g, 0.74 mmol), LiCl (1.87 g, 44.11 mmol), and 1.0 M aq. $Na_2CO_3$ (20 mL, 20 mmol), in EtOH (30 mL) and toluene (30 mL) was reacted for 4 h using the general procedure A for the Suzuki reaction. The crude product (5.74 g; dark brown oil) was purified by SGC using EtOAc:$CH_2Cl_2$=1:4 (v/v) as eluent to give (XIa-12) as a pale yellow powder (1.50 g, 7.57 mmol, 51%). $^1H$ NMR (400 MHz, $CDCl_3$) δ 1.68-1.75 (m, 2H), 1.81-1.88 (m, 2H), 2.23-2.29 (m, 2H), 2.47-2.53 (m, 2H), 6.10-6.14 (m, 1H), 6.50 (dd, J 2.0, 3.5 Hz, 1H), 7.30 (d, J=2.4 Hz, 1H), 7.92 (d, J=1.7 Hz, 1H), 8.40 (d, J=1.8 Hz, 1H), 7.88 (s, 1H), 9.07 (br s, 1H).

5-(1,4-Dioxa-spiro[4.5]dec-7-en-8-yl)-1H-pyrrolo[2,3-b]pyridine (XIa-14)

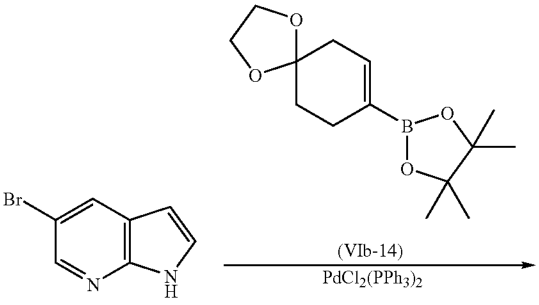

(X-a)

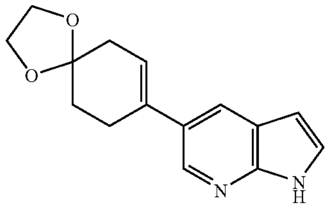

(XIa-14)

A mixture of (X-a) (1.00 g, 5.08 mmol), boronic ester (VIb-14) (2.15 g, 8.07 mmol), $PdCl_2(PPh_3)_2$ (378 mg, 0.54 mmol), LiCl (684 mg, 16.1 mmol), and 1.0 M aq. $Na_2CO_3$ (13.5 mL, 13.5 mmol), in EtOH (25 mL) and toluene (25 mL) was reacted for 3.5 h using the general procedure A for the Suzuki reaction. The crude product was purified by SGC using EtOAc:hexane=6:4 (v/v) as eluent (gradient elution) to give brown solid. This solid was washed with 10% then 20% and finally 30% EtOAc in hexane to give (XIa-14) (881 mg, 68%) as a white solid; $^1H$ NMR (400 MHz, $CDCl_3$) δ 1.98 (t, J=6.5 Hz, 2H), 2.49-2.52 (m, 2H), 2.72-2.76 (m, 2H), 4.04 (s, 4H), 5.97-5.99 (m, 1H), 6.47 (dd, J=2.0, 1.4 Hz, 1H), 7.30 (t, J=2.9 Hz, 1H), 7.92 (d, J=1.9 Hz, 1H), 8.41 (d, J=1.9 Hz, 1H), 9.34 (bs, NH).

5-Cyclohexyl-1H-pyrrolo[2,3-b]pyridine (XIb-16)

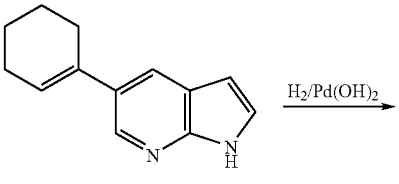

(XIa-12)

-continued

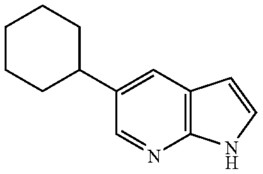

(XIb-16)

Compound (XIa-12) was hydrogenated using the general procedure for hydrogenation of 7-azaindoles. Thus, (XIa-12) (1.50 g, 7.57 mmol), methanol (100 mL) and 20% $Pd(OH)_2/C$ (Degussa type) (0.25 g) were stirred at RT under $H_2$ for 4 days. Filtration through a pad of Celite using MeOH: $CH_2Cl_2$=1:1 (200 mL) and concentration of the filtrate gave (XIb-16) as a brown solid (1.37 g, 6.84 mmol, 90%). $^1H$ NMR (400 MHz, $CDCl_3$) δ 1.24-1.59 (m, 5H), 1.76-2.00 (m, 5H), 2.66 (tt, J 3.4, 11.6 Hz, 1H), 6.48 (d, J 3.4 Hz, 1H), 7.33 (d, J=3.4 Hz, 1H), 7.81 (d, J=1.8 Hz, 1H), 8.22 (d, J=1.8 Hz, 1H), 9.58 (br s, 1H).

5-(1,4-Dioxa-spiro[4.5]dec-8-yl)-1H-pyrrolo[2,3-b]pyridine (XIb-19)

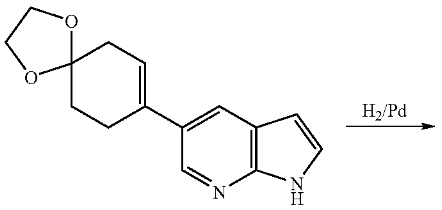

(XIa-14)

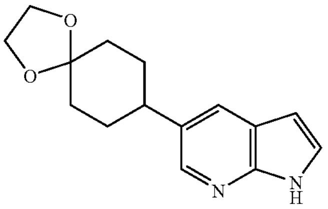

(XIb-19)

Compound (XIa-14) was hydrogenated using the general procedure for hydrogenation of 7-azaindoles. Thus, (XIa-14) (800 mg, 3.12 mmol), methanol (100 mL) and a $CH_2Cl_2$ (10 mL), and 10% Pd/C (catalytic amount) was stirred at RT under $H_2$ for 16.5 h. Filtration through a pad of Celite using MeOH:$CH_2Cl_2$ and concentration of the filtrate gave (XIb-19) as a white solid (795 mg, 99%); $^1H$ NMR (400 MHz, $CDCl_3$) δ 1.70-1.80 (m, 2H), 1.86-2.00 (m, 6H), 2.72 (m, 1H), 4.01 (s, 4H), 6.46 (dd, J=1.4, 3.4 Hz, 1H), 7.34 (m, 1H), 7.84 (d, J=1.5 Hz, 1H), 8.25 (bs, 1H), 10.21 (bs, NH).

5-(1,4-Dioxa-spiro[4.5]dec-8-yl)-1H-pyrrolo[2,3-b]pyridine (XIb-19)—an Alternative Method of Preparation

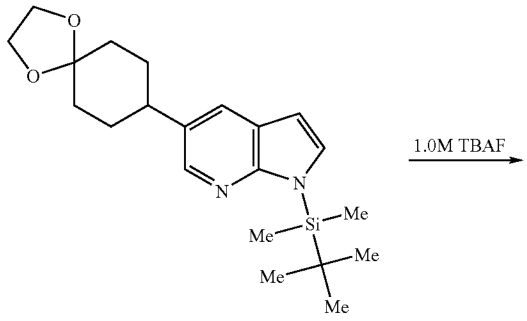

(XIIIb-19)

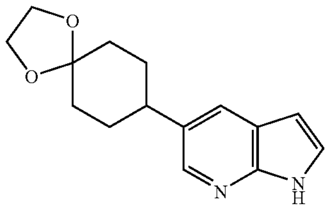

(XIb-19)

Compound (XIIIb-19) was deprotected using the general procedure B for deprotection of 7-azaindoles. Thus, (XIIIb-19) (4.23 g, 11.4 mmol) in THF (50 mL) and 1 M tetrabutylammonium fluoride in THF (22.7 mL, 22.7 mmol) were reacted over 75 min. The crude product was purified by SGC using hexane-EtOAc as eluent (in gradient) to afford the azaindole (XIb-19) (2.51 g, 86%). $^1H$ NMR (400 MHz, $CDCl_3$) δ 1.72-1.80 (m, 2H), 1.88-1.97 (m, 6H), 2.69-2.77 (m, 1H), 4.03 (s, 4H), 6.47 (dd, J=3.5, 2.0 Hz, 1H), 7.32 (dd, J=3.5, 2.5 Hz, 1H), 7.85 (d, J=2.0 Hz, 1H), 8.25 (d, J=2.0 Hz, 1H), 9.42 (bs, 1H).

4-((1r,4r)-4-(1H-pyrrolo[2,3-b]pyridin-5-yl)cyclohexyl)-1,4-oxazepane (XIb-40)

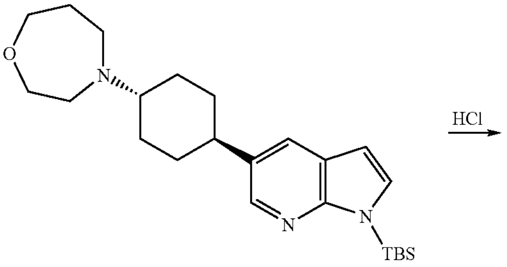

(XIIIb-40)

-continued

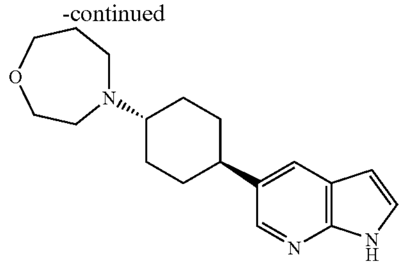

(XIb-40)

Azaindole (XIIIb-40) (1.5 g, 3.6 mmol) in MeOH (80 mL) and 12 M HCl (1.50 mL, 18.0 mmol) was deprotected over 45 min using the general procedure C for the deprotection of 7-azaindoles to afford azaindole (XIb-40) (1.27 g) an off-white powder that was used directly for the next transformations without further purification. $^1$H NMR (400 MHz, $CDCl_3$) δ 1.42-1.65 (m, 4H), 1.84-1.92 (m, 2H), 1.97-2.06 (m, 4H), 2.56-2.70 (m, 2H), 3.73-3.75 (m, 2H), 3.82 (t, J=6.0 Hz, 2H), 6.43 (q, J=2.0 Hz, 1H), 7.29 (q, J=2.5 Hz, 1H), 7.76 (d, J=2.0 Hz, 1H), 8.19 (d, J=2.0 Hz, 1H), 9.35 (br s, 1H).

4-(4-(1H-pyrrolo[2,3-b]pyridin-5-yl)cyclohex-3-enyl)morpholine (XIa-75)

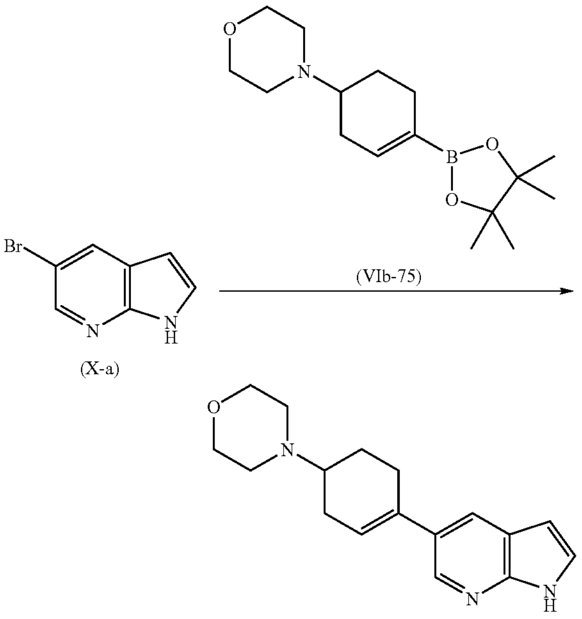

(X-a)

(XIa-75)

A mixture of (X-a) (18.00 g, 91.35 mmol), boronic ester (VIb-75) (31.40 g, 107.09 mmol), $PdCl_2(PPh_3)_2$ (3.21 g, 4.57 mmol), LiCl (11.62 g, 274.06 mmol), and 1.0 M aq. $Na_2CO_3$ (91.4 mL, 91.4 mmol), in EtOH (150 mL) and toluene (150 mL) was reacted for 5 h using the general procedure A for the Suzuki reaction. The reaction mixture was cooled, poured onto EtOAc (500 mL) and saturated aqueous $NaHCO_3$ (200 mL). The layers were separated and allowed to stand overnight. After 18 hrs, the aqueous layer was filtered to afford (XIa-75) as a pale brown powder (13.59 g). The aqueous filtrate was then further extracted with EtOAc (500 mL), the combined organic portions were dried over $MgSO_4$ and evaporated to afford a dark brown oil (33.37 g), which was triturated with MeOH (250 mL) to afford more (XIa-75) as a pale brown powder (2.76 g). Total yield of (XIa-75) 17.23 g (60.80 mmol, 63%). $^1$H NMR (400 MHz, $CDCl_3$) δ 1.57-1.73 (m, 1H), 2.17-2.31 (m, 2H), 2.44-2.75 (m, 8H), 3.80 (t, J=4.6 Hz, 4H), 6.05-6.09 (m, 1H), 6.50 (dd, J=2.0, 3.5 Hz, 1H), 7.31 (dd, J=2.5, 3.4 Hz, 1H), 7.92 (d, J=1.9 Hz, 1H), 8.40 (d, J=2.0 Hz, 1H), 8.82 (br s, 1H).

4-(4-(1H-pyrrolo[2,3-b]pyridin-5-yl)cyclohex-3-enyl)-1,4-oxazepane (XIa-134)

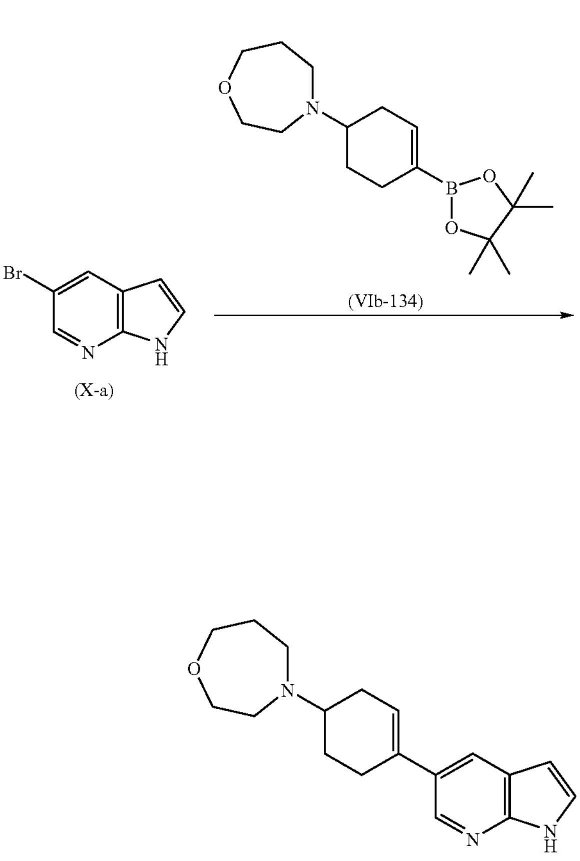

(X-a)

(XIa-134)

A mixture of (X-a) (10 g, 50.8 mmol), boronic ester (VIb-134) (17.15 g, 55.8 mmol), $PdCl_2(PPh_3)_2$ (3.92 g, 5.6 mmol), LiCl (6.93 g, 163.4 mmol), and 1.0 M aq. $Na_2CO_3$ (137 mL, 137 mmol) in EtOH (200 mL) and toluene (200 mL) was reacted for 2.5 h using the general procedure A for the Suzuki reaction. The reaction mixture was cooled, and partitioned between saturated brine (100 mL) and EtOAc (200 mL). The aqueous layer was extracted with EtOAc (3×150 mL). The combined organic solutions were dried ($MgSO_4$), filtered and concentrated to afford an orange powder. This was triturated with cold EtOAc and filtered to yield the Suzuki adduct (XIa-134) (12.65 g, 84%) as a tan solid. $^1$H NMR (400 MHz, $CDCl_3$) δ 1.64-1.74 (m, 1H), 1.89-1.92 (m, 2H), 2.10 (m, 1H), 2.20-2.27 (m, 1H), 2.39-2.46 (m, 1H), 2.60-2.64 (m, 2H), 2.86 (m, 4H), 2.95 (m, 1H), 3.76 (t, J=4.6 Hz, 2H), 3.83 (t, J=6.0 Hz, 2H), 6.05 (m, 1H), 6.4 (dd, J=2.0, 3.5 Hz, 1H), 7.29-7.30 (m, 1H), 7.89 (d, J=2.0 Hz, 1H), 8.37 (d, J=2.0 Hz, 1H), 9.21 (br s, 1H).

5-Cyclohexyl-3-iodo-1H-pyrrolo[2,3-b]pyridine (XIIb-16)

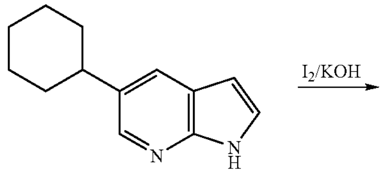

(XIb-16)

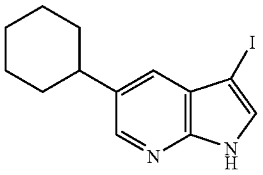

(XIIb-16)

To a solution of (XIb-16) (1.37 g, 6.84 mmol) in DMF (30 mL) was added KOH (0.77 g, 13.68 mmol) and the mixture was stirred for 5 min. Iodine (1.77 g, 6.98 mmol) was then added portionwise over 10 min, and the reaction was stirred at room temperature for 2 h. The solution was then diluted with EtOAc (250 mL) and washed with saturated aqueous $Na_2S_2O_3$ (2×50 mL). The organic layer was dried ($MgSO_4$) and concentrated to afford (XIIb-16) (1.92 g, 5.89 mmol, 86%) as a yellow powder. $^1H$ NMR (400 MHz, $CDCl_3$) δ 1.27-1.61 (m, 5H), 1.78-2.00 (m, 5H), 2.70 (tt, J=3.3, 11.5 Hz, 1H), 7.40 (d, J=2.0 Hz, 1H), 7.57 (d, J=2.0 Hz, 1H), 8.22 (d, J=2.0 Hz, 1H), 8.95 (br s, 1H).

3-iodo-5-(1,4-dioxaspiro[4.5]decan-8-yl)-1H-pyrrolo[2,3-b]pyridine (XIIb-19)

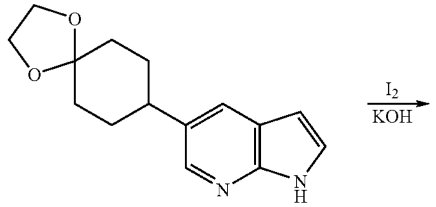

(XIb-19)

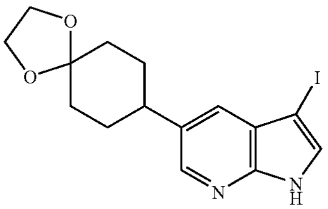

(XIIb-19)

To a stirred solution of the azaindole (XIb-19) (2.51 g, 9.72 mmol) in DMF (40 mL), was added crushed KOH pellets (2.05 g, 36.6 mmol) followed by $I_2$ (2.22 g, 8.7 mmol). The mixture was stirred at room temperature for 3.5 h and concentrated in vacuum. The residue was partitioned between EtOAc (100 mL) and saturated aqueous $NaHCO_3$ solution (40 mL). The aqueous layer was extracted with EtOAc (3×60 mL). The combined organic solutions were dried ($MgSO_4$), filtered and concentrated. The residue consisting of crude iodide (XIIb-19) was used for the preparation of (IXb-19) without any additional purification.

4-((1r,4r)-4-(3-iodo-1H-pyrrolo[2,3-b]pyridin-5-yl)cyclohexyl)-1,4-oxazepane (XIIb-40)

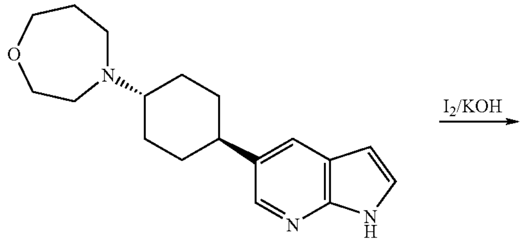

(XIb-40)

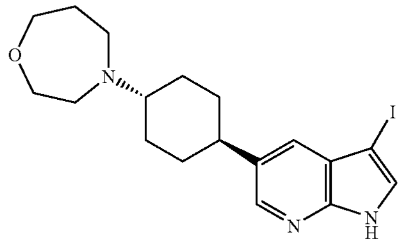

(XIIb-40)

To a stirred mixture of (XIb-40) (1.09 g, 3.6 mmol) and solid KOH (0.77 g, 13.7 mmol) in DMF (40 mL) was added iodine (0.83 g, 3.3 mmol) was added and the mixture was stirred for 3 h. The reaction mixture was partially concentrated in vacuo and partitioned between EtOAc (100 mL) and saturated $NaHCO_3$ (40 mL). The aqueous layer was extracted with EtOAc (3×60 mL). The combined organic solutions were dried ($MgSO_4$) and concentrated to afford iodide (XIIb-40), which was used directly in further steps without any additional purification. $^1H$ NMR (400 MHz, $CDCl_3$) δ 1.42-1.52 (m, 2H), 1.56-1.67 (m, 2H), 1.84-1.91 (m, 2H), 1.98-2.04 (m, 4H), 2.59-2.71 (m, 2H), 2.81-2.85 (m, 4H), 3.73-

3.75 (m, 2H), 3.81 (t, J=6.0 Hz, 2H), 7.39 (d, J=2.0 Hz, 1H), 7.54 (d, J=2.0 Hz, 1H), 8.18 (d, J=2.0 Hz, 1H), 9.83 (br s, 1H).

4-((1r,4r)-4-(1-(tert-butyldimethylsilyl)-1H-pyrrolo[2,3-b]pyridin-5-yl)cyclohexyl)morpholine (XIIIb-6) and 4-((1s,4s)-4-(1-(tert-butyldimethylsilyl)-1H-pyrrolo[2,3-b]pyridin-5-yl)cyclohexyl)morpholine (XIIIb-7)

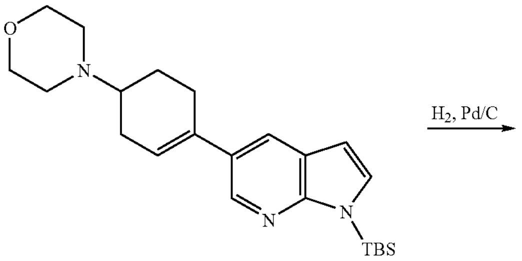

(XIIIa-75)

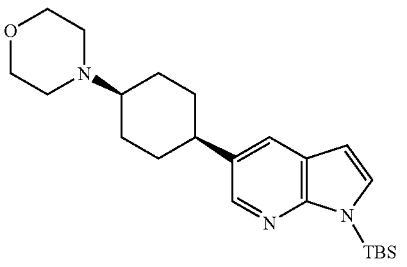

(XIIIb-7)

+

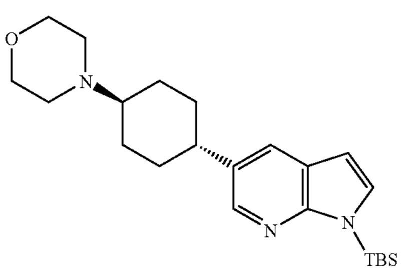

(XIIIb-6)

Compound (XIIIa-75) was hydrogenated using the general procedure for hydrogenation of 7-azaindoles. Thus, (XIIIa-75) (11.00 g, 27.66 mmol), ethanol (100 mL) and THF (100 mL), and $Pd(OH)_2$ (20% on carbon, Degussa-type) (2.00 g) was stirred at RT under $H_2$ for 22 h. Filtration through a pad of Celite using ethanol (500 mL) and concentration of the filtrate gave the crude mixture of cis and trans isomers. The isomers were separated by SGC using $EtOAc:CH_2Cl_2$ (gradient from 1:2 to 2:1 v/v) to give (XIIIb-7) (4.08 g, 10.21 mmol, 37%), followed by (XIIIb-6) (6.67 g, 16.69 mmol, 60%).

Data for the trans isomer (XIIIb-6): $^1$H NMR (400 MHz, $CDCl_3$) δ 0.56 (s, 6H), 0.87 (s, 9H), 1.30-1.65 (m, 5H), 1.89-2.13 (m, 4H), 2.38-2.76 (m, 5H), 3.58-3.94 (m, 4H), 6.42 (d, J=3.5 Hz, 1H), 7.16 (d, J=3.5 Hz, 1H), 7.61 (d, J=1.9 Hz, 1H), 8.08 (d, J=2.0 Hz, 1H).

1-(tert-butyldimethylsilyl)-5-(1,4-dioxaspiro[4.5]dec-7-en-8-yl)-1H-pyrrolo[2,3-b]pyridine (XIIIa-14)

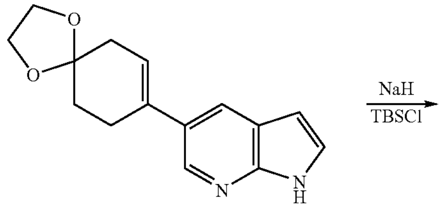

(XIa-14)

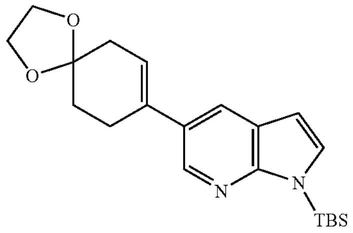

(XIIIa-14)

To a solution of azaindole (XIa-14) (4.0 g, 15.6 mmol) in DMF (35 mL) was added NaH (0.749 g, 18.7 mmol; 60% in oil) in one portion. After 10 min, tetrabutyldimethylsilyl chloride (3.06 g, 20.3 mmol) was added in 2 portions over 1 min. Following a further 19.5 h the mixture was diluted with EtOAc (100 mL) and saturated aqueous $NaHCO_3$ solution (35 mL) and partitioned. The aqueous layer was extracted with EtOAc (2×40 mL). The combined organic extracts were dried ($MgSO_4$), filtered and concentrated to afford a honey-coloured viscous oil. This was purified by SGC using hexane: EtOAc (gradient elution) to afford the silylated derivative (XIIIa-14) (4.37 g, 76%).

1-(tert-butyldimethylsilyl)-5-(1,4-dioxaspiro[4.5]decan-8-yl)-1H-pyrrolo[2,3-b]pyridine (XIIIb-19)

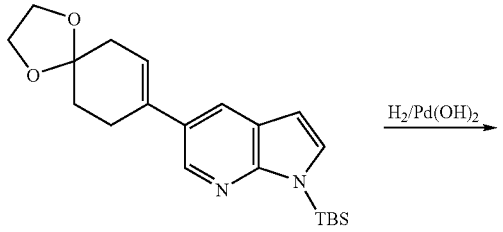

(XIIIa-14)

-continued

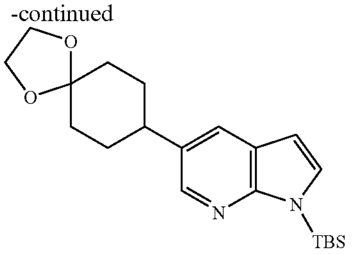

(XIIIb-19)

Compound (XIIIa-14) was hydrogenated using the general procedure for hydrogenation of 7-azaindoles. Thus, (XIIIa-14) (4.37 g, 11.8 mmol), EtOH (35 mL) and THF (35 mL), and $Pd(OH)_2$ (20% on carbon, Degussa-type) (1.00 g) was stirred at RT under $H_2$ for 24 h. Filtration through a pad of Celite using EtOH (500 mL), EtOAc (500 mL) and concentration of the filtrate gave (XIIIb-19) (4.23 g, 96%).

4-((1s,4s)-4-(1-(tert-butyldimethylsilyl)-1H-pyrrolo[2,3-b]pyridin-5-yl)cyclohexyl)-1,4-oxazepane (XIIIb-39) and 4-((1r,4r)-4-(1-(tert-butyldimethylsilyl)-1H-pyrrolo[2,3-b]pyridin-5-yl)cyclohexyl)-1,4-oxazepane (XIIIb-40)

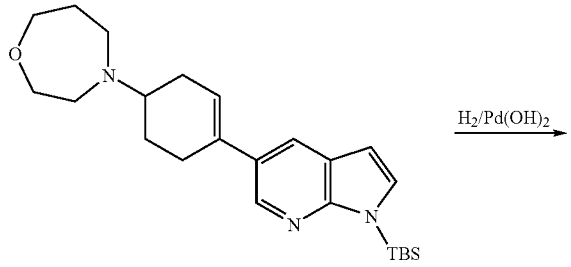

(XIIIa-134)

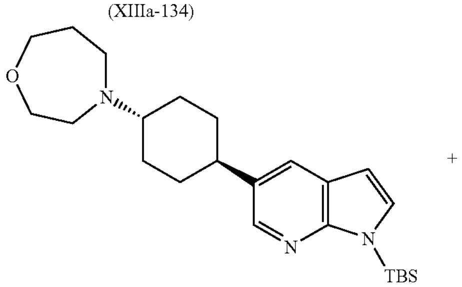

(XIIIb-40)

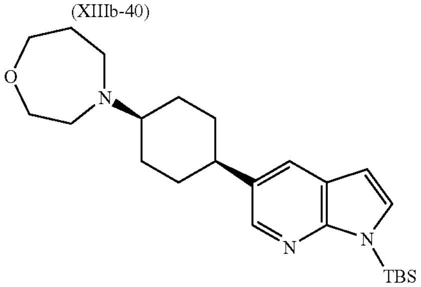

(XIIIb-39)

Compound (XIIIa-134) was hydrogenated using the general procedure for hydrogenation of 7-azaindoles. Thus, (XIIIa-134) (15.37 g, 37.3 mmol), ethanol (120 mL) and THF (120 mL), and $Pd(OH)_2$ (20% on carbon, Degussa-type) (3.50 g) was stirred at RT under $H_2$ for 23 h. Another portion of the catalyst (2.00 g) was added and stirring under $H_2$ continued for 23.5 h. Filtration through a pad of Celite using EtOH (500 mL), EtOAc (500 mL), $CH_2Cl_2$ (500 mL), 10% MeOH/$CH_2Cl_2$ (500 mL) and 10% MeOH/EtOAc (300 mL) and concentration of the filtrate gave the crude mixture of cis and trans isomers (15.44 g) as a viscous honey-coloured oil. The isomers were separated by SGC using EtOAc:MeOH=9:1 (v/v) to give cis isomer (XIIIb-39) (5.91 g, 38%), followed by mixed fractions (2.01 g, 13%) and (XIIIb-40) (4.19 g, 27%).

Data for the trans isomer (XIIIb-40): $^1H$ NMR (400 MHz, $CDCl_3$) δ 0.62 (s, 6H), 0.93 (s, 9H), 1.42-1.62 (m, 4H), 1.88 (m, 1H), 1.99-2.02 (m, 4H), 2.52-2.66 (m, 2H), 2.83 (m, 4H), 3.74 (m, 12H), 3.82 (t, J=6.0 Hz, 2H), 6.46 (d, J=3.4 Hz, 1H), 7.20 (d, J=3.4 Hz, 1H), 7.67 (d, J=2.1 Hz, 1H), 8.14 (d, J=2.1 Hz, 1H).

4-(4-(1-(tert-butyldimethylsilyl)-1H-pyrrolo[2,3-b]pyridin-5-yl)cyclohex-3-enyl)morpholine (XIIIa-75)

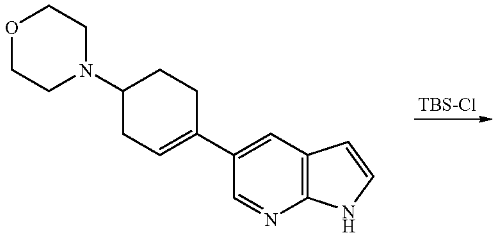

(XIa-75)

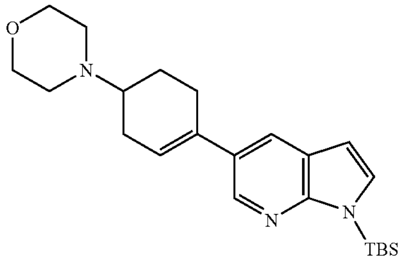

(XIIIa-75)

To a solution of (XIa-75) (17.23 g, 60.80 mmol) in DMF (250 mL) was added NaH (2.67 g, 60% in mineral oil, 66.67 mmol) portionwise over 30 min. The reaction mixture was allowed to stir for 10 min, then tert-butyldimethylchlorosilane (11.00 g, 72.96 mmol) was added portionwise over 10 min. After stirring at room temperature for 3 d, the reaction was quenched with saturated aqueous $NaHCO_3$ (250 mL) and extracted with EtOAc (800 mL). The organic layer was further washed with saturated aqueous $NaHCO_3$ (2×250 mL), dried over $MgSO_4$, and concentrated to give an oil (17.45 g). The crude product was purified by flash column chromatography to afford (XIIIa-75) (11.00 g, 27.66 mmol, 46%) as a colourless oil. $^1H$ NMR (400 MHz, $CDCl_3$) δ 0.60 (s, 6H), 0.89 (s, 9H), 1.53-1.64 (m, 1H), 2.10-2.25 (m, 2H), 2.37-2.68

(m, 8H), 3.74 (t, J=4.7 Hz, 4H), 5.99-6.03 (m, 1H), 6.46 (d, J=3.4 Hz, 1H), 7.18 (d, J=3.5 Hz, 1H), 7.79 (d, J=2.3 Hz, 1H), 8.32 (d, J=2.3 Hz, 1H).

4-(4-(1-(tert-butyldimethylsilyl)-1H-pyrrolo[2,3-b]pyridin-5-yl)cyclohex-3-enyl)-1,4-oxazepane (XIIIa-134)

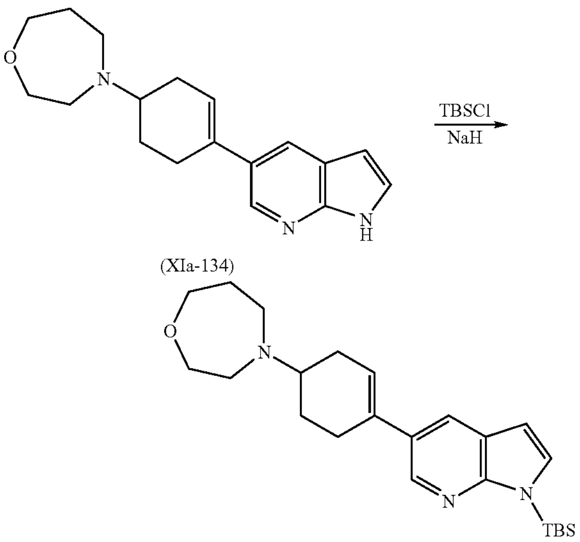

(XIa-134)

(XIIIa-134)

To a stirred solution of azaindole (XIa-134) (12.65 g, 42.5 mmol) in DMF (120 mL) was added 60% NaH dispersion in mineral oil (2.04 g, 51.0 mmol) portionwise over 3 min. After 15 min, tert-butyldimethylchlorosilane (8.33 g, 55.3 mmol) was added and the mixture stirred for a further 66 h. The mixture was diluted with EtOAc (150 mL) and saturated $NaHCO_3$ solution (100 mL) and partitioned. The aqueous layer was extracted with EtOAc (4×150 mL) and $CH_2Cl_2$ (100 mL). The combined organic extracts were dried ($MgSO_4$), filtered and concentrated to yield a honey coloured viscous oil. This was purified by means of SGC using hexane: $CH_2Cl_2$ (gradient elution from 100:0 to 0:100, v/v) followed by $CH_2Cl_2$:MeOH (gradient elution from 100:0 to 90:10, v/v) to afford the silylated azaindole (XIIIa-134) (15.37 g, 87%). $^1$H NMR (400 MHz, $CDCl_3$) δ 0.62 (s, 6H), 0.92 (s, 9H), 1.68 (m, 1H), 1.87-1.93 (m, 2H), 2.05-2.10 (m, 1H), 2.18-2.26 (m, 1H), 2.36-2.43 (m, 1H), 2.57-2.63 (m, 2H), 2.83-2.86 (m, 5H), 3.75 (t, J=4.7 Hz, 2H), 3.82 (t, J=6.0 Hz, 2H), 6.02-6.05 (m, 1H), 6.49 (d, J=3.5 Hz, 1H), 7.21 (d, J=3.5 Hz, 1H), 7.81 (d, J=2.3 Hz, 1H), 8.33 (d, J=2.3 Hz, 1H).

3-(1-Methyl-1H-pyrazol-4-yl)-5-(4,4,5,5-tetramethyl-[1,3,2]dioxaborolan-2-yl)-1-(2-trimethylsilanyl-ethoxymethyl)-1H-pyrrolo[2,3-b]pyridine (XIV-e)

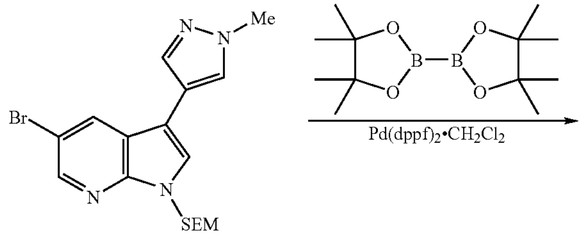

(III-e)

-continued

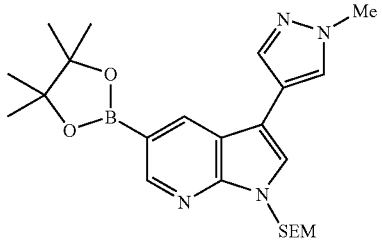

(XIV-e)

The compound was prepared using the general procedure for the synthesis of boronic pinacol esters. Bromide (III-e) (0.5 g, 1.23 mmol), bis(pinacolatodiboron) (468 mg, 1.84 mmol), potassium acetate (361 mg, 3.68 mmol) and dichloro [1,1'-bis(diphenylphosphino)ferrocene]palladium (II) dichloromethane adduct (35.1 mg, 0.043 mmol) in DMF (7.8 mL) was stirred at 80° C. for 31 h. The crude product was purified by SGC using hexane:EtOAc (gradient elution up to 70:30 v/v) to give boronic ester (XIV-e) as a light orange oil (339 mg, 61%); $^1$H NMR (400 MHz, $CDCl_3$) δ −0.062 (s, 9H), 0.92 (m, 2H), 1.39 (s, 12H), 3.55 (m, 2H), 4.01 (s, 3H), 5.72 (s, 2H), 7.41 (s, 1H), 7.71 (s, 1H), 7.78 (d, J=0.7 Hz, 1H), 8.45 (d, J=1.5 Hz, 1H), 8.73 (d, J=1.5 Hz, 1H).

Biological Activity

JNK1, JNK2, JNK3—SPA Assay

JNK1, JNK2, JNK3—SPA Assay

1. Compound is dissolved in DMSO to a convenient concentration and this is diluted in 10% DMSO to a five times concentrate of the desired starting concentration (frequently 1:100).
2. 10 μl of 500 mM EDTA is added to alternative wells of the Opti-plate row, which will receive kinase reaction plus DMSO. This creates the negative control.
3. For the JNK2 and JNK3 assay, compounds are prepared in six 2-fold dilutions with water and each concentration is tested in duplicate. For the JNK1 assay compounds are prepared in four 5-fold dilutions with water which are tested in triplicate. Controls are treated identically.
4. 20 μl per well of each compound concentration is transferred to an Opti-plate, in duplicate.
5. 30 μl (JNK2/3 SPA) or 50 μl (JNK1 SPA) of substrate solution (25 mM HEPES pH 7.5, 10 mM magnesium acetate with 3.33 μM ATP (JNK2/3) or 2 μM ATP (JNK1), approximately 7.5 kBq [γ-$^{33}$P] ATP, GST-c-Jun, in water) is added to each well.
6. 50 μl (JNK2/3 SPA) or 30 μl (JNK1 SPA) of kinase solution (JNK in 25 mM HEPES pH 7.5, 10 mM Mg Acetate) is added to each well.

| Kinase | Kinase per well (μg) | GST-c-Jun per well (μg) |
|---|---|---|
| JNK1 | 0.25 | 1 |
| JNK2 | 0.2 | 1.2 |
| JNK3 | 0.16 | 1.2 |

7. The plate is incubated for 30 minutes at room temperature.
8. 100 μl of bead/stop solution is added to each well (5 mg/ml glutathione-PVT-SPA beads, 40 mM ATP in PBS).
9. Plates are sealed and incubated for 30 minutes at room temperature, centrifuged for 10 minutes at 2500 g and counted.

10. The $IC_{50}$ values are calculated as the concentration of the compound being tested at which the phosphorylation of c-Jun is decreased to 50% of the control value. Example $IC_{50}$ values for the compounds of this invention are given in Tables 1 and 2.

TABLE 1

$IC_{50}$ values for compounds (I) against JNK3.

| Cpd # I- | $IC_{50}$ [nM] |
|---|---|
| 1 | 18 |
| 2 | 199 |
| 3 | 58 |
| 4 | 123 |
| 5 | 339 |
| 6 | 80 |
| 7 | 60 |
| 8 | 16 |
| 9 | 40 |
| 10 | 17 |
| 11 | 132 |
| 12 | 110 |
| 13 | 126 |
| 14 | 224 |
| 15 | 275 |
| 16 | 40 |
| 17 | 162 |
| 18 | 288 |
| 19 | 25 |
| 20 | 229 |
| 21 | 49 |
| 22 | 25 |
| 23 | 126 |
| 24 | 83 |
| 25 | 90 |
| 26 | 94 |
| 27 | 155 |
| 28 | 5500 |
| 29 | 98 |
| 30 | 170 |
| 31 | 480 |
| 32 | 79 |
| 33 | 110 |
| 34 | 2138 |
| 35 | 91 |
| 36 | 257 |
| 37 | 69 |
| 38 | 98 |
| 39 | 184 |
| 40 | 129 |
| 41 | 103 |
| 42 | 138 |
| 43 | 117 |
| 44 | 129 |
| 45 | 166 |
| 46 | 151 |
| 47 | 93 |
| 48 | 182 |
| 49 | 316 |
| 50 | 214 |
| 51 | 191 |
| 52 | 251 |
| 53 | 182 |
| 54 | 174 |
| 55 | 263 |
| 56 | 71 |
| 57 | 417 |
| 58 | >500 |
| 59 | >500 |
| 60 | >500 |
| 62 | 105 |
| 63 | 468 |
| 64 | 158 |
| 66 | 219 |
| 67 | 178 |
| 68 | 760 |
| 71 | 189 |

TABLE 1-continued $IC_{50}$ values for compounds (I) against JNK3.

| Cpd # I- | $IC_{50}$ [nM] |
|---|---|
| 72 | 259 |
| 73 | 74 |
| 74 | 63 |
| 75 | 89 |
| 76 | 251 |
| 77 | >500 |
| 78 | 288 |
| 79 | 117 |
| 80 | 148 |
| 93 | |
| 94 | |
| 95 | 1514 |
| 96 | 1698 |
| 101 | |
| 102 | |
| 103 | 263 |
| 104 | 138 |
| 105 | 320 |
| 106 | 500 |
| 107 | 288 |
| 108 | 204 |
| 109 | 302 |
| 110 | 355 |
| 111 | 263 |
| 112 | 500 |
| 113 | 316 |
| 114 | 224 |
| 115 | 347 |
| 116 | 309 |
| 117 | 288 |
| 118 | 257 |
| 119 | 257 |
| 120 | 500 |
| 121 | 363 |
| 122 | 295 |
| 123 | 323 |
| 124 | 257 |
| 125 | 263 |
| 126 | 281 |
| 127 | 398 |
| 128 | 794 |
| 129 | 191 |
| 130 | 692 |
| 131 | 251 |
| 133 | 468 |
| 136 | 76 |
| 137 | 45 |
| 138 | 148 |
| 139 | 83 |
| 140 | 87 |
| 141 | 288 |
| 142 | 155 |
| 143 | >500 |
| 145 | 167 |
| 146 | 832 |
| 147 | >1000 |
| 148 | 1000 |
| 149 | >500 |
| 151 | 347 |
| 153 | 288 |
| 154 | 62 |
| 155 exo | 219 |
| 155 endo | 174 |
| 156 | 1412 |
| 157 | 295 |
| 162 | >2000 |
| 163 | 1480 |

TABLE 2

IC$_{50}$ values for compounds (I) against JNK2 and JNK1.

| Cpd # | JNK2 IC$_{50}$ [nM] | JNK1 IC$_{50}$ [nM] |
|---|---|---|
| 3 | 501 | 178 |
| 6 | 123 | 74 |
| 7 | 162 | 98 |
| 10 | 65 | 31 |
| 16 | 135 | 74 |
| 23 | 1288 | 646 |
| 24 | 562 | 195 |
| 25 | 245 | 191 |
| 26 | 617 | 302 |
| 37 | 178 | 186 |
| 38 | 158 | 182 |
| 39 | 562 | 316 |
| 40 | 339 | 166 |
| 43 | 214 | 100 |
| 44 | 347 | 132 |

TABLE 2-continued

IC$_{50}$ values for compounds (I) against JNK2 and JNK1.

| Cpd # | JNK2 IC$_{50}$ [nM] | JNK1 IC$_{50}$ [nM] |
|---|---|---|
| 48 | 339 | 170 |
| 53 | 355 | 182 |
| 55 | 501 | 240 |
| 71 | 603 | 170 |
| 72 | 955 | 417 |

Selectivity of Compounds (I) Against a Panel of Kinases

Inhibitory potency of compounds (I) at a concentration of 1 micromolar and with ATP concentration of 10 micromolar was determined at Upstate/Millipore against a panel of 100 kinases representing all major families within the kinome. The results are presented in Table 3 and are expressed as percentage of remaining activity.

TABLE 3

Inhibitory profile of (I-6), (I-7), (I-16), (I-25), (I-26), (I-39), (I-40) and (I-80) against a panel of 100 kinases. Numbers represent the percentage of remaining activity.

| | I-6 | I-7 | I-16 | I-25 | I-26 | I-39 | I-40 | I-80 |
|---|---|---|---|---|---|---|---|---|
| Abl(h) | 107 | 104 | 64 | 133 | 124 | 143 | 142 | 99 |
| AMPK(r) | 77 | 87 | 88 | | | | | |
| ARK5(h) | 78 | 60 | | 102 | 77 | 76 | 130 | 55 |
| Aurora-A(h) | 87 | 86 | 38 | 137 | 110 | 152 | 149 | 76 |
| BrSK1(h) | | | | 81 | 97 | 98 | 96 | 76 |
| BTK(h) | | | | 109 | 110 | 117 | 120 | 98 |
| CaMKII(r) | 71 | 92 | 108 | 90 | 93 | 118 | 112 | 83 |
| CDK1/cyclinB(h) | 77 | 55 | 35 | 77 | 80 | 75 | 75 | 53 |
| CDK2/cyclinA(h) | 56 | 40 | | 64 | 77 | 82 | 65 | 36 |
| CDK2/cyclinE(h) | 1 | 36 | | 59 | 71 | 71 | 56 | 29 |
| CDK5/p35(h) | 0 | 23 | | 52 | 85 | 68 | 54 | 28 |
| CDK6/cyclinD3(h) | 94 | 101 | | 72 | 89 | 93 | 87 | 84 |
| CDK7/cyclinH/MAT1(h) | 14 | 45 | | 11 | 21 | 32 | 12 | 5 |
| CHK1(h) | 91 | 106 | 94 | 82 | 108 | 110 | 107 | 91 |
| CK18(h) | 14 | 64 | 43 | -8 | -5 | 43 | -1 | 12 |
| CK2(h) | 87 | 109 | | 120 | 103 | 116 | 119 | 116 |
| c-RAF(h) | 94 | 96 | 97 | 104 | 121 | 106 | 119 | 109 |
| CSK(h) | 113 | 110 | | 119 | 117 | 129 | 125 | 109 |
| cSRC(h) | 100 | 97 | 36 | 73 | 71 | 84 | 90 | 124 |
| DAPK1(h) | 110 | 4 | | 97 | 91 | 97 | 96 | 89 |
| eEF-2K(h) | 115 | 107 | | 100 | 98 | 105 | 110 | 110 |
| EGFR(h) | 118 | 118 | 119 | 140 | 109 | 108 | 125 | 124 |
| EphB2(h) | 123 | 123 | 91 | 87 | 106 | 108 | 98 | 78 |
| FAK(h) | 101 | 94 | | 94 | 90 | 98 | 96 | 93 |
| FGFR3(h) | 86 | 73 | | 88 | 102 | 110 | 107 | 96 |
| Fgr(h) | 108 | 96 | | 73 | 72 | 92 | 86 | 77 |
| Fms(h) | 85 | 74 | 57 | 86 | 93 | 81 | 79 | 81 |
| Fyn(h) | 88 | 82 | 28 | 83 | 81 | 105 | 104 | 147 |
| GRK5(h) | 83 | 91 | | 96 | 115 | 116 | 99 | 82 |
| GRK6(h) | 82 | 90 | | 79 | 78 | 90 | 70 | 87 |
| GSK3α(h) | 62 | 57 | 20 | 47 | 47 | 89 | 58 | 58 |
| GSK3β(h) | 82 | 73 | | 132 | 147 | 106 | 97 | 75 |
| HIPK3(h) | 109 | 103 | | 103 | 112 | 118 | 117 | 78 |
| IGF-1R(h) | 91 | 89 | 100 | 119 | 105 | 117 | 123 | 56 |
| IKKα(h) | 77 | 62 | | 29 | 37 | 52 | 50 | 57 |
| IKKβ(h) | 93 | 91 | 73 | 68 | 69 | 74 | 69 | 80 |
| IR(h) | 133 | 99 | | 153 | 152 | 147 | 130 | 93 |
| IRAK1(h) | 75 | 98 | | 55 | 67 | 83 | 55 | 58 |
| Itk(h) | | | | 74 | 86 | 105 | 88 | 62 |
| JAK2(h) | 118 | 121 | | 120 | 111 | 125 | 120 | 101 |
| JAK3(h) | 94 | 103 | | 94 | 86 | 90 | 93 | 104 |

TABLE 3-continued

Inhibitory profile of (I-6), (I-7), (I-16), (I-25), (I-26), (I-39), (I-40) and (I-80) against a panel of 100 kinases. Numbers represent the percentage of remaining activity.

| | | | | | | | | |
|---|---|---|---|---|---|---|---|---|
| JNK1α1(h) | 14 | 12 | | | | | | |
| JNK2α2(h) | 37 | 34 | | | | | | |
| JNK3(h) | 13 | 12 | 14 | 13 | 7 | 10 | 13 | 9 |
| KDR(h) | 93 | 100 | 54 | 79 | 81 | 88 | 78 | 78 |
| Lck(h) | 93 | 89 | 30 | 75 | 81 | 114 | 101 | 76 |
| LIMK1(h) | 107 | 103 | | 122 | 110 | 137 | 131 | 95 |
| Lyn(h) | 96 | 102 | | 107 | 112 | 108 | 120 | 88 |
| MAPK1(h) | 94 | 70 | | 104 | 84 | 76 | 114 | 92 |
| MAPK2(h) | 94 | 78 | | 96 | 92 | 100 | 104 | 79 |
| MAPKAP-K2(h) | 98 | 102 | 98 | 117 | 124 | 135 | 129 | 112 |
| MAPKAP-K3(h) | 108 | 117 | | 107 | 105 | 115 | 104 | 80 |
| MEK1(h) | 107 | 103 | 72 | 101 | 95 | 102 | 102 | 99 |
| Met(h) | 92 | 94 | | 117 | 132 | 138 | 130 | 79 |
| MKK4(m) | 117 | 82 | 77 | 93 | 73 | 74 | 113 | 111 |
| MKK6(h) | 118 | 108 | | 101 | 87 | 108 | 104 | 98 |
| MKK7β(h) | 77 | 64 | | 77 | 55 | 65 | 82 | 79 |
| MLCK(h) | 81 | 84 | 60 | 57 | 78 | 98 | 84 | 55 |
| MLK1(h) | 98 | 102 | | 107 | 101 | 102 | 117 | 74 |
| MST2(h) | 99 | 71 | 82 | 90 | 86 | 109 | 96 | 105 |
| MuSK(h) | 107 | 105 | | 92 | 94 | 104 | 98 | 91 |
| p70S6K(h) | 106 | 104 | 91 | 92 | 96 | 116 | 113 | 95 |
| PAK2(h) | 122 | 134 | 93 | 82 | 109 | 89 | 99 | 79 |
| PAK3(h) | 90 | 99 | | 58 | 73 | 80 | 82 | 79 |
| PAK5(h) | 93 | 113 | | 19 | 53 | 76 | 73 | 51 |
| PAK6(h) | 96 | 99 | | 62 | 87 | 102 | 86 | 76 |
| PAR-1Ba(h) | 49 | 69 | | 42 | 72 | 97 | 80 | 17 |
| PDGFRα(h) | 87 | 99 | | 100 | 105 | 109 | 109 | 87 |
| PDGFRβ(h) | 122 | 120 | 104 | 110 | 102 | 98 | 108 | 86 |
| PDK1(h) | 93 | 97 | 112 | 101 | 99 | 105 | 100 | 94 |
| PKA(h) | 121 | 119 | 109 | 105 | 103 | 109 | 103 | 96 |
| PKBα(h) | 102 | 116 | | 102 | 104 | 97 | 106 | 106 |
| PKCα(h) | 99 | 102 | | 106 | 106 | 81 | 84 | 64 |
| PKCβII(h) | 110 | 100 | 91 | 130 | 98 | 137 | 133 | 90 |
| PKCγ(h) | 101 | 92 | | 94 | 90 | 99 | 78 | 113 |
| PKCδ(h) | 107 | 102 | | 96 | 92 | 102 | 96 | 93 |
| PKCε(h) | 88 | 90 | | 94 | 99 | 101 | 98 | 90 |
| PKD2(h) | 13 | 47 | 116 | 5 | 10 | 34 | 2 | 7 |
| Plk3(h) | 124 | 120 | | 108 | 106 | 111 | 105 | 116 |
| PRAK(h) | 97 | 97 | | 81 | 90 | 78 | 104 | 84 |
| Pyk2(h) | 79 | 85 | | 93 | 98 | 112 | 100 | 91 |
| Ret(h) | 86 | 145 | 94 | 88 | 88 | 94 | 101 | 114 |
| RIPK2(h) | 57 | 79 | | 56 | 77 | 79 | 53 | 31 |
| ROCK-I(h) | 86 | 79 | | 129 | 89 | 86 | 88 | 65 |
| ROCK-II(h) | 4 | 39 | 29 | 18 | 29 | 50 | 24 | 37 |
| Rsk1(h) | 64 | 82 | 80 | 43 | 59 | 84 | 66 | 88 |
| SAPK2a(h) | 102 | 106 | | 97 | 107 | 105 | 98 | 100 |
| SAPK2b(h) | 106 | 112 | | 102 | 111 | 109 | 102 | 103 |
| SAPK3(h) | 110 | 104 | | 95 | 96 | 107 | 96 | 69 |
| SAPK4(h) | 105 | 106 | | 111 | 111 | 111 | 112 | 66 |
| SGK(h) | 80 | 79 | | 73 | 50 | 147 | 86 | 52 |
| SRPK1(h) | 104 | 104 | | 102 | 99 | 97 | 105 | 112 |
| Syk(h) | 104 | 86 | 95 | 82 | 81 | 102 | 105 | 35 |
| TBK1(h) | 92 | 76 | | 80 | 87 | 114 | 100 | 76 |
| Tie2(h) | 103 | 105 | | 115 | 128 | 111 | 115 | 82 |
| TrkA(h) | 83 | 49 | | 41 | 24 | 70 | 68 | 36 |
| TrkB(h) | 117 | 81 | 131 | 101 | 65 | 100 | 115 | 94 |
| WNK2(h) | 96 | 99 | | 88 | 94 | 99 | 94 | 80 |
| ZAP-70(h) | 118 | 116 | 101 | 115 | 130 | 115 | 118 | 124 |
| ZIPK(h) | 105 | 109 | | 87 | 90 | 102 | 101 | 100 |
| PI3Kβ(h) | 103 | 111 | | 98 | 98 | 102 | 101 | 108 |
| PI3Kγ(h) | 98 | 99 | | 94 | 93 | 96 | 97 | 96 |
| PI3Kδ(h) | 95 | 93 | | 99 | 96 | 97 | 101 | 98 |

<30% activity 30-70% activity

>70% activity

For comparison purposes Table 4 contains the relevant inhibitory data for reference compounds A-K containing a (hetero)aromatic ring at C(5) of the 7-azaindole system.

TABLE 4

Inhibitory profile of reference compounds A, B, C, D, E, F, G, H, J and K against a panel of 100 kinases. Numbers represent the percentage of remaining activity.

| | A | B | C | D | E | F | G | H | J | K |
|---|---|---|---|---|---|---|---|---|---|---|
| Abl(h) | 16 | 34 | 36 | 22 | 47 | 39 | 18 | 82 | 42 | 76 |
| AMPK(r) | 22 | 18 | 31 | 13 | 14 | 24 | | | | |
| ARK5(h) | | 0 | 0 | | | 4 | 20 | 8 | 1 | 7 |
| Aurora-A(h) | 12 | 14 | 14 | 11 | 20 | 5 | 27 | 106 | 55 | 19 |
| BrSK1(h) | | | | | | | 59 | 81 | 76 | 55 |
| BTK(h) | | | | | | | 78 | 104 | 24 | 45 |
| CaMKII(r) | 62 | 51 | 62 | 18 | 74 | 66 | 33 | 72 | 14 | 37 |
| CDK1/cyclinB(h) | 2 | 8 | 41 | 10 | 43 | 3 | 5 | 10 | 17 | 3 |
| CDK2/cyclinA(h) | 5 | 10 | 37 | | | 7 | 10 | 22 | 18 | 2 |
| CDK2/cyclinE(h) | 17 | 19 | 41 | | | 15 | 8 | 34 | 29 | 4 |
| CDK5/p35(h) | 2 | 12 | 35 | | | 11 | 8 | 3 | 24 | 6 |
| CDK6/cyclinD3(h) | 11 | 46 | 77 | | | 70 | 37 | 71 | 15 | 32 |
| CDK7/cyclinH/MAT1(h) | 13 | 18 | 8 | | | 14 | 25 | 52 | 5 | 14 |
| CHK1(h) | 17 | 13 | 14 | 36 | 13 | 16 | 62 | 63 | 46 | 59 |
| CK1δ(h) | 20 | 12 | 16 | 1 | 10 | 26 | 0 | 20 | -10 | -6 |
| CK2(h) | | 84 | 82 | | | 64 | 119 | 118 | 81 | 113 |
| c-RAF(h) | 88 | 95 | 106 | 94 | 101 | 41 | 73 | 98 | 90 | 57 |
| CSK(h) | | 109 | 102 | | | 107 | 102 | 87 | 97 | 108 |
| cSRC(h) | 46 | 56 | 28 | 8 | 73 | 66 | 44 | 45 | 5 | 17 |
| DAPK1(h) | | 4 | 2 | | | 6 | 68 | 79 | 29 | 49 |
| eEF-2K(h) | | 105 | 113 | | | 107 | 99 | 92 | 97 | 102 |
| EGFR(h) | 114 | 89 | 107 | 113 | 112 | 117 | 108 | 113 | 104 | 85 |
| EphB2(h) | 69 | 80 | 97 | 78 | 77 | 109 | 69 | 91 | 65 | 101 |
| FAK(h) | | 23 | 37 | | | 53 | 17 | 27 | 5 | 7 |
| FGFR3(h) | 21 | 30 | 41 | | | 13 | 33 | 71 | 23 | 25 |
| Fgr(h) | | 21 | 11 | | | 33 | 53 | 29 | 10 | 39 |
| Fms(h) | 14 | 25 | 24 | 10 | 39 | 10 | 22 | 53 | 13 | 12 |
| Fyn(h) | 19 | 51 | 42 | 19 | 54 | 63 | 55 | 66 | 13 | 36 |
| GRK5(h) | | 112 | 64 | | | 72 | 108 | 111 | 109 | 109 |
| GRK6(h) | | 94 | 75 | | | 75 | 95 | 87 | 77 | 59 |
| GSK3α(h) | 6 | 6 | 5 | 15 | 16 | 1 | 13 | 44 | 14 | 2 |
| GSK3β(h) | 23 | 22 | 16 | | | 5 | 47 | 125 | 34 | 9 |
| HIPK3(h) | | 13 | 20 | | | 32 | 3 | 92 | 0 | 11 |
| IGF-1R(h) | 71 | 79 | 61 | 3 | 107 | 82 | 25 | 56 | 5 | 5 |
| IKKα(h) | 5 | 13 | 23 | | | 6 | -5 | 0 | -9 | 4 |
| IKKβ(h) | | 51 | 57 | 13 | 55 | 58 | 12 | 39 | 15 | 12 |
| IR(h) | | 121 | 106 | | | 143 | 62 | 118 | 27 | 36 |
| IRAK1(h) | | 7 | 14 | | | 8 | 20 | 68 | 37 | 21 |
| Itk(h) | | | | | | | 5 | 43 | 2 | 5 |
| JAK2(h) | | 17 | 37 | | | 19 | 16 | 27 | 2 | 5 |
| JAK3(h) | | 12 | 49 | | | 31 | 18 | 34 | 11 | 8 |
| JNK1α1(h) | | 4 | 35 | | | 8 | | | | |
| JNK2α2(h) | | 12 | 61 | | | 28 | | | | |
| JNK3(h) | | 1 | 21 | 2 | 17 | 5 | 0 | 13 | -1 | 0 |
| KDR(h) | | 11 | 25 | 17 | 20 | 9 | 13 | 34 | 11 | 4 |
| Lck(h) | | 42 | 31 | 2 | 38 | 38 | 34 | 37 | 3 | 20 |
| LIMK1(h) | | 77 | 94 | | | 81 | 43 | 88 | 109 | 38 |
| Lyn(h) | | 105 | 94 | | | 75 | 67 | 44 | 27 | 51 |
| MAPK1(h) | 41 | 50 | 49 | | | 15 | 56 | 74 | 74 | 30 |
| MAPK2(h) | | 43 | 63 | | | 12 | 55 | 61 | 73 | 22 |
| MAPKAP-K2(h) | 90 | 107 | 96 | 99 | 107 | 98 | 92 | 101 | 106 | 119 |
| MAPKAP-K3(h) | | 104 | 115 | | | 104 | 95 | 101 | 109 | 101 |
| MEK1(h) | 88 | 56 | 59 | 39 | 24 | 31 | 68 | 85 | 60 | 27 |
| Met(h) | | 23 | 101 | | | 25 | 21 | 24 | 4 | 18 |
| MKK4(m) | 53 | 42 | 97 | 122 | 82 | 61 | 40 | 79 | 56 | 12 |
| MKK6(h) | 58 | 58 | 114 | | | 29 | 44 | 50 | 70 | 17 |
| MKK7β(h) | 49 | 40 | 89 | | | 43 | 28 | 83 | 21 | 8 |
| MLCK(h) | | 46 | 34 | 9 | 19 | 44 | 25 | 48 | 6 | 13 |
| MLK1(h) | | 9 | 21 | | | 9 | 4 | 3 | 3 | 2 |
| MST2(h) | 6 | 7 | 48 | 17 | 17 | 7 | 1 | 10 | 10 | -2 |
| MuSK(h) | | 43 | 62 | | | 47 | 26 | 36 | 13 | 15 |

TABLE 4-continued

Inhibitory profile of reference compounds A, B, C, D, E, F, G, H, J and K against a panel of 100 kinases.
Numbers represent the percentage of remaining activity.

| | | | | | | | | | | |
|---|---|---|---|---|---|---|---|---|---|---|
| p70S6K(h) | 34 | 27 | 25 | 16 | 11 | 35 | 47 | 71 | 42 | 37 |
| PAK2(h) | | 106 | 92 | 19 | 43 | 94 | 85 | 63 | 19 | 55 |
| PAK3(h) | | 60 | 56 | | | 85 | 57 | 30 | 5 | 34 |
| PAK5(h) | | 14 | 51 | | | 30 | 9 | 10 | -4 | 5 |
| PAK6(h) | | 70 | 59 | | | 56 | 40 | 74 | 18 | 18 |
| PAR-1Bα(h) | | 43 | 16 | | | 12 | 27 | 69 | 5 | 10 |
| PDGFRα(h) | 77 | 93 | 104 | | | 80 | 70 | 77 | 48 | 68 |
| PDGFRβ(h) | 30 | 97 | 104 | 57 | 89 | 93 | 82 | 80 | 59 | 90 |
| PDK1(h) | 7 | 40 | 61 | 92 | 73 | 59 | 69 | 83 | 89 | 60 |
| PKA(h) | 91 | 98 | 113 | 64 | 93 | 112 | 94 | 91 | 64 | 67 |
| PKBα(h) | | 102 | 98 | | | 107 | 86 | 89 | 89 | 85 |
| PKCα(h) | 85 | 60 | 37 | | | 65 | 70 | 95 | 27 | 35 |
| PKCβII(h) | 87 | 78 | 53 | 32 | 65 | 81 | 111 | 119 | 87 | 119 |
| PKCγ(h) | 76 | 92 | 85 | | | 39 | 91 | 91 | 38 | 77 |
| PKCδ(h) | 92 | 53 | 61 | | | 68 | 96 | 98 | 76 | 93 |
| PKCε(h) | 103 | 60 | 68 | | | 80 | 79 | 98 | 35 | 88 |
| PKD2(h) | 11 | 6 | 6 | 11 | 7 | 14 | 22 | 34 | 1 | 21 |
| Plk3(h) | | 122 | 121 | | | 125 | 98 | 110 | 108 | 88 |
| PRAK(h) | | 43 | 61 | | | 31 | 56 | 54 | 64 | 49 |
| Pyk2(h) | | 18 | 25 | | | 38 | 21 | 23 | 8 | 10 |
| Ret(h) | 11 | 4 | 19 | 6 | 31 | 17 | 12 | 11 | 2 | 5 |
| RIPK2(h) | | 30 | 44 | | | 28 | 42 | 56 | 42 | 26 |
| ROCK-I(h) | | 24 | 31 | | | 41 | 30 | 68 | 16 | 17 |
| ROCK-II(h) | 4 | 2 | 33 | 0 | 7 | 7 | 5 | 8 | 1 | 1 |
| Rsk1(h) | 24 | 23 | 27 | 18 | 23 | 16 | 28 | 58 | 27 | 27 |
| SAPK2a(h) | | 116 | 109 | | | 103 | 95 | 100 | 109 | 100 |
| SAPK2b(h) | 57 | 94 | 112 | | | 102 | 67 | 100 | 96 | 88 |
| SAPK3(h) | 77 | 90 | 121 | | | 121 | 49 | 51 | 74 | 12 |
| SAPK4(h) | 89 | 92 | 108 | | | 84 | 65 | 108 | 75 | 33 |
| SGK(h) | | 29 | 41 | | | 30 | 56 | 119 | 56 | 61 |
| SRPK1(h) | | 127 | 107 | | | 93 | 67 | 98 | 92 | 51 |
| Syk(h) | | 47 | 72 | 16 | 66 | 61 | 35 | 71 | 18 | 13 |
| TBK1(h) | | 11 | 16 | | | 27 | -1 | 28 | -6 | -8 |
| Tie2(h) | | 75 | 77 | | | 68 | 131 | 132 | 49 | 72 |
| TrkA(h) | 1 | 1 | 0 | | | 0 | 5 | 1 | -1 | 0 |
| TrkB(h) | 2 | 0 | 4 | 116 | 125 | -1 | 1 | 1 | 1 | 2 |
| WNK2(h) | | 77 | 88 | | | 85 | 71 | 87 | 84 | 58 |
| ZAP-70(h) | 98 | 119 | 119 | 92 | 103 | 108 | 97 | 97 | 112 | 109 |
| ZIPK(h) | | 71 | 45 | | | 87 | 59 | 70 | 21 | 39 |
| PI3Kβ(h) | | 100 | | | | 97 | 101 | 100 | 98 | 94 |
| PI3Kγ(h) | 72 | 88 | | | | 73 | 2 | 91 | 71 | 4 |
| PI3Kδ(h) | 72 | 94 | | | | 73 | 53 | 93 | 79 | 32 |

<30% activity
30-70% activity
>70% activity

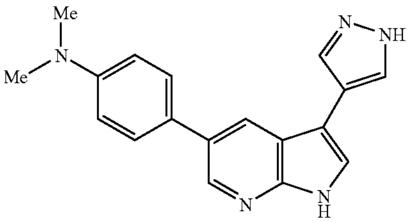

A

TABLE 4-continued
Inhibitory profile of reference compounds A, B, C, D, E, F, G, H, J and K against a panel of 100 kinases. Numbers represent the percentage of remaining activity.
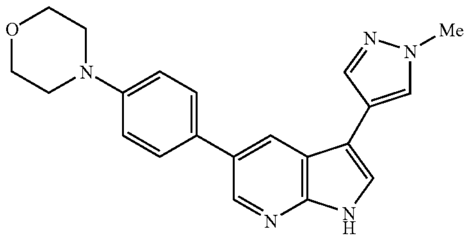
B
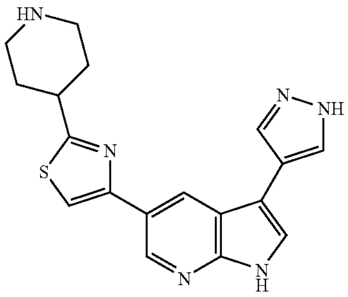
C
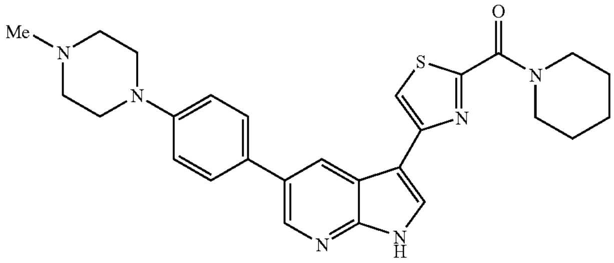
D
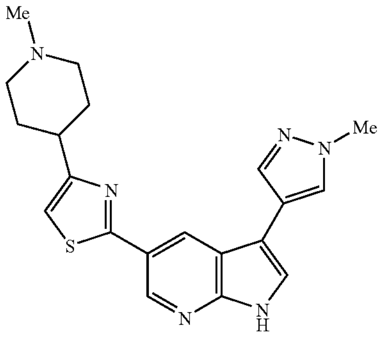
E
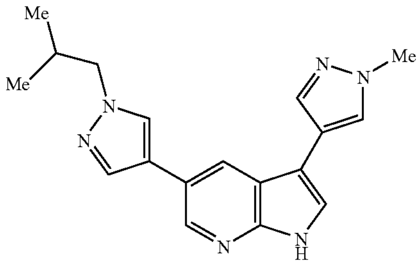
F TABLE 4-continued
Inhibitory profile of reference compounds A, B, C, D, E, F, G, H, J and K against a panel of 100 kinases.
Numbers represent the percentage of remaining activity.
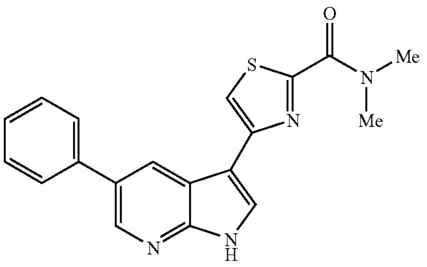
G
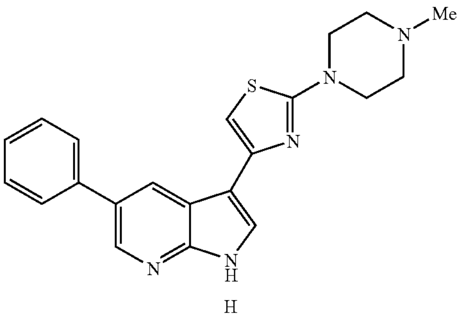
H
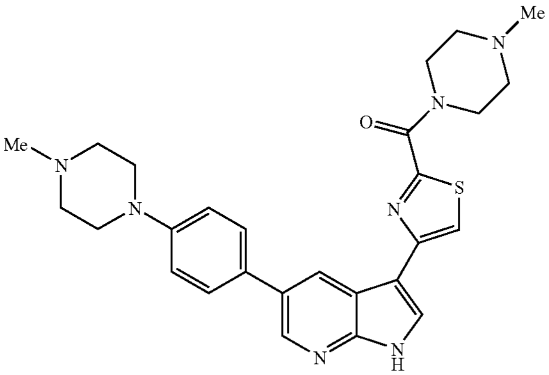
J
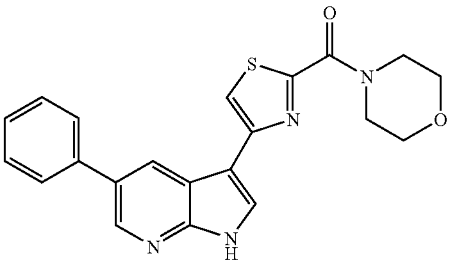
K Selectivity Expressed as Gini Coefficient Selectivity of compounds according to the present invention and reference compounds expressed as Gini coefficient (*J. Med. Chem.* 2007, 50, 5773-5779) is shown in Table 5. The individual Gini coefficients have been calculated using the data in Tables 3 and 4. Value Gini=0 corresponds to a totally non-selective compound; value Gini=1 reflects perfect selectivity (inhibition of a single target only)

TABLE 5

Selectivity of compounds (I) and reference compounds expressed as Gini coefficient.

| Non-aromatic C(5) group | | Aromatic C(5) group | |
|---|---|---|---|
| Compound (I) | Gini | Reference | Gini |
| 6 | 0.7173 | A | 0.3368 |
| 7 | 0.7006 | B | 0.3920 |
| 16 | 0.5745 | C | 0.4129 |
| 25 | 0.6769 | D | 0.2705 |
| 26 | 0.6727 | E | 0.3757 |
| 39 | 0.7661 | F | 0.3777 |
| 40 | 0.7684 | G | 0.3501 |
| 80 | 0.5741 | H | 0.4917 |
| | | J | 0.3286 |
| | | K | 0.2968 |
| Mean | 0.6813 ± 0.075 | Mean | 0.3633 ± 0.063 |

LPS-Induced TNFα Suppression in Mice

Experimental Protocol

The studies were carried out in male C57/B16 mice. Compounds (20 mg/kg; p.o.) were administered 30 minutes before injection of lipopolysaccharide (LPS). LPS was administered intraperitoneally at a dose of 10 mg/kg. Animals were sacrificed 1 hour following LPS injection. Blood was collected into heparinized tubes for measurement of plasma TNFα levels and spleens were collected for the measurement of c-Jun phosphorylation. Plasma TNFα was measured using an ELISA kit purchased from R&D systems. Spleens were homogenised, extracted in high salt (250 mM NaCl) lysis buffer with phosphatase inhibitors and c-Jun phosphorylation was measured using HTRF. The suppressive effect of compounds was calculated as the percentage reduction of the TNFα level in plasma and P-c-Jun level in spleen as compared with the vehicle-treated animals.

Results

The results are presented in Table 6.

TABLE 6

Percentage reduction in the level of TNFα and P-c-Jun for compounds (I).

| Cpd # I- | TNFα [%] | P-c-Jun [%] |
|---|---|---|
| 3 | 60 | 0 |
| 6 | 82 | 41 |
| 7 | 63 | 18 |
| 10 | 62 | 75 |
| 16 | 45 | 20 |
| 19 | 9 | 32 |
| 23 | 61 | 2 |
| 24 | 57 | 23 |
| 25 | 80 | 25 |

TABLE 6-continued

Percentage reduction in the level of TNFα and P-c-Jun for compounds (I).

| Cpd # I- | TNFα [%] | P-c-Jun [%] |
|---|---|---|
| 26 | 71 | 16 |
| 37 | 51 | −3 |
| 39 | 67 | 10 |
| 40 | 61 | 35 |
| 43 | 74 | 0 |
| 44 | 58 | 17 |
| 71 | 86 | 7 |
| 72 | 84 | 15 |
| 136 | 87 | 42 |
| 137 | 45 | 15 |
| 139 | 54 | 31 |
| 141 | 43 | 4 |
| 154 | 60 | 33 |

MOG (35-55)-Induced Experimental Autoimmune Encephalomyelitis (EAE) in C57/B16J Mice Experimental Protocol Reagents PBS 0.01M phosphate buffer, 0.0027M potassium chloride, 0.137M sodium chloride pH 7.4 (prepared from tablets—Sigma, Poole, Dorset. UK.)

*Mycobacterium tuberculosis* H37 RA: Difco Laboratories, Detroit Mich., USA

MOG peptide (35-55) synthesised by Rachel Striesow, Advanced Biotechnology Centre, Imperial College Faculty of Medicine, Charing Cross Campus, Fulham Palace Road, London, W6 8RF.

Pertussis Toxin—Calbiochem (Merck Bioscience (UK), Beeston, Nottingham. UK)

Freund's Incomplete Adjuvant (Difco Laboratories, Detroit Mich., USA)

Animals

Specific pathogen-free male C57/B16J mice will be obtained at the age of 6-8 weeks (20-24 g) from Charles River UK Ltd. (Margate, UK). Mice will be purchased and acclimatised for a period of at least 3 days before the start of the experiment The mice will be housed in transparent plastic cages with wire covers (270 W×370 L×230 H mm) 2 animals per cage, in a room with a constant temperature (20-24° C.) and humidity (40-70%) and a 12 h light-dark cycle (lightened from 6 A.M. to 6 P.M.). Animals will be provided with pellet food (RM1 E, Specialist Diet Services, Witham, UK) and tap water ad libitum.

Methods

MOG (35-55) adjuvant was prepared as follows:

1. Prepare a 20 ml syringe by removing the plunger and plugging the injection end with a bung (we use the cut off end of a Treff Pellet Mixer (2.5 mL), Anachem, Lutons, Bedfordshire. UK.)
2. Add 5 ml of 2 mg/ml MOG 35-55 in PBS
3. Add 5 ml of Freunds incomplete adjuvant supplemented (IFA) with 5 mg/ml (25 mg total) *Mycobacterium Tuberculosis* H37ra to the 20 ml syringe
4. Cover with a double layer of parafilm and vortex mixture for 1 minute.

5. Sonicate (15 min; Decon FS Minor sonicating water bath)
6. Emulsify by repeated passing between two 20 ml syringes (20 passes; syringes connected with PVC tubing, secured with cable ties).
7. Check emulsion—place drop of emulsion onto water. Drop should stay as entity, if drop dissipates quickly repeat step 5.
8. Dispense 10 ml aliquots into 10 ml syringes and maintain either frozen (−80° C.) or on ice until used.

Induction Protocol

1. At day 0 mice were injected sc. in two sites on the lower flanks with 0.1 ml of MOG (35-55) adjuvant. Mice also receive 30 ng pertussis toxin in 100 μl of PBS iv or ip.
2. At day 2 mice received 30 ng of pertussis toxin in 100 μl of PBS iv or ip.
3. At day 7 mice were injected sc. in two sites on the medial flanks with 0.1 mL of MOG (35-55) adjuvant.
4. Mice were observed daily for clinical symptoms.

Points to Note

Sites of adjuvant injection should not be areas that are involved in scruffing of animals. Manipulation of sc. sites leads to reduced induction and peak scores.

Pertussis toxin, MTB, MOG and IFA should all be batch tested as some batches reduce induction and peak scores.

Animals must be more than 20 g on induction of disease, otherwise, there is a mortality rate of about 20% (normally less than 5%).

Chronic Mouse EAE Scoring

Animals receive two scores. One gives an accurate assessment of the animals' disability (cumulative score). The second reflects the overall severity of the animal (peak score).

Peak score=maximum score reached

Cumulative score=Sum of scores from each section e.g. if mouse has FT, IRR, HLP, peak score is 4, cumulative score is 7.

| | | |
|---|---|---|
| Slightly Floppy Tail (half tail paralysis)/ Slight Tail Spasticity | SFT/STSp | 0.5 |
| Floppy Tail/Tail Spasticity | FT/TSp | 1 |
| Slightly Impaired Righting Reflex | SIRR | 1.5 |
| Impaired Righting Reflex | IRR | 2 |
| Slight Hind Limb Weakness/Hind Limb Weakness in one leg | SHLW/ HLWx1 | 2.5 |
| Slight Hind Limb Spasticity/Hind Limb Spasticity in one leg | SHLSp/ HLSpx1 | 2.5 |
| Hind Limb Weakness/Hind Limb Spasticity | HLW/HLSp | 3 |
| Hind Limb Weakness in one leg and Paralysis in the other/'Very' Hind Limb Weakness in both legs/Hind Limb Spasticity Causing Immobility of One Limb/Very Hind Limb Spasticity | HLW/P/ VHLW/ HLW/SP/ VHLSp | 3.5 |
| Hind Limb Paralysis/Hind Limb Spasticity Causing Immobility of Both Hind Limbs | HLP/HLP(Sp) | 4 |
| Slight Fore Limb Weakness/Fore Limb Weakness in one leg/Slight Fore Limb Spasticity | SFLW/FLWx1/ SFLSp | 4.5 |
| Fore Limb Weakness/Fore Limb Spasticity | FLW/FLSp | 5 |
| Fore Limb Weakness in one leg and Paralysis in the other/'Very' Fore Limb Weakness/ Fore Limb Spasticity Causing Immobility of One Fore Limb/Very Fore Limb Spasticity | FLW/P/VFLW/ FLW/Sp/ VFLSp | 5.5 |
| Fore Limb Paralysis/Fore Limb Spasticity Causing Immobility of Both Fore Limbs | FLP/FLP (Sp) | 6 |
| Moribund | Mori | 7 |

Short Description of Scores

Tail

Slightly Floppy Tail—Up to 50% of tail without tone.

Floppy Tail—More than 50% of tail without tone.

Hind Limb Weakness

Slight Hind Limb Weakness—Impaired gate but legs still load bearing.

Hind Limb Weakness—Impaired gate and loss of load bearing in hind limbs.

Very Hind Limb Weakness—Inability to move hind limb through more than 50% of stride and non load bearing.

Hind Limb Paralysis—Complete loss of movement of hind limbs

Fore Limb Weakness

Slights Forelimb Weakness—Reduced grip in forelimbs.

Forelimb Weakness—Reduced grip in forelimbs leading to problems with forward movement.

Very Forelimb Weakness—Limbs still moving but inability to move.

Forelimb Paralysis—Complete loss of movement in forelimbs.

Spasticity

Spasticity scores are comparable in disability with weakness scores but due to rigidity rather than loss of muscle tone.

References

Nicole Heijmans et al. Journal of Neuroimmunology, 167, (2005) 23-33

Dusanka S. Skundric et al. Journal of Neuroimmunology, 136 (2003) 34-45

S Amor et al, Journal of Immunology, 150, (1993) 5666-5672

Baker et al. Journal of Neuroimmunology, 28, (1990) 261-271

Results

The results of EAE experiments for (I-6), (I-25) and (I-40) and reference aromatic compound A are shown in FIGS. 1-13. The drug was administered at the appearance of symptoms (score 1; floppy tail).

Figure 2:
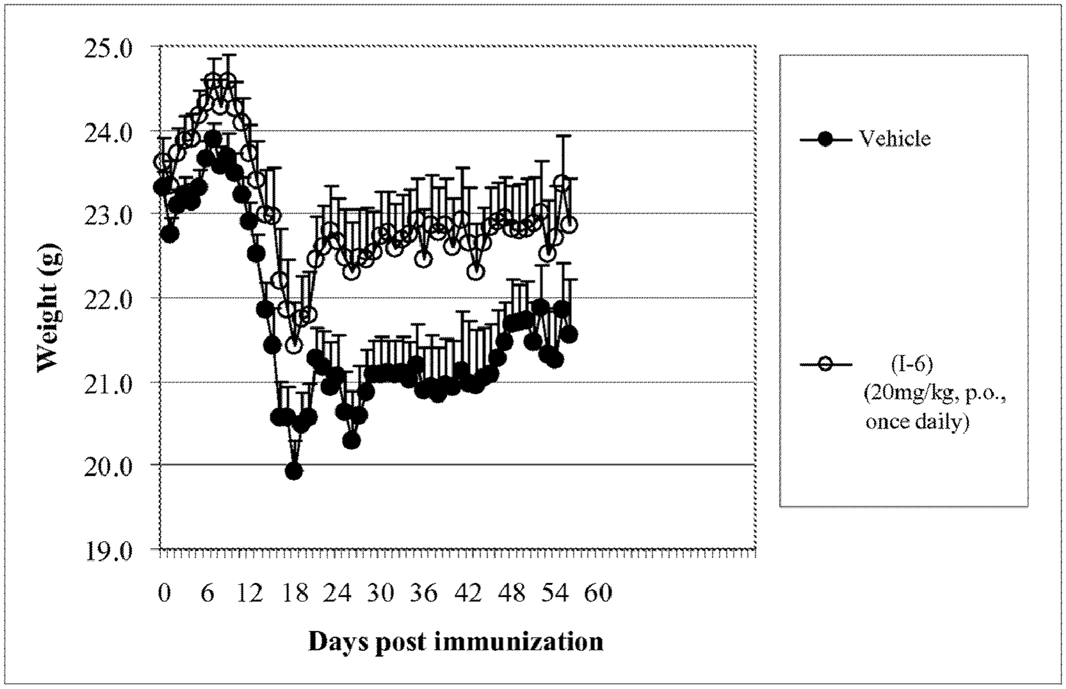
FIG. 2 shows the effect of compound I-6 (20 mg/kg, p.o., once daily) on animals' weight in the EAE experiment in mice.
Figure 3:
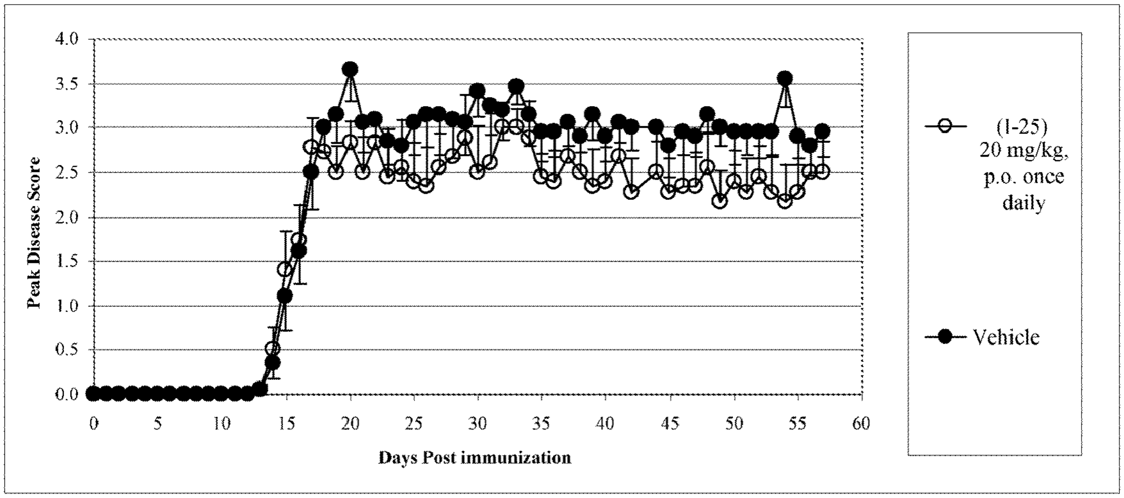
FIG. 3 shows the effect of compound I-25 (20 mg/kg, p.o., once daily) on peak disease score in the EAE experiment in mice.
Figure 4:
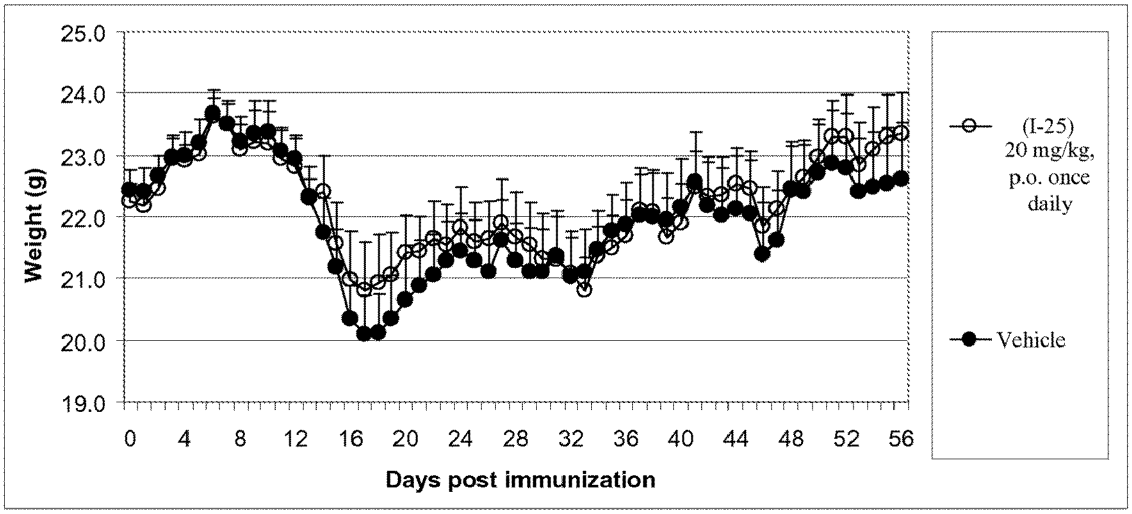
FIG. 4 shows the effect of compound I-25 (20 mg/kg, p.o., once daily) on animals' weight in the EAE experiment in mice.
Figure 5:
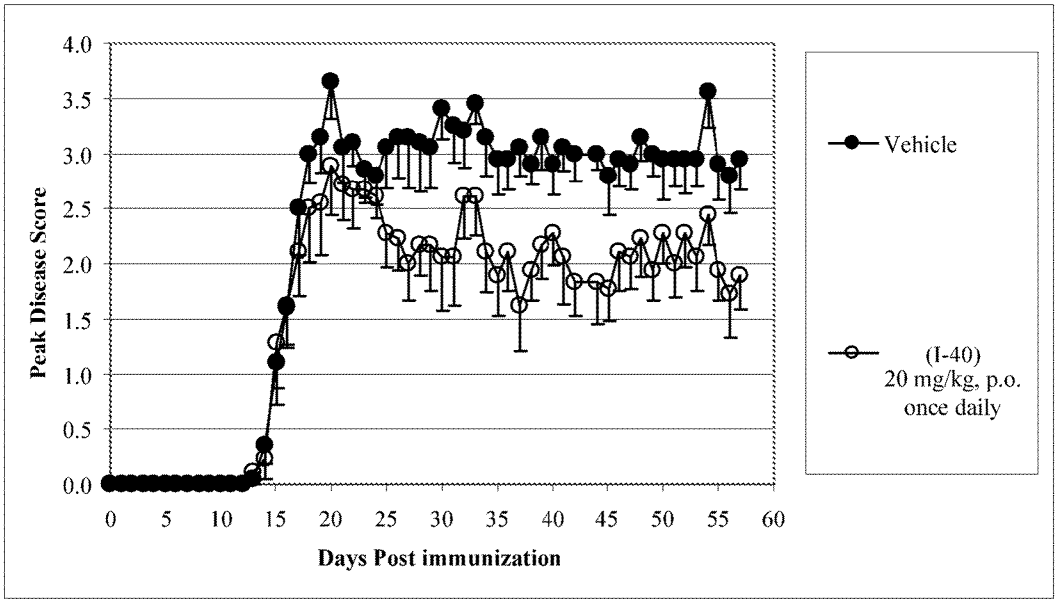
FIG. 5 shows the effect of compound I-40 (20 mg/kg, p.o., once daily) on peak disease score in the EAE experiment in mice.
Figure 6:
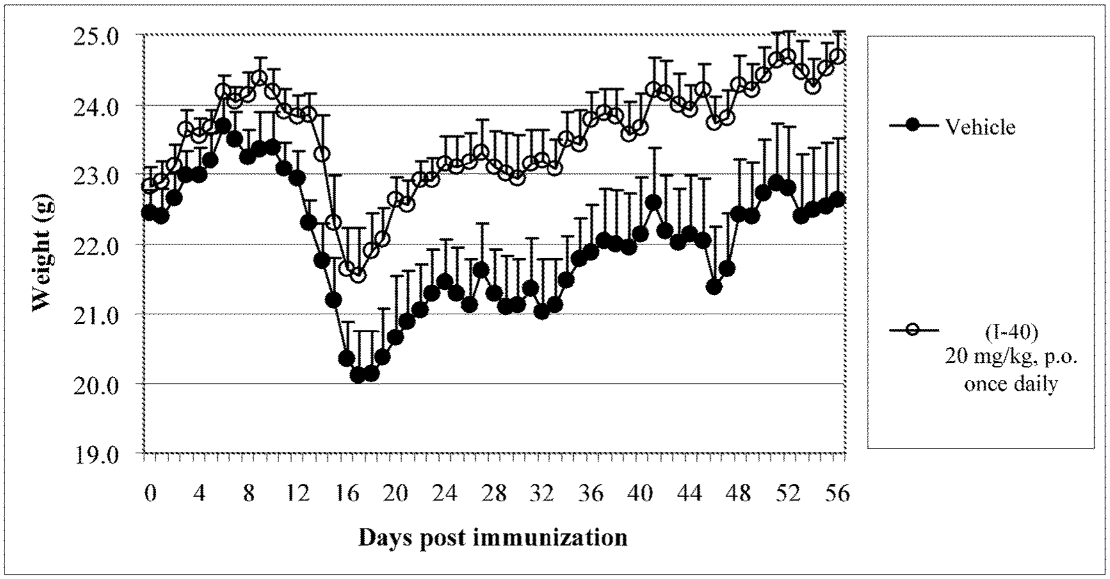
FIG. 6 shows the effect of compound I-40 (20 mg/kg, p.o., once daily) on animals' weight in the EAE experiment in mice.
Figure 7:
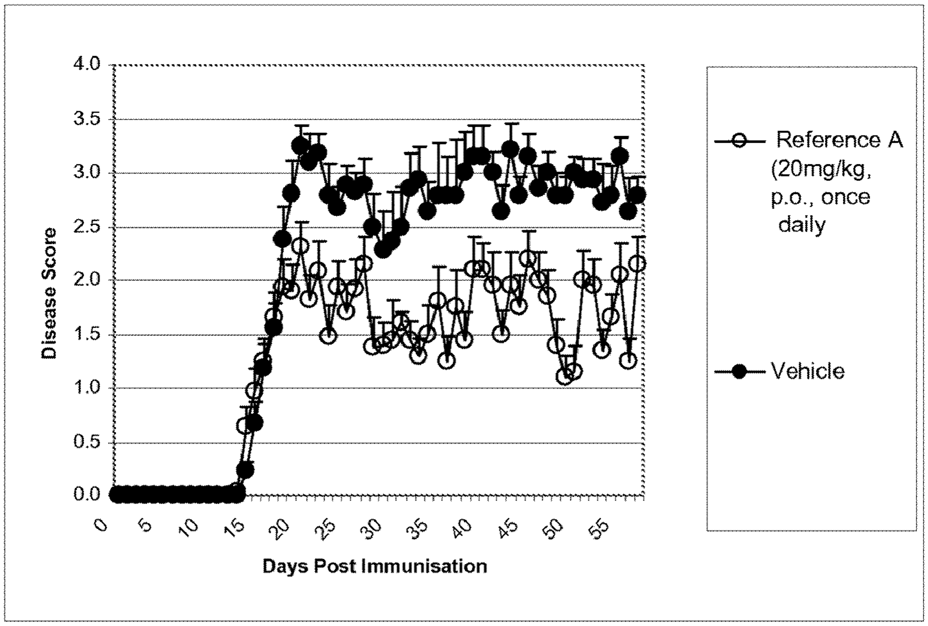
FIG. 7 shows the effect of reference compound A (20 mg/kg, p.o., once daily) on peak disease score in the EAE experiment in mice.
Figure 8:
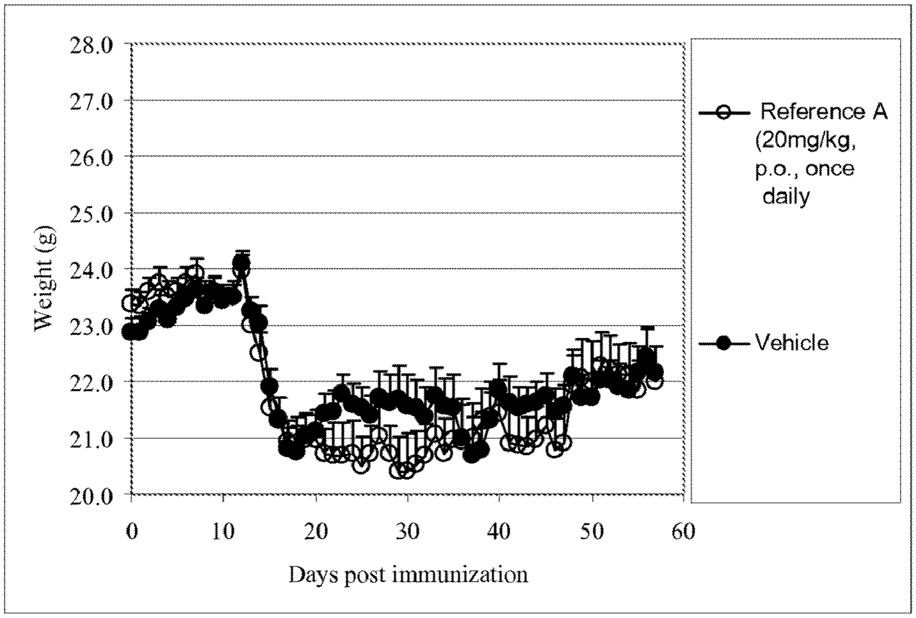
FIG. 8 shows the effect of reference compound A (20 mg/kg, p.o., once daily) on animals' weight in the EAE experiment in mice.

FIG. 1 shows the effect of (I-6) (20 mg/kg, p.o., once daily) on peak disease score in the EAE experiment in mice;

FIG. 2 shows the effect of (I-6) (20 mg/kg, p.o., once daily) on animals' weight in the EAE experiment in mice;

FIG. 3 shows the effect of (I-25) (20 mg/kg, p.o., once daily) on peak disease score in the EAE experiment in mice;

FIG. 4 shows the effect of (I-25) (20 mg/kg, p.o., once daily) on animals' weight in the EAE experiment in mice;

FIG. 5 shows the effect of (I-40) (20 mg/kg, p.o., once daily) on peak disease score in the EAE experiment in mice;

FIG. 6 shows the effect of (I-40) (20 mg/kg, p.o., once daily) on animals' weight in the EAE experiment in mice;

FIG. 7 shows the effect of reference compound A (20 mg/kg, p.o., once daily) on peak disease score in the EAE experiment in mice;

FIG. 8 shows the effect of reference compound A (20 mg/kg, p.o., once daily) on animals' weight in the EAE experiment in mice.

Figure 9:
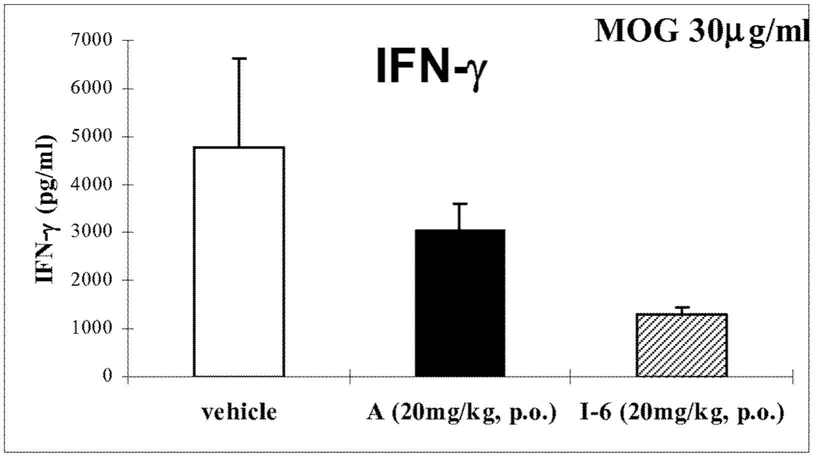
FIG. 9 shows MOG-induced IFN-gamma production from spleen cells of MOG-immunized mice after treatment with compound I-6 (20 mg/kg, p.o., once daily) and compound A (20 mg/kg, p.o., once daily).

FIG. 9: shows MOG-induced IFN-gamma production from spleen cells of MOG-immunized mice after treatment with (I-6) (20 mg/kg, p.o., once daily) and compound A (20 mg/kg, p.o., once daily).

Figure 10:
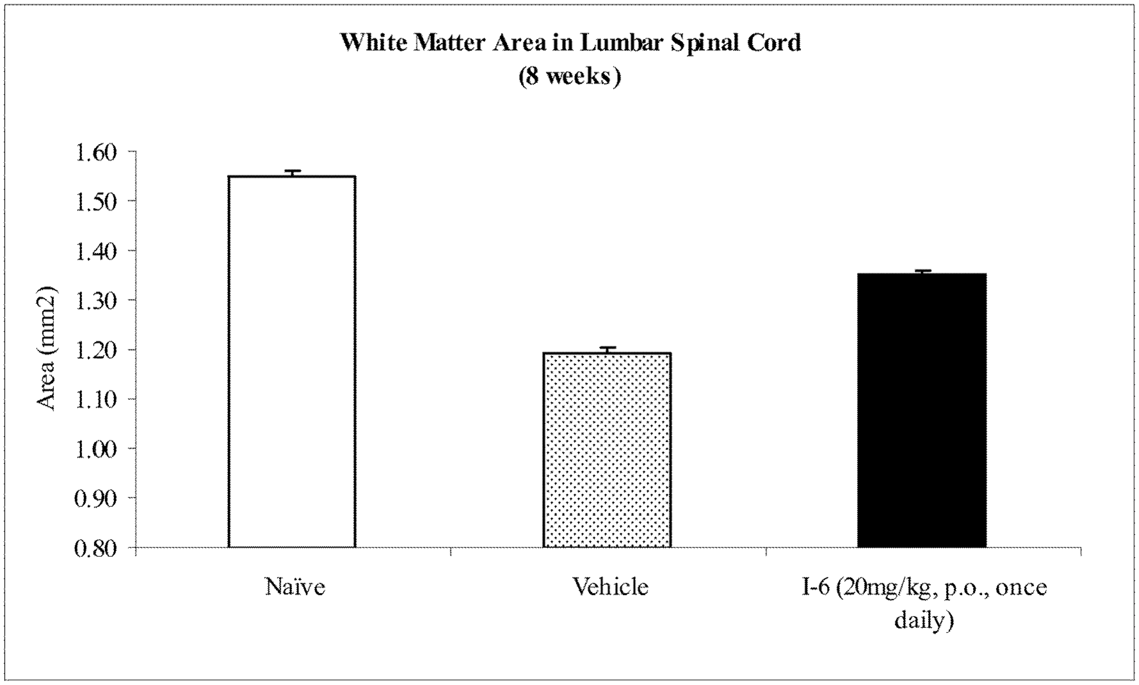
FIG. 10 shows the preservation of a total white matter area in the lumbar spinal cord of mice following MOG-induced EAE after treatment with compound I-6 (20 mg/kg, p.o., once daily).

FIG. 10: shows the preservation of a total white matter area in the lumbar spinal cord of mice following MOG-induced EAE after treatment with (I-6) (20 mg/kg, p.o., once daily).

Figure 11:
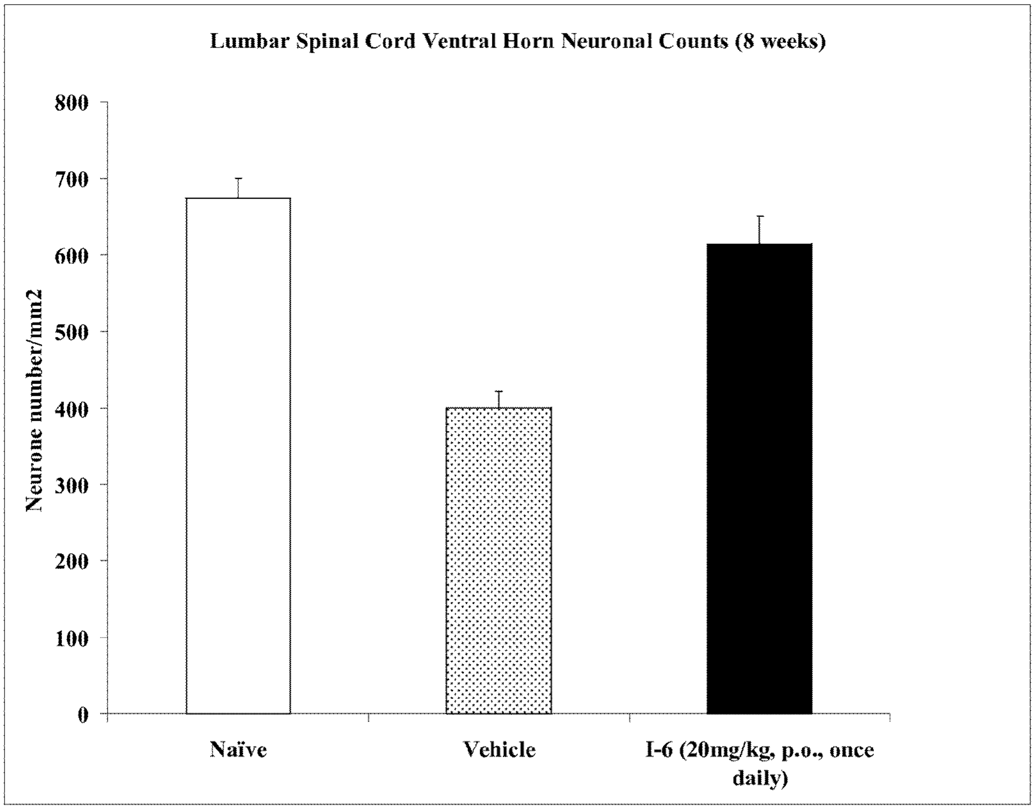
FIG. 11 shows the preservation of neuronal numbers in the ventral horn of the lumbar spinal cords of mice following MOG-induced EAE after treatment with compound 1-6 (20 mg/kg, p.o., once daily).

FIG. 11: shows the preservation of neuronal numbers in the ventral horn of the lumbar spinal cords of mice following MOG-induced EAE after treatment with (I-6) (20 mg/kg, p.o., once daily).

Figure 12:
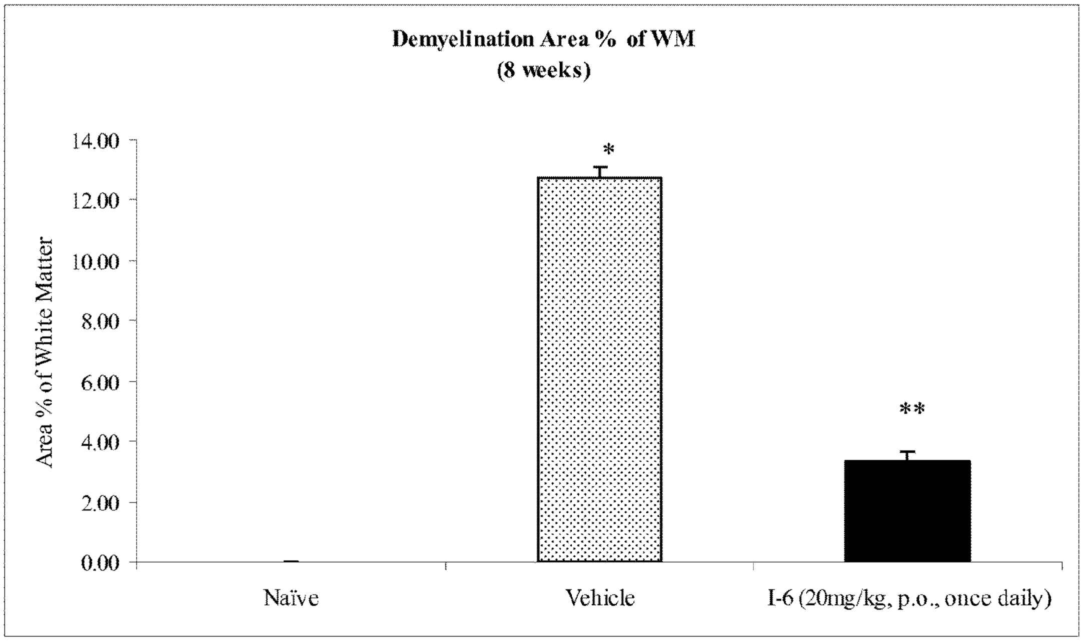
FIG. 12 shows the decrease in demyelination in the lumbar spinal cord of mice following MOG-induced EAE after treatment with compound I-6 (20 mg/kg, p.o., once daily).

FIG. 12: shows the decrease in demyelination in the lumbar spinal cord of mice following MOG-induced EAE after treatment with (I-6) (20 mg/kg, p.o., once daily).

Figure 13:
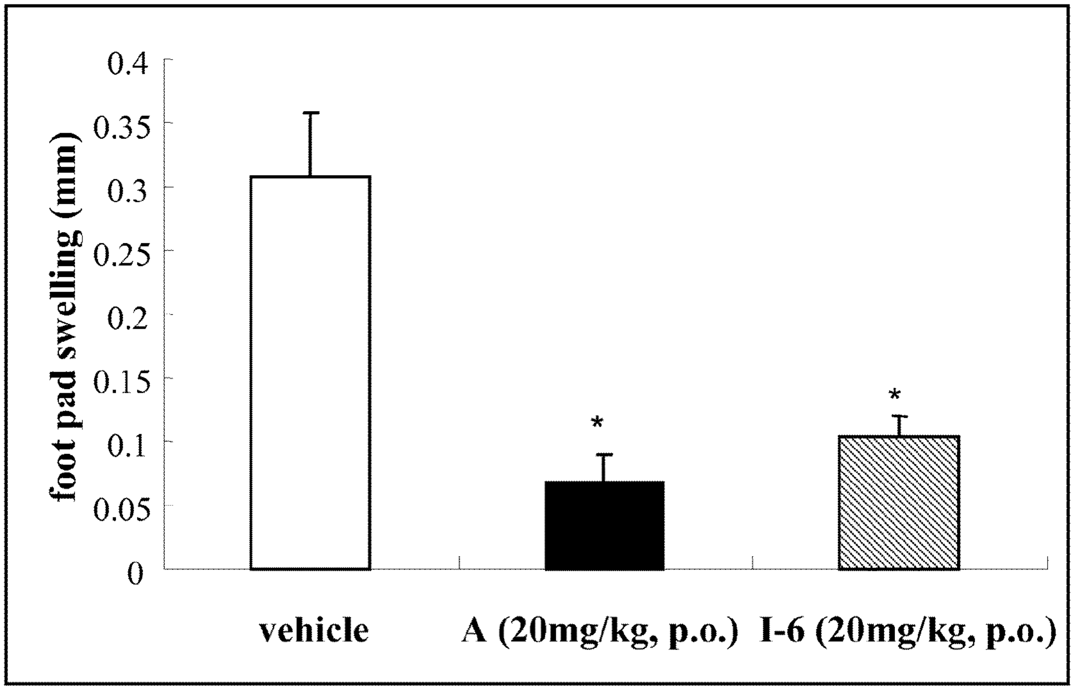
FIG. 13 shows MOG-induced Delayed Type Hypersensitivity (DTH) responses in MOG-immunized mice Biozzi Relapsing-Remitting EAE.

FIG. 13: shows MOG-induced Delayed Type Hypersensitivity (DTH) responses in MOG-immunized mice

Biozzi Relapsing-Remitting EAE

Experimental Protocol

Reagents

PBS 0.01M phosphate buffer, 0.0027M potassium chloride, 0.137M sodium chloride pH 7.4 (prepared from tablets—Sigma, Poole, Dorset. UK.)

Lyophilized Biozzi Spinal Cord Homogenate.—Prepared by homogenizing whole Biozzi spinal cords in PBS. The homogenate was then lyophilized and stored at −80° C. till required.

Freund's Complete Adjuvant (Difco Laboratories, Detroit Mich., USA)

Animals

Specific pathogen-free male Biozzi ABH mice will be obtained at the age of 6-8 weeks (20-24 g) from Harlan UK Ltd. (Bicester, UK). Mice will be purchased and acclimatised for a period of at least 7 days before the start of the experiment The mice will be housed in transparent plastic cages with wire covers (270 W×370 L×230 H mm) 2 animals per cage, in a room with a constant temperature (20-24° C.) and humidity (40-70%) and a 12 h light-dark cycle (lightened from 6 A.M. to 6 P.M.). Animals will be provided with pellet food (RM1 E, Specialist Diet Services, Witham, UK) and tap water ad libitum.

Equipment

Balance: AT201 (Mettler-Toledo AG, Greifensee, Switzerland) for chemicals and tubes.

Balance: LA4200 (Satorius Ltd, Epsom, UK) for animals.

Polytron homogeniser: PT300; PT-DA 3020/2S probe (Kinematica AG, Switzerland) for inoculum preparation Plastipack disposable syringes, (Scientific Laboratory Supplies Ltd., Wilford, UK)

Methods

Biozzi adjuvant was prepared as follows:

1. Prepare a 20 ml syringe by removing the plunger and plugging the injection end with a bung (we use the cut off end of a Treff Pellet Mixer (2.5 ml), Anachem, Lutons, Bedfordshire. UK.)
2. Add 6 ml of PBS to 40 mg Lyophilized Biozzi Spinal Cord Homogenate
3. Add 6 ml of Freunds complete adjuvant supplemented (CFA) and 56 μg/ml m. butyricum to the 20 ml syringe
4. Cover with a double layer of parafilm and vortex mixture for 1 minute.

4 Sonicate (15 min; Decon FS Minor sonicating water bath)

5 Emulsify by repeated passing between two 20 ml syringes (20 passes; syringes connected with PVC tubing, secured with cable ties).

6 Check emulsion—place drop of emulsion onto water. Drop should stay as entity, if drop dissipates quickly repeat step 5.

7 Dispense 10 ml aliquots into 10 ml syringes and maintain either frozen (−80° C.) or on ice until used.

Induction Protocol

1) At day 0 mice were injected sc. in two sites on the lower flanks with 0.15 ml of Biozzi adjuvant (therefore 0.3 ml in total).

2) At day 7 mice were injected sc. in two sites on the medial flanks with 0.15 ml of Biozzi adjuvant (therefore 0.3 ml adjuvant in total).

3) Mice were observed daily for clinical symptoms.

Points to Note

Sites of adjuvant injection should not be areas that are involved in scruffing of animals. Manipulation of sc. sites leads to reduced induction and peak scores.

Chronic Mouse EAE Scoring

Animals receive two scores. One gives an accurate assessment of the animals' disability (cumulative score). The second reflects the overall severity of the animal (peak score).

Peak score=maximum score reached

Cumulative score=Sum of scores from each section eg if mouse has FT, IRR, HLP, peak score is 4, cumulative score is 7.

| | | |
|---|---|---|
| Slightly Floppy Tail (half tail paralysis)/ Slight Tail Spasticity | SFT/STSp | 0.5 |
| Floppy Tail/Tail Spasticity | FT/TSp | 1 |
| Slightly Impaired Righting Reflex | SIRR | 1.5 |
| Impaired Righting Reflex | IRR | 2 |
| Slight Hind Limb Weakness/Hind Limb Weakness in one leg | SHLW/ HLWx1 | 2.5 |
| Slight Hind Limb Spasticity/Hind Limb Spasticity in one leg | SHLSp/ HLSpx1 | 2.5 |
| Hind Limb Weakness/Hind Limb Spasticity | HLW/HLSp | 3 |
| Hind Limb Weakness in one leg and Paralysis in the other/'Very' Hind Limb Weakness in both legs/Hind Limb Spasticity Causing Immobility of One Limb/Very Hind Limb Spasticity | HLW/P/ VHLW/ HLW/SP/ VHLSp | 3.5 |
| Hind Limb Paralysis/Hind Limb Spasticity Causing Immobility of Both Hind Limbs | HLP/HLP(Sp) | 4 |
| Slight Fore Limb Weakness/Fore Limb Weakness in one leg/Slight Fore Limb Spasticity | SFLW/FLWx1/ SFLSp | 4.5 |
| Fore Limb Weakness/Fore Limb Spasticity | FLW/FLSp | 5 |
| Fore Limb Weakness in one leg and Paralysis in the other/'Very' Fore Limb Weakness/ | FLW/P/VFLW/ FLW/Sp/ | 5.5 |

-continued

| | | |
|---|---|---|
| Fore Limb Spasticity Causing Immobility of One Fore Limb/Very Fore Limb Spasticity | VFLSp | |
| Fore Limb Paralysis/Fore Limb Spasticity Causing Immobility of Both Fore Limbs | FLP/FLP (Sp) | 6 |
| Moribund | Mori | 7 |

Short Description of Scores

Tail

Slightly Floppy Tail—Up to 50% of tail without tone.

Floppy Tail—More than 50% of tail without tone.

Hind Limb Weakness

Slight Hind Limb Weakness—Impaired gate but legs still load bearing.

Hind Limb Weakness—Impaired gate and loss of load bearing in hind limbs.

Very Hind Limb Weakness—Inability to move hind limb through more than 50% of stride and non load bearing.

Hind Limb Paralysis—Complete loss of movement of hind limbs

Fore Limb Weakness

Slights Forelimb Weakness—Reduced grip in forelimbs.

Forelimb Weakness—Reduced grip in forelimbs leading to problems with forward movement.

Very Forelimb Weakness—Limbs still moving but inability to move.

Forelimb Paralysis—Complete loss of movement in forelimbs.

Spasticity

Spasticity scores are comparable in disability with weakness scores but due to rigidity rather than loss of muscle tone.

References

Nicole Heijmans et al. Journal of Neuroimmunology, 167, (2005) 23-33

Dusanka S. Skundric et al. Journal of Neuroimmunology, 136 (2003) 34-45

S Amor et al, Journal of Immunology, 150, (1993) 5666-5672

Baker et al. Journal of Neuroimmunology, 28, (1990) 261-271

Results

Figure 14:
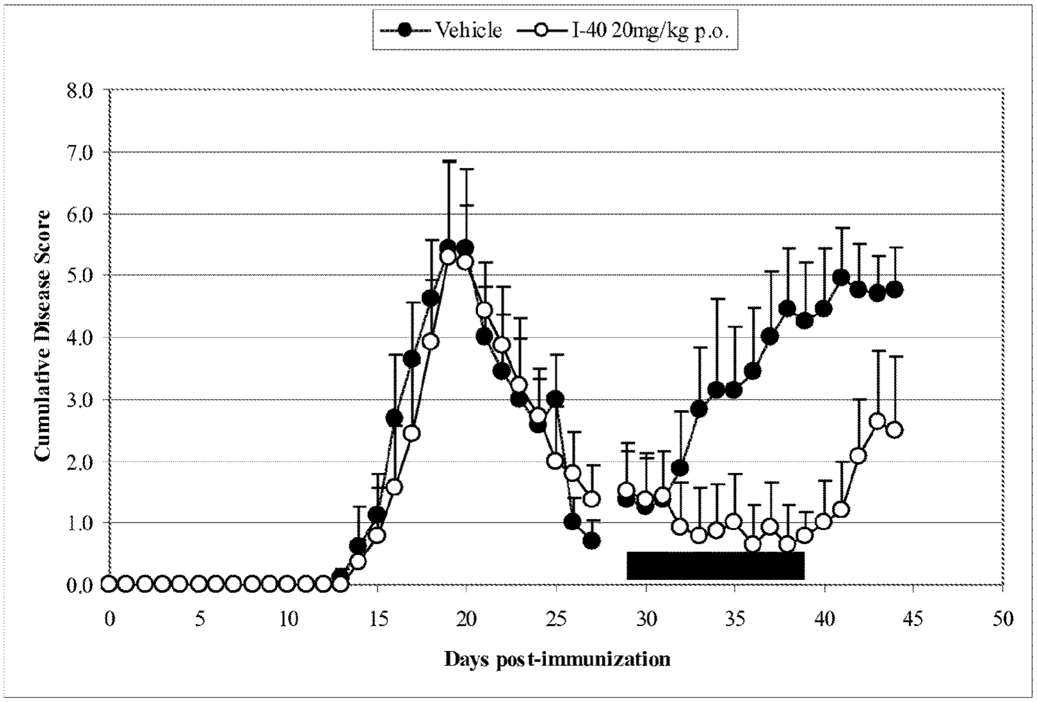
FIG. 14 shows the effect of compound I-40 (20 mg/kg, p.o., once daily) on cumulative disease score in Biozzi mice following spinal cord homogenate-induced relapsing-remitting EAE.

The results of Biozzi relapsing-remitting EAE experiments for (I-40) are shown in FIG. 14. Only animals which developed full hind limb paralysis in the first phase of disease were entered into the study when they developed another phase of disease.

FIG. 14 shows the effect of (I-40) (20 mg/kg, p.o., once daily) on cumulative disease score in Biozzi mice following spinal cord homogenate-induced relapsing-remitting EAE.

MBP-induced EAE in Lewis Rat

Experimental Protocol

On day 0, Lewis rats were immunised subcutaneously in the dorsal surface of each hind foot with 20 μl inoculum containing 20 μg MBP emulsified in Freund's complete adjuvant containing *M. tuberculosis* (final concentration 3 mg/ml). Lewis rats were assigned to vehicle or treatment groups. Rats received the relevant treatment from day 5 for the entire course of the study. Rats received vehicle (0.5% methyl cellulose in MilliQ water), 5, 10 or 20 mg/kg of compounds, orally once daily. Rats were the culled on day 21 post induction, plasma and tissue were taken for further analysis.

Results

The results of EAE experiments for (I-6) and (I-40) are shown in FIGS. 15-18. The drug was administered from day 5 post induction of the disease.

Figure 15:
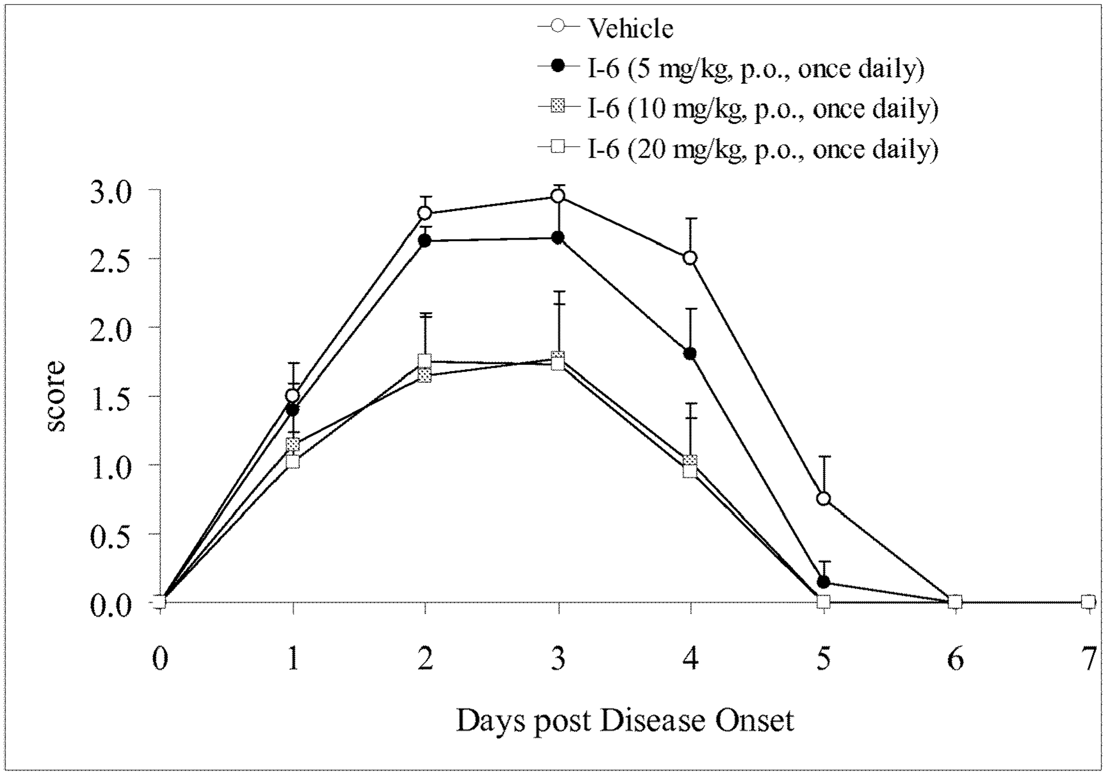
FIG. 15 shows the effect of compound I-6 (5, 10 and 20 mg/kg, p.o., once daily) on scores post-onset of disease following MBP-induced EAE in Lewis rats.
Figure 16:
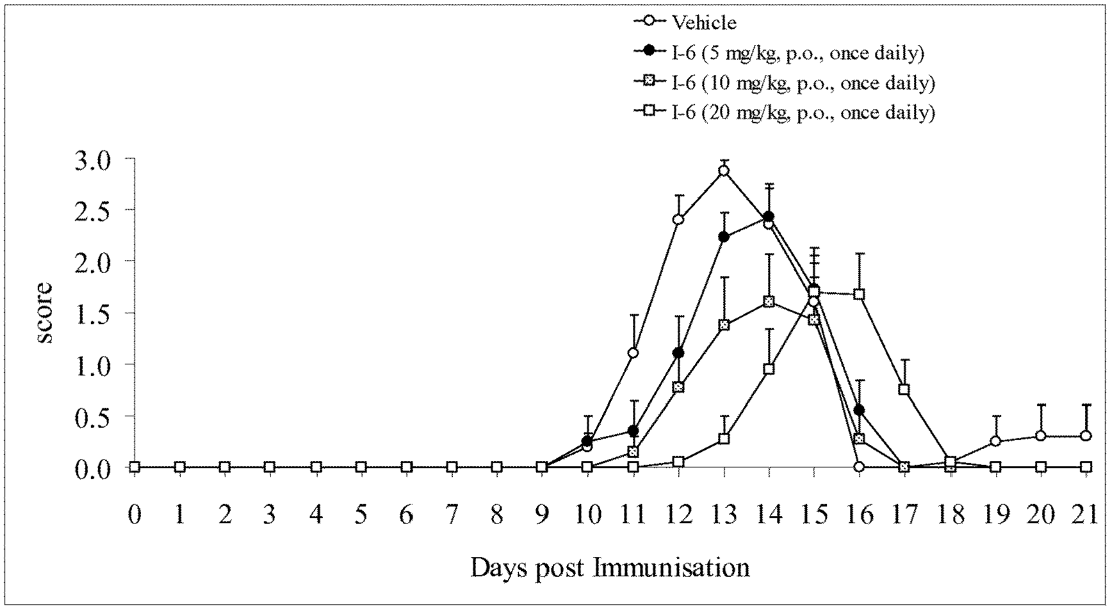
FIG. 16 shows the effect of compound I-6 (5, 10 and 20 mg/kg, p.o., once daily) on disease scores following MBP-induced EAE in Lewis rats.
Figure 17:
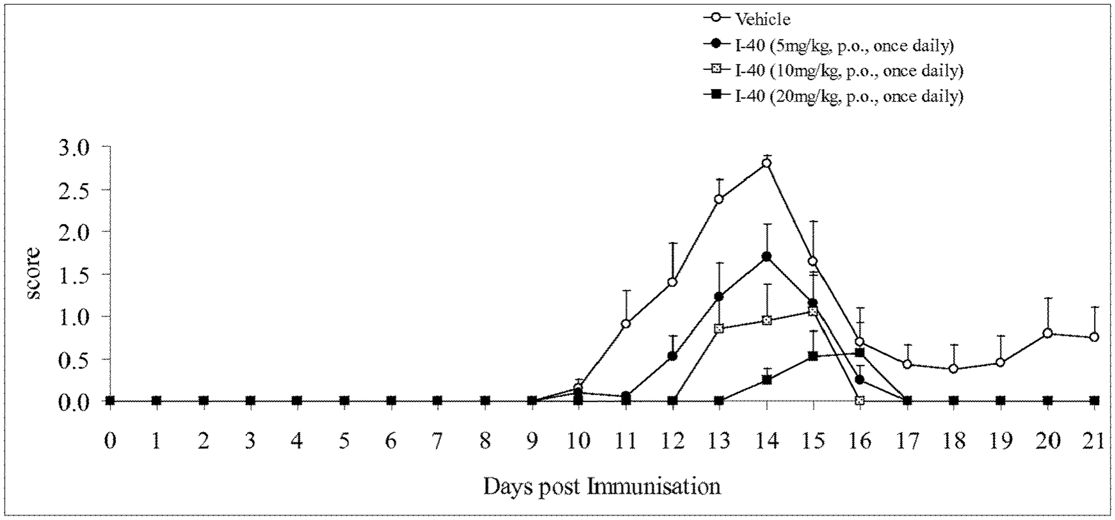
FIG. 17 shows the effect of compound I-40 (5, 10 and 20 mg/kg, p.o., once daily) on disease scores following MBP-induced EAE in Lewis rats.
Figure 18:
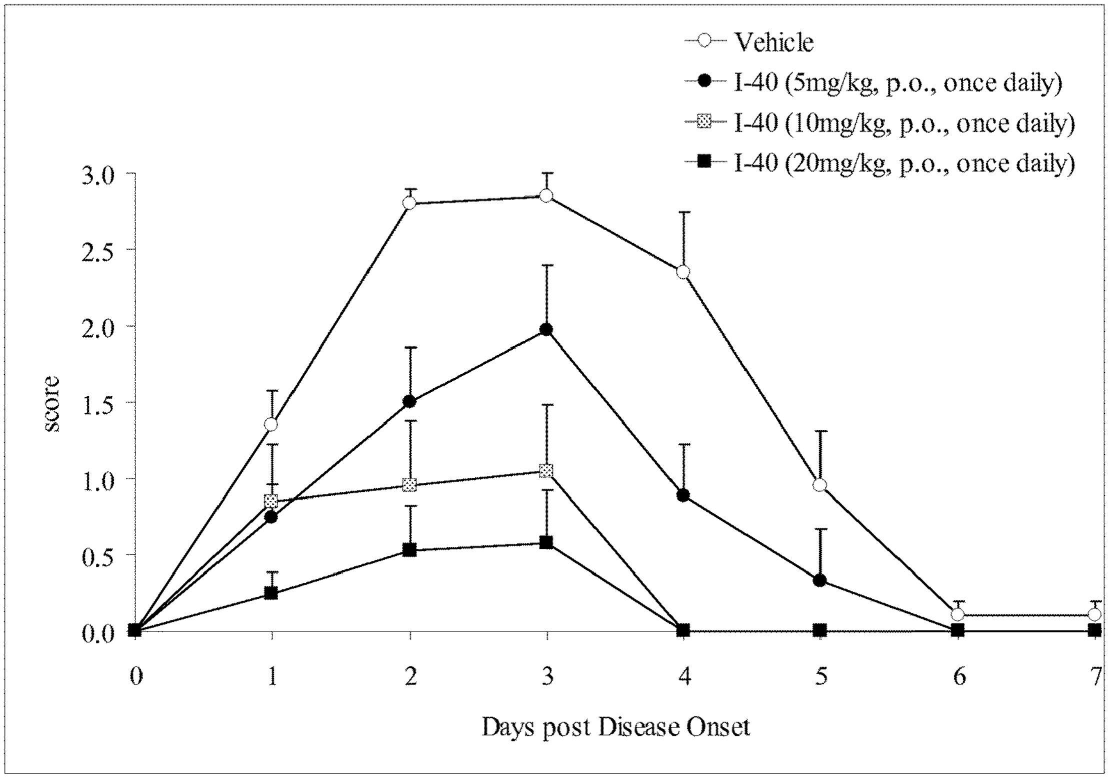
FIG. 18 shows the effect of compound I-40 (5, 10 and 20 mg/kg, p.o., once daily) on scores post-onset of disease following MBP-induced EAE in Lewis rats.

FIG. 15 shows the effect of (I-6) (5, 10 and 20 mg/kg, p.o., once daily) on scores post-onset of disease following MBP-induced EAE in Lewis rats FIG. 16 shows the effect of (I-6) (5, 10 and 20 mg/kg, p.o., once daily) on disease scores following MBP-induced EAE in Lewis rats FIG. 17 shows the effect of (I-40) (5, 10 and 20 mg/kg, p.o., once daily) on disease scores following MBP-induced EAE in Lewis rats FIG. 18 shows the effect of (I-40) (5, 10 and 20 mg/kg, p.o., once daily) on scores post-onset of disease following MBP-induced EAE in Lewis rats Suppression of Arthritis Development in Collagen-Induced Arthritis (CIA) in a Partial Therapeutic Regimen.

Experimental Protocol

DBA1/J mice were immunized with bCII/CFA at day 0 then boosted at day 21 with bCII/IFA. Compounds were given oral dosing daily at the dose indicated from day 19 after induction of antibodies to collagen II. Arthritis development was monitored over the course of study by measuring the arthritis score.

Results

Figure 19:
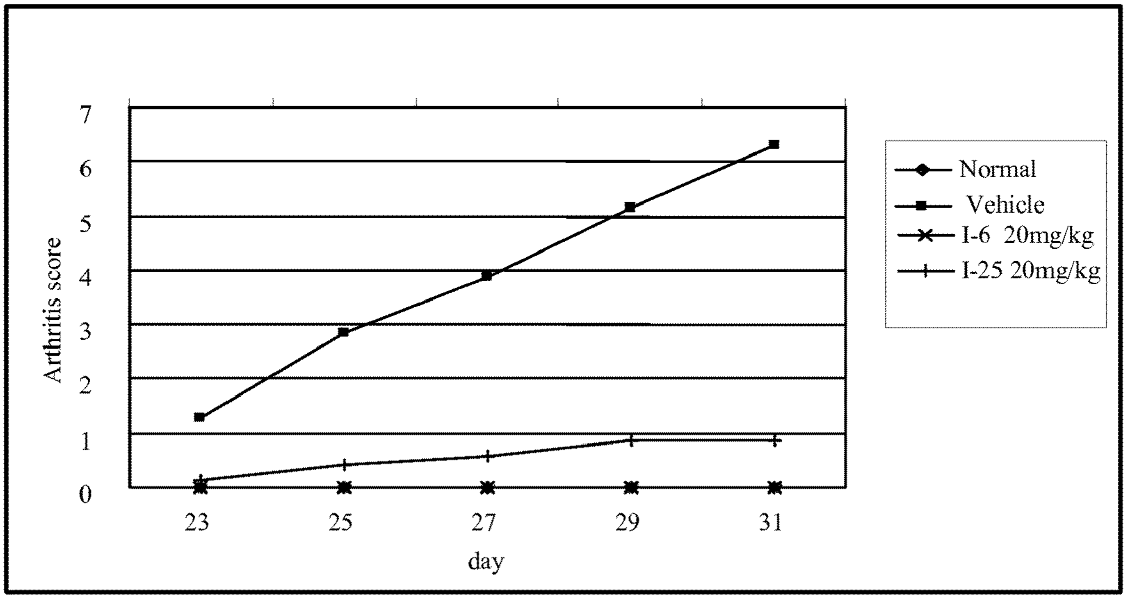
FIG. 19 shows the effect of compound I-6 and compound 1-25 (20 mg/kg, p.o., once daily) on arthritis score in the CIA model in mice.

The results for compounds (I-6) and (I-25) are shown in FIG. 19, which shows the effect of (I-6) and (I-25) (20 mg/kg, p.o., once daily) on arthritis score in the CIA model in mice.

Adjuvant-induced Arthritis in Rats

Experimental Protocol

Adjuvant was injected into the F344 rat hind paw at day 0. The volumes of adjuvant injected and un-injected paws were measured plethysmographically. Edema density was calculated as follows: Edema density=[(the paw volume after adjuvant injection)−(the paw volume before adjuvant injection)]/(the paw volume before adjuvant injection). Compounds were administered PO once daily from day 0 for 18 days.

Results

Figure 20:
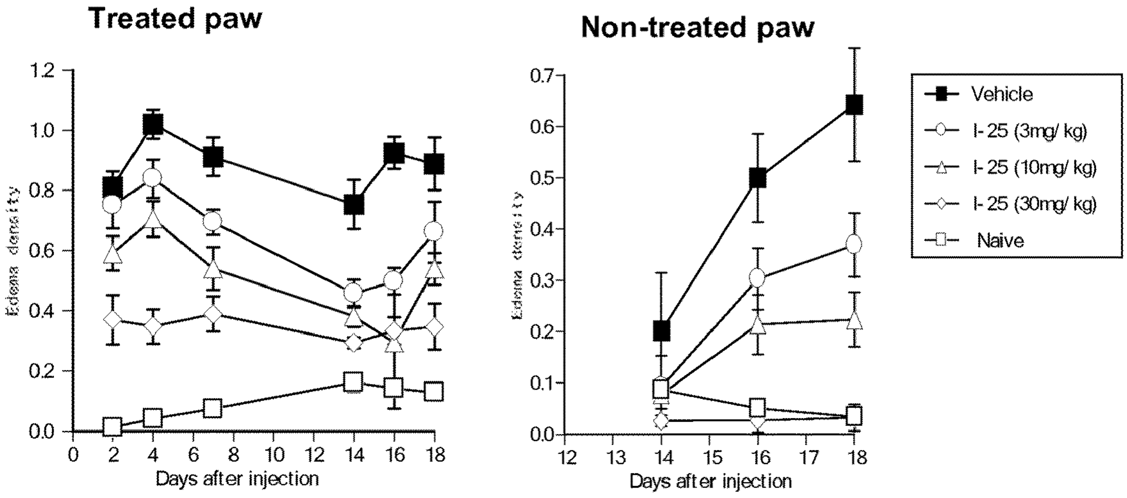
FIG. 20 shows the effect of compound I-25 (3, 10, 30 mg/kg, p.o., once daily) on edema density following adjuvant-induced arthritis in rats.

The results for compound (I-25) are shown in FIG. 20, which shows the effect of (I-25) (3, 10, 30 mg/kg, p.o., once daily) on edema density following adjuvant-induced arthritis in rats Suppression of Urinary Protein Excretion and Urinary Albumin Excretion as Well as Suppression of Nephromegaly in the Streptozotocin-Induced Diabetic Nephropathy Model in Rat Experimental Protocol Dahl/s male rats 7 week old were administered with streptozotocin (50 mg/kg iv). A week later compounds were given by oral dosing daily at the dose indicated. Development of symptoms was monitored over 4 week period of study by urine sampling and evaluation of urinary protein excretion and urinary albumin excretion. At the end of the experiment the kidney weight was established.

Results

The results for compound (I-6) are shown in FIGS. 21-26.

Figure 21:
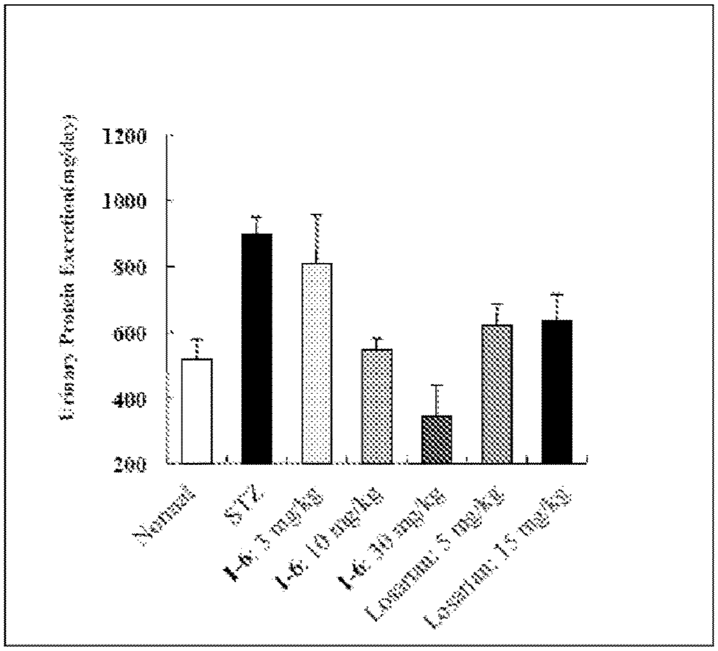
FIG. 21 shows the effect of compound I-6 (3, 10 and 30 mg/kg) and Losartan (5 and 15 mg/kg) on urinary protein excretion.
Figure 22:
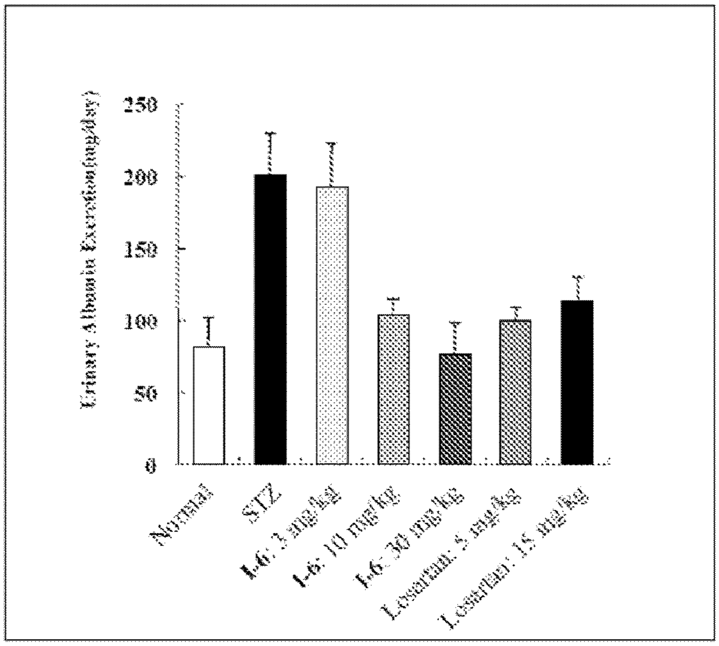
FIG. 22 shows the effect of compound I-6 (3, 10 and 30 mg/kg) and Losartan (5 and 15 mg/kg) on urinary albumin excretion.
Figure 23:
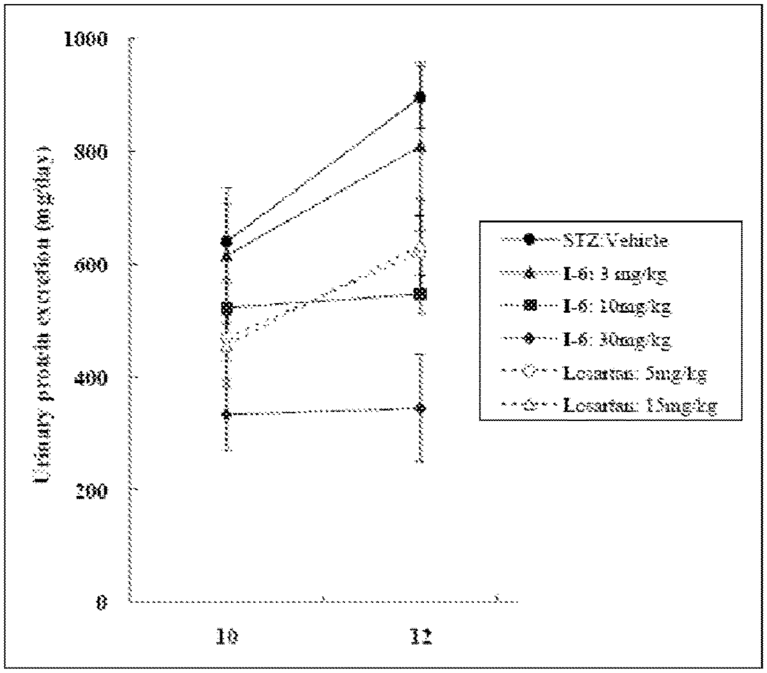
FIG. 23 shows the effect of compound I-6 (3, 10 and 30 mg/kg) and Losartan (5 and 15 mg/kg) on the time course of urinary protein excretion.
Figure 24:
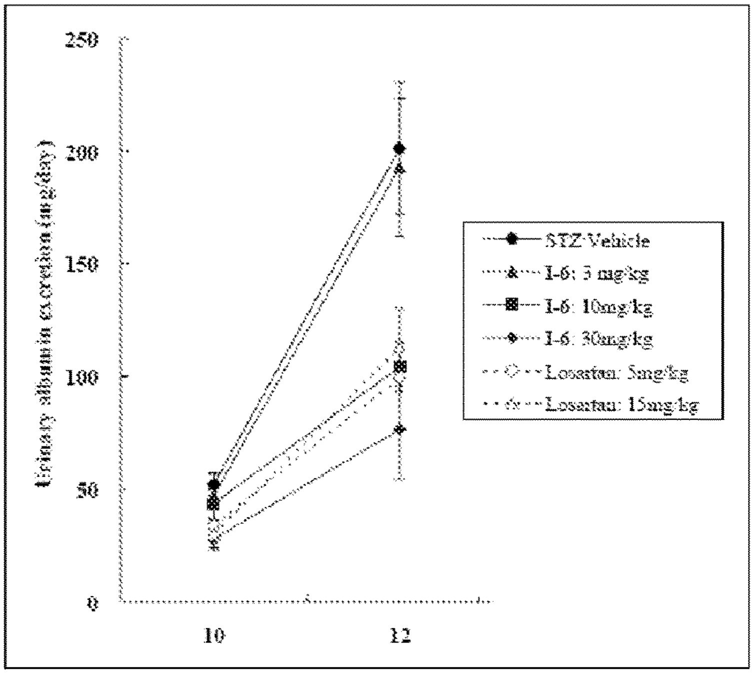
FIG. 24 shows the effect of compound I-6 (3, 10 and 30 mg/kg) and Losartan (5 and 15 mg/kg) on the time course of urinary albumin excretion.
Figure 25:
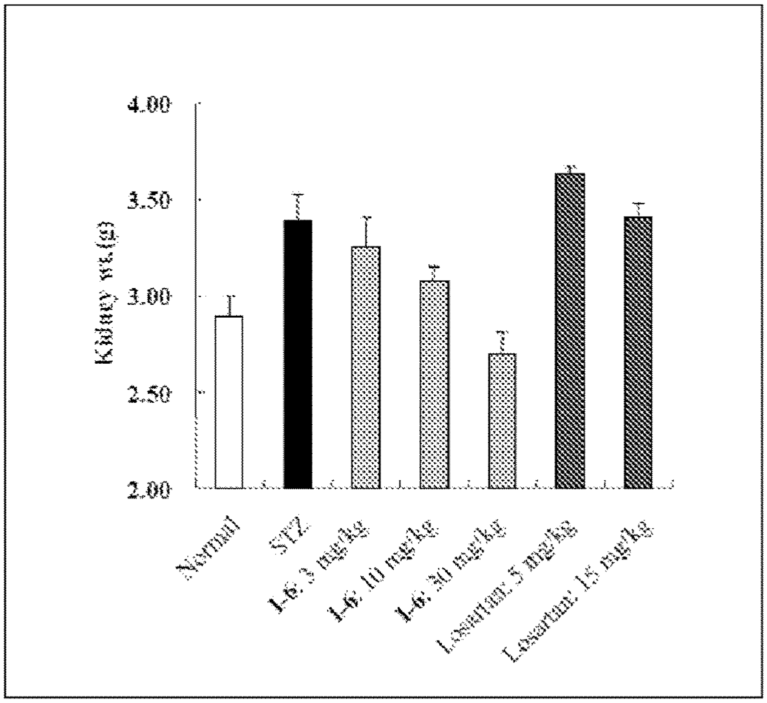
FIG. 25 shows the effect of compound I-6 (3, 10 and 30 mg/kg) and Losartan (5 and 15 mg/kg) on kidney weight.
Figure 26:
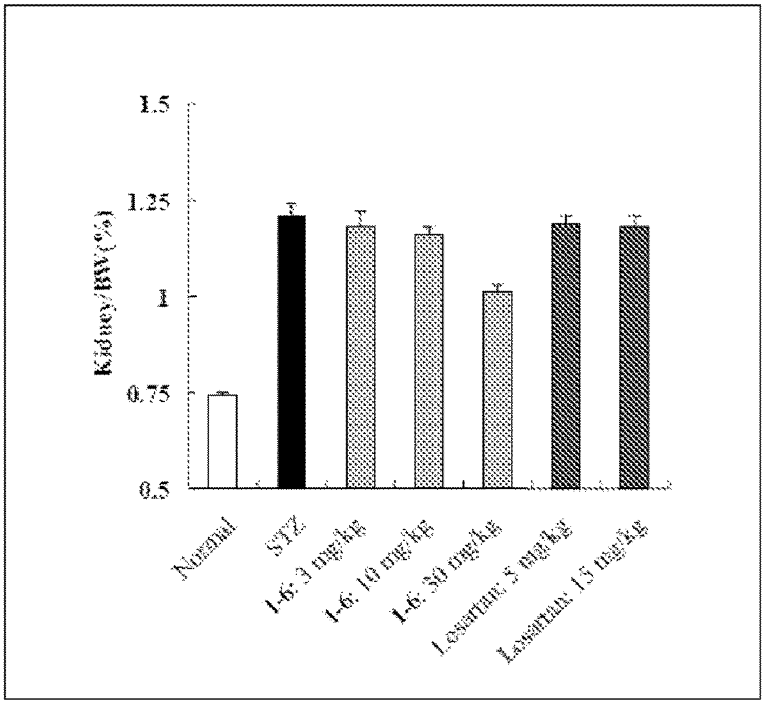
FIG. 26 shows the effect of compound I-6 (3, 10 and 30 mg/kg) and Losartan (5 and 15 mg/kg) on the ratio of kidney weight/body weight.

FIG. 21 shows the effect of (I-6) (3, 10 and 30 mg/kg) and Losartan (5 and 15 mg/kg) on urinary protein excretion;

FIG. 22 shows the effect of (I-6) (3, 10 and 30 mg/kg) and Losartan (5 and 15 mg/kg) on urinary albumin excretion;

FIG. 23 shows the effect of (I-6) (3, 10 and 30 mg/kg) and Losartan (5 and 15 mg/kg) on the time course [weeks] of urinary protein excretion;

FIG. 24 shows the effect of (I-6) (3, 10 and 30 mg/kg) and Losartan (5 and 15 mg/kg) on the time course [weeks] of urinary albumin excretion;

FIG. 25 shows the effect of (I-6) (3, 10 and 30 mg/kg) and Losartan (5 and 15 mg/kg) on kidney weight; and FIG. 26 shows the effect of (I-6) (3, 10 and 30 mg/kg) and Losartan (5 and 15 mg/kg) on the ratio of kidney weight/body weight.

The invention claimed is:

1. A compound of formula (I);

or a pharmaceutically acceptable salt thereof, (I)

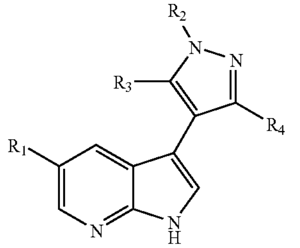

wherein $R^1$ represents a 5-7 membered non-aromatic hydrocarbon cyclic group substituted with 1-4 substituent(s) selected from the group consisting of a halogen atom, a cyano group, a hydroxyl group, an oxo group, an ethylenedioxy group, a $C_{1-6}$ alkyl group, a $C_{1-6}$ alkoxy group, a $C_{1-6}$ hydroxyalkyl group, —C(O)OH, —$CONH_2$, a $NHR^5$ group, a $NR^5R^6$ group and —$R^a$—$R^b$;

wherein $R^a$ represents a single bond or —$CH_2$—;

wherein $R^b$ represents a 4-8 membered non-aromatic heterocyclic group, a $C_{6-10}$ aryl group or a 5-7 membered heteroaryl group, substituted with 1-4 substituent(s) selected from the group consisting of a halogen atom and a $C_{1-6}$ alkyl group;

wherein $R^5$ and $R^6$ are independently selected from a $C_{1-6}$ alkyl group, a $C_{1-6}$ alkoxy group, a $C_{1-6}$ hydroxyalkyl group or a 6-membered non-aromatic heterocyclic group wherein two or more positions on $R^1$ are optionally bridged by a group —X— wherein X is O, $CH_2$, $CH_2$—$CH_2$, $NR^7$, $CH_2$—$CH_2$—$CH_2$, $CH_2$—$CH(CH_2$—)—$CH_2$ or $N(R^7)$—$CH(CH_2$—)$CH_2$ to form a bicyclic or tricyclic ring system, wherein $R^7$ is selected from hydrogen or a $C_{1-6}$ alkyl group and wherein said bridge may be optionally and substituted with one or more of a $C_{1-6}$ alkyl group, a cyano group, $CO_2NH_2$, a $C_{1-6}$ hydroxyalkyl group, an oxo group, a hydroxy group, a $C_{1-6}$ alkylamino group or a 6-membered non-aromatic heterocyclic group wherein $R^2$ represents a hydrogen atom, a $C_{1-6}$ alkyl group optionally substituted with a 4-7 membered non-aromatic heterocyclic group or a $C_{1-6}$ haloalkyl group $R^3$ represents a hydrogen atom or a $C_{1-6}$ alkyl group and $R^4$ represents a hydrogen atom or a $C_{1-6}$ alkyl group.

2. A compound or a pharmaceutically acceptable salt as claimed in claim 1 wherein the compound is of formula (Ia);

(Ia)

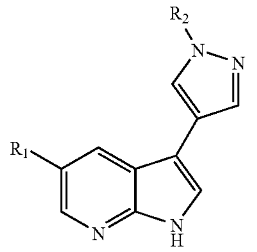

wherein $R^1$ represents a 5-7 membered non-aromatic hydrocarbon cyclic group substituted with 1-4 substituent(s) selected from the group consisting of a halogen atom, an oxo group, an ethylenedioxy group, a $C_{1-6}$ alkyl group, a $C_{1-6}$ alkoxy group, a $C_{1-6}$ hydroxyalkyl group, —C(O)OH, a ($C_{1-6}$ alkyl)amino group, a di($C_{1-6}$ alkyl) amino group and —$R^a$—$R^b$;

wherein $R^a$ represents a single bond or —$CH_2$—;

wherein $R^b$ represents a 4-7 membered non-aromatic heterocyclic group, a $C_{6-10}$ aryl group or a 5-7 membered heteroaryl group, substituted with 1-4 substituent(s) selected from the group consisting of a halogen atom and a $C_{1-6}$ alkyl group;

wherein $R^2$ represents a hydrogen atom, a $C_{1-6}$ alkyl group optionally substituted with a 4-7 membered non-aromatic heterocyclic group or a $C_{1-6}$ haloalkyl group.

3. A compound or a pharmaceutically acceptable salt as claimed in claim 2;

wherein $R^1$ represents a 5-7 membered non-aromatic hydrocarbon cyclic group substituted with 1-4 substituent(s) selected from the group consisting of a halogen atom, an oxo group, an ethylenedioxy group, a $C_{1-6}$ alkyl group, a $C_{1-6}$ alkoxy group, a $C_{1-6}$ hydroxyalkyl group, —C(O)OH, and —$R^a$—$R^b$; and wherein $R^a$, $R^b$ and $R^2$ are as defined for claim 2.

4. A compound or a pharmaceutically acceptable salt thereof according to claim 1 wherein $R^1$ represents a cyclopentyl group, a cyclohexyl group, a cycloheptyl group, a cyclopentenyl group, a cyclohexenyl group, a cycloheptenyl group, a cyclohexadienyl group, borane, norborane, adamantane, 7-oxabicyclo[2.2.1]hept-2,3-ene, 7-oxabicyclo[2.2.1]heptane, or 7-aminobicyclo[2.2.1]hept-2,3-ene, each of which may be substituted with 1-4 substituent(s) selected from the group consisting of a halogen atom, an oxo group, an ethylenedioxy group, a $C_{1-6}$ alkyl group, a $C_{1-6}$ alkoxy group, a $C_{1-6}$ hydroxyalkyl group, —C(O)OH, a ($C_{1-6}$ alkyl)amino group, a di($C_{1-6}$ alkyl)amino group and —$R^a$—$R^b$;

wherein $R^a$ represents a single bond or —$CH_2$—;

wherein $R^b$ represents a 4-7 membered non-aromatic heterocyclic group, a $C_{6-10}$ aryl group or a 5-6 membered heteroaryl group, substituted with 1-4 substituent(s) selected from the group consisting of a halogen atom and a $C_{1-6}$ alkyl group.

5. A compound or a pharmaceutically acceptable salt thereof according to claim 1, wherein $R^1$ represents a cyclohexyl group substituted with 1-4 substituent(s) selected from the group consisting of a halogen atom, an oxo group, an ethylenedioxy group, a $C_{1-6}$ alkyl group, a $C_{1-6}$ alkoxy group, a $C_{1-6}$ hydroxyalkyl group, —C(O)OH, a ($C_{1-6}$ alkyl)amino group, a di($C_{1-6}$ alkyl)amino group and —$R^a$—$R^b$;

wherein $R^a$ represents a single bond or —$CH_2$—;

wherein $R^b$ represents a 4-7 membered non-aromatic heterocyclic group, a $C_{6-10}$ aryl group or a 5-6 membered heteroaryl group, substituted with 1-4 substituent(s) selected from the group consisting of a halogen atom and a $C_{1-6}$ alkyl group.

6. A compound or a pharmaceutically acceptable salt thereof according to claim 1 wherein $R^1$ represents a 5-7 membered non-aromatic hydrocarbon cyclic group substituted with 1-4 substituent(s) selected from the group consisting of a fluorine atom, an oxo group, an ethylenedioxy group, methyl group, ethyl group, t-butyl group, methoxy group, methylamino group, dimethylamino group, diethylamino group, azetidinyl group, piperidyl group, fluoropiperidyl group, pyrrolidinyl group, methylpiperazinyl group, isopropylpiperazinyl group, methyldiazepanyl group, morpholino group, oxazepanyl group, oxazocanyl group, pyrimidyloxy group and fluorophenoxy group.

7. A compound or a pharmaceutically acceptable salt thereof according to claim 1 wherein $R^1$ represents a 5-7 membered non-aromatic hydrocarbon cyclic group substituted with 1-4 substituent(s) selected from the group consisting of a methylpiperazinyl group, a morpholino group, an oxazocanyl group and an oxazepanyl group.

8. A compound or a pharmaceutically acceptable salt thereof according to claim 1 wherein $R^1$ represents a cyclohexyl group substituted with 1-4 substituent(s) selected from the group consisting of a methylpiperazinyl group, a morpholino group, an oxazocanyl group and an oxazepanyl group.

9. A compound or a pharmaceutically acceptable salt thereof according to claim 1 wherein $R^2$ represents a methyl group, a morpholinoethyl group or a trifluoromethyl group.

10. A compound or a pharmaceutically acceptable salt thereof according to claim 1 wherein $R^2$ represents a methyl group.

11. A compound or a pharmaceutically acceptable salt thereof according to claim 1 wherein $R^3$ represents hydrogen or a methyl group.

12. A compound or a pharmaceutically acceptable salt thereof according to any according to claim 1 wherein $R^4$ represents hydrogen or a methyl group.

13. A compound selected from the following group or a pharmaceutically acceptable salt thereof;

I-6

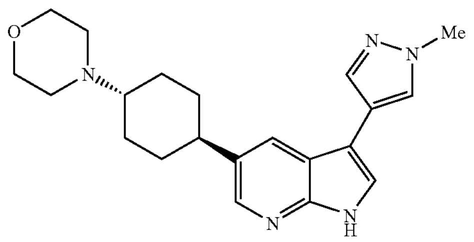

-continued

I-7

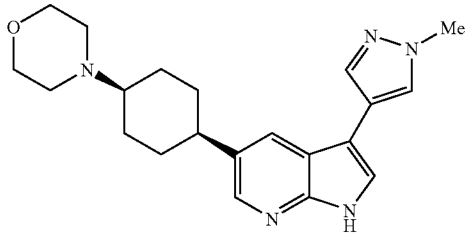

I-23

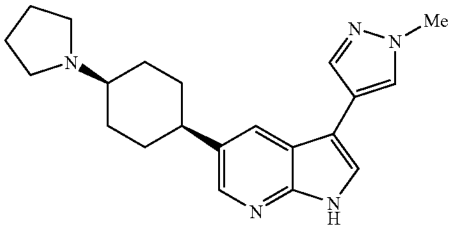

I-24

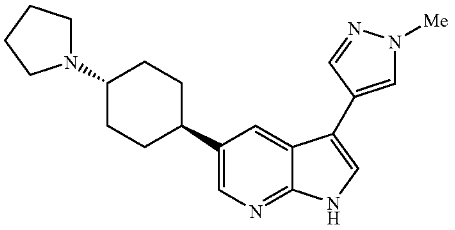

I-25

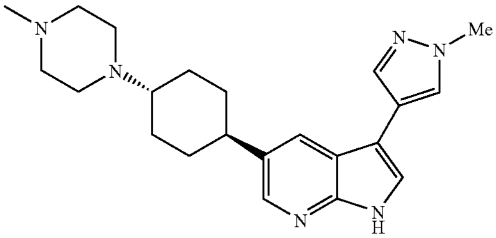

I-26

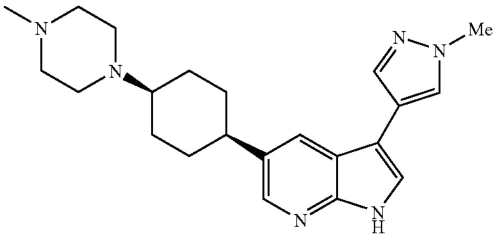

I-37

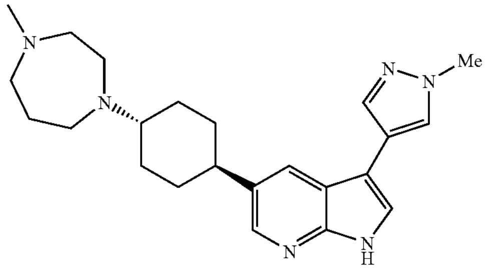

-continued
I-38
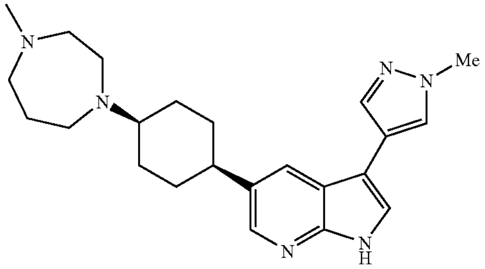
I-39
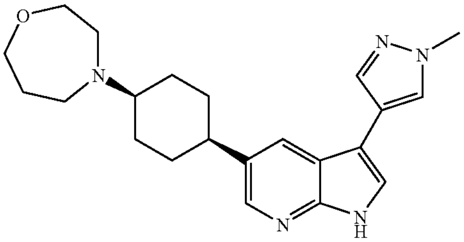
I-40
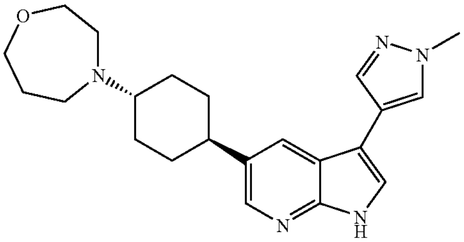
I-41
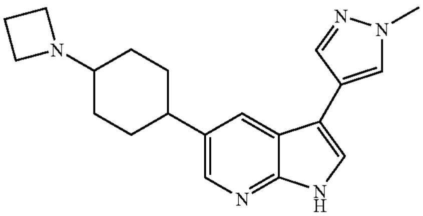
I-43
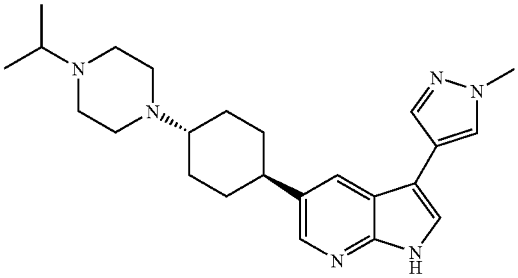
I-44
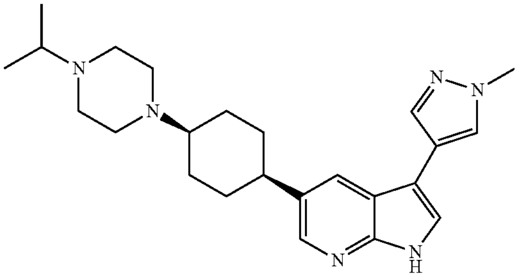
-continued
I-45
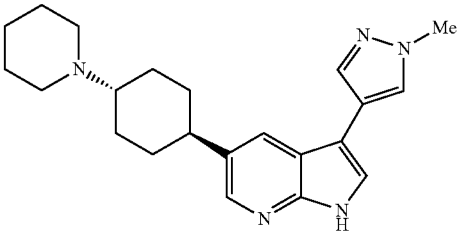
I-46
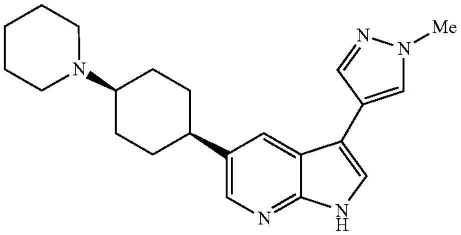
14. A pharmaceutical composition comprising a compound according to claim 1.
15. A compound of the formula:
I-6
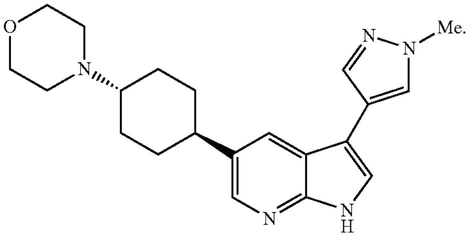
or a pharmaceutically acceptable salt thereof.
16. A compound of the formula:
I-40
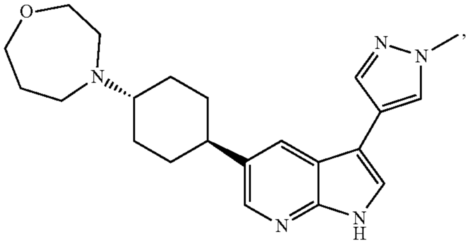
or a pharmaceutically acceptable salt thereof.
* * * * *

UNITED STATES PATENT AND TRADEMARK OFFICE

CERTIFICATE OF CORRECTION

PATENT NO. : 8,178,552 B2
APPLICATION NO. : 12/536342
DATED : May 15, 2012
INVENTOR(S) : Piotr Pawel Graczyk et al.

It is certified that error appears in the above-identified patent and that said Letters Patent is hereby corrected as shown below:

On the cover page, column 1, please insert the following new field:

-- (30) Foreign Application Priority Data:

Feb. 6, 2007 (GB) ...................... 0702265.0 --

Signed and Sealed this
Seventh Day of August, 2012

David J. Kappos

*Director of the United States Patent and Trademark Office*